(12) United States Patent
Pujala et al.

(10) Patent No.: US 12,325,720 B2
(45) Date of Patent: Jun. 10, 2025

(54) ECTONUCLEOTIDE PYROPHOSPHATASE-PHOSPHODIESTERASE-1 (ENPP1) INHIBITORS AND USES THEREOF

(71) Applicant: 1cBio, Inc., Moraga, CA (US)

(72) Inventors: Brahmam Pujala, Greater Noida (IN); Amantullah Ansari, Greater Noida (IN); Shreya Sapra, Greater Noida (IN); Pradeep S. Jadhavar, Greater Noida (IN); Dhananjay Pendharkar, Noida (IN); Sreekanth A. Ramachandran, Greater Noida (IN); Uzma Saeed, Okhla (IN); Abhinandan Danodia, Greater Noida (IN); Farha Khan, Noida (IN); Sagar Patni, Noida (IN); Sanjeev Soni, Greater Noida (IN); Ashu Gupta, Noida (IN); Sarvajit Chakravarty, Edmond, OK (US); Balaji Dashrath Sathe, Greater Noida (IN)

(73) Assignee: 1cBio, Inc., Moraga, CA (US)

( * ) Notice: Subject to any disclaimer, the term of this patent is extended or adjusted under 35 U.S.C. 154(b) by 0 days.

(21) Appl. No.: 18/743,025

(22) Filed: Jun. 13, 2024

(65) Prior Publication Data

US 2024/0352046 A1    Oct. 24, 2024

Related U.S. Application Data

(63) Continuation of application No. 17/515,758, filed on Nov. 1, 2021.

(60) Provisional application No. 63/192,605, filed on May 25, 2021, provisional application No. 63/107,818, filed on Oct. 30, 2020.

(51) Int. Cl.

| | |
|---|---|
| *C07D 403/04* | (2006.01) |
| *C07D 401/14* | (2006.01) |
| *C07D 403/14* | (2006.01) |
| *C07D 471/04* | (2006.01) |
| *C07D 487/04* | (2006.01) |
| *C07D 491/056* | (2006.01) |
| *C07F 5/02* | (2006.01) |
| *C07F 9/6558* | (2006.01) |

(52) U.S. Cl.
CPC ............ *C07F 5/025* (2013.01); *C07D 401/14* (2013.01); *C07D 403/04* (2013.01); *C07D 403/14* (2013.01); *C07D 471/04* (2013.01); *C07D 487/04* (2013.01); *C07D 491/056* (2013.01); *C07F 9/65583* (2013.01)

(58) Field of Classification Search
CPC .. C07D 401/14; C07D 403/04; C07D 403/14; C07D 471/04; C07D 487/04; C07D 491/056
See application file for complete search history.

(56) References Cited

U.S. PATENT DOCUMENTS

| | | |
|---|---|---|
| 2019/0160029 A1 | 5/2019 | Pinsky et al. |
| 2020/0085782 A1 | 3/2020 | Gallatin et al. |
| 2020/0085828 A1 | 3/2020 | Gallatin et al. |
| 2020/0101141 A1 | 4/2020 | Moseley et al. |
| 2021/0253556 A1 | 8/2021 | Kasibhatla et al. |
| 2022/0056052 A1 | 2/2022 | Hawley et al. |

(Continued)

FOREIGN PATENT DOCUMENTS

| | | |
|---|---|---|
| EP | 0324298 A1 | 7/1989 |
| WO | WO2006001511 A1 | 1/2006 |
| WO | WO2016071293 A2 | 5/2016 |

(Continued)

OTHER PUBLICATIONS

E. Forcellini, et al. Synthesis and biological evaluation of novel quinazoline-4-piperidinesulfamide derivatives as inhibitors of NPP1, European Journal of Medicinal Chemistry, 2018, vol. 147, ISSN 0223-5234, pp. 130-149, https://doi.org/10.1016/j.ejmech.2018.01.094. (Year: 2018).*

(Continued)

*Primary Examiner* — Medhanit W Bahta
*Assistant Examiner* — Manahil Mirghani Ali Abdalhameed
(74) *Attorney, Agent, or Firm* — Sheppard Mullin Richter & Hampton LLP

(57) ABSTRACT

The present invention discloses compounds useful in treatment of conditions associated with dysfunction of ectonucleotide pyrophosphatase/phosphodiesterase-1 (ENPP1) enzyme. Specifically, the present invention discloses compound of formula (J) which exhibit inhibitory activity against ENPP1. Method of treating conditions associated with over-expression of ENPP1 gene with such compound is disclosed. Uses thereof, pharmaceutical composition, and kits are also disclosed.

11 Claims, 1 Drawing Sheet

Formula (J)

(56) References Cited

U.S. PATENT DOCUMENTS

2022/0135598 A1* 5/2022 Pujala .................. C07D 403/04 514/64

FOREIGN PATENT DOCUMENTS

| WO | WO2019046778 | A1 | | 3/2019 | | |
|----|--------------|----|---|--------|---|---|
| WO | WO2019051269 | A1 | | 3/2019 | | |
| WO | WO2019076358 | A1 | | 4/2019 | | |
| WO | WO2019177971 | A1 | | 9/2019 | | |
| WO | WO-2019191504 | A1 | * | 10/2019 | ........... | A61K 47/545 |
| WO | WO2020140001 | A1 | | 7/2020 | | |
| WO | WO2020160333 | A1 | | 8/2020 | | |
| WO | WO2020163366 | A1 | | 8/2020 | | |
| WO | WO2020185859 | A1 | | 9/2020 | | |
| WO | WO2020190912 | A1 | | 9/2020 | | |
| WO | WO2020210649 | A1 | | 10/2020 | | |
| WO | WO2021061803 | A1 | | 4/2021 | | |
| WO | WO2021225969 | A1 | | 11/2021 | | |
| WO | WO2021226136 | A1 | | 11/2021 | | |
| WO | WO2021231726 | A1 | | 11/2021 | | |
| WO | WO2021243031 | A1 | | 12/2021 | | |
| WO | WO2021257614 | A1 | | 12/2021 | | |
| WO | WO2022006545 | A1 | | 1/2022 | | |

OTHER PUBLICATIONS

Carozza et al., "Structure-Aided Development of Small-Molecule Inhibitors of ENPP1, the Extracellular Phosphodiesterase of the Immunotransmitter cGAMP," Cell Chemical Biology, vol. 27, Issue 11, pp. 1347-1358.

Extended European Search Report, dated Jul. 26, 2024, regarding Application No. EP21885500, 16 pages.

International Preliminary Report on Patentability, dated May 2, 2023, regarding International Application No. PCT/IB2021/060074, 7 pages.

International Search Report, dated Feb. 1, 2022, regarding International Application No. PCT/IB2021/060074, 4 pages.

Talamas et al., "Discovery of N-[4-[6-tert-butyl-5-methoxy-8-(6-methoxy-2-oxo-1H-pyridin-3-yl)-3-quinolyl]phenyl]methanesulfonamide (RG7109), a Potent Inhibitor of the Hepatitis C Virus NS5B Polymerase," Journal of Medicinal Chemistry, 2014, vol. 57, Issue 5, pp. 1914-1931.

* cited by examiner

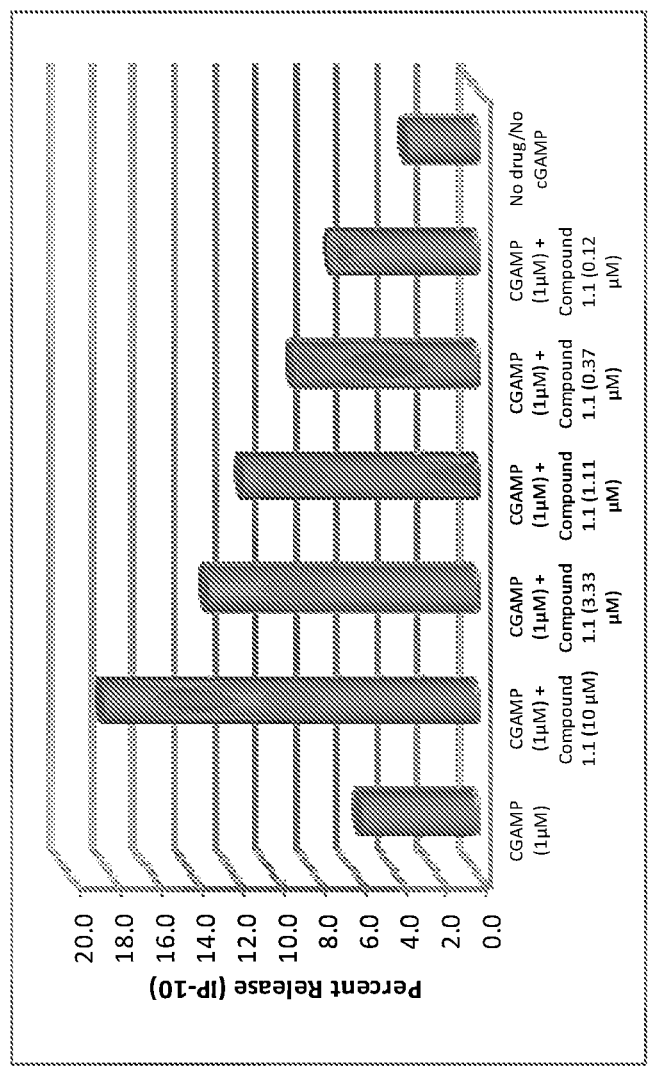

ECTONUCLEOTIDE PYROPHOSPHATASE-PHOSPHODIESTERASE-1 (ENPP1) INHIBITORS AND USES THEREOF

CROSS-REFERENCE TO RELATED APPLICATIONS

This application is a continuation of U.S. patent application Ser. No. 17/515,758, filed Nov. 1, 2021, which claims the priority benefits of U.S. Provisional Application No. 63/107,818, filed on Oct. 30, 2020; and U.S. Provisional Application No. 63/192,605, filed on May 25, 2021, disclosures of which are incorporated herein by reference in its entireties.

FIELD OF THE INVENTION

The present invention generally relates to compounds possessing anti-cancer activity useful in the treatment of proliferative disorders. The invention also provides method of synthesis of said compounds, method of using said compounds, pharmaceutical compositions comprising said compounds and method of using thereof.

BACKGROUND OF THE INVENTION

ENPP1, ectonucleotide pyrophosphatase/phosphodiesterase 1, is a type II transmembrane glycoprotein with pyrophosphatase and phosphodiesterase activity, expressed highly in bone and cartilage. ATP is an identified substrate of ENPP1, which is hydrolyzed to AMP and PPi. CD73 converts AMP to adenosine and inorganic phosphate (Pi). ENPP1 hydrolysis of pyrophosphate bonds (such as in ATP) and phosphodiester bonds (such as in oligonucleotides) to produce nucleoside 5'-monophosphates, as part of the functions mediated by nucleotide pyrophosphatases/phosphodiesterase (NPPs), which is necessary in a wide range of cellular processes including nucleotide recycling, purinergic receptor signaling and ATP-mediated apoptosis.

Recently, ENPP1 has been found to play an important role in the immunological responses to various stimuli through the cyclic GMP-AMP synthase (cGAS)-stimulator of interferon genes (STING) pathway. Damage associated molecular patterns (DAMPs) as well as pathogen associated molecular patterns (PAMPs) activate the immune system via STING. cGAS senses cytosolic DNA and catalyzes the conversion of GTP and ATP to cyclic GMP-AMP (cGAMP). Subsequently, 2,3'-cGAMP activates STING to initiate an inflammatory response via the TANK-binding kinase 1 (TBK1)-Interferon Regulatory Factor (IRF) 3 pathway to produce type 1 interferons (IFNs) and other cytokines. A link between the cGAS-STING pathway and ENPP1 has emerged whereby the hydrolysis of cGAMP by ENPP1 attenuates cGAS-STING signaling. ENPP1 plays a regulatory function in immune cells such as neutrophils, macrophages, dendritic cells, natural killer cells, and B lymphocytes. ENPP1 expression is heightened in M2 macrophages in the presence of cancer and promotes tumor growth and spread. The role of ENPP1 in cancer is exemplified by the observations of enhanced tumor metastasis to the bone from breast cancer, for example, by over-expression of ENPP1.

Recent reports suggest that the cyclic dinucleotides, a substrate for ENPP1, stimulate innate immunity via STING-dependent activation of interferon genes. ENPP1 inhibition of STING pathway activation is critical for tumor control, similar to that of checkpoint inhibitors such as anti PD-1 or PD-L1 which are promising immunotherapeutics for various cancers.

Since STING activation is a promising therapeutic strategy to cure cancer, more and more compounds that activate the STING pathway have been reported. ENPP1, as a highly potent cGAMP-degradation enzyme, makes the application of ENPP1 inhibitors for anti-tumor therapy.

ADP-ribosylation is a conserved post-translational protein modification that plays a role in all major cellular processes, particularly DNA repair, transcription, translation, stress response and cell death. Poly(ADP-ribosyl)ation (PARylation) mediated by poly ADP-ribose polymerases (PARPs) plays a key role in DNA damage repair. Suppression of PARylation by PARP inhibitors impairs DNA damage repair and induces apoptosis of tumor cells with repair defects. Thus, PARP inhibitors have been approved by the US FDA for various types of cancer treatment. However, recent studies suggest that dePARylation also plays a key role in DNA damage repair. Instead of antagonizing PARylation, dePARylation acts as a downstream step of PARylation in DNA damage repair. Protein PARylation can be reversed by the macrodomain containing proteins PARG, TARG1, MacroD1 and MacroD2, and ENPP1. Recently it is known that ENPP1 play a role in dePARylation process by h hydrolysing the ester bond known to link proteins to ADP-ribose as well as consecutive ADP-ribose subunits. DePARylation inhibitors represent a novel class of inhibitors alternative to PARP inhibition, and may overcome chemoresistance of PARPi. Thus, ENPP1 inhibitors can also play an important role in DNA damage repair process.

Based on the above principles, there is an urgent and growing need of a class of anti-tumor compounds which can inhibit ENPP1 and treat various types of cancer.

SUMMARY OF THE INVENTION

In one aspect, the present invention provides a compound of formula (IA):

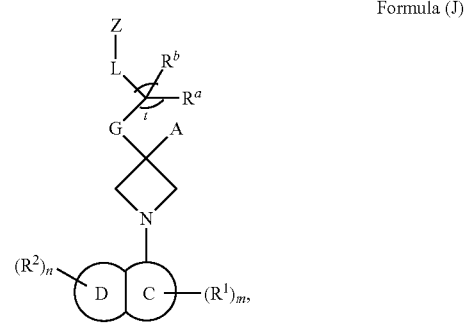

Formula (J)

or a salt thereof, wherein A, G, $R^a$, $R^b$, L, Z, C, D, $R^1$, $R^2$, m, n and t are as detailed herein.

In some aspects, the compound of formula (J) or a salt thereof, is a compound of formula (IA) or a salt thereof, as detailed herein.

In some aspects, the compound of formula (J) or a salt thereof, is a compound of formula (I) or a salt thereof, as detailed herein.

In some aspects, the compound of formula (J) or a salt thereof, is a compound of formula (II) or a salt thereof, as detailed herein.

In some aspects, the compound of formula (J) or a salt thereof, is a compound of formula (III) or a salt thereof, as detailed herein.

In some aspects, the compound of formula (J) or a salt thereof, is a compound of formula (IV) or a salt thereof, as detailed herein.

In some aspects, the compound of formula (J) or a salt thereof, is any of the compounds of formula (IV-1) to (IV-11) or a salt thereof, as detailed herein.

In some aspects, the compound of formula (J) or a salt thereof, is a compound of formula (V) or a salt thereof, as detailed herein.

In some aspects, the compound of formula (J) or a salt thereof, any of the compounds of formula (V-1) to (V-11) or a salt thereof, as detailed herein.

In some aspects, the compound of formula (J) or a salt thereof, is a compound of formula (VI) or a salt thereof, as detailed herein.

In some aspects, the compound of formula (J) or a salt thereof, is a compound of formula (VII) or a salt thereof, as detailed herein.

In some aspects, the compound of formula (J) or a salt thereof, is a compound of formula (VIII) or a salt thereof, as detailed herein.

In some aspects, the compound of formula (J) or a salt thereof, is a compound of formula (IX) or a salt thereof, as detailed herein.

In some aspects, the compound of formula (J) or a salt thereof, is a compound of formula (X) or a salt thereof, as detailed herein.

In some aspects, the compound of formula (J) or a salt thereof, is a compound of formula (XI) or a salt thereof, as detailed herein.

In some aspects, the compound of formula (J) or a salt thereof, is a compound of formula (XII) or a salt thereof, as detailed herein.

In some aspects, the compound of formula (J) or a salt thereof, is any of compounds of formula (XII-1) to (XII-6) or a salt thereof, as detailed herein.

In some aspects, the compound of formula (J) or a salt thereof, is a compound of formula (XIII) or a salt thereof, as detailed herein.

In some aspects, the compound of formula (J) or a salt thereof, is any of compounds of formula (XIII-1) to (XIII-9) or a salt thereof, as detailed herein.

In some aspects, the present invention provides method of treating a disease or disorder associated with ENPP1 enzyme in an individual in need thereof, wherein the method comprises administering to the individual an effective amount of a compound of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)), or a salt thereof.

In some aspects, the present invention provides method of treating cancer in an individual in need thereof, wherein the method comprises administering to the individual an effective amount of a compound of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)), or a salt thereof.

In some aspects, the present invention provides method of inhibiting ENPP1 enzyme in an individual in need thereof, wherein the method comprises administering to the individual an effective amount of a compound of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)), or a salt thereof.

In some aspects, the present invention provides method of treating a disease or disorder associated with ENPP1 enzyme in an individual in need thereof, wherein the method comprises administering to the individual an effective amount of a compound of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)), or a salt thereof in combination with other therapeutic agents.

In some aspects, the present invention also provides pharmaceutical compositions, comprising a compound of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)), or a salt thereof, and at least one pharmaceutically acceptable excipient.

In some aspects, the present invention provides method of treating a disease or disorder associated with ENPP1 enzyme in an individual in need thereof, wherein the method comprises administering to the individual a pharmaceutical composition comprising an effective amount of a compound of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)), or a salt thereof.

In some aspects, the present invention provides uses of the compound of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)), or a salt thereof in the manufacture of the medicament for treatment of a disease or disorder associated with this ENPP1 gene.

In some aspects, the present invention provides processes for synthesizing compounds disclosed herein and intermediates used to synthesize the disclosed compounds.

BRIEF DESCRIPTION OF THE DRAWINGS

FIG. 1 is a bar-graph of the IP-10 release in THP-1 cell lines for a compound of the present invention.

DETAILED DESCRIPTION OF THE INVENTION

Definitions

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_6$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Carbonyl" refers to the group C=O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to imidazolyl, pyrrolyl, pyrazolyl, 1,2,4-triazolyl, thiophenyl, furanyl, thiazolyl, isothiazolyl, 1,3,4-thiadiazolyl oxazolyl, isoxazolyl, 1,3,4-oxadiazolyl, pyridyl, pyrimidyl, pyridazinyl, pyrazinyl, indolyl, indazolyl, benzoimidazolyl, pyrrolopyridinyl, pyrrolopyridazinyl, pyrrolopyrimidinyl, pyrazolopyridinyl, pyrazolopyrimidinyl, imidazopyridinyl, purinyl, benzofuranyl, furopyridinyl, benzooxazolyl, benzothiophenyl, benzothiazolyl, oxazolopyridinyl, thiazolopyridinyl, thienopyridinyl, quinolinyl, quinolonyl, naphthyridinyl, quinazolinyl, pyridopyrimidinyl, cinnolinyl or pyridopyridazinyl and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, aziridinyl, azetidinyl, oxetanyl, morpholinyl, thiomorpholinyl, azepanyl tetrahydropyranyl, dihydropyranyl, piperidinyl, piperazinyl, pyrrolidinyl, thiazolinyl, thiazolidinyl, tetrahydrofuranyl, tetrahydrothiophenyl, and the like.

"Oxo" refers to the moiety =O.

"ENPP1" refers to Ectonucleotide Pyrophosphatase Phosphodiesterase 1.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "medicament" or "pharmaceutical composition" refers to an pharmaceutical formulation in administrable form comprising at least one pharmaceutically active ingredient and one or more pharmaceutically acceptable carrier.

A "pharmaceutically acceptable carrier" or "pharmaceutically acceptable excipient" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late-stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations. in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Compounds

In one aspect, provided is a compound of the formula (J):

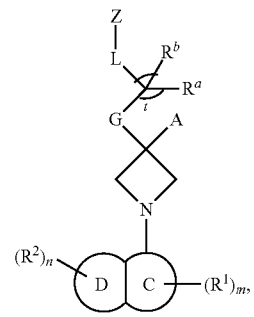

Formula (J)

or a salt thereof, wherein
C is 5- to 6-membered heteroaryl optionally substituted with $R^1$;
D is $C_6$- aryl or 5- to 6-membered heteroaryl, each of which is optionally substituted with $R^2$, wherein D is fused to C;
A is hydrogen, $C_1$-$C_6$ alkyl, or $C_6$- aryl, each of which is optionally substituted with halogen;
G is a bond, —$CH_2$— or —$CH_2$—$CH_2$—;
$R^a$ and $R^b$ are independently hydrogen or $C_1$-$C_6$ alkyl;

or $R^a$ and $R^b$ are taken together with the atoms to which they are attached to form a $C_3$-$C_6$ cycloalkyl ring;
or any one of $R^a$ and $R^b$, and A are taken together along with the atoms to which they are attached to form a $C_4$-$C_6$ cycloalkyl ring;

L is a bond, linear or branched $C_1$-$C_6$ alkylene or linear or branched $C_2$-$C_6$ alkenylene;

t is 0 or 1;

provided that when t is 0 then L is linear or branched $C_2$-$C_6$ alkenylene;

Z is —$NR^cS(O)_2NH_2$, —$NR^cS(O)_2CH_3$, —$SO_2NH_2$, —$NR^cC(O)CH_3$, —C(O)OH, —$CONH_2$, $NR^cCONH_2$, —CONH(OH), —$B(OH)_2$—$P(O)(OH)_2$, —$SO_2OH$, —$NR^cS(O)_2CF_3$, —$NR^cS(O)_2NHCH_3$, or —$NR^cCH_2C_6$- aryl-$S(O)_2NH_2$.

each $R^1$ and $R^2$ are independently hydrogen, oxo, $C_1$-$C_6$ alkyl, $C_2$-$C_6$ alkenyl, $C_2$-$C_6$ alkynyl, $C_3$-$C_6$ cycloalkyl, adamantly, 3- to 6-membered heterocyclyl, $C_6$- aryl, 5- to 6-membered heteroaryl, —CN, halogen, $C_1$-$C_6$alkoxy, $C_1$-$C_6$haloalkoxy, —$OR^{10}$, —$SR^{10}$, —$S(O)_2R^{10}$, —$S(O)_2NR^{11}R^{12}$, —$NR^{10}S(O)_2R^{11}$, —$NR^{11}R^{12}$, —$C(O)R^{10}$, —$NR^{10}C(O)R^{11}$, —$NR^{10}C(O)NR^{11}R^{12}$, —$C(O)OR^{10}$, —$C(O)ONR^{11}R^{12}$, —$C(O)NR^{11}R^{12}$, wherein each of which is optionally substituted by $R^9$;

or any two of $R^2$ are taken together with the atoms to which they attached to form a $C_5$-$C_6$ cycloalkyl, 5- to 6-membered heterocyclyl, $C_6$- aryl or 5- to 6-membered heteroaryl, wherein each of which is optionally substituted by $R^9$;

$R^9$ is oxo, $C_2$-$C_6$ alkenyl, $C_2$-$C_6$ alkynyl, $C_3$-$C_6$ cycloalkyl, 3- to 6-membered heterocyclyl, $C_6$- aryl, 5- to 6-membered heteroaryl, —CN, halogen, $C_1$-$C_6$ alkoxy, $C_1$-$C_6$ haloalkoxy, $C_1$-$C_6$ haloalkyl, —$OR^{13}$, —$SR^{13}$, —$S(O)_2R^{13}$, —$S(O)_2NR^{14}R^{15}$, —$NR^3S(O)_2R^4$, —$NR^{14}R^{15}$, —$C(O)R^{13}$, —$NR^{13}C(O)R^{14}$, —$NR^{13}C(O)NR^{14}R^{15}$, —$C(O)OR^{13}$, —$C(O)ONR^{14}R^{15}$, —$C(O)NR^{14}R^{15}$ or $C_1$-$C_6$ alkyl optionally substituted by oxo, OH or halogen;

$R^c$ is hydrogen, $C_1$-$C_6$ alkyl, $C_3$-$C_6$ cycloalkyl, —($C_1$-$C_6$ alkylene)$C_3$-$C_6$ cycloalkyl, 3- to 6-membered heterocyclyl, —($C_1$-$C_6$ alkylene) 3- to 6-membered heterocyclyl, —($C_1$-$C_6$ alkylene)$C_6$- aryl, 5- to 6-membered heteroaryl, —($C_1$-$C_6$ alkylene) 5- to 6-membered heteroaryl, $C_1$-$C_6$ haloalkyl, —($C_1$-$C_6$ alkylene)$OR^{13}$, —($C_1$-$C_6$ alkylene)$SR^{13}$, —($C_1$-$C_6$ alkylene)$S(O)_2R^{13}$, —($C_1$-$C_6$ alkylene)$S(O)_2NR^{14}R^{15}$, —($C_1$-$C_6$ alkylene)$NR^{13}S(O)_2R^1$, —($C_1$-$C_6$ alkylene)$NR^{14}R^{15}$, —($C_1$-$C_6$ alkylene)$C(O)R^{13}$, —($C_1$-$C_6$ alkylene)$NR^{13}C(O)R^4$, —($C_1$-$C_6$ alkylene)$NR^{13}C(O)NR^{14}R^{15}$, —($C_1$-$C_6$ alkylene)$C(O)OR^{13}$, —($C_1$-$C_6$ alkylene) C(O)$ONR^1R^{15}$ or —($C_1$-$C_6$ alkylene)-$C(O)NR^{14}R^{15}$, each of which is optionally substituted with $R^d$;

$R^d$ is hydrogen, halogen, —OH, oxo, —CN, $C_1$-$C_6$ haloalkyl, $C_1$-$C_6$ alkoxy, $C_1$-$C_6$ haloalkoxy, —COOH or $C_1$-$C_6$ alkyl optionally substituted with —OH, halogen, CN or oxo;

each $R^{10}$, $R^{11}$ and $R^{12}$ is independently hydrogen, $C_1$-$C_6$ alkyl, $C_2$-$C_6$ alkenyl, $C_2$-$C_6$ alkynyl, $C_3$-$C_6$ cycloalkyl, —($C_1$-$C_6$ alkylene)$C_3$-$C_6$ cycloalkyl-, 3- to 6-membered heterocyclyl or, —($C_1$-$C_6$ alkylene) 3- to 6-membered heterocyclyl, wherein each of $R^{10}$, $R^{11}$ and $R^{12}$ is independently optionally substituted by oxo, $C_2$-$C_6$ alkenyl, $C_2$-$C_6$ alkynyl, —CN, halogen, $C_1$-$C_6$alkoxy or $C_1$-$C_6$ alkyl optionally substituted by oxo, OH, halogen;

or $R^{11}$ and $R^{12}$ are taken together with the atoms to which they attached to form a 3-6 membered heterocyclyl optionally substituted by oxo, OH, halogen or $C_1$-$C_6$ alkyl optionally substituted by oxo, OH or halogen;

each $R^{13}$, $R^{14}$ and $R^{15}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl or 3- to 6-membered heterocyclyl, wherein each of $R^{10}$, $R^{11}$ and $R^{12}$ is independently optionally substituted by oxo, —OH, $C_2$-$C_6$ alkenyl, $C_2$-$C_6$ alkynyl, —CN, halogen or $C_1$-$C_6$ alkyl optionally substituted by oxo, OH, halogen;

or $R^{14}$ and $R^{15}$ are taken together with the atoms to which they attached to form a 3-6 membered heterocyclyl optionally substituted by oxo, OH, halogen, or $C_1$-$C_6$ alkyl optionally substituted by oxo, OH or halogen;

m is 0, 1 or 2; and n is 0, 1, 2, 3 or 4;

provided that when Z is —$NR^cS(O)_2CH_3$, —$CONH_2$ or —C(O)OH, G is a bond and t is 1 then L is not a bond; and the compound is not:

1-[7-(4-Bromo-2,6-dimethylphenyl)-2,5-dimethyl-7H-pyrrolo[2,3-d]pyrimidin-4-yl]-3-azetidinebutanoic acid;

1-[7-(4-Bromo-2,6-dimethylphenyl)-2,5-dimethyl-7H-pyrrolo[2,3-d]pyrimidin-4-yl]-3-azetidinepentanoic acid; or Acetamide, N-[[1-(6-fluoro-2-benzoxazolyl)-3-azetidinyl]methyl]-N-methyl.

In one aspect, provided is a compound of the formula (IA):

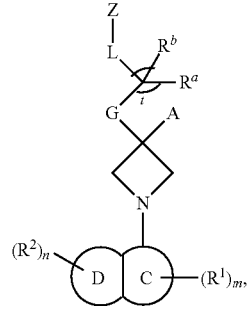

Formula (IA)

or a salt thereof, wherein

C is 5- to 6-membered heteroaryl optionally substituted with $R^1$;

D is $C_6$- aryl or 5- to 6-membered heteroaryl, each of which is optionally substituted with $R^2$, wherein D is fused to C;

A is hydrogen, $C_1$-$C_6$ alkyl, or $C_6$- aryl, each of which is optionally substituted with halogen;

G is a bond, —$CH_2$— or —$CH_2$—$CH_2$—;

$R^a$ and $R^b$ are independently hydrogen or $C_1$-$C_6$ alkyl;

or $R^a$ and $R^b$ are taken together with the atoms to which they are attached to form a $C_3$-$C_6$ cycloalkyl ring;

or any one of $R^a$ and $R^b$, and A are taken together along with the atoms to which they are attached to form a $C_4$-$C_6$ cycloalkyl ring;

L is a bond, linear or branched $C_1$-$C_6$ alkylene or linear or branched $C_2$-$C_6$ alkenylene;

t is 0 or 1;

provided that when t is 0 then L is linear or branched $C_2$-$C_6$ alkenylene;

Z is —$NR^cS(O)_2NH_2$, —$NR^cS(O)_2CH_3$, —$SO_2NH_2$, —$NR^cC(O)CH_3$, —C(O)OH, —$CONH_2$, $NR^cCONH_2$,

—CONH(OH), —B(OH)$_2$—P(O)(OH)$_2$, —SO$_2$OH, —NR$^c$S(O)$_2$CF$_3$ or —NR$^c$S(O)$_2$NHCH$_3$;

R$^c$ is hydrogen, C$_1$-C$_6$ alkyl, C$_3$-C$_6$ cycloalkyl, or C$_1$-C$_6$ haloalkyl;

each R$^1$ and R$^2$ are independently hydrogen, oxo, C$_1$-C$_6$ alkyl, C$_2$-C$_6$ alkenyl, C$_2$-C$_6$ alkynyl, C$_3$-C$_6$ cycloalkyl, adamantly, 3- to 6-membered heterocyclyl, —, 5- to 6-membered heteroaryl, —CN, halogen, C$_1$-C$_6$alkoxy, C$_1$-C$_6$haloalkoxy, —OR$^{10}$, —SR$^{10}$, —S(O)$_2$R$^{10}$, —S(O)$_2$NR$^{11}$R$^{12}$, —NR$^{10}$S(O)$_2$R$^{11}$, —NR$^{11}$R$^{12}$, —C(O)R$^{10}$, —NR$^{10}$C(O)R$^{11}$, —NR$^{10}$C(O)NR$^{11}$R$^{12}$, —C(O)OR$^{10}$, —C(O)ONR$^{11}$R$^{12}$, —C(O)NR$^{11}$R$^{12}$, wherein each of which is optionally substituted by R$^9$;

or any two of R$^2$ are taken together with the atoms to which they attached to form a C$_5$-C$_6$ cycloalkyl, 5- to 6-membered heterocyclyl, C$_6$- aryl or 5- to 6-membered heteroaryl, wherein each of which is optionally substituted by R$^9$;

R$^9$ is oxo, C$_2$-C$_6$ alkenyl, C$_2$-C$_6$ alkynyl, C$_3$-C$_6$ cycloalkyl, 3- to 6-membered heterocyclyl, C$_6$- aryl, 5- to 6-membered heteroaryl, —CN, halogen, C$_1$-C$_6$ alkoxy, C$_1$-C$_6$ haloalkoxy, C$_1$-C$_6$ haloalkyl, —OR$^{13}$, —SR$^{13}$, —S(O)$_2$R$^{13}$, —S(O)$_2$NR$^{14}$R$^{13}$, —NR$^{13}$S(O)$_2$R$^{14}$, —NR$^{14}$R$^{15}$, —C(O)R$^{13}$, —NR$^{13}$C(O)R$^{14}$, —NR$^{13}$C(O)NR$^{14}$R$^{15}$, —C(O)OR$^{13}$, —C(O)ONR$^{14}$R$^{15}$, —C(O)NR$^{14}$R$^{15}$ or C$_1$-C$_6$ alkyl optionally substituted by oxo, OH or halogen;

each R$^{10}$, R$^{11}$ and R$^{12}$ is independently hydrogen, C$_1$-C$_6$ alkyl, C$_2$-C$_6$ alkenyl, C$_2$-C$_6$ alkynyl, C$_3$-C$_6$ cycloalkyl or 3- to 6-membered heterocyclyl, wherein each of R$^{10}$, R$^{11}$ and R$^{12}$ is independently optionally substituted by oxo, C$_2$-C$_6$ alkenyl, C$_2$-C$_6$ alkynyl, —CN, halogen, C$_1$-C$_6$ alkoxy or C$_1$-C$_6$ alkyl optionally substituted by oxo, OH, halogen;

or R$^{11}$ and R$^{12}$ are taken together with the atoms to which they attached to form a 3-6 membered heterocyclyl optionally substituted by oxo, OH, halogen or C$_1$-C$_6$ alkyl optionally substituted by oxo, OH or halogen;

each R$^{13}$, R$^{14}$ and R$^{15}$ is independently hydrogen, C$_1$-C$_6$ alkyl, C$_2$-C$_6$ alkenyl, C$_2$-C$_6$ alkynyl, C$_3$-C$_6$ cycloalkyl or 3- to 6-membered heterocyclyl, wherein each of R$^{10}$, R$^{11}$ and R$^{12}$ is independently optionally substituted by oxo, C$_2$-C$_6$ alkenyl, C$_2$-C$_6$ alkynyl, —CN, halogen or C$_1$-C$_6$ alkyl optionally substituted by oxo, OH, halogen;

or R$^{14}$ and R$^{15}$ are taken together with the atoms to which they attached to form a 3-6 membered heterocyclyl optionally substituted by oxo, OH, halogen, or C$_1$-C$_6$ alkyl optionally substituted by oxo, OH or halogen;

m is 0, 1 or 2; and n is 0, 1, 2, 3 or 4.

In one aspect, provided is a compound of the formula (I):

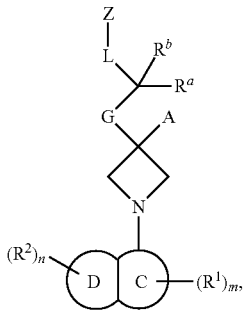

Formula (I)

or a salt thereof, wherein

C is 5- to 6-membered heteroaryl optionally substituted with R$^1$;

D is C$_6$- aryl or 5- to 6-membered heteroaryl, each of which is optionally substituted with R$^2$, wherein D is fused to C;

A is hydrogen or C$_1$-C$_6$ alkyl;

G is a bond, —CH$_2$— or —CH$_2$—CH$_2$—;

R$^a$ and R$^b$ are independently hydrogen or C$_1$-C$_6$ alkyl;

or R$^a$ and R$^b$ are taken together with the atoms to which they are attached to form a C$_3$-C$_6$ cycloalkyl ring;

or any one of R$^a$ and R$^b$, and A are taken together along with the atoms to which they are attached to form a C$_4$-C$_6$ cycloalkyl ring;

L is a bond or linear or branched C$_1$-C$_6$ alkylene;

Z is —NR$^c$S(O)$_2$NH$_2$, —NR$^c$S(O)$_2$CH$_3$, —SO$_2$NH$_2$, —NR$^c$C(O)CH$_3$, —C(O)OH, —CONH$_2$, NR$^c$-CONH$_2$, —CONH(OH), —B(OH)$_2$ or —P(O)(OH)$_2$;

R$^c$ is hydrogen, C$_1$-C$_6$ alkyl or C$_3$-C$_6$ cycloalkyl;

each R$^1$ and R$^2$ are independently hydrogen, oxo, C$_1$-C$_6$ alkyl, C$_2$-C$_6$ alkenyl, C$_2$-C$_6$ alkynyl, C$_3$-C$_6$ cycloalkyl, 3- to 6-membered heterocyclyl, C$_6$- aryl, 5- to 6-membered heteroaryl, —CN, halogen, C$_1$-C$_6$alkoxy, C$_1$-C$_6$haloalkoxy, —OR$^{10}$, —SR$^{10}$, —S(O)$_2$R$^{10}$, —S(O)$_2$NR$^{11}$R$^{12}$, —NR$^{10}$S(O)$_2$R$^{11}$, —NR$^{11}$R$^{12}$, —C(O)R$^{10}$, —NR$^{10}$C(O)R$^{11}$, —NR$^{10}$C(O)NR$^{11}$R$^{12}$, —C(O)OR$^{10}$, —C(O)ONR$^{11}$R$^{12}$, —C(O)NR$^{11}$R$^{12}$, wherein each of which is optionally substituted by R$^1$;

or any two of R$^2$ are taken together with the atoms to which they attached to form a C$_5$-C$_6$ cycloalkyl, 5- to 6-membered heterocyclyl, C$_6$- aryl or 5- to 6-membered heteroaryl, wherein each of which is optionally substituted by R$^9$;

R$^9$ is oxo, C$_2$-C$_6$ alkenyl, C$_2$-C$_6$ alkynyl, C$_3$-C$_6$ cycloalkyl, 3- to 6-membered heterocyclyl, C$_6$- aryl, 5- to 6-membered heteroaryl, —CN, halogen, C$_1$-C$_6$ alkoxy, C$_1$-C$_6$ haloalkoxy, C$_1$-C$_6$ haloalkyl, —OR$^{13}$, —SR$^{13}$, —S(O)$_2$R$^{13}$, —S(O)$_2$NR$^{14}$R$^{13}$, —NR$^3$S(O)$_2$R$^4$, —NR$^{14}$R$^{15}$, —C(O)R$^{13}$, —NR$^{13}$C(O)R$^{14}$, —NR$^{13}$C(O)NR$^{14}$R$^{15}$, —C(O)OR$^{13}$, —C(O)ONR$^{14}$R$^{15}$, —C(O)NR$^{14}$R$^{15}$ or C$_1$-C$_6$ alkyl optionally substituted by oxo, OH or halogen;

each R$^{10}$, R$^{11}$ and R$^{12}$ is independently hydrogen, C$_1$-C$_6$ alkyl, C$_2$-C$_6$ alkenyl, C$_2$-C$_6$ alkynyl, C$_3$-C$_6$ cycloalkyl or 3- to 6-membered heterocyclyl, wherein each of R$^{10}$, R$^{11}$ and R$^{12}$ is independently optionally substituted by oxo, C$_2$-C$_6$ alkenyl, C$_2$-C$_6$ alkynyl, —CN, halogen, C$_1$-C$_6$ alkoxy or C$_1$-C$_6$ alkyl optionally substituted by oxo, OH, halogen;

or R$^{11}$ and R$^{12}$ are taken together with the atoms to which they attached to form a 3-6 membered heterocyclyl optionally substituted by oxo, OH, halogen or C$_1$-C$_6$ alkyl optionally substituted by oxo, OH or halogen;

each R$^{13}$, R$^{14}$ and R$^{15}$ is independently hydrogen, C$_1$-C$_6$ alkyl, C$_2$-C$_6$ alkenyl, C$_2$-C$_6$ alkynyl, C$_3$-C$_6$ cycloalkyl or 3- to 6-membered heterocyclyl, wherein each of R$^{10}$, R$^{11}$ and R$^{12}$ is independently optionally substituted by oxo, C$_2$-C$_6$ alkenyl, C$_2$-C$_6$ alkynyl, —CN, halogen or C$_1$-C$_6$ alkyl optionally substituted by oxo, OH, halogen;

or R$^{14}$ and R$^{15}$ are taken together with the atoms to which they attached to form a 3-6 membered heterocyclyl optionally substituted by oxo, OH, halogen, or C$_1$-C$_6$ alkyl optionally substituted by oxo, OH or halogen;

m is 0, 1 or 2; and n is 0, 1, 2, or 4.

In some embodiments of a compound of formula (J), A is hydrogen. In some embodiments of a compound of formula (J), A is $C_1$-$C_6$ alkyl. In some embodiments of a compound of formula (J), A is methyl. In some embodiments of a compound of formula (J), A is $C_1$-$C_6$ alkyl optionally substituted by halogen. In some embodiments of a compound of formula (J), A is —$CF_3$. In some embodiments of a compound of formula (J), A is $C_6$- aryl. In some embodiments of a compound of formula (J), A is phenyl.

In some embodiments of a compound of formula (J), G is a bond. In some embodiments of a compound of formula (J), G is —$CH_2$—. In some embodiments of a compound of formula (J), G is —$CH_2$—$CH_2$—. In some embodiments of a compound of formula (J), G is a bond, and the A, C, D, L, Z, $R^a$, $R^b$, $R^1$, $R^2$, m, n and t are as detailed herein. In some embodiments of a compound of formula (J), G is —$CH_2$—, and the A, C, D, L, Z, $R^a$, $R^b$, $R^1$, $R^2$, m, n and t are as detailed herein. In some embodiments of a compound of formula (J), G is —$CH_2$—$CH_2$—, and the A, C, D, L, Z, $R^a$, $R^b$, $R^1$, $R^2$, m, n and t are as detailed herein.

In some embodiments of a compound of formula (J), $R^a$ and $R^b$ are independently hydrogen or $C_1$-$C_6$ alkyl. In some embodiments of a compound of formula (J), $R^a$ and $R^b$ both are hydrogen. In some embodiments of a compound of formula (J), any one of $R^a$ and $R^b$ is hydrogen and other is $C_1$-$C_6$ alkyl. In some embodiments of a compound of formula (J), $R^a$ and $R^b$ both are $C_1$-$C_6$ alkyl. In some embodiments of a compound of formula (J), any one of $R^a$ and $R^b$ is hydrogen and other is methyl. In some embodiments of a compound of formula (J), any one of $R^a$ and $R^b$ is hydrogen and other is ethyl. In some embodiments of a compound of formula (J), $R^a$ and $R^b$ both are methyl.

In some embodiments of a compound of formula (J), $R^a$ and $R^b$ are taken together with the atoms to which they attached to form a $C_3$-$C_6$ cycloalkyl ring. In some embodiments of a compound of formula (J), $R^a$ and $R^b$ are taken together with the atoms to which they attached to form a cycloproplyl ring.

In some embodiments of a compound of formula (J), any one of $R^a$ and $R^b$, and A are taken together along with the atoms to which they are attached to form a $C_4$-$C_6$ cycloalkyl. In some embodiments of a compound of formula (J), any one of $R^a$ and $R^b$, and A are taken together along with the atoms to which they are attached to form a cyclobutyl ring. In some embodiments of a compound of formula (J), any one of $R^a$ and $R^b$, and A are taken together along with the atoms to which they are attached to form a cyclopentyl ring. In some embodiments of a compound of formula (J), any one of $R^a$ and $R^b$, and A are taken together along with the atoms to which they are attached to form a cyclohexyl ring.

In some embodiments of a compound of formula (J), any one of $R^a$ and $R^b$, and A are taken together along with the atoms to which they are attached to form a $C_4$-$C_6$ cycloalkyl ring, in such case other one of $R^a$ or $R^b$ is hydrogen. In some embodiments of a compound of formula (J), any one of $R^a$ and $R^b$, and A are taken together along with the atoms to which they are attached to form a cyclobutyl ring, in such case other one of $R^a$ or $R^b$ is hydrogen. In some embodiments of a compound of formula (J), any one of $R^a$ and $R^b$, and A are taken together along with the atoms to which they are attached to form a cyclopentyl ring, in such case other one of $R^a$ or $R^b$ is hydrogen. In some embodiments of a compound of formula (J), any one of $R^a$ and $R^b$, and A are taken together along with the atoms to which they are attached to form a cyclohexyl ring, in such case other one of $R^a$ or $R^b$ is hydrogen.

In some embodiments of a compound of formula (J), G is a bond, $CH_2$ or —$CH_2$—$CH_2$—; and any one of $R^a$ and $R^b$, and A are taken together along with the atoms to which they are attached to form a $C_4$-$C_6$ cycloalkyl ring. In some embodiments of a compound of formula (J), G is $CH_2$; and any one of $R^a$ and $R^b$, and A are taken together along with the atoms to which they are attached to form a cyclobutyl ring. In some embodiments of a compound of formula (J), G is $CH_2$; and any one of $R^a$ and $R^b$, and A are taken together along with the atoms to which they are attached to form a cyclopentyl ring. In some embodiments of a compound of formula (J), G is $CH_2$—$CH_2$—; and any one of $R^a$ and $R^b$, and A are taken together along with the atoms to which they are attached to form a cyclohexyl ring.

In some embodiments of a compound of formula (J), L is a bond, or $C_1$-$C_6$ alkylene or $C_2$-$C_6$ alkenylene. The $C_1$-$C_6$ alkylene or $C_2$-$C_6$ alkenylene can be a linear or branched. In some embodiments of a compound of formula (J), L is a bond. In some embodiments of a compound of formula (J), L is a $C_1$-$C_6$ alkylene. In some embodiments of a compound of formula (J), L is —$CH_2$—. In some embodiments of a compound of formula (J), L is —$C_2H_4$—. In some embodiments of a compound of formula (J), L is —$C_3H_6$—. In some embodiments of a compound of formula (J), L is —CH($CH_3$)—. In some embodiments of a compound of formula (J), L is —C($CH_3$)$_2$—. In some embodiments of a compound of formula (J), L is —CH($CH_3$)—$CH_2$—. In some embodiments of a compound of formula (J), L is —$CH_2$—CH($CH_3$)—. In some embodiments of a compound of formula (J), L is —C($CH_3$)$_2$—$CH_2$—. In some embodiments of a compound of formula (J), L is —$CH_2$—C($CH_3$)$_2$—. In some embodiments of a compound of formula (J), L is —CH($C_2H_5$)—$CH_2$—.

In some embodiments of a compound of formula (J), L is a $C_2$-$C_6$ alkynelene. The $C_2$-$C_6$ alkenylene can be a linear or branched. In some embodiments of a compound of formula (J), L is a —CH═CH—. In some embodiments of a compound of formula (J), L is a —$CH_2$—CH═CH—.

In some embodiments of a compound of formula (J), t is 0 or 1. In some embodiments of a compound of formula (J), t is 0. In some embodiments of a compound of formula (J), t is 1.

In some embodiments of a compound of formula (J), when t is 0 then $R^a$ and $R^b$ are absent and L is $C_2$-$C_6$ alkynelene. In some embodiments of a compound of formula (J), when t is 0 then $R^a$ and $R^b$ are absent and L is —CH═CH—.

In some embodiments of a compound of formula (J), when t is 1 then $R^a$ and $R^b$ are present and L is a bond or $C_1$-$C_6$ alkylene. In some embodiments of a compound of formula (J), when t is 1 then $R^a$ and $R^b$ are present and L is a bond. In some embodiments of a compound of formula (J), when t is 1 then $R^a$ and $R^b$ are present and L is $C_1$-$C_6$ alkylene. In some embodiments of a compound of formula (J), when t is 1 then $R^a$ and $R^b$ are present and L is —$CH_2$—. In some embodiments of a compound of formula (J), when t is 1 then $R^a$ and $R^b$ are present and L is —$CH_2$—$CH_2$—. Wherein $R^a$ and $R^b$ are independently selected from hydrogen or $C_1$-$C_6$ alkyl.

In some embodiments of a compound of formula (J), when t is 1 then $R^a$ and $R^b$ are present and any one of $R^a$ and $R^b$, and A are taken together along with the atoms to which they are attached to form a $C_4$-$C_6$ cycloalkyl ring, in such case other one of $R^a$ or $R^b$ is hydrogen. In some embodiments of a compound of formula (J), when t is 1 then $R^a$ and $R^b$ are present and any one of $R^a$ and $R^b$, and A are taken together along with the atoms to which they are attached to form a cyclobutyl ring, in such case other one of $R^a$ or $R^b$ is hydrogen.

In some embodiments of a compound of formula (J), Z is selected from —NR$^c$SO$_2$NH$_2$, —NR$^c$S(O)$_2$CH$_3$, —SO$_2$NH$_2$, —NR$^c$C(O)CH$_3$, —C(O)OH, —CONH$_2$, NR$^c$CONH$_2$, —CONH(OH), —B(OH)$_2$, —P(O)(OH)$_2$, —SO$_2$OH, —NR$^c$S(O)$_2$CF$_3$, —NR$^c$S(O)$_2$NHCH$_3$ or —NR$^c$CH$_2$C$_6$- aryl-S(O)$_2$NH$_2$. In some embodiments of a compound of formula (J), Z is —NR$^c$S(O)$_2$NH$_2$. In some embodiments of a compound of formula (J), Z is —NR$^c$S(O)$_2$CH$_3$. In some embodiments of a compound of formula (J), Z is —SO$_2$NH$_2$. In some embodiments of a compound of formula (J), Z is —NR$^c$C(O)CH$_3$. In some embodiments of a compound of formula (J), Z is —C(O)OH. In some embodiments of a compound of formula (J), Z is —CONH$_2$. In some embodiments of a compound of formula (J), Z is —NR$^c$CONH$_2$. In some embodiments of a compound of formula (J), Z is —CONH(OH). In some embodiments of a compound of formula (J), Z is —B(OH)$_2$. In some embodiments of a compound of formula (J), Z is —P(O)(OH)$_2$. In some embodiments of a compound of formula (J), Z is-SO$_2$OH. In some embodiments of a compound of formula (J), Z is-NR$^c$S(O)$_2$CF$_3$. In some embodiments of a compound of formula (J), Z is —NR$^c$S(O)$_2$NHCH$_3$. In some embodiments of a compound of formula (J), Z is —NR$^c$CH$_2$C$_6$- aryl-S(O)$_2$NH. In some embodiments of a compound of formula (J), R$^c$ is selected from hydrogen, $C_1$-$C_6$ alkyl, $C_3$-$C_6$ cycloalkyl or $C_1$-$C_6$ haloalkyl. In some embodiments of a compound of formula (J), R$^c$ is methyl. In some embodiments of a compound of formula (J), R$^c$ is ethyl. In some embodiments of a compound of formula (J), R$^c$ is isopropyl. In some embodiments of a compound of formula (J), R$^c$ is n-propyl. In some embodiments of a compound of formula (J), R$^c$ is cyclopropyl. In some embodiments of a compound of formula (J), R$^c$ is

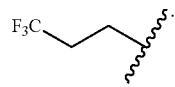

In some embodiments of a compound of formula (J), R$^c$ is

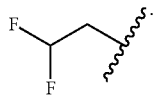

In some embodiments of a compound of formula (J), R$^c$ is

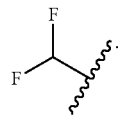

In some embodiments of a compound of formula (J) R$^c$ is —(C$_1$-C$_6$ alkylene)C$_3$-C$_6$ cycloalkyl optionally substituted with R$^d$. In some embodiments of a compound of formula (J) R$^c$ is 3- to 6-membered heterocyclyl optionally substituted with R$^d$. In some embodiments of a compound of formula (J) R$^c$ is —(C$_1$-C$_6$ alkylene) 3- to 6-membered heterocyclyl optionally substituted with R$^d$. In some embodiments of a compound of formula (J) R$^c$ is —(C$_1$-C$_6$ alkylene)C$_6$- aryl optionally substituted with R$^d$. In some embodiments of a compound of formula (J) R$^c$ is 5- to 6-membered heteroaryl optionally substituted with R$^d$. In some embodiments of a compound of formula (J) R$^c$ is —(C$_1$-C$_6$ alkylene) 5- to 6-membered heteroaryl optionally substituted with R$^d$. In some embodiments of a compound of formula (J) R$^c$ is —(C$_1$-C$_6$ alkylene)OR$^{13}$. In some embodiments of a compound of formula (J) R$^c$ is —(C$_1$-C$_6$ alkylene)SR$^{13}$. In some embodiments of a compound of formula (J) R$^c$ is —(C$_1$-C$_6$ alkylene)S(O)$_2$R$^{13}$. In some embodiments of a compound of formula (J) R$^c$ is —(C$_1$-C$_6$ alkylene)S(O)$_2$NR$^{14}$R$^{15}$. In some embodiments of a compound of formula (J) R$^c$ is —(C$_1$-C$_6$ alkylene)NR$^{13}$S(O)$_2$R$^{14}$. In some embodiments of a compound of formula (J) R$^c$ is —(C$_1$-C$_6$ alkylene)NR$^{14}$R$^{15}$. In some embodiments of a compound of formula (J) R$^c$ is —(C$_1$-C$_6$ alkylene)C(O)R$^{13}$. In some embodiments of a compound of formula (J) R$^c$ is —(C$_1$-C$_6$ alkylene)NR$^{13}$C(O)R$^{14}$. In some embodiments of a compound of formula (J) R$^c$ is —(C$_1$-C$_6$ alkylene)NR$^{13}$C(O)NR$^{14}$R$^{15}$. In some embodiments of a compound of formula (J) R$^c$ is —(C$_1$-C$_6$ alkylene)C(O)OR$^{13}$. In some embodiments of a compound of formula (J) R$^c$ is —(C$_1$-C$_6$ alkylene) C(O)ONR$^{14}$R$^{15}$. In some embodiments of a compound of formula (J) R$^c$ is —(C$_1$-C$_6$ alkylene)-C(O)NR$^{14}$R$^{15}$.

In some embodiments of a compound of formula (J), —C$_1$-C$_6$ alkylene of any R$^c$ group may be optionally substituted with R$^d$.

In some embodiments of a compound of formula (J), —C$_1$-C$_6$ alkylene of any R$^c$ group is leanear or branched.

In some embodiments of a compound of formula (J) R$^c$ is selected from the group consisting of methyl, ethyl, isopropyl, n-propyl, n-butyl, cyclopropyl, cyclobutyl, cyclopentyl,

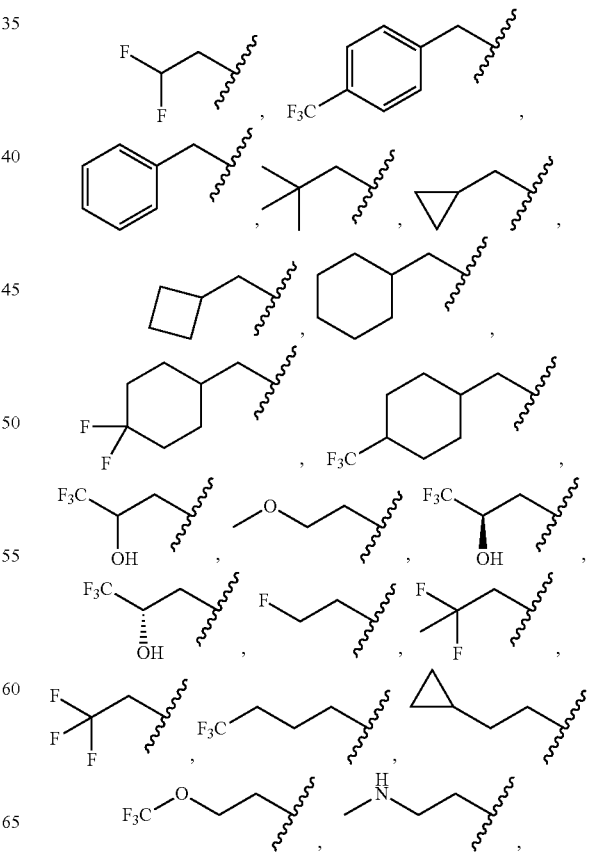

-continued
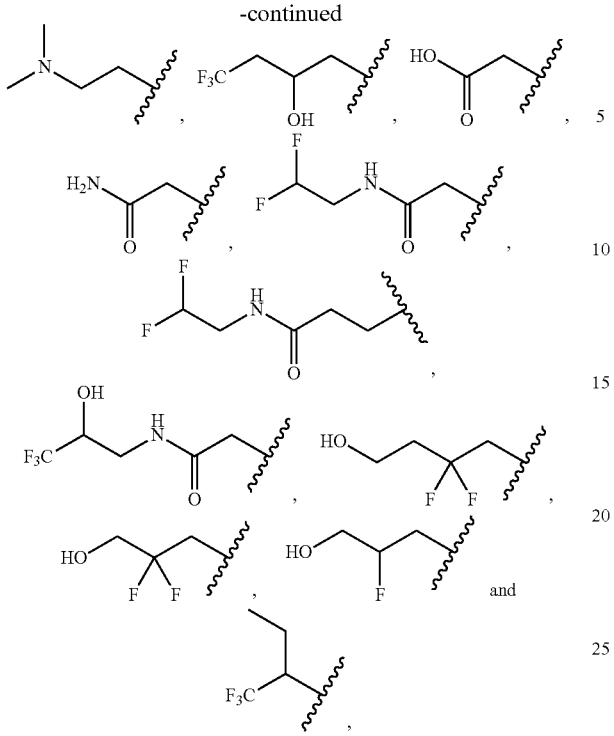
wherein wavy lines denote the attachment points.
In some embodiments of a compound of a formula (J), Z is selected from the group consisting of
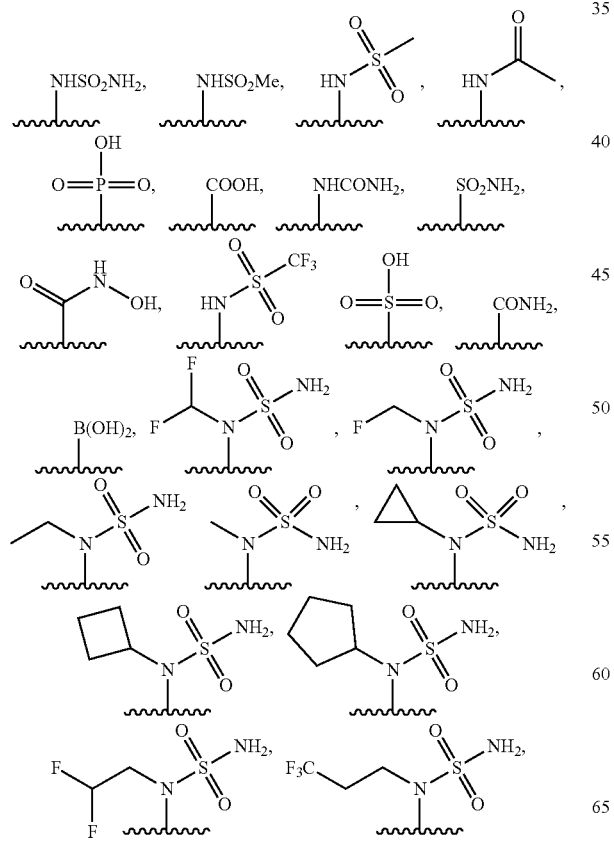
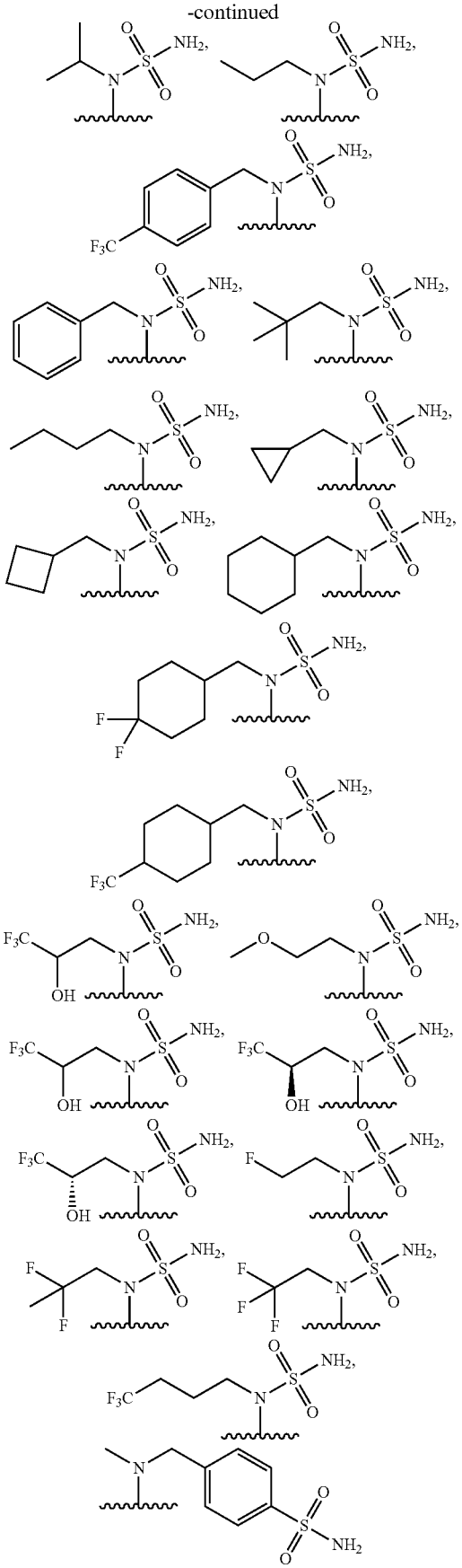

-continued

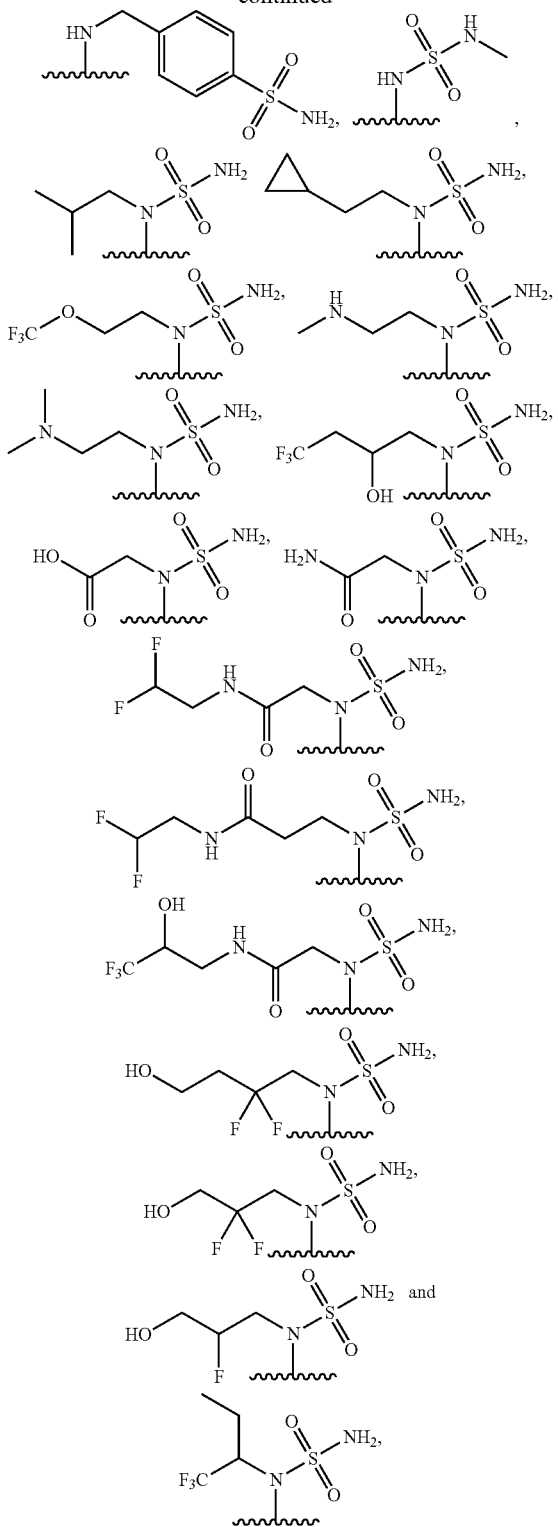

wherein wavy lines denote the attachment points.

In some embodiments of a compound of formula (J), Z is —NR$^c$SO$_2$NH$_2$.

In some embodiments of a compound of formula (J), Z is —NHSO$_2$NH$_2$. In some embodiments of a compound of formula (J), Z is

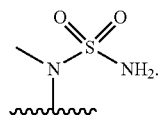

In some embodiments of a compound of formula (J), Z is

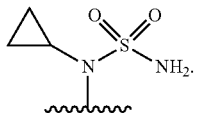 [SMILES: *N(C1CC1)S(N)(=O)=O]

In some embodiments of a compound of formula (J), Z is

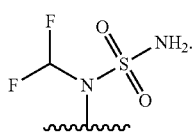

In some embodiments of a compound of formula (J), Z is

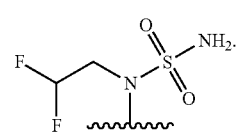 [SMILES: *N(CC(F)F)S(N)(=O)=O]

In some embodiments of a compound of formula (J), Z is

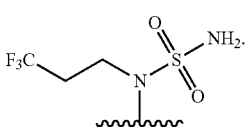 [SMILES: *N(CCC(F)(F)F)S(N)(=O)=O]

In some embodiments of a compound of formula (J), Z is

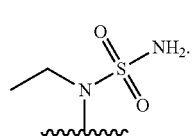 [SMILES: *N(CC)S(N)(=O)=O]

In some embodiments of a compound of formula (J), Z is

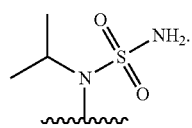 [SMILES: *N(C(C)C)S(N)(=O)=O]

In some embodiments of a compound of formula (J), Z is

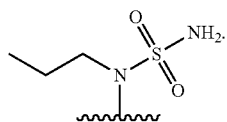 [SMILES: *N(CCC)S(N)(=O)=O]

In some embodiments of a compound of formula (J), Z is —NHS(O)$_2$CH$_3$.
In some embodiments of a compound of formula (J), Z is —SO$_2$NH$_2$.
In some embodiments of a compound of formula (J), Z is —NHC(O)CH$_3$.
In some embodiments of a compound of formula (J), Z is —C(O)OH.
In some embodiments of a compound of formula (J), Z is —CONH$_2$.
In some embodiments of a compound of formula (J), Z is —NHCONH$_2$.
In some embodiments of a compound of formula (J), Z is —CONH(OH).
In some embodiments of a compound of formula (J), Z is —B(OH)$_2$.
In some embodiments of a compound of formula (J), Z is —P(O)(OH)$_2$.
In some embodiments of a compound of formula (J), Z is —S(O)$_2$$_0$H.
In some embodiments of a compound of formula (J), Z is —NR$^c$S(O)$_2$CF$_3$.
In some embodiments of a compound of formula (J), Z is —NR$^c$S(O)$_2$NHCH$_3$.
In some embodiments of a compound of formula (J), Z is —NR$^c$CH$_2$C$_6$- aryl-S(O)$_2$NH$_2$.
In some embodiments of a compound of formula (J), Z is —NHCH$_2$C$_6$- aryl-S(O)$_2$NH$_2$.
In some embodiments of a compound of formula (J), Z is —N(CH$_3$)CH$_2$C$_6$- aryl-S(O)$_2$NH$_2$.
In some embodiments of a compound of formula (J), G, R$^a$, R$^b$, L, t and Z together is selected from the group consisting of

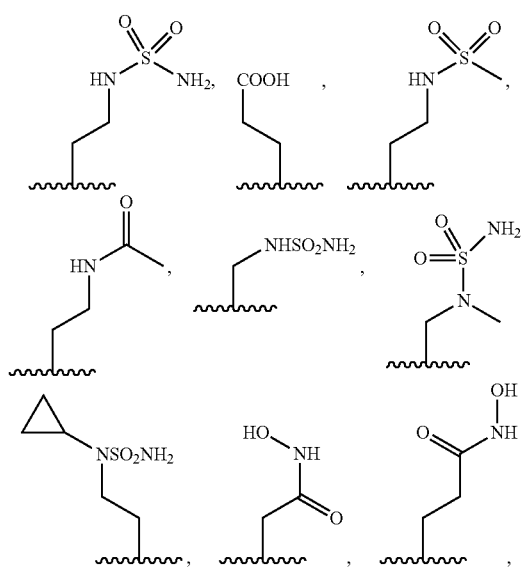

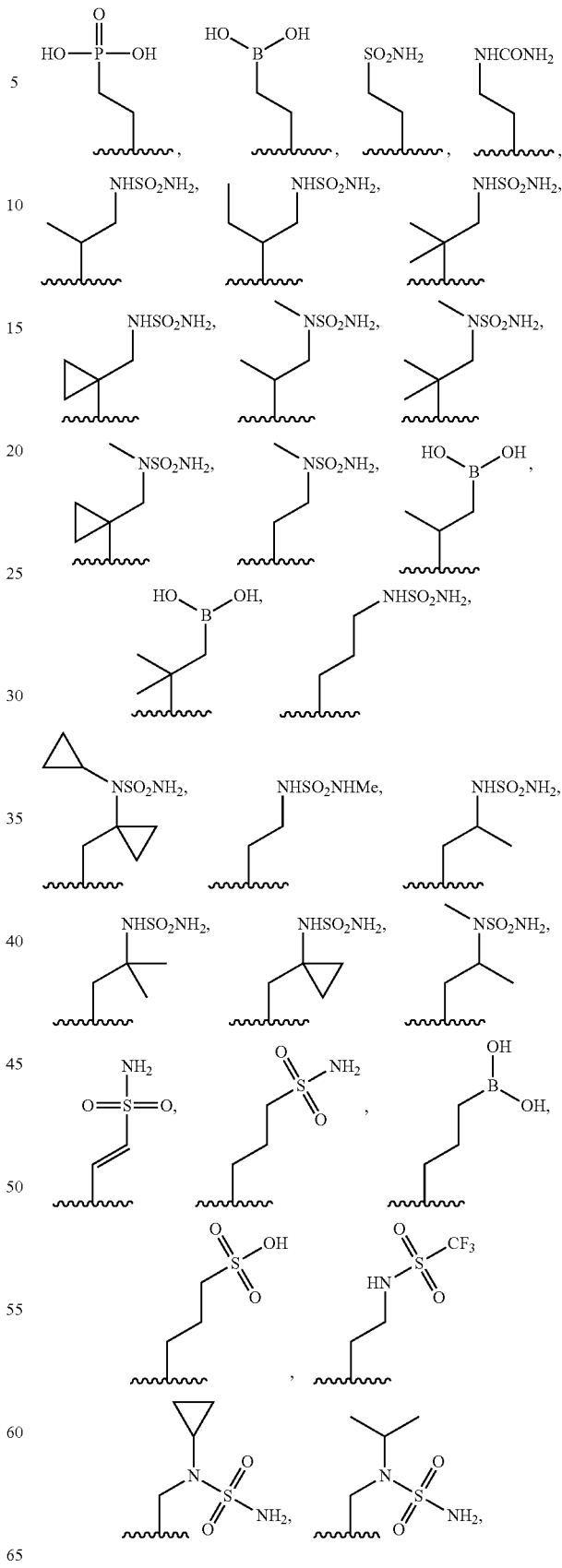

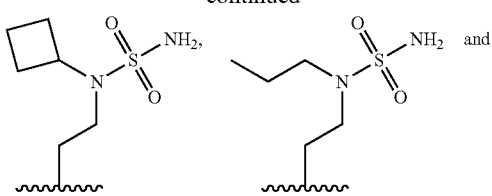
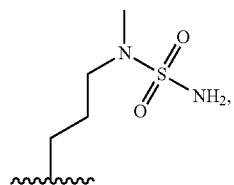 [SMILES: *CCCN(C)S(N)(=O)=O]

wherein wavy lines denote the attachment points.

In some embodiments of a compound of formula (J), when any one of $R^a$ and $R^b$, and A are taken together along with the atoms to which they are attached to form a $C_4$-$C_6$ cycloalkyl ring then L and Z together is selected from the group consisting of

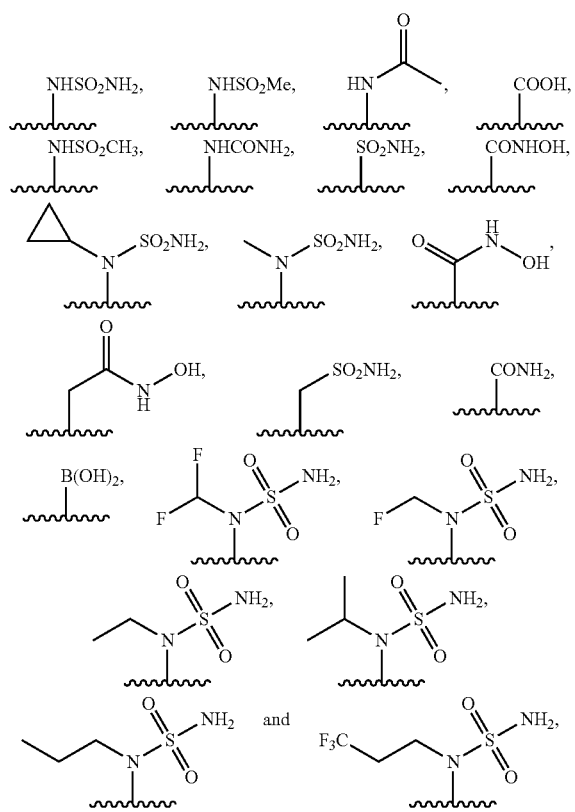

wherein wavy lines denote the attachment points.

In some embodiments of a compound of formula (J), when any one of $R^a$ and $R^b$, and A are taken together along with the atoms to which they are attached to form a $C_4$-$C_6$ cycloalkyl ring then L and Z together is selected from the group consisting of

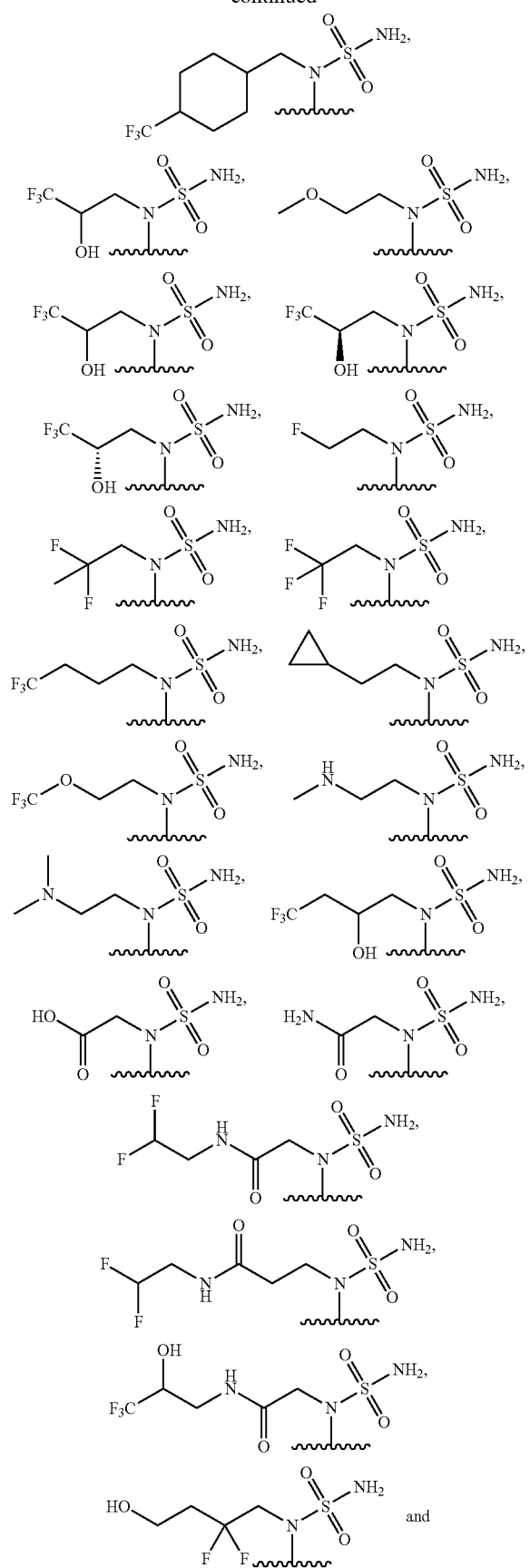
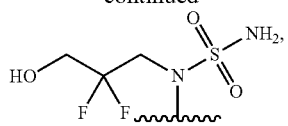
wherein wavy lines denote the attachment points.
In some embodiments of a compound of formula (J), when any one of $R^a$ and $R^b$, and A are taken together along with the atoms to which they are attached to form a cyclobutyl ring (which forms with the azetidine an azaspiroheptane ring) then L and Z together is selected from the group consisting of
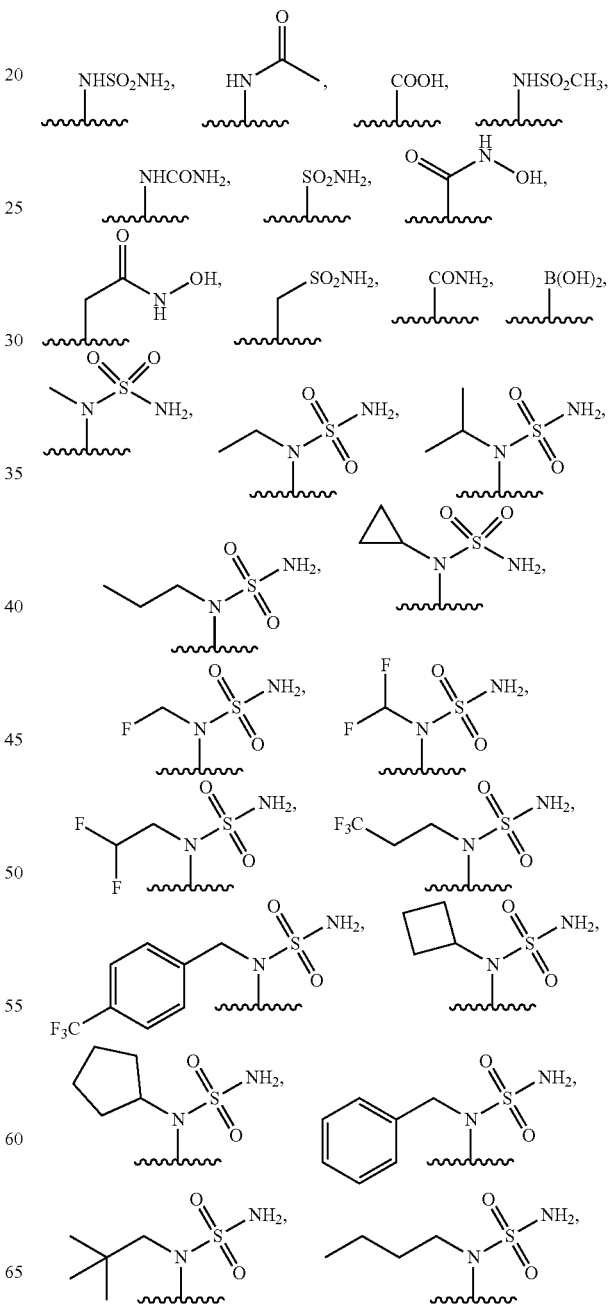

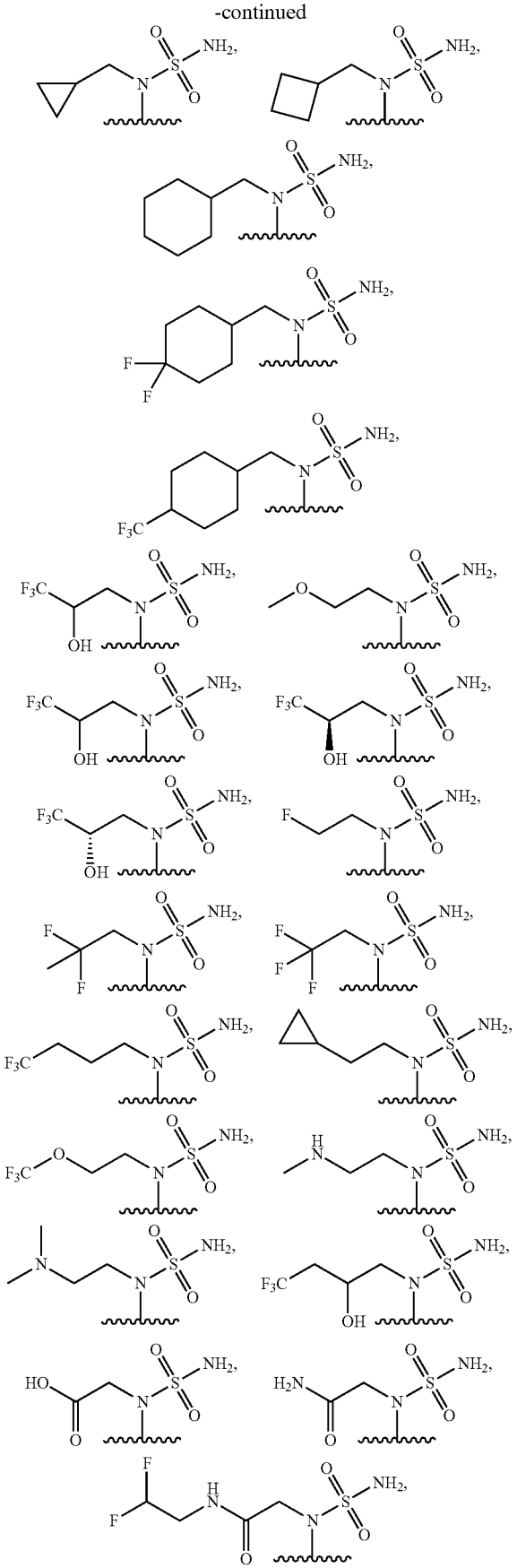

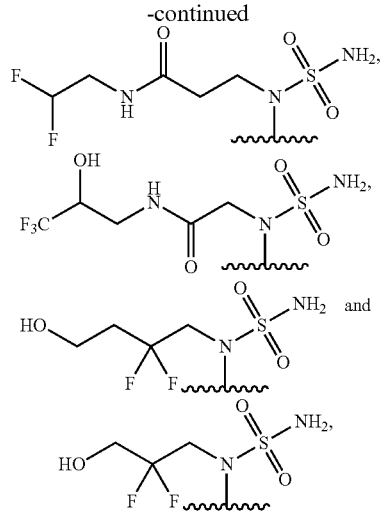

wherein wavy lines denote the attachment points.

In some embodiments of a compound of formula (J), C is 5- to 6-membered heteroaryl optionally substituted with $R^1$. In embodiments of a compound of formula (J), C is 5-membered heteroaryl optionally substituted with $R^1$. In embodiments of a compound of formula (J), C is 6-membered heteroaryl optionally substituted with $R^1$. In embodiments of a compound of formula (J), C is selected from the group consisting of imidazole, pyrazole, pyrrole, pyridine, pyrimidine, pyridone, pyrimidone, pyridazine, pyridazinone and triazine, wherein each of which is optionally substituted with $R^1$. In some embodiments of the compound of formula (J), the $R^1$ is selected from hydrogen, oxo, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$- aryl, 5- to 6-membered heteroaryl, —CN, —CONR$^{11}$R$^{12}$ or —NR$^{11}$R$^{12}$, wherein each of which is optionally substituted by $R^9$. In some embodiments of the compound of formula (J), the $R^1$ is selected from hydrogen, oxo, methyl, ethyl, ethylene, propynyl, cyclopropyl, cyclobutyl, cyclopentyl, cyclohexyl, adamantly, oxetanyl, tetrahydropyranyl, pyrazolyl, pyridyl, pyrimidyl, phenyl, —CONH$_2$, —NH$_2$, —CHF$_2$, —CF$_3$, Cl, and —CN; wherein each of which is optionally further substituted with pyridyl, F, $CF_3$ and $CHF_2$.

In some embodiments of the compound of formula (J), the D is $C_6$- aryl or 5- to 6-membered heteroaryl, each of which is optionally substituted with $R^2$; wherein D is fused to C. In some embodiments of the compound of formula (J), the D is $C_6$- aryl optionally substituted with $R^2$; wherein D is fused to C. In some embodiments of the compound of formula (J), the D is 5- to 6-membered heteroaryl optionally substituted with $R^2$; wherein D is fused to C. In some embodiments of the compound of formula (J), the D is 5-membered heteroaryl optionally substituted with $R^2$; wherein D is fused to C. In some embodiments of the compound of formula (J), the D is 6-membered heteroaryl optionally substituted with $R^2$; wherein D is fused to C. In some embodiments of the compound of formula (J), the D is selected from the group consisting of phenyl, pyrrole, pyrazole, imidazole, pyridine, thiophene and pyrimidine optionally substituted with $R^2$; wherein each of which is fused to C. In some embodiments of the compound of formula (J), $R^2$ is selected from hydrogen, halogen, oxo, $C_1$-$C_6$ alkyl, $C_1$-$C_6$ alkoxy, $C_3$-$C_6$ cycloalkyl, —OR$^{10}$, —CN and $C_6$- aryl; wherein each of which is optionally substituted by $R^9$. In some embodiments of the compound of formula (J), $R^2$ is selected from hydrogen, fluorine, bromine, chloro, oxo, methyl, ethyl, isopropyl, methoxy, ethoxy, propoxy, phenyl, 4-methoxypheyl, —CN, —OCH$_2$F, —OCH$_2$OCH$_3$, —(OCH$_2$CH$_2$)morpholine, 4-hydroxycyclohexyl, —CF$_3$, cyclopropyl and phenyl.

In some embodiments of the compound of formula (J), any two of R$^2$ are taken together with the atoms to which they attached to form a C$_5$-C$_6$ cycloalkyl, 5- to 6-membered heterocyclyl, C$_6$- aryl or 5- to 6-membered heteroaryl, wherein each of which is optionally substituted by R$^9$. In some embodiments of the compound of formula (J), any two of R$^2$ are taken together with the atoms to which they attached to form imidazole, dioxole and dihydro dioxine, wherein each of which is optionally substituted with methyl.

In some embodiments of a compound of formula (J), m is 0. In some embodiments of a compound of formula (J), m is 1. In some embodiments of a compound of formula (J), m is 2.

In some embodiments of a compound of formula (J), n is 0. In some embodiments of a compound of formula (J), n is 1. In some embodiments of a compound of formula (J), n is 2. In some embodiments of a compound of formula (J), n is 3. In some embodiments of a compound of formula (J), n is 4.

In some embodiments of a compound of formula J. C. D. R$^1$ and R$^2$ together is selected from the group consisting of

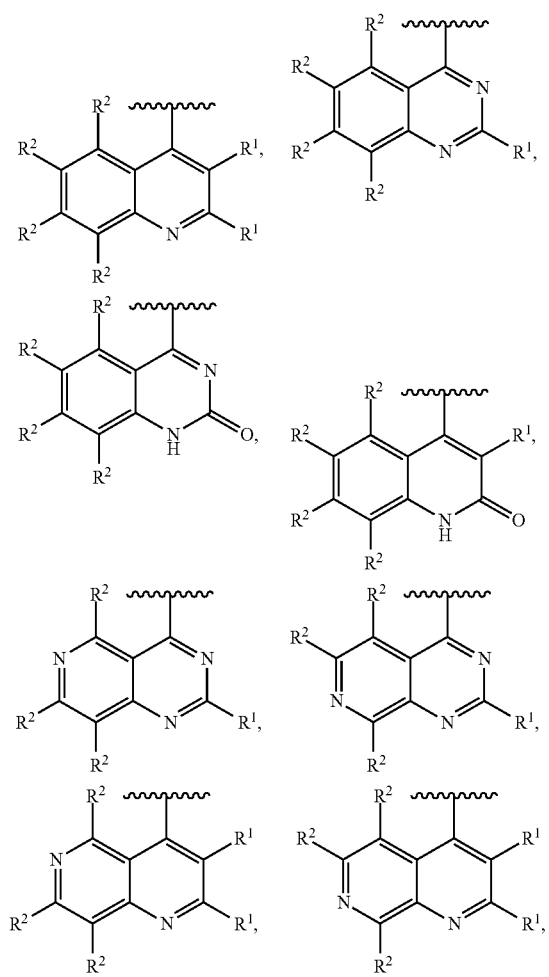

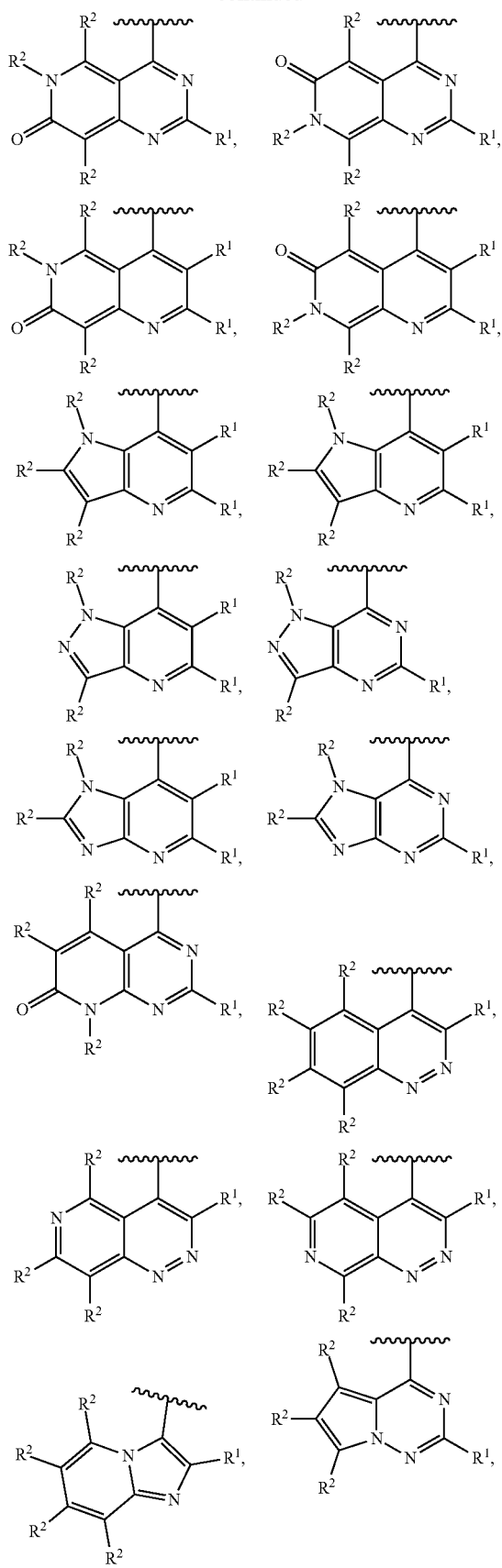

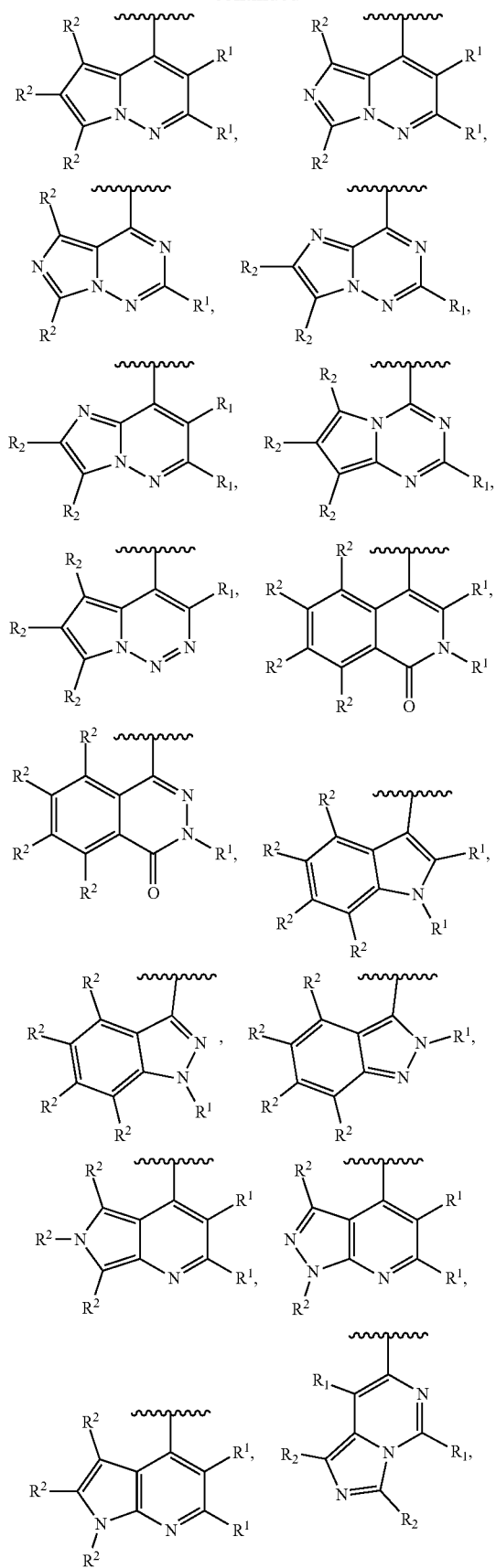
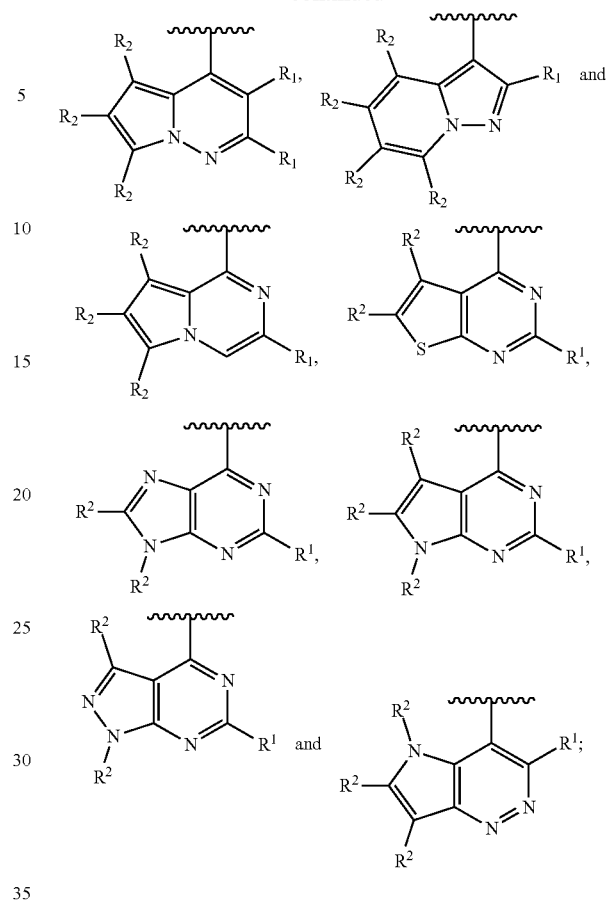
wherein wavy lines denote the attachment points.
In some embodiments of a compound of formula (J), C, D, $R^1$ and $R^2$ together is C, selected from the group consisting
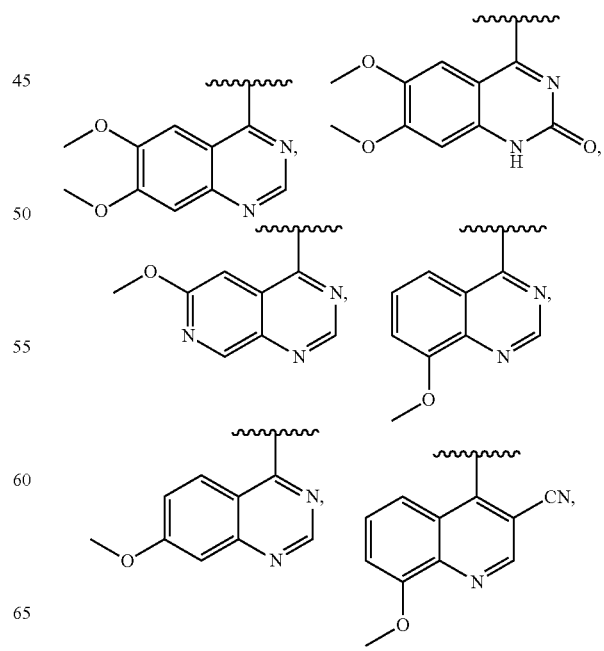

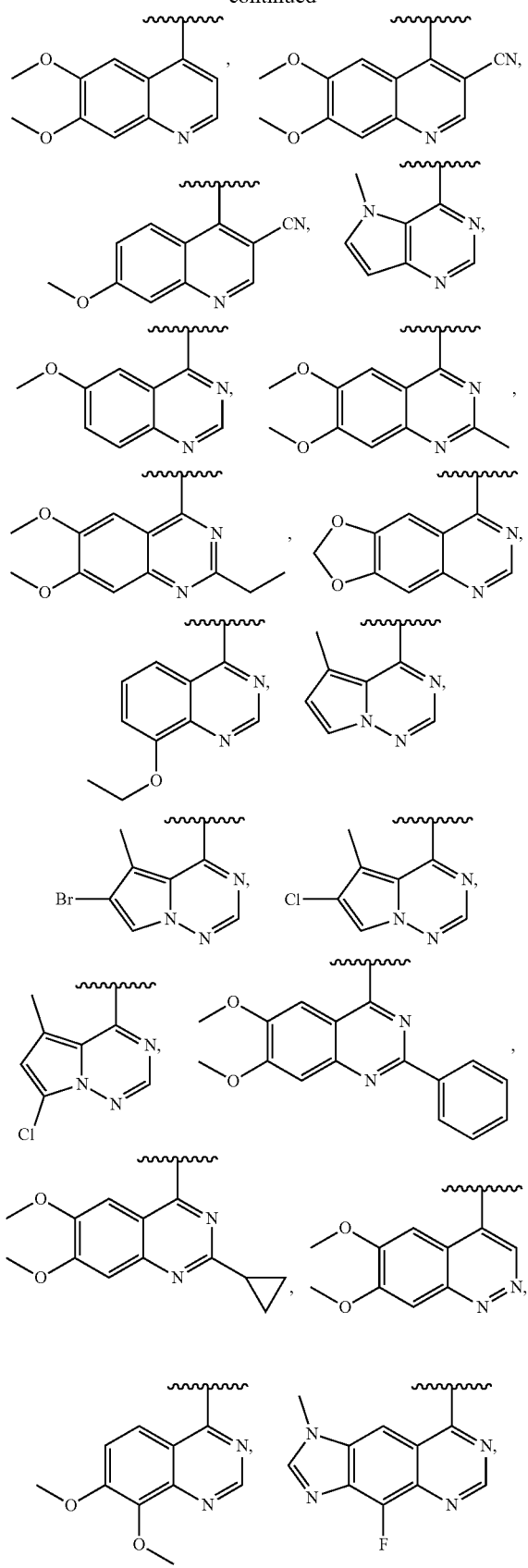
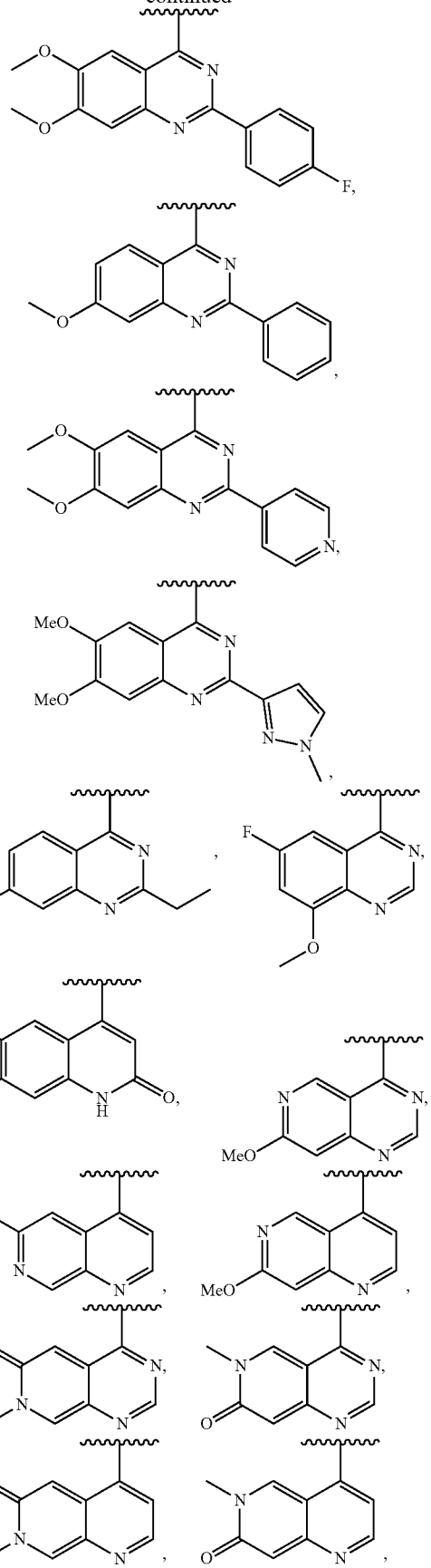

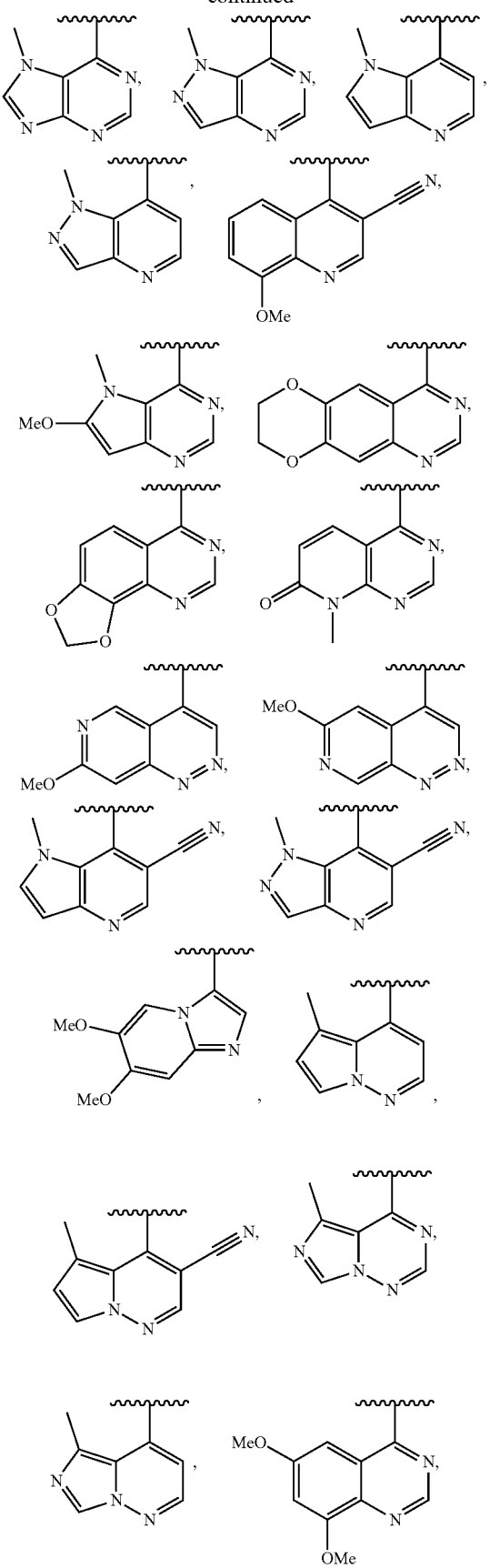
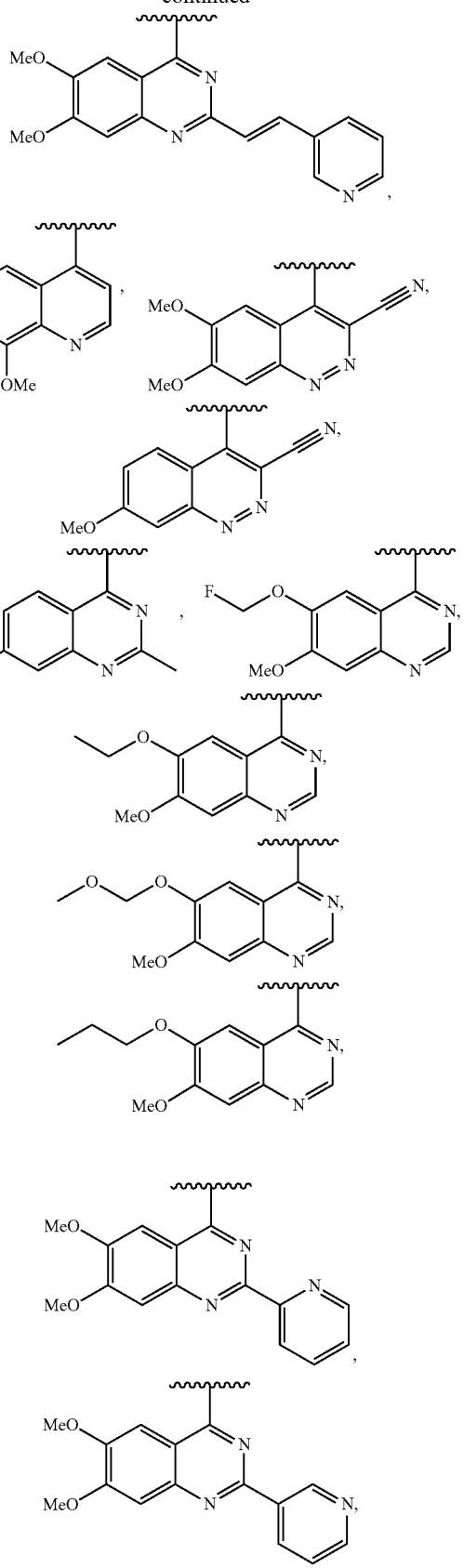

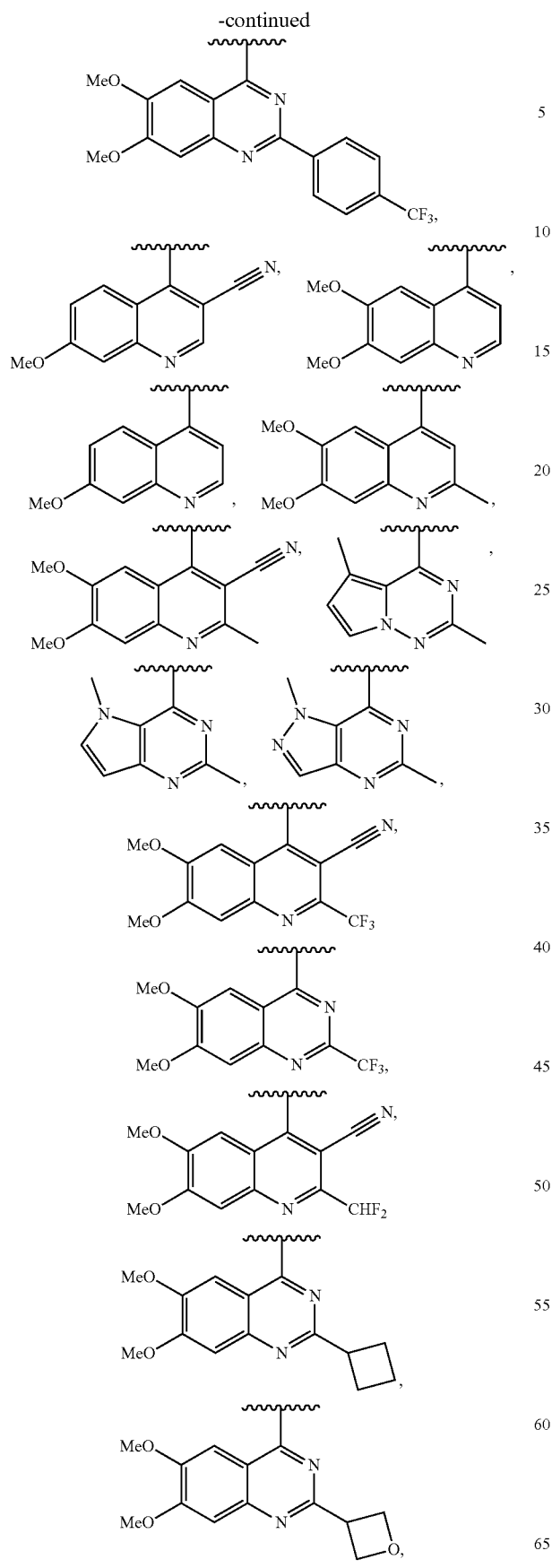
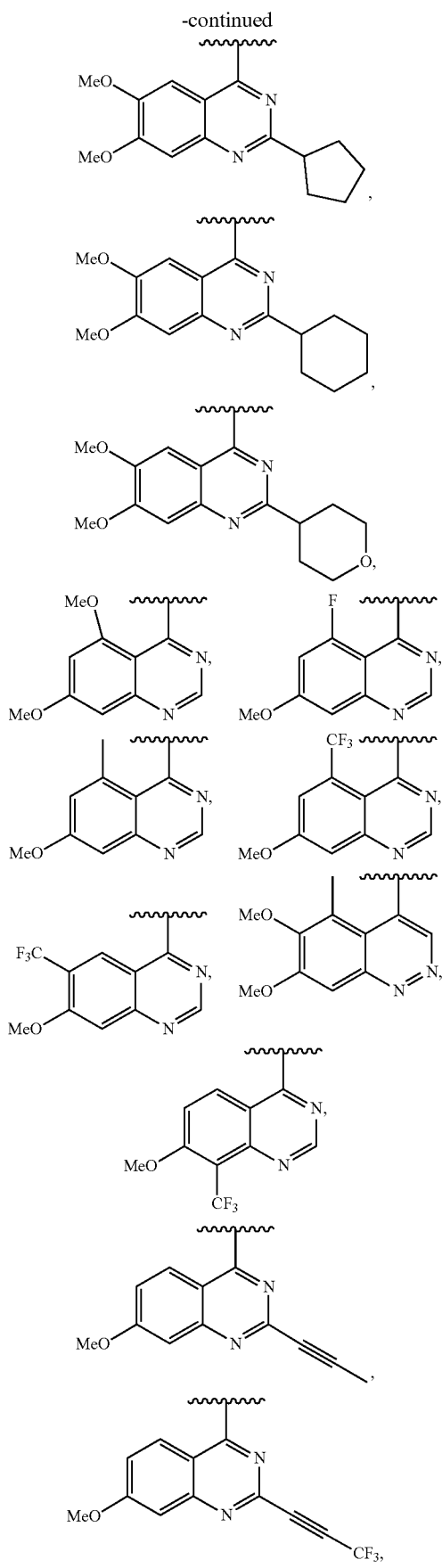

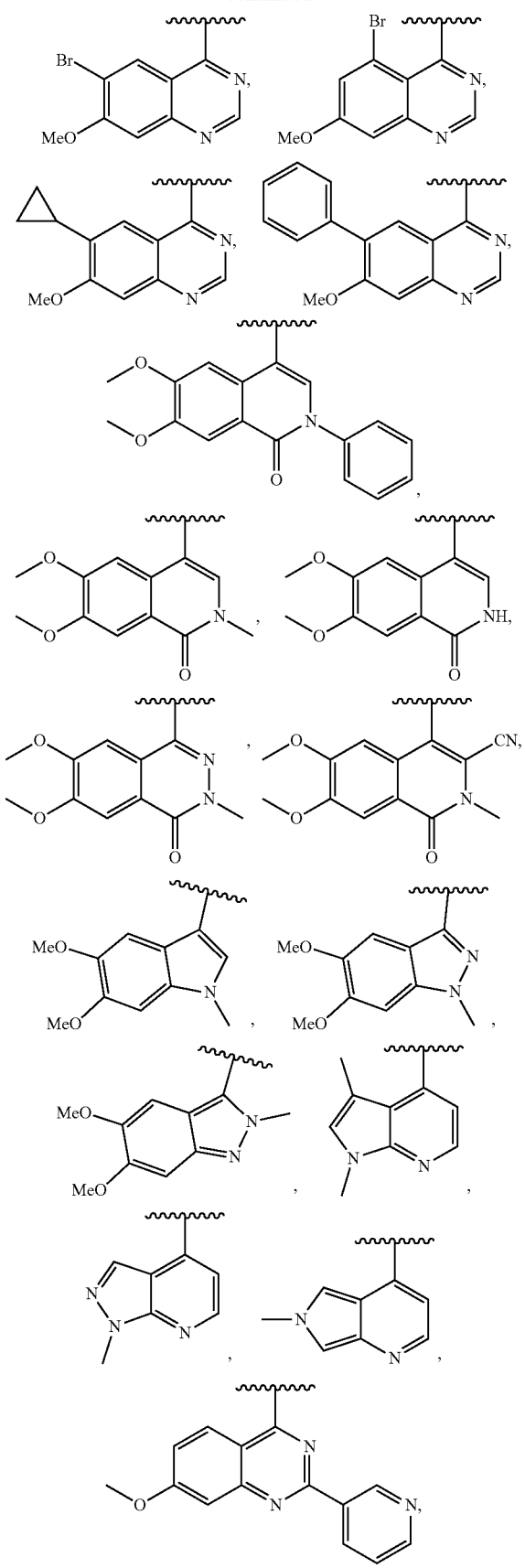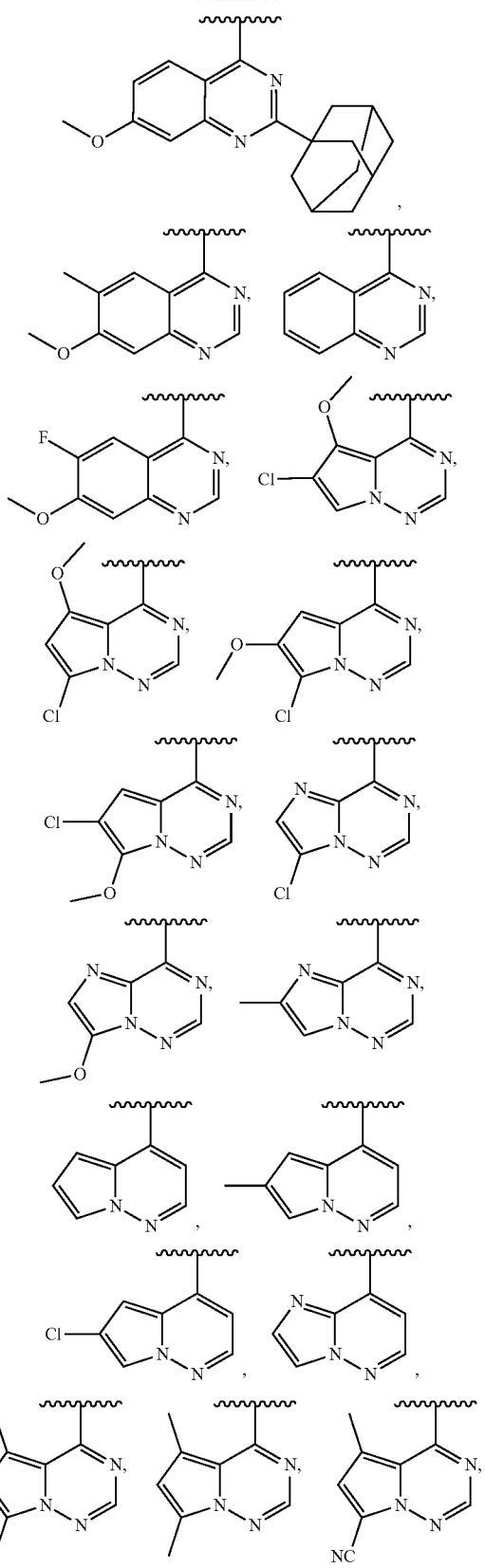

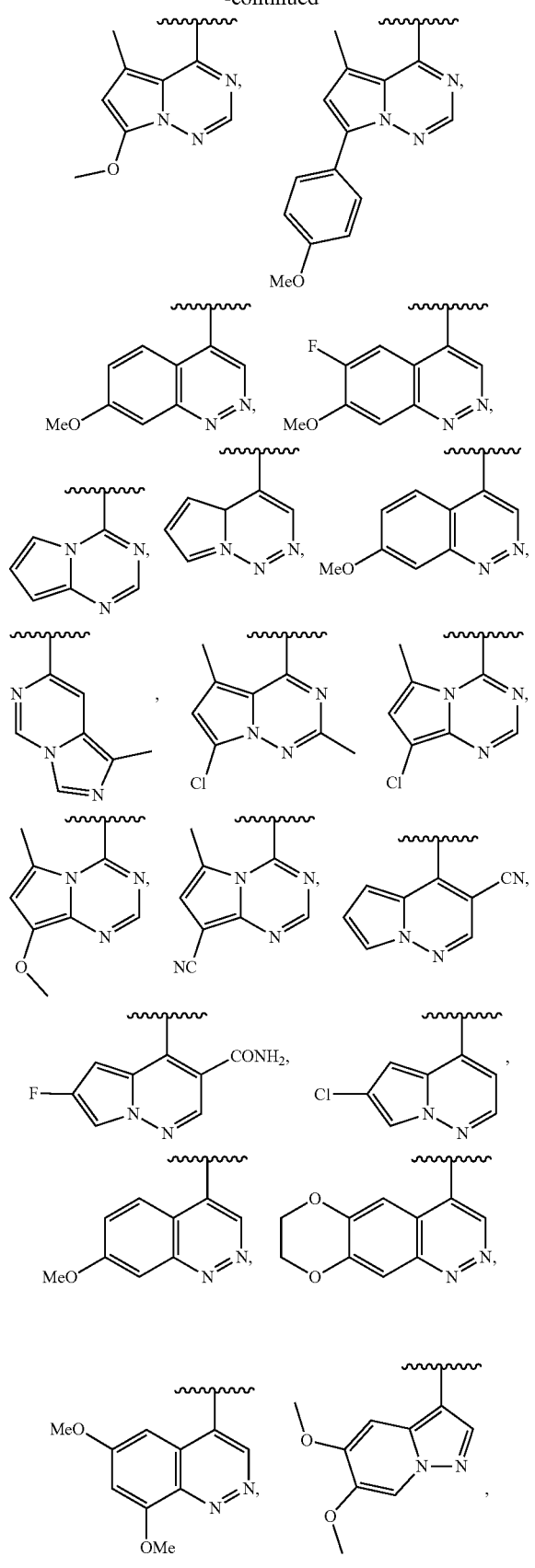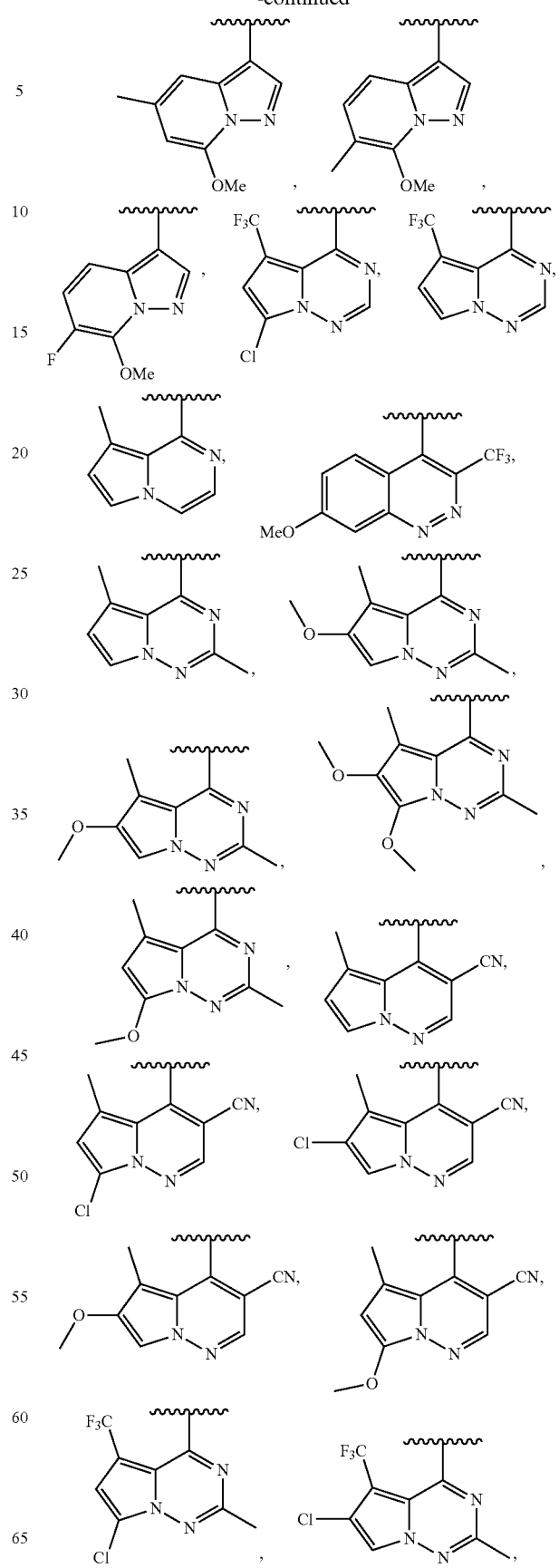

-continued

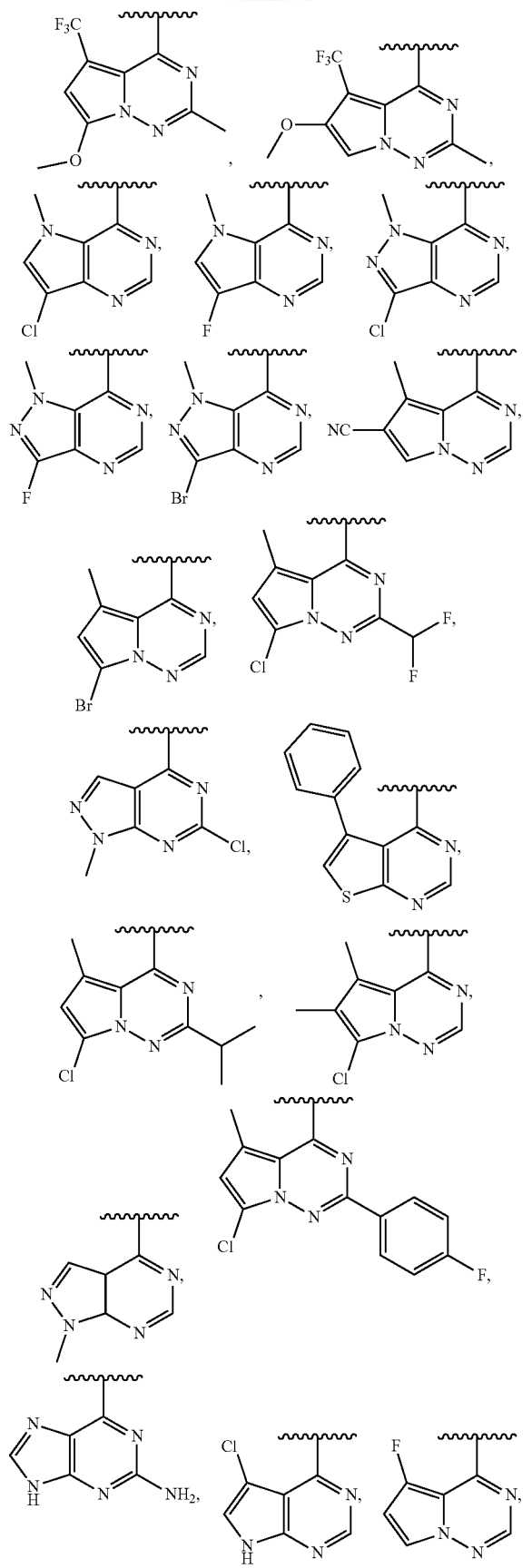

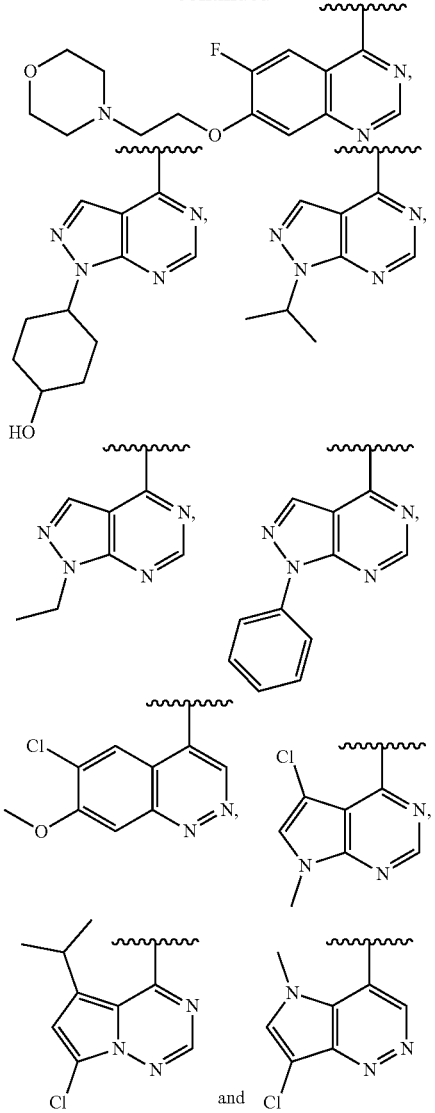

wherein wavy lines denote the attachment points.

It is understood that each description of A, G, $R^a$, $R^b$, L, Z, C, D, $R^1$, $R^2$, $R^c$, m, n and t may be independently combined with each description of A, G, $R^a$, $R^b$, L, Z, C, D, $R^1$, $R^2$, $R^c$, m, n and t the same as if each and every combination were specifically and individually listed.

In some embodiments, provided is a compound of formula (II):

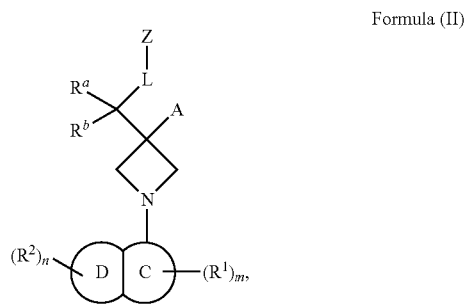

Formula (II)

or a salt thereof, wherein A, $R^a$, $R^b$, L, Z, C, D, $R^1$, $R^2$ m and n are as detailed herein.

In some embodiments, provided is a compound of formula (III):

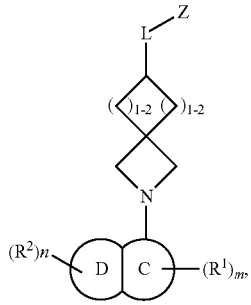

Formula (III)

or a salt thereof, wherein L, Z, C, D, $R^1$, $R^2$, m and n are as detailed herein.

In some embodiments, provided is a compound of formula (IV):

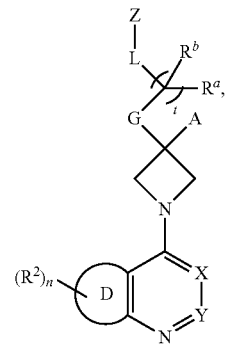

Formula (IV)

or a salt thereof, wherein
X is N or $CR^1$;
Y is N or $CR^1$; provided that at same time X and Y both are not N;
and A, G, $R^a$, $R^b$, L, Z, D, $R^1$, $R^2$, n and t are as detailed herein.

In some embodiments, provided is a compound of any one of formula (IV-1) to (IV-11):

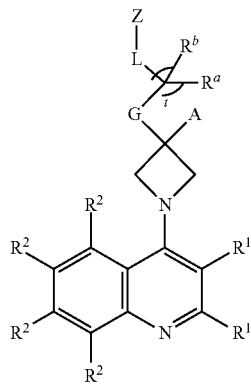

(IV-1)

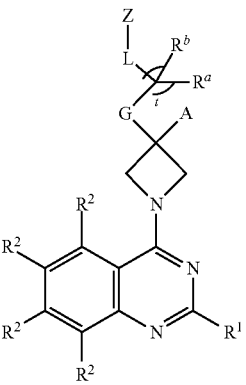

(IV-2)

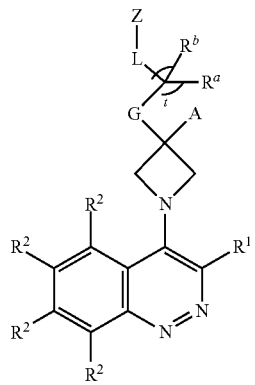

(IV-3)

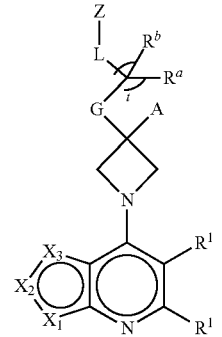

(IV-4)

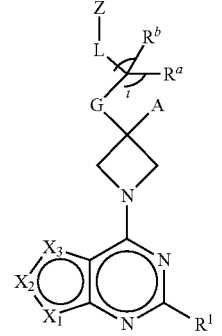

(IV-5)

47

-continued

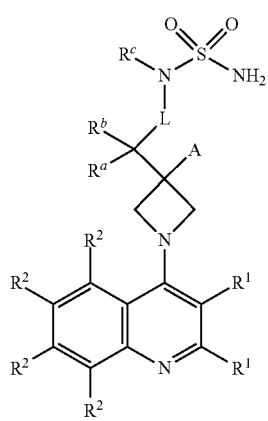
(IV-6)

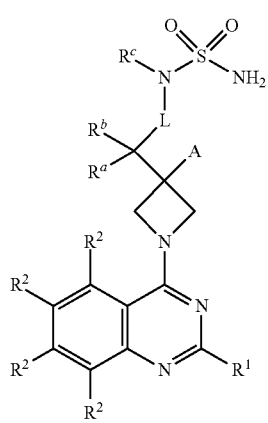
(IV-7)

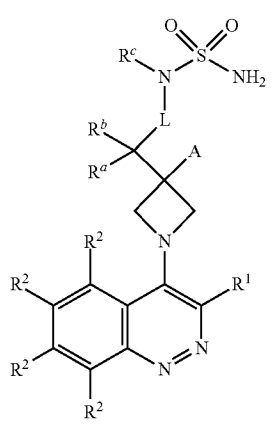
(IV-8)

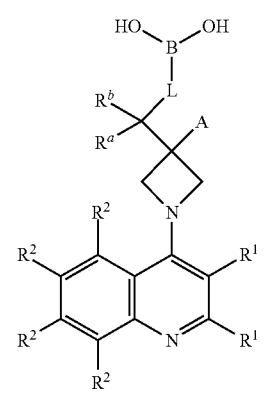
(IV-9)

48

-continued

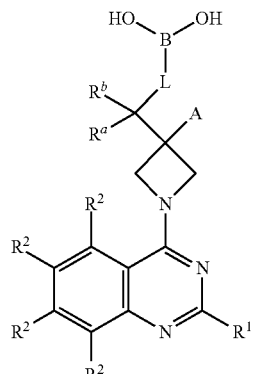
(IV-10)

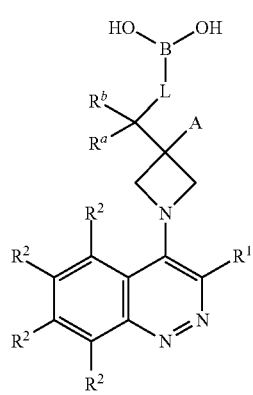
(IV-11)

or a salt thereof, wherein $X_1$, $X_2$ and $X_3$ are independently N, $NR^2$ or $CR^2$;

provided that any one of $X_1$, $X_2$ and $X_3$ is $NR^2$ and others are N or $CR^2$;

and A, G, $R^a$, $R^b$, L, Z, $R^1$, $R^2$ and t are as detailed herein.

In some embodiments, provided is a compound of formula (V):

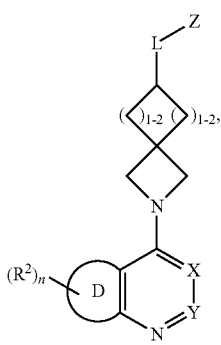
Formula (V)

or a salt thereof, wherein

X is N or $CR^1$;

Y is N or $CR^1$; provided that at same time X and Y both are not N;

and L, Z, D, $R^1$, $R^2$ and n are as detailed herein.

In some embodiments, provided is a compound of any one of formula (V-1) to (V-11):

(V-1) 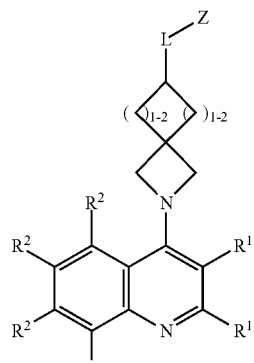
(V-2) 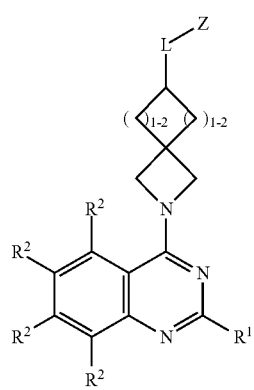
(V-3) 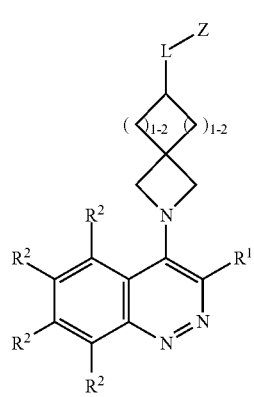
(V-4) 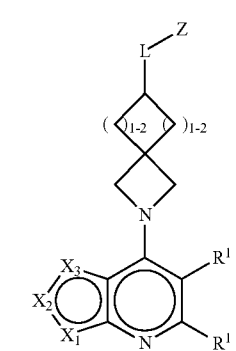
-continued
(V-5) 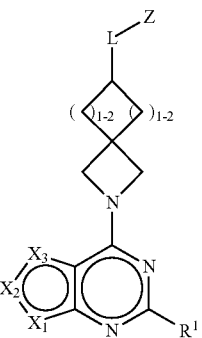
(V-6) 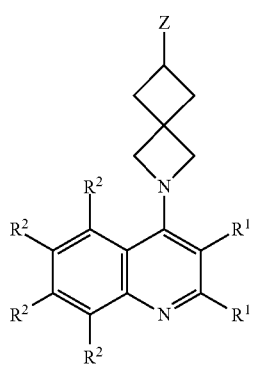
(V-7) 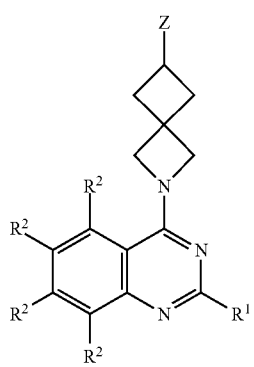
(V-8) 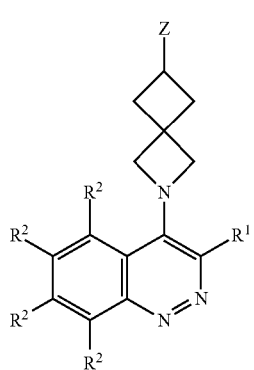

-continued (V-9)
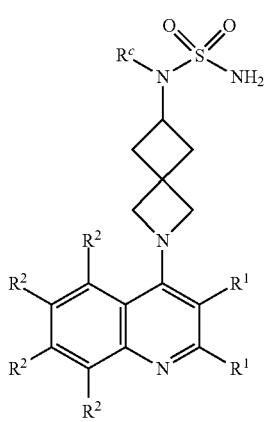

(V-10)
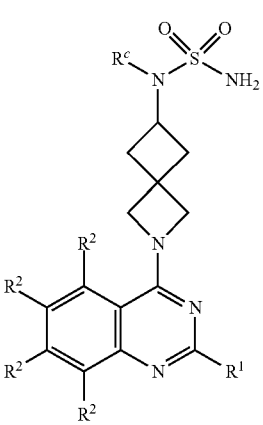

(V-11)
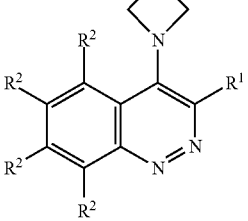

or a salt thereof, wherein
$X_1$, $X_2$ and $X_3$ are independently N, $NR^2$ or $CR^2$;
provided that any one of $X_1$, $X_2$ and $X_3$ is $NR^2$ and others are N or $CR^2$;
and L, Z, $R^1$ and $R^2$ are as detailed herein.

In some embodiments, provided is a compound of formula (VI):

Formula (VI)
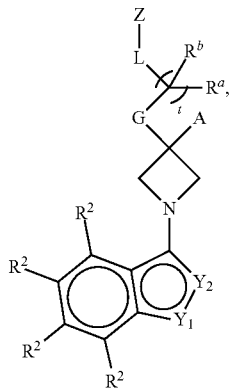

or a salt thereof, wherein
$Y_1$ is N or $NR^1$;
$Y_2$ is N, $NR^1$ or $CR^1$; provided that any one of $Y_1$ and $Y_2$ is $NR^1$ and other one is other than $NR^1$;
and A, G, $R^a$, $R^b$, L, Z, $R^1$, $R^2$ and t are as detailed herein.

In some embodiments, provided is a compound of formula (VII):

Formula (VII)
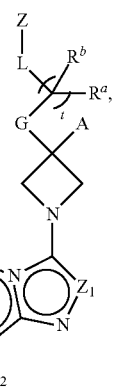

or a salt thereof, wherein
$Z_1$ is N or $CR^1$;
and A, G, $R^a$, $R^b$, L, Z, $R^1$, $R^2$ and t are as detailed herein.

In some embodiments, provided is a compound of formula (VIII):

Formula (VIII)
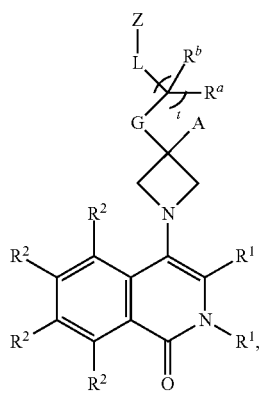

or a salt thereof, wherein, A, G, $R^a$, $R^b$, L, Z, $R^1$, $R^2$ and t are as detailed herein.

In some embodiments, provided is a compound of formula (IX):

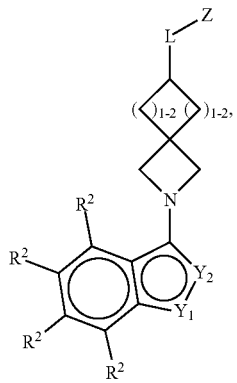

Formula (IX)

or a salt thereof, wherein
$Y_1$ is N or $NR^1$;
$Y_2$ is N, $NR^1$ or $CR^1$; provided that any one of $Y_1$ and $Y_2$ is $NR^1$ and other one is other than $NR^1$;
and L, Z, $R^1$ and $R^2$ are as detailed herein.

In some embodiments, provided is a compound of formula (X):

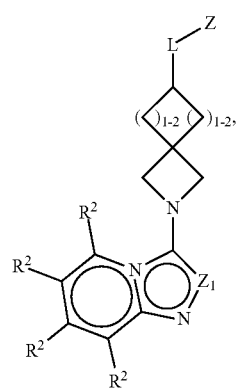

Formula (X)

or a salt thereof, wherein
$Z_1$ is N or $CR^1$;
and L, Z, $R^1$ and $R^2$ are as detailed herein.

In some embodiments, provided is a compound of formula (XI):

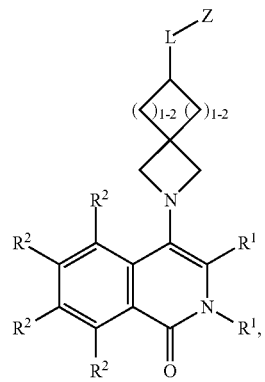

Formula (XI)

or a salt thereof, wherein L, Z, $R^1$ and $R^2$ are as detailed herein.

In some embodiments, provided is a compound of formula (XII):

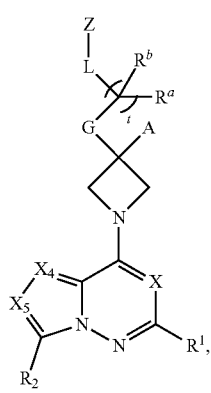

Formula (XII)

or a salt thereof, wherein,
X is N or $CR^1$;
$X_4$ and $X_5$ is independently N or $CR^2$; provided that at same time both are not N; and A, G, $R^a$, $R^b$, L, Z, $R^1$, $R^2$ and t are as detailed herein.

In some embodiments, provided is a compound of any one of formula (XII-1) to (XII-6):

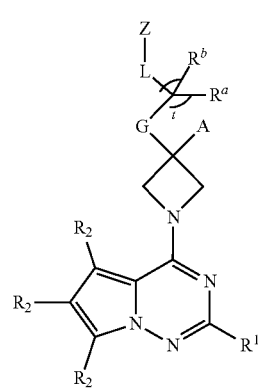

(XII-1)

-continued (XII-2)
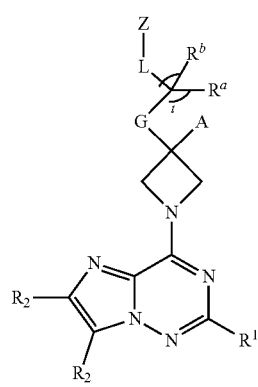

(XII-3)
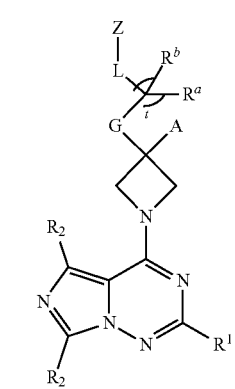

(XII-4)
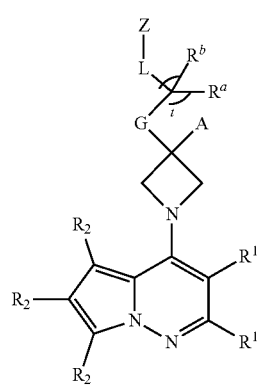

(XII-5)
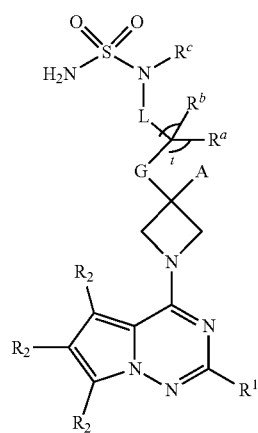

-continued (XII-6)
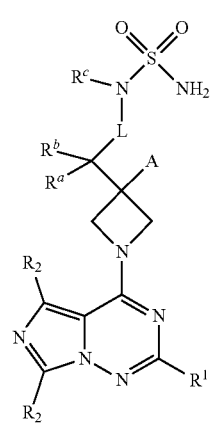

or a salt thereof, wherein A, G, $R^a$, $R^b$, L, Z, $R^1$, $R^2$, $R^c$ and t are as detailed herein.

In some embodiments, provided is a compound of formula (XIII):

Formula (XIII)
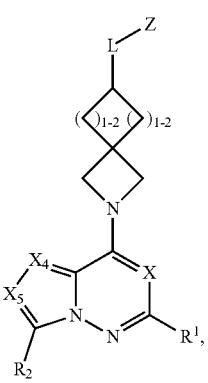

or a salt thereof, wherein
X is N or $CR^1$;
$X_4$ and $X_5$ is independently N or $CR^2$; provided that at same time both are not N; and L, Z, $R^1$ and $R^2$ are as detailed herein.

In some embodiments, provided is a compound of any one of formula (XIII-1) to (XIII-9):

(XIII-1)
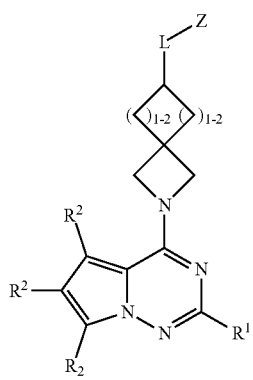

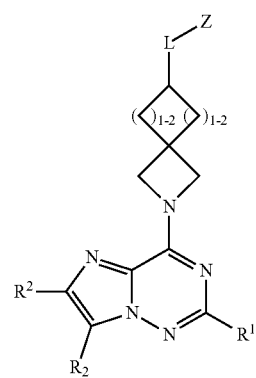
(XIII-2)
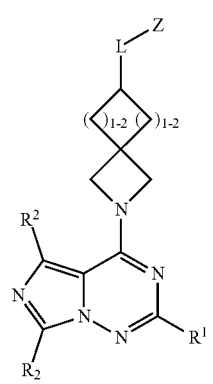
(XIII-3)
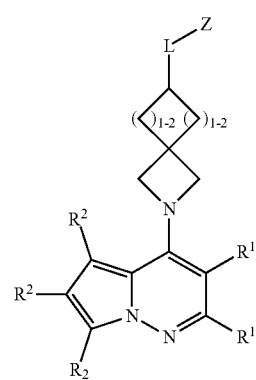
(XIII-4)
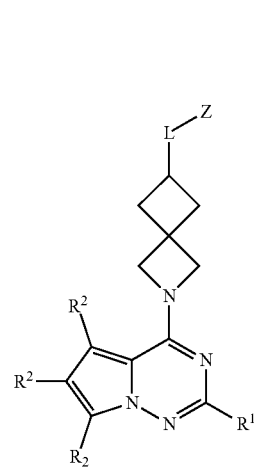
(XIII-5)
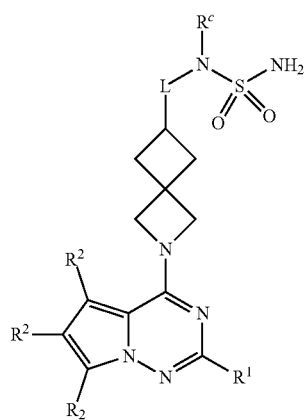
(XIII-6)
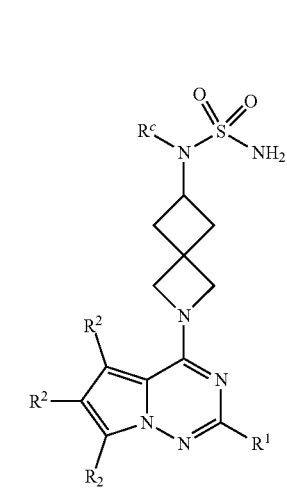
(XIII-7)
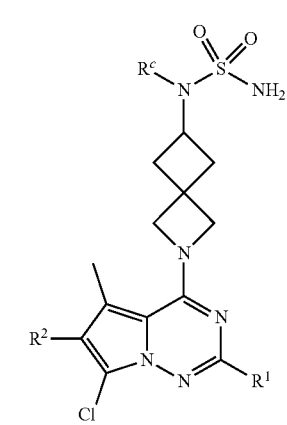
(XIII-8)

-continued (XIII-9)

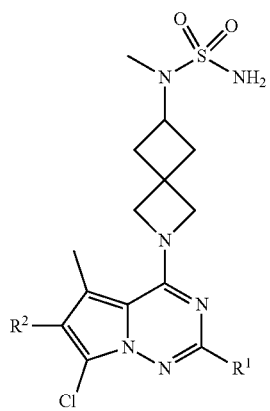

or a salt thereof, wherein L, Z, $R^1$, $R^2$ and $R^c$ are as detailed herein.

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)) are listed in table-1 and table-2. It is understood that individual enantiomers and diastereomers are included in the generic compound structures shown in table-1 and table-2. Specific synthetic methods for preparing compounds of table-1 are provided examples herein.

TABLE 1

| S.No. | Compounds |
|---|---|
| 1.1 | 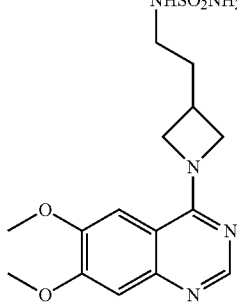 |
| 1.2 | 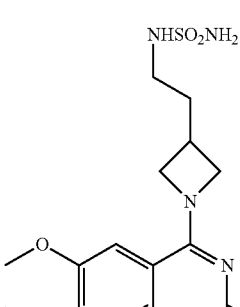 |
| 1.3 | 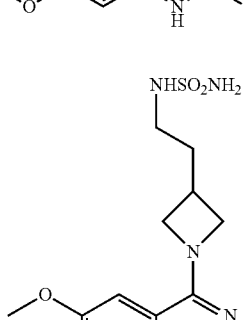 |
| 1.4 | 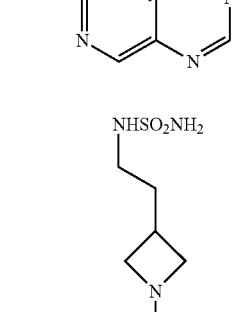 |

TABLE 1-continued
Compounds
| S.No. | Compounds |
|---|---|
| 1.5 | 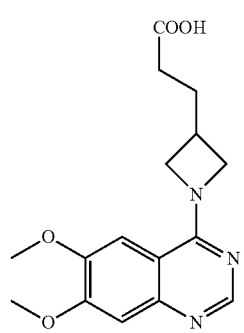 [SMILES: COc1cc2ncnc(N3CC(CCC(=O)O)C3)c2cc1OC] |
| 1.6 | 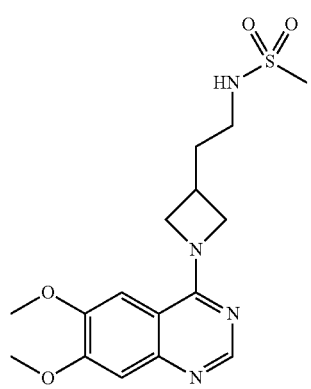 |
| 1.7 | 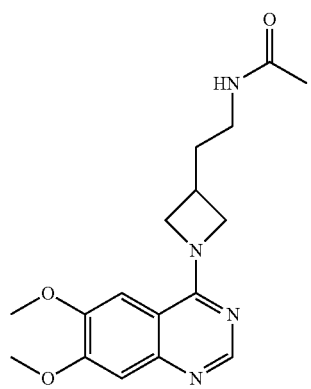 [SMILES: COc1cc2ncnc(N3CC(CCNC(C)=O)C3)c2cc1OC] |
| 1.8 | 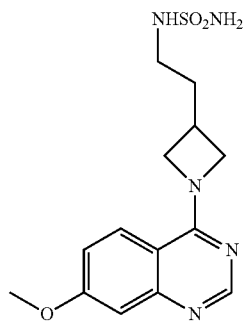 |
| 1.9 | 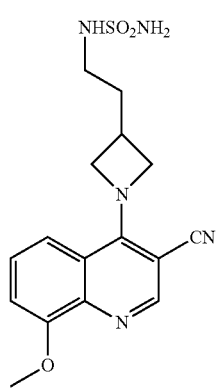 |
| 1.10 | 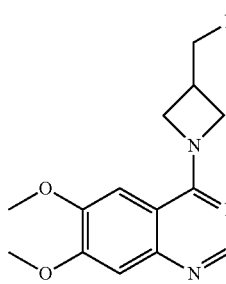 |
| 1.11 | 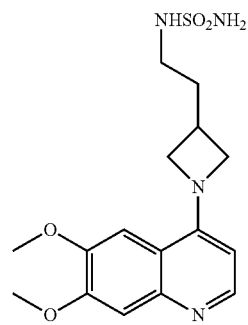 |
| 1.12 | 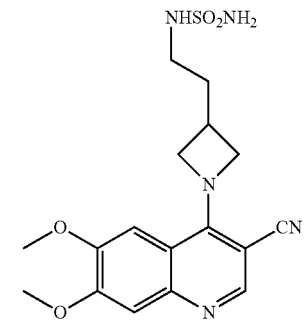 |

TABLE 1-continued

| S.No. | Compounds |
|---|---|
| 1.13 | 3-cyano-7-methoxyquinolin-4-yl azetidine with ethyl-NHSO$_2$NH$_2$ |
| 1.14 | 5-methyl-5H-pyrrolo[3,2-d]pyrimidin-4-yl azetidine with ethyl-NHSO$_2$NH$_2$ |
| 1.15 | 6,7-dimethoxyquinazolin-4-yl 2-azaspiro[3.3]heptane with NHSO$_2$NH$_2$ |
| 1.16 | 6-methoxyquinazolin-4-yl azetidine with ethyl-NHSO$_2$NH$_2$ |
| 1.17 | 6,7-dimethoxy-2-methylquinazolin-4-yl azetidine with ethyl-NHSO$_2$NH$_2$ |
| 1.18 | [1,3]dioxolo[4,5-g]quinazolin-8-yl azetidine with ethyl-NHSO$_2$NH$_2$ |
| 1.19 | 8-ethoxyquinazolin-4-yl azetidine with ethyl-NHSO$_2$NH$_2$ |
| 1.20 | 5-methylpyrrolo[2,1-f][1,2,4]triazin-4-yl azetidine with ethyl-NH-S(=O)$_2$-NH$_2$ |

TABLE 1-continued
| S.No. | Compounds |
|---|---|
| 1.21 | 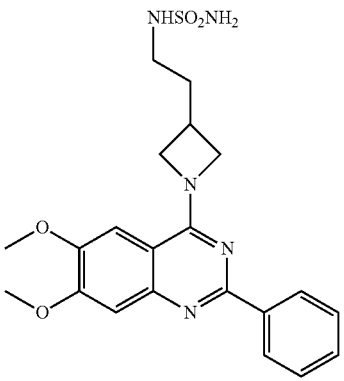 |
| 1.22 | 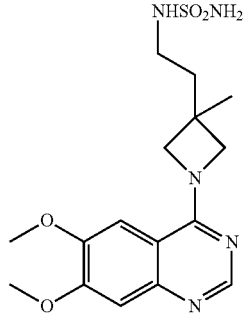 |
| 1.23 | 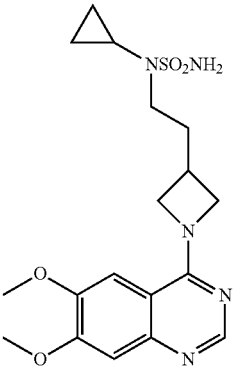 |
| 1.24 | 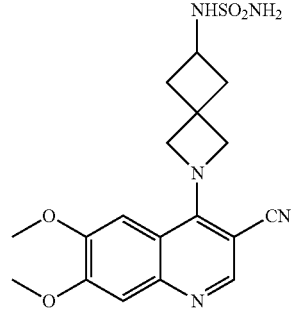 |
TABLE 1-continued
| S.No. | Compounds |
|---|---|
| 1.25 | 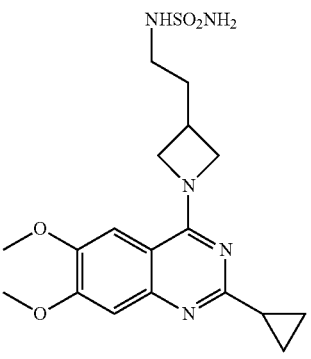 |
| 1.26 | 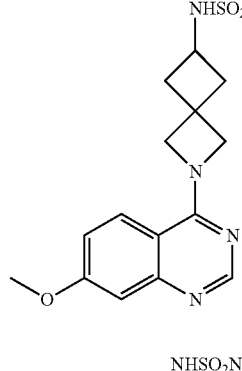 |
| 1.27 | 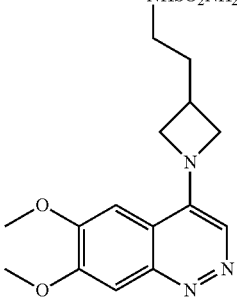 |
| 1.28 | 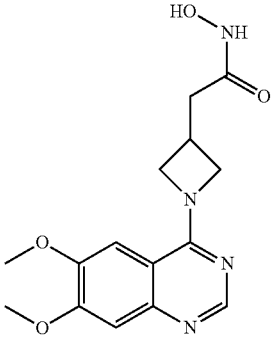 [SMILES: COc1cc2ncnc(N3CC(CC(=O)NO)C3)c2cc1OC] |

TABLE 1-continued

| S.No. | Compounds |
|---|---|
| 1.29 | (phosphonic acid ethyl-azetidinyl-6,7-dimethoxyquinazoline) |
| 1.30 | (boronic acid propyl-azetidinyl-6,7-dimethoxyquinazoline) |
| 1.31 | (NHSO₂NH₂ ethyl-azetidinyl-7,8-dimethoxyquinazoline) |
| 1.32 | (NHSO₂NH₂ ethyl-azetidinyl-N-methyl-imidazo-fluoroquinazoline) |
| 1.33 | (NHSO₂NH₂ ethyl-azetidinyl-6,7-dimethoxy-2-(4-fluorophenyl)quinazoline) |
| 1.34 | (NHSO₂NH₂ ethyl-azetidinyl-7-methoxy-2-phenylquinazoline) |
| 1.35 | (NHSO₂NH₂ ethyl-azetidinyl-6,7-dimethoxy-2-(pyridin-4-yl)quinazoline) |
| 1.36 | (NHSO₂NH₂ ethyl-azetidinyl-6,7-dimethoxy-2-(1-methylpyrazol-3-yl)quinazoline) |

TABLE 1-continued

| S.No. | Compounds |
|---|---|
| 1.37 | (2-ethyl-7-methoxyquinazolin-4-yl azetidine with ethyl sulfamoylamino chain) |
| 1.38 | (6-fluoro-8-methoxyquinazolin-4-yl azetidine with ethyl sulfamoylamino chain) |
| 1.39 | (6,7-dimethoxyquinazolin-4-yl azetidine with propyl sulfonamide chain) |
| 1.40 | (7-methoxyquinazolin-4-yl azetidine with N-methyl sulfamoylamino ethyl chain) |
| 1.41 | (6-bromo-7-methoxyquinazolin-4-yl azetidine with ethyl NHSO$_2$NH$_2$ chain) |
| 1.42 | (2-cyclopropyl-7-methoxyquinazolin-4-yl azetidine with ethyl NHSO$_2$NH$_2$ chain) |
| 1.43 | (2-difluoromethyl-6,7-dimethoxyquinazolin-4-yl azetidine with ethyl NHSO$_2$NH$_2$ chain) |
| 1.44 | (7-methoxy-2-(pyridin-3-yl)quinazolin-4-yl azetidine with ethyl sulfamoylamino chain) |

TABLE 1-continued
Compounds
| S.No. | Compounds |
|---|---|
| 1.45 | 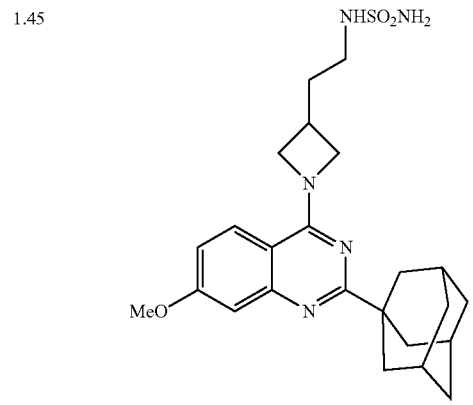 |
| 1.46 | 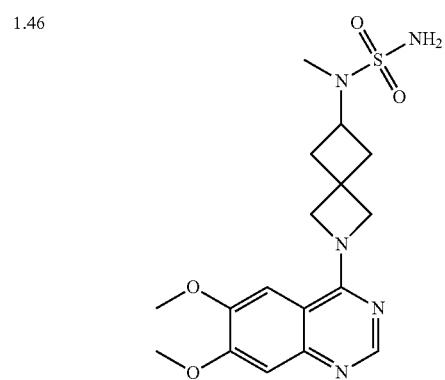 |
| 1.47 | 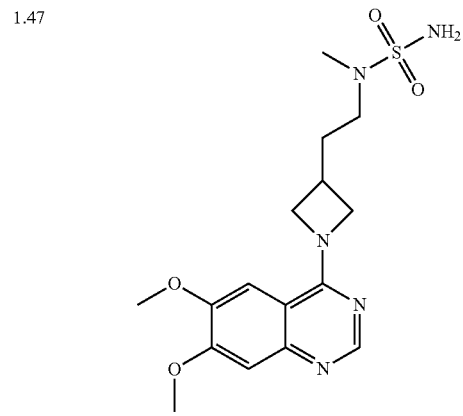 |
| 1.48 | 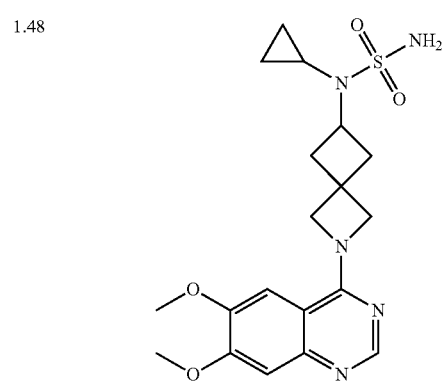 |
TABLE 1-continued
Compounds
| S.No. | Compounds |
|---|---|
| 1.49 | 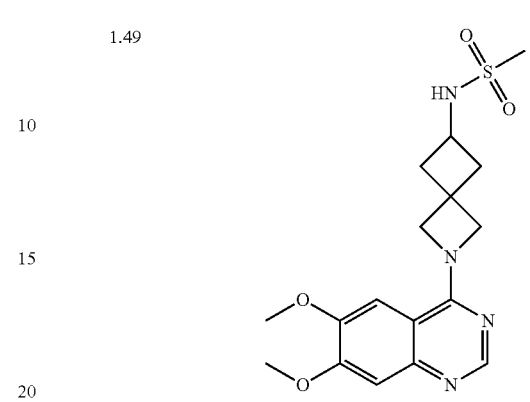 |
| 1.50 | 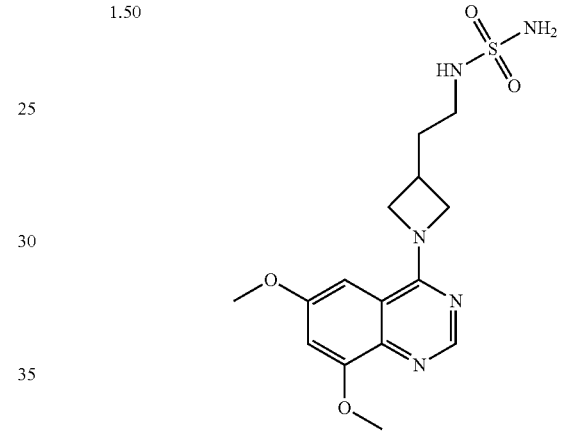 |
| 1.51 | 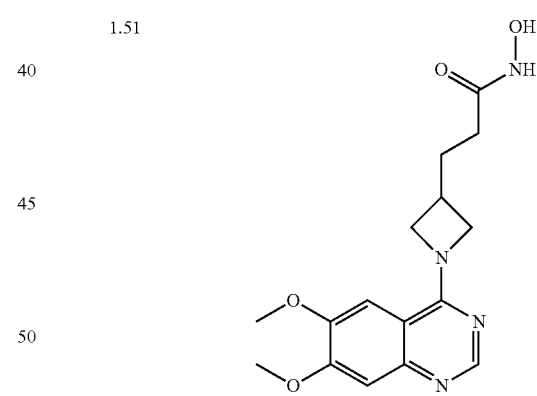 |
| 1.52 | 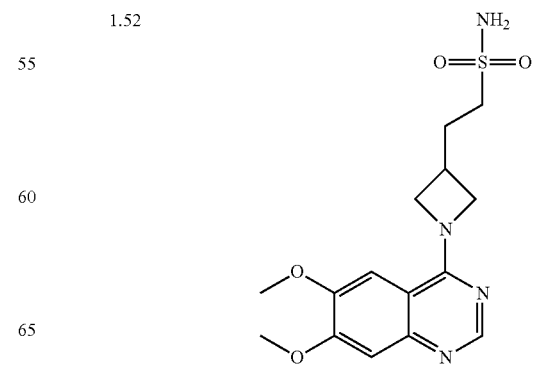 |

TABLE 1-continued
Compounds
| S.No. | Compounds |
|---|---|
| 1.53 | 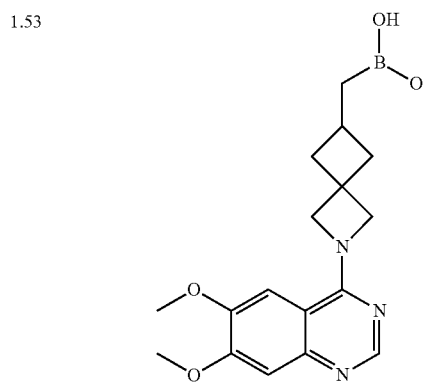 |
| 1.54 | 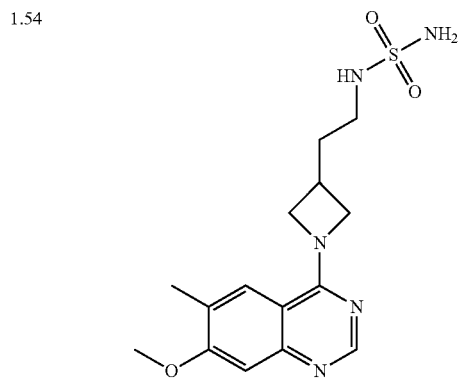 |
| 1.55 | 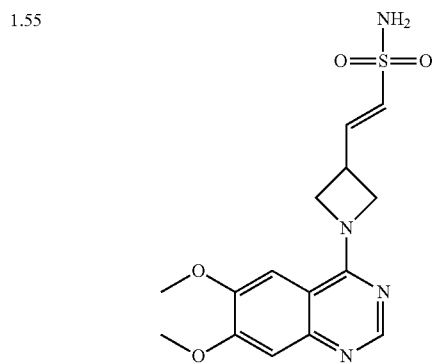 |
| 1.56 | 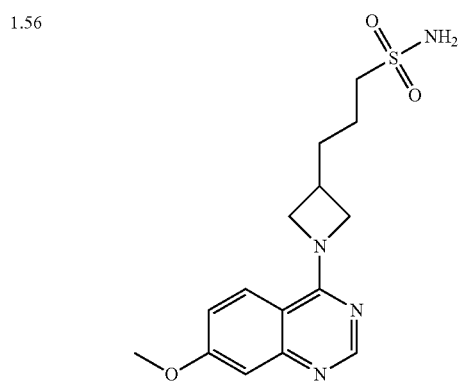 |
| 1.57 | 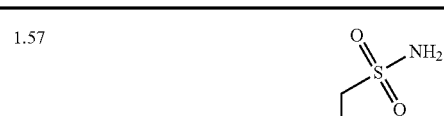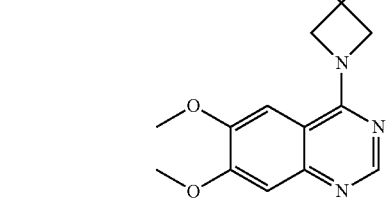 |
| 1.58 | 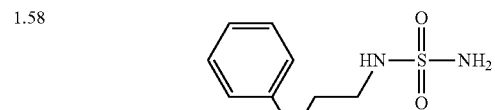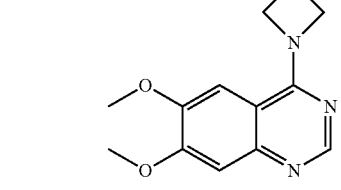 |
| 1.59 | 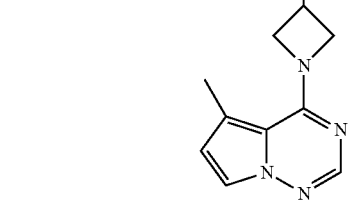 |
| 1.60 | 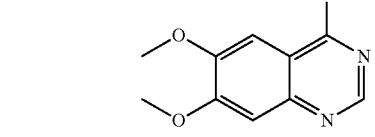 |

TABLE 1-continued
| S.No. | Compounds |
|---|---|
| 1.61 | 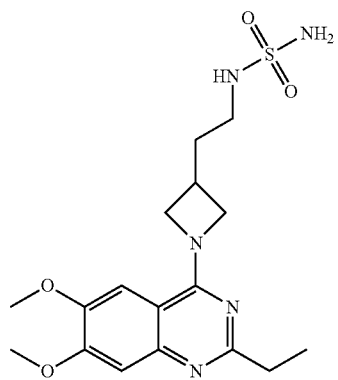 [SMILES: CCc1nc(N2CC(CCNS(N)(=O)=O)C2)c2cc(OC)c(OC)cc2n1] |
| 1.62 | 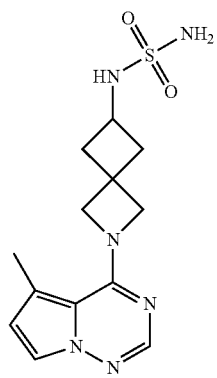 [SMILES: Cc1ccn2ncnc(N3CC4(CC(NS(N)(=O)=O)C4)C3)c12] |
| 1.63 | 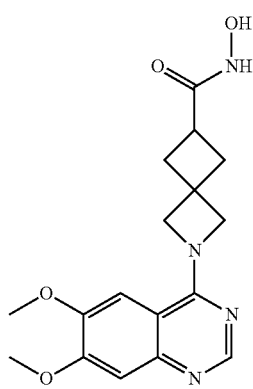 [SMILES: COc1cc2ncnc(N3CC4(CC(C(=O)NO)C4)C3)c2cc1OC] |
| 1.64 | 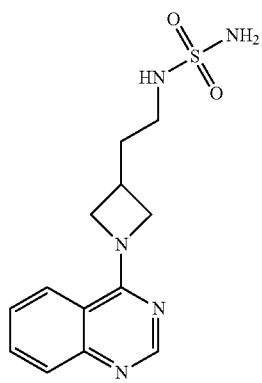 [SMILES: NS(=O)(=O)NCCC1CN(c2ncnc3ccccc23)C1] |
TABLE 1-continued
| S.No. | Compounds |
|---|---|
| 1.65 | 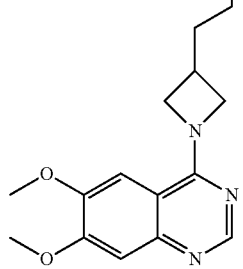 |
| 1.66 | 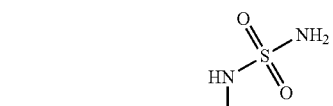 |
| 1.67 | 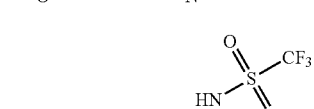 |
| 1.68 | 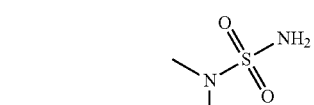 |

TABLE 1-continued

| S.No. | Compounds |
|---|---|
| 1.69 | (structure) |
| 1.70 | (structure) |
| 1.71 | (structure) |
| 1.72 | (structure) |
| 1.73 | (structure) |
| 1.74 | (structure) |
| 1.75 | (structure) |

TABLE 1-continued
| S.No. | Compounds |
|---|---|
| 1.76 | 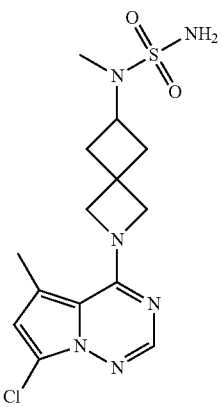 [SMILES: Cc1cc(Cl)n2ncnc(N3CC4(CC(N(C)S(N)(=O)=O)C4)C3)c12] |
| 1.77 | 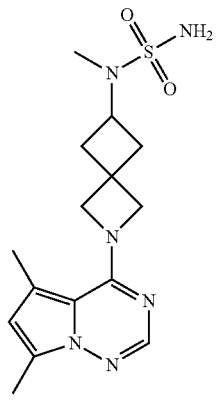 [SMILES: Cc1cc(C)n2ncnc(N3CC4(CC(N(C)S(N)(=O)=O)C4)C3)c12] |
| 1.78 | 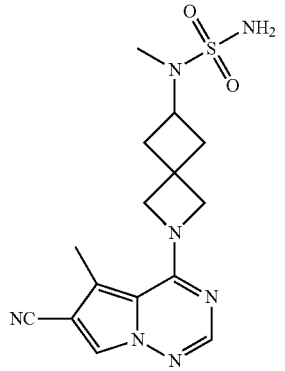 [SMILES: Cc1c(C#N)cn2ncnc(N3CC4(CC(N(C)S(N)(=O)=O)C4)C3)c12] |
| 1.79 | 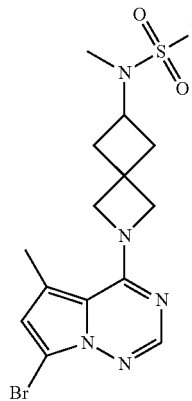 |
| 1.80 | 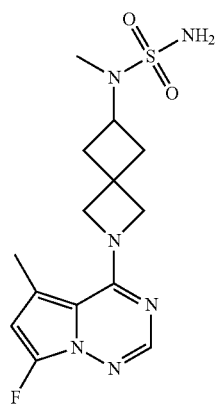 [SMILES: Cc1cc(F)n2ncnc(N3CC4(CC(N(C)S(N)(=O)=O)C4)C3)c12] |
| 1.81 | 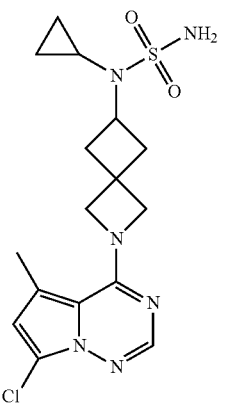 [SMILES: Cc1cc(Cl)n2ncnc(N3CC4(CC(N(C5CC5)S(N)(=O)=O)C4)C3)c12] |
| 1.82 | 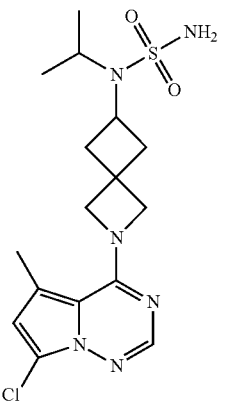 [SMILES: Cc1cc(Cl)n2ncnc(N3CC4(CC(N(C(C)C)S(N)(=O)=O)C4)C3)c12] |

TABLE 1-continued
| S.No. | Compounds |
|---|---|
| 1.83 | 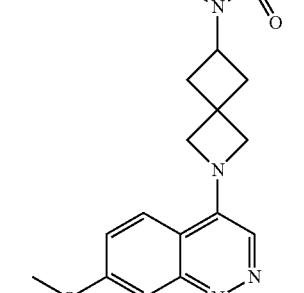 |
| 1.84 | |
| 1.85 | |
| 1.86 | |
TABLE 1-continued
| S.No. | Compounds |
|---|---|
| 1.87 | 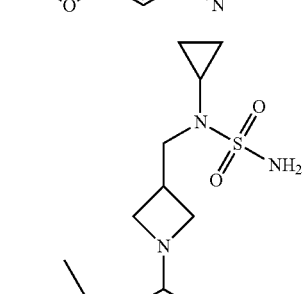 |
| 1.88 | |
| 1.89 | |
| 1.90 | |

TABLE 1-continued
Compounds
| S.No. | Compounds |
|---|---|
| 1.91 | 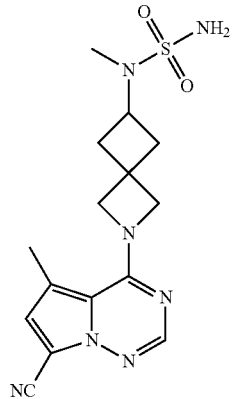 [SMILES: Cc1cc(C#N)n2ncnc(N3CC4(CC(N(C)S(N)(=O)=O)C4)C3)c12] |
| 1.92 | 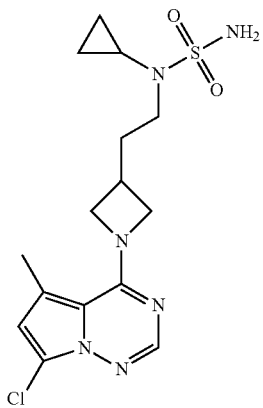 [SMILES: Cc1cc(Cl)n2ncnc(N3CC(CCN(C4CC4)S(N)(=O)=O)C3)c12] |
| 1.93 | 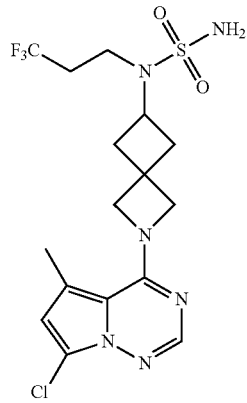 [SMILES: Cc1cc(Cl)n2ncnc(N3CC4(CC(N(CCC(F)(F)F)S(N)(=O)=O)C4)C3)c12] |
TABLE 1-continued
Compounds
| S.No. | Compounds |
|---|---|
| 1.94 | 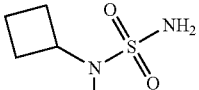 |
| 1.95 | 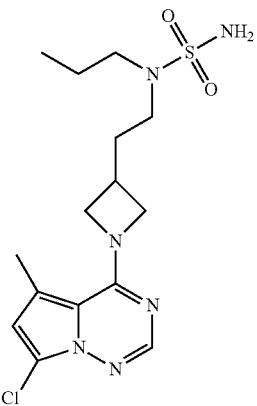 [SMILES: CCCN(CCC1CN(c2ncnn3c(Cl)cc(C)c23)C1)S(N)(=O)=O] |
| 1.96 | 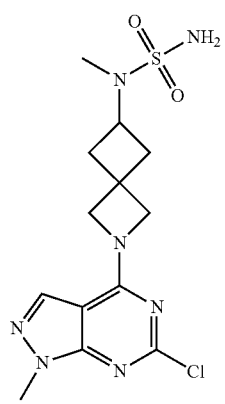 [SMILES: CN(C1CC2(C1)CN(c1nc(Cl)nc3c1cnn3C)C2)S(N)(=O)=O] |

TABLE 1-continued
Compounds
| S.No. | Compounds |
|---|---|
| 1.97 | 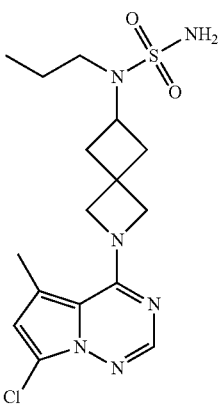 [SMILES: CCCN(C1CC2(C1)CN(c1ncnn3c(Cl)cc(C)c13)C2)S(N)(=O)=O] |
| 1.98 | 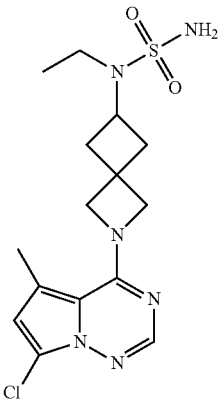 [SMILES: CCN(C1CC2(C1)CN(c1ncnn3c(Cl)cc(C)c13)C2)S(N)(=O)=O] |
| 1.99 | 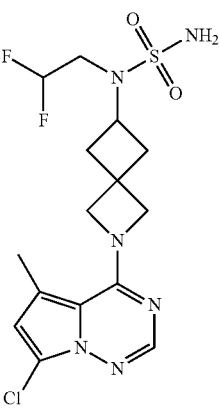 [SMILES: Cc1cc(Cl)n2ncnc(N3CC4(CC(N(CC(F)F)S(N)(=O)=O)C4)C3)c12] |
TABLE 1-continued
Compounds
| S.No. | Compounds |
|---|---|
| 1.100 | 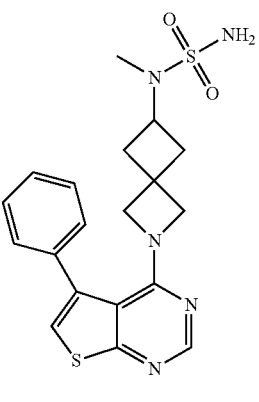 [SMILES: CN(C1CC2(C1)CN(c1ncnc3scc(-c4ccccc4)c13)C2)S(N)(=O)=O] |
| 1.101 | 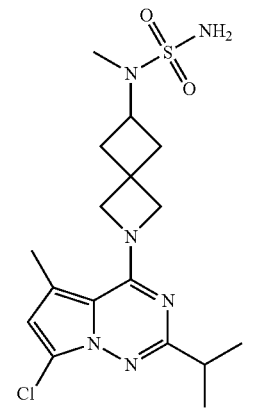 [SMILES: Cc1cc(Cl)n2nc(C(C)C)nc(N3CC4(CC(N(C)S(N)(=O)=O)C4)C3)c12] |
| 1.102 | 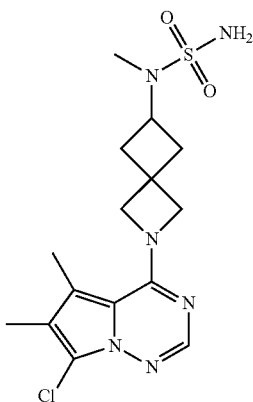 [SMILES: Cc1c(C)c2c(N3CC4(CC(N(C)S(N)(=O)=O)C4)C3)ncnn2c1Cl] |

TABLE 1-continued
| S.No. | Compounds |
|---|---|
| 1.103 | 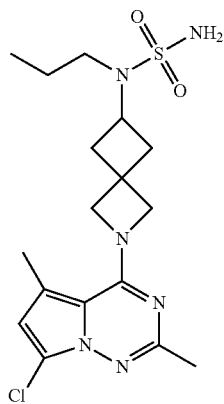 [SMILES: CCCN(C1CC2(C1)CN(c1nc(C)nn3c(Cl)cc(C)c13)C2)S(N)(=O)=O] |
| 1.104 | 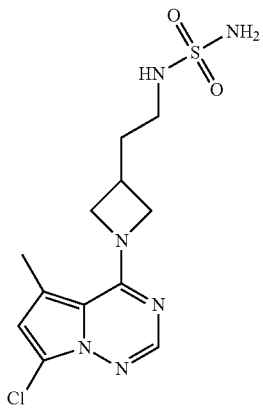 [SMILES: Cc1cc(Cl)n2ncnc(N3CC(CCNS(N)(=O)=O)C3)c12] |
| 1.105 | 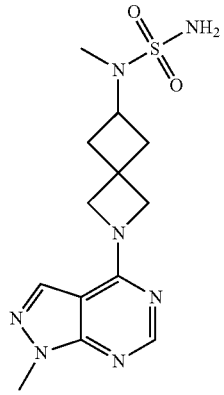 [SMILES: CN(C1CC2(C1)CN(c1ncnc3c1cnn3C)C2)S(N)(=O)=O] |† |
| S.No. | Compounds |
|---|---|
| 1.106 | 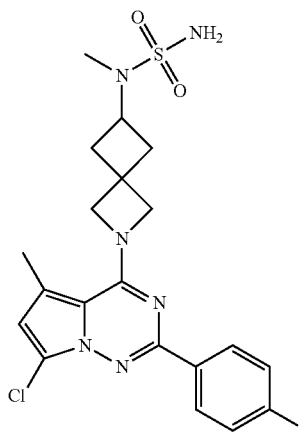 |
| 1.107 | 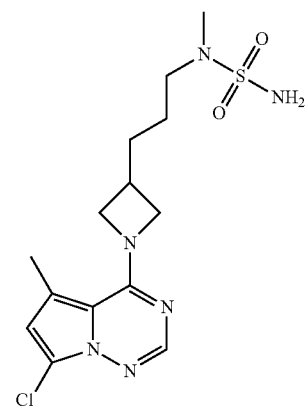 [SMILES: Cc1cc(Cl)n2ncnc(N3CC(CCCN(C)S(N)(=O)=O)C3)c12] |
| 1.108 | 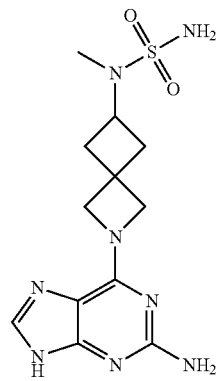 [SMILES: CN(C1CC2(C1)CN(c1nc(N)nc3[nH]cnc13)C2)S(N)(=O)=O] |

TABLE 1-continued
| S.No. | Compounds |
|---|---|
| 1.109 | 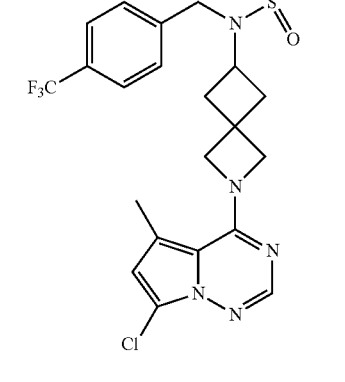 |
| 1.110 | 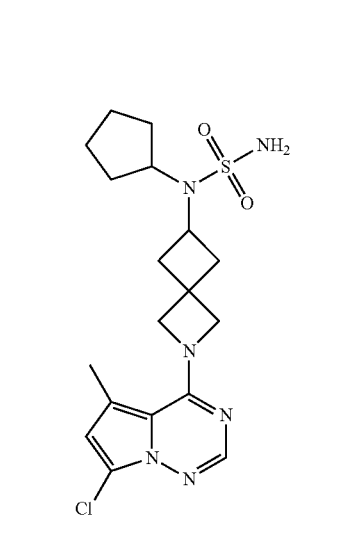 [SMILES: Cc1cc(Cl)n2ncnc(N3CC4(CC(N(C5CCCC5)S(N)(=O)=O)C4)C3)c12] |
| 1.111 | 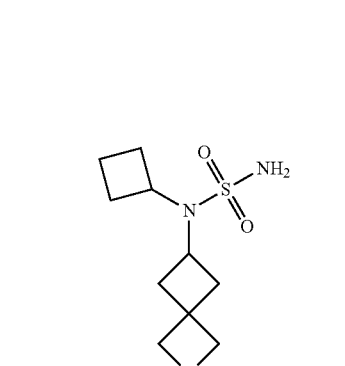 |
| 1.112 | 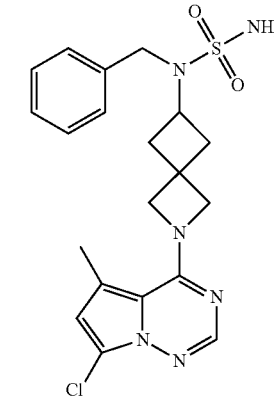 |
| 1.113 | 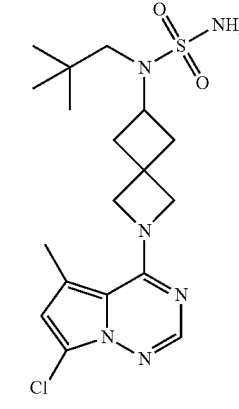 |
| 1.114 | 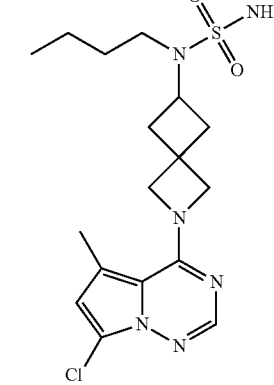 |

TABLE 1-continued
| S.No. | Compounds |
|---|---|
| 1.115 | 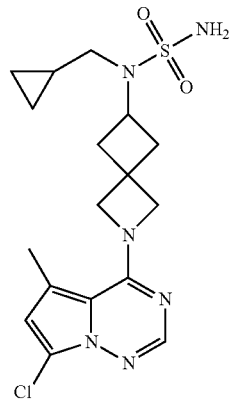 [SMILES: Cc1cc(Cl)n2ncnc(N3CC4(CC(N(CC5CC5)S(N)(=O)=O)C4)C3)c12] |
| 1.116 | 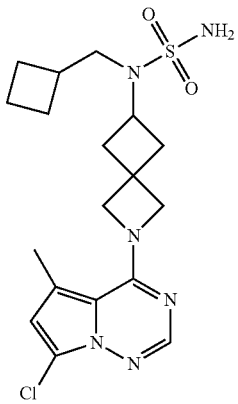 [SMILES: Cc1cc(Cl)n2ncnc(N3CC4(CC(N(CC5CCC5)S(N)(=O)=O)C4)C3)c12] |
| 1.117 | 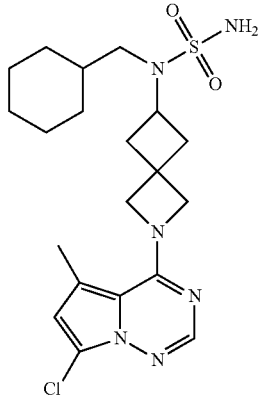 [SMILES: Cc1cc(Cl)n2ncnc(N3CC4(CC(N(CC5CCCCC5)S(N)(=O)=O)C4)C3)c12] |
TABLE 1-continued
| S.No. | Compounds |
|---|---|
| 1.118 | 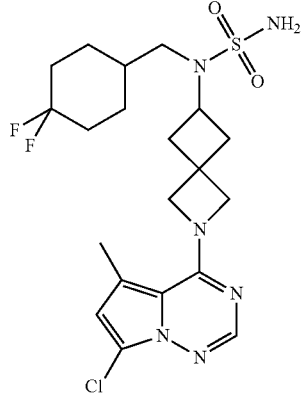 [SMILES: Cc1cc(Cl)n2ncnc(N3CC4(CC(N(CC5CCC(F)(F)CC5)S(N)(=O)=O)C4)C3)c12] |
| 1.119 | 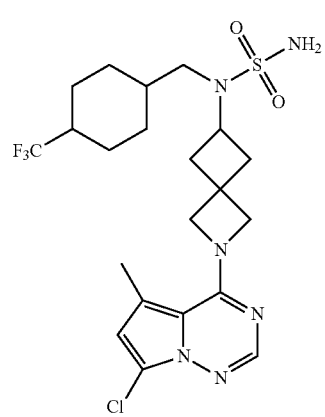 [SMILES: Cc1cc(Cl)n2ncnc(N3CC4(CC(N(CC5CCC(C(F)(F)F)CC5)S(N)(=O)=O)C4)C3)c12] |
| 1.120 | 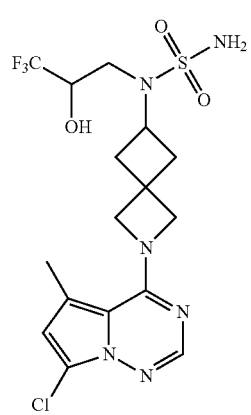 [SMILES: Cc1cc(Cl)n2ncnc(N3CC4(CC(N(CC(O)C(F)(F)F)S(N)(=O)=O)C4)C3)c12] |

TABLE 1-continued
Compounds
| S.No. | Compounds |
|---|---|
| 1.121 | 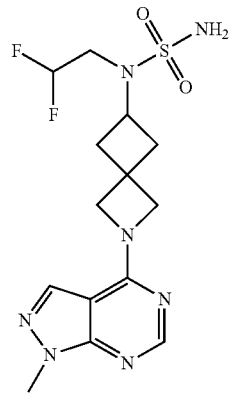 [SMILES: Cn1ncc2c(N3CC4(CC(N(CC(F)F)S(N)(=O)=O)C4)C3)ncnc21] |
| 1.122 | 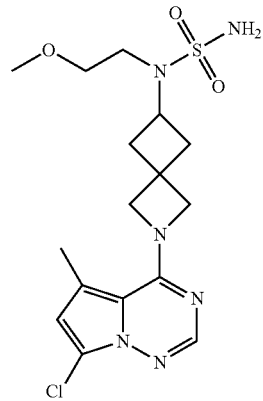 [SMILES: COCCN(C1CC2(C1)CN(c1ncnn3c(Cl)cc(C)c13)C2)S(N)(=O)=O] |
| 1.123 | 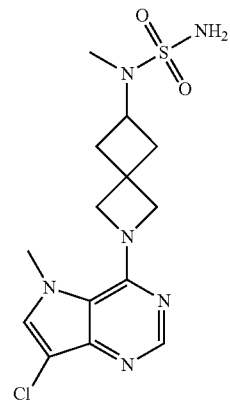 [SMILES: CN(C1CC2(C1)CN(c1ncnc3c(Cl)cn(C)c13)C2)S(N)(=O)=O] |
| 1.124 | 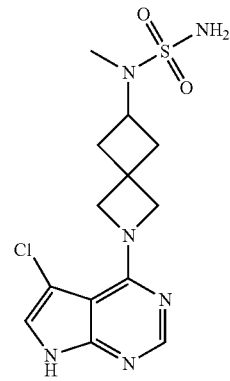 [SMILES: CN(C1CC2(C1)CN(c1ncnc3[nH]cc(Cl)c13)C2)S(N)(=O)=O] |
| 1.125 | 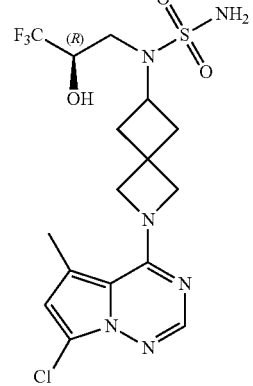 |
| 1.126 | 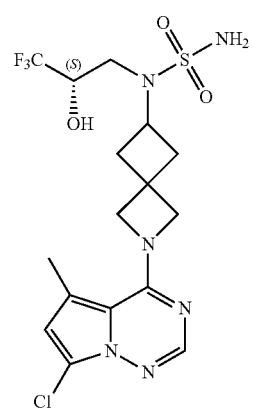 |

TABLE 1-continued

| S.No. | Compounds |
|---|---|
| 1.127 | (structure) |
| 1.128 | (structure) |
| 1.129 | (structure) |
| 1.130 | (structure) |
| 1.131 | (structure) |
| 1.132 | (structure) |
| 1.133 | (structure) |

TABLE 1-continued
| S.No. | Compounds |
|---|---|
| 1.134 | 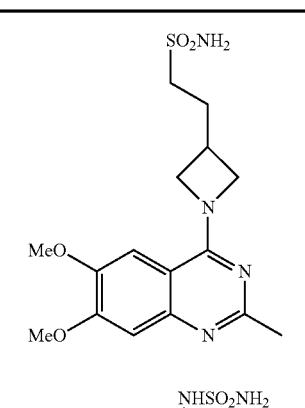 |
| 1.135 | 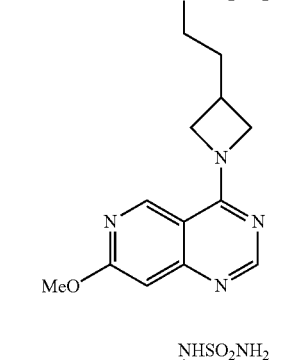 |
The compounds illustrated in table-2 are prepared in a manner analogous to the techniques used in connection with the preparation of the table-1 compounds and in accordance, using appropriate, analogous starting materials and by utilizing the general synthetic schemes illustrated below.
TABLE 2
| S.No. | Compounds |
|---|---|
| 2.1 | 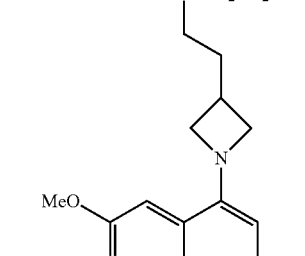 |
| 2.2 | |
| 2.3 | |
| 2.4 | |
| 2.5 | 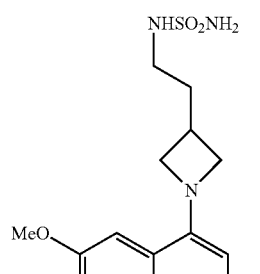 |

TABLE 2-continued
| S.No. | Compounds |
|---|---|
| 2.6 | 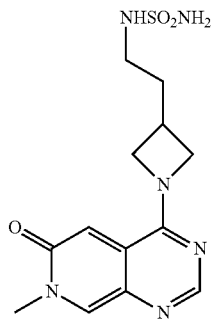 |
| 2.7 | 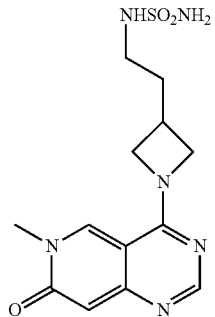 |
| 2.8 | 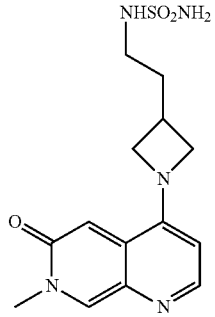 |
| 2.9 | 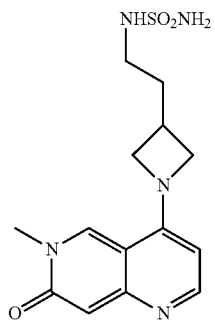 |
| 2.10 | 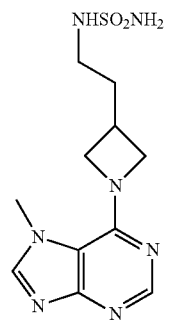 |
| 2.11 | 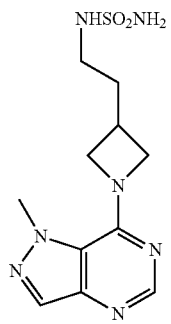 |
| 2.12 | 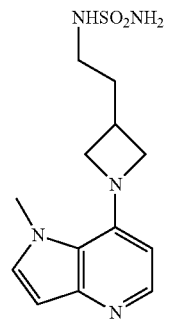 |
| 2.13 | 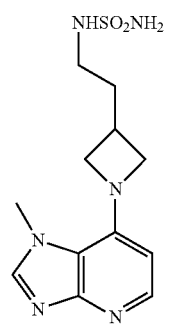 |

TABLE 2-continued
Compounds
| S.No. | Compounds |
|---|---|
| 2.14 | 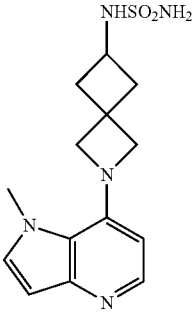 |
| 2.15 | 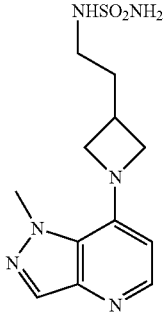 |
| 2.16 | 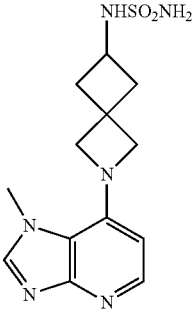 |
| 2.17 | 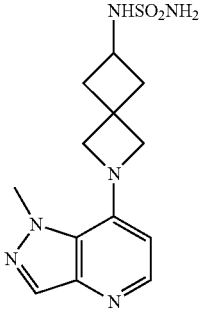 |
TABLE 2-continued
Compounds
| S.No. | Compounds |
|---|---|
| 2.18 | 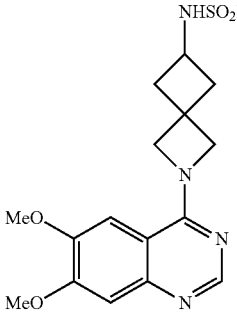 |
| 2.19 | 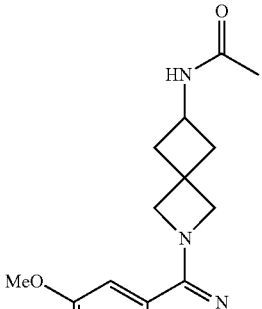 |
| 2.20 | 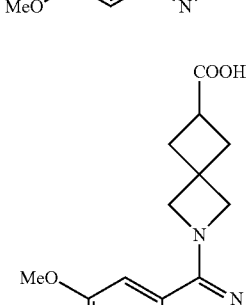 |
| 2.21 | 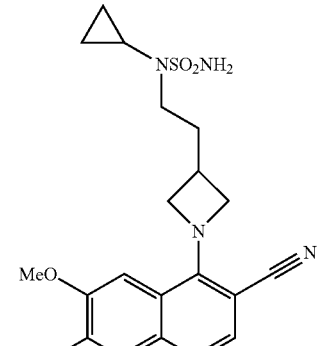 |

TABLE 2-continued

| S.No. | Compounds |
|---|---|
| 2.22 | (structure) |
| 2.23 | (structure) |
| 2.24 | (structure) |
| 2.25 | (structure) |
| 2.26 | (structure) |
| 2.27 | (structure) |
| 2.28 | (structure) |
| 2.29 | (structure) |

TABLE 2-continued
| S.No. | Compounds |
|---|---|
| 2.30 | 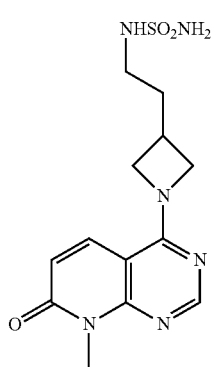 |
| 2.31 | 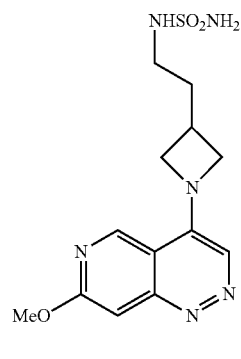 |
| 2.32 | 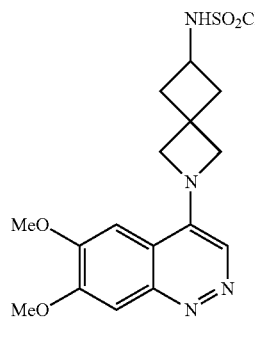 |
| 2.33 | 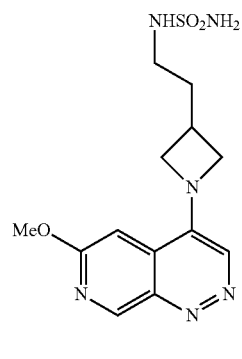 |
| 2.34 | 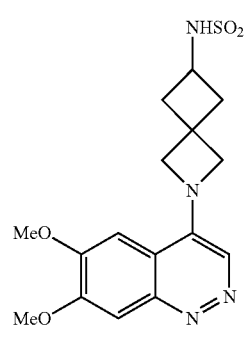 |
| 2.35 | 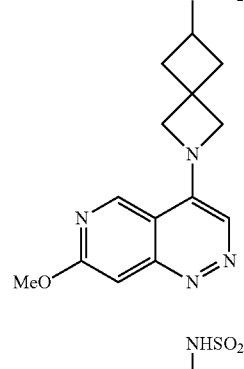 |
| 2.36 | 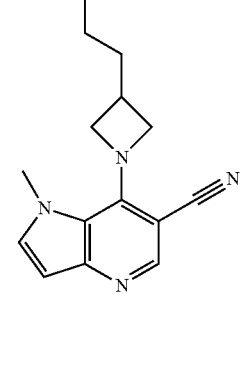 |
| 2.37 | |

TABLE 2-continued

| S.No. | Compounds |
|---|---|
| 2.38 | (2-(1-(6-cyano-1-methyl-1H-pyrazolo[4,3-b]pyridin-7-yl)azetidin-3-yl)ethyl)sulfamide |
| 2.39 | (2-(1-(6,7-dimethoxyimidazo[1,2-a]pyridin-3-yl)azetidin-3-yl)ethyl)sulfamide |
| 2.40 | (2-(1-(5-methylpyrrolo[2,1-f][1,2,4]triazin-4-yl)azetidin-3-yl)ethyl)sulfamide |
| 2.41 | (2-(1-(4-methylpyrrolo[1,2-b]pyridazin-7-yl)azetidin-3-yl)ethyl)sulfamide |
| 2.42 | (2-(1-(3-cyano-5-methylpyrrolo[1,2-b]pyridazin-4-yl)azetidin-3-yl)ethyl)sulfamide |
| 2.43 | (2-(1-(8-methylimidazo[5,1-f][1,2,4]triazin-4-yl)azetidin-3-yl)ethyl)sulfamide |
| 2.44 | (2-(1-(8-methylimidazo[1,5-b]pyridazin-7-yl)azetidin-3-yl)ethyl)sulfamide |
| 2.45 | (1-(6-cyano-1-methyl-1H-pyrrolo[3,2-b]pyridin-7-yl)-2,6-diazaspiro[3.3]heptan-2-yl)sulfamide |

TABLE 2-continued

| S.No. | Compounds |
|---|---|
| 2.46 | (1-methyl-1H-pyrazolo[4,3-b]pyridin-7-yl)-2-azaspiro[3.3]heptane with NHSO₂NH₂ |
| 2.47 | (6-cyano-1-methyl-1H-pyrazolo[4,3-b]pyridin-7-yl)-2-azaspiro[3.3]heptane with NHSO₂NH₂ |
| 2.48 | 2-(1-(6-methoxy-8-methoxyquinazolin-4-yl)azetidin-3-yl)ethyl-NHSO₂NH₂ |
| 2.49 | (6-fluoro-8-methoxyquinazolin-4-yl)-2-azaspiro[3.4]octane-carboxamide N-OH |
| 2.50 | 2-(1-(7-methoxy-8-methoxy-2-methylquinazolin-4-yl)azetidin-3-yl)-2-methylpropyl-NHSO₂NH₂ |
| 2.51 | 2-(1-(6,7-dimethoxy-2-(2-(pyridin-3-yl)vinyl)quinazolin-4-yl)azetidin-3-yl)ethyl-NHSO₂NH₂ |
| 2.52 | 2-(1-(6,7-dimethoxy-5-methylcinnolin-4-yl)azetidin-3-yl)ethyl-NHSO₂NH₂ |
| 2.53 | (6,7-dimethoxyquinazolin-4-yl)-2-azaspiro[3.3]heptane with NHCONH₂ |

TABLE 2-continued
| S.No. | Compounds |
|---|---|
| 2.54 | 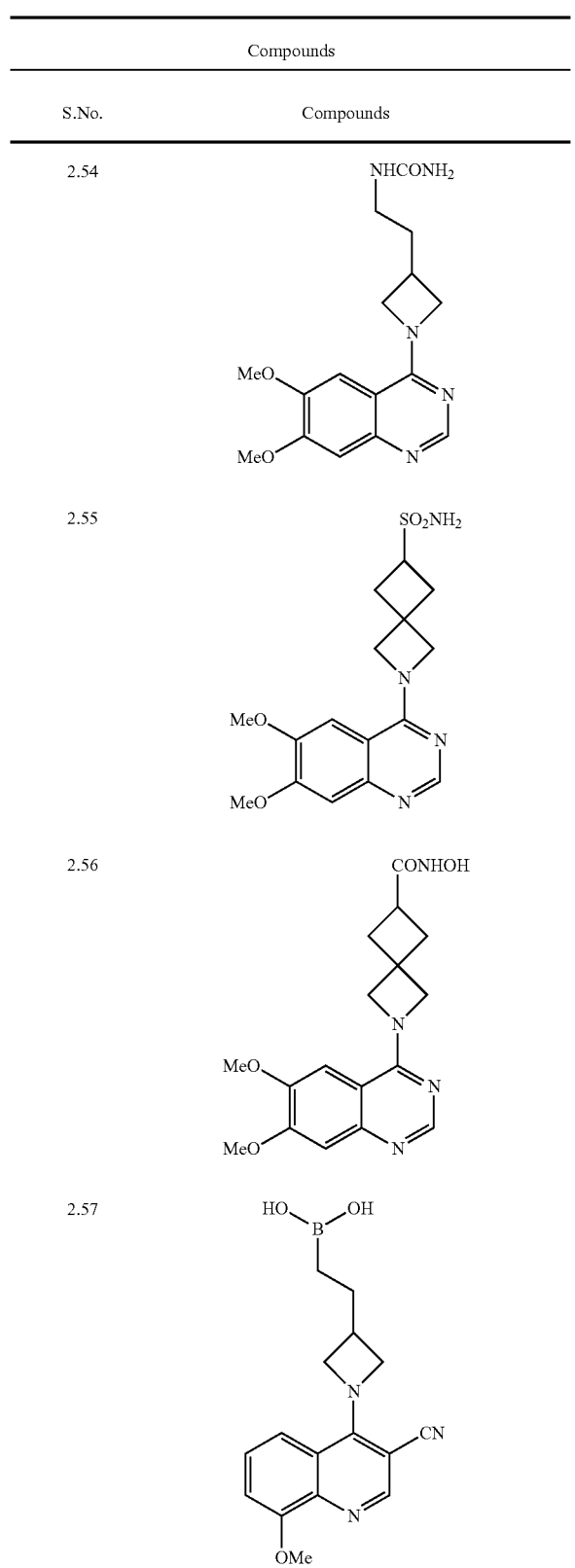 |
| 2.55 | |
| 2.56 | |
| 2.57 | |
TABLE 2-continued
| S.No. | Compounds |
|---|---|
| 2.58 | 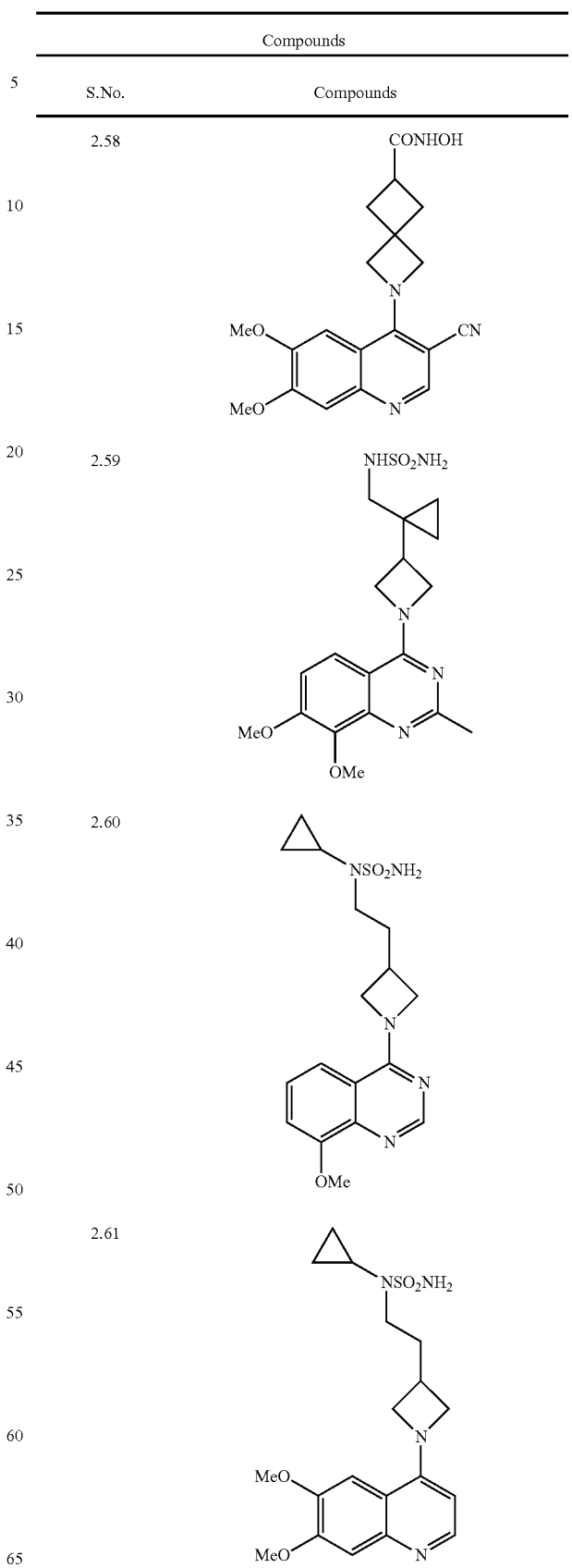 |
| 2.59 | |
| 2.60 | |
| 2.61 | |

TABLE 2-continued
| S.No. | Compounds |
|---|---|
| 2.62 | 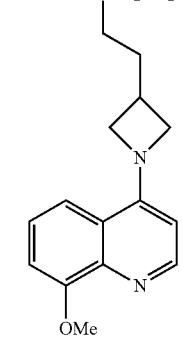 |
| 2.63 | |
| 2.64 | |
| 2.65 | |
| 2.66 | 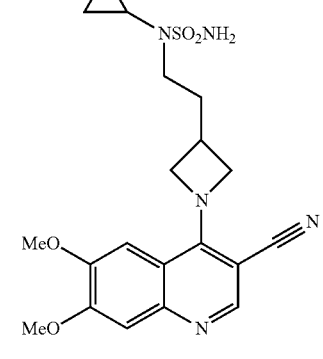 |
| 2.67 | |
| 2.68 | |
| 2.69 | |

TABLE 2-continued

| S.No. | Compounds |
|---|---|
| 2.70 | cyclopropyl-N(SO₂NH₂)-CH₂CH₂-(3-methylazetidin-3-yl)-N-(8-methoxyquinazolin-4-yl) |
| 2.71 | cyclopropyl-N(SO₂NH₂)-CH₂CH₂-(3-methylazetidin-3-yl)-N-(6,7-dimethoxyquinazolin-4-yl) |
| 2.72 | H₂NSO₂NH-CH₂CH₂-(azetidin-3-yl)-N-(6,7-dimethoxy-3-cyanocinnolin-4-yl) |
| 2.73 | H₂NSO₂NH-CH₂CH₂-(azetidin-3-yl)-N-(7-methoxy-3-cyanocinnolin-4-yl) |
| 2.74 | ethyl-N(SO₂NH₂)-(2-azaspiro[3.3]heptan-6-yl)-N-(6,7-dimethoxycinnolin-4-yl) |
| 2.75 | isopropyl-N(SO₂NH₂)-(2-azaspiro[3.3]heptan-6-yl)-N-(6,7-dimethoxycinnolin-4-yl) |
| 2.76 | methyl-N(SO₂NH₂)-(2-azaspiro[3.3]heptan-6-yl)-N-(7-methoxyquinazolin-4-yl) |
| 2.77 | cyclopropyl-N(SO₂NH₂)-(2-azaspiro[3.3]heptan-6-yl)-N-(7-methoxyquinazolin-4-yl) |

TABLE 2-continued

| S.No. | Compounds |
|---|---|
| 2.78 | (structure) |
| 2.79 | (structure) |
| 2.80 | (structure) |
| 2.81 | (structure) |
| 2.82 | (structure) |
| 2.83 | (structure) |
| 2.84 | (structure) |
| 2.85 | (structure) |

TABLE 2-continued

| S.No. | Compounds |
|---|---|
| 2.86 | (structure) |
| 2.87 | (structure) |
| 2.88 | (structure) |
| 2.89 | (structure) |
| 2.90 | (structure) |
| 2.91 | (structure) |
| 2.92 | (structure) |
| 2.93 | (structure) |

TABLE 2-continued
| S.No. | Compounds |
|---|---|
| 2.94 | 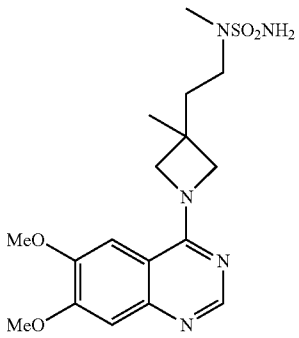 |
| 2.95 | 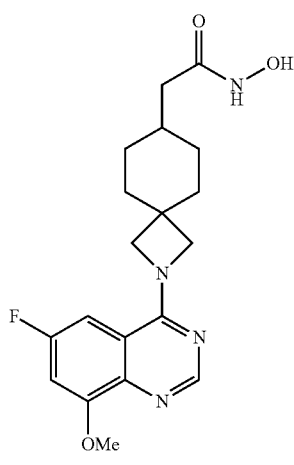 [SMILES: COc1cc(F)cc2c(N3CC4(CCC(CC(=O)NO)CC4)C3)ncnc12] |
| 2.96 | 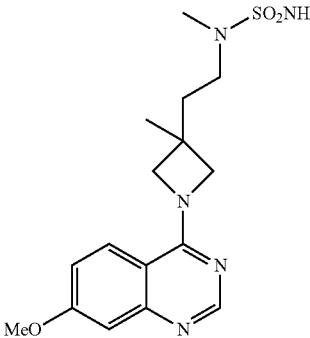 |
| 2.97 | 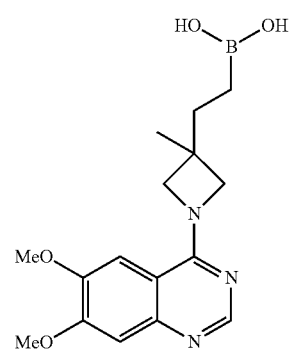 [SMILES: COc1cc2ncnc(N3CC(C)(CCB(O)O)C3)c2cc1OC] |
| 2.98 | 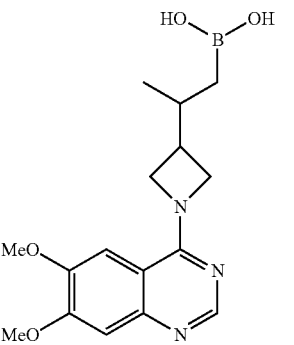 [SMILES: COc1cc2ncnc(N3CC(C(C)CB(O)O)C3)c2cc1OC] |
| 2.99 | 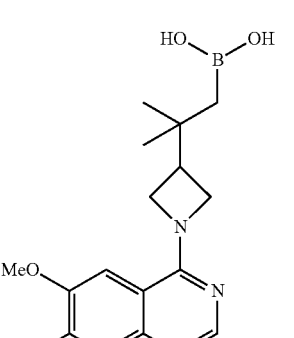 |
| 2.100 | 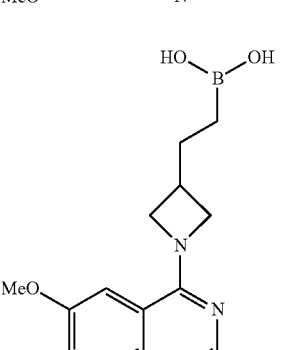 |
| 2.101 | 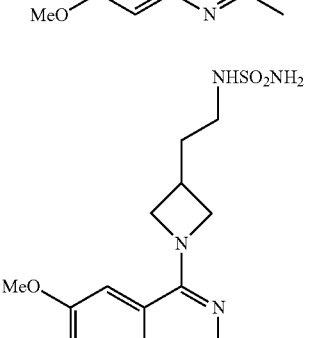 |

TABLE 2-continued

| S.No. | Compounds |
|---|---|
| 2.102 | [structure] |
| 2.103 | [structure] |
| 2.104 | [structure] |
| 2.105 | [structure] |
| 2.106 | [structure] |
| 2.107 | [structure] |
| 2.108 | [structure] |
| 2.109 | [structure] |

TABLE 2-continued
| S.No. | Compounds |
|---|---|
| 2.110 | 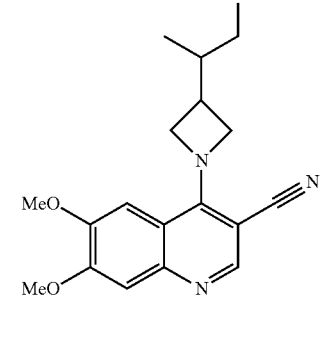 |
| 2.111 | |
| 2.112 | |
| 2.113 | |
| 2.114 | 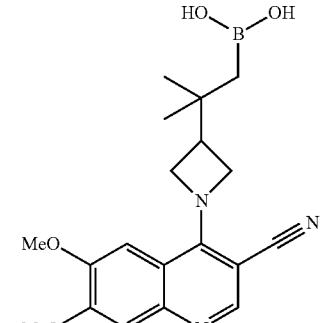 |
| 2.115 | |
| 2.116 | |
| 2.117 | |

TABLE 2-continued
Compounds
| S.No. | Compounds |
|---|---|
| 2.118 | 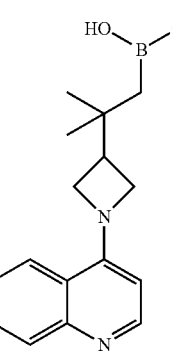 |
| 2.119 | 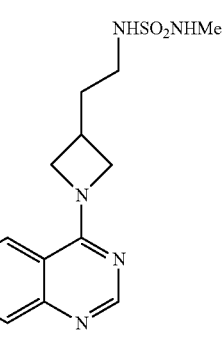 |
| 2.120 | 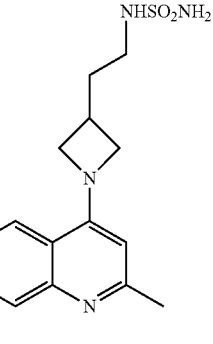 |
| 2.121 | 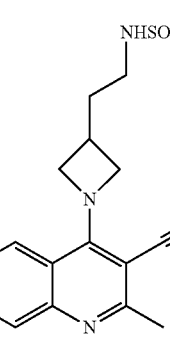 |
| 2.122 | 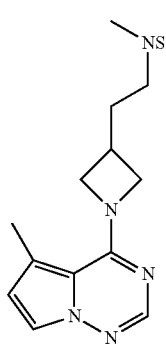 |
| 2.123 | 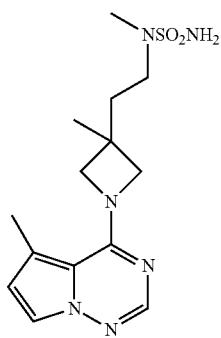 |
| 2.124 | 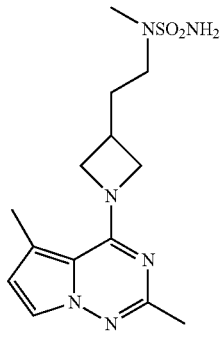 |
| 2.125 | 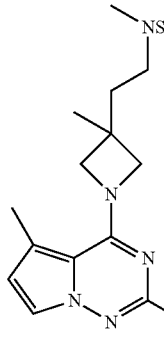 |

TABLE 2-continued
| S.No. | Compounds |
|---|---|
| 2.126 |  |
| 2.127 |  |
| 2.128 |  |
| 2.129 |  |
TABLE 2-continued
| S.No. | Compounds |
|---|---|
| 2.130 | 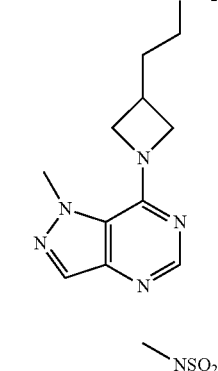 |
| 2.131 | 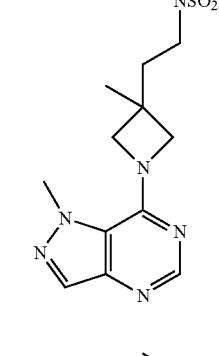 |
| 2.132 | 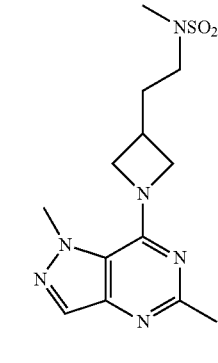 |
| 2.133 | 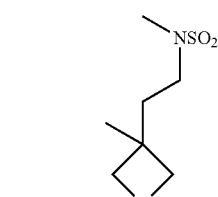 |

TABLE 2-continued
| S.No. | Compounds |
|---|---|
| 2.134 | 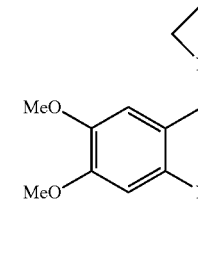 |
| 2.135 | 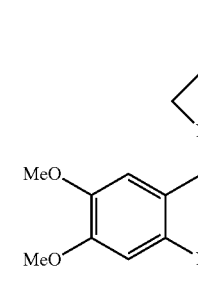 |
| 2.136 | 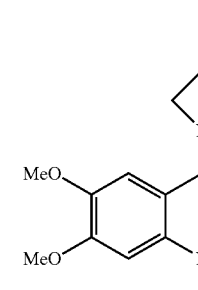 |
| 2.137 | 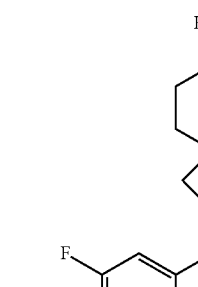 |
| 2.138 | 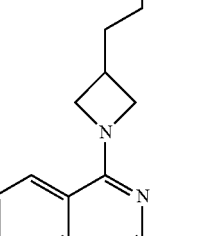 |
| 2.139 | 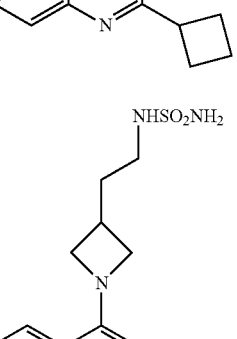 |
| 2.140 | 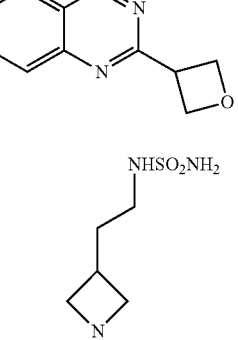 |
| 2.141 | 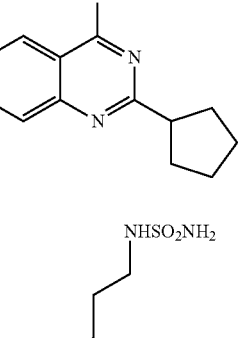 |

TABLE 2-continued
| S.No. | Compounds |
|---|---|
| 2.142 | 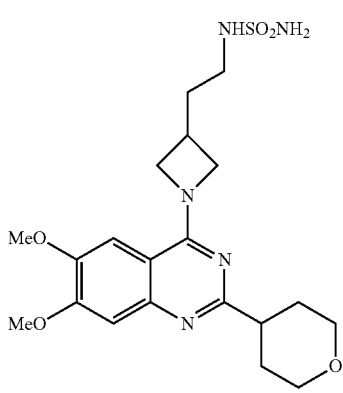 |
| 2.143 | 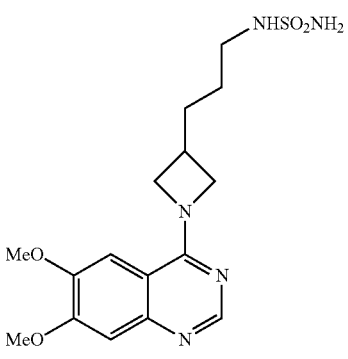 |
| 2.144 | 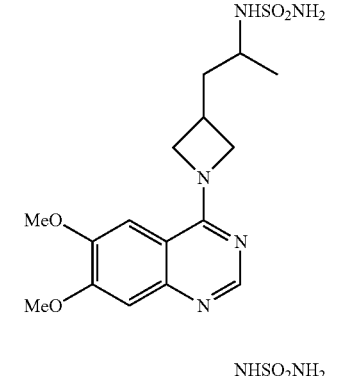 |
| 2.145 | 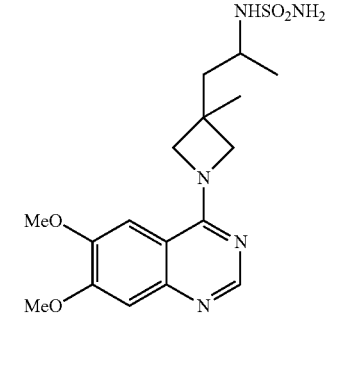 |
| 2.146 | 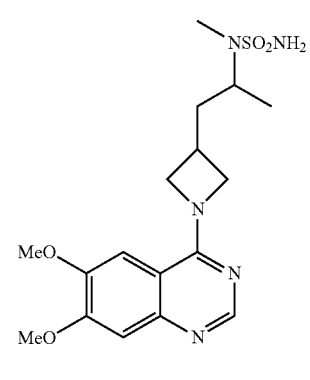 |
| 2.147 | 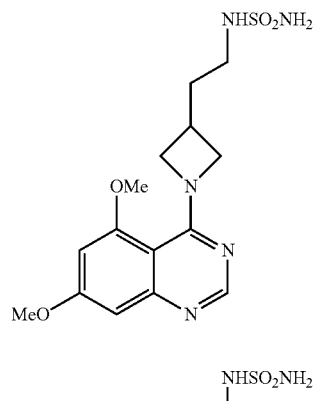 |
| 2.148 | 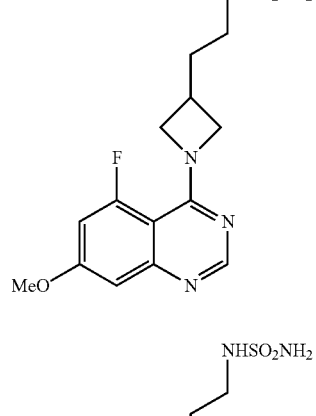 |
| 2.149 | 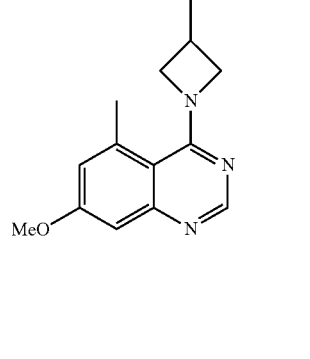 |

TABLE 2-continued

| S.No. | Compounds |
|---|---|
| 2.150 | 5-CF3, 7-MeO-quinazolin-4-yl azetidine with 2-(NHSO2NH2)ethyl substituent |
| 2.151 | 6-CF3, 7-MeO-quinazolin-4-yl azetidine with 2-(NHSO2NH2)ethyl substituent |
| 2.152 | 7-MeO, 8-CF3-quinazolin-4-yl azetidine with 2-(NHSO2NH2)ethyl substituent |
| 2.153 | 6,7-diMeO-quinazolin-4-yl 2-azaspiro[3.4]octane with CH2SO2NH2 substituent |
| 2.154 | 7-MeO, 2-(propynyl)-quinazolin-4-yl azetidine with 2-(NHSO2NH2)ethyl substituent |
| 2.155 | 7-MeO, 2-(CF3-ethynyl)-quinazolin-4-yl azetidine with 2-(NHSO2NH2)ethyl substituent |
| 2.156 | 7-MeO-quinazolin-4-yl 2-azaspiro[3.3]heptane with B(OH)2 substituent |
| 2.157 | 7-MeO-quinazolin-4-yl azetidine with 2,2-dimethyl-2-(N-methyl-NHSO2NH2)ethyl substituent |

TABLE 2-continued
| S.No. | Compounds |
|---|---|
| 2.158 | 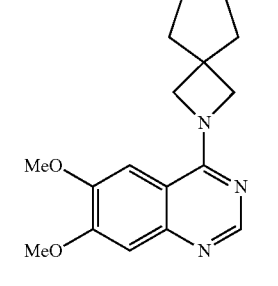 |
| 2.159 | 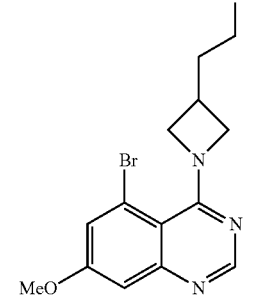 |
| 2.160 | 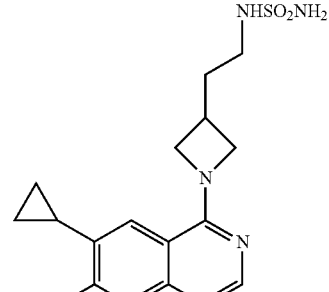 |
| 2.161 | 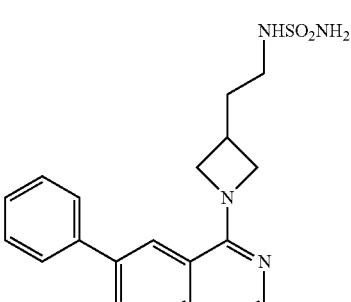 |
| 2.162 | 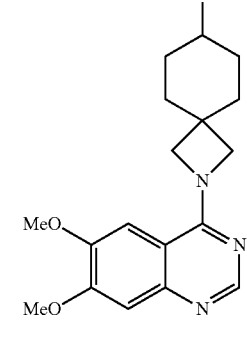 |
| 2.163 | 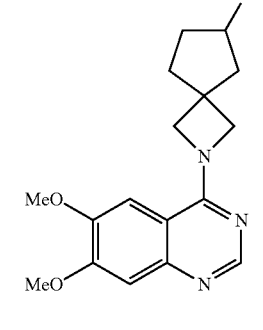 |
| 2.164 | 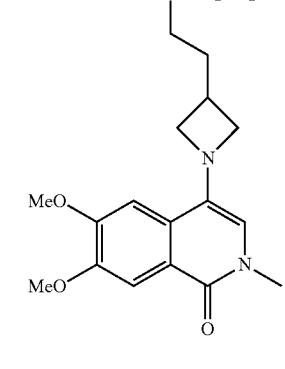 |
| 2.165 | 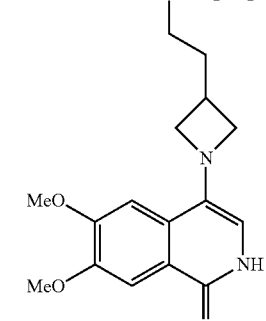 |

TABLE 2-continued
| S.No. | Compounds |
|---|---|
| 2.166 | 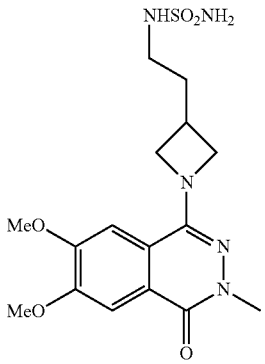 |
| 2.167 | 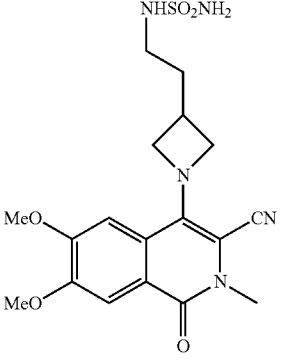 |
| 2.168 | 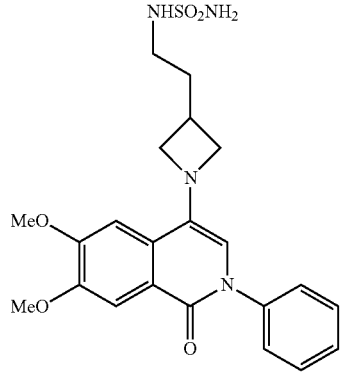 |
| 2.169 | 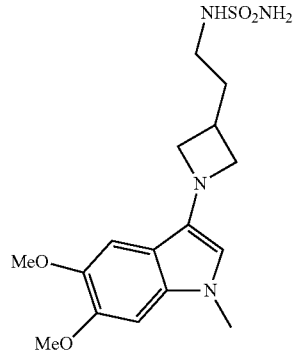 |
| 2.170 | 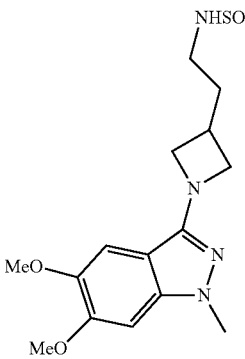 |
| 2.171 | 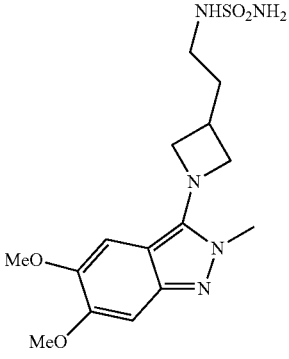 |
| 2.172 | 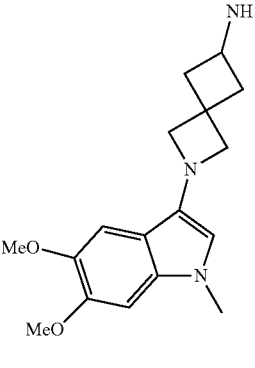 |
| 2.173 | 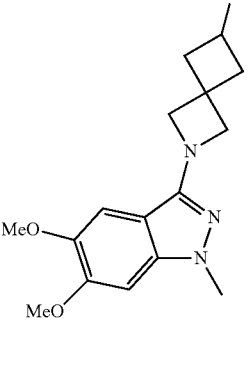 |

TABLE 2-continued
| S.No. | Compounds |
|---|---|
| 2.174 | 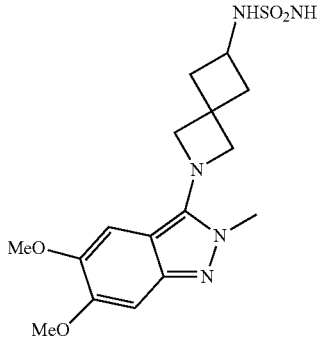 |
| 2.175 | 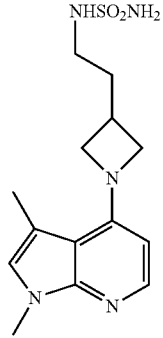 |
| 2.176 | 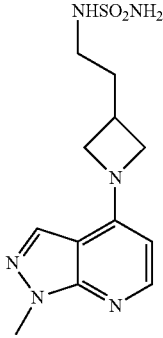 |
| 2.177 | 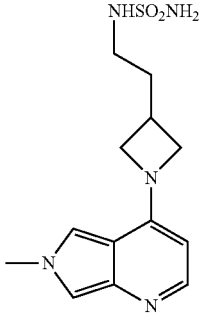 |
| 2.178 | 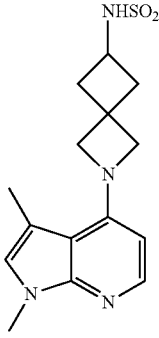 |
| 2.179 | 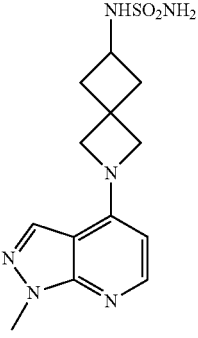 |
| 2.180 | 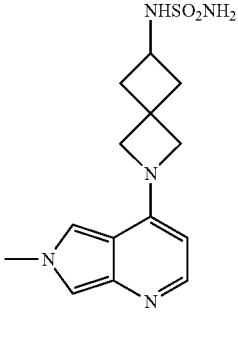 |
| 2.181 | 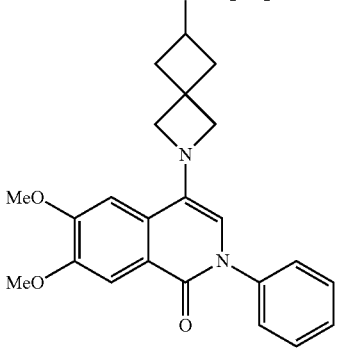 |

TABLE 2-continued

| S.No. | Compounds |
|---|---|
| 2.182 | (structure) |
| 2.183 | (structure) |
| 2.184 | (structure) |
| 2.185 | (structure) |
| 2.186 | (structure) |
| 2.187 | (structure) |
| 2.188 | (structure) |

TABLE 2-continued
| S.No. | Compounds |
|---|---|
| 2.189 | 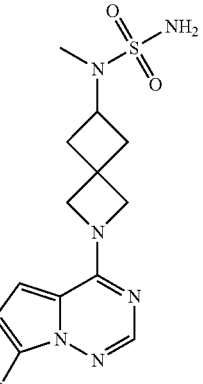 |
| 2.190 | Compound No. 1.81 of table-1 |
| 2.191 | Compound No. 1.98 of table-1 |
| 2.192 | 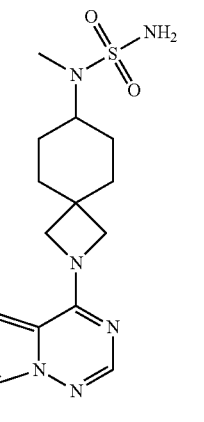 |
| 2.193 | 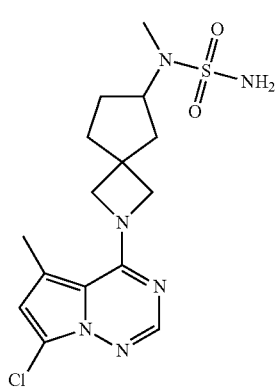 [SMILES: Cc1cc(Cl)n2ncnc(N3CC4(CCC(N(C)S(N)(=O)=O)C4)C3)c12] |
| 2.194 | 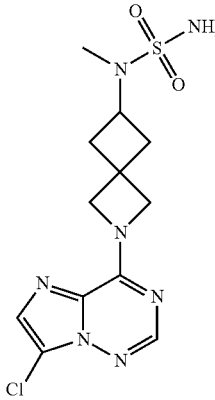 |
| 2.195 | 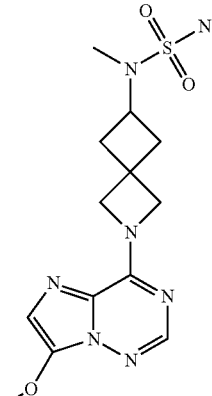 |
| 2.196 | 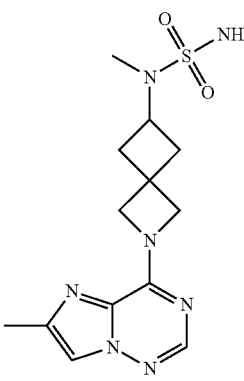 |
| 2.197 | 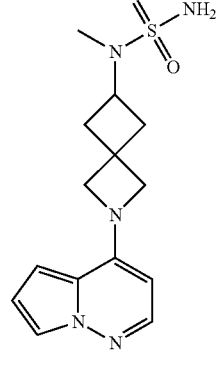 |

TABLE 2-continued
| S.No. | Compounds |
|---|---|
| 2.198 | 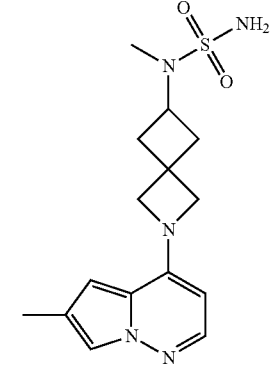 [SMILES: Cc1cc2c(N3CC4(CC(N(C)S(N)(=O)=O)C4)C3)ccnn2c1] |
| 2.199 | |
| 2.200 | |
| 2.201 | Compound No. 1.80 of table-1 |
| 2.202 | Compound No. 1.77 of table-1 |
| 2.203 | Compound No. 1.91 of table-1 |
TABLE 2-continued
| S.No. | Compounds |
|---|---|
| 2.204 | 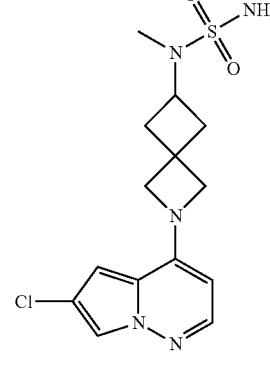 |
| 2.205 | |
| 2.206 | Compound No. 1.84 of table-1 |
| 2.207 | 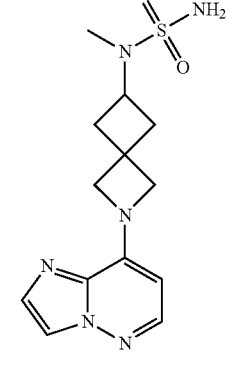 |
| 2.208 | Compound No. 1.87 of table-1 |

TABLE 2-continued

| S.No. | Compounds |
|---|---|
| 2.209 | (structure) |
| 2.210 | (structure) |
| 2.211 | (structure) |
| 2.212 | (structure) |
| 2.213 | (structure) |
| 2.214 | (structure) |
| 2.215 | Compound No. 1.86 of table-1 |
| 2.216 | (structure) |
| 2.217 | (structure) |

TABLE 2-continued

| S.No. | Compounds |
|---|---|
| 2.218 | |
| 2.219 | |
| 2.220 | |
| 2.221 | |
| 2.222 | |
| 2.223 | |
| 2.224 | |

TABLE 2-continued

| S.No. | Compounds |
|---|---|
| 2.225 | |
| 2.226 | |
| 2.227 | |
| 2.228 | |
| 2.229 | |
| 2.230 | |
| 2.231 | |
| 2.232 | |

TABLE 2-continued
| S.No. | Compounds |
|---|---|
| 2.233 | 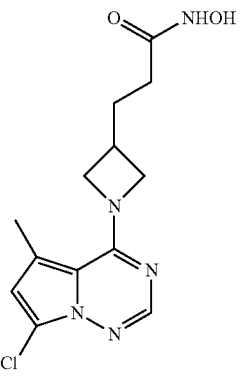 |
| 2.234 | 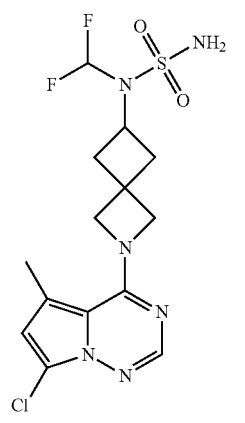 [SMILES: Cc1cc(Cl)n2ncnc(N3CC4(CC(N(C(F)F)S(N)(=O)=O)C4)C3)c12] |
| 2.235 | 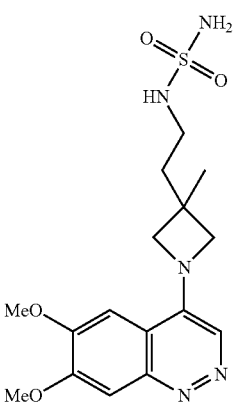 [SMILES: COc1cc2nncc(N3CC(C)(CCNS(N)(=O)=O)C3)c2cc1OC] |
| 2.236 | 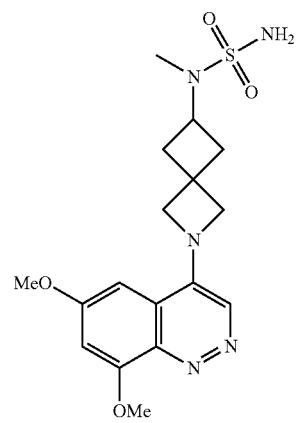 [SMILES: COc1cc(OC)c2nncc(N3CC4(CC(N(C)S(N)(=O)=O)C4)C3)c2c1] |
| 2.237 | Compound No. 1.99 of table-1 |
| 2.238 | Compound No. 1.82 of table-1 |
| 2.239 | Compound No. 1.97 of table-1 |
| 2.240 | 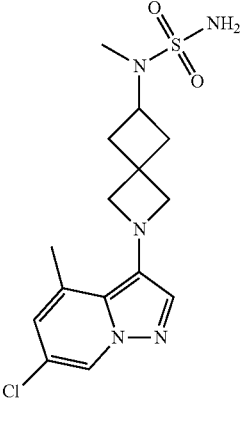 [SMILES: Cc1cc(Cl)cn2ncc(N3CC4(CC(N(C)S(N)(=O)=O)C4)C3)c12] |
| 2.241 | 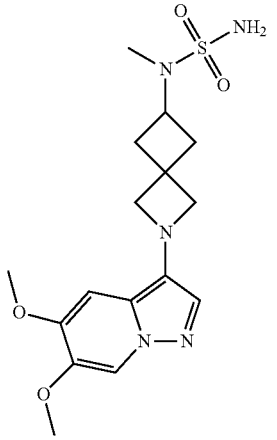 [SMILES: COc1cc2c(N3CC4(CC(N(C)S(N)(=O)=O)C4)C3)cnn2cc1OC] |

TABLE 2-continued

| S.No. | Compounds |
|---|---|
| 2.242 | (structure) |
| 2.243 | (structure) |
| 2.244 | (structure) |
| 2.245 | (structure) |
| 2.246 | Compound No. 1.93 of table-1 |
| 2.247 | (structure) |
| 2.248 | (structure) |

TABLE 2-continued

Compounds

| S.No. | Compounds |
|---|---|
| 2.249 | (structure) |
| 2.250 | (structure) |
| 2.251 | (structure) |
| 2.252 | (structure) |
| 2.253 | (structure) |
| 2.254 | (structure) |
| 2.255 | (structure) |
| 2.256 | (structure) |

TABLE 2-continued
| S.No. | Compounds |
|---|---|
| 2.257 | 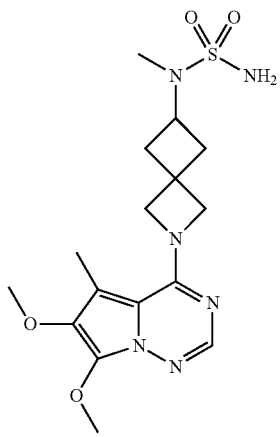 [SMILES: COc1c(C)c2c(N3CC4(CC(N(C)S(N)(=O)=O)C4)C3)ncnn2c1OC] |
| 2.258 | 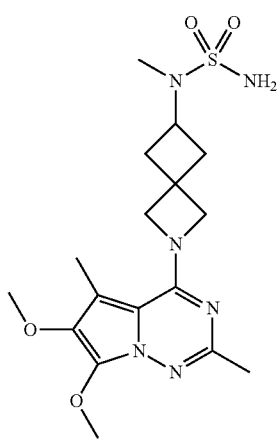 |
| 2.259 | 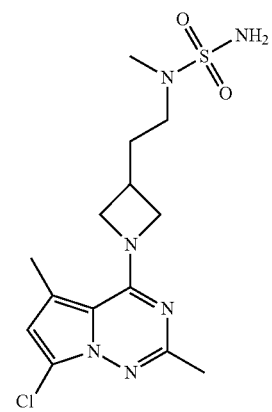 [SMILES: Cc1nc(N2CC(CCN(C)S(N)(=O)=O)C2)c2c(C)cc(Cl)n2n1] |
TABLE 2-continued
| S.No. | Compounds |
|---|---|
| 2.260 | 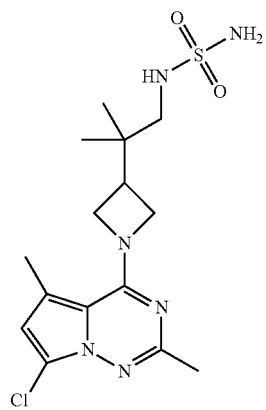 [SMILES: Cc1nc(N2CC(C(C)(C)CNS(N)(=O)=O)C2)c2c(C)cc(Cl)n2n1] |
| 2.261 | 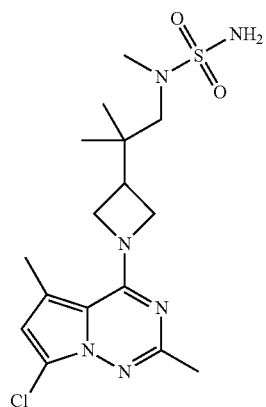 [SMILES: Cc1nc(N2CC(C(C)(C)CN(C)S(N)(=O)=O)C2)c2c(C)cc(Cl)n2n1] |
| 2.262 | 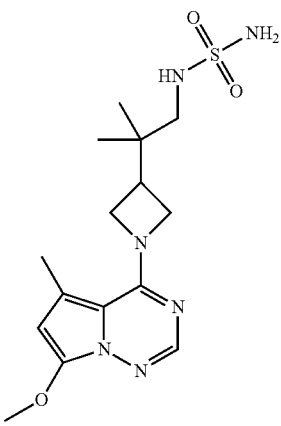 [SMILES: COc1cc(C)c2c(N3CC(C(C)(C)CNS(N)(=O)=O)C3)ncnn12] |

TABLE 2-continued
| S.No. | Compounds |
|---|---|
| 2.263 | 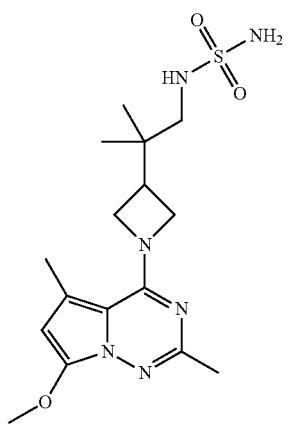 [SMILES: COc1cc(C)c2c(N3CC(C(C)(C)CNS(N)(=O)=O)C3)nc(C)nn12] |
| 2.264 | 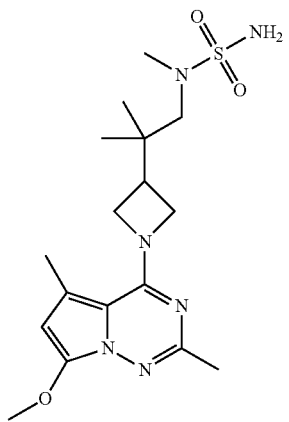 [SMILES: COc1cc(C)c2c(N3CC(C(C)(C)CN(C)S(N)(=O)=O)C3)nc(C)nn12] |
| 2.265 | 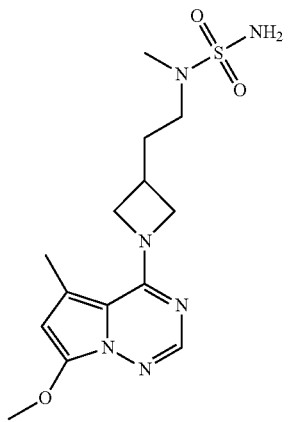 [SMILES: COc1cc(C)c2c(N3CC(CCN(C)S(N)(=O)=O)C3)ncnn12] |
TABLE 2-continued
| S.No. | Compounds |
|---|---|
| 2.266 | 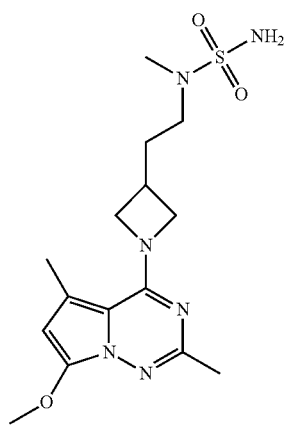 [SMILES: COc1cc(C)c2c(N3CC(CCN(C)S(N)(=O)=O)C3)nc(C)nn12] |
| 2.267 | 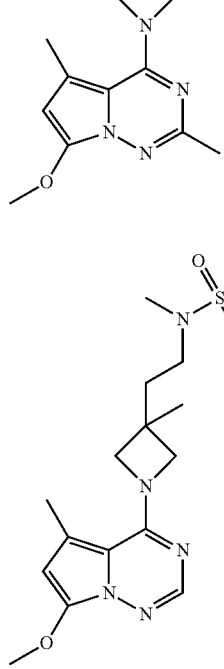 |
| 2.268 | 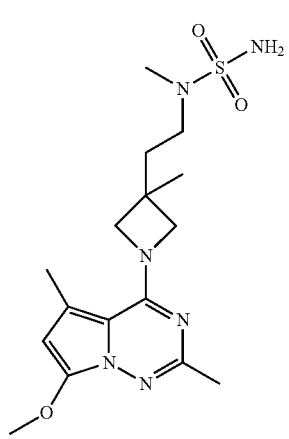 [SMILES: COc1cc(C)c2c(N3CC(C)(CCN(C)S(N)(=O)=O)C3)nc(C)nn12] |

TABLE 2-continued

| S.No. | Compounds |
|---|---|
| 2.269 | |
| 2.270 | |
| 2.271 | |
| 2.272 | |
| 2.273 | |
| 2.274 | |
| 2.275 | |
| 2.276 | |

TABLE 2-continued

| S.No. | Compounds |
|---|---|
| 2.277 | (structure) |
| 2.278 | (structure) |
| 2.279 | (structure) |
| 2.280 | (structure) |
| 2.281 | (structure) |
| 2.282 | (structure) |
| 2.283 | (structure) |
| 2.284 | Compound No. 1.123 of table-1 |

TABLE 2-continued

| S.No. | Compounds |
|---|---|
| 2.285 | |
| 2.286 | |
| 2.287 | |
| 2.288 | |
| 2.289 | Compound No. 1.127 of table-1 |
| 2.290 | |
| 2.291 | |

TABLE 2-continued

| S.No. | Compounds |
|---|---|
| 2.292 | (structure) |
| 2.293 | (structure) |
| 2.294 | (structure) |
| 2.295 | (structure) |
| 2.296 | (structure) |
| 2.297 | (structure) |
| 2.298 | (structure) |

TABLE 2-continued
Compounds
| S.No. | Compounds |
|---|---|
| 2.299 | 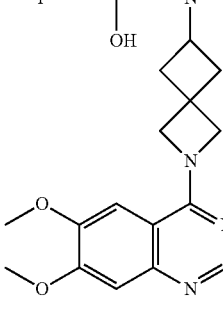 |
| 2.300 | |
| 2.301 | |
| 2.302 | |
TABLE 2-continued
Compounds
| S.No. | Compounds |
|---|---|
| 2.303 | 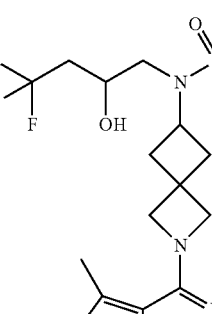 |
| 2.304 | |
| 2.305 | |
| 2.306 | |

TABLE 2-continued
| S.No. | Compounds |
|---|---|
| 2.307 | 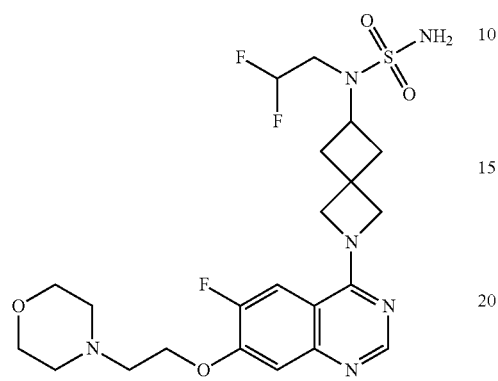 |
| 2.308 | 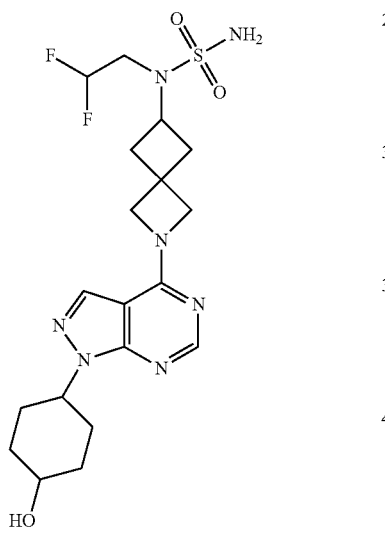 |
| 2.309 | 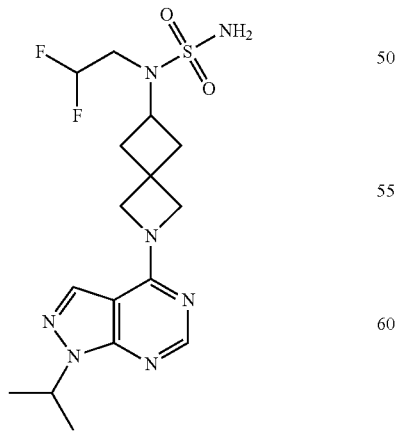 |
| 2.310 | 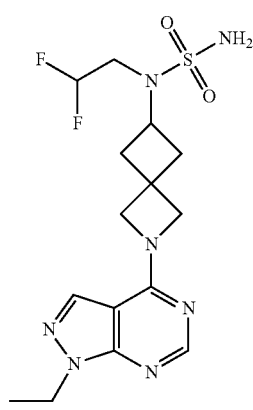 [SMILES: CCn1ncc2c(N3CC4(CC(N(CC(F)F)S(N)(=O)=O)C4)C3)ncnc21] |
| 2.311 | 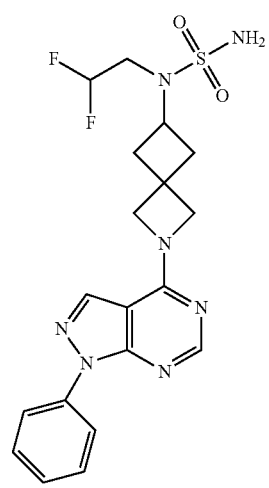 [SMILES: NS(=O)(=O)N(CC(F)F)C1CC2(C1)CN(c1ncnc3c1cnn3-c1ccccc1)C2] |
| 2.312 | 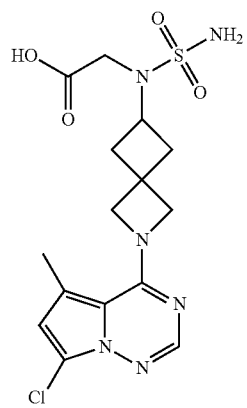 [SMILES: Cc1cc(Cl)n2ncnc(N3CC4(CC(N(CC(=O)O)S(N)(=O)=O)C4)C3)c12] |

TABLE 2-continued
| S.No. | Compounds |
|---|---|
| 2.313 | 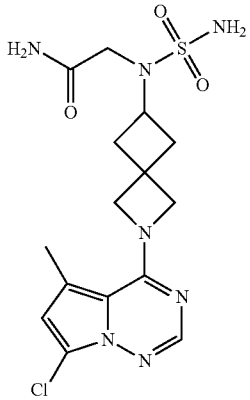 [SMILES: Cc1cc(Cl)n2ncnc(N3CC4(CC(N(CC(N)=O)S(N)(=O)=O)C4)C3)c12] |
| 2.314 | 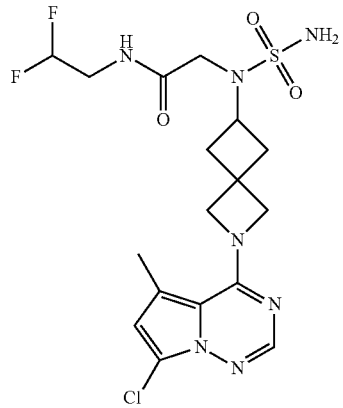 [SMILES: Cc1cc(Cl)n2ncnc(N3CC4(CC(N(CC(=O)NCC(F)F)S(N)(=O)=O)C4)C3)c12] |
| 2.315 | 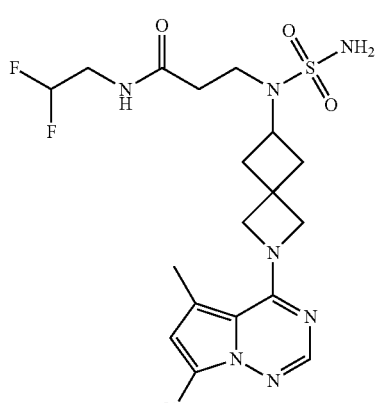 |
TABLE 2-continued
| S.No. | Compounds |
|---|---|
| 2.316 | 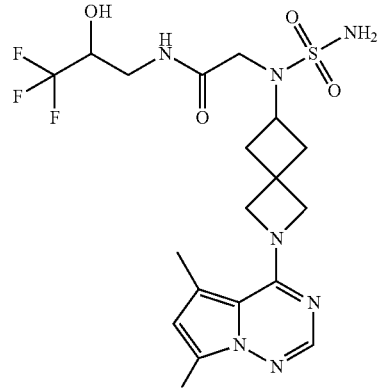 |
| 2.317 | 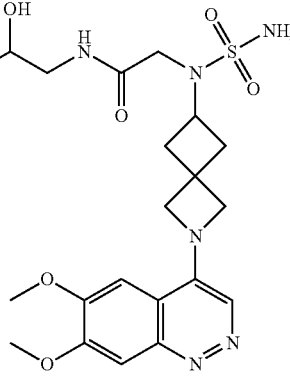 |
| 2.318 | 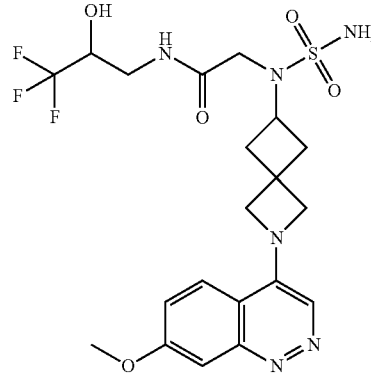 |
| 2.319 | 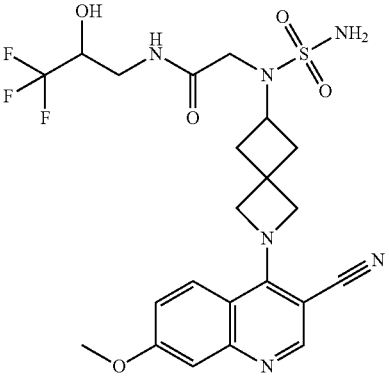 [SMILES: COc1ccc2c(N3CC4(CC(N(CC(=O)NCC(O)C(F)(F)F)S(N)(=O)=O)C4)C3)c(C#N)cnc2c1] |

TABLE 2-continued

Compounds

| S.No. | Compounds |
|---|---|
| 2.320 | (structure) |
| 2.321 | (structure) |
| 2.322 | (structure) |
| 2.323 | (structure) |
| 2.324 | (structure) |
| 2.325 | (structure) |
| 2.326 | (structure) |
| 2.327 | (structure) |

TABLE 2-continued
| S.No. | Compounds |
|---|---|
| 2.328 | 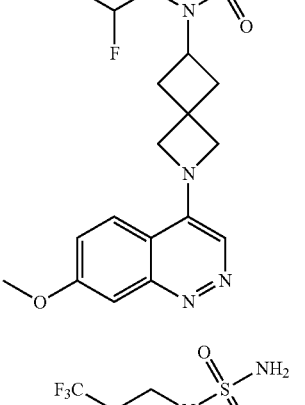 |
| 2.329 | 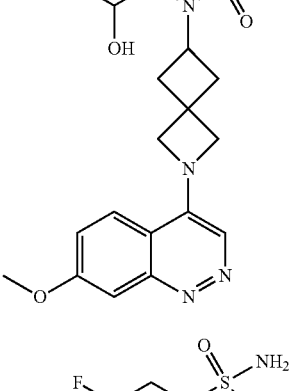 |
| 2.330 | 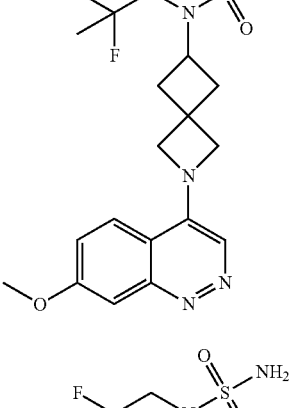 |
| 2.331 | 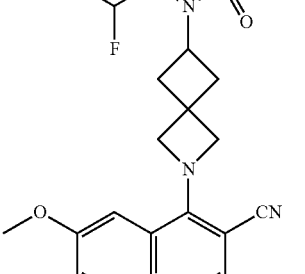 |
| 2.332 | 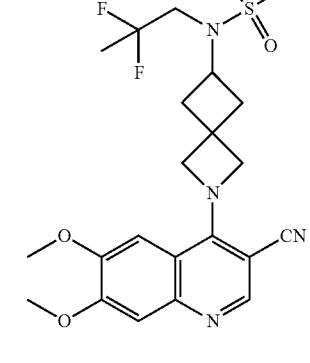 |
| 2.333 | 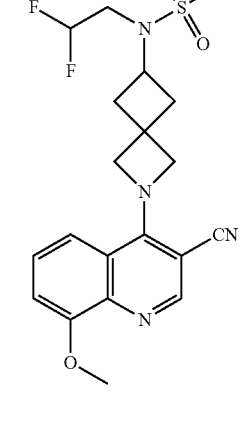 |
| 2.334 | 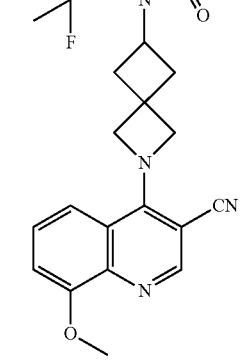 |

TABLE 2-continued
| S.No. | Compounds |
|---|---|
| 2.335 | 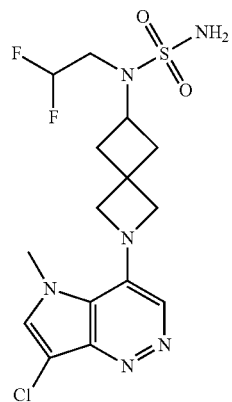 [SMILES: Cn1cc(Cl)c2nncc(N3CC4(CC(N(CC(F)F)S(N)(=O)=O)C4)C3)c21] |
| 2.336 | 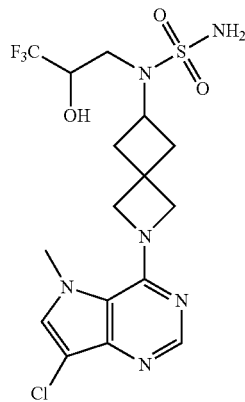 [SMILES: Cn1cc(Cl)c2ncnc(N3CC4(CC(N(CC(O)C(F)(F)F)S(N)(=O)=O)C4)C3)c21] |
| 2.337 | 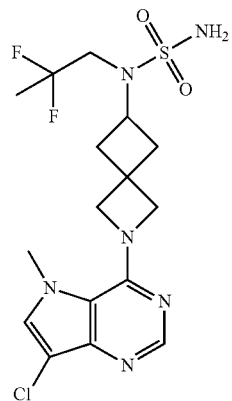 [SMILES: Cn1cc(Cl)c2ncnc(N3CC4(CC(N(CC(C)(F)F)S(N)(=O)=O)C4)C3)c21] |
TABLE 2-continued
| S.No. | Compounds |
|---|---|
| 2.338 | 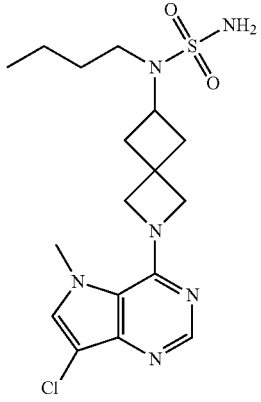 [SMILES: CCCCN(C1CC2(C1)CN(c1ncnc3c(Cl)cn(C)c13)C2)S(N)(=O)=O] |
| 2.339 | 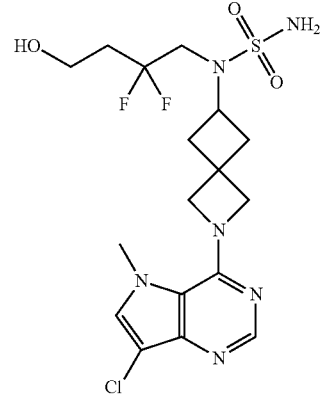 [SMILES: Cn1cc(Cl)c2ncnc(N3CC4(CC(N(CC(F)(F)CCO)S(N)(=O)=O)C4)C3)c21] |
| 2.340 | 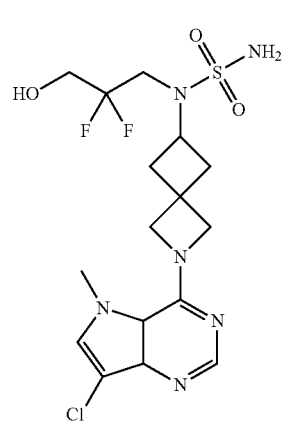 [SMILES: CN1C=C(Cl)C2N=CN=C(N3CC4(CC(N(CC(F)(F)CO)S(N)(=O)=O)C4)C3)C21] |

TABLE 2-continued
| S.No. | Compounds |
|---|---|
| 2.341 | 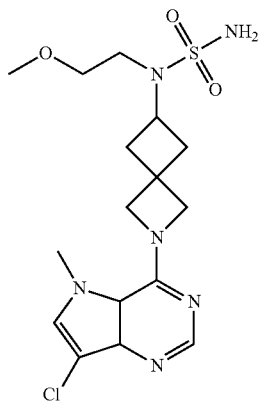 [SMILES: COCCN(C1CC2(C1)CN(C1=NC=NC3C(Cl)=CN(C)C13)C2)S(N)(=O)=O] |
| 2.342 | 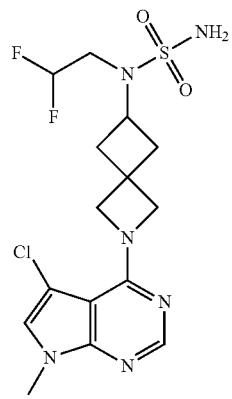 [SMILES: Cn1cc(Cl)c2c(N3CC4(CC(N(CC(F)F)S(N)(=O)=O)C4)C3)ncnc21] |
| 2.343 | 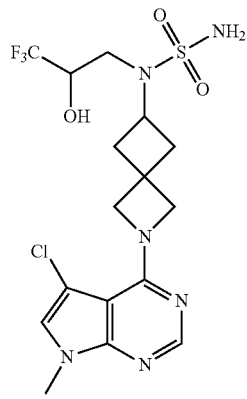 [SMILES: Cn1cc(Cl)c2c(N3CC4(CC(N(CC(O)C(F)(F)F)S(N)(=O)=O)C4)C3)ncnc21] |
| 2.344 | 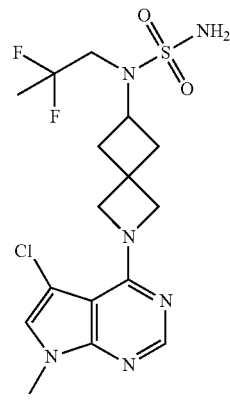 [SMILES: Cn1cc(Cl)c2c(N3CC4(CC(N(CC(C)(F)F)S(N)(=O)=O)C4)C3)ncnc21] |
| 2.345 | 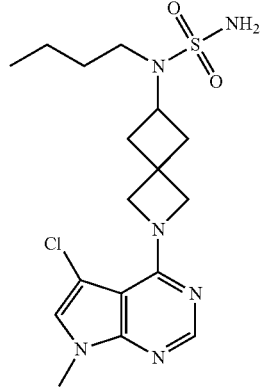 [SMILES: CCCCN(C1CC2(C1)CN(c1ncnc3c1c(Cl)cn3C)C2)S(N)(=O)=O] |
| 2.346 | 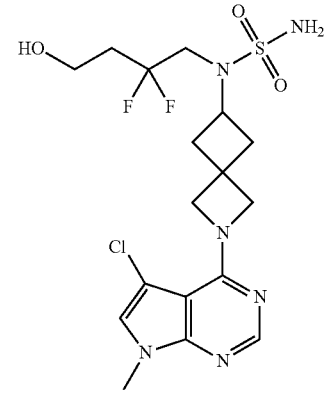 [SMILES: Cn1cc(Cl)c2c(N3CC4(CC(N(CC(F)(F)CCO)S(N)(=O)=O)C4)C3)ncnc21] |

TABLE 2-continued
| S.No. | Compounds |
|---|---|
| 2.347 | 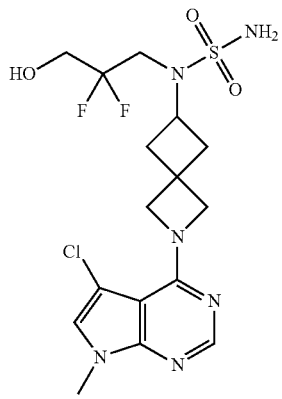 [SMILES: Cn1cc(Cl)c2c(N3CC4(CC(N(CC(F)(F)CO)S(N)(=O)=O)C4)C3)ncnc21] |
| 2.348 | 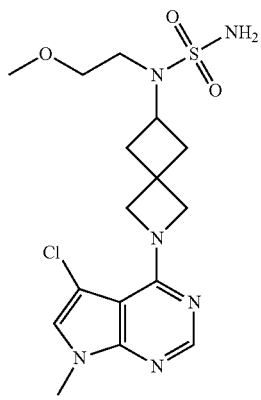 [SMILES: COCCN(C1CC2(C1)CN(c1ncnc3c1c(Cl)cn3C)C2)S(N)(=O)=O] |
| 2.349 | 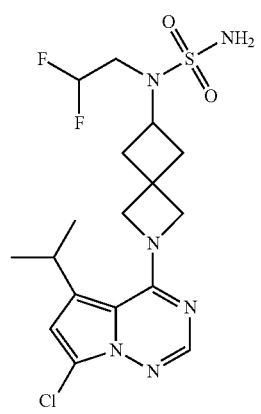 [SMILES: CC(C)c1cc(Cl)n2ncnc(N3CC4(CC(N(CC(F)F)S(N)(=O)=O)C4)C3)c12] |
| 2.350 | 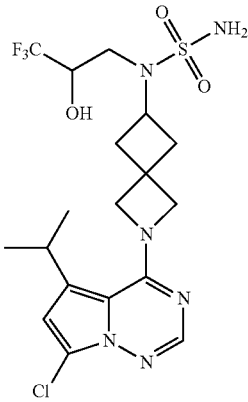 [SMILES: CC(C)c1cc(Cl)n2ncnc(N3CC4(CC(N(CC(O)C(F)(F)F)S(N)(=O)=O)C4)C3)c12] |
| 2.351 | 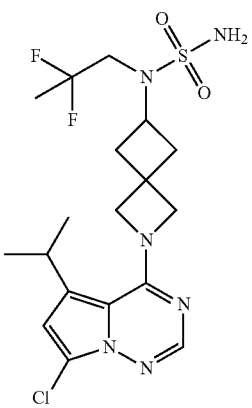 [SMILES: CC(C)c1cc(Cl)n2ncnc(N3CC4(CC(N(CC(C)(F)F)S(N)(=O)=O)C4)C3)c12] |
| 2.352 | 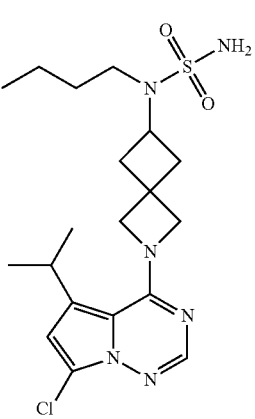 [SMILES: CCCCN(C1CC2(C1)CN(c1ncnn3c(Cl)cc(C(C)C)c13)C2)S(N)(=O)=O] |

TABLE 2-continued

| S.No. | Compounds |
|---|---|
| 2.353 | (structure) |
| 2.354 | (structure) |
| 2.355 | (structure) |
| 2.356 | (structure) |
| 2.357 | (structure) |
| 2.358 | (structure) |

TABLE 2-continued

| S.No. | Compounds |
|---|---|
| 2.359 | 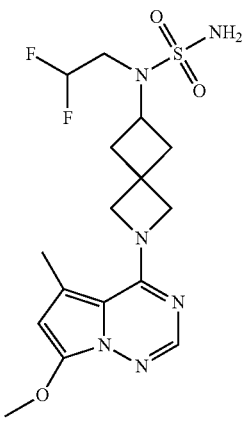 [SMILES: COc1cc(C)c2c(N3CC4(CC(N(CC(F)F)S(N)(=O)=O)C4)C3)ncnn12] |
| 2.360 | 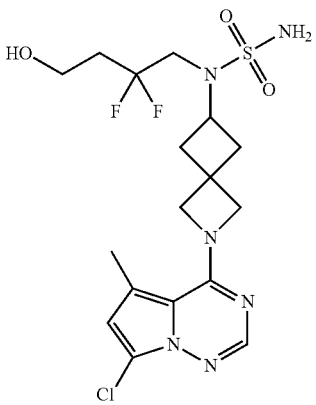 [SMILES: Cc1cc(Cl)n2ncnc(N3CC4(CC(N(CC(F)(F)CCO)S(N)(=O)=O)C4)C3)c12] |
| 2.361 | 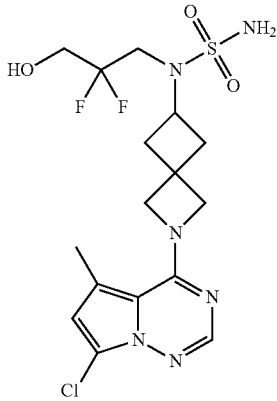 [SMILES: Cc1cc(Cl)n2ncnc(N3CC4(CC(N(CC(F)(F)CO)S(N)(=O)=O)C4)C3)c12] |
| 2.362 | 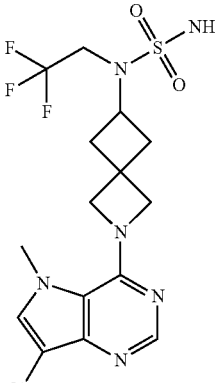 |

In some embodiments, provided herein are compounds described in table-1 and table-2, or a salt, polymorph, solvate, enantiomer, stereoisomer or tautomer thereof, and uses thereof.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds described herein may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (J), or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) are useful in compound or substrate tissue distribution studies. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate In some embodiments, compounds of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)) are synthesized according to general Scheme 1 to 8.

General Synthetic Scheme:

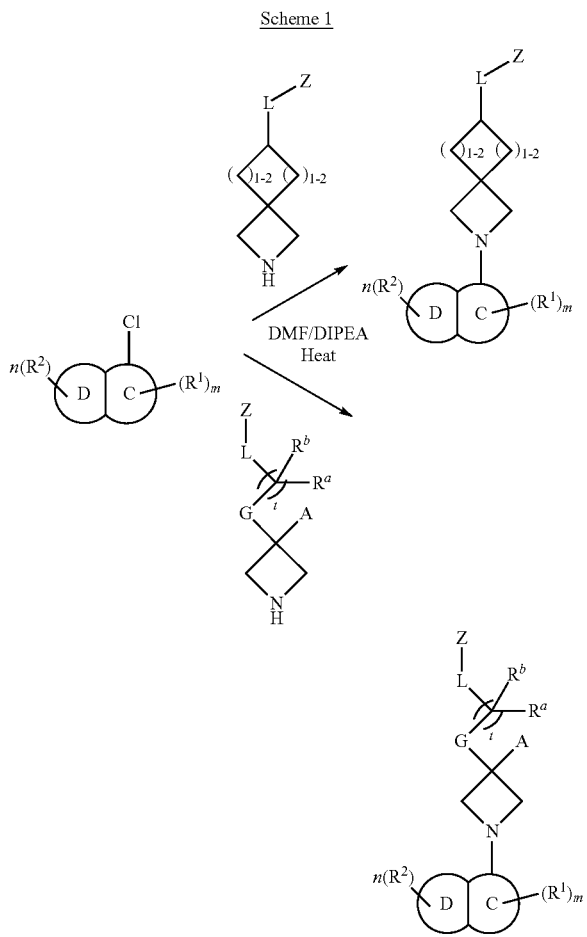

Scheme 1 wherein A, G, $R^a$, $R^b$, L, Z, C, D, $R^1$, $R^2$, m, n and t are as detailed herein.

Scheme 2
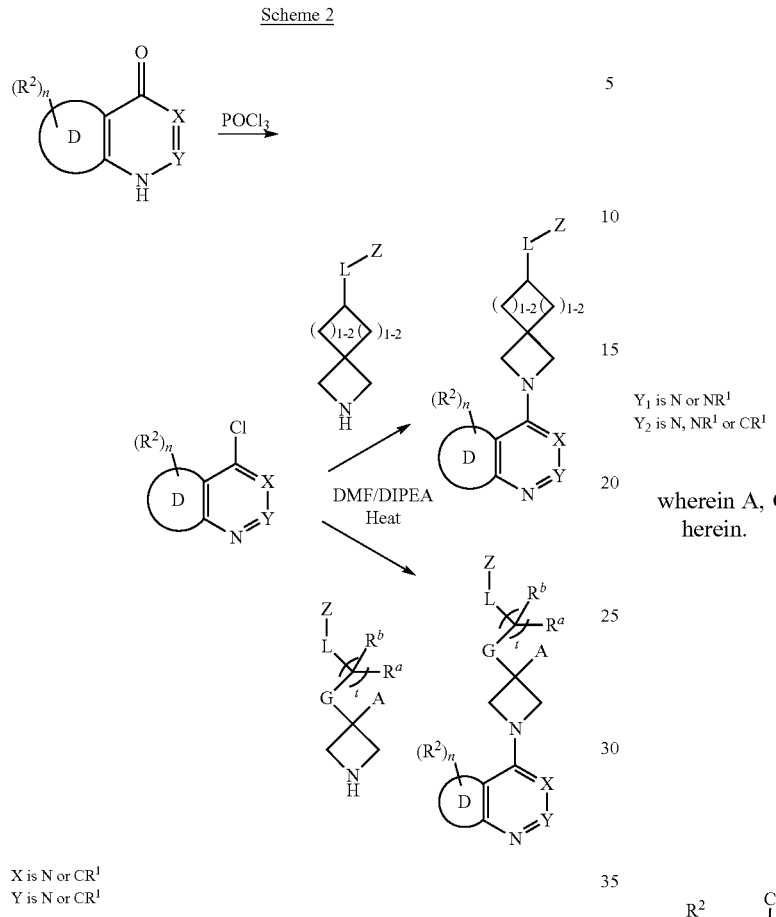
X is N or CR[1]
Y is N or CR[1]
wherein A, G, R[a], R[b], L, Z, C, R[1], R[2], n and t are as detailed herein.
Scheme 3
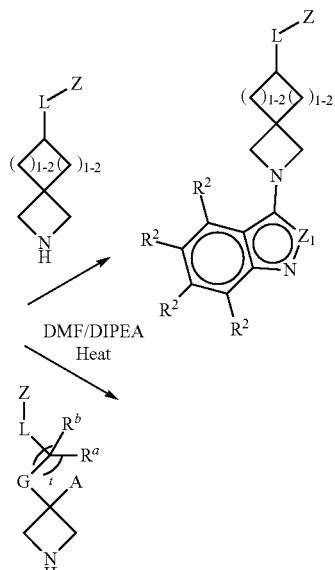
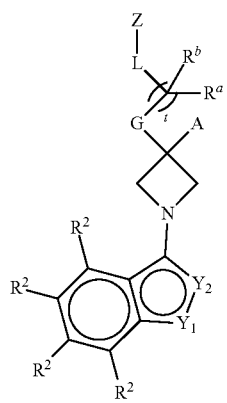
$Y_1$ is N or NR[1]
$Y_2$ is N, NR[1] or CR[1]
wherein A, G, R[a], R[b], L, Z, R[1], R[2] and t are as detailed herein.
Scheme 4
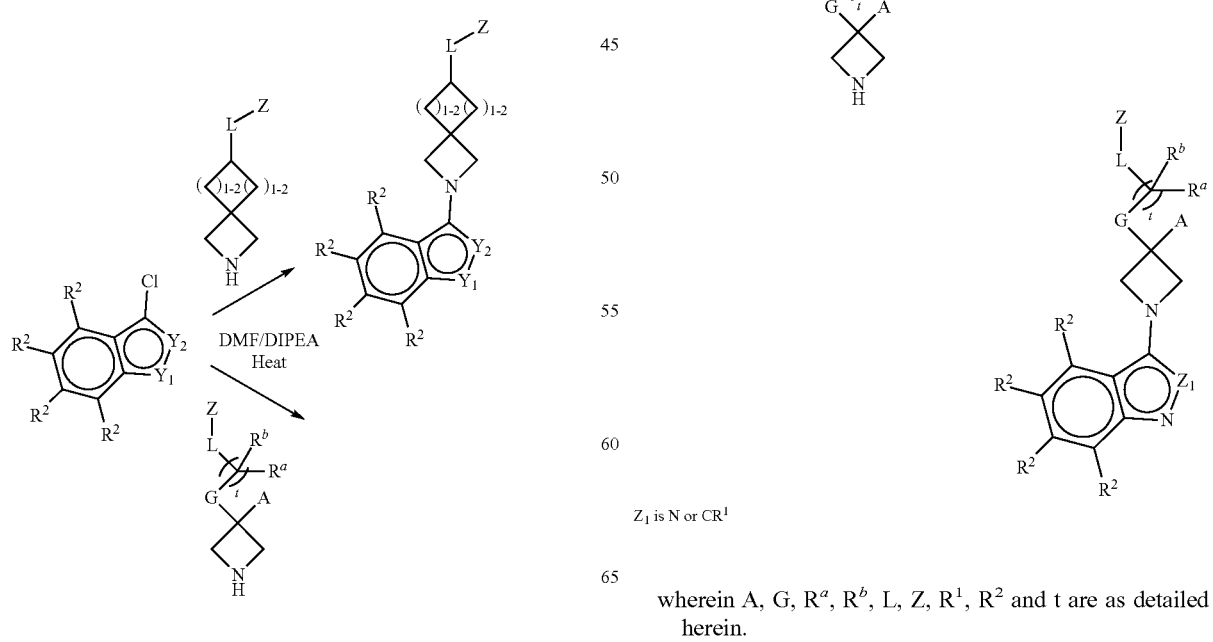
$Z_1$ is N or CR[1]
wherein A, G, R[a], R[b], L, Z, R[1], R[2] and t are as detailed herein.

Scheme 5
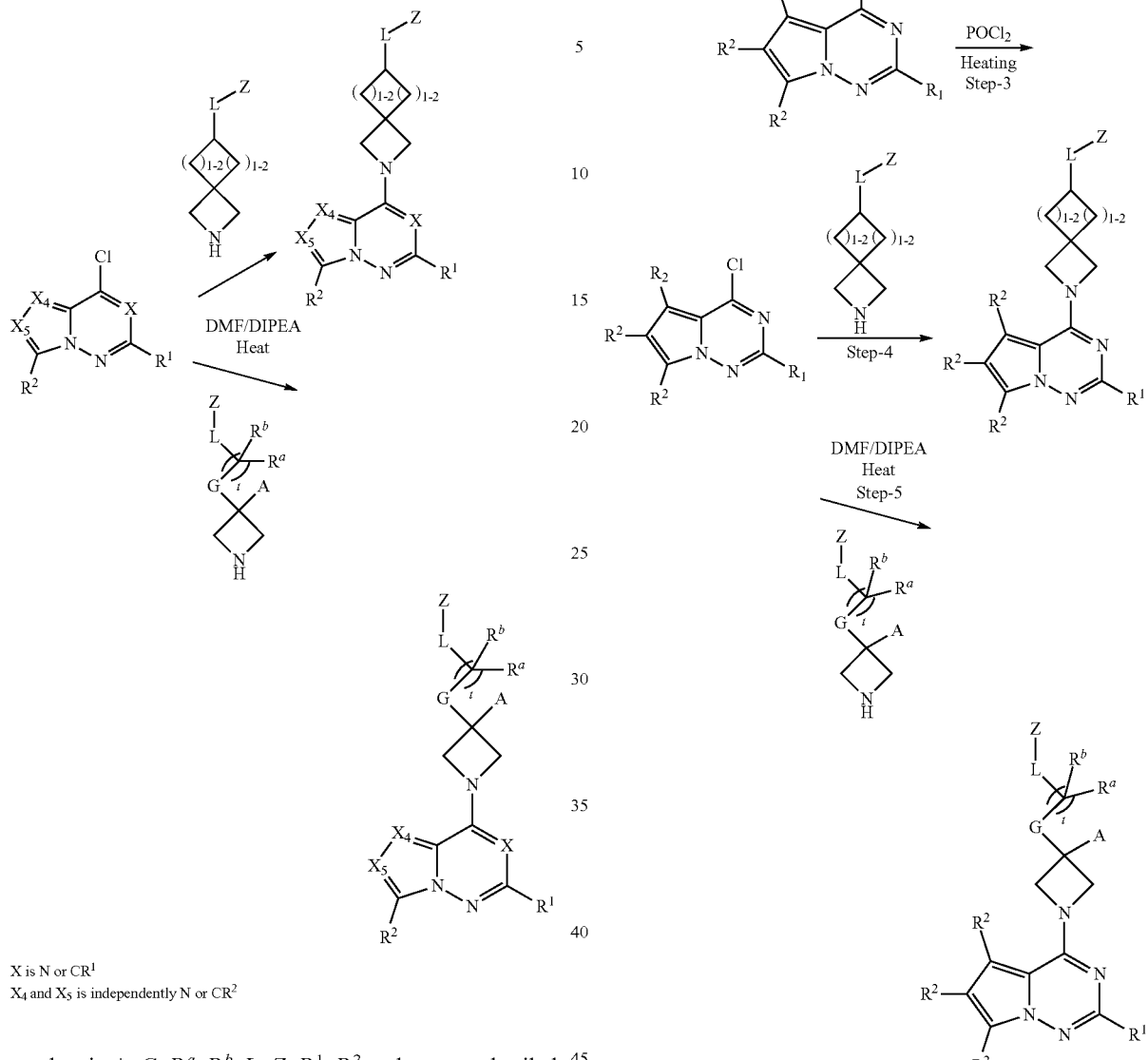
X is N or CR[1]
X[4] and X[5] is independently N or CR[2]
wherein A, G, $R^a$, $R^b$, L, Z, $R^1$, $R^2$ and t are as detailed herein.
wherein A, G, $R^a$, $R^b$, L, Z, $R^1$, $R^2$ and t are as detailed herein.
Scheme-6
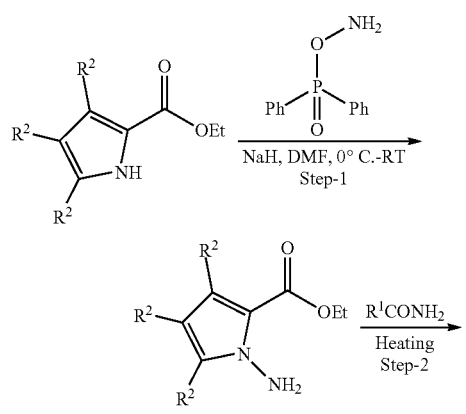
Scheme-7
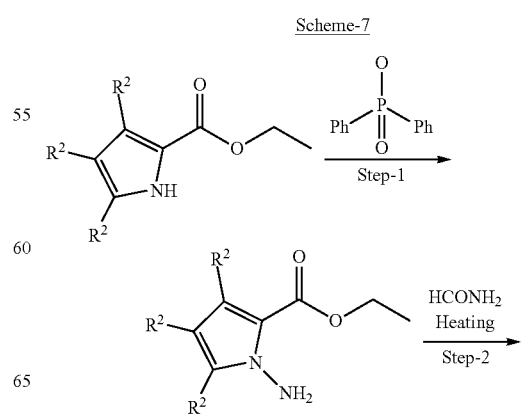

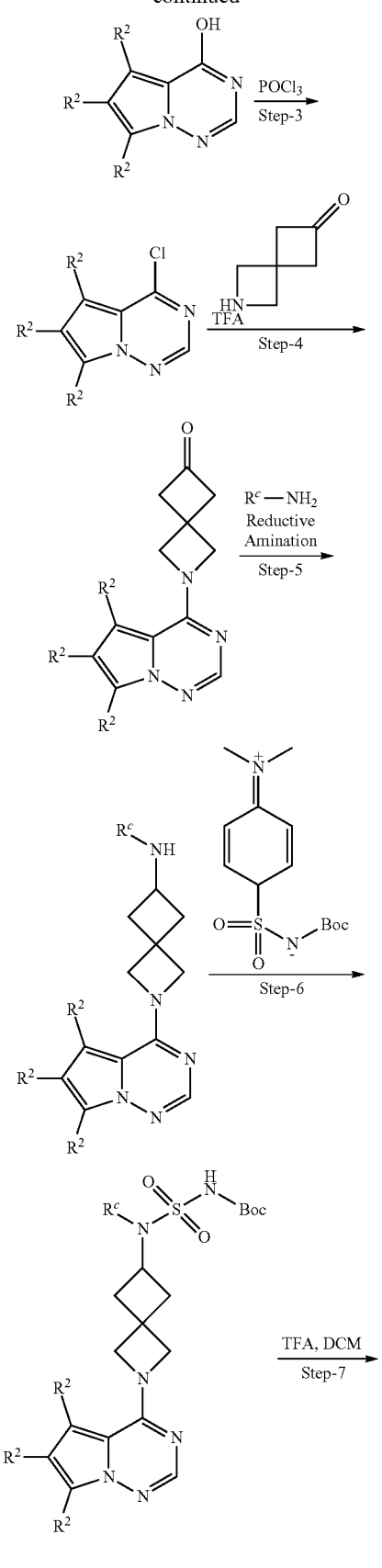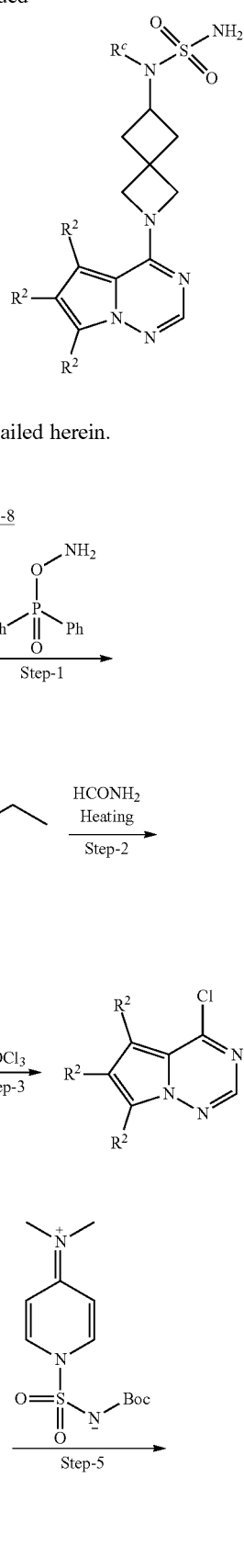
wherein $R^2$ and $R^c$ are as detailed herein.
Scheme-8

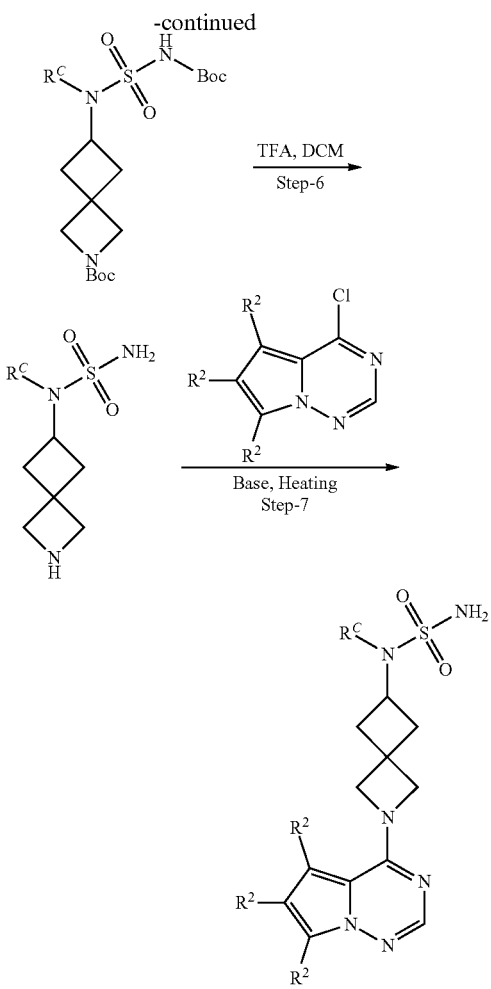

wherein $R^2$ and $R^c$ are as detailed herein.

In some cases, enantiomers or diastereomers are synthesized chirally pure. In some cases, stereoisomers are separated to give single enantiomers or diastereomers as single, unknown stereoisomers, and are arbitrarily drawn as single isomers. Where appropriate, information is given on separation method and elution time and order.

Pharmaceutical Compostions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington's Pharmaceutical Sciences, Mack Publishing Company, Philadelphia, PA, $20^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a salt thereof can be incorporated in tablet in an amount ranging from about 1 mg to about 1000 mg.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease in an individual comprising administering an effective amount of a compounds of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)) or any embodiment, variation or aspect thereof or the present compounds or the compounds detailed or described herein) or a pharmaceutically acceptable salt thereof, to the individual. Further provided herein is a method of treating a proliferative disease in an individual, comprising administering an effective amount of the compounds of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)) or a pharmaceutically acceptable salt thereof, to the individual. Also provided herein is a method of treating cancer in an individual comprising administering an effective amount of the compounds of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)) or a pharmaceutically acceptable salt thereof, to the individual. In some embodiments, the compound is administered to the individual according to a dosage and/or method of administration described herein.

Another aspect of the invention relates to a method of treating a disease or disorder associated with ENPP1. The method involves administering to a patient in need of a treatment for diseases or disorders associated with ENPP1 an effective amount of the compositions and compounds of the present invention (collectively, a compound of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9)) or a pharmaceutically acceptable salt thereof.

Another aspect of the invention is directed to a method inhibiting ENPP1. The method involves administering to a patient in need thereof an effective amount of the compositions or compounds of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9) or a pharmaceutically acceptable salt thereof.

Aspects of the present disclosure include methods for inhibiting the hydrolase activity of ENPP1 against cGAMP provides for increased levels of cGAMP and/or downstream modulation (e.g., activation) of the STING pathway. It is also known that cGAMP is present in the extracellular space and that ENPP1 can control extracellular levels of cGAMP. ENPP1 inhibition can modulate STING activity, and thus it is used in the treatment of a variety of diseases, e.g., as a target for cancer immunotherapy. As such, the subject methods can provide for selective extracellular inhibition of ENPP1 activity (e.g., hydrolase activity of cGAMP) to increase extracellular levels of cGAMP and activate the stimulator of interferon genes (STING) pathway. In some instances, the subject method is a method for increasing a STING mediated response in a subject. In some instances, the subject method is a method for modulating an immune response in a subject.

A "STING mediated response" refers to any response that is mediated by STING, including, but not limited to, immune responses, e.g., to bacterial pathogens, viral pathogens, and eukaryotic pathogens. STING also functions in certain autoimmune diseases initiated by inappropriate recognition of self DNA as well as for the induction of adaptive immunity in response to DNA vaccines. By increasing a STING mediated response in a subject is meant an increase in a STING mediated response in a subject as compared to a control subject (e.g., a subject who is not administered a subject compound). In some cases, the subject is human and the subject compounds and methods provide for activation of human STING. In some cases, the STING mediated response includes modulation of an immune response. In some instances, the subject method is a method of modulating an immune response in a subject.

In some cases, the STING mediated response includes increasing the production of an interferon (e.g., a type I interferon (IFN), type III interferon (IFN)) in a subject. Interferons (IFNs) are proteins having a variety of biological activities, e.g., antiviral, immunomodulating and antiproliferative. IFNs are relatively small, species-specific, single chain polypeptides, produced by mammalian cells in response to exposure to a variety of inducers such as viruses, polypeptides, mitogens and the like. Interferons protect animal tissues and cells against viral attack and are an important host defense mechanism. Interferons may be classified as Type-I, Type-II and Type-III interferons. Mammalian Type-I interferons of interest include IFN-α, IFN-β, IFN-k, IFN-δ, IFN-ε, IFN-τ, IFN-ω, and IFN-ζ.

Interferons find use in the treatment of a variety of cancers since these molecules have anti-cancer activity that acts at multiple levels. Interferon proteins can directly inhibit the proliferation of human tumor cells. In some cases, the anti-proliferative activity is also synergistic with a variety of approved chemotherapeutic agents such as cisplatin, 5FU and paclitaxel. The immunomodulatory activity of interferon proteins can also lead to the induction of an anti-tumor immune response. This response includes activation of NK cells, stimulation of macrophage activity and induction of major histocompatibility complex (MHC) class I surface expression, leading to the induction of anti-tumor cytotoxic T lymphocyte activity. In addition, interferons play a role in cross-presentation of antigens in the immune system. Moreover, some studies further indicate that IFN-β protein may have anti-angiogenic activity. Angiogenesis, new blood vessel formation, is critical for the growth of solid tumors. IFN-β may inhibit angiogenesis by inhibiting the expression of pro-angiogenic factors such as bFGF and VEGF. Interferon proteins may also inhibit tumor invasiveness by modulating the expression of enzymes, such as collagenase and elastase, which are important in tissue remodeling.

Another aspect of the invention relates to ENPP1 inhibitor, inhibit the hydrolysis of cGAMP. The method comprises administering to a patient in need thereof an effective amount of the compositions or compounds of the present invention of formula (J), (IA), (I), (II), (III), (IV), (IV-1) to (IV-11), (V), (V-1) to (V-11), (VI), (VII), (VIII), (IX), (X), (XI), (XII), (XII-1) to (XII-6), (XIII) and (XIII-1) to (XIII-9), or a pharmaceutically acceptable salt thereof.

One therapeutic use of the compounds or compositions of the present invention which inhibit ENPP1 is to provide treatment to patients or subjects suffering from cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors. Targeted treatments for these cancers and cell proliferative diseases are not currently available to patients suffering from these conditions. Therefore, there is a need for new therapeutic agents selective to these conditions.

Another therapeutic use of the compounds or compositions of the present invention which inhibit ENPP1 is to provide treatment to patients or subjects suffering from cell proliferative diseases and cancers including sarcomas and carcinomas. In some embodiments, examples such as sarcomas and carcinomas are cancer that may be treated as solid tumors. In some embodiments, examples such as leukemia are the cancer that may be treated as liquid tumors. Present invention may treat different types of cancers that include, but are not limited to, adrenocortical cancer, bladder cancer, brain tumors, breast cancer, prostate cancer, colorectal cancer, colon cancer, endometrial cancer, gallbladder cancer, gastric cancer, head and neck cancer, hematopoietic cancer, kidney cancer, leukemia, oral cancer, uterine carcinoma, Hodgkin lymphoma, liver cancer, lung cancer, pancreatic cancer, prostate cancer, ovarian cancer, sarcoma, skin cancer and thyroid cancer. In some embodiments, the breast cancer is classified as carcinoma of breast (ER negative or ER positive), mammary adenocarcinoma, primary breast ductal carcinoma, mammary ductal carcinoma (ER positive, ER negative or HER2 positive), triple negative breast cancer (TNBC), HER2 positive breast cancer or luminal breast cancer. In some embodiments, the breast cancer is unclassified. In some embodiments, a basal-like TNBC, an immunomodulatory TNBC, mesenchymal TNBC (mesenchymal or mesenchymal stem-like) or a luminal androgen receptor TNBC are triple negative breast. In some embodiments, prostate adenocarcinoma is prostate cancer. In some embodiments, the ovary adenocarcinoma is ovarian cancer. In some embodiments, lung carcinoma, adenocarcinoma, non-small lung carcinoma, mucoepidermoid, anaplastic large cell are lung cancer. In some embodiments, the lung cancer is unclassified. In some embodiments, the colon adenocarcinomas, colon carcinoma, metastatic colorectal cancer, colon adenocarcinoma from a metastatic site lymph node are colon cancer. In some embodiments astrocytoma, glioblastoma, meduloblastoma, neuroblastoma or meningioma are brain tumor. In some embodiments, stomach cancer is gastric cancer. In some embodiments, cholangiocarcinoma or hepatoblastoma, hepatocellular carcinoma are liver cancers. In some embodiments, liver cancer is derived from hepatitis B virus. In some embodiments, liver cancer is virus negative. In some embodiments, medullary thyroid cancer or follicular thyroid cancer, papillary thyroid carcinomas are classified as thyroid cancer. In some embodiments, uterine papillary serous carcinoma or uterine clear cell carcinoma, high grade endometroid cancer are endometrial cancer. In some embodiments, gallbladder adenocarcinoma or squamous cell gallbladder carcinoma are gallbladder cancer. In some embodiments, renal cell carcinoma or urothelial cell carcinoma are classified as kidney cancer. In some embodiments, adrenal cortical carcinoma adrenocortical is cancer. In some embodiments, fibrosarcoma or Ewing's sarcoma, osteosarcoma, rhabdomiosarcoma and synovial sarcoma are classified as sarcoma. In some embodiments, basal cell carcinoma, melanoma or squamous carcinoma are classified as skin cancer. In some embodiments, cancer of the trachea, laryngeal cancer, nasopharyngeal cancer and oropharyngeal cancer are classified as head and neck cancer. In some embodiments, acute lymphoblastic leukemia, acute promyelocytic leukemia, chronic myelogenous leukemia, chronic lymphocytic leukemia, mantle cell lymphoma or multiple myeloma are classified as leukemia.

The disclosed compounds of the invention can be administered in effective amounts to treat or prevent a disorder and/or prevent the development thereof in subjects.

Combination Therapy

The compound of the present invention may be administered either simultaneously with, or before or after, one or more other therapeutic agents. The compound of the present invention may be administered separately, by the same or different route of administration, or together in the same pharmaceutical composition as the other agents.

In some embodiments, the methods described herein comprise the additional step of co-administering to a subject in need thereof a second therapy e.g., an additional cancer therapeutic agent or an additional cancer treatment. In one embodiment, the other therapeutic agent is selected from: vascular endothelial growth factor (VEGF) receptor inhibitors, topoisomerase II inhibitors, smoothened inhibitors, alkylating agents, chemotherapy agents, anti-tumor antibiotics, anti-metabolites, retinoids, immunomodulatory agents including but not limited to anti-cancer vaccines, CTLA-4, LAG-3 and PD-1/PDL-1 antagonists, nitrosoureas, antitumor antibiotics, plant (vinca) alkaloids, steroid hormones, taxanes, nucleoside analogs, steroids, anthracyclines, thyroid hormone replacement drugs, thymidylatetargeted drugs, Chimeric Antigen Receptor/T cell therapies, Chimeric Antigen Receptor/NK cell therapies, apoptosis regulator inhibitors (e.g., B cell CLL/lymphoma 2 (BCL-2) BCL-2-like 1 (BCLXL) inhibitors), CARP-1/CCAR1 (Cell division cycle and apoptosis regulator 1) inhibitors, colonystimulating factor-1 receptor (CSF1R) inhibitors, CD47 inhibitors, and other cell therapies.

In some embodiments, the additional cancer therapeutic agent is alkylating agents. Examples of alkylating agents, include but are not limited to, temozolomide, dactinomycin, melphalan, altretamine, carmustine, bendamustine, busulfan, carboplatin, lomustine, cisplatin, chlorambucil, cyclophosphamide, dacarbazine, altretamine, ifosfamide, procarbazine, mechlorethamine, streptozocin and thiotepa.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

In some embodiments, the additional cancer therapeutic agent is a PARP inhibitors such as Olaparib, Rucaparib, Niraparib and Talazoparib.

Other possible additional therapeutic modalities include tyrosine kinase inhibitors, cyclin-dependent kinase inhibitors, gene therapy, hormonal therapy, peptide and dendritic cell vaccines, synthetic chlorotoxins, and radiolabeled drugs and antibodies.

In some embodiments, the compound of the present invention may be administered either simultaneously with, or before or after, one or more other immunotherapeutic agents which modulate the immune targets like TIM-3 (T-cell immunoglobulin and mucin domain-3), LAG-3 (Lymphocyte-associated gene 3), TIGIT (T cell immunoreceptor with Ig and ITIM domains), VISTA (V-domain Ig suppressor of T cell activation), A2a (Adenosine A2a receptor), A2b (Adenosine A2b receptor), IDO (Indoleamine-pyrrole 2,3-dioxygenase), TDO (tryptophan-2,3-dioxygenase), Arginase, CD73, CD39, OX40, CD160, BTLA, TCR (T-cell receptor), CD28, GITR (glucocorticoid-induced TNFR family related protein), HVEM, CD226, CD96 and B7-$H_3$.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits:

The present disclosure further provides kits for carrying out the methods of the invention, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf-life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual The invention can be further understood by reference to the following examples, which are provided by way of illustration and are not meant to be limiting.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure.

UPLC-MS Standard Procedures

Method-1:

Instrument: Waters Acquity UPLC-MS SQD 3100; Column: Acquity BEH Shield RP 18, 50×2.1 mm, 1.7 µm; Eluent A: 0.05% Trifluoroacetic acid in Water, Eluent B: Acetonitrile; Gradient: 10% B to 90% B in 4.5 min, hold for 3 min, 90% B to 10% B in 0.5 min (Run Time: 10.0 min); Flow rate: 0.35 mL/min; Temperature: 25° C., PDA scan: 210 nm-400 nm.

EXAMPLES

Example-1: Synthesis of (2-(1-(6,7-dimethoxyquinazolin-4-yl)azetidin-3-yl)ethyl)aminisulfonamide, (Compound 1.1)

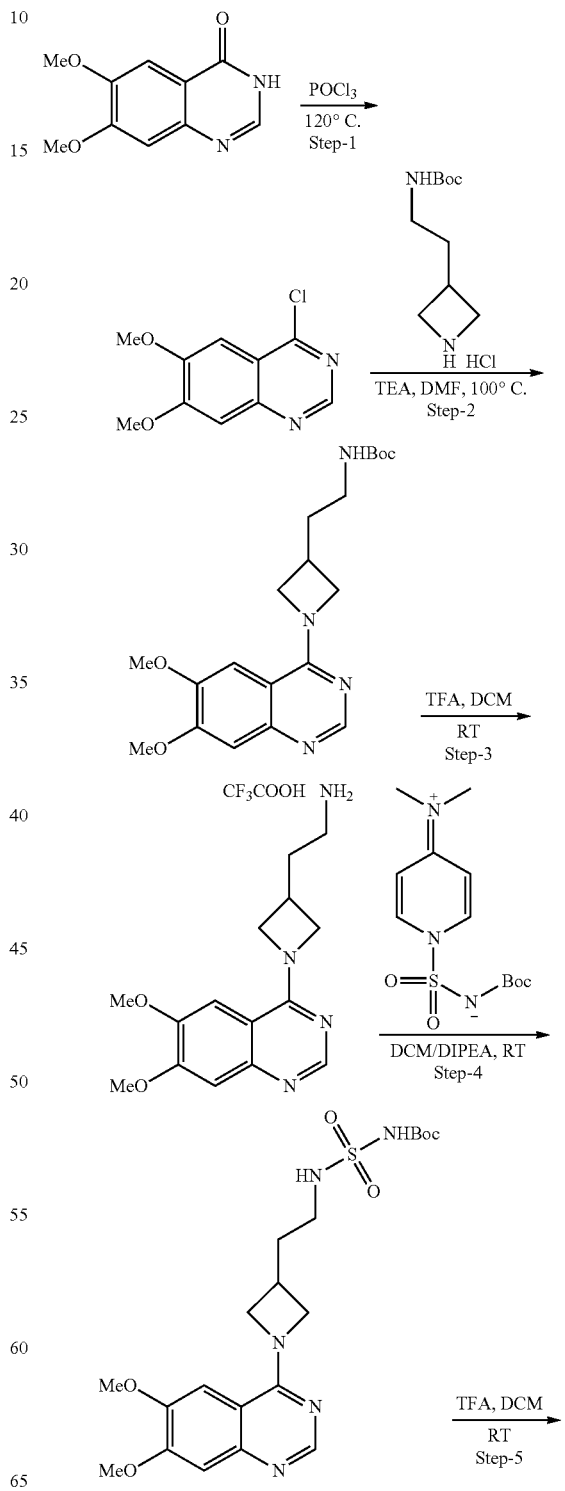

-continued

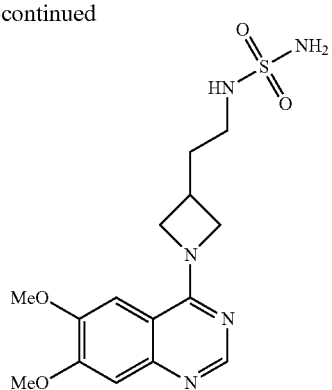

Step-1: Synthesis of 4-chloro-6,7-dimethoxyquinazoline: A mixture of 6,7-dimethoxyquinazolin-4 (3H)-one (1 g, 4.86 mol, 1 eq) in POCl$_3$ (2.5 mL) was allowed to stir at 120° C. for 2 h. Progress of reaction was monitored by TLC. After completion reaction mixture was cooled to RT, diluted with cold water (100 mL) and allowed to stir for 5 minutes. Solid was filtered, washed with water and dried under vacuum to afford 4-chloro-6,7-dimethoxyquinazoline (800 mg, 74%). LCMS: 225 [M+1]$^+$ Step-2: Synthesis of tert-butyl 2-(1-(6,7-dimethoxyquinazolin-4-yl)azetidin-3-yl)ethylcarbamate: A suspension of 4-chloro-6,7-dimethoxyquinazoline (200 mg, 0.89 mol, 1.0 eq), tert-butyl 2-(azetidin-3-yl)ethylcarbamate hydrochloride (211 mg, 0.89 mmol, 1.0 eq) and triethylamine (0.25 mL, 1.78 mmol, 2.0 eq) in DMF (2.5 mL) was allowed to stir at 100° C. for 1 h. Reaction mixture was cooled to RT, diluted with cold water (50 mL) and allowed to stir at RT for 10 minutes. Solid was filtered, washed with water and dried under vacuum to afford tert-butyl 2-(1-(6,7-dimethoxyquinazolin-4-yl)azetidin-3-yl)ethylcarbamate (240 mg, 69%). LCMS: 389 [M+1]$^+$ Step-3: Synthesis of 2-(1-(6,7-dimethoxyquinazolin-4-yl)azetidin-3-yl)ethanamine 2,2,2-trifluoroacetate: To a solution of tert-butyl 2-(1-(6,7-dimethoxyquinazolin-4-yl)azetidin-3-yl)ethylcarbamate (240 mg, 0.61 mmol, 1 eq) in DCM (5 mL) was added TFA (5 mL) and the mixture was allowed to stir at RT for 3 h. Progress of reaction was monitored by TLC. After completion, reaction mixture was concentrated under reduced pressure to get residue which was triturated with diethylether (20 mL) to afford 2-(1-(6,7-dimethoxyquinazolin-4-yl)azetidin-3-yl)ethanamine 2,2,2-trifluoroacetate (200 mg, 81%). LCMS: 289 [M+1]$^+$ Step-4: Synthesis of tert-butyl N-(2-(1-(6,7-dimethoxyquinazolin-4-yl)azetidin-3-yl)ethyl)sulfamoylcarbamate: To a solution of -(1-(6,7-dimethoxyquinazolin-4-yl)azetidin-3-yl)ethanamine 2,2,2-trifluoroacetate (200 mg, 0.49 mmol, 1 eq) in dichloromethane (40 ML) were added N-(tert-butoxycarbonyl)-N-[4-(dimethylazaniumylidene)-1,4-dihydropyridin-1ylsulfonyl]azanide (149 mg. 0.49 mmol, 1 eq) and N,N-diisopropylethylamine (0.17 mL, 0.99 mmol, 2 eq) and the reaction mixture was allowed to stir at RT for 24 h. Progress of reaction was monitored by LCMS. After completion, reaction mixture was diluted with water (50 mL) and extracted with ethyl acetate (3×100 mL). Combined organic layer was washed with brine (50 mL) and dried over anhydrous sodium sulfate. Removal of solvent under reduced pressure afforded tert-butyl N-(2-(1-(6,7-dimethoxyquinazolin-4-yl)azetidin-3-yl)ethyl)sulfamoylcarbamate (200 mg, 86%) which was used in the next step without purification. LCMS: 468[M+1]$^+$ Step-5: Synthesis of (2-(1-(6,7-dimethoxyquinazolin-4-yl)azetidin-3-yl)ethyl)aminisulfonamide: To a solution of tert-butyl N-(2-(1-(6,7-dimethoxyquinazolin-4-yl)azetidin-3-yl)ethyl)sulfamoylcarbamate (200 mg, 0.42 mmol, 1 eq) in DCM (5 mL) was added TFA (5 mL) and the resulting mixture was allowed to stir at RT for 2 h. Progress of reaction was monitored by TLC. After completion, reaction mixture was concentrated under reduced pressure to afford crude which was purified by reversed phase HPLC to afford (2-(1-(6,7-dimethoxyquinazolin-4-yl)azetidin-3-yl)ethyl) aminisulfonamide (50 mg, 32%). LCMS: 368 [M+1]$^+$; $^1$H NMR (400 MHz, DMSO-d$_6$) δ ppm 8.31 (s, 1H), 7.19 (s, 1H), 7.10 (s, 1H), 6.56 (brs, 1H), 6.50 (s, 2H), 4.60-4.50 (m, 2H), 4.18-4.06 (m, 2H), 3.87 (s, 3H), 7.86 (s, 3H), 2.95-2.83 (m, 3H), 1.88-1.78 (m, 2H).

Example-2: Synthesis of (2-(1-(6,7-dimethoxy-2-oxo-1,2-dihydroquinazolin-4-yl)azetidin-3-yl)ethyl)aminosulfonamide, (Compound 1.2)

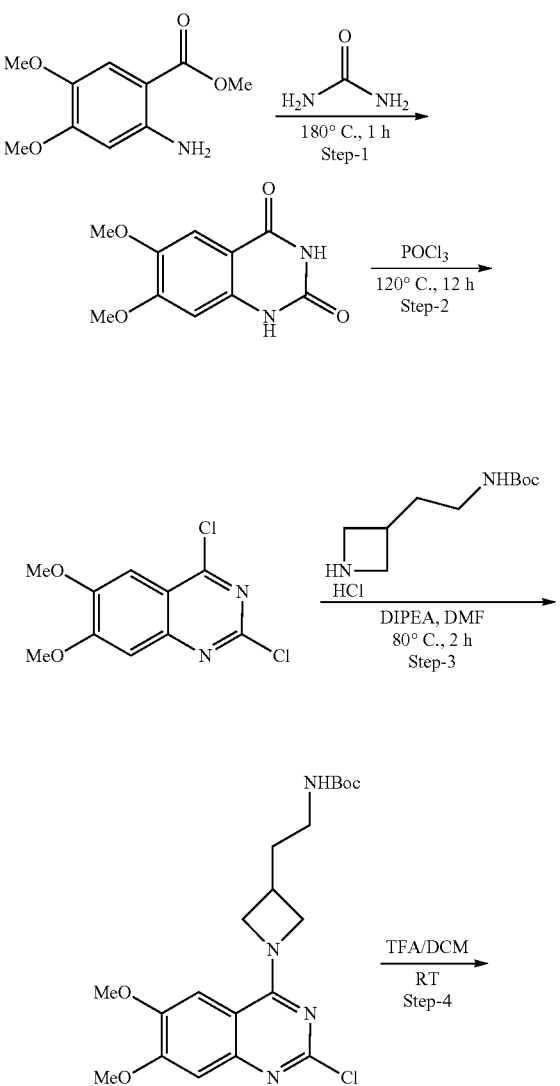

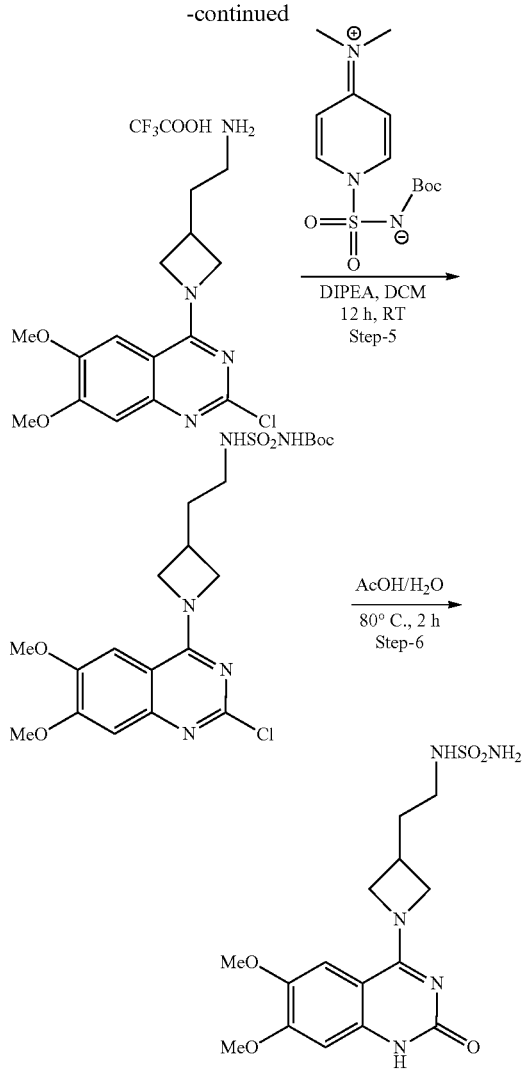

Step-1: Synthesis of 6,7-dimethoxyquinazoline-2,4 (1H, 3H)-dione: A solid mix of of methyl 2-amino-4,5-dimethoxybenzoate (500 mg, 2.36 mmol, 1 eq) and urea (300 mg) was fused at 180° C. for 1 h. Progress of reaction was monitored by TLC. After completion, reaction mixture was cooled to RT, diluted with cold water (100 mL) and allowed to stir for 5 minutes. Solid was filtered, washed with water and dried under vacuum to afford 6,7-dimethoxyquinazoline-2,4 (1H,3H)-dione (30 mg, 8%). LCMS: 2[M+1]$^+$ Step-2: Synthesis of 2,4-dichloro-6,7-dimethoxyquinazoline: A mixture of 6,7-dimethoxyquinazolin-4 (3H)-one (360 mg, 1.62 mmol, 1 eq) in POCl$_3$ (0.5 mL) was allowed to stir at 120° C. for 12 h. Progress of reaction was monitored by TLC. After completion, reaction mixture was cooled to RT, diluted with cold water (100 mL) and allowed to stir for 5 minutes. Solid was filtered, washed with water and dried under vacuum to afford 2,4-dichloro-6,7-dimethoxyquinazoline (300 mg, 72%). LCMS: 258[M+1]$^+$ Step-3: Synthesis of tert-butyl 2-(1-(2-chloro-6,7-dimethoxyquinazolin-4-yl)azetidin-3-yl)ethylcarbamate: A suspension of to 2,4-dichloro-6,7-dimethoxyquinazolin-4-yl)azetidin-3-yl)ethylcarbamate: A suspension of to 2,4-dichloro-6,7-dimethoxyquinazoline (50 mg, 0.19 mmol, 1.0 eq), tert-butyl 2-(azetidin-3-yl)ethylcarbamate hydrochloride (45.7 mg, 0.19 mmol, 1.0 eq) and N,N diisopropylethylamine (50 mg, 0.38 mmol, 2.0 eq) in DMF (5 mL) was allowed to stir at 80° C. for 2 h. Progress of reaction was monitored by TLC. Reaction mixture was cooled to RT, diluted with cold water (10 mL) and extracted with ethyl acetate (3×20 mL). Combined organic layer was dried over anhydrous sodium sulfate. Removal of solvent under reduced pressure gave crude which was purified by Combi-Flash to afford tert-butyl 2-(1-(2-chloro-6,7-dimethoxyquinazolin-4-yl)azetidin-3-yl)ethylcarbamate (38 mg, 47%). LCMS: 422 [M+1]$^+$ Step-4: Synthesis 2-(1-(2-chloro-6,7-dimethoxyquinazolin-4-yl)azetidin-3-yl)ethanamine 2,2,2-trifluoroacetate: To a solution of tert-butyl 2-(1-(2-chloro-6,7-dimethoxyquinazolin-4-yl)azetidin-3-yl)ethylcarbamate (38 mg, 0.09 mmol, 1 eq) in DCM (5 mL) was added TFA (1 mL) and the mixture was allowed to stir at RT for 2 h. Progress of reaction was monitored by TLC. After completion, reaction mixture was concentrated under reduced pressure to get residue which was triturated with diethyl ether (5 mL) to afford 2-(1-(2-chloro-6,7-dimethoxyquinazolin-4-yl)azetidin-3-yl)ethanamine 2,2,2-trifluoroacetate (37 mg, 97%). LCMS: 322 [M+1]$^+$ Step-5: Synthesis of tert-butyl N-(2-(1-(2-chloro-6,7-dimethoxyquinazolin-4-yl)azetidin-3-yl)ethyl)sulfamoylcarbamate: To a solution of 2-(1-(2-chloro-6,7-dimethoxyquinazolin-4-yl)azetidin-3-yl)ethanamine 2,2,2-trifluoroacetate (37 mg, 0.08 mmol, 1 eq) in dichloromethane (5 mL) were added N-(tert-butoxycarbonyl)-N-[4-(dimethylazanium-ylidene)-1,4-dihydropyridin-1ylsulfonyl]azanide (31.89 mg. 0.10 mmol, 1.2 eq) and N,N-diisopropylethylamine (20.64 mg, 0.16 mmol, 2 eq) and the reaction mixture was allowed to stir at RT for 24 h. Progress of reaction was monitored by LCMS. After completion, reaction mixture was diluted with water (50 mL) and extracted with ethyl acetate (3×100 mL). Combined organic layer was washed with brine (50 mL) and dried over anhydrous sodium sulfate. Removal of solvent under reduced pressure to obtain the crude which was purified by Combi-Flash to afforded tert-butyl N-(2-(1-(2-chloro-6,7-dimethoxyquinazolin-4-yl)azetidin-3-yl)ethyl)sulfamoylcarbamate (30 mg, 68%) LCMS: 501[M+1]$^+$ Step-6: Synthesis of (2-(1-(6,7-dimethoxy-2-oxo-1,2-dihydroquinazolin-4-yl)azetidin-3-yl)ethyl)aminosulfonamide: To a solution of tert-butyl N-(2-(1-(6,7-dimethoxyquinazolin-4-yl)azetidin-3-yl)ethyl)sulfamoylcarbamate (30 mg, 0.05 mmol, 1 eq) in acetic acid (5 mL) was added water (2 drops) and the resulting mixture was allowed to stir at 80° C. for 2 h. Progress of reaction was monitored by LCMS. After completion, reaction mixture was concentrated under reduced pressure to afford crude which was purified by reversed phase HPLC to afford (2-(1-(6,7-dimethoxy-2-oxo-1,2-dihydroquinazolin-4-yl)azetidin-3-yl)ethyl)amiosulfonamide (50 mg, 32%). LCMS: 383 [M+1]$^+$; $^1$H NMR (400 MHz, DMSO-d$_6$) δ ppm 10.45 (brs, 1H), 8.16 (brs, 1H), 7.52 (s, 1H), 6.76 (s, 2H), 6.67 (s, 1H), 3.80 (s, 6H), 3.70-3.60 (m, 3H), 3.4-3.1 (m, 2H), 2.98 (brs, 1H), 1.98 (brs, 2H), 1.65 s (brs, 1H).

Example-3: Synthesis of (2-(1-(6-methoxypyrido[3,4-d]pyrimidin-4-yl)azetidin-3-yl)ethyl)aminisulfonamide, (Compound 1.3)

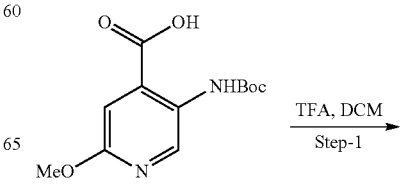

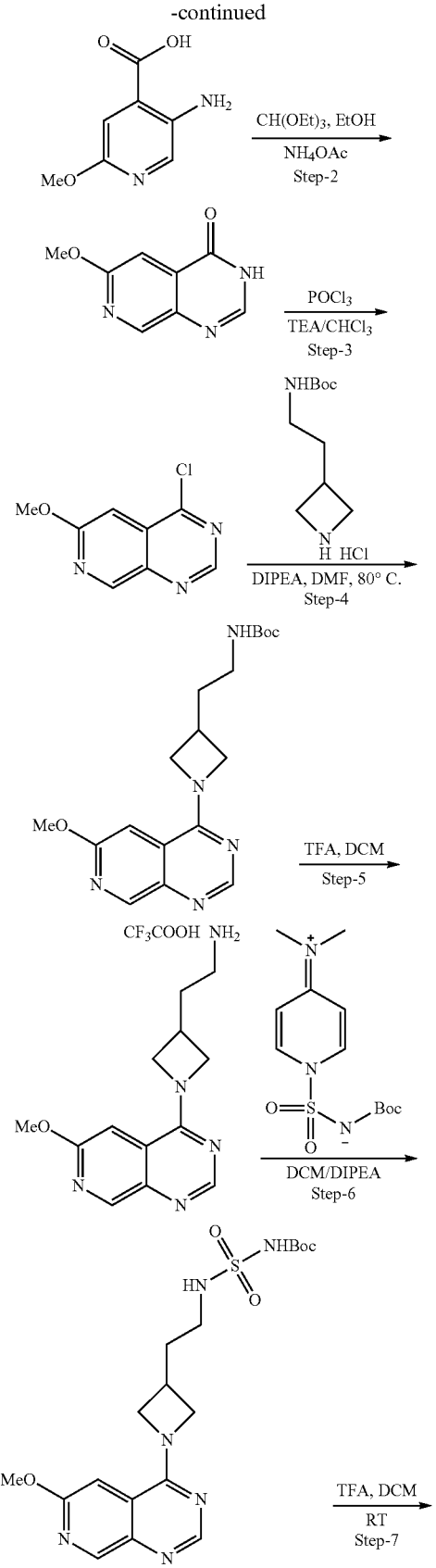

Step-1: Synthesis of 5-amino-2-methoxyisonicotinic acid: To a solution of 5-(tert-butoxycarbonylamino)-2-methoxyisonicotinic acid (2 g, 7.4 mmol, 1 eq) in DCM (15 mL) was added TFA (15 mL) and the reaction mixture was allowed to stir at RT for 3 h. Progress of reaction was monitored by TLC. After completion, reaction mixture was concentrated under reduced pressure to get crude which was triturated using diethyl ether to afford 5-amino-2-methoxyisonicotinic acid (1 g, 80%). LCMS: 169[M+1]+

Step-2: Synthesis of 6-methoxypyrido[3,4-d]pyrimidin-4(3H)-one: To a solution of 5-amino-2-methoxyisonicotinic acid (0.5 g, 2.9 mmol, 1 eq) in ethanol (5 mL) were added triethylorthoformate (0.79 mL, 4.7 mmol, 1.6 eq) and ammonium acetate (0.29 g, 3.7 mmol, 1.3 eq.) and the reaction mixture was allowed to stir at 90° C. for 16 h. After completion, reaction mixture was filtered and washed with hexane to get 6-methoxypyrido[3,4-d]pyrimidin-4 (3H)-one as white solid (370 mg, 70%). LCMS: 178[M+1]+

Step-3: Synthesis of 4-cloro-6-methoxypyrido[3,4-d]pyrimidine: To a solution of 6-methoxypyrido[3,4-d]pyrimidin-4 (3H)-one (0.28 g, 1.5 mmol, 1 eq) in CHCl₃ (10 mL) were added POCl₃ (0.5 mL, 5.3 mmol, 3.5 eq) and triethylamine (0.8 mL, 5.6 mmol, 3.7 eq) and the reaction mixture was allowed to stir at 80° C. for 16 h. Progress of reaction was monitored by TLC. After completion, reaction mixture was cooled to RT, concentrated under reduced pressure to get residue, to which saturated aq. NaHCO₃ solution (50 mL) was added and extracted with ethyl acetate (3×100 mL). Combined organic layer was washed with brine (3×50 mL) and dried over anhydrous sodium sulfate. Removal of solvent under reduced pressure afforded crude which was purified using Combi-Flash to afford 4-chloro-6-methoxypyrido[3,4-d]pyrimidine (0.2 g, 65%). LCMS: 196 [M+1]+

Step-4: Synthesis of tert-butyl 2-(1-(6-methoxypyrido[3,4-d]pyrimidin-4-yl)azetidin-3-yl)ethylcarbamate: A suspension of -chloro-6-methoxypyrido[3,4-d]pyrimidine (40 mg, 0.20 mmol, 1 eq), tert-butyl 2-(azetidin-3-yl)ethylcarbamate hydrochloride (50 mg, 0.20 mmol, 1.0 eq) and DIPEA (0.07 mL, 0.41 mmol, 2.0 eq) in DMF (2 mL) was allowed to stir at 80° C. for 2 h. Progress of reaction was monitored by TLC. After completion, reaction mixture was diluted with cold water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(1-(6-methoxypyrido[3,4-d]pyrimidin-4-yl)azetidin-3-yl)ethylcarbamate (0.1 g) which was used in the next step without purification. LCMS: 360[M+1]+

Step-5: Synthesis of 2-(1-(6-methoxypyrido[3,4-d]pyrimidin-4-yl)azetidin-3-yl)ethanamine 2,2,2-trifluoroacetate: To a solution of tert-butyl 2-(1-(6-methoxypyrido[3,4-d]pyrimidin-4-yl)azetidin-3-yl)ethylcarbamate (200 mg, 0.05 mmol, 1 eq) in DCM (2 mL) was added TFA (2 mL) and allowed to stir at RT for 2 h. Progress of reaction was monitored by TLC. After completion, reaction mixture was concentrated under reduced pressure to afford crude which was triturated with diethyl ether to afford 2-(1-(6-methoxypyrido[3,4-d]pyrimidin-4-yl)azetidin-3-yl)ethanamine 2,2,2-trifluoroacetate (200 mg, 97%). LCMS: 260 [M+1]+

Step-6: Synthesis of tert-butyl N-(2-(1-(6-methoxypyrido[3,4-d]pyrimidin-4-yl)azetidin-3-yl)ethyl)sulfamoylcarbamate: To a solution of 2-(1-(6-methoxypyrido[3,4-d]pyrimidin-4-yl)azetidin-3-yl)ethanamine 2,2,2-trifluoroacetate (200 mg, 0.53 mmol, 1 eq) in dichloromethane (25 mL) were added N-(tert-butoxycarbonyl)-N-[4-(dimethylazanium-ylidene)-1,4-dihydropyridin-1ylsulfonyl]azanide (161 mg, 0.53 mmol, 1 eq) and N,N-diisopropylethylamine (0.18 mL, 0.6 mmol, 2 eq) and the reaction mixture was allowed to stir at RT for 16 h. Progress of reaction was monitored by LCMS. After completion, reaction mixture was concentrated under reduced pressure to get residue which was purified by reversed phase HPLC to afford tert-butyl N-(2-(1-(6-methoxypyrido[3,4-d]pyrimidin-4-yl)azetidin-3-yl)ethyl)sulfamoylcarbamate (60 mg, 26%). LCMS:439[M+1]+

Step-7: Synthesis of (2-(1-(6-methoxypyrido[3,4-d]pyrimidin-4-yl)azetidin-3-yl)ethyl)aminisulfonamide: To a solution of tert-butyl N-(2-(1-(6-methoxypyrido[3,4-d]pyrimidin-4-yl)azetidin-3-yl)ethyl)sulfamoylcarbamate (30 mg, 0.06 mmol, 1 eq) in DCM (5 mL) was added TFA (1 mL) and allowed to stir at RT for 2 h. Progress of reaction was monitored by TLC. After completion, reaction mixture was concentrated under reduced pressure to afford crude which was triturated with diethyl ether to afford desired product as TFA salt which was basified with ammonia solution (0.2 mL, 7N in MeOH) and lyophillized to afford (2-(1-(6-methoxypyrido[3,4-d]pyrimidin-4-yl)azetidin-3-yl)ethyl)aminisulfonamide (19 mg, 82%). LCMS:339 [M+1]+; 1H NMR (400 MHz, DMSO-d6) δ ppm 8.84 (s, 1H), 8.43 (s, 1H), 7.09 (s, 1H), 6.98 (s, 1H), 6.59 (brs, 1H), 6.55 (s, 2H), 4.60-4.20 (brs, 4H), 3.97 (s, 3H), 2.98-2.82 (m, 3H), 1.90-1.78 (m, 2H).

Example-4: Synthesis of (2-(1-(8-methoxyquinazolin-4-yl)azetidin-3-yl)ethyl)aminosulfonamide, (Compound 1.4)

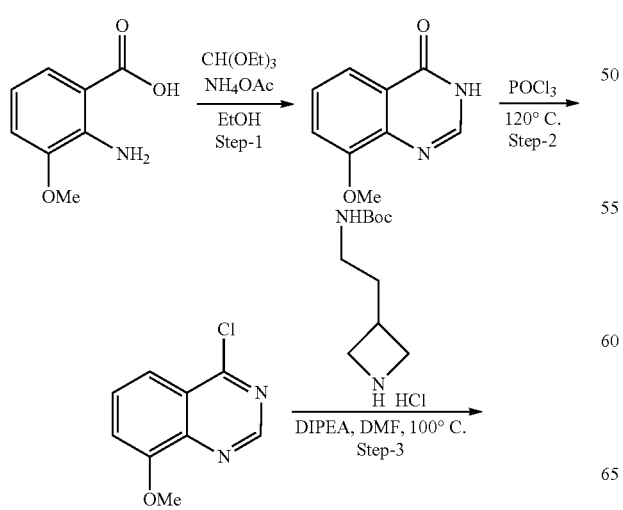

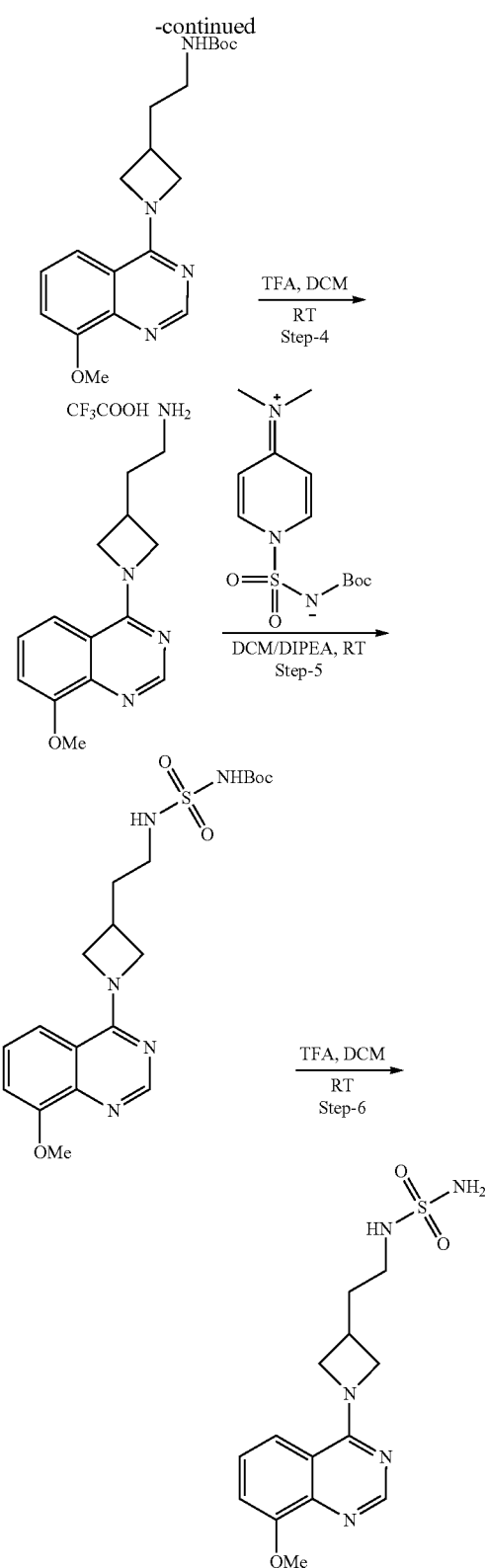

Step-1: Synthesis of 8-methoxyquinazolin-4 (3H)-one: To a solution of 2-amino-3-methoxybenzoic acid (1 g, 5.9 mmol, 1 eq) in ethanol (10 mL) were added triethylorthoformate (2.58 mL, 15 mmol, 2.6 eq) and ammonium acetate (1.06 g, 13.7 mmol, 2.3 eq.) and the reaction mixture was allowed to stir at 90° C. for 32 h. After completion, reaction mixture was filtered and washed with hexane to get 8-methoxyquinazolin-4 (3H)-one as white solid (0.9 g, 86%) LCMS: 177 [M+1]+

Step-2: Synthesis of 4-chloro-8-methoxyquinazoline: A mixture of 8-methoxyquinazolin-4 (3H)-one (0.15 g, 0.85 mmol, 1 eq) in POCl$_3$ (1.63 mL) was allowed to stir at 120° C. for 2 h. Progress of reaction was monitored by TLC. After completion, reaction mixture was cooled to RT, diluted with cold water (100 mL) and extracted with ethyl acetate (3×100 mL). Combined organic layer was washed with brine (50 mL) and dried over anhydrous sodium sulfate. Removal of solvent under reduced pressure afforded crude 4-chloro-8-methoxyquinazoline (0.1 g, 61%) which was used in the next step without purification. LCMS: 195 [M+1]+

Step-3: Synthesis of tert-butyl 2-(1-(8-methoxyquinazolin-4-yl)azetidin-3-yl)ethylcarbamate: A suspension of 4-chloro-8-methoxyquinazoline (40 mg, 0.20 mmol, 1 eq), tert-butyl 2-(azetidin-3-yl)ethylcarbamate hydrochloride (50 mg, 0.20 mmol, 1.0 eq) and DIPEA (0.07 mL, 0.41 mmol, 2.0 eq) in DMF (1 mL) was allowed to stir at 80° C. for 2 h. Progress of reaction was monitored by TLC. After completion, reaction mixture was diluted with cold water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(1-(8-methoxyquinazolin-4-yl)azetidin-3-yl)ethylcarbamate (0.08 g) which was used in the next step without purification. LCMS: 359 [M+1]+

Step-4: Synthesis of 2-(1-(8-methoxyquinazolin-4-yl)azetidin-3-yl)ethanamine 2,2,2-trifluoroacetate: To a solution of tert-butyl 2-(1-(8-methoxyquinazolin-4-yl)azetidin-3-yl) ethylcarbamate (80 mg, 0.22 mmol, 1 eq) in DCM (4 mL) was added TFA (4 ML) and the mixture was allowed to stir at RT for 2 h. Progress of reaction was monitored by TLC. After completion, reaction mixture was concentrated under reduced pressure to get 2-(1-(8-methoxyquinazolin-4-yl) azetidin-3-yl)ethanamine 2,2,2-trifluoroacetate (0.1 g) which was used in the next step without purification. LCMS: 259 [M+1]+

Step-5: Synthesis of tert-butyl N-(2-(1-(8-methoxyquinazolin-4-yl)azetidin-3-yl)ethyl)sulfamoylcarbamate: To a solution of 2-(1-(8-methoxyquinazolin-4-yl)azetidin-3-yl) ethanamine 2,2,2-trifluoroacetate (100 mg, 0.26 mmol, 1 eq) in dichloromethane (20 mL) were added N-(tert-butoxycarbonyl)-N-[4-(dimethylazaniumylidene)-1,4-dihydropyridin-1ylsulfonyl]azanide (161 mg. 0.53 mmol, 2 eq) and N,N-diisopropylethylamine (0.18 mL, 1.07 mmol, 4 eq) and the reaction mixture was allowed to stir at RT for 48 h. Progress of reaction was monitored by LCMS. After completion, reaction mixture was concentrated under reduced pressure to get residue which was purified by reversed phase HPLC to afford tert-butyl N-(2-(1-(8-methoxyquinazolin-4-yl)azetidin-3-yl)ethyl)sulfamoylcarbamate (35 mg, 30%). LCMS: 438 [M+1]+

Step-6: Synthesis of (2-(1-(8-methoxyquinazolin-4-yl) azetidin-3-yl)ethyl)aminosulfonamide: To a solution of tert-butyl N-(2-(1-(8-methoxyquinazolin-4-yl)azetidin-3-yl) ethyl)sulfamoylcarbamate (35 mg, 0.80 mmol, 1 eq) in DCM (3 mL) was added TFA (1.5 mL) and allowed to stir at RT for 1 h. Progress of reaction was monitored by TLC. After completion, reaction mixture was concentrated under reduced pressure to afford crude which was triturated with diethyl ether to afford (2-(1-(8-methoxyquinazolin-4-yl)azetidin-3-yl)ethyl)aminosulfonamide (10 mg, 38%) as TFA salt. LCMS: 338 [M+1]+; ¹H NMR (400 MHz, DMSO-d$_6$) δ ppm 13.85 (brs, 1H), 8.62 (s, 1H), 7.70-7.58 (m, 3H), 6.60 (brs, 1H), 6.55 (s, 2H), 5.18-5.00 (m, 1H), 4.75-4.50 (m, 2H), 4.22-4.10 (m, 1H), 4.03 (s, 3H), 3.02-2.90 (m, 3H), 1.98-1.82 (m, 2H).

Example-5: Synthesis of 3-(1-(6,7-dimethoxyquinazolin-4-yl)azetidin-3-yl)propanoic acid, (Compound 1.5)

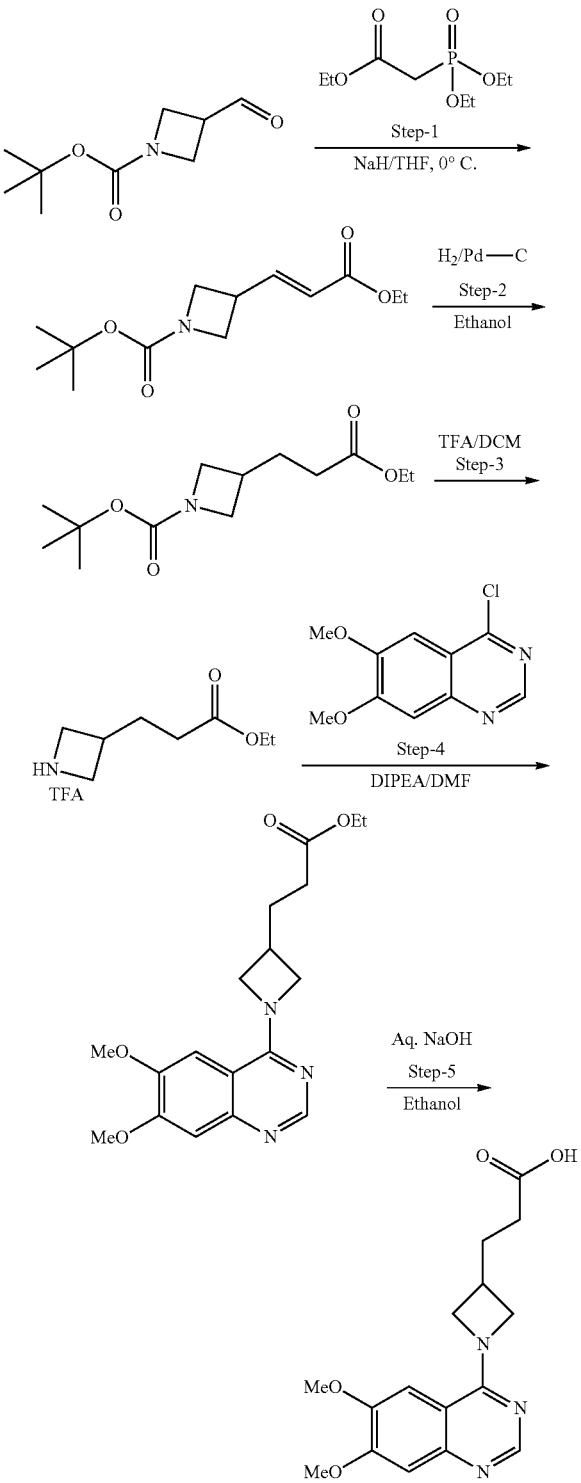

Step-1: Synthesis of (E)-tert-butyl 3-(3-ethoxy-3-oxo-prop-1-enyl)azetidine-1-carboxylate: To a solution of ethyl 2-(diethoxyphosphoryl)acetate (0.220 g, 1.188 mmol, 1 eq) in THF (10 mL) was added sodium hydride (0.072 g, 1.782 mmol, 1.5 eq) at 0° C. and the reaction mixture was allowed to stir at 0° C. for 5 minutes, followed by addition of tert-butyl 3-formylazetidine-1-carboxylate (0.319 g, 1.426 mmol, 1.2 eq) and then the reaction mixture was allowed to stir at 0° C. for 30 minutes. After completion, reaction mixture was diluted with water (50 mL) and extracted with ethyl acetate (3×50 mL). Combined organic layer was washed with brine (50 mL) and dried over anhydrous sodium sulfate. Removal of solvent under reduced pressure afforded (E)-tert-butyl 3-(3-ethoxy-3-oxoprop-1-enyl)azetidine-1-carboxylate (0.3 g, 99%) which was used in the next step without purification.

Step-2: Synthesis of tert-butyl 3-(3-ethoxy-3-oxopropyl)azetidine-1-carboxylate: To a solution of (E)-tert-butyl 3-(3-ethoxy-3-oxoprop-1-enyl)azetidine-1-carboxylate (0.3 g, 1.175 mmol, 1 eq) in ethanol (20 mL) was added Pd—C (0.1 g) and the reaction mixture was allowed to stir at RT under $H_2$ atmosphere for 2 h. After completion, reaction mixture was filtered through celite-bed and bed was washed with ethyl acetate (50 mL). Removal of solvent under reduced pressure afforded tert-butyl 3-(3-ethoxy-3-oxopropyl)azetidine-1-carboxylate (0.3 g, 99%).

Step-3: Synthesis of ethyl 3-(azetidin-3-yl)propanoate: To a solution of tert-butyl 3-(3-ethoxy-3-oxopropyl)azetidine-1-carboxylate (0.3 g, 1.17 mmol, 1 eq) in DCM (10 mL) was added trifluoroacetic acid (3 mL). The reaction mixture was allowed to stir at RT for overnight. After completion, removal of solvent under reduced pressure afforded crude ethyl 3-(azetidin-3-yl)propanoate (0.350 g) which was used in the next step without purification.

Step-4: Synthesis of ethyl 3-(1-(6,7-dimethoxyquinazolin-4-yl)azetidin-3-yl)propanoate: To a solution of 4-chloro-6,7-dimethoxyquinazoline (0.120 g, 0.534 mmol, 1 eq) in DMF (2 mL) were added DIPEA (0.28 mL, 1.60 mmol, 3 eq) and ethyl 3-(azetidin-3-yl)propanoate (0.100 g, 0.641 mmol, 1.2 eq) and the mixture was allowed to stir at 80° C. for 5 h. After completion, reaction mixture was diluted with water (50 mL) and extracted with ethyl acetate (3×80 mL). Combined organic layer was washed with brine (2×50 mL) and dried over anhydrous sodium sulfate. Removal of solvent under reduced pressure afford crude which was purified by Combi-Flash on silica gel using ethyl acetate-hexane system as eluent to afford ethyl 3-(1-(6,7-dimethoxyquinazolin-4-yl)azetidin-3-yl)propanoate (0.080 g, 43%).

Step-5: Synthesis of 3-(1-(6,7-dimethoxyquinazolin-4-yl)azetidin-3-yl)propanoic acid: To a solution of 3-(1-(6,7-dimethoxyquinazolin-4-yl)azetidin-3-yl)propanoate (0.080 g, 0.232 mmol, 1 eq) in ethanol (10 mL) was added aq. NaOH (0.3 mL) and the reaction mixture was allowed to stir at RT for 2 h. Progress of reaction was monitored by TLC. After completion, reaction mixture was concentrated under reduced pressure to get residue which was purified by reversed phase HPLC to afford 3-(1-(6,7-dimethoxyquinazolin-4-yl)azetidin-3-yl)propanoic acid (02 mg, 3%). LCMS: 318[M+1]$^+$; $^1$H NMR (400 MHz, DMSO-$d_6$) δ ppm 8.32 (s, 1H), 7.20 (m, 1H), 7.10 (s, 1H), 4.55 (brs, 2H), 4.07 (brs, 2H), 3.86 (s, 6H), 2.68 (brs, 1H), 2.05 (brs, 2H), 1.82 (brs, 2H).

Example-6: Synthesis of N-(2-[1-(6,7-dimethoxy-quinazolin-4-yl)azetidin-3-yl]ethyl)methanesulfonamide, (Compound 1.6)

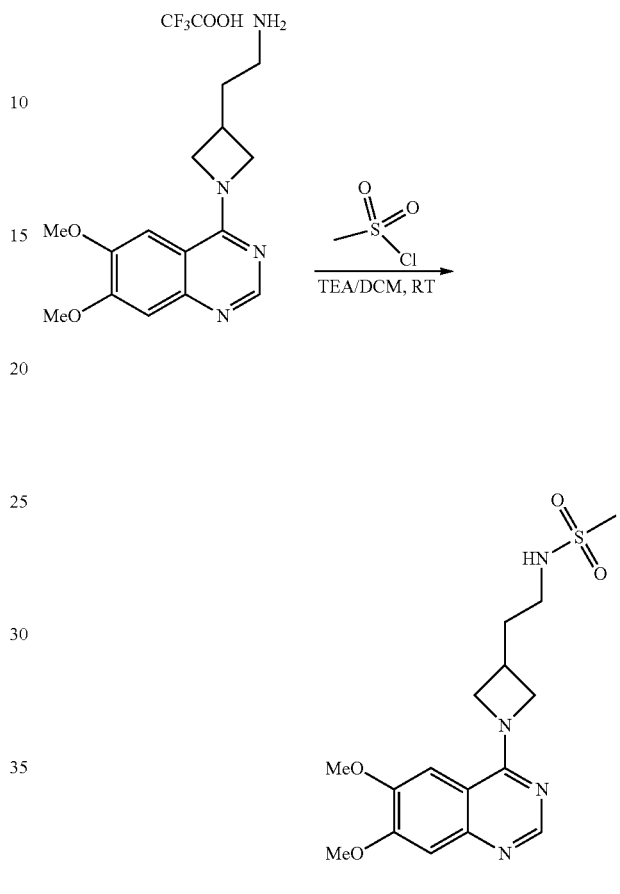

To a solution of 2-(1-(6,7-dimethoxyquinazolin-4-yl)azetidin-3-yl)ethanamine 2,2,2-trifluoroacetate (87 mg, 0.22 mmol, 1 eq) in dichloromethane (10 mL) were added methane sulphonyl chloride (27 mg. 0.24 mmol, 1.1 eq) and triethylamine (45 mg, 0.45 mmol, 2 eq) and the reaction mixture was allowed to stir at RT for 2 h. Progress of reaction was monitored by LCMS. After completion, reaction mixture was diluted with water (20 mL) and extracted with ethyl acetate (3×25 mL). Combined organic layer was washed with brine (50 mL) and dried over anhydrous sodium sulfate. Removal of solvent under reduced pressure afforded crude which was purified by reversed phase HPLC to afford N-(2-(1-(6,7-dimethoxyquinazolin-4-yl)azetidin-3-yl)ethyl)methanesulfonamide (9 mg, 11%). LCMS: 367 [M+1]$^+$; $^1$H NMR (400 MHz, DMSO-$d_6$) δ ppm 8.46 (s, 1H), 7.22 (s, 1H), 7.19 (s, 1H), 7.06 (brs, 1H), 4.65 (brs, 2H), 4.25 (brs, 2H), 3.92 (s, 3H), 3.90 (s, 3H), 3.05-2.80 (m, 3H), 2.90 (s, 3H), 1.88-1.80 (m, 2H).

223

Example-7: Synthesis of N-(2-[1-(6,7-dimethoxy-quinazolin-4-yl)azetidin-3-yl]ethyl)acetamide, (Compound 1.7)

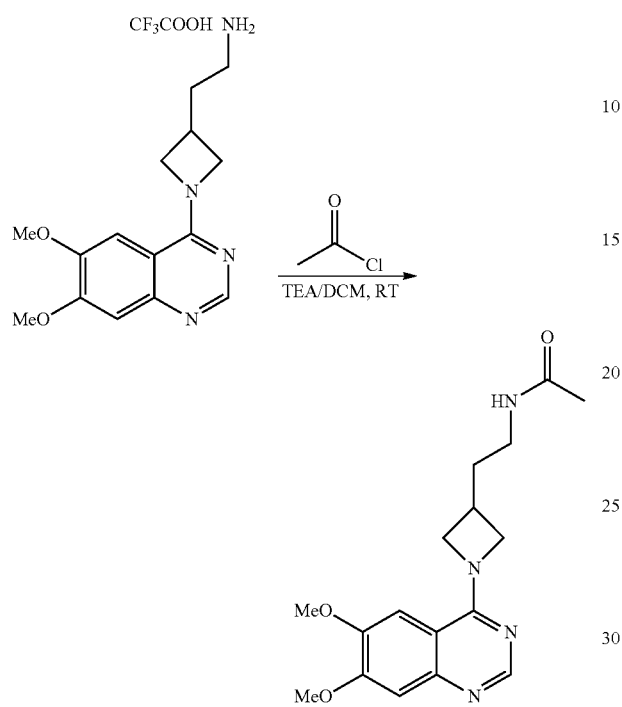

To a solution of 2-(1-(6,7-dimethoxyquinazolin-4-yl)aze-tidin-3-yl)ethanamine 2,2,2-trifluoroacetate (88 mg, 0.22 mmol, 1 eq) in dichloromethane (10 mL) were added acetyl chloride (20 mg, 0.25 mmol, 1.1 eq) and triethylamine (45 mg, 0.45 mmol, 2 eq) and the reaction mixture was allowed to stir at RT for 2 h. Progress of reaction was monitored by LCMS. After completion, reaction mixture was diluted with water (20 mL) and extracted with ethyl acetate (3×25 mL). Combined organic layer was washed with brine (50 mL) and dried over anhydrous sodium sulfate. Removal of solvent under reduced pressure afforded crude which was purified by reversed phase HPLC to afford (N-{2-[1-(6,7-dimethoxy-quinazolin-4-yl)azetidin-3-yl]ethyl}acetamide (11 mg, 15%). LCMS: 331 [M+1]$^+$; $^1$H NMR (400 MHz, DMSO-d$_6$) δ ppm 8.31 (s, 1H), 7.83 (brs, 1H), 7.20 (s, 1H), 7.10 (s, 1H), 4.60-4.50 (m, 2H), 4.18-4.01 (m, 2H), 3.90 (s, 3H), 3.87 (s, 3H), 3.10-3.00 (m, 2H), 2.80-2.70 (m, 1H), 1.80-1.70 (m, 2H), 1.80 (s, 3H).

Example-8: Synthesis of (2-(1-(7-methoxyquinazo-lin-4-yl)azetidin-3-yl)ethyl)aminisulfonamide, (Compound 1.8)

224

-continued

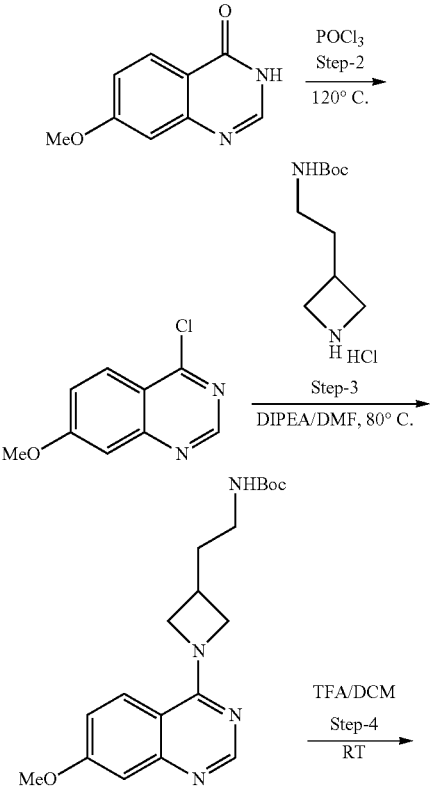

-continued

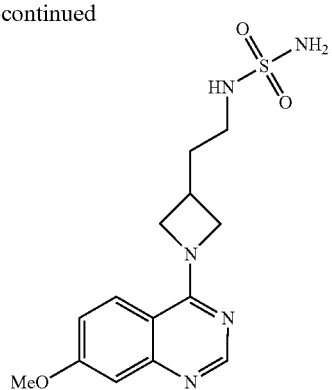

Step-1: Synthesis of 7-methoxyquinazolin-4 (3H)-one: To a solution of 2-amino-4-methoxybenzoic acid (1 g, 5.9 mmol, 1 eq) in ethanol (10 mL) were added triethylorthoformate (1.59 mL, 9.5 mmol, 1.6 eq) and ammonium acetate (0.59 g, 7.7 mmol, 1.3 eq.) and the reaction mixture was allowed to stir at 90° C. for 16 h. Progress of reaction was monitored by LTC. After completion, reaction mixture was cooled to RT, filtered, washed with hexane and dried to afford 7-methoxyquinazolin-4 (3H)-one (700 mg, 67%). LCMS: 177 [M+1]+

Step-2: Synthesis of 4-chloro-7-methoxyquinazoline: A mixture of 7-methoxyquinazolin-4 (3H)-one (0.2 g, 1.1 mmol, 1 eq) in POCl3 (2 mL) was allowed to stir at 120° C. for 2 h. Progress of reaction was monitored by TLC. After completion, reaction mixture was cooled to RT, diluted with cold water (100 mL) and extracted with ethyl acetate (3×100 mL). Combined organic layer was washed with water (3×50 mL) followed by brine (50 mL) and dried over anhydrous sodium sulfate. Removal of solvent under reduced pressure afforded 4-chloro-7-methoxyquinazoline (0.1 g, 45%) which was used in the next step without purification. LCMS: 195 [M+1]+

Step-3: Synthesis of tert-butyl 2-(1-(7-methoxyquinazolin-4-yl)azetidin-3-yl)ethylcarbamate: A suspension of 4-chloro-7-methoxyquinazoline (40 mg, 0.20 mmol, 1 eq), tert-butyl 2-(azetidin-3-yl)ethylcarbamate hydrochloride (50 mg, 0.20 mmol, 1.0 eq) and DIPEA (0.07 mL, 0.41 mmol, 2.0 eq) in DMF (1 mL) was allowed to stir at 80° C. for 2 h. Progress of reaction was monitored by TLC. After completion, reaction mixture was diluted with cold water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(1-(7-methoxyquinazolin-4-yl)azetidin-3-yl)ethylcarbamate (0.1 g) crude which was used in the next step without purification. LCMS: 359 [M+1]+

Step-4: Synthesis of 2-(1-(7-methoxyquinazolin-4-yl)azetidin-3-yl)ethanamine 2,2,2-trifluoroacetate: To a solution of tert-butyl 2-(1-(7-methoxyquinazolin-4-yl)azetidin-3-yl)ethylcarbamate (100 mg, 0.27 mmol, 1 eq) in DCM (5 mL) was added TFA (4 mL) and the mixture was allowed to stir at RT for 1 h. Progress of reaction was monitored by TLC. After completion, reaction mixture was concentrated under reduced pressure to afford crude 2-(1-(7-methoxyquinazolin-4-yl)azetidin-3-yl)ethanamine 2,2,2-trifluoroacetate (200 mg) which was used in the next step without purification. LCMS: 259 [M+1]+

Step-5: Synthesis of tert-butyl N-(2-(1-(7-methoxyquinazolin-4-yl)azetidin-3-yl)ethyl)sulfamoylcarbamate: To a solution of 2-(1-(7-methoxyquinazolin-4-yl)azetidin-3-yl)ethanamine 2,2,2-trifluoroacetate (200 mg, 0.53 mmol, 1 eq) in dichloromethane (50 mL) were added N-(tert-butoxycarbonyl)-N-[4-(dimethylazaniumylidene)-1,4-dihydropyridin-1ylsulfonyl]azanide (342 mg. 1.13 mmol, 2.1 eq) and N,N-diisopropylethylamine (0.37 mL, 2.14 mmol, 4 eq) and the reaction mixture was allowed to stir at RT for 48 h. Progress of reaction was monitored by LCMS. After completion, reaction mixture was concentrated under reduced pressure to get crude residue which was purified by reversed phase HPLC to afford tert-butyl N-(2-(1-(7-methoxyquinazolin-4-yl)azetidin-3-yl)ethyl)sulfamoylcarbamate (16 mg, 7%). LCMS: 438 [M+1]+

Step-6: Synthesis of (2-(1-(7-methoxyquinazolin-4-yl)azetidin-3-yl)ethyl)aminisulfonamide: To a solution of tert-butyl N-(2-(1-(7-methoxyquinazolin-4-yl)azetidin-3-yl)ethyl)sulfamoylcarbamate (16 mg, 0.036 mmol, 1 eq) in DCM (2 mL) was added TFA (1 mL) and allowed to stir at RT for 2 h. Progress of reaction was monitored by TLC. After completion, reaction mixture was concentrated under reduced pressure to afford crude which was triturated with diethyl ether to afford (2-(1-(7-methoxyquinazolin-4-yl)azetidin-3-yl)ethyl)aminisulfonamide (10 mg, 83%). LCMS: 338 [M+1]+; 1H NMR (400 MHz, DMSO-d6) δ ppm 8.44 (s, 1H), 8.00 (d, 1H), 7.25 (d, 1H), 7.11 (s, 1H), 6.30 (brs, 1H), 6.31 (s, 2H), 4.75 (brs, 2H), 4.30 (brs, 2H), 3.94 (s, 3H), 3.00-3.82 (m, 3H), 1.90-1.80 (m, 2H).

Example-9: Synthesis of (2-(1-(3-cyano-8-methoxyquinolin-4-yl)azetidin-3-yl)ethyl)aminisulfonamide, (Compound 1.9)

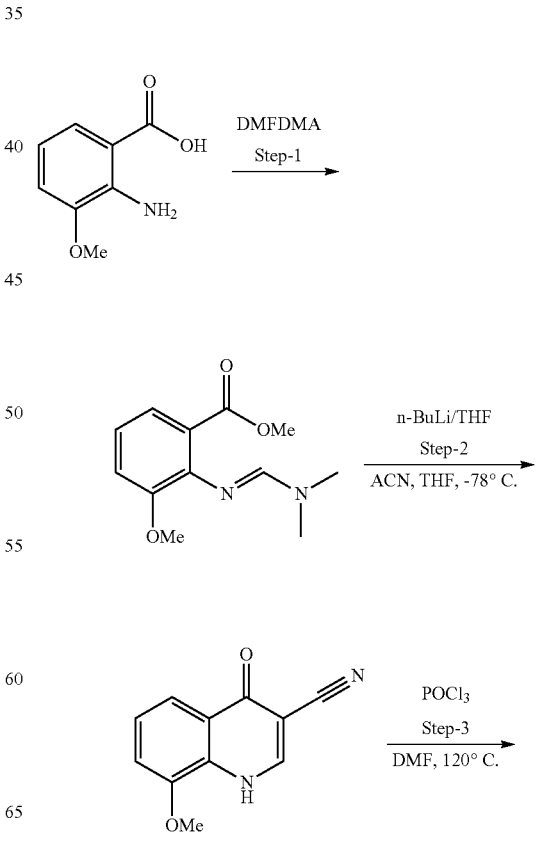

227
-continued

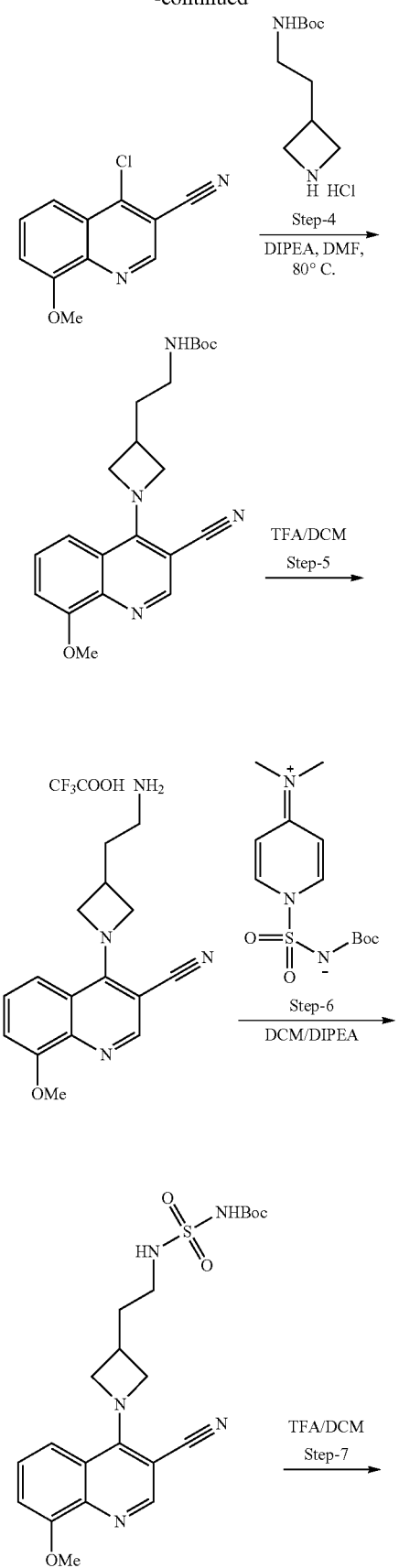

228
-continued

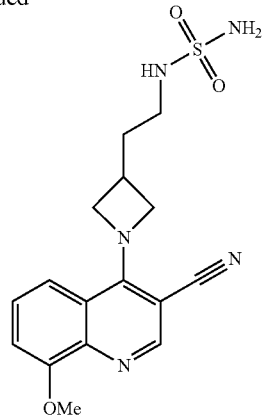

Step-1: Synthesis of 2-amino-3-methoxybenzoic acid: A mixture of 2-amino-3-methoxybenzoic acid (2 g, 11.9 mmol, 1 eq) in DMF-DMA (13.6 mL) was refluxed for 6 h. Reaction mixture was concentrated under reduced pressure at 70° C. to afford crude product which was purified by trituration with hexane at −78° C. to afford (E)-methyl 2-((dimethylamino)methyleneamino)-3-methoxybenzoate (1.4 g, 50%). LCMS: 237 [M+1]⁺

Step-2: Synthesis of 8-methoxy-4-oxo-1,4-dihydroquinoline-3-carbonitrile: To a solution of n-BuLi (2.5 M in hexane, 1.37 mL, 3.4 mmol, 2.71 eq) in THF (2 mL) at −78° C. was added a solution of CH₃CN (0.18 mL, 3.5 mmol, 2.77 eq) in THF (3.5 mL) drop wise over a time period of 10 minute and the resulting mixture was allowed to stir at the same temperature for 15 minutes. To the reaction mixture was then added a solution of (E)-methyl 2-((dimethylamino)methyleneamino)-3-methoxybenzoate (0.3 g, 1.2 mmol, 1 eq) in THF (2.5 mL) over a period of 30 minutes at −78° C., and then allowed to stir at the same temperature for additional 30 minutes. Reaction mixture was treated with acetic acid (0.43 mL) and warmed to room temperature. Solvent was evaporated under reduced pressure, the residue was truturated with cold water (20 mL), filtered and dried under vacuum to afford 8-methoxy-4-oxo-1,4-dihydroquinoline-3-carbonitrile (0.2 g, 79%) as white solid. LCMS: 201[M+1]⁺

Step-3: Synthesis of 4-chloro-8-methoxyquinoline-3-carbonitrile: To stirred solution of 8-methoxy-4-oxo-1,4-dihydroquinoline-3-carbonitrile (0.1 g, 0.49 mmol, 1 eq) in POCl₃ (1 mL) was added DMF (5 drops) and the mixture was allowed to stir at 120° C. for 1 h. Progress of reaction was monitored by TLC. After completion, reaction mixture was cooled to RT, diluted with cold water (100 mL) and triturated. Precipitate was filtered and dried under vacuum to afford 4-chloro-8-methoxyquinoline-3-carbonitrile (30 mg, 28%) as white solid. LCMS: 219 [M+1]⁺

Step-4: Synthesis of tert-butyl 2-(1-(3-cyano-8-methoxyquinolin-4-yl)azetidin-3-yl)ethylcarbamate: A suspension of 4-chloro-8-methoxyquinoline-3-carbonitrile (30 mg, 0.13 mmol, 1 eq), tert-butyl 2-(azetidin-3-yl)ethylcarbamate hydrochloride (35 mg, 0.13 mmol, 1.0 eq) and DIPEA (0.05 mL, 0.27 mmol, 2.0 eq) in DMF (1 mL) was allowed to stir at 80° C. for 2 h. Progress of reaction was monitored by TLC. After completion, reaction mixture was diluted with cold water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(1-(3-cyano-8-methoxyquinolin-4-yl)azetidin-3-yl)ethylcarbamate (0.08 g) which was used in the next step without purification. LCMS: 383 [M+1]+

Step-5: Synthesis of 4-(3-(2-aminoethyl)azetidin-1-yl)-8-methoxyquinoline-3-carbonitrile 2,2,2-trifluoroacetate: To a solution of tert-butyl 2-(1-(3-cyano-8-methoxyquinolin-4-yl)azetidin-3-yl)ethylcarbamate (80 mg, 0.2 mmol, 1 eq) in DCM (4 mL) was added TFA (3 mL) and the mixture was allowed to stir at RT for 1 h. Progress of reaction was monitored by TLC. After completion, reaction mixture was concentrated under reduced pressure to afford 4-(3-(2-aminoethyl)azetidin-1-yl)-8-methoxyquinoline-3-carbonitrile 2,2,2-trifluoroacetate (0.15 g) which was used in the next step without purification. LCMS: 283 [M+1]+

Step-6: Synthesis of tert-butyl N-(2-(1-(3-cyano-8-methoxyquinolin-4-yl)azetidin-3-yl)ethyl)sulfamoylcarbamate: To a solution of 4-(3-(2-aminoethyl)azetidin-1-yl)-8-methoxyquinoline-3-carbonitrile 2,2,2-trifluoroacetate (150 mg, 0.37 mmol, 1 eq) in dichloromethane (25 ML) were added N-(tert-butoxycarbonyl)-N-[4-(dimethylazaniumylidene)-1,4-dihydropyridin-1ylsulfonyl]azanide (171 mg. 0.55 mmol, 1.5 eq) and N,N-diisopropylethylamine (0.28 mL, 1.48 mmol, 4 eq) and the reaction mixture was allowed to stir at RT for 48 h. Progress of reaction was monitored by LCMS. After completion, reaction mixture was concentrated under reduced pressure to get residue which was purified by reversed phase HPLC to afford tert-butyl N-(2-(1-(3-cyano-8-methoxyquinolin-4-yl)azetidin-3-yl)ethyl)sulfamoylcarbamate (30 mg, 17%). LCMS: 462 [M+1]+

Step-7: Synthesis of (2-(1-(3-cyano-8-methoxyquinolin-4-yl)azetidin-3-yl)ethyl)aminisulfonamide: To a solution of tert-butyl N-(2-(1-(3-cyano-8-methoxyquinolin-4-yl)azetidin-3-yl)ethyl)sulfamoylcarbamate (30 mg, 0.06 mmol, 1 eq) in DCM (2 mL) was added TFA (0.5 mL) and allowed to stir at RT for 1 h. Progress of reaction was monitored by TLC. After completion, reaction mixture was concentrated under reduced pressure to afford crude which was triturated using diethyl ether to afford desired compound as TFA salt which was basified using 7 N $NH_3$ in methanol to afford (2-(1-(3-cyano-8-methoxyquinolin-4-yl)azetidin-3-yl)ethyl)aminisulfonamide (27 mg). LCMS: 362 [M+1]+; $^1$H NMR (400 MHz, DMSO-d6) δ ppm 8.39 (s, 1H), 7.71 (d, 1H), 7.39 (t, 1H), 7.24 (d, 1H), 6.58-6.47 (m, 3H), 4.90-4.80 (m, 2H), 4.46-4.38 (m, 2H), 3.88 (s, 3H), 2.90-2.88 (m, 3H), 1.88-1.78 (m, 2H).

Example-10: Synthesis of N-((1-(6,7-dimethoxyquinazolin-4-yl)azetidin-3-yl)methyl) aminisulfonamide, (Compound 1.10)

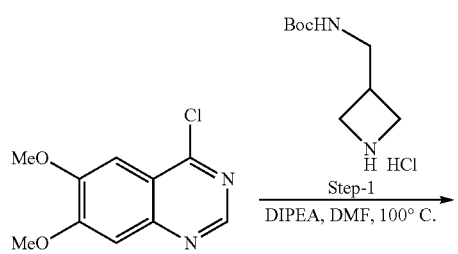

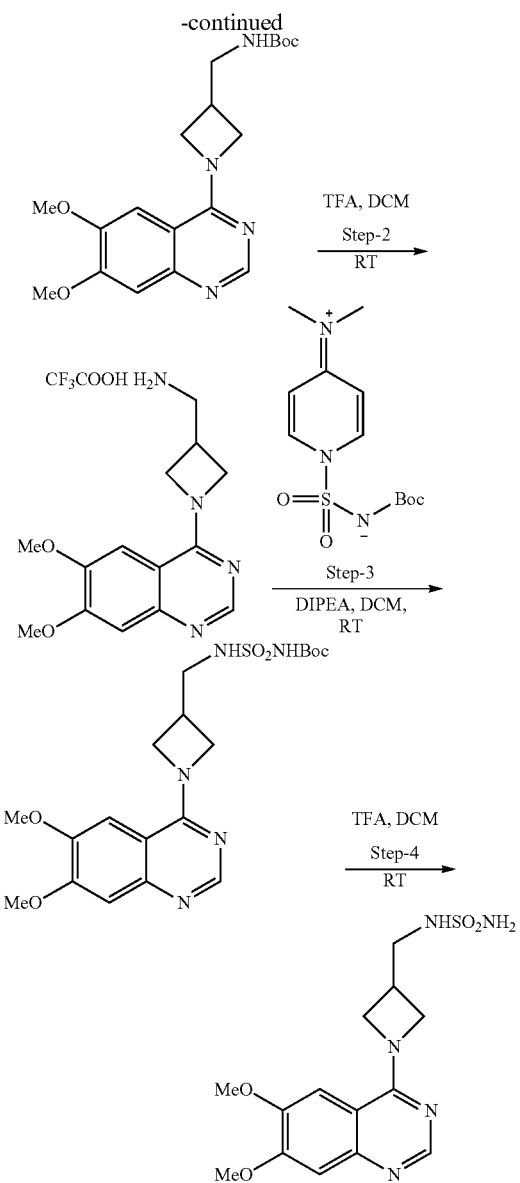

Step-1: Synthesis of tert-butyl (1-(6,7-dimethoxyquinazolin-4-yl)azetidin-3-yl)methylcarbamate: A suspension of 4-chloro-6,7-dimethoxyquinazoline (50 mg, 0.22 mmol, 1.0 eq), tert-butyl azetidin-3-ylmethylcarbamate hydrochloride (50 mg, 0.22 mmol, 1.0 eq) and N, N-Diisopropylethylamine (57 mg, 0.44 mmol, 2.0 eq) in DMF (1 mL) was allowed to stir at 80° C. for 2 h. Progress of reaction was monitored by TLC. After completion, reaction mixture was diluted with water (10 mL) and extracted with ethyl acetate (3×25 mL). Combined organic layer was washed with water (5×50 mL) followed by brine (50 mL) and dried over anhydrous sodium sulfate. Removal of solvent under reduced pressure afforded tert-butyl (1-(6,7-dimethoxyquinazolin-4-yl)azetidin-3-yl)methylcarbamate which was used in the next step without purification (83 mg, 100%). LCMS: 374 [M+1]+

Step-2: Synthesis of (1-(6,7-dimethoxyquinazolin-4-yl)azetidin-3-yl)methanamine 2,2,2-trifluoroacetate: To a solution of tert-butyl (1-(6,7-dimethoxyquinazolin-4-yl)azetidin-3-yl)methylcarbamate (83 mg, 0.22 mmol, 1 eq) in DCM (5 mL) was added TFA (1 mL) and the mixture was allowed to stir at RT for 2 h. Progress of reaction was monitored by TLC. After completion, reaction mixture was concentrated under reduced pressure to get crude which was triturated with diethyl ether (10 mL) to afford (1-(6,7-dimethoxyquinazolin-4-yl)azetidin-3-yl)methanamine 2,2,2-trifluoroacetate (80 mg, 93%). LCMS: 274[M+1]$^+$ Step-3: Synthesis of tert-butyl N-((1-(6,7-dimethoxyquinazolin-4-yl)azetidin-3-yl)methyl)sulfamoylcarbamate: To a solution of 1-(6,7-dimethoxyquinazolin-4-yl)azetidin-3-yl)methanamine 2,2,2-trifluoroacetate (80 mg, 0.20 mmol, 1 eq) in dichloromethane (5 mL) were added N-(tert-butoxycarbonyl)-N-[4-(dimethylazaniumylidene)-1,4-dihydropyridin-1ylsulfonyl]azanide (93 mg. 0.30 mmol, 1.5 eq) and N,N-diisopropylethylamine (51.6 mg, 0.40 mmol, 2 eq) and the reaction mixture was allowed to stir at RT for 24 h. Progress of reaction was monitored by LCMS. After completion, solvent was removed under reduced pressure to afford crude which was purified by reversed phase HPLC to tert-butyl N-((1-(6,7-dimethoxyquinazolin-4-yl)azetidin-3-yl)methyl)sulfamoylcarbamate (18 mg, 20%). LCMS: 454 [M+1]$^+$ Step-4: Synthesis of N-((1-(6,7-dimethoxyquinazolin-4-yl)azetidin-3-yl)methyl) aminisulfonamide: To a solution of tert-butyl N-((1-(6,7-dimethoxyquinazolin-4-yl)azetidin-3-yl)methyl)sulfamoylcarbamate (9 mg, 0.02 mmol, 1 eq) in DCM (3 mL) was added TFA (0.5 mL) and the resulting mixture was allowed to stir at RT for 2 h. Progress of reaction was monitored by TLC. After completion, reaction mixture was concentrated under reduced pressure to afford crude which was purified by trituration with ether and pentane to afford (1-(6,7-dimethoxyquinazolin-4-yl)azetidin-3-yl)methylaminosulfonamide (50 mg, 71%). LCMS: 354 [M+1]$^+$; $^1$H NMR (400 MHz, DMSO-d$_6$) δ ppm 14.00 (brs, 1H), 8.61 (s, 1H), 7.28 (s, 1H), 7.16 (s, 1H), 6.85 (brs, 1H), 6.62 (brs, 2H), 5.00-4.20 (m, 4H), 3.96 (s, 3H), 3.94 (s, 3H), 3.30-3.18 (m, 2H), 3.10-2.98 (m, 1H).

Example-11: Synthesis of (2-(1-(6,7-dimethoxyquinolin-4-yl)azetidin-3-yl)ethyl)aminosulfonamide, (Compound 1.11)

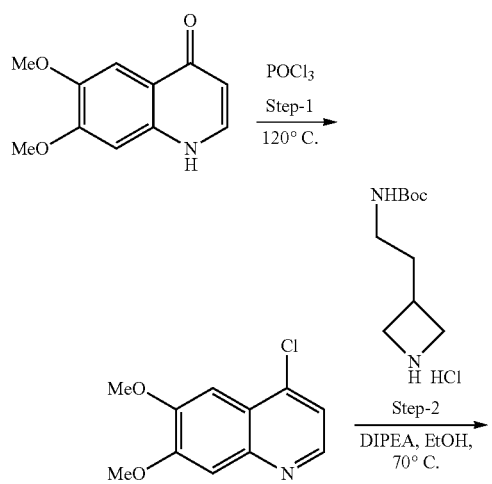

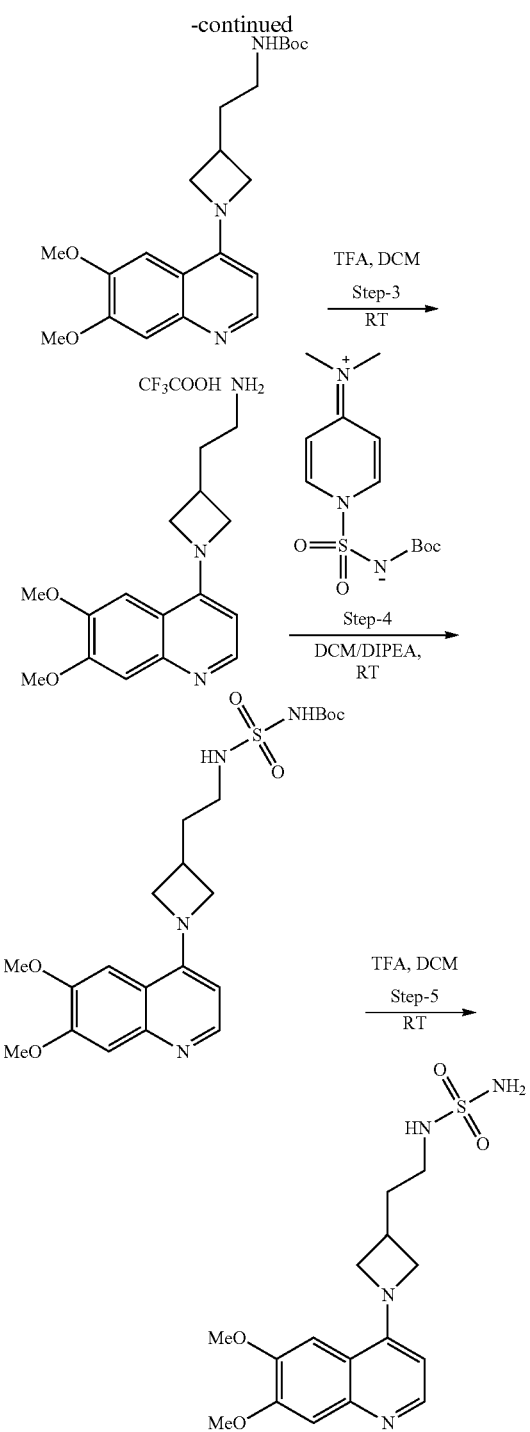

Step-1: Synthesis of 4-chloro-6,7-dimethoxyquinoline: A mixture of 6,7-dimethoxyquinolin-4 (1H)-one (1 g, 4.87 mmol, 1 eq) in POCl$_3$ (2 mL) was allowed to stir at 120° C. for 12 h. Progress of reaction was monitored by TLC. After completion, reaction mixture poured on crushed ice and extracted with ethyl acetate (3×50 mL). Combined organic layer was washed with brine (20 mL) and dried over anhydrous sodium sulfate. Solvent was removed under reduced pressure to afford 4-chloro-6,7-dimethoxyquinoline (500 mg, 46%). LCMS: 224 [M+1]$^+$ Step-2: Synthesis of tert-butyl 2-(1-(6,7-dimethoxyquinolin-4-yl)azetidin-3-yl)ethylcarbamate: A suspension of 4-chloro-6,7-dimethoxyquinoline (50 mg, 0.22 mmol, 1.0 eq), tert-butyl 2-(azetidin-3-yl)ethylcarbamate hydrochloride (53 mg, 0.22 mmol, 1.0 eq) and N,N-diisopropylethylamine (56 mg, 0.44 mmol, 2.0 eq) in ethanol (1 mL) was allowed to stir at 70° C. for 48 h. Progress of reaction was monitored by TLC After completion, reaction mixture was removed under reduced pressure to afford tert-butyl 2-(1-(6,7-dimethoxyquinolin-4-yl)azetidin-3-yl)ethylcarbamate which is carried further without purification (50 mg, 58%). LCMS: 387 [M+1]+

Step-3: Synthesis of 2-(1-(6,7-dimethoxyquinolin-4-yl)azetidin-3-yl)ethanamine 2,2,2-trifluoroacetate: To a solution of tert-butyl 2-(1-(6,7-dimethoxyquinolin-4-yl)azetidin-3-yl)ethylcarbamate (50 mg, 0.13 mmol, 1 eq) in DCM (2.5 mL) was added TFA (1 mL) and the mixture was allowed to stir at RT for 2 h. Progress of reaction was monitored by TLC. After completion, reaction mixture was concentrated under reduced pressure to get residue which was triturated with diethyl ether (10 mL) to afford 2-(1-(6,7-dimethoxyquinolin-4-yl)azetidin-3-yl)ethanamine 2,2,2-trifluoroacetate (50 mg, 96%). LCMS:287[M+1]+

Step-4: Synthesis of tert-butyl N-(2-(1-(6,7-dimethoxyquinolin-4-yl)azetidin-3-yl)ethyl)sulfamoylcarbamate: To a solution of 2-(1-(6,7-dimethoxyquinolin-4-yl)azetidin-3-yl) ethanamine 2,2,2-trifluoroacetate (50 mg, 0.12 mmol, 1 eq) in dichloromethane (5 mL) were added N-(tert-butoxycarbonyl)-N-[4-(dimethylazaniumylidene)-1,4-dihydropyridin-1ylsulfonyl]azanide (37 mg. 0.12 mmol, 1.5 eq) and N,N-diisopropylethylamine (31 mg, 0.24 mmol, 2 eq) and the reaction mixture was allowed to stir at RT for 24 h. Progress of reaction was monitored by LCMS. After completion, solvent was removed under reduced pressure to afford crude which was purified by reversed phase HPLC to afford tert-butyl N-(2-(1-(6,7-dimethoxyquinolin-4-yl)azetidin-3-yl)ethyl)sulfamoylcarbamate (18 mg, 32%). LCMS: 467 [M+1]+

Step-5: Synthesis of (2-(1-(6,7-dimethoxyquinolin-4-yl)azetidin-3-yl)ethyl)aminosulfonamide: To a solution of tert-butyl N-(2-(1-(6,7-dimethoxyquinolin-4-yl)azetidin-3-yl) ethyl)sulfamoylcarbamate (17 mg, 0.036 mmol, 1 eq) in DCM (3 mL) was added TFA (0.5 mL) and the resulting mixture was allowed to stir at RT for 2 h. Progress of reaction was monitored by TLC. After completion, reaction mixture was concentrated under reduced pressure to afford crude which was purified by reversed phase HPLC to afford (2-(1-(6,7-dimethoxyquinolin-4-yl)azetidin-3-yl)ethyl)aminosulfonamide as TFA salt (10 mg, 56%). LCMS: 367 [M+1]+; 1H NMR (400 MHz, DMSO-d6) δ ppm 13.28 (brs, 1H), 8.27 (d, s 1H), 7.39 (s, 1H), 7.25 (s, 1H), 6.60 (brs, 1H), 6.55 (s, 2H), 6.31 (d, 1H), 5.17 (brs, 1H), 4.74 (brs, 1H), 4.45 (brs, 1H), 4.02 (brs, 1H), 3.95 (s, 6H), 3.03-2.90 (m, 3H), 1.90-1.81 (m, 2H).

Example-12: Synthesis of (2-(1-(3-cyano-6,7-dimethoxyquinolin-4-yl)azetidin-3-yl)ethyl)aminisulfonamide, (Compound 1.12)

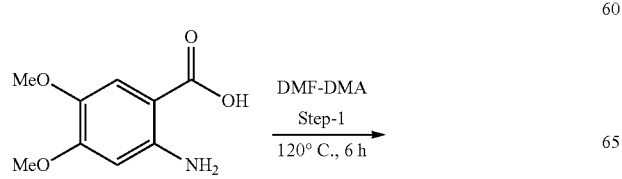

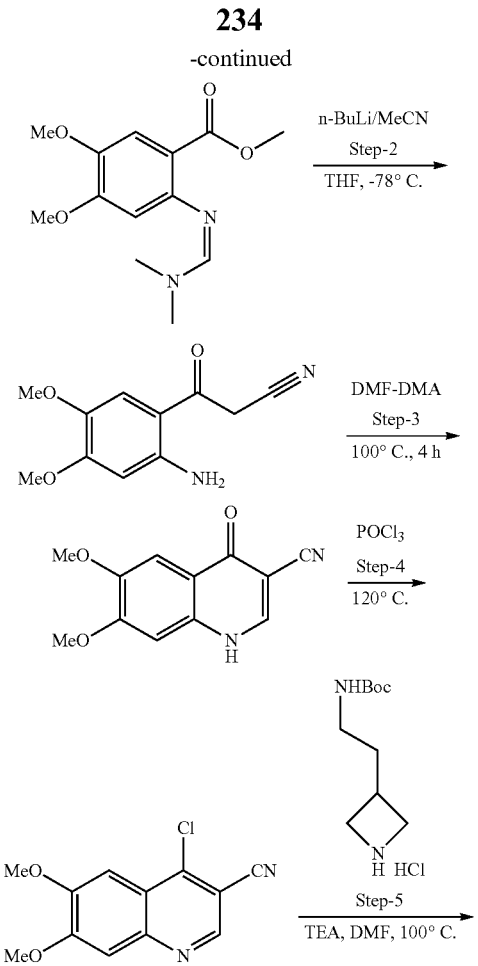

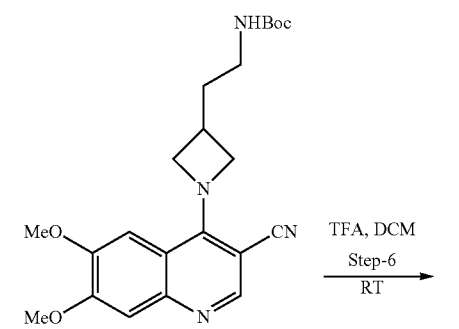

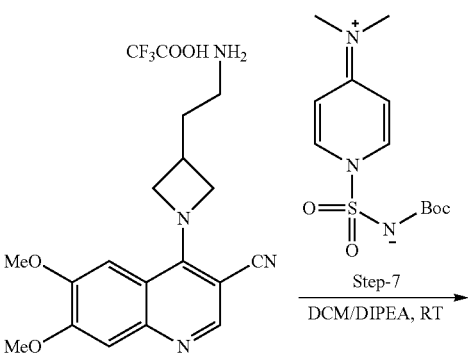

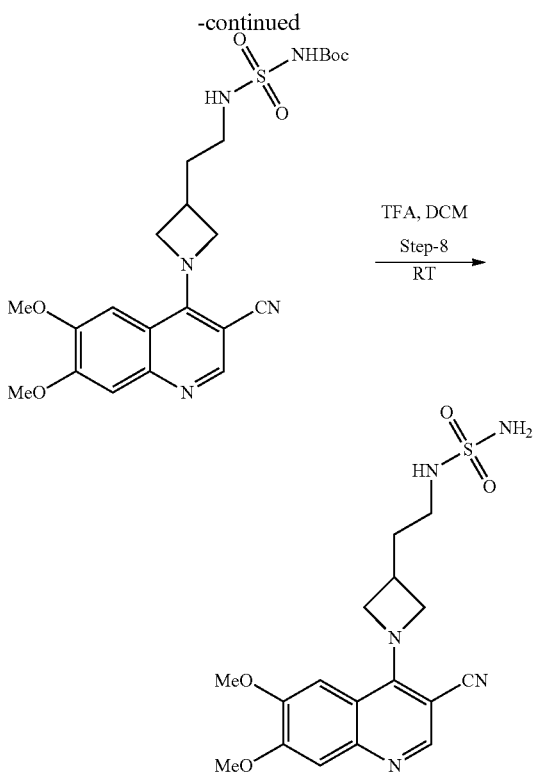

Step-1: Synthesis of (Z)-methyl 2-((dimethylamino)methyleneamino)-4,5-dimethoxybenzoate: A mixture of 2-amino-4,5-dimethoxybenzoic acid (2 g, 100 mol, 1 eq) in DMF-DMA (12 mL) was allowed to stir at 120° C. for 6 h. Progress of reaction was monitored by TLC. After completion, reaction mixture was cooled to RT, concentrated under reduced pressure at 70° C. to get crude residue which was purified by trituration with pentane to afford (Z)-methyl 2-((dimethylamino)methyleneamino)-4,5-dimethoxybenzoate (1.8 g, 68%).

Step-2: Synthesis of 3-(2-amino-4,5-dimethoxyphenyl)-3-oxopropanenitrile: To a solution of 2.5 M n-BuLi in THF (1.7 mL, 4.25 mmol, 2.2 eq) in THF (10 mL) at −78° C. was added a solution of MeCN (0.25 mL, 4.25 mmol, 2.2 eq) in THF (5 mL) drop wise and the resulting mixture was allowed to stir at the same temperature for 10 minutes. To the mixture was then added a solution of (Z)-methyl 2-((dimethylamino)methyleneamino)-4,5-dimethoxybenzoate (500 mg, 1.9 mmol, 1 eq) in THF (10 mL) and the mixture was allowed to stir at −78° C. for 2.5 h. To the reaction mixture was added acetic acid (0.6 mL), the reaction mixture was gradually warmed to RT and allowed to stir overnight. Reaction mixture was filtered, solid was dried to get crude which was purified by Combi-Flash on silica gel using ethyl acetate-hexane system as eluent to afford 3-(2-amino-4,5-dimethoxyphenyl)-3-oxopropanenitrile (200 mg, 48%).

Step-3: Synthesis of 6,7-dimethoxy-4-oxo-1,4-dihydroquinoline-3-carbonitrile: To a solution of 3-(2-amino-4,5-dimethoxyphenyl)-3-oxopropanenitrile (200 mg, 0.90 mmol, 1 eq) in dioxane (5 mL) was added DMF-DMA (0.25 mL, 1.8 mmol, 2 eq) and the resulting mixture was allowed to stir at 100° C. for 4 h. Progress of reaction was monitored by TLC. After completion, reaction mixture was cooled to RT and concentrated under reduced pressure at 70° C. to afford crude which was purified by trituration with diethyl ether to afford 6,7-dimethoxy-4-oxo-1,4-dihydroquinoline-3-carbonitrile (100 mg, 48%). LCMS: 231[M+1]$^+$ Step-4: Synthesis of 4-chloro-6,7-dimethoxyquinoline-3-carbonitrile: A mixture of 6,7-dimethoxy-4-oxo-1,4-dihydroquinoline-3-carbonitrile (100 mg 0.43 mmol, 1 eq) in POCl$_3$ (0.5 mL) was allowed to stir at 120° C. for 12 h. Progress of reaction was monitored by TLC. After completion, reaction mixture was diluted with ice-cold water (100 mL) and extracted with ethyl acetate (3×20 mL). Combined organic layer was washed with water (3×50 mL) followed by brine (20 mL) and dried over anhydrous sodium sulfate. Solvent was removed under reduced pressure afforded 4-chloro-6,7-dimethoxyquinoline-3-carbonitrile (80 mg, 74.76%). LCMS: 248 [M+1]$^+$ Step-5: Synthesis of tert-butyl 2-(1-(3-cyano-6,7-dimethoxyquinolin-4-yl)azetidin-3-yl)ethylcarbamate: A suspension of 4-chloro-6,7-dimethoxyquinoline-3-carbonitrile (50 mg, 0.20 mmol, 1.0 eq), tert-butyl 2-(azetidin-3-yl)ethylcarbamate hydrochloride (47.5 mg, 0.20 mmol, 1.0 eq) and N,N-diisopropylethylamine (51.6 mg, 0.40 mmol, 2.0 eq) in DMF (1 mL) was allowed to stir at 80° C. for 2 h. Progress of reaction was monitored by TLC. After completion, reaction mixture was diluted with water (10 mL) and extracted with ethyl acetate (3×25 mL). Combined organic layer was washed with brine (50 mL) and dried over anhydrous sodium sulfate. Removal of solvent under reduced pressure gave tert-butyl 2-(1-(3-cyano-6,7-dimethoxyquinolin-4-yl)azetidin-3-yl)ethylcarbamate (80 mg, 100%). LCMS: 374 [M+1]$^+$ Step-6: Synthesis of 4-(3-(2-aminoethyl)azetidin-1-yl)-6,7-dimethoxyquinoline-3-carbonitrile 2,2,2-trifluoroacetate: To a solution of tert-butyl 2-(1-(3-cyano-6,7-dimethoxyquinolin-4-yl)azetidin-3-yl)ethylcarbamate (80 mg, 0.19 mmol, 1 eq) in DCM (5 mL) was added TFA (2 mL) and the mixture was allowed to stir at RT for 2 h. Progress of reaction was monitored by TLC. After completion, reaction mixture was concentrated under reduced pressure to get crude, which was triturated with diethyl ether (10 mL) to afford 4-(3-(2-aminoethyl)azetidin-1-yl)-6,7-dimethoxyquinoline-3-carbonitrile 2,2,2-trifluoroacetate (80 mg, 97%). LCMS: 312[M+1]$^+$ Step-7: Synthesis of tert-butyl N-(2-(1-(3-cyano-6,7-dimethoxyquinolin-4-yl)azetidin-3-yl)ethyl)sulfamoylcarbamate: To a solution of 4-(3-(2-aminoethyl)azetidin-1-yl)-6,7-dimethoxyquinoline-3-carbonitrile 2,2,2-trifluoroacetate (80 mg, 0.18 mmol, 1 eq) in dichloromethane (5 ML) were added N-(tert-butoxycarbonyl)-N-[4-(dimethylazaniumylidene)-1,4-dihydropyridin-1ylsulfonyl]azanide (84 mg. 0.30 mmol, 1.5 eq) and N,N-diisopropylethylamine (46 mg, 0.36 mmol, 2 eq) and the reaction mixture was allowed to stir at RT for 24 h. Progress of reaction was monitored by LCMS. After completion, solvent was removed under reduced pressure to afford crude which was purified by reversed phase HPLC to tert-butyl N-(2-(1-(3-cyano-6,7-dimethoxyquinolin-4-yl)azetidin-3-yl)ethyl)sulfamoylcarbamate (10 mg, 10%). LCMS: 492[M+1]$^+$ Step-8: Synthesis of (2-(1-(3-cyano-6,7-dimethoxyquinolin-4-yl)azetidin-3-yl)ethyl)aminisulfonamide: To a solution of tert-butyl N-(2-(1-(3-cyano-6,7-dimethoxyquinolin-4-yl)azetidin-3-yl)ethyl)sulfamoylcarbamate (9 mg, 0.018 mmol, 1 eq) in DCM (3 mL) was added TFA (0.5 mL) and the resulting mixture was allowed to stir at RT for 2 h. Progress of reaction was monitored by TLC. After completion, reaction mixture was concentrated under reduced pressure to afford crude which was triturated with diethyl ether to afford (2-(1-(3-cyano-6,7-dimethoxyquinolin-4-yl)azetidin-3-yl)ethyl)aminisulfonamide (5 mg, 55%). LCMS: 392 [M+1]$^+$;

¹H NMR (400 MHz, DMSO-d₆) δ ppm 8.80 (s, 1H), 7.42 (s, 1H), 7.17 (s, 1H), 6.60 (brs, 1H), 6.55 (s, 2H), 5.20-5.02 (m, 2H), 4.78-4.42 (m, 2H), 3.99 (s, 3H), 3.98 (s, 3H), 3.00-2.83 (m, 3H), 1.96-1.83 (m, 2H).

Example-13: Synthesis of 4-(3-(2-sulfamoylaminoethyl)azetidin-1-yl)-7-methoxyquinoline-3-carbonitrile, (Compound 1.13)

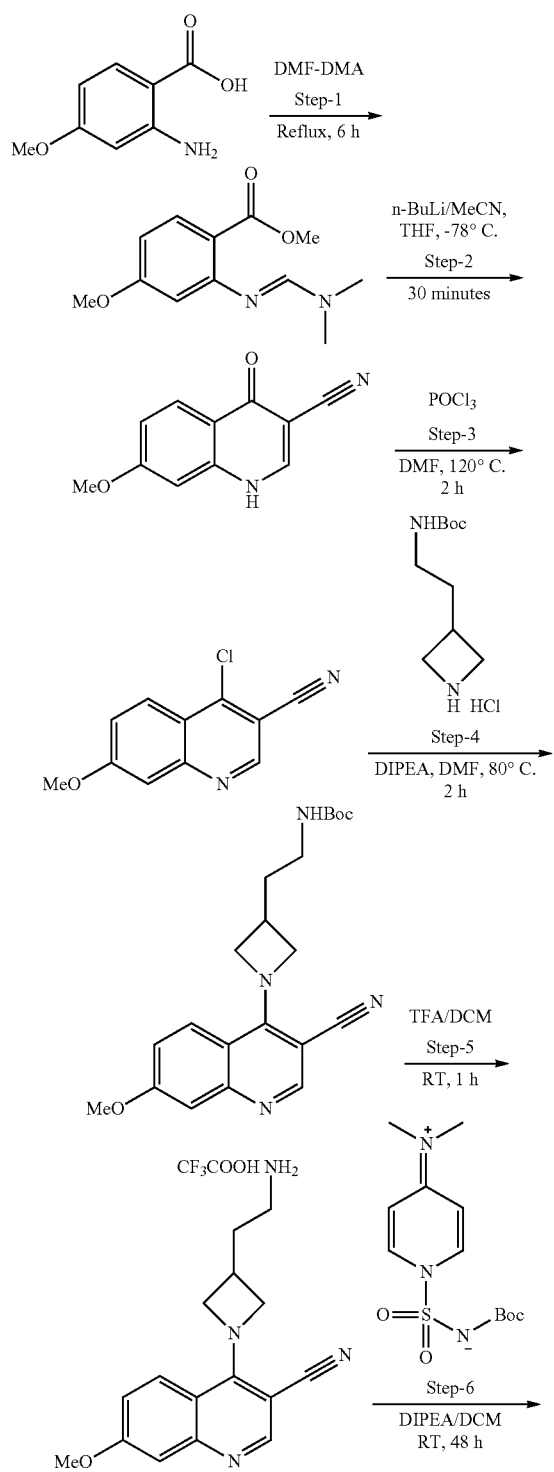

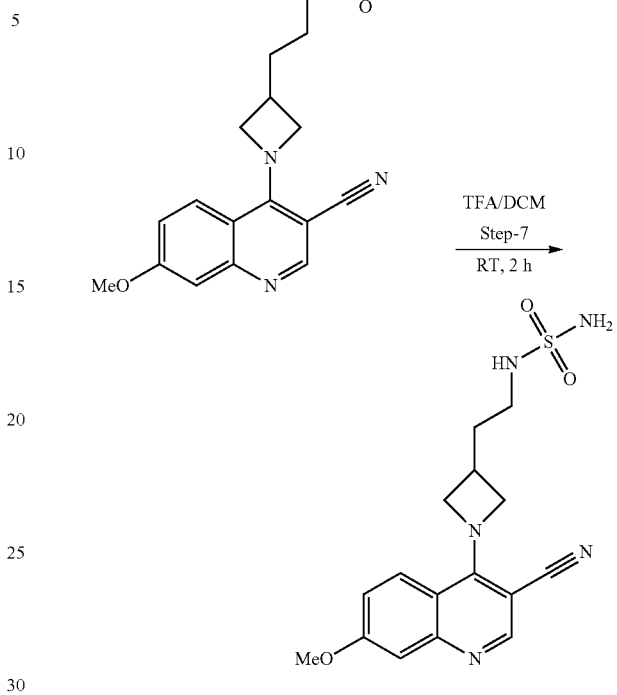

Step-1: Synthesis of (E)-methyl 2-((dimethylamino)methyleneamino)-4 methoxybenzoate: A mixture of (E)-methyl 2-((dimethylamino)methyleneamino)-4-methoxybenzoate (2 g, 11.9 mmol, 1 eq) in DMF-DMA (13.6 mL) was refluxed for 6 h. Progress of reaction was monitored by TLC. After completion, reaction mixture was concentrated under reduced pressure at 70° C. to afford oily crude which was purified by trituration with hexane at −78° C. to afford (E)-methyl 2-((dimethylamino)methyleneamino)-4-methoxybenzoate (1.4 g, 50%). LCMS: 237 [M+1]⁺

Step-2: Synthesis of 7-methoxy-4-oxo-1,4-dihydroquinoline-3-carbonitrile: To a solution of a solution n-BuLi (2.5 M in hexane, 1.37 mL, 3.4 mmol, 2.71 eq) in THF (2 mL) at −78° C. was added a solution of CH₃CN (0.18 mL, 3.5 mmol, 2.77 eq) in THF (3.5 mL) drop wise over a period of 10 minutes. The white suspension formed was then stirred for 15 minutes. To the suspension was added a solution of (E)-methyl 2-((dimethylamino)methyleneamino)-4-methoxybenzoate (0.3 g, 1.2 mmol, 1 eq) of THF (2.5 mL) over a period of 30 minutes. The resulting mixture was then allowed to stir at −78° C. for additional 30 minutes. During this period, the mixture gradually became clear. To the mixture was then added acetic acid (0.43 mL) and the thick slurry formed was stirred and warmed to room temperature. Reaction mixture was concentrated under vacuum and residue was diluted with cold water (50 mL). Solid was collected by filtration, washed with water and dried under vacuum to afford 7-methoxy-4-oxo-1,4-dihydroquinoline-3-carbonitrile (0.08 g, 31%) as white solid. LCMS: 201 [M+1]⁺

Step-3: Synthesis of 4-chloro-7-methoxyquinoline-3-carbonitrile: To a solution of 7-methoxy-4-oxo-1,4-dihydroquinoline-3-carbonitrile (0.1 g, 0.49 mmol, 1 eq) in POCl₃ (1 mL) was added DMF (5 drops) and the mixture was allowed to stir at 120° C. for 2 h. Progress of reaction was monitored by TLC. After completion, reaction mixture was cooled to RT, diluted with cold water (100 mL) and filtered. Solid was dried under vacuum to afford 4-chloro-7-methoxyquinoline-3-carbonitrile (60 mg, 60%) as white solid. LCMS: 219 [M+1]$^+$ Step-4: Synthesis of tert-butyl 2-(1-(3-cyano-7-methoxyquinolin-4-yl)azetidin-3-yl)ethylcarbamate: A mixture of 4-chloro-7-methoxyquinoline-3-carbonitrile (46 mg, 0.21 mmol, 1 eq), tert-butyl 2-(azetidin-3-yl)ethylcarbamate hydrochloride (50 mg, 0.21 mmol, 1.0 eq) and DIPEA (0.07 mL, 0.42 mmol, 2.0 eq) in DMF (2 mL) was allowed to stir at 80° C. for 2 h. Progress of reaction was monitored by TLC. After completion, reaction mixture was diluted with cold water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(1-(3-cyano-7-methoxyquinolin-4-yl)azetidin-3-yl)ethylcarbamate (0.12 g, crude) which was used in the next step without purification. LCMS: 383 [M+1]$^+$ Step-5: Synthesis 4-(3-(2-aminoethyl)azetidin-1-yl)-7-methoxyquinoline-3-carbonitrile 2,2,2-trifluoroacetate: To a solution of tert-butyl 2-(1-(3-cyano-7-methoxyquinolin-4-yl)azetidin-3-yl)ethylcarbamate (120 mg, 0.3 mmol, 1 eq) in DCM (4 mL) was added TFA (3 mL) and the resulting mixture was allowed to stir at RT for 1 h. Progress of reaction was monitored by TLC. After completion, reaction mixture was concentrated under reduced pressure to get 4-(3-(2-aminoethyl)azetidin-1-yl)-7-methoxyquinoline-3-carbonitrile 2,2,2-trifluoroacetate (0.15 g) which was used in the next step without purification. LCMS: 283 [M+1]$^+$ Step-6: Synthesis of tert-butyl N-(2-(1-(3-cyano-7-methoxyquinolin-4-yl)azetidin-3-yl)ethyl)sulfamoylcarbamate: To a solution of 4-(3-(2-aminoethyl)azetidin-1-yl)-7-methoxyquinoline-3-carbonitrile 2,2,2-trifluoroacetate (150 mg, 0.37 mmol, 1 eq) in dichloromethane (25 ML) were added N-(tert-butoxycarbonyl)-N-[4-(dimethylazaniumylidene)-1,4-dihydropyridin-1ylsulfonyl]azanide (171 mg. 0.55 mmol, 1.5 eq) and N,N-diisopropylethylamine (0.28 mL, 1.48 mmol, 4 eq) and the reaction mixture was allowed to stir at RT for 48 h. Progress of reaction was monitored by LCMS. After completion, reaction mixture was concentrated under reduced pressure to get residue which was purified by reversed phase HPLC to afford tert-butyl N-(2-(1-(3-cyano-7-methoxyquinolin-4-yl)azetidin-3-yl)ethyl)sulfamoylcarbamate (25 mg, 14%). LCMS: 462 [M+1]$^+$ Step-7: Synthesis of 4-(3-(2-sulfamoylaminoethyl)azetidine-1-yl)-7-methoxyquinoline-3-carbonitrile: To a solution of tert-butyl N-(2-(1-(3-cyano-7-methoxyquinolin-4-yl)azetidin-3-yl)ethyl)sulfamoylcarbamate (25 mg, 0.05 mmol, 1 eq) in DCM (2.5 mL) was added TFA (0.5 mL) and the resulting mixture allowed to stir at RT for 2 h. Progress of reaction was monitored by TLC. After completion, reaction mixture was concentrated under reduced pressure to afford crude which was triturated using diethyl ether to afford 4-(3-(2-sulfamoylaminoethyl)azetidine-1-yl)-7-methoxyquinoline-3-carbonitrile (14 mg, 74%) as TFA salt. LCMS: 362 [M+1]$^+$; $^1$H NMR (400 MHz, DMSO-d6) δ ppm 8.46 (s, 1H), 8.02 (d, 1H), 7.22 (s, 1H), 7.10 (d, 2H), 6.60-6.50 (m, 3H), 4.95-4.86 (m, 2H), 4.50-4.40 (m, 2H), 3.90 (s, 3H), 2.95-2.80 (m, 3H), 1.90-1.80 (m, 2H).

Example-14: Synthesis of 4-(3-(2-sulfamoylaminoethyl)azetidine-1-yl)-5-methyl-5H-pyrrolo[3,2-d] pyrimidine, (Compound 1.14)

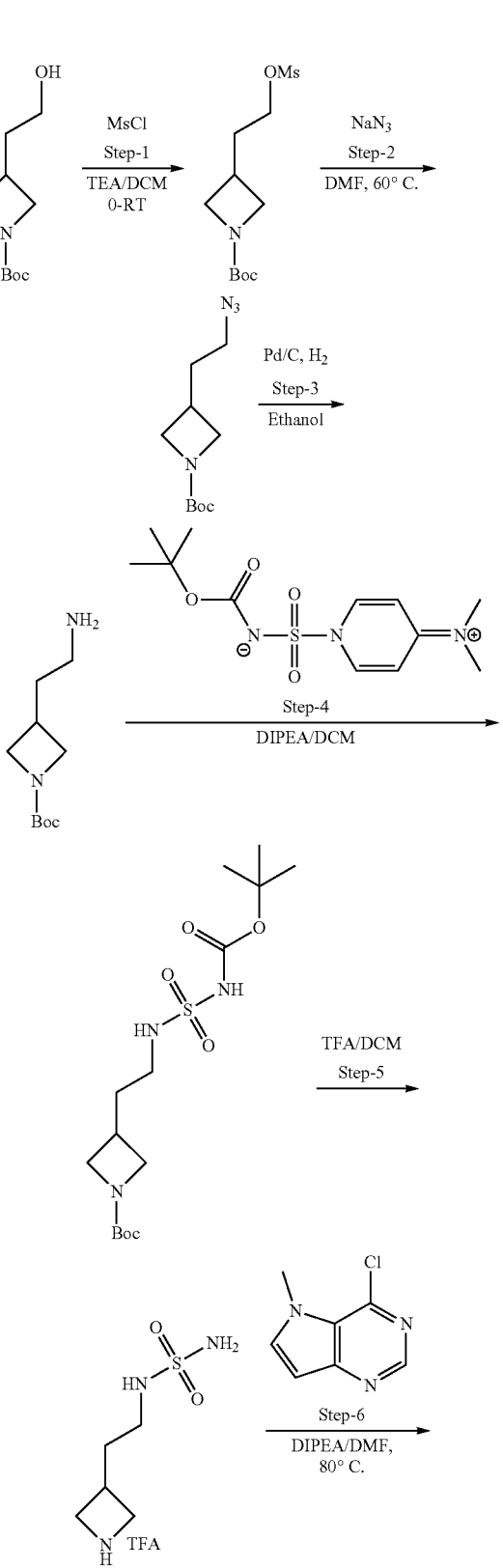

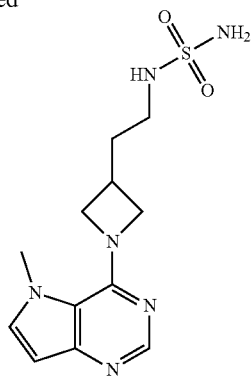

Step-1: Synthesis of tert-butyl 3-(2-(methylsulfonyloxy)ethyl)azetidine-1-carboxylate: To a solution of tert-butyl 3-(2-hydroxyethyl)azetidine-1-carboxylate (2 g, 9.93 mmol, 1 eq) in DCM (50 mL) was added triethylamine (3.4 mL, 24.83 mmol, 2.5 eq) and the reaction mixture was allowed to stir at 0° C. for 5 minutes. To the mixture was added methane sulfonyl chloride (2.27 g, 19.87 mmol, 2 eq) and the reaction mixture to stir at 0° C. for 10 minutes followed by stirring at RT for 2 h. Progress of reaction is monitored by $^1$H NMR. After completion, reaction mixture was diluted with water (100 mL) and extracted with ethyl acetate (3×100 mL). Combined organic layer was washed with brine (150 mL) and dried over anhydrous sodium sulfate. Removal of solvent under reduced pressure afforded tert-butyl 3-(2-(methylsulfonyloxy)ethyl)azetidine-1-carboxylate (3.8 g, Crude) which was used in the next step without purification.

Step-2: Synthesis of tert-butyl 3-(2-azidoethyl)azetidine-1-carboxylate: To a solution of tert-butyl 3-(2-(methylsulfonyloxy)ethyl)azetidine-1-carboxylate (3.7 g, 13.25 mmol, 1 eq) in DMF (30 mL), was added sodium azide (3.4 g, 52.98 mmol, 4 eq) and the reaction mixture was allowed to stir at 60° C. for 2 h. Progress of reaction is monitored by $^1$H NMR. After completion, reaction mixture was diluted with water (100 mL) and extracted with diethyl ether (3×150 mL). Combined organic layer was washed with water (2×100 mL) followed by brine (150 mL) and dried over anhydrous sodium sulfate. Removal of solvent under reduced pressure afforded tert-butyl 3-(2-azidoethyl)azetidine-1-carboxylate (2.9 g, Crude) which was used in the next step without purification.

Step-3: Synthesis of tert-butyl 3-(2-aminoethyl)azetidine-1-carboxylate: To a solution of tert-butyl 3-(2-azidoethyl)azetidine-1-carboxylate (2.9 g, 12.81 mmol, 1 eq) in ethanol (100 mL) was added Pd/C (1.2 g) and the reaction mixture was allowed to stir at RT under H$_2$ atmosphere using balloon for 3 h. Progress of reaction was monitored by TLC. After completion, reaction mixture was filtered through celite-bed. Removal of solvent under reduced pressure afforded crude tert-butyl 3-(2-aminoethyl)azetidine-1-carboxylate (2.5 g, Crude) which was used in the next step without purification.

Step-4: Synthesis of tert-butyl 3-(2-(N-(tert-butoxycarbonyl)sulfamoylamino)ethyl)azetidine-1-carboxylate: To a solution of tert-butyl 3-(2-aminoethyl)azetidine-1-carboxylate (1 g, 4.99 mmol, 1 eq) in dichloromethane (50 mL) were added N-(tert-butoxycarbonyl)-N-[4-(dimethylazanium-ylidene)-1,4-dihydropyridin-1ylsulfonyl]azanide (1.8 mg, 5.99 mmol, 1.2 eq) and N,N-diisopropylethylamine (1.73 mL, 9.98 mmol, 2 eq) and the reaction mixture was allowed to stir at RT for 48 h. Progress of reaction was monitored by TLC. After completion, reaction mixture was concentrated under reduced pressure to get crude which was purified by Combi-Flash using ethyl acetate-hexane system as eluent to afford tert-butyl 3-(2-(N-(tert-butoxycarbonyl)sulfamoylamino)ethyl)azetidine-1-carboxylate (0.45 g, 24%).

Step-5: Synthesis of 3-(2-sulfamoylaminoethyl)azetidine: To a solution of tert-butyl 3-(2-(N-(tert-butoxycarbonyl)sulfamoylamino)ethyl)azetidine-1-carboxylate (0.420 g, 1.11 mmol, 1 eq) in DCM (10 mL) was added TFA (3 mL) and the mixture was allowed to stir at RT for 1.5 h. Progress of reaction was monitored by $^1$H NMR. After completion, reaction mixture was concentrated under reduced pressure to afford crude which was triturated with diethyl ether to afford 3-(2-sulfamoylaminoethyl)azetidine (0.3 g, 98%) as TFA salt.

Step-6: Synthesis of 4-(3-(2-sulfamoylaminoethyl)azetidine-1-yl)-5-methyl-5H-pyrrolo[3,2-d]pyrimidine: A mixture of 4-chloro-5-methyl-5H-pyrrolo[3,2-d]pyrimidine (60 mg, 0.34 mmol, 2 eq), 3-(2-sulfamoylaminoethyl)azetidine trifluoroacetate (50 mg, 0.17 mmol, 1.0 eq) and DIPEA (0.05 mL, 0.34 mmol, 2.0 eq) in DMF (1.5 mL) was allowed to stir at 80° C. for 5 h. Progress of reaction was monitored by TLC. After completion, reaction mixture was concentrated under reduced pressure to get crude which was triturated using diethylether, ethylacetate and ethanol to afford 4-(3-(2-sulfamoylaminoethyl)azetidine-1-yl)-5-methyl-5H-pyrrolo[3,2-d]pyrimidine (7 mg, 13%). LCMS: 311 [M+1]$^+$; $^1$H NMR (400 MHz, DMSO-d6) δ ppm 8.57 (s, 1H), 8.00 (d, 1H), 6.61-6.45 (m, 4H), 4.70-4.58 (m, 2H), 4.25-4.17 (m, 2H), 4.00 (s, 3H), 3.00-2.80 (m, 3H), 1.90-1.80 (m, 2H).

Example-15: Synthesis of 4-(6-sulfamoylamino-2-azaspiro[3.3]heptan-2-yl)-6,7-dimethoxyquinazoline, (Compound 1.15)

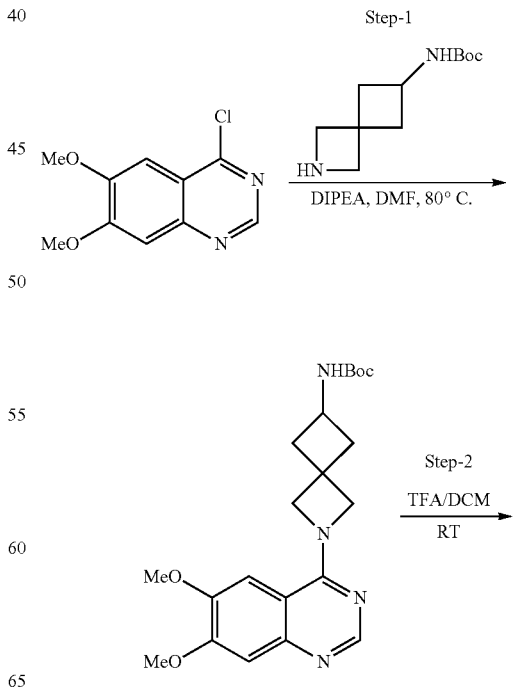

-continued

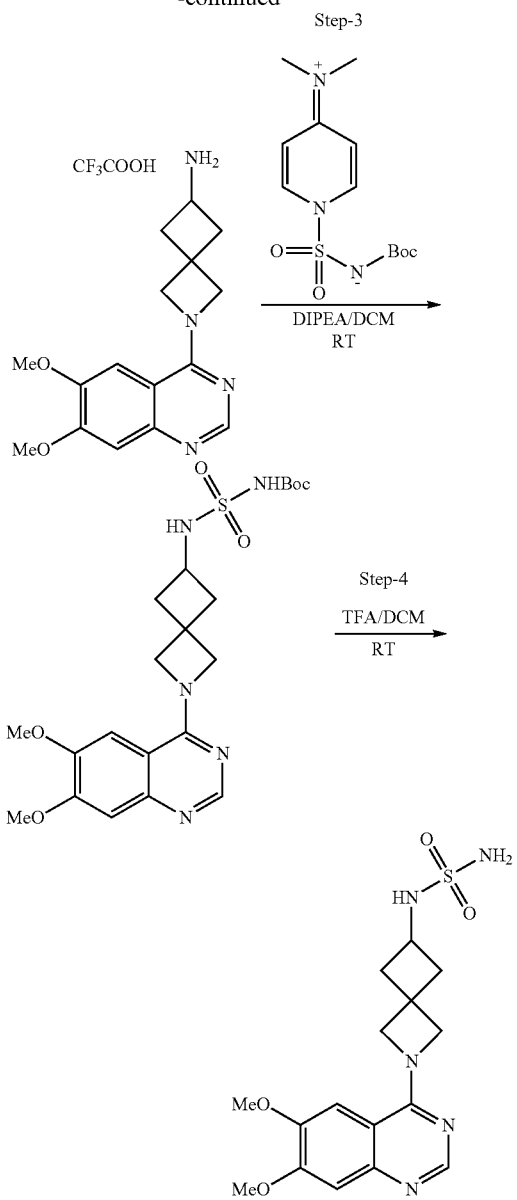

Step-1: Synthesis of tert-butyl 2-(6,7-dimethoxyquinazolin-4-yl)-2-azaspiro[3.3]heptan-6-ylcarbamate: A suspension of 4-chloro-6,7-dimethoxyquinazoline (100 mg, 0.44 mmol, 1.0 eq), tert-butyl 2-azaspiro[3.3]heptan-6-ylcarbamate (90 mg, 0.44 mmol, 1.0 eq) and DIPEA (0.15 mL, 0.88 mmol, 2.0 eq) in DMF (1.5 mL) was allowed to stir at 80° C. for 2 h. Progress of reaction was monitored by TLC. After completion, reaction mixture was diluted with water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(6,7-dimethoxyquinazolin-4-yl)-2-azaspiro[3.3]heptan-6-ylcarbamate (0.12 g, 67%) which was used in the next step without purification. LCMS: 401 [M+1]$^+$ Step-2: Synthesis of 2-(6,7-dimethoxyquinazolin-4-yl)-2-azaspiro[3.3]heptan-6-amine 2,2,2-trifluoroacetate: To a solution of tert-butyl 2-(6,7-dimethoxyquinazolin-4-yl)-2-azaspiro[3.3]heptan-6-ylcarbamate (120 mg, 0.29 mmol, 1 eq) in DCM (4 mL) was added TFA (2.5 mL) and the resulting mixture was allowed to stir at RT for 1 h. Progress of reaction was monitored by TLC. After completion, reaction mixture was concentrated under reduced pressure to afford 2-(6,7-dimethoxyquinazolin-4-yl)-2-azaspiro[3.3]heptan-6-amine 2,2,2-trifluoroacetate (120 mg, 97%) which was used in the next step without purification. LCMS: 301 [M+1]$^+$ Step-3: Synthesis of tert-butyl N-(2-(6,7-dimethoxyquinazolin-4-yl)-2-azaspiro[3.3]heptan-6-yl)sulfamoylcarbamate: To a solution of 2-(6,7-dimethoxyquinazolin-4-yl)-2-azaspiro[3.3]heptan-6-amine 2,2,2-trifluoroacetate (150 mg, 0.36 mmol, 1 eq) in dichloromethane (30 mL) were added N-(tert-butoxycarbonyl)-N-[4-(dimethylazaniumylidene)-1,4-dihydropyridin-1ylsulfonyl]azanide (163 mg. 0.54 mmol, 1.5 eq) and N,N-diisopropylethylamine (0.12 mL, 0.72 mmol, 2 eq) and the reaction mixture was allowed to stir at RT for 16 h. Progress of reaction was monitored by LCMS. After completion, reaction mixture was concentrated under reduced pressure to afford crude product which was purified using reversed phase HPLC to afford tert-butyl N-(2-(6,7-dimethoxyquinazolin-4-yl)-2-azaspiro[3.3]heptan-6-yl)sulfamoylcarbamate (55 mg, 32%). LCMS: 480 [M+1]$^+$ Step-4: Synthesis of 4-(6-sulfamoylamino-2-azaspiro[3.3]heptan-2-yl)-6,7-dimethoxyquinazoline: To a solution of tert-butyl N-(2-(6,7-dimethoxyquinazolin-4-yl)-2-azaspiro[3.3]heptan-6-yl)sulfamoylcarbamate (25 mg, 0.05 mmol, 1 eq) in DCM (3 mL) was added TFA (1 mL) and allowed to stir at RT for 1 h. Progress of reaction was monitored by TLC. After completion, reaction mixture was concentrated under reduced pressure to afford crude which was triturated using diethyl ether and pentane to afford 4-(6-Sulfamoylamino-2-azaspiro[3.3]heptan-2-yl)-6,7-dimethoxyquinazoline (20 mg, 80%) as TFA salt. LCMS: 380 [M+1]$^+$; $^1$H NMR (400 MHz, DMSO-d6) δ ppm 14.20 (brs, 1H), 8.65 (s, 1H), 7.29 (s, 1H), 7.21 (s, 1H), 6.92 (d, 1H), 6.55 (s, 2H), 4.70 (brs, 4H), 4.96 (s, 6H), 3.80-3.60 (m, 1H), 2.70-2.50 (m, 2H), 2.40-2.20 (m, 2H).

Example-16: Synthesis of 4-(3-(2-sulfamoylamino-ethyl)azetidine-1-yl)-6-methoxyquinazoline, (Compound 1.16)

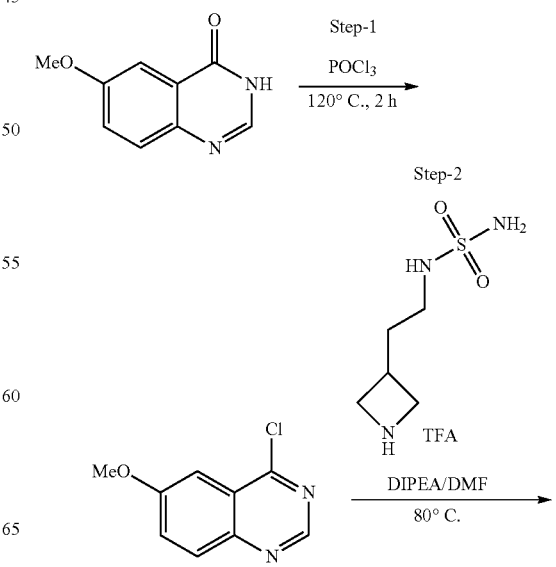

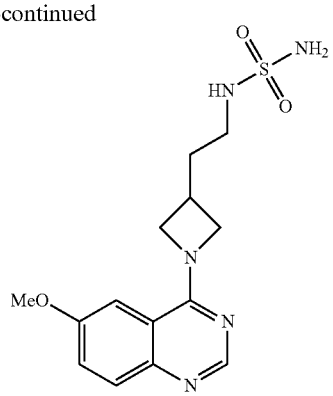

Step-1: Synthesis of 4-chloro-6-methoxyquinazoline: A mixture of 6-methoxyquinazolin-4 (3H)-one (0.2 g, 1.1 mmol, 1 eq) in POCl$_3$ (2 mL) was allowed to stir at 120° C. for 2 h. Progress of reaction was monitored by TLC. After completion, reaction mixture was cooled to RT, diluted with cold water (100 mL) and extracted with ethyl acetate (3×100 mL). Combined organic layer was washed with water (3×50 mL) and dried over anhydrous sodium sulfate. Removal of solvent under reduced pressure afforded 6-methoxyquinazolin-4 (3H)-one (0.15 g, 68%) which was used in the next step without purification. LCMS: 195 [M+1]$^+$ Step-2: Synthesis of 4-(3-(2-sulfamoylaminoethyl)azetidine-1-yl)-6-methoxyquinazoline: A suspension of 6-methoxyquinazolin-4 (3H)-one (70 mg, 0.34 mmol, 2 eq), 3-(2-sulfamoylaminoethyl)azetidine trifluoroacetate (50 mg, 0.17 mmol, 1.0 eq) and DIPEA (0.06 mL, 0.34 mmol, 2.0 eq) in DMF (1 mL) was allowed to stir at 80° C. for 5 h. Progress of reaction was monitored by TLC. After completion, reaction mixture was concentrated under reduced pressure to afford residue which was triturated with ether, ethyl acetate and then pentane to get crude which was purified by reversed phase HPLC to afford 4-(3-(2-sulfamoylaminoethyl)azetidine-1-yl)-6-methoxyquinazoline (7 mg, 12%). LCMS: 338 [M+1]$^+$; $^1$H NMR (400 MHz, DMSO-d6) δ ppm 8.37 (s, 1H), 7.66 (d, 1H), 7.42 (d, 1H), 7.24 (s, 1H), 6.59 (brs, 1H), 6.52 (s, 2H), 4.60 (brs, 2H), 4.17 (brs, 2H), 3.87 (s, 3H), 2.96-2.80 (m, 3H), 1.90-1.80 (m, 2H).

Example-17: Synthesis of 4-(3-(2-sulfamoylaminoethyl)azetidine-1-yl)-6,7-dimethoxy-2-methylquinazoline, (Compound 1.17)

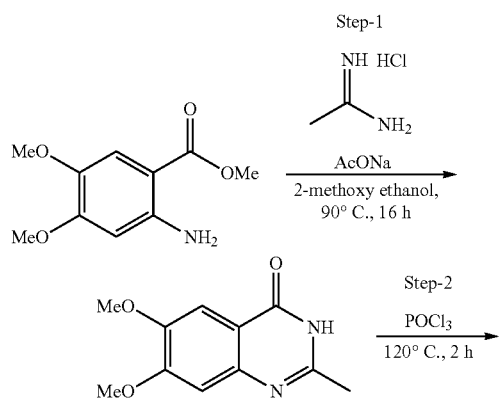

Step-1: Synthesis of 6,7-dimethoxy-2-methylquinazolin-4 (3H)-one: A mixture of methyl 2-amino-4,5-dimethoxybenzoate (0.5 g, 2.5 mmol, 1 eq), acetamidine hydrochloride (0.48 g, 5 mmol, 2.0 eq) and in anhydrous sodium acetate (0.416 g, 5 mmol, 2.0 eq) 2-methoxyethanol (6 mL) was allowed to stir at 90° C. for 16 h. Progress of reaction was monitored by TLC. Reaction mixture was cooled to RT, solid was filtered, washed with hexane and dried to afford 6,7-dimethoxy-2-methylquinazolin-4 (3H)-one (247 mg, 43%) as white solid. LCMS: 221 [M+1]$^+$ Step-2: Synthesis of 4-chloro-6,7-dimethoxy-2-methylquinazoline: A mixture of 6,7-dimethoxy-2-methylquinazolin-4 (3H)-one (0.25 g, 1.1 mmol, 1 eq) in POCl$_3$ (2 mL) was allowed to stir at 120° C. for 2 h. Progress of reaction was monitored by TLC. After completion, reaction mixture was cooled to RT, diluted with cold water (100 mL) and extracted with ethyl acetate (3×100 mL). Combined organic layer was washed with water (3×50 mL) and dried over anhydrous sodium sulfate. Removal of solvent under reduced pressure afforded 4-chloro-6,7-dimethoxy-2-methylquinazoline (0.2 g, 74%) which was used in the next step without purification. LCMS: 239 [M+1]$^+$ Step-3: Synthesis of 4-(3-(2-sulfamoylaminoethyl)azetidine-1-yl)-6,7-dimethoxy-2-methylquinazoline: A suspension of 4-chloro-6,7-dimethoxy-2-methylquinazoline (80 mg, 0.34 mmol, 2 eq), 3-(2-sulfamoylaminoethyl)azetidine trifluoroacetate (50 mg, 0.17 mmol, 1.0 eq) and DIPEA (0.06 mL, 0.34 mmol, 2.0 eq) in DMF (1 mL) was allowed to stir at 80° C. for 5 h. Progress of reaction was monitored by TLC. After 3 h, reaction mixture was concentrated under reduced pressure to afford crude which was purified using reversed phase HPLC to afford 4-(3-(2-sulfamoylaminoethyl)azetidine-1-yl)-6,7-dimethoxy-2-methylquinazoline (12 mg, 18%). LCMS: 382 [M+1]$^+$; $^1$H NMR (400 MHz, DMSO-d6) δ ppm 7.19 (s, 1H), 7.05 (s, 1H), 6.60-6.45 (m,

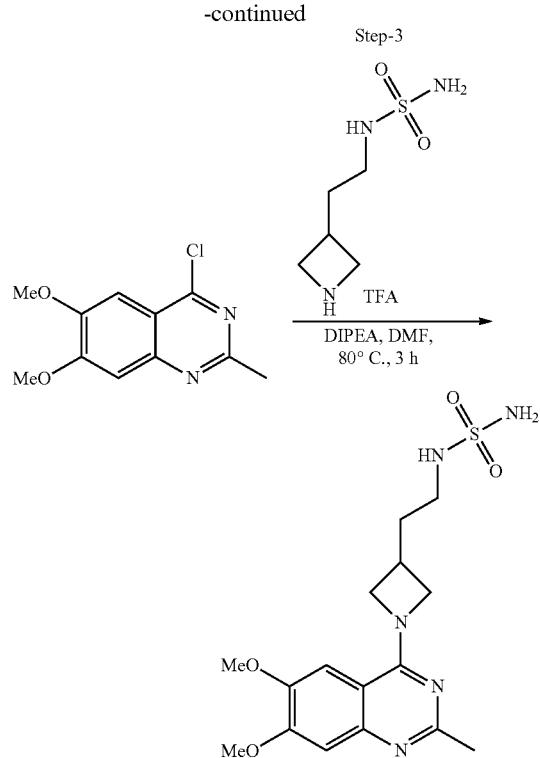

3H), 4.61-4.50 (m, 2H), 4.18-4.02 (m, 2H), 3.88 (s, 3H), 3.86 (s, 3H), 2.95-2.2.80 (m, 3H), 2.4 (s, 3H), 1.90-1.80 (m, 2H).

Example-18: Synthesis of 8-(3-(2-sulfamoylamino-ethyl)azetidine-1-yl)-[1,3]dioxolo[4,5-g]quinazoline, (Compound 1.18)

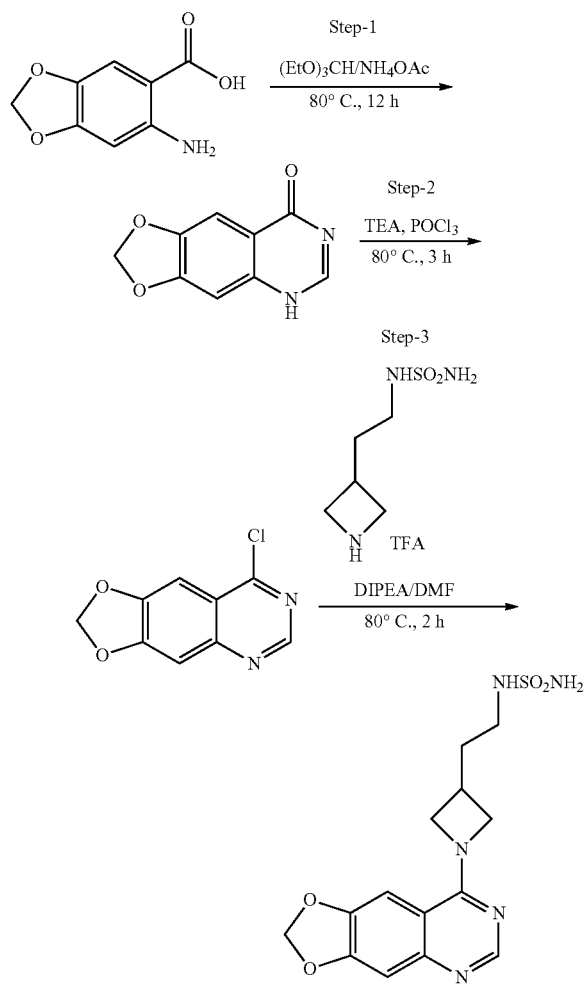

Step-1: Synthesis of [1,3]dioxolo[4,5-g]quinazolin-8 (5H)-one: A mixture of 6-amino-1,3-benzodioxole-5-carboxylic acid (300 mg, 1.65 mmol, 1 eq), triethylorthoformate (391 mg, 2.65 mmol, 1.6 eq) and ammonium acetate (165 mg, 2.14 mmol, 1.3 eq) in ethanol (10 mL) was stirred at 80° C. for 12 h. Progress of reaction was monitored by TLC. After completion, reaction mixture was cooled to RT. The solid obtained was filtered, washed with ether (10 mL) and dried under vacuum to afford [1,3]dioxolo[4,5-g]quinazolin-8 (5H)-one (247 mg, 78%). LCMS: 190[M+1]$^+$ Step-2: Synthesis of 8-chloro[1,3]dioxolo[4,5-g]quinazoline: To the stirred solution of [1,3]dioxolo[4,5-g]quinazolin-8 (5H)-one (150 mg, 0.78 mmol, 1 eq) in triethylamine (3 mL) was added POCl$_3$ (0.8 mL, 7.89 mmol, 10 eq) and the reaction mixture was heated at 80° C. for 3 h. Progress of reaction was monitored by TLC. After completion, reaction mixture was cooled to RT, diluted with ice cold water (10 mL) and extracted with ethyl acetate (3×10 mL). The organic layer was evaporated under reduced pressure to obtain 8-chloro[1,3]dioxolo[4,5-g]quinazoline (100 mg, 61%). LCMS: 208[M+1]$^+$ Step-3: Synthesis of N-{2-[1-([1,3]dioxolo[4,5-g]quinazolin-8-yl)azetidin-3-yl]ethyl}sulfuric diamide: A suspension of 8-chloro[1,3]dioxolo[4,5-g]quinazoline (100 mg, 0.48 mmol, 1.0 eq), N-[2-(azetidin-3-yl)ethyl]sulfuric diamide trifloroacetic acid (132 mg, 0.48 mmol, 1.0 eq) and N,N diisopropylethylamine (124 mg, 0.96 mmol, 2.0 eq) in DMF (2 mL) was allowed to stir at 80° C. for 2 h. Progress of reaction was monitored by TLC. Reaction mixture was cooled to RT, DMF was removed under reduced pressure, triturated with ether (10 mL) and ethyl acetate (10 mL). Solid obtained was purified by reversed phase HPLC to afford N-{2-[1-([1,3]dioxolo[4,5-g]quinazolin-8-yl)azetidin-3-yl]ethyl}sulfuric diamide (10 mg, 6%). LCMS: 350 [M+1]$^+$; $^1$H NMR (400 MHz, DMSO-d$_6$) δ ppm 8.31 (s, 1H), 7.27 (s, 1H), 7.10 (s, 1H), 6.60 (brs, 1H), 6.52 (s, 2H), 6.20 (s, 2H), 4.60-4.45 (m, 2H), 4.18-4.02 (m, 2H), 2.95-2.78 (m, 3H), 1.88-1.78 (m, 2H).

Example-19: Synthesis of 4-(3-(2-sulfamoylamino-ethyl)azetidine-1-yl)-8-ethoxyquinazoline, (Compound 1.19)

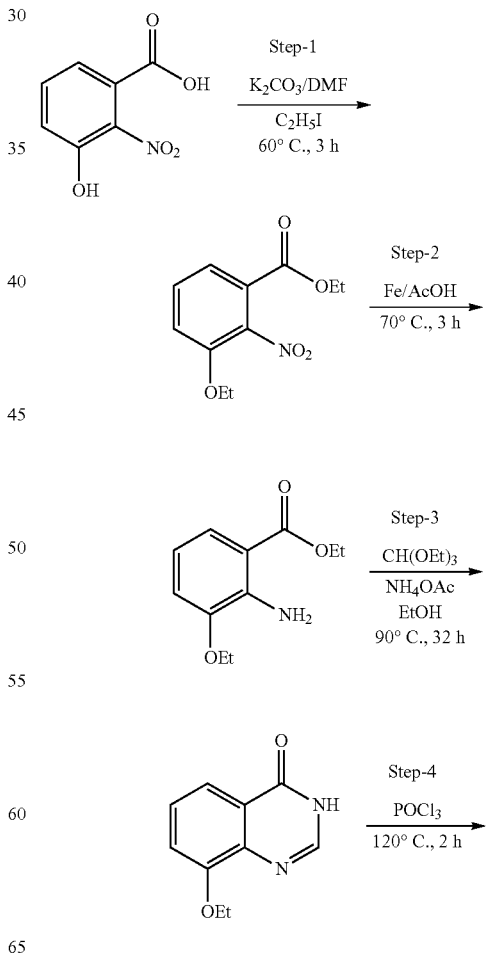

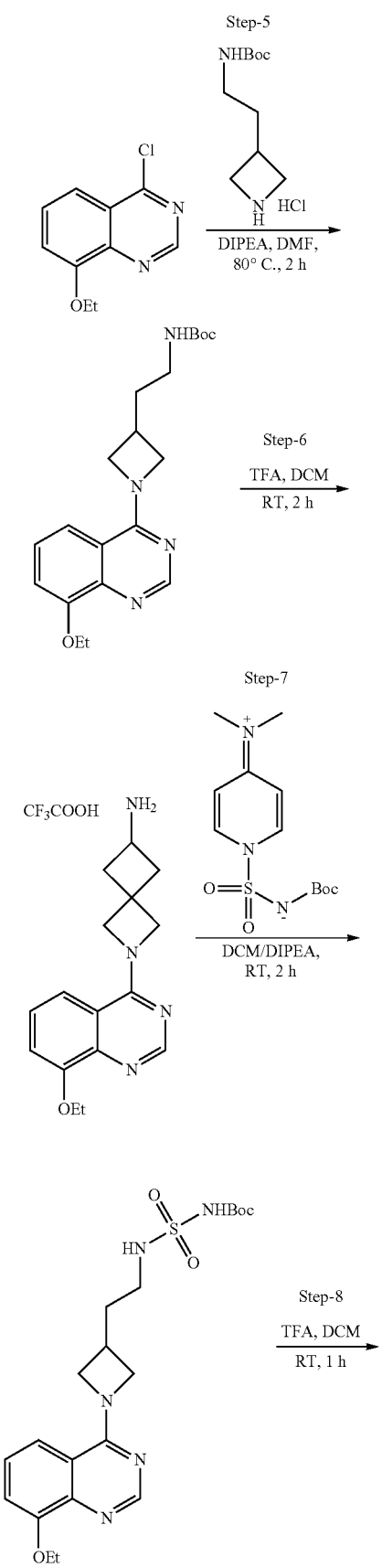

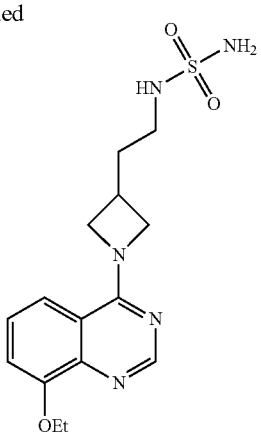

Step-1: Synthesis of ethyl 3-ethoxy-2-nitrobenzoate: To a solution of 3-hydroxy-2-nitrobenzoic acid (1 g, 5.4 mmol, 1 eq) in DMF (10 mL) were added K2CO₃ (3.8 gm, 27 mmol, 5 eq) and ethyl iodide (2.2 ml, 27 mmol, 5 eq.) and the reaction mixture was allowed to stir at 60° C. for 3 h. Progress of reaction was monitored by TLC. After completion, reaction mixture was diluted with cold water (100 mL) and stirred for 5 minutes. Solid was filtered, washed with water and dried under vacuum to get ethyl 3-ethoxy-2-nitrobenzoate as white solid (0.8 g, 62%).

Step-2: Synthesis of ethyl 2-amino-3-ethoxybenzoate: To a solution of ethyl 3-ethoxy-2-nitrobenzoate (0.8 g, 3.3 mmol, 1 eq) in acetic acid (5 mL) was added iron powder (1.28 g, 23 mmol, 7 eq) and the reaction mixture was allowed to stir at 70° C. for 3 h. Progress of reaction was monitored by TLC. After completion, reaction mixture was filtered, filtrate was diluted with water and extracted with ethyl acetate (3×50 ml). Combined organic layer was washed with brine (50 mL) and dried over anhydrous sodium sulfate. Removal of solvent under reduced pressure afforded crude which was purified by Combi-Flash using ethyl acetate-hexane system as eluent to get ethyl 2-amino-3-ethoxybenzoate (0.4 g, 58%).

Step-3: Synthesis of 8-ethoxyquinazolin-4 (3H)-one: To a solution of 2-amino-3-ethoxybenzoate (0.4 g, 1.9 mmol, 1 eq) in ethanol (5 mL) were added triethyl orthoformate (0.45 mL, 3 mmol, 1.6 eq) and ammonium acetate (0.19 g, 2.4 mmol, 1.3 eq.) and the reaction mixture was allowed to stir at 90° C. for 32 h. Progress of reaction was monitored by TLC. After completion, reaction mixture was filtered, washed with hexane and dried under vacuum to get 8-ethoxyquinazolin-4 (3H)-one as white solid (0.3 g, 83%). LCMS: 190 [M+1]⁺

Step-4: Synthesis of 4-chloro-8-ethoxyquinazoline: A mixture of 8-ethoxyquinazolin-4 (3H)-one (0.2 g, 1 mmol, 1 eq) in POCl₃ (2 mL) was allowed to stir at 120° C. for 2 h. Progress of reaction was monitored by TLC. After completion, reaction mixture was cooled to RT, diluted with cold water (100 mL) and extracted with ethyl acetate (3×100 mL). Combined organic layer was washed with water (3×50 mL) followed by brine (50 mL) and dried over anhydrous sodium sulfate. Removal of solvent under reduced pressure afforded 4-chloro-8-ethoxyquinazoline (0.1 g) which was used in the next step without purification.

Step-5: Synthesis of tert-butyl 2-(1-(8-ethoxyquinazolin-4-yl)azetidin-3-yl)ethylcarbamate: A suspension of 4-chloro-8-ethoxyquinazoline (100 mg, 0.48 mmol, 1 eq), tert-butyl 2-(azetidin-3-yl)ethylcarbamate hydrochloride (96 mg, 0.48 mmol, 1.0 eq) and DIPEA (0.17 mL, 0.96 mmol, 2.0 eq) in DMF (1 mL) was allowed to stir at 80° C. for 2 h. Progress of reaction was monitored by TLC. After completion, reaction mixture was diluted with cold water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(1-(8-ethoxyquinazolin-4-yl)azetidin-3-yl)ethylcarbamate (80 mg, 45%) which was used in the next step without purification. LCMS: 373 [M+1]$^+$ Step-6: Synthesis of 2-(1-(8-ethoxyquinazolin-4-yl)azetidin-3-yl)ethanamine 2,2,2-trifluoroacetate: To a solution of tert-butyl 2-(1-(8-ethoxyquinazolin-4-yl)azetidin-3-yl)ethylcarbamate (100 mg, 0.22 mmol, 1 eq) in DCM (4 mL) was added TFA (2 mL) and the mixture was allowed to stir at RT for 2 h. Progress of reaction was monitored by TLC. After completion, reaction mixture was concentrated under reduced pressure to get 2-(1-(8-ethoxyquinazolin-4-yl)azetidin-3-yl)ethanamine 2,2,2-trifluoroacetate (0.1 g) which was used in the next step without purification. LCMS: 273 [M+1]$^+$ Step-7: Synthesis of tert-butyl N-(2-(1-(8-ethoxyquinazolin-4-yl)azetidin-3-yl)ethyl)sulfamoylcarbamate: To a solution of 2-(1-(8-methoxyquinazolin-4-yl)azetidin-3-yl)ethanamine 2,2,2-trifluoroacetate (100 mg, 0.24 mmol, 1 eq) in dichloromethane (15 mL) were added N-(tert-butoxycarbonyl)-N-[4-(dimethylazaniumylidene)-1,4-dihydropyridin-1ylsulfonyl]azanide (132 mg. 0.43 mmol, 1.2 eq) and N,N-diisopropylethylamine (0.12 mL, 0.48 mmol, 2 eq) and the reaction mixture was allowed to stir at RT for 48 h. Progress of reaction was monitored by LCMS. After completion, reaction mixture was concentrated under reduced pressure to get residue which was purified by reversed phase HPLC to afford tert-butyl N-(2-(1-(8-ethoxyquinazolin-4-yl)azetidin-3-yl)ethyl)sulfamoylcarbamate (15 mg, 14%). LCMS: 452 [M+1]$^+$ Step-8: Synthesis of Synthesis of 4-(3-(2-sulfamoylaminoethyl)azetidine-1-yl)-8-ethoxyquinazoline: To a solution of tert-butyl N-(2-(1-(8-ethoxyquinazolin-4-yl)azetidin-3-yl)ethyl)sulfamoylcarbamate (15 mg, 0.033 mmol, 1 eq) in DCM (3 mL) was added TFA (1 mL) and the resulting mixture was allowed to stir at RT for 1 h. Progress of reaction was monitored by TLC. After completion, reaction mixture was concentrated under reduced pressure to afford crude which was triturated with diethyl ether to afford Synthesis of 4-(3-(2-sulfamoylaminoethyl)azetidine-1-yl)-8-ethoxyquinazoline (6 mg, 39%) as TFA salt. LCMS: 352 [M+1]$^+$; $^1$H NMR (400 MHz, DMSO-d$_6$) δ ppm 13.65 (brs, 1H), 8.64 (s, 1H), 7.62 (brs, 3H), 6.60 (brs, 1H), 6.55 (s, 2H), 5.02 (brs, 1H), 4.80-4.50 (m, 2H), 4.30 (q, 2H), 4.18 (brs, 1H), 3.00-2.83 (m, 3H), 1.93-1.83 (m, 2H), 1.45 (t, 3H)

Example-20: Synthesis of 4-(3-(2-sulfamoylaminoethyl)azetidine-1-yl)-5-methylpyrrolo[1,2-f][1,2,4]triazine, (Compound 1.20)

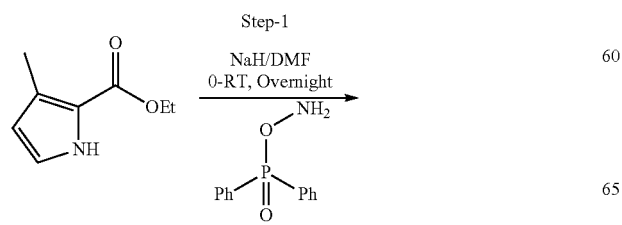

Step-1

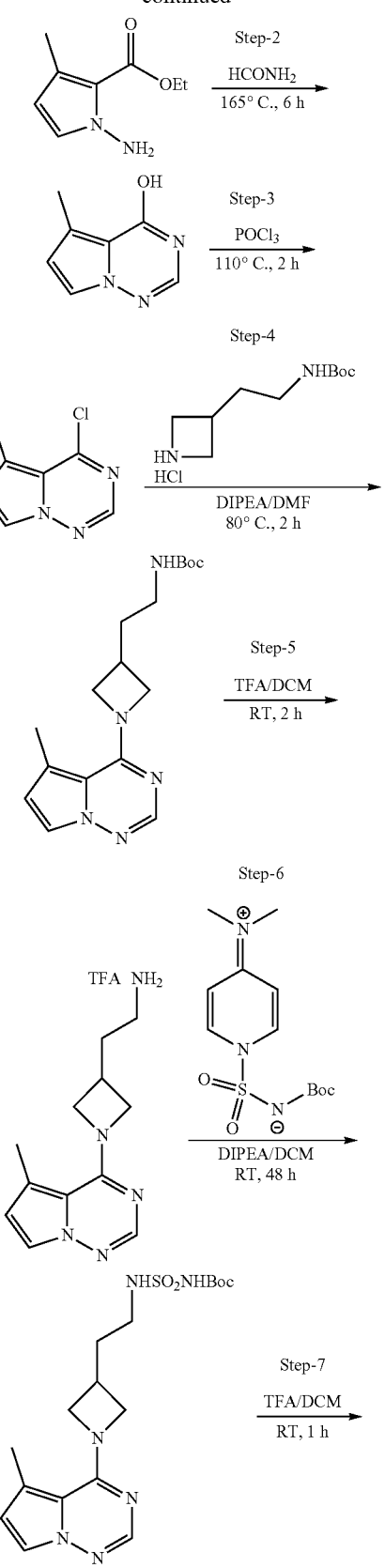

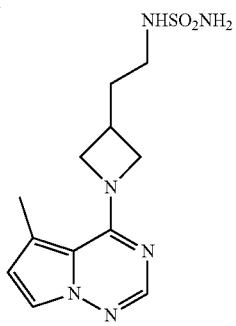

Step-1: Synthesis of ethyl 1-amino-3-methyl-1H-pyrrole-2-carboxylate: To a solution of sodium hydride (0.372 g, 0.0093 mmol, 1.43 eq) in DMF (60 mL) was added a solution of ethyl 3-methyl-1H-pyrrole-2-carboxylate (1 g, 0.0065 mmol, 1.0 eq) in DMF (20 mL) at 0° C. and the reaction mixture was allowed to stir at 0° C. for 30 minutes, followed by addition of O-(diphenylphosphoryl)hydroxylamine (2.68 g, 0.0115 mmol, 1.76 eq) portion wise. The reaction mixture was allowed to stir at RT for overnight. Progress of reaction is monitored using TLC. After completion, DMF was removed under reduced pressure, residue was diluted with water (100 mL) and extracted with ethyl acetate (3×100 mL). Combined organic layer was washed with brine (150 mL) and dried over anhydrous sodium sulfate. Removal of solvent under reduced pressure afforded ethyl 1-amino-3-methyl-1H-pyrrole-2-carboxylate (0.6 g, 55%).

Step-2: Synthesis of 5-methylpyrrolo[1,2-f][1,2,4]triazin-4-ol: A solution of ethyl 1-amino-3-methyl-1H-pyrrole-2-carboxylate (0.2 g, 1.189 mmol, 1 eq) in formamide (2 mL) was allowed to stir at 165° C. for 6 h. Progress of reaction is monitored by TLC. After completion, reaction mixture was diluted with cold water (30 mL) and allowed to stir for 10 minutes. Solid was filtered, washed with water followed by hexane and dried under vacuum to afford 5-methylpyrrolo[1,2-f][1,2,4]triazin-4-ol (0.05 g, 28%).

Step-3: Synthesis of 4-chloro-5-methylpyrrolo[1,2-f][1,2,4]triazine: A mixture of 5-methylpyrrolo[1,2-f][1,2,4]triazin-4-ol (0.050 g, 0.335 mmol, 1 eq) in phosphoryl trichloride (2 mL) was allowed to stir at 110° C. for 2 h. Progress of reaction is monitored by TLC. After completion, reaction mixture was diluted with cold water (30 mL) and extracted with ethyl acetate (3×15 mL). Combined organic layer was washed with brine (20 mL) and dried over anhydrous sodium sulfate. Removal of solvent under reduced pressure afforded 4-chloro-5-methylpyrrolo[1,2-f][1,2,4]triazine (0.050 g, 89%).

Step-4: Synthesis of tert-butyl 2-(1-(5-methylpyrrolo[1,2-f][1,2,4]triazin-4-yl)azetidin-3-yl)ethylcarbamate: A suspension of 4-chloro-5-methylpyrrolo[1,2-f][1,2,4]triazine (50 mg, 0.298 mmol, 1 eq), tert-butyl 2-(azetidin-3-yl)ethylcarbamate hydrochloride (70 mg, 0.298 mmol, 1.0 eq) and DIPEA (0.1 mL, 0.596 mmol, 2.0 eq) in DMF (1 mL) was allowed to stir at 80° C. for 2 h. Progress of reaction was monitored by TLC. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure afforded tert-butyl 2-(1-(5-methylpyrrolo[1,2-f][1,2,4]triazin-4-yl)azetidin-3-yl)ethylcarbamate (0.06 g) which was used in the next step without purification. LCMS: 332[M+1]$^+$ Step-5: Synthesis of 2-(1-(5-methylpyrrolo[1,2-f][1,2,4]triazin-4-yl)azetidin-3-yl)ethanamine: To a solution of tert-butyl 2-(1-(5-methylpyrrolo[1,2-f][1,2,4]triazin-4-yl)azetidin-3-yl)ethylcarbamate (60 mg, 0.181 mmol, 1 eq) in DCM (10 mL) was added TFA (2 mL) and the mixture was allowed to stir at RT for 2 h. Progress of reaction was monitored by TLC. After completion, reaction mixture was concentrated under reduced pressure to get 2-(1-(5-methylpyrrolo[1,2-f][1,2,4]triazin-4-yl)azetidin-3-yl)ethanamine (0.05 g) which was used in the next step without purification.

Step-6: Synthesis of tert-butyl N-(2-(1-(5-methylpyrrolo[1,2-f][1,2,4]triazin-4-yl)azetidin-3-yl)ethyl)sulfamoylcarbamate: To a solution of 2-(1-(5-methylpyrrolo[1,2-f][1,2,4]triazin-4-yl)azetidin-3-yl)ethanamine (50 mg, 0.152 mmol, 1 eq) in dichloromethane (10 mL) were added N-(tert-butoxycarbonyl)-N-[4-(dimethylazaniumylidene)-1,4-dihydropyridin-1ylsulfonyl]azanide (68.84 mg. 0.228 mmol, 1.5 eq) and N,N-diisopropylethylamine (0.3 mL, 0.304 mmol, 2 eq) and the reaction mixture was allowed to stir at RT for 48 h. Progress of reaction was monitored by LCMS. After completion, reaction mixture was concentrated under reduced pressure to get residue which was purified by reversed phase HPLC to afford N-(2-(1-(5-methylpyrrolo[1,2-f][1,2,4]triazin-4-yl)azetidin-3-yl)ethyl)sulfamoylcarbamate (18 mg, 32%). LCMS: 411[M+1]$^+$ Step-7: Synthesis of 4-(3-(2-sulfamoylaminoethyl)azetidine-1-yl)-5-methylpyrrolo[1,2-f][1,2,4]triazine: To a solution of N-(2-(1-(5-methylpyrrolo[1,2-f][1,2,4]triazin-4-yl)azetidin-3-yl)ethyl)sulfamoylcarbamate (18 mg, 0.044 mmol, 1 eq) in DCM (3 mL) was added TFA (0.5 mL) and allowed to stir at RT for 1 h. Progress of reaction was monitored by TLC. After completion, reaction mixture was concentrated under reduced pressure to afford crude which was triturated with diethyl ether to afford 4-(3-(2-sulfamoylaminoethyl)azetidine-1-yl)-5-methylpyrrolo[1,2-f][1,2,4]triazine (10 mg, 77%) as TFA salt. LCMS: 311[M+1]$^+$; $^1$H NMR (400 MHz, DMSO-d$_6$) δ ppm 7.79 (s, 1H), 7.60 (s, 1H), 6.60-6.45 (m, 4H), 4.50-4.40 (m, 2H), 4.07-3.95 (m, 2H), 2.90-2.70 (m, 3H), 2.41 (s, 3H), 1.87-1.77 (m, 2H).

Example-21: Synthesis of 4-(3-(2-sulfamoylaminoethyl)azetidine-1-yl)-6,7-dimethoxy-2-phenylquinazoline, (Compound 1.21)

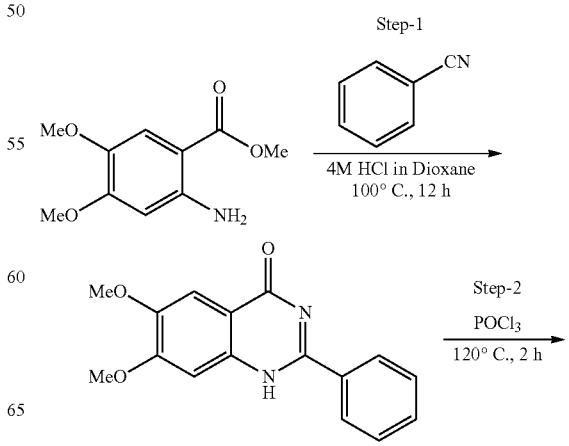

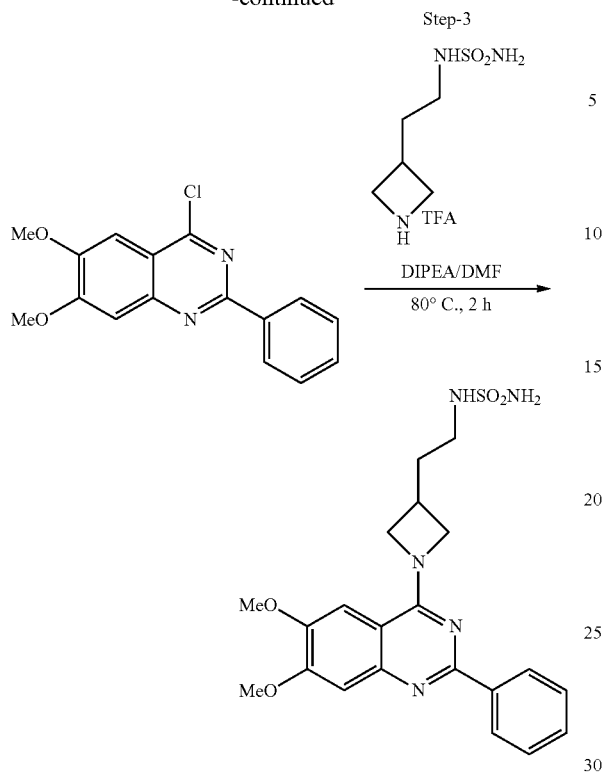

Step-1: Synthesis of 6,7-dimethoxy-2-phenylquinazolin-4 (1H)-one: A mixture of methyl 2-amino-4,5-dimethoxybenzoate (500 mg, 1.65 mmol, 1 eq) and benzonitrile (244 mg, 2.65 mmol, 1.6 eq) in 4M HCl in dioxane (10 mL) was sonicated for 30 minutes and then heated at 100° C. for 12 h. Progress of reaction was monitored by TLC. After completion, reaction mixture was cooled to RT, poured into ice-cold water and stirred for 15 minutes. The solid obtained was filtered and dried under vacuum to afford 6,7-dimethoxy-2-phenylquinazolin-4 (1H)-one (250 mg, 37%). LCMS: 282[M+1]$^+$ Step-2: Synthesis of 4-chloro-6,7-dimethoxy-2-phenylquinazoline: To a stirred solution of 6,7-dimethoxy-2-phenylquinazolin-4 (1H)-one (250 mg, 0.88 mmol, 1 eq) in POCl$_3$ (2.5 mL) was stirred at 120° C. for 2 h. Progress of reaction was monitored by TLC. After completion, reaction mixture was cooled to RT, poured into ice-cold water (20 mL) and stirred for 15 minutes. Solid was filtered and dried under vacuum to afford 4-chloro-6,7-dimethoxy-2-phenylquinazoline (200 mg, 75%). LCMS: 300[M+1]$^+$ Step-3: Synthesis of 4-(3-(2-sulfamoylaminoethyl)azetidine-1-yl)-6,7-dimethoxy-2-phenylquinazoline: A suspension of 4-chloro-6,7-dimethoxy-2-phenylquinazoline (54 mg, 0.18 mmol, 1.0 eq), N-[2-(azetidin-3-yl)ethyl]sulfuric diamide trifloroacetic acid (50 mg, 0.18 mmol, 1.0 eq) and N,N diisopropylethylamine (46 mg, 0.36 mmol, 2.0 eq) in DMF (2 mL) was allowed to stir at 80° C. for 2 h. Progress of reaction was monitored by TLC. Reaction mixture was cooled to RT, concentrated under vacuum to get semi-solid residue which was triturated with ether, ethyl acetate and then with pentane to afford crude solid which was purified by reversed phase HPLC to afford 4-(3-(2-sulfamoylaminoethyl)azetidine-1-yl)-6,7-dimethoxy-2-phenylquinazoline (3 mg, 4%). LCMS:350[M+1]$^+$; $^1$H NMR (400 MHz, DMSO-d$_6$) δ ppm 8.39 (d, 2H), 7.70-7.30 (m, 3H), 7.30 (s, 2H), 6.60 (brs, 1H), 6.53 (s, 2H), 4.80-4.55 (m, 2H), 4.40-4.20 (m, 2H), 3.97 (s, 3H), 3.93 (s, 3H), 3.00-2.90 (m, 3H), 1.94-1.84 (m, 2H).

Example-22: Synthesis of 4-(3-Methyl-3-(2-sulfamoylaminoethyl)azetidine-1-yl)-6,7-dimethoxyquinazoline, (Compound 1.22)

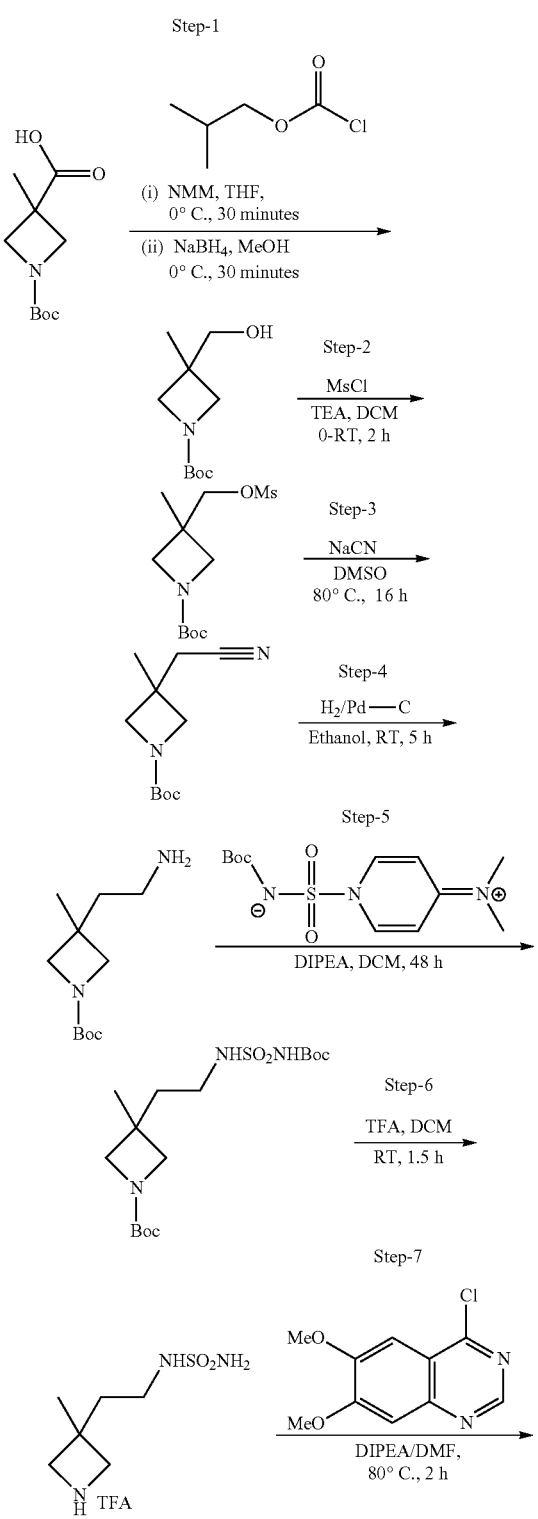

-continued

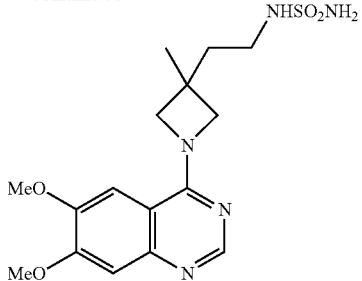

Step-1: Synthesis of tert-butyl 3-(hydroxymethyl)-3-methylazetidine-1-carboxylate: To a solution of 1-(tert-butoxycarbonyl)-3-methylazetidine-3-carboxylic acid (1.5 g, 6.97 mmol, 1 eq) in THF (20 mL) was added N-methylmorpholine (NMM) (2.3 mL, 20.9 mmol, 3 eq) and isobutyl chloroformate (1.08 ml, 8.37 mmol, 1.2 eq) and the reaction mixture was allowed to stir at 0° C. for 30 minutes. Progress of reaction is monitored by TLC. After consumption of carboxylic acid, reaction mixture was filtered through cotton plug, filtrate was cooled to 0° C. and to it was added a freshly prepared solution of $NaBH_4$ (3 g, 81.08 mmol, 12 eq) in MeOH (50 ml) at 0° C. in one portion. Reaction mixture was then allowed to stir for 30 minutes. Progress of reaction was monitored by $^1H$ NMR. After completion, reaction mixture was diluted with aq. saturated $NH_4Cl$ solution (100 mL) and extracted with ethyl acetate (3×100 mL). Combined organic layer was washed with brine (150 mL) and dried over anhydrous sodium sulfate. Removal of solvent under reduced pressure gave crude oil which was purified by Combi-Flash on silica gel using ethyl acetate-hexane system as eluent to afford tert-butyl 3-(hydroxymethyl)-3-methylazetidine-1-carboxylate (1 g, 71%).

Step-2: Synthesis of tert-butyl 3-methyl-3-((methylsulfonyloxy)methyl)azetidine-1-carboxylate: To a solution of tert-butyl 3-(hydroxymethyl)-3-methylazetidine-1-carboxylate (0.5 g, 2.48 mmol, 1 eq) in DCM (10 mL) was added triethylamine (0.67 mL, 4.97 mmol, 2 eq) and the reaction mixture was allowed to stir at 0° C. for 5 minutes. To the mixture was added methane sulfonyl chloride (0.42 g, 3.73 mmol, 1.5 eq) and the reaction mixture to stir at 0° C. for 10 minutes followed by stirring at RT for 2 h. Progress of reaction is monitored by $^1H$ NMR. After completion, reaction mixture was diluted with water (100 mL) and extracted with ethyl acetate (3×100 mL). Combined organic layer was washed with brine (150 mL) and dried over anhydrous sodium sulfate. Removal of solvent under reduced pressure afforded tert-butyl 3-methyl-3-((methylsulfonyloxy)methyl)azetidine-1-carboxylate (0.5 g, Crude) which was used in the next step without purification.

Step-3: Synthesis of tert-butyl 3-(cyanomethyl)-3-methylazetidine-1-carboxylate: To a solution of tert-butyl 3-methyl-3-((methylsulfonyloxy)methyl)azetidine-1-carboxylate (0.5 g, 1.79 mmol, 1 eq) in DMSO (1 mL) was added sodium cyanide (0.22 g, 4.48 mmol, 2.5 eq) and the reaction mixture was allowed to stir at 80° C. for 16 h. Progress of reaction was monitored by $^1H$ NMR. After completion, reaction mixture was diluted with water (100 mL) and extracted with diethyl ether (3×150 mL). Combined organic layer was washed with water (2×100 mL) followed by brine (150 mL) and dried over anhydrous sodium sulfate. Removal of solvent under reduced pressure afforded tert-butyl 3-(cyanomethyl)-3-methylazetidine-1-carboxylate (0.3 g) which was used in the next step without purification.

Step-4: Synthesis of tert-butyl 3-(2-aminoethyl)-3-methylazetidine-1-carboxylate: To a solution of tert-butyl 3-(cyanomethyl)-3-methylazetidine-1-carboxylate (0.3 g, 1.42 mmol, 1 eq) in ethanol (50 mL) was added Pd—C (0.3 g) and the reaction mixture was allowed to stir at RT under $H_2$ atmosphere using balloon for 5 h. Progress of reaction was monitored by TLC. After completion, reaction mixture was filtered through celite-bed. Filtrate was concentrated under reduced pressure to afford tert-butyl 3-(2-aminoethyl)-3-methylazetidine-1-carboxylate (0.25 g, Crude) which was used in the next step without purification.

Step-5: Synthesis of tert-butyl 3-(2-(N-(tert-butoxycarbonyl)sulfamoylamino)ethyl)-3-methylazetidine-1-carboxylate To a solution of tert-butyl 3-(2-aminoethyl)-3-methylazetidine-1-carboxylate (0.25 g, 1.16 mmol, 1 eq) in dichloromethane (10 ML) were added N-(tert-butoxycarbonyl)-N-[4-(dimethylazaniumylidene)-1,4-dihydropyridin-1ylsulfonyl]azanide (0.421 mg, 1.4 mmol, 1.2 eq) and N,N-diisopropylethylamine (0.4 mL, 2.2 mmol, 2 eq) and the reaction mixture was allowed to stir at RT for 48 h. Progress of reaction was monitored by TLC. After completion, reaction mixture was concentrated under reduced pressure to get crude which was purified by Combi-Flash using ethyl acetate-hexane system as eluent to afford tert-butyl 3-(2-(N-(tert-butoxycarbonyl)sulfamoylamino)ethyl)-3-methylazetidine-1-carboxylate (0.1 g, 22%).

Step-6: Synthesis of 3-methyl-3-(2-sulfamoylaminoethyl)azetidine trifluoroacetate: To a solution of tert-butyl 3-(2-(N-(tert-butoxycarbonyl)sulfamoylamino)ethyl)-3-methylazetidine-1-carboxylate (0.1 g, 0.25 mmol, 1 eq) in DCM (5 mL) was added TFA (1 mL) and the mixture was allowed to stir at RT for 1.5 h. Progress of reaction was monitored by $^1H$ NMR. After completion, reaction mixture was concentrated under reduced pressure to afford crude which was triturated with diethyl ether to afford 3-Methyl-3-(2-sulfamoylaminoethyl)azetidine trifluoroacetate (0.1 g).

Step-7: Synthesis of 4-(3-Methyl-3-(2-sulfamoylaminoethyl)azetidine-1-yl)-6,7-dimethoxyquinazoline: A mixture of 4-chloro-6,7-dimethoxyquinazoline (88 mg, 0.39 mmol, 1.2 eq), -Methyl-3-(2-sulfamoylaminoethyl)azetidine trifluoroacetate (100 mg, 0.32 mmol, 1.0 eq) and DIPEA (0.11 mL, 0.65 mmol, 2.0 eq) in DMF (1 mL) was allowed to stir at 80° C. for 2 h. Progress of reaction was monitored by TLC. After completion, reaction mixture was concentrated under reduced pressure to get residue which was purified by reversed phase HPLC to afford 4-(3-Methyl-3-(2-sulfamoylaminoethyl)azetidine-1-yl)-6,7-dimethoxyquinazoline (8 mg, 6%). LCMS: 382 [M+1]$^+$; $^1H$ NMR (400 MHz, DMSO-d6) δ ppm 8.45 (s, 1H), 7.23 (s, 1H), 7.16 (s, 1H), 6.58 (s, 3H), 4.60-4.17 (m, 4H), 3.88 (s, 3H), 3.86 (s, 3H), 3.01-2.90 (m, 2H), 1.89-1.80 (m, 2H).

Example-23: Synthesis of 4-(3-(2-((sulfamoyl)(cyclopropyl)amino)ethyl)azetidine-1-yl)-6,7-dimethoxyquinazoline, (Compound 1.23)

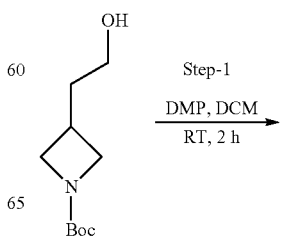

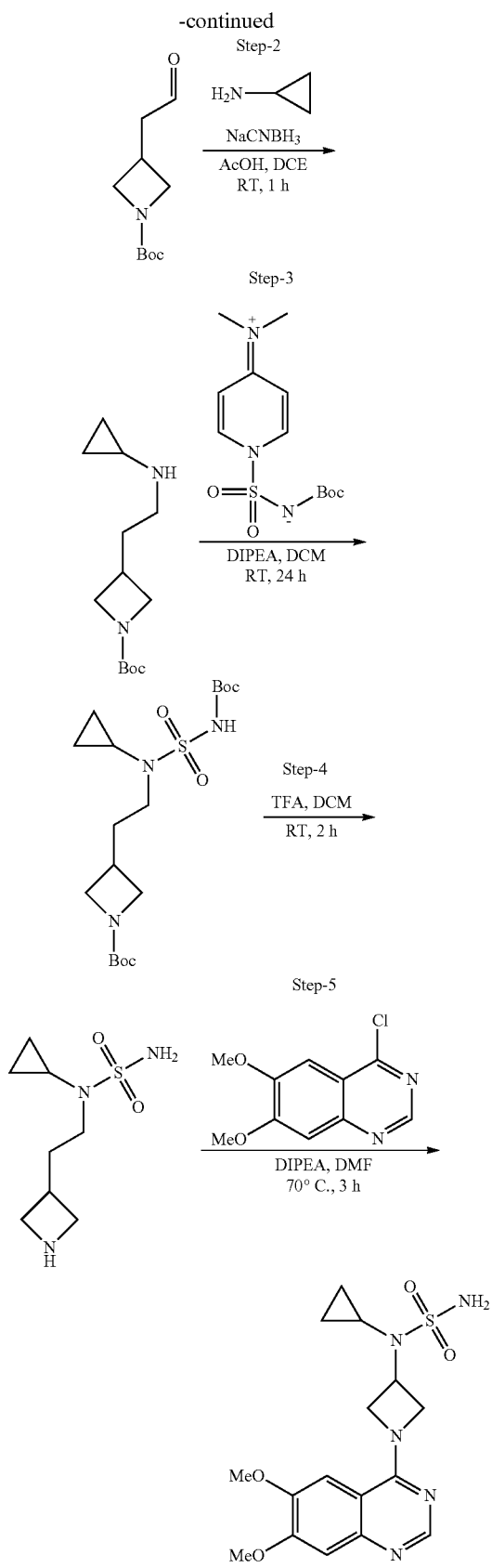

Step-1: Synthesis of tert-butyl 3-(2-oxoethyl)azetidine-1-carboxylate: To a solution of the tert-butyl 3-(2-hydroxy-ethyl)azetidine-1-carboxylate (0.5 g, 2.48 mmol, 1 eq) in dichloromethane (18 mL) at 0° C. was added Dess-Martin peridionane (DMP) (3.1 g, 7.46 mmol 3.0 eq) and the reaction mixture was stirred at RT for 2 h. Progress of reaction was monitored by TLC. After completion, reaction mixture poured on crushed ice and extracted with ethyl acetate (3×50 mL). Combined organic layer was washed with brine (20 mL) and dried over anhydrous sodium sulfate. Removal of solvent under reduced pressure gave crude which was triturated with pentane (100 mL) at 0° C. and filtered. Filtrate was concentrated under vacuum to afford tert-butyl 3-(2-oxoethyl)azetidine-1-carboxylate (0.350 g, 35%).

Step-2: Synthesis of tert-butyl 3-(2-(cyclopropylamino) ethyl)azetidine-1-carboxylate: To a stirred solution of tert-butyl 3-(2-oxoethyl)azetidine-1-carboxylate (0.350 g, 1.76 mmol, 1.0 eq) in DCE (20 mL) were added cyclopropyl amine (0.1 g, 1.76 mmol, 1.0 eq), acetic acid (0.3 mL, 5.27 mmol, 3.0 eq) and the reaction mixture was allowed to stir at RT for 1 h. to the mixture was then added NaCNBH$_3$ (0.332 g, 5.27 mmol, 3.0 eq) and the reaction mixture was stirred at room temperature for 1 h. Progress of reaction was monitored by TLC. After completion, reaction mixture was diluted with ice-cold water (50 mL) and extracted with ethyl acetate (3×50 mL). Combined organic layer was washed with brine (20 mL) and dried over anhydrous sodium sulfate. Removal of solvent under reduced pressure afforded tert-butyl 3-(2-(cyclopropylamino)ethyl)azetidine-1-carboxylate (0.130 g, 36%) which was used in the next step without purification.

Step-3: Synthesis of tert-butyl 3-(2-((N-(tert-butoxycarbonyl)sulfamoyl) (cyclopropyl)amino)ethyl)azetidine-1-carboxylate: To a solution of tert-butyl 3-(2-(cyclopropylamino)ethyl)azetidine-1-carboxylate (130 mg, 0.541 mmol, 1 eq) in dichloromethane (5 ML) were added N-(tert-butoxycarbonyl)-N-[4-(dimethylazaniumylidene)-1,4-dihydropyridin-1ylsulfonyl]azanide (0.195 mg. 0.649 mmol, 1.5 eq) and N,N-diisopropylethylamine (31 mg, 0.24 mmol, 2 eq) and the reaction mixture was allowed to stir at RT for 24 h. Progress of reaction was monitored by LCMS. After completion, solvent was removed under reduced pressure to afford crude which was purified by reversed phase HPLC to afford tert-butyl 3-(2-((N-(tert-butoxycarbonyl)sulfamoyl) (cyclopropyl)amino)ethyl)azetidine-1-carboxylate (100 mg, 32%).

Step-4: Synthesis of 3-(2-((sulfamoyl)(cyclopropyl) amino)ethyl)azetidine trifluoroacetate: To a solution of tert-butyl 3-(2-((N-(tert-butoxycarbonyl)sulfamoyl) (cyclopropyl)amino)ethyl)azetidine-1-carboxylate (100 mg, 0.238 mmol, 1 eq) in DCM (5 mL) was added TFA (1 mL) and the mixture was allow to stir at RT for 2 h. Progress of reaction was monitored by TLC. After completion, reaction mixture was concentrated under reduced pressure to get oily residue which was triturated with diethyl ether (10 mL) to afford 3-(2-((sulfamoyl)(cyclopropyl)amino)ethyl)azetidine trifluoroacetate (70 mg, 93%).

Step-5: Synthesis of 4-(3-(2-((sulfamoyl)(cyclopropyl) amino)ethyl)azetidine-1-yl)-6,7-dimethoxyquinazoline: A suspension of 4-chloro-6,7-dimethoxyquinazoline (70 mg, 0.22 mmol, 1.0 eq), 3-(2-((sulfamoyl)(cyclopropyl)amino) ethyl)azetidine trifluoroacetate (54 mg, 0.24 mmol, 1.1 eq) and N,N-diisopropylethylamine (56 mg, 0.26 mmol, 1.2 eq) in DMF (1 mL) was allowed to stir at 80° C. for 3 h. Progress of reaction was monitored by LCMS. After completion, solvent was removed under reduced pressure to afford crude which was purified by reversed phase HPLC to afford 4-(3-(2-((sulfamoyl)(cyclopropyl)amino)ethyl)azetidine-1- yl)-6,7-dimethoxyquinazoline (20 mg, 23%). LCMS: 408 [M+1]⁺; ¹H NMR (400 MHz, DMSO-d6) δ ppm 8.35 (s, 1H), 7.22 (s, 1H), 7.15 (s, 1H), 6.85 (s, 2H), 4.56 (brs., 2H), 4.13 (brs, 2H), 3.91 (s, 3H), 3.88 (s, 3H), 3.18-3.09 s (m, 2H), 2.84-2.70 (m, 1H), 2.39-2.30 (m, 1H), 2.03-1.95 (m, 2H), 0.8 (brs, 4H).

Example-24: Synthesis of 4-(6-sulfamoylamino-2-azaspiro[3.3]heptan-2-yl)-6,7-dimethoxyquinoline-3-carbonitrile, (Compound 1.24)

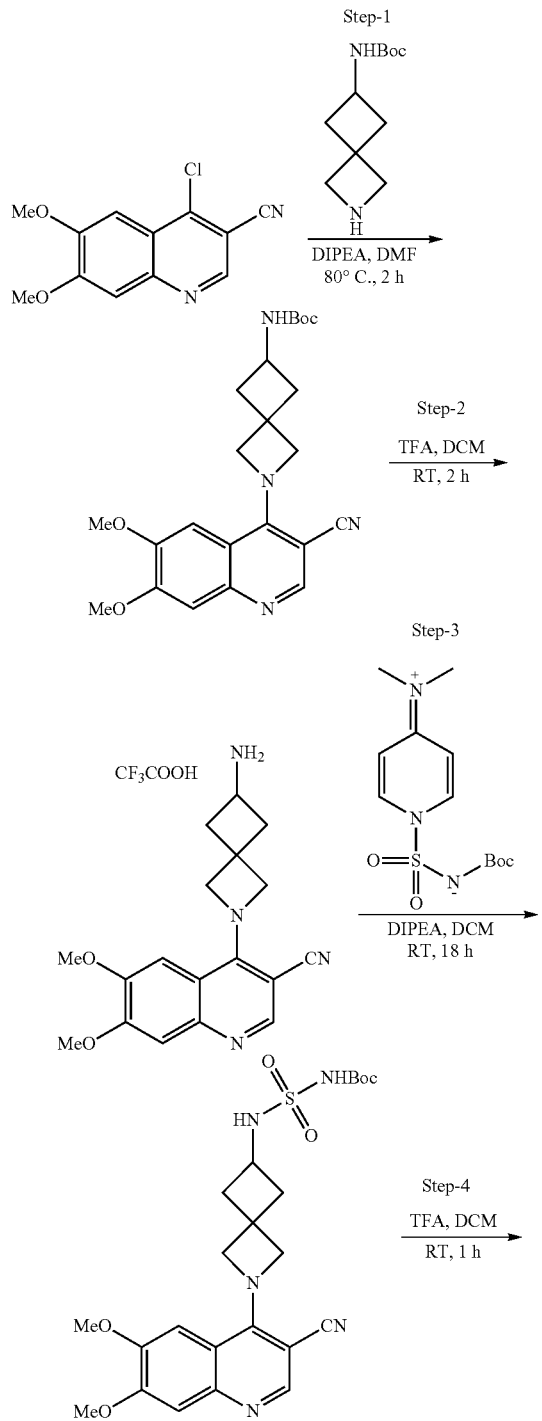

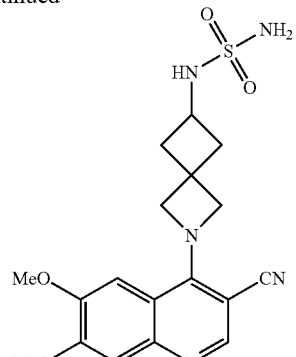

Step-1: Synthesis of tert-butyl 2-(3cyano-6,7-dimethoxyquinolin-4-yl)-2-azaspiro[3.3]heptan-6-ylcarbamate: A suspension of 4-chloro-6,7-dimethoxyquinoline-3-carbonitrile (70 mg, 0.28 mmol, 1.2 eq), tert-butyl 2-azaspiro[3.3]heptan-6-ylcarbamate (50 mg, 0.23 mmol, 1.0 eq) and DIPEA (0.08 mL, 0.47 mmol, 2.0 eq) in DMF (1 mL) was allowed to stir at 80° C. for 2 h. Progress of reaction was monitored by TLC. After completion, reaction mixture was diluted with cold water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(3-cyano-6,7-dimethoxyquinolin-4-yl)-2-azaspiro[3.3]heptan-6-ylcarbamate (0.1 g, crude) which was used in the next step without purification. LCMS: 425 [M+1]⁺

Step-2: Synthesis of 4-(6-amino-2-azaspiro[3.3]heptan-2-yl)-6,7-dimethoxyquinoline-3-carbonitrile 2,2,2-trifluoroacetate: To a solution of tert-butyl 2-(3-cyano-6,7-dimethoxyquinolin-4-yl)-2-azaspiro[3.3]heptan-6-ylcarbamate (100 mg, 0.23 mmol, 1 eq) in DCM (5 mL) was added TFA (1 mL) and the mixture was allowed to stir at RT for 2 h. Progress of reaction was monitored by TLC. After completion, reaction mixture was concentrated under reduced pressure to get 4-(6-amino-2-azaspiro[3.3]heptan-2-yl)-6,7-dimethoxyquinoline-3-carbonitrile 2,2,2-trifluoroacetate (0.1 g, crude) which was used in the next step without purification. LCMS: 325 [M+1]⁺

Step-3: Synthesis of tert-butyl N-(2-(3-cyano-6,7-dimethoxyquinolin-4-yl)-2-azaspiro[3.3]heptan-6-yl)sulfamoylcarbamate: To a solution of 4-(6-amino-2-azaspiro[3.3]heptan-2-yl)-6,7-dimethoxyquinoline-3-carbonitrile 2,2,2-trifluoroacetate (100 mg, 0.30 mmol, 1 eq) in dichloromethane (15 mL) were added N-(tert-butoxycarbonyl)-N-[4-(dimethylazaniumylidene)-1,4-dihydropyridin-1ylsulfonyl]azanide (111 mg. 0.37 mmol, 1.2 eq) and N,N-diisopropylethylamine (0.1 mL, 0.61 mmol, 2 eq) and the reaction mixture was allowed to stir at RT for 48 h. Progress of reaction was monitored by LCMS. After completion, reaction mixture was concentrated under reduced pressure to get residue which was purified by reversed phase HPLC to afford tert-butyl N-(2-(3-cyano-6,7-dimethoxyquinolin-4-yl)-2-azaspiro[3.3]heptan-6-yl)sulfamoylcarbamate (35 mg, 23%). LCMS: 504 [M+1]⁺

Step-4: Synthesis of 4-(6-sulfamoylamino-2-azaspiro[3.3]heptan-2-yl)-6,7-dimethoxyquinoline-3-carbonitrile: To a solution of tert-butyl N-(2-(3-cyano-6,7-dimethoxyquinolin-4-yl)-2-azaspiro[3.3]heptan-6-yl)sulfamoylcarbamate (35 mg, 0.069 mmol, 1 eq) in DCM (4 mL) was added TFA (0.8 mL) and allowed to stir at RT for 1 h. Progress of reaction was monitored by TLC. After completion, reaction mixture was concentrated under reduced pressure to afford crude which was triturated with diethyl ether to afford 4-(6-sulfamoylamino-2-azaspiro[3.3]heptan-2-yl)-6,7-dimethoxyquinoline-3-carbonitrile (20 mg, 56%) as TFA salt. LCMS: 404 [M+1]$^+$; $^1$H NMR (400 MHz, DMSO-d6) δ ppm 8.78 (s, 1H), 7.40 (s, 1H), 7.24 (s, 1H), 6.90 (d, 1H), 7.54 (s, 2H), 5.0.8 (s, 2H), 4.97 (s, 2H), 3.95 (s, 3H), 3.78-3.60 (m, 1H), 2.70-2.60 (m, 2H), 2.32-2.20 (m, 2H).

Example-25: Synthesis of 4-(3-(2-sulfamoylaminoethyl)azetidine-1-yl)-6,7-dimethoxy-2-phenylquinazoline, (Compound 1.25)

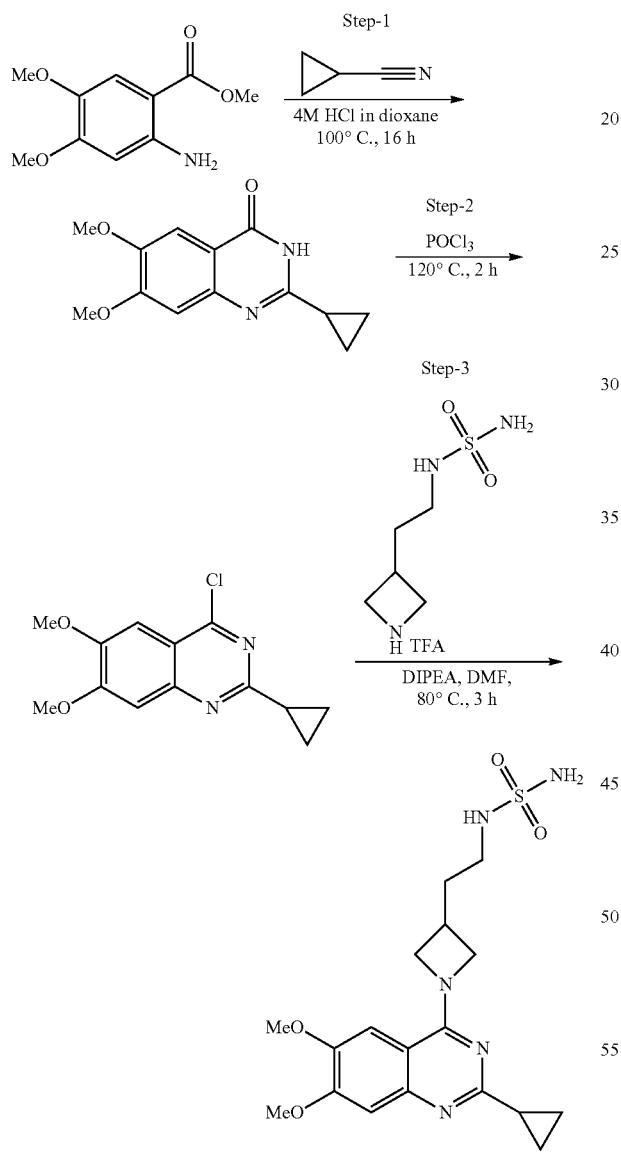

Step-1: Synthesis of 2-cyclopropyl-6,7-dimethoxyquinazolin-4 (3H)-one: A mixture of methyl 2-amino-4,5-dimethoxybenzoate (1 g, 4.7 mmol, 1 eq) and cyclopropyl cyanide (1.04 mL, 14 mmol, 3 eq) in 4M HCl in dioxane (10 mL) was allowed to stir at 100° C. for 16 h. Progress of reaction was monitored by TLC. After completion, reaction mixture was poured to saturated aq. sodium carbonate solution (50 mL) and allowed to stir for 5 minutes. Precipitate was filtered and dried under vacuum to afford 2-cyclopropyl-6,7-dimethoxyquinazolin-4 (3H)-one (900 mg, 78%) as white solid. LCMS: 247 [M+1]$^+$ Step-2: Synthesis of 4-chloro-2-cyclopropyl-6,7-dimethoxyquinazoline: A mixture of 2-cyclopropyl-6,7-dimethoxyquinazolin-4 (3H)-one (0.2 g, 0.81 mmol, 1 eq) in POCl$_3$ (2 mL) was allowed to stir at 120° C. for 2 h. Progress of reaction was monitored by TLC. After completion, reaction mixture was cooled to RT, diluted with cold water (100 mL) and extracted with ethyl acetate (3×100 mL). Combined organic layer was washed with water (3×50 mL) and dried over anhydrous sodium sulfate. Removal of solvent under reduced pressure afforded 4-chloro-2-cyclopropyl-6,7-dimethoxyquinazoline (0.15 g, 70%) which was used in the next step without purification. LCMS: 265 [M+1]$^+$ Step-3: Synthesis of 4-(3-(2-sulfamoylaminoethyl)azetidine-1-yl)-2-cyclopropyl-6,7-dimethoxyquinazoline: A suspension of 4-chloro-2-cyclopropyl-6,7-dimethoxyquinazoline (90 mg, 0.34 mmol, 2 eq), 3-(2-sulfamoylaminoethyl) azetidine trifluoroacetate (50 mg, 0.17 mmol, 1.0 eq) and DIPEA (0.06 mL, 0.34 mmol, 2.0 eq) in DMF (1 mL) was allowed to stir at 80° C. for 3 h. Progress of reaction was monitored by TLC. After 3 h, reaction mixture was concentrated under reduced pressure to afford crude which was purified using reversed phase HPLC to afford 4-(3-(2-sulfamoylaminoethyl)azetidine-1-yl)-2-cyclopropyl-6,7-dimethoxyquinazoline (20 mg, 19%). LCMS: 408 [M+1]$^+$; $^1$H NMR (400 MHz, DMSO-d6) δ ppm 7.17 (s, 1H), 7.00 (s, 1H), 6.60-6.47 (m, 3H), 4.58-4.45 (m, 2H), 4.10-4.02 (m, 2H), 3.87 (s, 3H), 3.85 (s, 3H), 2.92-2.78 (m, 3H), 1.99-1.82 (m, 3H), 1.00-0.80 (m, 4H).

Example-26: Synthesis of 4-(6-sulfamoylamino-2-azaspiro[3.3]heptan-2-yl)-7-methoxyquinazoline, (Compound 1.26)

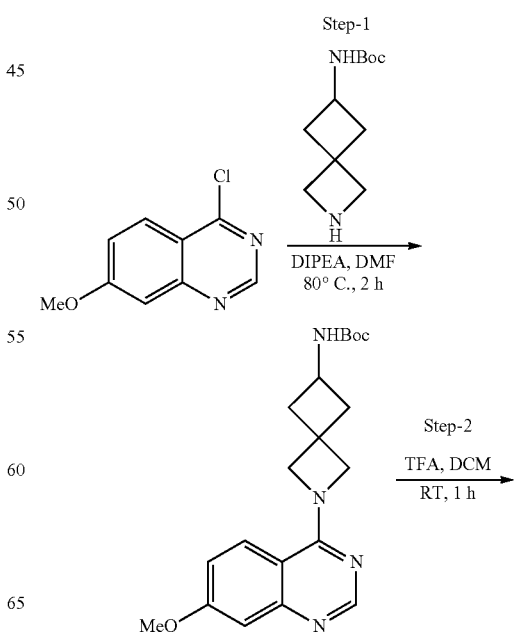

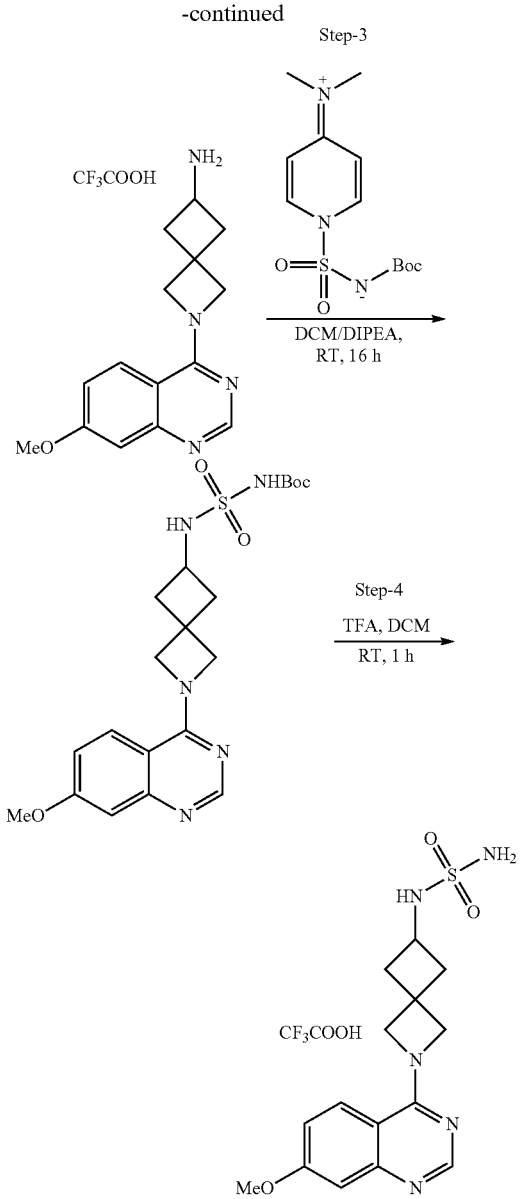

monitored by TLC. After completion, reaction mixture was concentrated under reduced pressure to get 2-(7-methoxyquinazolin-4-yl)-2-azaspiro[3.3]heptan-6-amine 2,2,2-trifluoroacetate (0.15 g) which was used in the next step without purification. LCMS: 271 [M+1]$^+$ Step-3: Synthesis of tert-butyl N-(2-(7-methoxyquinazolin-4-yl)-2-azaspiro[3.3]heptan-6-yl)sulfamoylcarbamate:

To a solution of 2-(7-methoxyquinazolin-4-yl)-2-azaspiro [3.3]heptan-6-amine 2,2,2-trifluoroacetate (150 mg, 0.39 mmol, 1 eq) in dichloromethane (20 ML) were added N-(tert-butoxycarbonyl)-N-[4-(dimethylazaniumylidene)-1, 4-dihydropyridin-1ylsulfonyl]azanide (176 mg. 0.58 mmol, 1.5 eq) and N,N-diisopropylethylamine (0.13 mL, 0.78 mmol, 2 eq) and the reaction mixture was allowed to stir at RT for 16 h. Progress of reaction was monitored by LCMS. After completion, reaction mixture was concentrated under reduced pressure to get residue which was purified by reversed phase HPLC to afford tert-butyl N-(2-(7-methoxyquinazolin-4-yl)-2-azaspiro[3.3]heptan-6-yl)sulfamoylcarbamate (30 mg, 17%). LCMS: 450 [M+1]$^+$ Step-4: Synthesis of 4-(6-sulfamoylamino-2-azaspiro [3.3]heptan-2-yl)-7-methoxyquinazoline: To a solution of tert-butyl N-(2-(7-methoxyquinazolin-4-yl)-2-azaspiro[3.3] heptan-6-yl)sulfamoylcarbamate (30 mg, 66 mmol, 1 eq) in DCM (3 mL) was added TFA (1 mL) and allowed to stir at RT for 1 h. Progress of reaction was monitored by TLC. After completion, reaction mixture was concentrated under reduced pressure to afford crude which was triturated with diethyl ether to afford 4-(6-sulfamoylamino-2-azaspiro[3.3] heptan-2-yl)-7-methoxyquinazoline (15 mg, 50%) as TFA salt. LCMS: 350 [M+1]$^+$; $^1$H NMR (400 MHz, DMSO-d6) δ ppm 14.00 (brs, 1H), 8.67 (s, 1H), 7.98 (d, 1H), 7.08 (d, 1H), 7.18 (s, 1H), 6.90 (d, 1H), 6.53 (s, 2H), 4.65 (brs, 4H), 3.98 (s, 3H), 2.70-2.60 (m, 1H), 2.67-2.50 (m, 2H), 2.30-2.30 (m, 2H).

Example-27: Synthesis of 4-(3-(2-sulfamoylaminoethyl)azetidine-1-yl)-6,7-dimethoxycinnoline, (Compound 1.27)

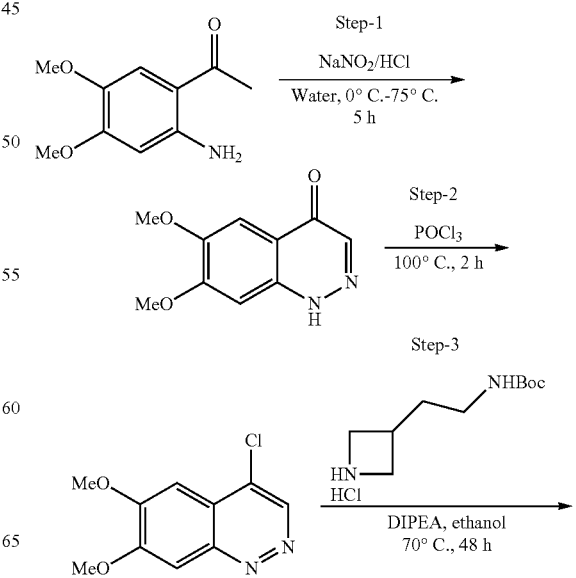

Step-1: Synthesis of tert-butyl 2-(7-methoxyquinazolin-4-yl)-2-azaspiro[3.3]heptan-6-ylcarbamate: A suspension of 4-chloro-7-methoxyquinazoline (55 mg, 0.28 mol, 1 eq), tert-butyl 2-azaspiro[3.3]heptan-6-ylcarbamate (50 mg, 0.23 mmol, 1.0 eq) and DIPEA (0.1 mL, 0.47 mmol, 2.0 eq) in DMF (1 L) was allowed to stir at 80° C. for 2 h. Progress of reaction was monitored by TLC. After 2 h, reaction mixture was diluted with cold water (50 mL) and extracted with ethyl acetate (3×100 mL). Combined organic layer was washed with brine (3×50 mL) and dried over anhydrous sodium sulfate. Removal of solvent under reduced pressure afforded tert-butyl 2-(7-methoxyquinazolin-4-yl)-2-azaspiro[3.3] heptan-6-ylcarbamate (0.1 g) which was used in the next step without purification. LCMS: 371 [M+1]$^+$ Step-2: Synthesis of 2-(7-methoxyquinazolin-4-yl)-2-azaspiro[3.3]heptan-6-amine 2,2,2-trifluoroacetate: To a solution of tert-butyl 2-(7-methoxyquinazolin-4-yl)-2-azaspiro[3.3]heptan-6-ylcarbamate (100 mg, 0.27 mmol, 1 eq) in DCM (4 mL) was added TFA (2 mL) and the mixture was allowed to stir at RT for 1 h. Progress of reaction was

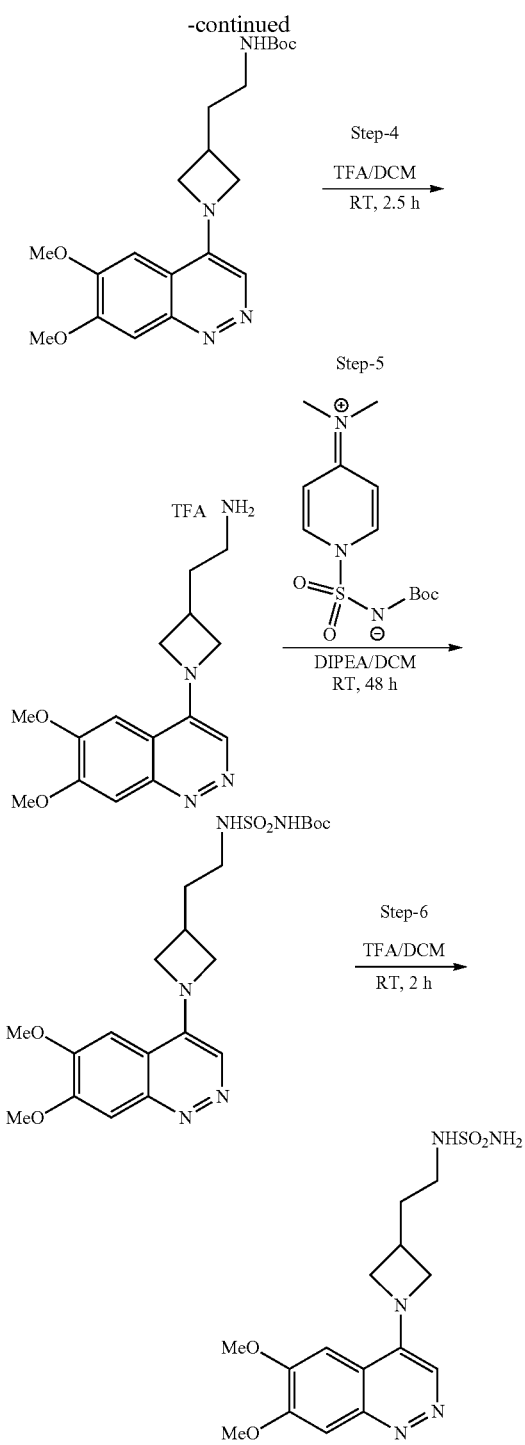

Step-1: Synthesis of 6,7-dimethoxycinnoline-4 (1H)-one: To a solution of 1-(2-amino-4,5-dimethoxyphenyl)ethanone (1 g, 5.12 mmol, 1 eq) in a solution of Conc·HCl (36 mL) and water (5 mL) at 0° C. was added a solution of sodium nitrite (0.353 g, 5.12 mmol, 1 eq) in water (2 mL) dropwise. The mixture was allowed to stir at 0° C. for 1 h followed by stirring at 75° C. for 4 h. Progress of reaction was monitored by ¹H NMR. After completion, reaction mixture was cooled to RT, precipitates was filtered, dissolved in water (150 mL) and basified with aq. NaOH up to pH 12 and then neutralized with 2M HCl solution. Precipitate was filtered, washed with hexane and dried under vacuum to afford 6,7-dimethoxycinnoline-4 (1H)-one (0.6 g, 57%). LCMS: 207 [M+1]⁺

Step-2: Synthesis of 4-chloro-6,7-dimethoxycinnoline: A mixture of 6,7-dimethoxycinnoline-4 (1H)-one (0.6 g, 2.90 mmol, 1 eq) in POCl₃ (3 mL) was allowed to stir at 100° C. for 2 h. Progress of reaction was monitored by TLC. After completion, reaction mixture was cooled to RT, diluted with ice-cold water (20 mL) and extracted with ethyl acetate (3×30 mL). Combined organic layer was washed with brine (50 mL) and dried over anhydrous sodium sulfate. Removal of solvent under reduced pressure afforded 4-chloro-6,7-dimethoxycinnoline (0.5 g, 77%).

Step-3: Synthesis of tert-butyl 2-(1-(6,7-dimethoxycinnoline-4-yl)azetidin-3-yl)ethylcarbamate: A suspension of 4-chloro-6,7-dimethoxycinnoline (50 mg, 0.222 mmol, 1 eq), tert-butyl 2-(azetidin-3-yl)ethylcarbamate hydrochloride (52 mg, 0.222 mmol, 1.0 eq) and DIPEA (57 mg, 0.444 mmol, 2.0 eq) in ethanol (5 mL) was allowed to stir at 70° C. for 48 h. Progress of reaction was monitored by TLC. After completion, reaction mixture was concentrated under reduced pressure to afford crude which was triturated with pentane to afford tert-butyl 2-(1-(6,7-dimethoxycinnoline-4-yl)azetidin-3-yl)ethylcarbamate (70 mg) which was used in the next step without purification. LCMS: 389 [M+1]⁺

Step-4: Synthesis of 2-(1-(6,7-dimethoxycinnoline-4-yl)azetidin-3-yl)ethanamine: To a solution of tert-butyl 2-(1-(6,7-dimethoxycinnoline-4-yl)azetidin-3-yl)ethylcarbamate (70 mg, 0.181 mmol, 1 eq) in DCM (5 mL) was added TFA (2 mL) and the mixture was allowed to stir at RT for 2.5 h. Progress of reaction was monitored by LCMS. After completion, reaction mixture was concentrated under reduced pressure to get 2-(1-(6,7-dimethoxycinnoline-4-yl)azetidin-3-yl)ethanamine (70 mg) which was used in the next step without purification.

Step-5: Synthesis of tert-butyl N-(2-(1-(6,7-dimethoxycinnoline-4-yl)azetidin-3-yl)ethyl)sulfamoylcarbamate: To a solution of 2-(1-(6,7-dimethoxycinnoline-4-yl)azetidin-3-yl)ethanamine (70 mg, 0.174 mmol, 1 eq) in dichloromethane (10 mL) were added N-(tert-butoxycarbonyl)-N-[4-(dimethylazaniumylidene)-1,4-dihydropyridin-1ylsulfonyl]azanide (104 mg. 0.348 mmol, 2 eq) and N,N-diisopropylethylamine (44 mg, 0.348 mmol, 2 eq) and the reaction mixture was allowed to stir at RT for 48 h. Progress of reaction was monitored by LCMS. After completion, reaction mixture was concentrated under reduced pressure to get crude residue which was purified by reversed phase HPLC to afford tert-butyl N-(2-(1-(6,7-dimethoxycinnoline-4-yl)azetidin-3-yl)ethyl)sulfamoylcarbamate (20 mg, 18%). LCMS: 468[M+1]⁺

Step-6 Synthesis of 4-(3-(2-sulfamoylaminoethyl)azetidine-1-yl)-6,7-dimethoxycinnoline: To a solution of N-(2-(1-(6,7-dimethoxycinnoline-4-yl)azetidin-3-yl)ethyl)sulfamoylcarbamate (20 mg, 0.028 mmol, 1 eq) in DCM (5 mL) was added TFA (1 mL) and allowed to stir at RT for 2 h. Progress of reaction was monitored by TLC. After completion, reaction mixture was concentrated under reduced pressure to afford crude which was triturated with diethyl ether to afford 4-(3-(2-sulfamoylaminoethyl)azetidine-1-yl)-6,7-dimethoxycinnoline (6 mg, 40%) as TFA salt. LCMS: 468 [M+1]⁺; ¹H NMR (400 MHz, DMSO-d6) δ ppm 14.82 (brs, 1H), 8.11 (s, 1H), 7.30 (s, 1H), 7.20 (s, 1H), 6.63 (brs, 1H), 6.55 (s, 2H), 5.40-4.20 (brs, 4H), 4.00 (s, 3H), 3.99 (s, 3H), 3.18-2.90 (m, 3H), 1.96-1.85 (m, 2H).

Example-28: Synthesis of 2-(1-(6,7-dimethoxyquinazolin-4-yl)azetidin-3-yl)-N-hydroxyacetamide, (Compound 1.28)

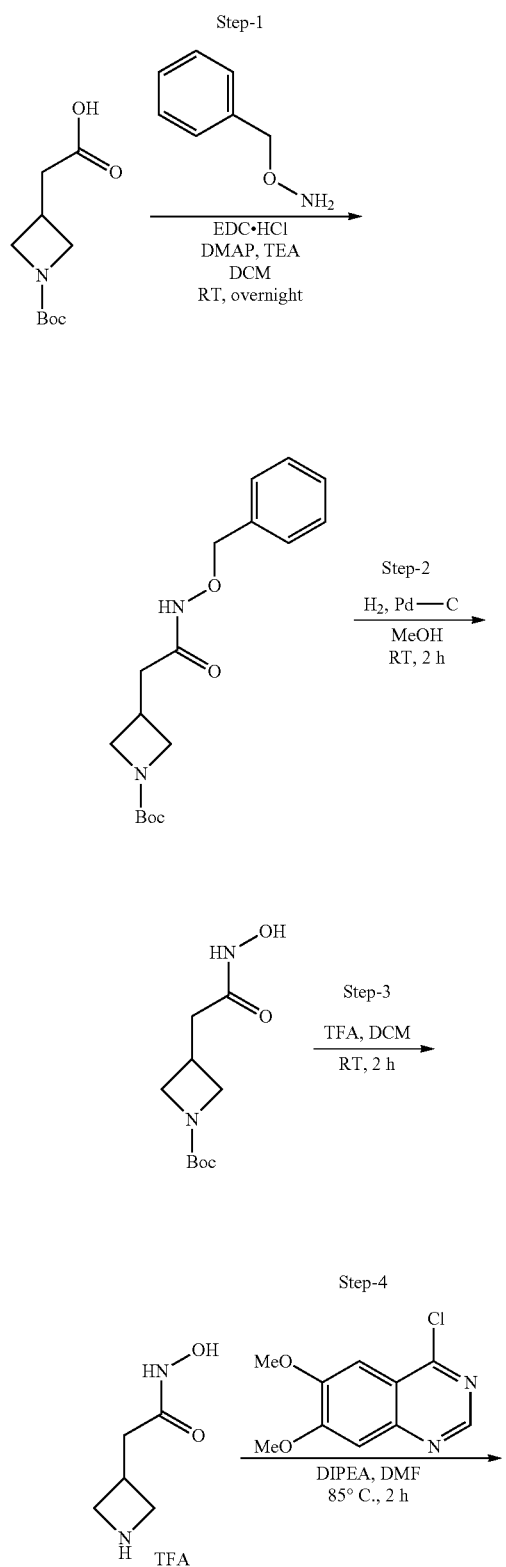

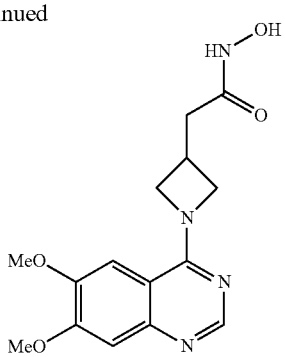

Step-1: Synthesis of tert-butyl 3-(2-(benzyloxyamino)-2-oxoethyl)azetidine-1-carboxylate: To a solution of 2-(1-(tert-butoxycarbonyl)azetidin-3-yl)acetic acid (1 g, 4.646 mmol, 1 eq) and O-benzylhydroxylamine (0.815 g, 5.110 mmol, 1.1 eq) in DCM (50 mL) were added N-(3-dimethylaminopropyl)-N'-ethylcarbodiimide hydrochloride (1.06 g, 5.575 mmol, 1.2 eq), 4-(dimethylamino)pyridine (0.851 g, 6.969 mmol, 1.5 eq) and triethylamine (1.9 mL, 13.938 mmol, 3 eq) and the reaction mixture was allowed to stir at RT overnight. Progress of reaction is monitored using TLC. After completion, removal of solvent is done under reduced pressure gave residue which was diluted with water (100 mL) and extracted with ethyl acetate (3×100 mL). Combined organic layer was washed with dil·HCl (50 mL) followed by brine (150 mL) and dried over anhydrous sodium sulfate. Removal of solvent under reduced pressure afforded tert-butyl 3-(2-(benzyloxyamino)-2-oxoethyl)azetidine-1-carboxylate (1.5 g, Crude) which was used in the next step without purification.

Step-2: Synthesis of tert-butyl 3-(2-(hydroxyamino)-2-oxoethyl)azetidine-1-carboxylate: To a solution of tert-butyl 3-(2-(benzyloxyamino)-2-oxoethyl)azetidine-1-carboxylate (0.5 g, 1.561 mmol, 1 eq) in methanol (20 mL) was added Pd—C (0.1 g) and the reaction mixture was allowed to stir at RT under $H_2$ atmosphere for 2 h. After completion, reaction mixture was filtered through celite bed and bed was washed with methanol (20 mL). Combined filtrate was concentrated under reduced pressure to afford tert-butyl 3-(2-(hydroxyamino)-2-oxoethyl)azetidine-1-carboxylate (0.360 g, Crude) which was used in the next step without purification.

Step-3: Synthesis of 2-(azetidin-3-yl)-N-hydroxyacetamide: To a solution of tert-butyl 3-(2-(hydroxyamino)-2-oxoethyl)azetidine-1-carboxylate (0.350 g, 1.520 mmol, 1 eq) in DCM (4 mL) was added TFA (1 mL) and mixture was allowed to stir at RT for 2 h. Progress of reaction was monitored by $^1$H NMR. After completion, reaction mixture was concentrated under reduced pressure to afford crude which was triturated with diethyl ether to afford 2-(azetidin-3-yl)-N-hydroxyacetamide (0.350 g, crude) as TFA salt.

Step-4: Synthesis of 2-(1-(6,7-dimethoxyquinazolin-4-yl)azetidin-3-yl)-N-hydroxyacetamide: To a solution of 2-(azetidin-3-yl)-N-hydroxyacetamide (0.1 g, 0.440 mmol, 1 eq) in DMF (1.5 mL) were added N,N-diisopropylethylamine (0.2 mL, 1.100 mmol, 2.5 eq) and 4-chloro-6,7-dimethoxyquinazoline (1.73 mL, 9.986 mmol, 2 eq) and the reaction mixture was allowed to stir at 85° C. for 2 h. Progress of reaction was monitored by LCMS. After completion, reaction mixture was concentrated under reduced pressure, triturated with diethyl ether and ethyl acetate, to get residue which was purified by reversed HPLC to afford 2-(1-(6,7- dimethoxyquinazolin-4-yl)azetidin-3-yl)-N-hydroxyacetamide (2 mg, 2%). LCMS: 319 [M+1]$^+$; $^1$H NMR (400 MHz, DMSO-d6) δ ppm 10.6 (s, 1H), 8.61 (s, 1H), 7.32 (s, 2H), 4.8 (brs, 2H), 4.4 (brs, 2H), 3.98 (s, 6H), 3.6 (s, 1H), 3.15 (brs, 2H).

Example-29: Synthesis of 2-(1-(6,7-dimethoxyquinazolin-4-yl)azetidin-3-yl)ethylphosphonic acid, (Compound 1.29)

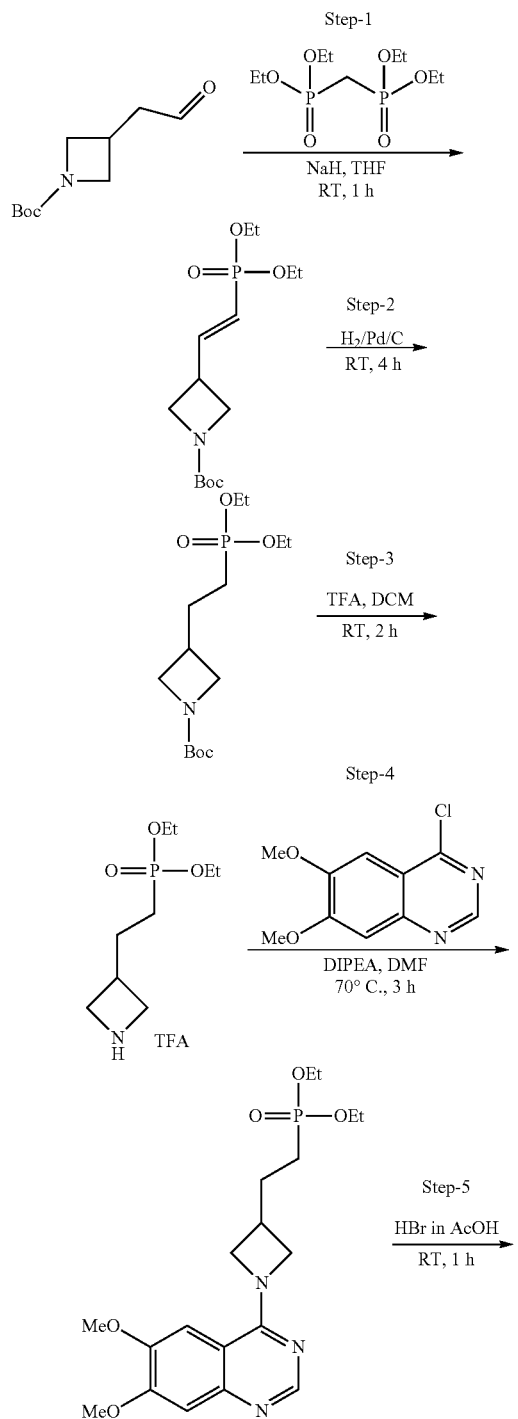

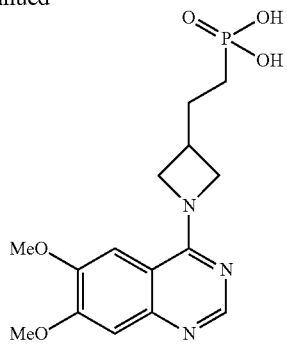

Step-1: Synthesis of (E)-tert-butyl 3-(2-(diethoxyphosphoryl)vinyl)azetidine-1-carboxylate: To a suspension of sodium hydride (60% in mineral oil, 0.052 g, 1.29 mmol, 1.2 eq) in THF (20 mL) was added tetraethyl methylenediphosphonate (0.3 mL g, 1.189 mmol, 1.1 eq) dropwise at 0° C. and the mixture was allowed to stir at the same temperature for 30 minutes. To this mixture was added a solution of tert-butyl 3-(2-oxoethyl)azetidine-1-carboxylate (0.2 g, 1.081 mmol, 1.0 eq) in THF (5 mL) and the resulting mixture was allowed to stir at room temperature for 2 h. Progress of reaction was monitored by TLC. After completion, reaction mixture was diluted with saturated aq. NH$_4$Cl (100 mL) and extracted with ethyl acetate (3×30 ml). Combined organic layer was washed with brine, dried over anhydrous Na$_2$SO$_4$ and evaporated to dryness under vacuum to afford (E)-tert-butyl 3-(2-(diethoxyphosphoryl)vinyl)azetidine-1-carboxylate (0.3 g, 94%). LCMS: 320 [M+1]$^+$ Step-2: Synthesis of tert-butyl 3-(2-(diethoxyphosphoryl) ethyl)azetidine-1-carboxylate: To a solution of (E)-tert-butyl 3-(2-(diethoxyphosphoryl)vinyl)azetidine-1-carboxylate (0.3 g, 0.940 mmol, 1.0 eq) in ethanol (50 mL) was added Pd/C (0.1 g) and the reaction mixture was allowed to stir at RT under H$_2$ atmosphere using balloon for 2 h. Progress of reaction was monitored by TLC. After completion, reaction mixture was filtered through celite-bed. Removal of solvent under reduced pressure afforded tert-butyl 3-(2-(diethoxyphosphoryl)ethyl)azetidine-1-carboxylate (0.25 g, 83%). LCMS: 322[M+1]$^+$ Step-3: Synthesis of diethyl 2-(azetidin-3-yl)ethylphosphonate: To a solution of tert-butyl 3-(2-(diethoxyphosphoryl)ethyl)azetidine-1-carboxylate (0.250 g, 0.778 mmol, 1 eq) in DCM (5 mL) was added TFA (1 mL) and the mixture was allowed to stir at RT for 2 h. Progress of reaction was monitored by TLC. After completion, reaction mixture was concentrated under reduced pressure to get oily residue which was triturated with diethyl ether (10 mL) to afford diethyl 2-(azetidin-3-yl)ethylphosphonate (0.2 g, 81%). LCMS: 222[M+1]$^+$ Step-4: Synthesis of diethyl 2-(1-(6,7-dimethoxyquinazolin-4-yl)azetidin-3-yl)ethylphosphonate: A suspension of 4-chloro-6,7-dimethoxyquinazoline (0.2 g, 0.8928 mmol, 1.0 eq), diethyl 2-(azetidin-3-yl)ethylphosphonate (0.215 mg, 0.9821 mmol, 1.1 eq) and N,N-diisopropylethylamine (0.185 mL, 1.071 mmol, 1.2 eq) in DMF (3 mL) was allowed to stir at 80° C. for 3 h. Progress of reaction was monitored by LCMS. After completion, reaction mixture was cooled to RT and diluted with ice-cold water (10 mL). Precipitate was filtered, washed with water followed by pentane and dried under reduced pressure to afford diethyl 2-(1-(6,7-dimethoxyquinazolin-4-yl)azetidin-3-yl)ethylphosphonate (0.120 mg, 49%). LCMS:410[M+1]$^+$ Step-5: Synthesis of 2-(1-(6,7-dimethoxyquinazolin-4-yl)azetidin-3-yl)ethylphosphonic acid: A mixture of diethyl 2-(1-(6,7-dimethoxyquinazolin-4-yl)azetidin-3-yl)ethylphosphonate (120 mg, 0.2933 mmol, 1.0 eq) in a solution of HBr in acetic acid (3 mL) was stirred at 80° C. for 3 h. Progress of reaction was monitored by TLC. After completion, solvent was removed under reduced pressure to afford crude which was purified by reversed phase HPLC to afford 2-(1-(6,7-dimethoxyquinazolin-4-yl)azetidin-3-yl)ethylphosphonic acid (7 mg, 6.79%). LCMS:354[M+1]$^+$; $^1$H NMR (400 MHz, D$_2$O:DMSO-d6) δ ppm 8.21 (s, 1H), 7.76 (s, 1H), 7.22 (s, 1H), 3.90 (s, 3H), 3.88 (s, 3H), 3.78-3.62 (m, 2H), 3.30-3.18 (m, 2H), 2.30-2.18 (m, 2H), 1.65-1.38 (m, 3H).

Example-30: Synthesis of 2-(1-(6,7-dimethoxyquinazolin-4-yl)azetidin-3-yl)ethylboronic acid, (Compound 1.30)

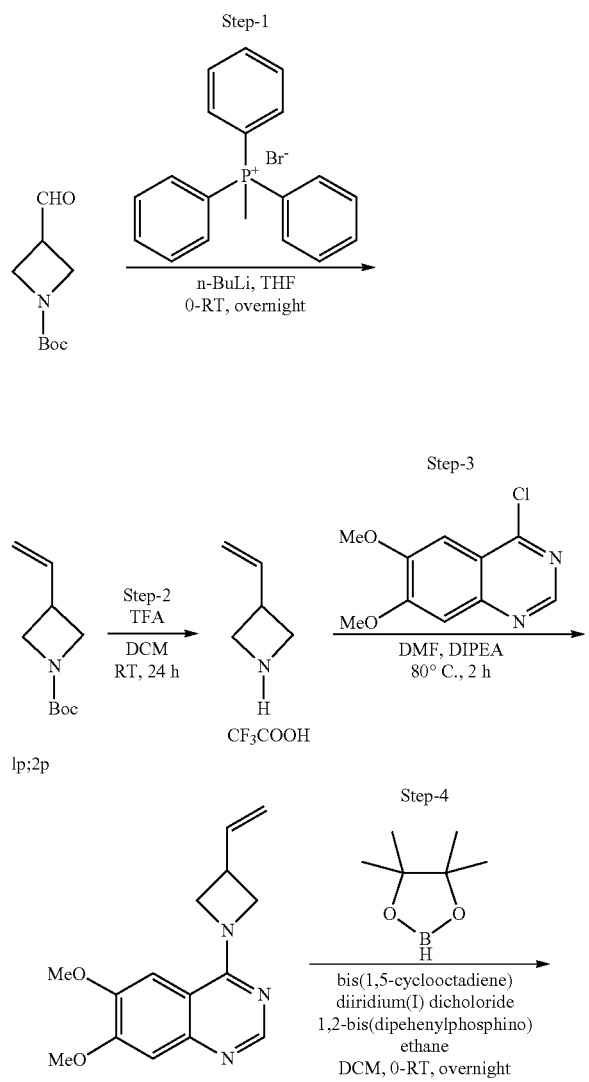

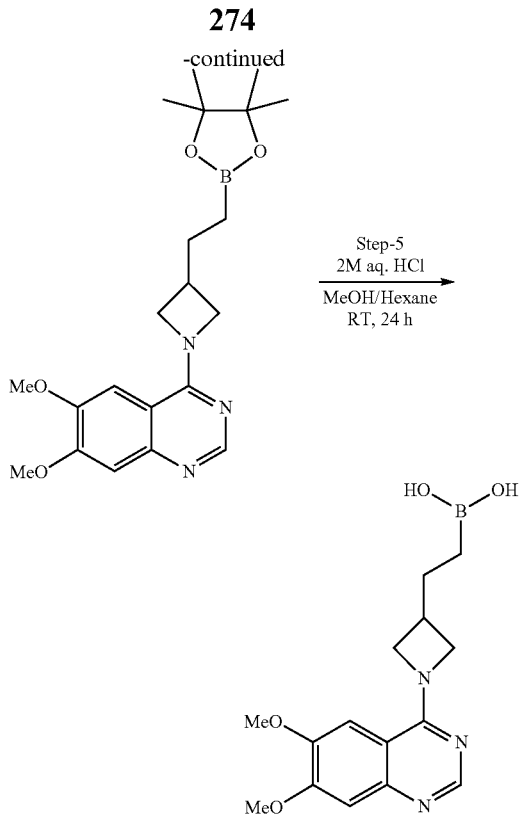

Step-1: Synthesis of tert-butyl 3-vinylazetidine-1-carboxylate: To a solution of methyltriphenylphosphonium bromide (1 g, 2.85 mmol, 2.6 eq) in THF (2 mL) was added n-butyllithium (2.5 mol/L solution in n-hexane, 1.3 mL, 3.24 mmol, 3 eq) at 0° C. under a nitrogen atmosphere, and the mixture was stirred at the same temperature for 10 minutes. To the reaction mixture a solution of tert-butyl 3-formylazetidine-1-carboxylate (200 mg, 1.08 mmol, 1.0 eq) in THF (2 mL) was added at the same temperature, and the mixture was stirred overnight at room temperature. To the reaction solution was added an aqueous ammonium chloride solution (10 mL), and the mixture was extracted with ethyl acetate (3×30 mL). The combined organic layer was washed with water and brine, dried over sodium sulfate, and concentrated. The residue was purified by normal phase silica gel column chromatography (eluent: ethyl acetate/n-hexane) to obtain tert-butyl 3-vinylazetidine-1-carboxylate (90 mg, 48%).

Step-2: Synthesis of 3-vinylazetidine 2,2,2-trifluoroacetate: To a solution of tert-butyl 3-ethenylazetidine-1-carboxylate (80 mg, 0.44 mmol, 1.0 eq) in methylene chloride (4 mL) was added 0.4 mL TFA at 0° C., and the reaction mixture was stirred at RT for 48 h. The reaction solution was concentrated and triturated with ether-hexane to get the semisolid (60 mg, 69%) which was used as such for next step without purification.

Step-3: Synthesis of 6,7-dimethoxy-4-(3-vinylazetidin-1-yl)quinazoline: To a solution of 3-vinylazetidine 2,2,2-trifluoroacetate (60 mg, 0.35 mmol, 1.0 eq) in DMF (2 mL) were added 4-chloro-6,7-dimethoxyquinazoline (80 mg. 0.35 mmol, 1.0 eq) and N,N-diisopropylethylamine (0.135 g, 1.05 mmol, 3.0 eq) and the reaction mixture was allowed to stir at 80° C. for 2 h. Progress of reaction was monitored by LCMS. After completion, reaction mixture was diluted with water (20 mL) and extracted with ethyl acetate (3×30 mL). Combined organic layer was washed with brine (30 mL), dried over anhydrous sodium sulfate and concentrated under vacuum to get the residue which was purified by silica gel column chromatography (Eluent: ethyl acetate/n-hexane) to obtain the title compound (50 mg, 52%). LCMS: 272[M+1]+

Step-4: Synthesis of 6,7-dimethoxy-4-(3-(2-(4,4,5,5-tetramethyl-1,3,2-dioxaborolan-2-yl)ethyl)azetidin-1-yl)quinazoline: To a solution of 6,7-dimethoxy-4-(3-vinylazetidin-1-yl)quinazoline (50 mg, 0.18 mmol, 1.0 eq) in DCM (4 mL) was added bis(1,5-cyclooctadiene)diiridium(I) dichloride (3 mg, 4 mol %) and 1,2-bis(diphenylphosphino)ethane (4 mg, 8 mol %) and the reaction mixture was allowed to stir at RT under nitrogen for 30 min. The reaction was cooled to 0° C. and pinacolborane (0.034 g, 0.27 mmol, 1.5 eq) was added dropwise. The reaction was allowed to stir at RT for overnight. Progress of reaction was monitored by LCMS. The reaction was quenched by addition of water (10 mL) and extracted with DCM (3×25 mL). Combined organic layer was washed with brine (30 mL), dried over anhydrous sodium sulfate and concentrated under vacuum to get the residue which was purified by normal phase silica gel column chromatography (eluent: ethyl acetate/n-hexane) to obtain the title compound (30 mg, 41%). LCMS: 400[M+1]+

Step-5: Synthesis of 2-(1-(6,7-dimethoxyquinazolin-4-yl)azetidin-3-yl)ethylboronic acid: To a solution of 6,7-dimethoxy-4-(3-(2-(4,4,5,5-tetramethyl-1,3,2-dioxaborolan-2-yl)ethyl)azetidin-1-yl)quinazoline (20 mg, 0.02 mmol, 1 eq) in MeOH:Hexane (1:1, 2 mL) was added 2 M aqueous HCl (0.4 mL) and the resulting reaction mixture was allowed to stir at RT for 24 h. The reaction mixture was concentrated under reduced pressure to afford crude product which was purified by RP-HPLC to afford 2-(1-(6,7-dimethoxyquinazolin-4-yl)azetidin-3-yl)ethylboronic acid (1 mg, 6%). LCMS: 318 [M+1]+; 1H NMR (400 MHz, CD3OD) δ ppm 8.26 (s, 2H), 7.31 (s, 1H), 7.10 (s, 1H), 4.66 (brs, 2H), 4.18 (brs, 2H), 3.95 (s, 3H), 3.97 (s, 3H), 2.82-2.78 (m, 2H), 1.97-1.92 (m, 1H), 1.82-1.74 (m, 2H).

Example-31: Synthesis of 4-(3-(2-sulfamoylaminoethyl)azetidine-1-yl)-7,8-dimethoxyquinazoline, (Compound 1.31)

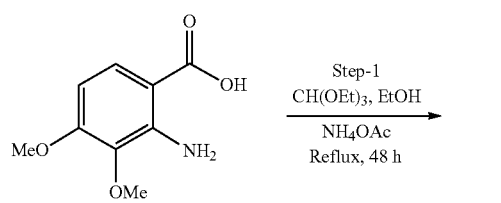

Step-1
CH(OEt)3, EtOH
NH4OAc
Reflux, 48 h

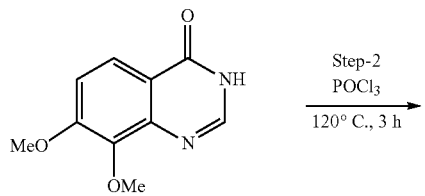

Step-2
POCl3
120° C., 3 h

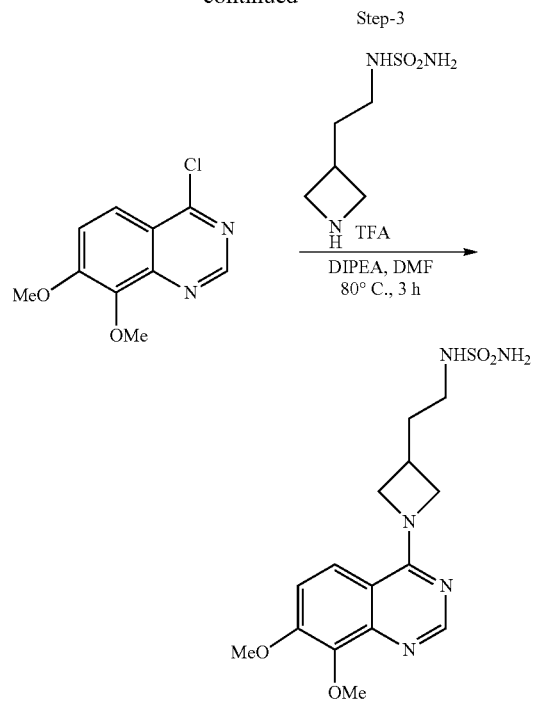

Step-1: Synthesis of 7,8-dimethoxyquinazolin-4 (3H)-one: To a solution of 2-amino-3,4-dimethoxybenzoic acid (0.25 g, 1.26 mmol, 1 eq) in ethanol (3.5 mL) were added triethylorthoformate (0.43 mL, 2.6 mmol, 2.1 eq) and ammonium acetate (0.38 g, 4.9 mmol, 3.9 eq.) and the reaction mixture was allowed to stir under reflux for 48 h. Progress of reaction was monitored by TLC. After completion, reaction mixture was cooled to RT, solid was filtered, washed with hexane and dried under vacuum to afford 7,8-dimethoxyquinazolin-4 (3H)-one (0.19 g, 73%). LCMS: 207 [M+1]+

Step-2: Synthesis of 4-chloro-7,8-dimethoxyquinazoline: A mixture of 7,8-dimethoxyquinazolin-4 (3H)-one (0.1 g, 0.48 mmol, 1 eq) in POCl3 (1 mL) was allowed to stir at 120° C. for 3 h. Progress of reaction was monitored by TLC. After completion reaction mixture was cooled to RT, diluted with cold water (100 mL) and extracted with ethyl acetate (3×100 mL). Combined organic layer was washed with water (3×50 mL) followed by brine (50 mL) and dried over anhydrous sodium sulfate. Removal of solvent under reduced pressure afforded 4-chloro-7,8-dimethoxyquinazoline (0.1 g, 92%) which was used in the next step without purification. LCMS: 225 [M+1]+

Step-3: Synthesis of 4-(3-(2-sulfamoylaminoethyl)azetidine-1-yl)-7,8-dimethoxyquinazoline: A suspension of 4-chloro-7,8-dimethoxyquinazoline (76 mg, 0.34 mmol, 2 eq), 3-(2-sulfamoylaminoethyl)azetidine trifluoroacetate (50 mg, 0.17 mmol, 1.0 eq) and DIPEA (0.06 mL, 0.34 mmol, 2.0 eq) in DMF (1.5 mL) was allowed to stir at 80° C. for 3 h. After 3 h, reaction mixture was concentrated under reduced pressure to afford crude product which was purified using reversed phase HPLC to afford 4-(3-(2-sulfamoylaminoethyl)azetidine-1-yl)-7,8-dimethoxyquinazoline (3.96 mg, 6%). LCMS: 368[M+1]+; 1H NMR (400 MHz, DMSO-d6) δ ppm 8.38 (s, 1H), 7.69 (d, 1H), 7.28 (d, 1H), 6.57 (brs, 1H), 6.52 (s, 2H), 4.55 (brs, 2H), 4.08 (brs, 2H), 3.94 (s, 3H), 3.86 (s, 3H), 2.95-2.80 (m, 3H), 1.90-1.80 (m, 2H).

Example-32: Synthesis of 8-(3-(2-sulfamoylamino-ethyl)azetidine-1-yl)-4-fluoro-1-methyl-1H-imidazo[4,5-g]quinazoline, (Compound 1.32)

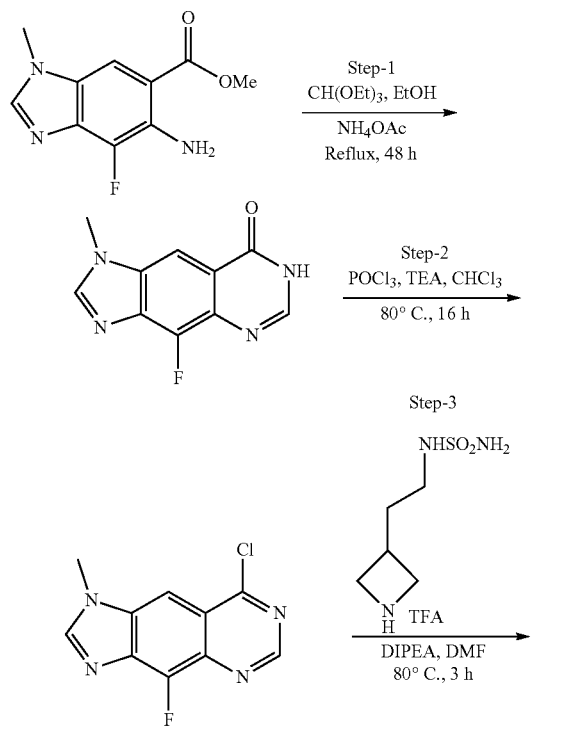

Step-1: Synthesis of 4-fluoro-1-methyl-1H-imidazo[4,5-g]quinazolin-8 (7H)-one: To a solution of methyl 5-amino-4-fluoro-1-methyl-1H-benzo[d]imidazole-6-carboxylate (0.25 g, 1.1 mmol, 1 eq) in ethanol (3 mL) were added triethylorthoformate (0.39 mL, 2.3 mmol, 2.1 eq) and ammonium acetate (0.33 g, 4.3 mmol, 3.9 eq.) and the reaction mixture was allowed to stir reflux for 48 h. Progress of reaction was monitored by TLC. After completion, reaction mixture was cooled to RT, solid was filtered to get residue which was triturated with diethyl ethe and ethanol to afford 4-fluoro-1-methyl-1H-imidazo[4,5-g]quinazolin-8 (7H)-one (0.13 g, 53%). LCMS: 219[M+1]$^+$ Step-2: Synthesis of 8-chloro-4-fluoro-1-methyl-1H-imidazo[4,5-g]quinazoline: To a solution of 4-fluoro-1-methyl-1H-imidazo[4,5-g]quinazolin-8 (7H)-one (50 mg, 0.22 mmol, 1 eq) in CHCl$_3$ (2 mL) were added POCl$_3$ (0.06 mL, 0.72 mmol, 3.15 eq) and triethylamine (0.1 mL, 0.76 mmol, 3.35 eq) and reaction mixture was allowed to stir at 80° C. for 16 h. Progress of reaction was monitored by TLC. After completion, reaction mixture was cooled to RT, diluted with cold water (100 mL) and extracted with ethyl acetate (3×100 mL). Combined organic layer was washed with brine (50 mL) and dried over anhydrous sodium sulfate. Removal of solvent under reduced pressure afforded 8-chloro-4-fluoro-1-methyl-1H-imidazo[4,5-g]quinazoline (40 mg, 54%) which was used in next step without purification. LCMS: 237 [M+1]$^+$ Step-3: Synthesis of 8-(3-(2-sulfamoylaminoethyl)azetidine-1-yl)-4-fluoro-1-methyl-1H-imidazo[4,5-g]quinazoline: A suspension of 8-chloro-4-fluoro-1-methyl-1H-imidazo[4,5-g]quinazoline (42 mg, 0.17 mmol, 1.5 eq), 3-(2-sulfamoylaminoethyl)azetidine trifluoroacetate (35 mg, 0.11 mmol, 1.0 eq) and DIPEA (0.04 mL, 0.23 mmol, 2 eq) in DMF (1 mL) was allowed to stir at 80° C. for 3 h. Progress of reaction was monitored by TLC. After completion, reaction mixture was concentrated under reduced pressure to afford crude product which was purified by reversed phase HPLC to afford 8-(3-(2-sulfamoylaminoethyl)azetidine-1-yl)-4-fluoro-1-methyl-1H-imidazo[4,5-g]quinazoline (1.6 mg, 3%). LCMS: 380[M+1]$^+$; $^1$H NMR (400 MHz, DMSO-d$_6$) δ ppm 8.56 (s, 1H), 8.40 (s, 1H), 7.85 s, 1H), 6.59 (brs, 1H), 6.56 (s, 2H), 4.66 (brs, 2H), 4.25 (brs, 2H), 3.96 (s, 3H), 3.00-2.82 (m, 3H), 1.92-1.81 (m, 2H).

Example-33: Synthesis of 4-(3-(2-sulfamoylamino-ethyl)azetidine-1-yl)-2-(4-fluorophenyl)-6,7-dimethoxyquinazoline, (Compound 1.33)

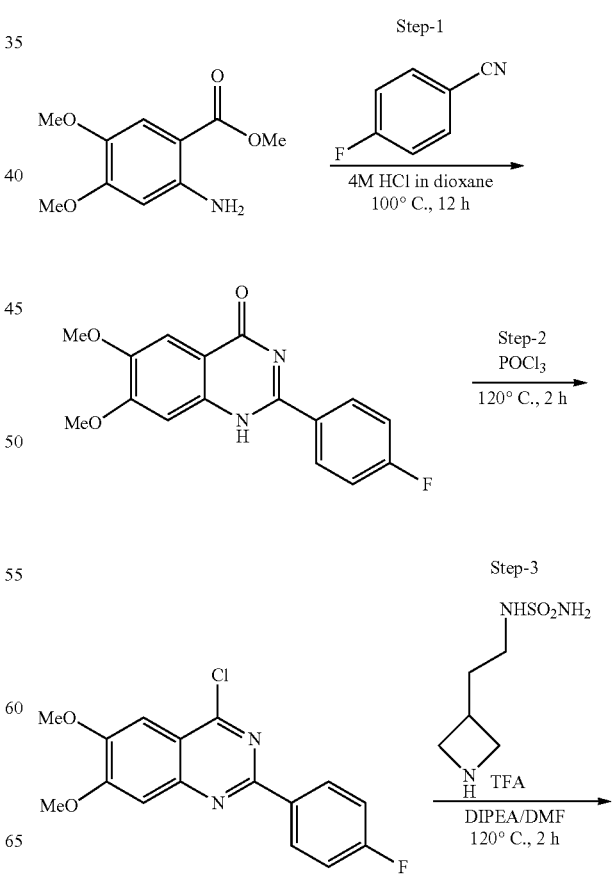

-continued

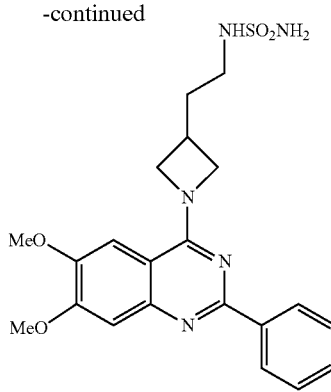

Step-1: Synthesis of 2-(4-fluorophenyl)-6,7-dimethoxyquinazolin-4 (1H)-one: A mixture of methyl 2-amino-4,5-dimethoxybenzoate (500 mg, 2.36 mmol, 1 eq) and 4-fluorobenzonitrile (315 mg, 2.60 mmol, 1.1 eq) was suspended in 4M HCl in dioxane (10 mL) and the resulting mixture was sonicated for 30 minutes. The reaction mixture was then allowed to stir at 100° C. for 12 h. Progress of reaction was monitored by TLC. After completion, reaction mixture was cooled to RT, diluted with ice cold water and stirred for 15 minutes. Solid was filtered, washed with water and dried under vacuum to afford 2-(4-fluorophenyl)-6,7-dimethoxyquinazolin-4 (1H)-one (250 mg, 35%). LCMS: 300[M+1]$^+$ Step-2: Synthesis of 4-chloro-2-(4-fluorophenyl)-6,7-dimethoxyquinazoline: A mixture of 2-(4-fluorophenyl)-6,7-dimethoxyquinazolin-4 (1H)-one (250 mg, 0.83 mmol, 1 eq) in POCl$_3$ (2.5 mL) was allowed to stir at 120° C. for 2 h. Progress of reaction was monitored by TLC. After completion, reaction mixture was cooled to RT, diluted with ice-cold water (50 mL) and stirred for 15 minutes. Solid was filtered and dried under vacuum to afford 4-chloro-2-(4-fluorophenyl)-6,7-dimethoxyquinazoline (200 mg, 75%). LCMS: 318[M+1]$^+$ Step-3: Synthesis of 4-(3-(2-sulfamoylaminoethyl)azetidine-1-yl)-2-(4-fluorophenyl)-6,7-dimethoxyquinazoline: A suspension of 4-chloro-2-(4-fluorophenyl)-6,7-dimethoxyquinazoline (50 mg, 0.15 mmol, 1.0 eq), 3-(2-sulfamoylaminoethyl)azetidine trifluoroacetate (43 mg, 0.15 mmol, 1.0 eq) and N,N diisopropylethylamine (38.7 mg, 0.30 mmol, 2.0 eq) in DMF (1 mL) was allowed to stir at 80° C. for 2 h. Progress of reaction was monitored by TLC. After completion, reaction mixture was cooled to RT, DMF was removed under reduced pressure to obtain crude which was purified by reversed phase HPLC to afford 4-(3-(2-sulfamoylaminoethyl)azetidine-1-yl)-2-(4-fluorophenyl)-6,7-dimethoxyquinazoline (13 mg, 18%). LCMS: 461 [M+1]$^+$; $^1$H NMR (400 MHz, DMSO-d$_6$) δ ppm 8.42 (dd, 2H), 7.60-7.38 (m, 3H), 7.30 (s, 1H), 6.62 (brs, 1H), 6.58 (s, 2H), 5.20-4.20 (m, 4H), 3.98 (s, 3H), 7.95 (s, 3H), 3.02-2.85 (m, 3H), 1.92-1.83 (m, 2H).

Example-34: Synthesis of 4-(3-(2-sulfamoylaminoethyl)azetidine-1-yl)-7-methoxy-2-phenylquinazoline, (Compound 1.34)

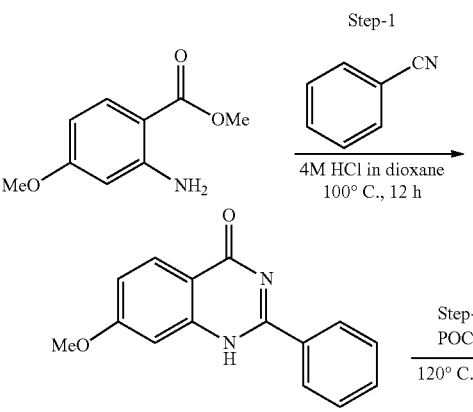

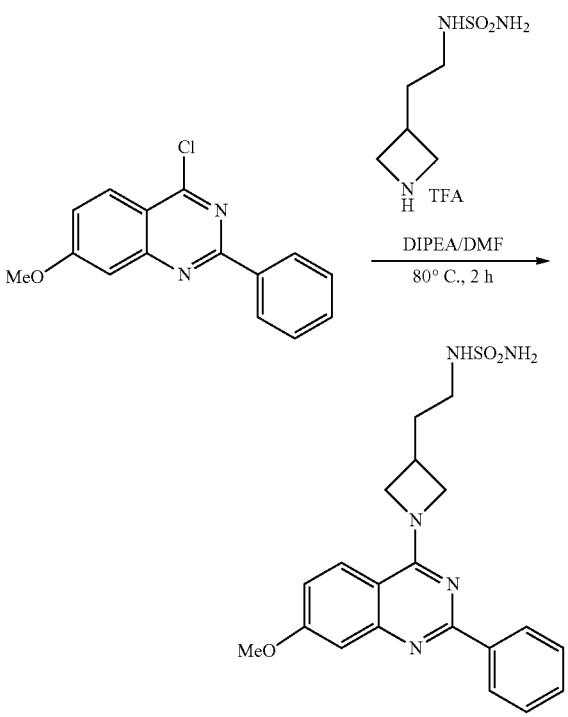

Step-1: Synthesis of 7-methoxy-2-phenylquinazolin-4 (1H)-one: A mixture of methyl 2-amino-4-methoxybenzoate (650 mg, 3.59 mmol, 1 eq) and benzonitrile (0.4 mL, 3.95 mmol, 1.1 eq) in 4M HCl in dioxane (10 mL) was stirred at 100° C. for 12 h. Progress of reaction was monitored by TLC. After completion, reaction mixture was cooled to RT, diluted with ice cold water and stirred for 15 minutes. Solid obtained was filtered and dried under vacuum to afford 7-methoxy-2-phenylquinazolin-4 (1H)-one (500 mg, 55%). LCMS: 252 [M+1]$^+$ Step-2: Synthesis of 4-chloro-7-methoxy-2-phenylquinazoline: A mixture of 7-methoxy-2-phenylquinazolin-4 (1H)-one (165 mg, 0.65 mmol, 1 eq) in POCl$_3$ (0.6 mL) was heated at 120° C. for 2 h. Progress of reaction was monitored by TLC. After completion, reaction mixture was cooled to RT, diluted with ice-cold water (10 mL) and stirred for 15 minutes. Solid was filtered and dried under vacuum to 4-chloro-7-methoxy-2-phenylquinazoline (100 mg, 56%). LCMS: 270[M+1]$^+$ Step-3: Synthesis of 4-(3-(2-sulfamoylaminoethyl)azetidine-1-yl)-7-methoxy-2-phenylquinazoline: A suspension of 4-chloro-7-methoxy-2-phenylquinazoline (50 mg, 0.18 mmol, 1.0 eq), N-[2-(azetidin-3-yl)ethyl]sulfuric diamide trifloroacetic acid (54 mg, 0.15 mmol, 1.0 eq) and N,N diisopropylethylamine (47 mg, 0.30 mmol, 2.0 eq) in DMF (1 mL) was allowed to stir at 80° C. for 2 h. Progress of reaction was monitored by TLC. Reaction mixture was cooled to RT, DMF was removed under reduced pressure to give crude which was purified by reversed phase HPLC to afford 4-(3-(2-sulfamoylaminoethyl)azetidine-1-yl)-7-methoxy-2-phenylquinazoline (13 mg, 17%). LCMS: 413 [M+1]$^+$; 8.45 (d, 2H), 8.20 (s, 1H), 7.88 (d, 1H), 7.47 (brs, 3H), 7.20 (s, 1H), 7.04 (d, 1H), 6.01-6.50 (m, 3H), 4.65 (brs, 2H), 4.20 (brs, 2H), 3.91 (s, 3H), 3.00-2.82 (m, 3H), 1.92-1.80 (m, 2H).

Example-35: Synthesis of 4-(3-(2-sulfamoylaminoethyl)azetidine-1-yl)-6,7-dimethoxy-2-(pyridin-4-yl)quinazoline, (Compound 1.35)

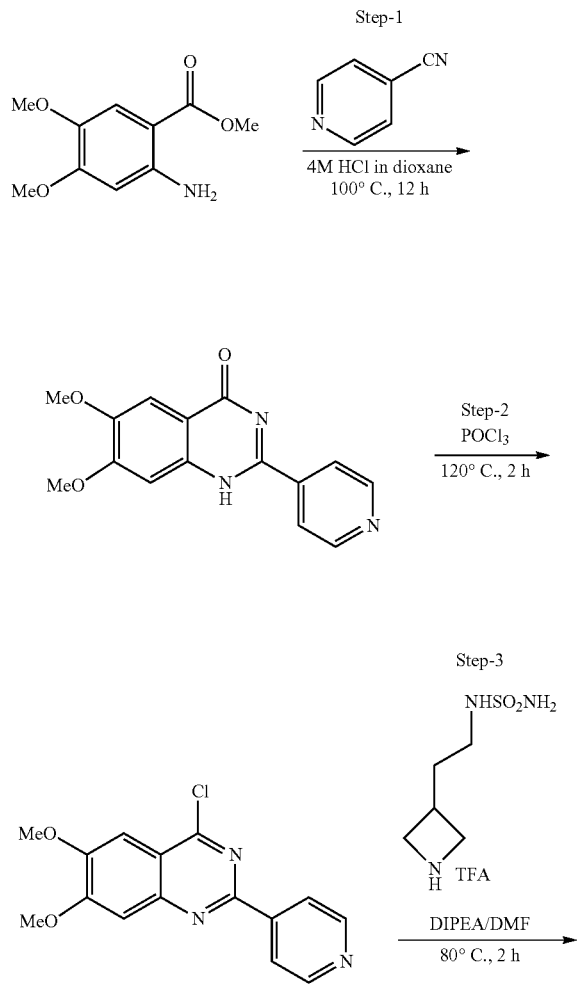

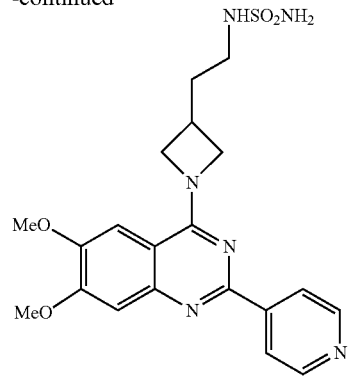

Step-1: Synthesis of 6,7-dimethoxy-2-(pyridin-4-yl)quinazolin-4 (1H)-one: A mixture of methyl 2-amino-4,5-dimethoxybenzoate (1 g, 4.73 mmol, 1 eq) and pyridine-4-carbonitrile (541 mg, 2.60 mmol, 1.1 eq) in 4M HCl in dioxane (10 mL) was stirred at 100° C. for 12 h. Progress of reaction was monitored by TLC. After completion, reaction mixture was cooled to RT, diluted with ice cold water and stirred for 15 minutes. Solid was filtered and dried under vacuum to afford 6,7-dimethoxy-2-(pyridin-4-yl)quinazolin-4 (1H)-one (410 mg, 30%). LCMS: 283[M+1]$^+$ Step-2: Synthesis of 4-chloro-6,7-dimethoxy-2-(pyridin-4-yl)quinazoline: A mixture of 6,7-dimethoxy-2-(pyridin-4-yl)quinazolin-4 (1H)-one (200 mg, 0.90 mmol, 1 eq) in POCl$_3$ (0.6 mL) was stirred at 120° C. for 2 h. Progress of reaction was monitored by TLC. After completion, reaction mixture was cooled to RT, diluted with ice cold water (10 mL) and stirred for 15 minutes. Solid was filtered and dried under vacuum to afford 4-chloro-6,7-dimethoxy-2-(pyridin-4-yl)quinazoline (100 mg, 47%). LCMS: 301[M+1]$^+$ Step-3: Synthesis of 4-(3-(2-sulfamoylaminoethyl)azetidine-1-yl)-6,7-dimethoxy-2-(pyridin-4-yl)quinazoline: A suspension of 4-chloro-6,7-dimethoxy-2-(pyridin-4-yl)quinazoline (50 mg, 0.16 mmol, 1.0 eq), 3-(2-sulfamoylaminoethyl)azetidine trifluoroacetate (49 mg, 0.15 mmol, 1.0 eq) and N,N diisopropylethylamine (42 mg, 0.30 mmol, 2.0 eq) in DMF (1 mL) was allowed to stir at 80° C. for 2 h. Progress of reaction was monitored by TLC. Reaction mixture was cooled to RT, DMF was removed under reduced pressure, crude obtained was purified by reversed phase HPLC to afford 4-(3-(2-sulfamoylaminoethyl)azetidine-1-yl)-6,7-dimethoxy-2-(pyridin-4-yl)quinazoline (13 mg, 17%). LCMS: 461[M+1]$^+$; $^1$H NMR (400 MHz, DMSO-d$_6$) δ ppm 8.70 (d, 2H), 8.29 (s, 1H), 8.28 (s, 1H), 7.24 (d, 2H), 6.60 (brs, 1H), 6.57 (s, 2H), 4.68 (brs, 2H), 4.25 (brs, 2H), 3.95 (s, 3H), 3.91 (s, 3H), 3.00-2.81 (m, 3H), 1.92-1.80 (m, 2H).

Example-36: Synthesis of 6,7-dimethoxy-2-(1-methylpyrazol-3-yl)-4-[3-[2-(sulfamoylamino)ethyl]azetidin-1-yl]quinazoline, (Compound 1.36)

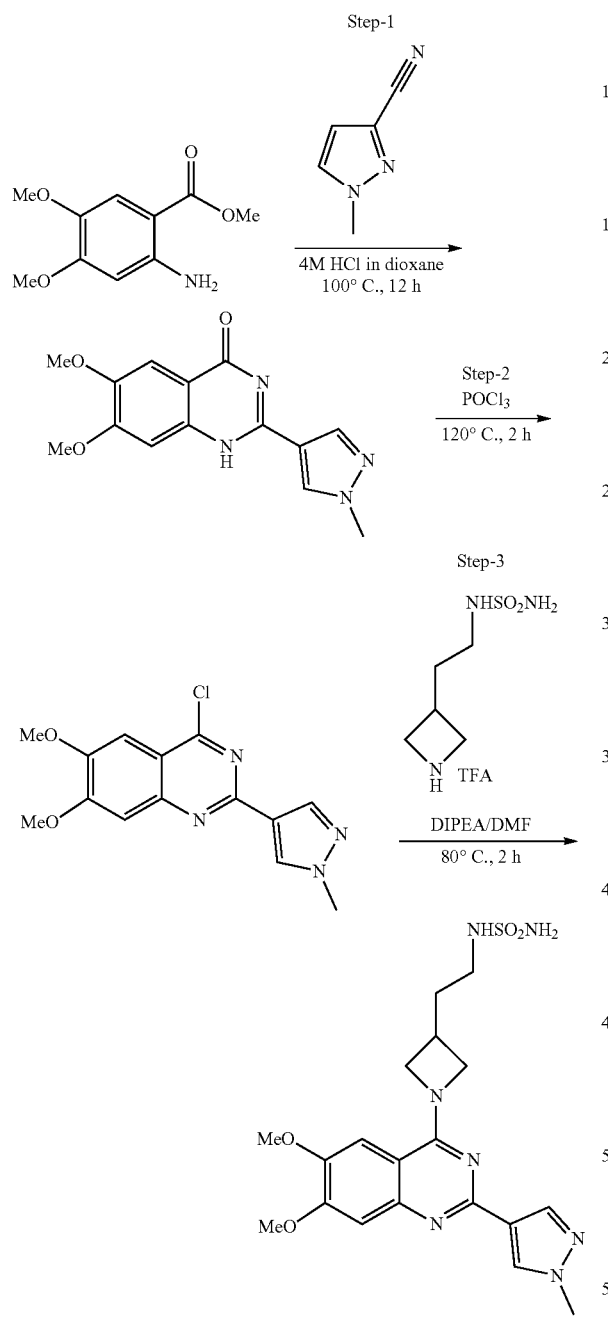

Step-1: Synthesis of 6,7-dimethoxy-2-(1-methylpyrazol-3-yl)quinazoline 4 (1H)-one: A mixture of methyl 2-amino-4,5-dimethoxy-benzoate (500 mg, 2.36 mmol, 1 eq) and 1-methylpyrazole-3-carbonitrile (279 mg, 2.60 mmol, 1.1 eq) in 4M HCl in dioxane (5 mL) was sonicated for 30 minutes and then stirred at 100° C. for 12 h. Progress of reaction was monitored by TLC. After completion, reaction mixture was cooled to RT, poured into ice-cold water and stirred for 15 minutes. The solid obtained was filtered and dried under vacuum to afford 6,7-dimethoxy-2-(1-methylpyrazol-3-yl)quinazoline 4 (1H)-one (415 mg, 56%). LCMS: 287 [M+1]+

Step-2: Synthesis of 4-chloro-6,7-dimethoxy-2-(1-methylpyrazol-3-yl)quinazoline: To a stirred solution of 6,7-dimethoxy-2-(1-methylpyrazol-3-yl)quinazoline 4 (1H)-one (200 mg, 0.69 mmol, 1 eq) in POCl₃ (1 mL) was stirred at 120° C. for 2 h. Progress of reaction was monitored by TLC. After completion, reaction mixture was cooled to RT, poured into ice-cold water (20 mL) and stirred for 15 minutes. Solid was filtered and dried under vacuum to afford 4-chloro-6,7-dimethoxy-2-(1-methylpyrazol-3-yl)quinazoline (76 mg, 35%). LCMS: 305 [M+1]+

Step-3: Synthesis of 6,7-dimethoxy-2-(1-methylpyrazol-3-yl)-4-[3-[2-(sulfamoylamino)ethyl]azetidin-1-yl]quinazoline: A suspension of 4-chloro-6,7-dimethoxy-2-(1-methylpyrazol-3-yl)quinazoline (50 mg, 0.164 mmol, 1.0 eq), N-[2-(azetidin-3-yl)ethyl]sulfuric diamide trifloroacetic acid (49 mg, 0.164 mmol, 1.0 eq) and N,N diisopropylethylamine (60 mg, 0.32 mmol, 2.0 eq) in DMF (2 mL) was allowed to stir at 80° C. for 2 h. Progress of reaction was monitored by TLC. Reaction mixture was cooled to RT, concentrated under vacuum to get semi-solid residue which was triturated with ether, ethyl acetate and then with pentane to afford crude solid which was purified by reversed phase HPLC to afford 6,7-dimethoxy-2-(1-methylpyrazol-3-yl)-4-[3-[2-(sulfamoylamino)ethyl]azetidin-1-yl]quinazoline (3 mg, 4%). LCMS: 448 [M+1]+; ¹H NMR (400 MHz, DMSO-d6) δ ppm 13.90 (brs, 1H), 7.95 (s, 1H), 7.58 (s, 1H), 7.28 (s, 1H), 7.00 (s, 1H), 6.60 (s, 1H), 6.58 (s, 2H), 4.80 (brs, 2H), 4.42 (brs, 2H), 4.02 (s, 3H), 3.98 (s, 6H), s 3.03-2.90 (m, 3H), 2.00-1.82 (m, 2H).

Example-37: Synthesis of 2-ethyl-7-methoxy-4-[3-[2-(sulfamoylamino)ethyl]azetidin-1-yl]quinazoline, (Compound 1.37)

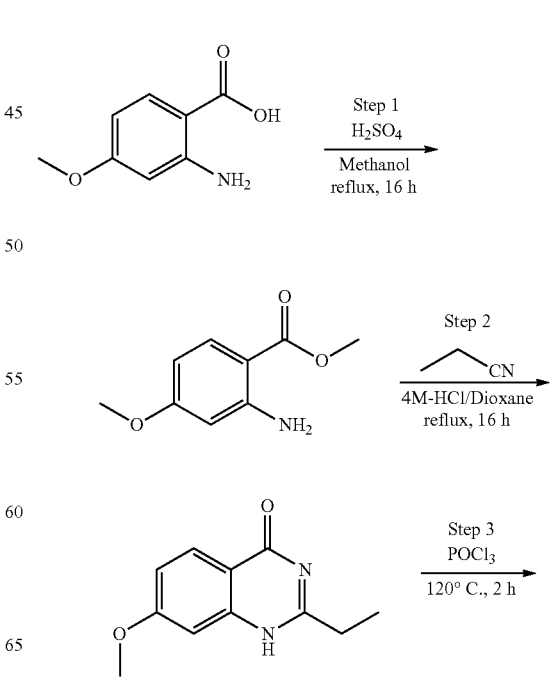

Step 4

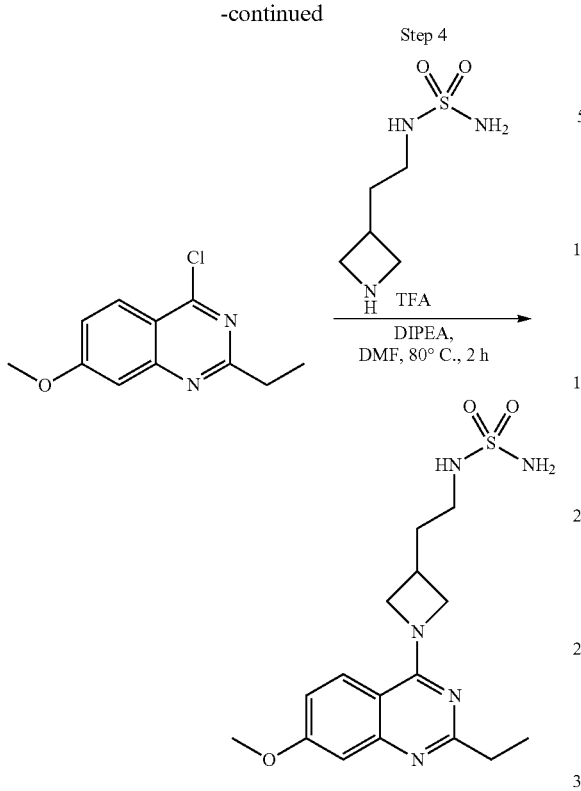

Step Step-1: Synthesis of methyl 2-amino-4-methoxy-benzoate: To a mixture of 2-amino-4-methoxy-benzoic acid (5 g, 29.94 mmol, 1 eq) in methanol (100 mL) was added $H_2SO_4$ (6 mL) and then allowed to reflux for 16 h. Progress of reaction was monitored by TLC. After completion, reaction mixture was cooled to RT, and concentrated under reduced pressure, neutralized with sodium bicarbonate and diluted with water (100 mL), extracted with ethyl acetate (300 mL). Organic layer was concentrated under reduced pressure to afford the title compound (3.9 g, 78%). LCMS: 182[M+1]$^+$ Step-2: Synthesis of 2-ethyl-7-methoxy-1H-quinazolin-4-one: A mixture of methyl 2-amino-4-methoxy-benzoate (800 mg, 4.41 mmol, 1 eq) and propanenitrile (330 mg, 4.48 mmol, 1.1 eq) in 4M HCl in dioxane (09 mL) was sonicated for 30 minutes and followed by heating at 100° C. for 12 h. Progress of reaction was monitored by TLC. After completion, reaction mixture was cooled to RT, poured into ice-cold water and stirred for 15 minutes. The solid obtained was filtered and dried under vacuum to afford the title compound (350 mg, 38%). LCMS: 205[M+1]$^+$ Step-3: Synthesis of 4-chloro-2-ethyl-7-methoxy-quinazoline: A stirred solution of 2-ethyl-7-methoxy-1H-quinazolin-4-one (200 mg, 0.98 mmol, 1 eq) in POCl$_3$ (0.5 mL) was allowed to heat at 120° C. for 2 h. Progress of reaction was monitored by TLC. After completion, reaction mixture was cooled to RT, poured into ice-cold water (20 mL) and stirred for 15 minutes. Solid was filtered and dried under vacuum to afford the title compound (90 mg, 41%). LCMS: 223[M+1]$^+$ Step-4: Synthesis of 2-ethyl-7-methoxy-4-[3-[2-(sulfamoylamino)ethyl]azetidin-1-yl]quinazoline: A suspension of 4-chloro-2-ethyl-7-methoxy-quinazoline (90 mg, 0.40 mmol, 1.0 eq), N-[2-(azetidin-3-yl)ethyl]sulfuric diamide trifloroacetic acid (118 mg, 0.40 mmol, 1.0 eq) and N,N diisopropylethylamine (150 mg, 0.81 mmol, 2.0 eq) in DMF (2 mL) was allowed to stir at 80° C. for 2 h. Progress of reaction was monitored by TLC. Reaction mixture was cooled to RT, concentrated under vacuum to get semi-solid residue which was triturated with ether, ethyl acetate and then with pentane to afford crude solid which was purified by RP-HPLC to afford the title compound (24 mg, 16%). LCMS: 366[M+1]$^+$; $^1$H NMR (400 MHz, DMSO-d6) δ ppm 7.85 (d, J=9.21 Hz, 1H), 7.11-6.99 (m, 2H), 6.61-6.47 (m, 3H), 4.59 (br. s., 2H), 4.15 (br. s., 2H), 3.88 (s, 3H), 2.98-2.81 (m, 3H), 2.70 (q, J=7.75 Hz, 2H), 1.91 (s, 1H), 1.85 (q, J=6.72 Hz, 2H), 1.26 (t, J=7.45 Hz, 3H).

Example-38: Synthesis of (2-(7-fluoro-6-methoxy-quinazolin-4-yl)azetidin-3-yl))aminosulfonamide, (Compound 1.38)

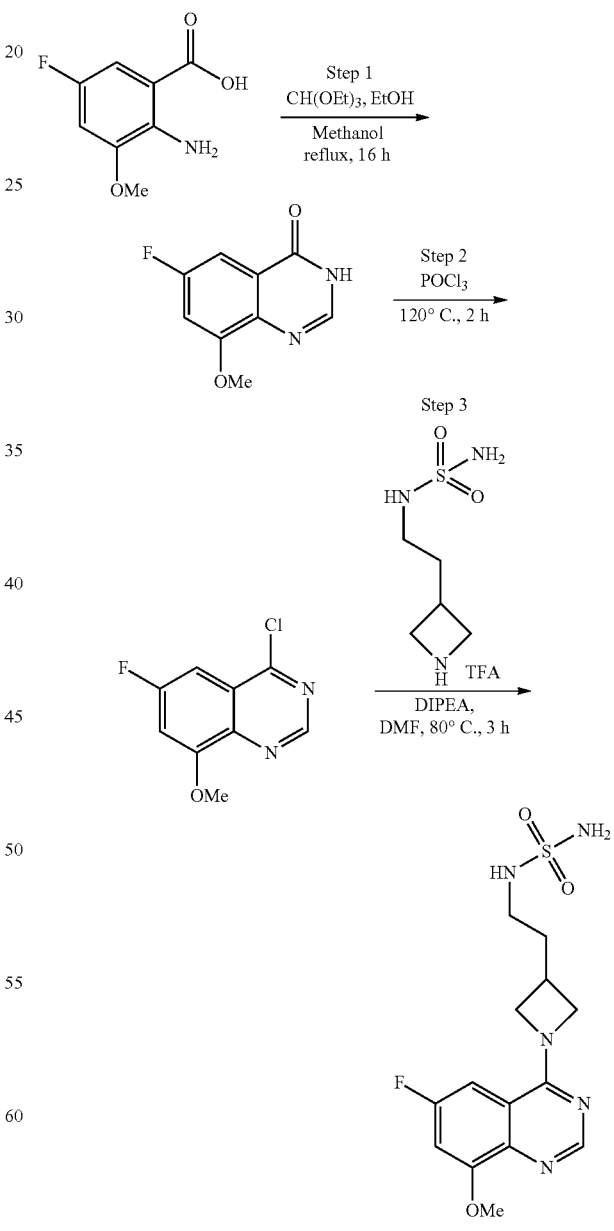

Step-1: Synthesis of 6-fluoro-8-methoxyquinazolin-4 (3H)-one: To a stirred solution of 2-amino-5-fluoro-3- methoxybenzoic acid (0.5 g, 2.7 mmol, 1 eq) in ethanol (6 mL) was added triethylorthoformate (0.8 mL, 4.8 mmol, 1.8 eq) and ammonium acetate (0.58 g, 7.5 mmol, 2.8 eq.). The resulting reaction mixture was allowed to stir at 90° C. for 48 h. After 48 h, reaction mixture was cooled to RT, filtered and washed with hexane to afford the title compound (0.39 g, 74%). LCMS: 195[M+1]$^+$ Step-2: Synthesis of 4-chloro-6-fluoro-8-methoxyquinazoline: A mixture of 6-fluoro-8-methoxyquinazolin-4 (3H)-one in POCl$_3$ (1.5 mL) was allowed to stir at 120° C. for 2 h. Progress of reaction of reaction was monitored by TLC. After completion, reaction mixture was poured into cold water (100 mL), precipitates so obtained were filtered, dried under vacuum to afford title compound (0.11 g, 67%) which was used as such for next step without purification. LCMS: 213[M+1]$^+$ Step-3: Synthesis of (2-(7-fluoro-6-methoxyquinazolin-4-yl)azetidin-3-yl))aminosulfonamide: A suspension of 4-chloro-6-fluoro-8-methoxyquinazoline (54 mg, 0.25 mmol, 1.5 eq), N-[2-(azetidin-3-yl)ethyl]sulfuric diamide trifloroacetic acid (50 mg, 0.17 mmol, 1.0 eq) and DIPEA (0.06 mL, 0.34 mmol, 2.0 eq) in DMF (1 mL) was allowed to stir at 80° C. for 3 h. After 3 h, reaction mixture was concentrated under reduced pressure to afford crude which was purified using RP-HPLC to afford the title compound (6 mg, 10%). LCMS: 356 [M+1]$^+$; $^1$HNMR (400 MHz, DMSO-d6) δ ppm 8.39 (s, 1H), 7.23 (d, J=10.09 Hz, 1H), 7.17 (d, J=9.65 Hz, 1H), 6.48-6.60 (m, 3H), 4.56 (br. s., 2H), 4.13 (br. s., 2H), 3.92 (s, 3H), 2.92 (d, J=6.14 Hz, 2H), 2.84 (br. s., 1H), 1.84 (d, J=7.02 Hz, 2H).

Example-39: Synthesis of 3-(1-(6,7-dimethoxyquinazolin-4-yl)azetidin-3-yl)propane-1-sulfonamide, (Compound 1.39)

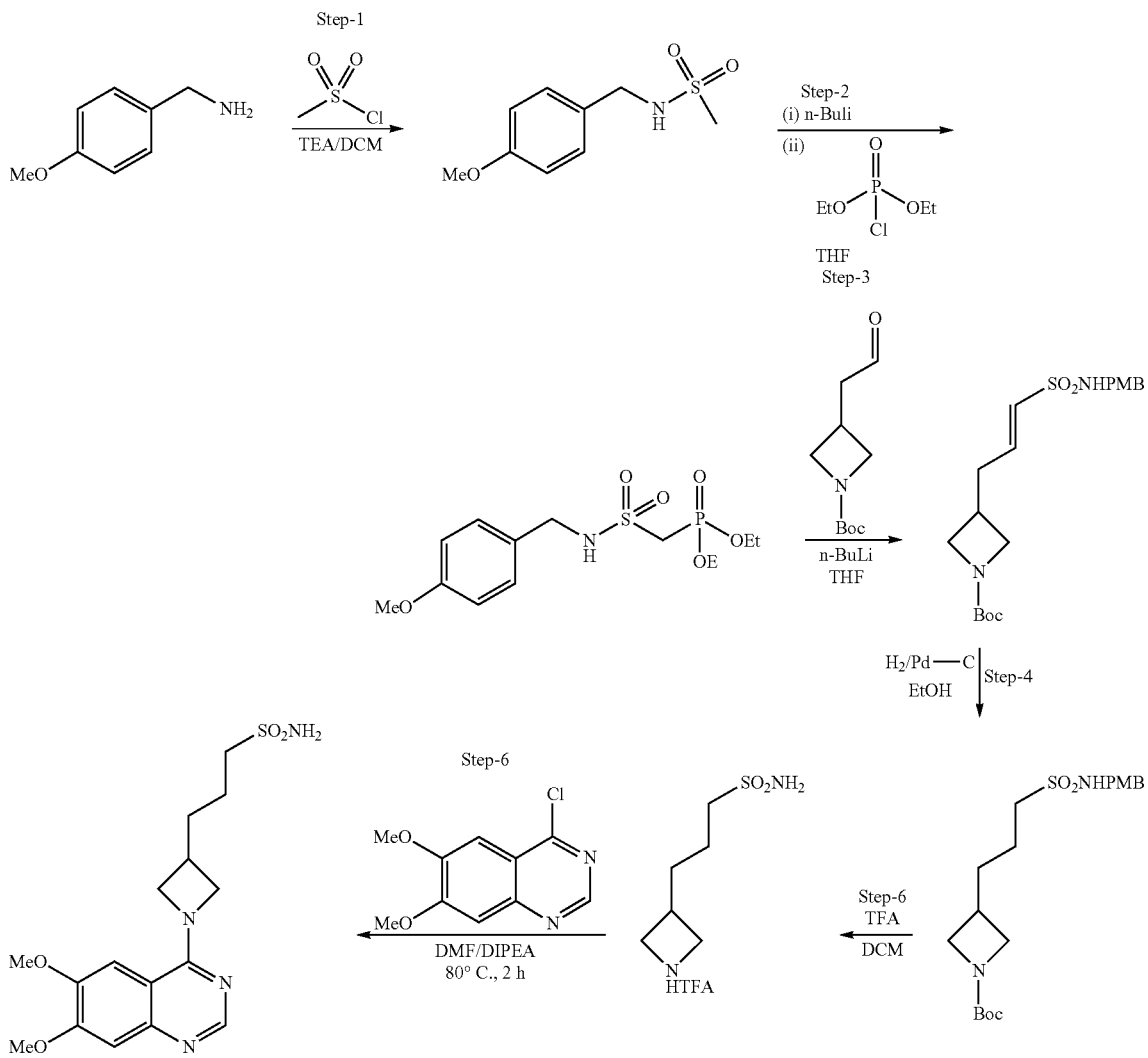

Step-1: Synthesis of N-(4-methoxybenzyl)methanesulfonamide: To a solution of 4-methoxybenzylamine (2 g, 14 mmol, 1.0 eq) in DCM (20 mL) was added triethylamine (3.96 mL, 29 mmol, 2 eq) and the reaction mixture was allowed to stir at 0° C. for 5 min. To this mixture was added methane sulfonyl chloride (1.35 mL, 17 mmol, 1.2 eq) and the reaction mixture was stirred at 0° C. for 10 min followed by stirring at RT for 2 h. Progress of reaction was monitored by $^1$H NMR. After completion, reaction mixture was diluted with water (100 mL) and extracted with ethyl acetate (3×100 mL). Combined organic layer was washed with brine (150 mL) and dried over anhydrous sodium sulfate. Removal of solvent under reduced pressure afforded the title compound (2.5 g), which was used for next step without purification.

Step-2: Synthesis of diethyl(N-(4-methoxybenzyl)sulfamoyl)methylphosphonate: N-(4-methoxybenzyl)methanesulfonamide (2 g, 9.2 mmol, 1 eq) was dissolved in THF (20 ml) and cooled to −78° C. To this solution was added 2.5 M n-BuLi (7.6 mL, 18 mmol, 2 eq) dropwise under nitrogen and the reaction was stirred at the same temperature for 1 h. Diethyl chlorophosphate (0.8 mL, 4.6 mmol, 0.5 eq) in THF (2 mL) was added dropwise to the reaction mixture at the same temperature. The reaction was warmed to 0° C. and stirred for 1 h. The reaction mixture was quenched with $NH_4Cl$ solution and extracted with EtOAc (3×100 mL). Combined organic layer was washed with water (2×100 mL) followed by brine (150 mL) and dried over anhydrous sodium sulfate. Removal of solvent under reduced pressure provided crude product which was purified by normal phase silica gel column chromatography using ethyl acetate-hexane system as eluent to afford the title compound (0.8 g, 24%)

Step-3: Synthesis of diethyl(N-(4-methoxybenzyl)sulfamoyl)methylphosphonate: Diethyl(N-(4-methoxybenzyl)sulfamoyl)methylphosphonate (0.5 g, 1.4 mmol, 1 eq) was dissolved in THF (20 mL) and cooled the reaction mixture to −78° C. To this reaction mixture 2.5 M n-BuLi (1.2 mL, 2.9 mmol, 2.1 eq) was added dropwise under nitrogen atmosphere. The reaction mixture was stirred at same temperature for 15 min. Then added solution of tert-butyl 3-(2-oxoethyl)azetidine-1-carboxylate (0.28 g, 1.4 mmol, 1 eq) in THF (2 mL) dropwise. Warmed the reaction mixture to RT and stirred at RT for 16 h. Then quenched the reaction mixture with saturated $NH_4Cl$ solution and extracted with EtOAc (3×100 mL). Combined organic layer was washed with water (2×100 mL) followed by brine (150 mL) and dried over anhydrous sodium sulfate. Removal of solvent under reduced pressure provided crude product which was purified by normal phase silica gel column chromatography using ethyl acetate-hexane system as eluent to afford the title compound (0.18 g, 32%)

Step-4: Synthesis of tert-butyl 3-(3-(N-(4-methoxybenzyl)sulfamoyl)propyl)azetidine-1-carboxylate: To a solution of diethyl(N-(4-methoxybenzyl)sulfamoyl)methylphosphonate (0.18 g, 0.45 mmol, 1 eq) in ethanol (10 mL) was added Pd/C (0.09 g) and the reaction mixture was allowed to stir at RT under $H_2$ atmosphere (using balloon) for 3 h. Progress of reaction was monitored by TLC. After completion, reaction mixture was filtered through celite-bed. Removal of solvent under reduced pressure afforded crude (0.18 g) which was used for next step without purification.

Step-5: Synthesis of 3-(azetidin-3-yl)propane-1-sulfonamide trifluoracetate: To a solution of tert-butyl 3-(3-(N-(4-methoxybenzyl)sulfamoyl)propyl)azetidine-1-carboxylate (0.05 g, 0.13 mmol, 1 eq) in DCM (2 mL) was added TFA (0.5 mL) and the mixture was allowed to stir at RT for 16 h. Progress of reaction was monitored by $^1H$ NMR. After completion, reaction mixture was concentrated under reduced pressure to afford crude which was triturated with diethyl ether to afford the title compound (40 mg) which was used for next step without purification.

Step 6: Synthesis of 3-(1-(6,7-dimethoxyquinazolin-4-yl)azetidin-3-yl)propane-1-sulfonamide: A suspension of 6,7-dimethoxyquinazolin-4 (3H)-one (30 mg, 0.14 mmol, 2 eq), 3-(azetidin-3-yl)propane-1-sulfonamide trifluoracetate (38 mg, 0.2 mmol, 1.0 eq) and DIPEA (0.04 mL, 0.3 mmol, 2.0 eq) in DMF (1 mL) was allowed to stir at 80° C. for 2 h. Progress of reaction was monitored by TLC. After completion, reaction mixture was concentrated under reduced pressure to afford residue which was triturated with ether, ethyl acetate and then pentane to get crude which was purified by RP-HPLC to afford the title compound (5 mg, 10%). LCMS: 367[M+1]$^+$; $^1H$ NMR (400 MHz, DMSO-d$_6$) δ ppm 8.33 (s, 1H), 7.19 (s, 1H), 7.12 (s, 1H), 6.77 (s, 2H), 4.58 (br. s., 2H), 4.12 (br. s., 2H), 3.82-3.93 (m, 6H), 2.97-3.04 (m, 2H), 2.78 (br. s., 1H), 1.75 (s, 4H).

Example-40: Synthesis of 4-(3-(2-sulfamoylmethyl-aminoethyl)azetidine-1-yl)-7-methoxyquinazoline, (Compound 1.40)

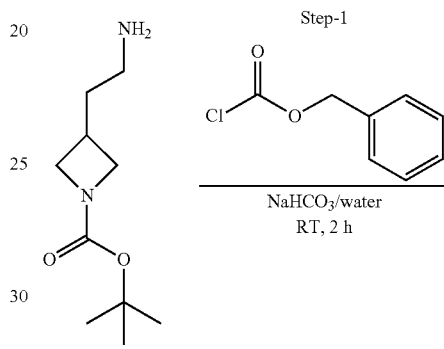

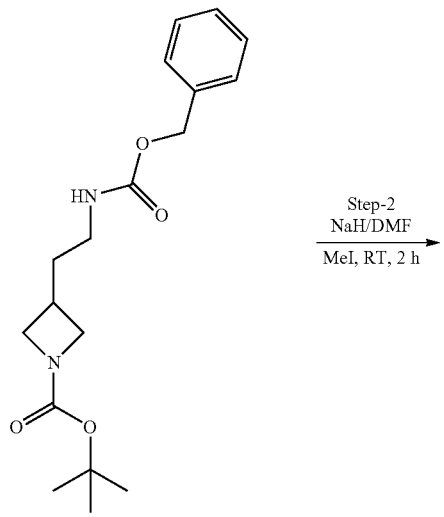

-continued

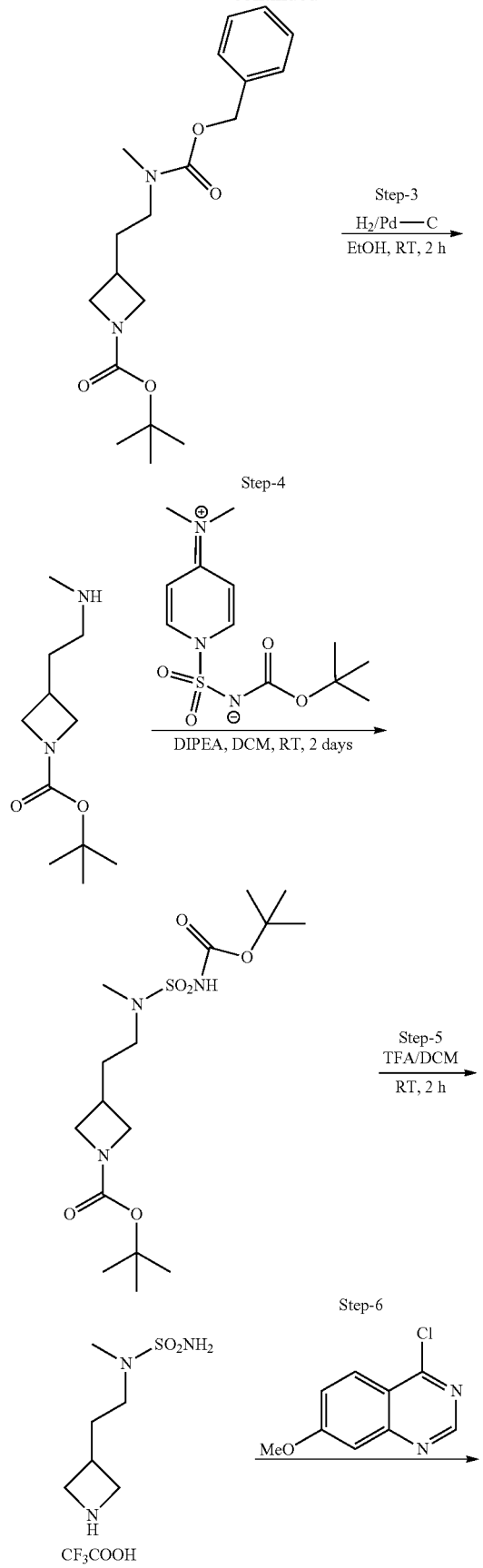

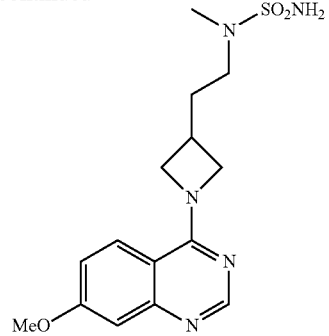

Step-1: Synthesis of tert-butyl 3-(2-(benzyloxycarbonylamino)ethyl)azetidine-1-carboxylate: To a mixture of tert-butyl 3-(2-aminoethyl)azetidine-1-carboxylate (200 mg, 1 mmol, 1 eq) and NaHCO$_3$ (168 mg, 2 mmol, 2 eq) in water (5 mL) was added benzyl carbonochloridate (171 mg, 1 mmol, 1 eq) and the resulting mixture was allowed to stir at RT for 2 h. Progress of reaction was monitored by TLC. After completion, reaction mixture was diluted with water (30 mL) and extracted with ethyl acetate (3×50 mL). Combined organic layer was washed with water (50 mL) followed brine (50 mL) and dried over anhydrous sodium sulphate. Removal of solvent under reduced pressure afforded tert-butyl 3-(2-(benzyloxycarbonylamino)ethyl)azetidine-1-carboxylate (250 mg, 64%).

Step-2: Synthesis of tert-butyl 3-(2-((benzyloxycarbonyl)(methyl)amino)ethyl)azetidine-1-carboxylate: To a solution of tert-butyl 3-(2-(benzyloxycarbonylamino)ethyl)azetidine-1-carboxylate (250 mg, 0.75 mmol, 1 eq) in DMF (5 mL) at RT was added NaH (60 mg, 1.5 mmol, 2 eq) and the reaction mixture was stirred at RT for 10 minutes. To the mixture was then added methyl iodide (213 mg, 1.50 mmol, 2 eq) and the reaction mixture was stirred at RT for 2 h. Progress of reaction was monitored by TLC. After completion, reaction mixture was diluted with water (30 mL) and extracted with diethyl ether (3×50 mL). Combined organic layer was washed with water (2×50 mL) followed by brine (50 mL) and dried over anhydrous sodium sulphate. Removal of solvent gave tert-butyl 3-(2-((benzyloxycarbonyl)(methyl)amino)ethyl)azetidine-1-carboxylate (210 mg, 81%) which was used in the next step without purification.

Step-3 Synthesis of tert-butyl 3-(2-(methylamino)ethyl)azetidine-1-carboxylate: To a solution of tert-butyl 3-(2-((benzyloxycarbonyl)(methyl)amino)ethyl)azetidine-1-carboxylate (210 mg) in ethanol (30 mL) was added 10% Pd—C (100 mg) and the resulting mixture was hydrogenated at RT by nitrogen purging for 2 h. Progress of reaction was monitored by TLC. After completion, reaction mixture was filtered through celite bed and bed was washed with ethanol (10 mL). Combined filtrate was concentrated to afford tert-butyl 3-(2-(methylamino)ethyl)azetidine-1-carboxylate (130 mg, crude) which was used I the next step without purification.

Step-4: Synthesis of tert-butyl 3-(2-((N-(tert-butoxycarbonyl)sulfamoyl)(methyl)amino)ethyl)azetidine-1-carboxylate: To a solution of tert-butyl 3-(2-(methylamino)ethyl)azetidine-1-carboxylate (150 mg, 0.70 mmol, 1 eq) in dichloromethane (10 mL) were added N-(tert-butoxycarbonyl)-N-[4-(dimethylazaniumylidene)-1,4-dihydropyridin-1ylsulfonyl]azanide (317 mg 1.05 mmol, 1.5 eq) and N,N-diisopropylethylamine (271 mg, 2.10 mmol, 3 eq) and the reaction mixture was allowed to stir at RT for 2 days.

Progress of reaction was monitored by TLC. After completion, reaction mixture was diluted with water (50 mL) and extracted with ethyl acetate (3×100 mL). Combined organic layer was washed with brine (50 mL) and dried over anhydrous sodium sulfate. Removal of solvent under reduced pressure afforded crude which was purified by Combi-Flash on silica gel using ethyl acetate-hexane system as eluent to afford tert-butyl 3-(2-((N-(tert-butoxycarbonyl)sulfamoyl)(methyl)amino)ethyl)azetidine-1-carboxylatexylate (180 mg, 75%).

Step-5: Synthesis of 3-(2-sulfamoylmethylaminoethyl)azetidine trifluoroacetate: To a solution of tert-butyl 3-(2-((N-(tert-butoxycarbonyl)sulfamoyl)(methyl)amino)ethyl)azetidine-1-carboxylatexylate (180 mg, 0.46 mmol, 1 eq) in DCM (5 mL) was added TFA (1.5 mL) and the mixture was allowed to stir at RT for 2 h. Progress of reaction was monitored by $^1$H NMR. After completion, reaction mixture was concentrated under reduced pressure to afford crude which was triturated with diethyl ether to afford 3-(2-sulfamoylmethylaminoethyl)azetidine trifluoroacetate (160 mg, 86%).

Step-6: Synthesis of 4-(3-(2-sulfamoylmethylaminoethyl)azetidine-1-yl)-7-methoxyquinazoline: A mixture of 4-chloro-7-methoxyquinazoline (50 mg, 0.256 mmol, 1.2 eq), 3-(2-sulfamoylmethylaminoethyl)azetidine trifluoroacetate (63 mg, 0.205 mmol, 1.0 eq) and DIPEA (0.138 mL, 0.768 mmol, 3.0 eq) in DMF (1 mL) was allowed to stir at 80° C. for 2 h. Progress of reaction was monitored by TLC. After completion, reaction mixture was concentrated under reduced pressure to get crude which was triturated with diethyl ether, ethyl acetate and ether to afford 4-(3-(2-sulfamoylmethylaminoethyl)azetidine-1-yl)-7-methoxyquinazoline (20 mg, 27%). LCMS: 352 [M+1]$^+$; $^1$H NMR (400 MHz, DMSO-d6) δ ppm 8.38 (s, 1H), 7.83 (d, 1H), 7.10 (s, 1H), 7.06 (d, 1H), 6.72 (brs, 1H), 4.55 (brs, 2H), 4.12 (brs, 2H), 3.86 (s, 3H), 3.00-2.90 (m, 2H), 2.89-2.72 (m, 1H), 2.65 (s, 3H), 1.95-1.84 (m, 2H).

Example-41: Synthesis of 4-(3-(2-sulfamoylaminoethyl)azetidine-1-yl)-6-bromo-7-methoxyquinazoline, (Compound 1.41)

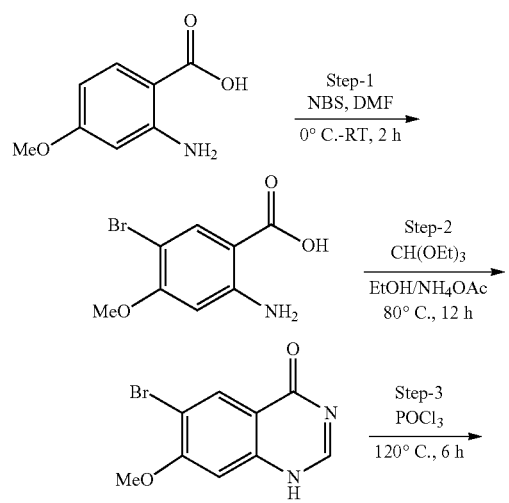

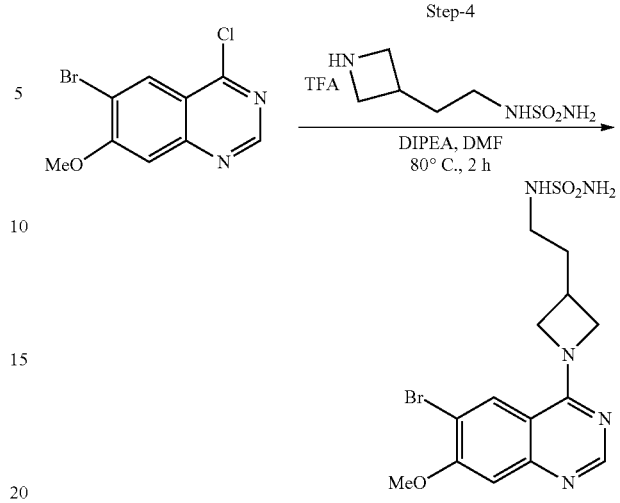

Step-1: Synthesis of 2-amino-5-bromo-4-methoxybenzoic acid: To a solution of 2-amino-4-methoxybenzoic acid (1 g, 5.92 mmol, 1 eq) in DMF (30 mL) was added N-bromosuccinimide (1.17 g, 6.58 mmol, 1.1 eq) at 0° C. and the reaction mixture was allowed to stir at 0° C. for 5 minutes followed by stirring at RT for 2 h. Progress of reaction was monitored by TLC. After completion, reaction mixture was cooled to RT; solid was filtered to get residue which was triturated with hexane to afford 2-amino-5-bromo-4-methoxybenzoic acid (0.950 g, 65%).

Step-2: Synthesis of 6-bromo-7-methoxyquinazolin-4(1H)-one: To a solution of 2-amino-5-bromo-4-methoxybenzoic acid (0.950 g, 3.86 mmol, 1 eq) in ethanol (15 mL) were added triethylorthoformate (1.03 mL, 6.18 mmol, 1.6 eq) and ammonium acetate (0.386 g, 5.02 mmol, 1.3 eq.) and the reaction mixture was allowed to stir at 80° C. for 12 h. Progress of reaction was monitored by TLC. After completion, reaction mixture was cooled to RT, solid was filtered to get residue which was triturated with diethyl ether and ethanol to afford 6-bromo-7-methoxyquinazolin-4(1H)-one (0.380 g, 39%).

Step-3: Synthesis of 6-bromo-4-chloro-7-methoxyquinazoline: A suspension of 6-bromo-7-methoxyquinazolin-4(1H)-one (0.180 g, 0.71 mmol, 1 eq) in POCl$_3$ (1 mL) was allowed to stir at 120° C. for 6 h. Progress of reaction was monitored by TLC. After completion, reaction mixture was cooled to RT, diluted with cold water (20 mL) and extracted with ethyl acetate (3×15 mL). Combined organic layer was washed with brine (50 mL) and dried over anhydrous sodium sulfate. Removal of solvent under reduced pressure afforded crude which was purified by Combi-Flash on silica gel using ethyl acetate-hexane system as eluent to afford 6-bromo-4-chloro-7-methoxyquinazoline (80 mg, 42%).

Step-4: Synthesis of 4-(3-(2-sulfamoylaminoethyl)azetidine-1-yl)-6-bromo-7-methoxyquinazoline: A suspension of 6-bromo-4-chloro-7-methoxyquinazoline (80 mg, 0.29 mmol, 1.0 eq), 3-(2-sulfamoylaminoethyl)azetidine trifluoroacetate (80 mg, 0.292 mmol, 1.0 eq) and DIPEA (0.3 mL, 1.75 mmol, 6 eq) in DMF (0.8 mL) was allowed to stir at 80° C. for 3 h. Progress of reaction was monitored by TLC. After completion, reaction mixture was concentrated under reduced pressure to afford crude product which was purified by reversed phase HPLC to afford 4-(3-(2-sulfamoylaminoethyl)azetidine-1-yl)-6-bromo-7-methoxyquinazoline (10 mg, 8%). LCMS: 417 [M+1]$^+$; $^1$H NMR (400 MHz, DMSO-d$_6$) δ ppm 8.56 (s, 1H), 8.40 (s, 1H), 8.05 s, 1H), 7.23 (s, 1H), 6.55 (t, 1H), 6.52 (s, 2H), 4.56 (brs, 2H), 4.14 (brs, 2H), 3.98 (s, 3H), 2.98-2.80 (m, 3H), 1.90-1.80 (m, 2H).

Example-42: Synthesis of 1-(cyclopropylmethyl)-7-methoxy-4-[3-[2-(sulfamoylamino)ethyl]azetidin-1-yl]quinazoline, (Compound 1.42)

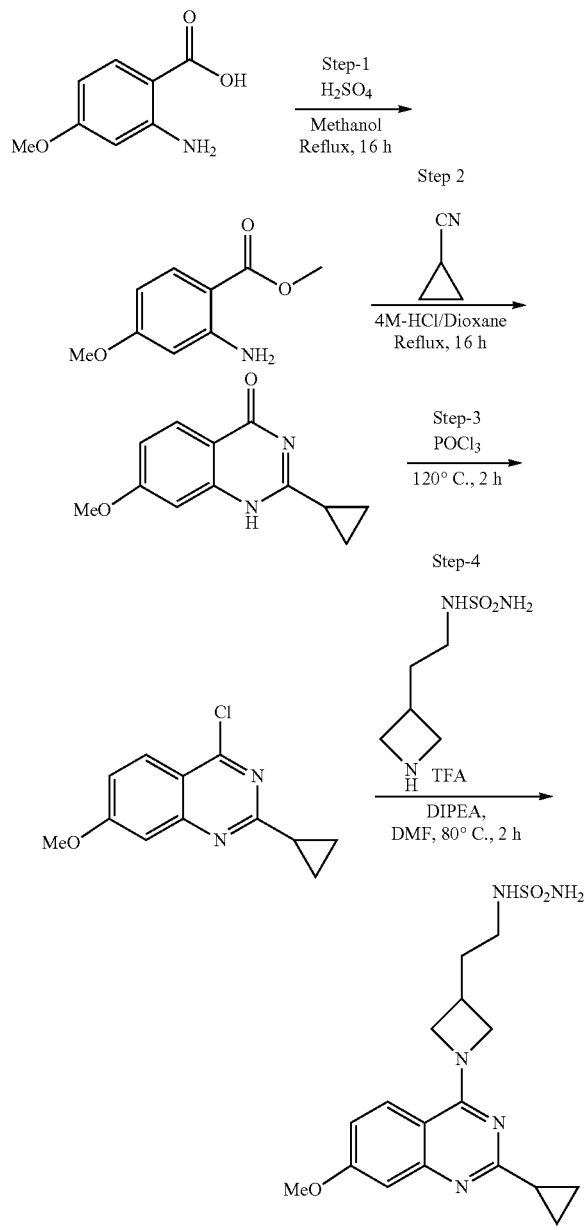

Step-1: Synthesis of methyl 2-amino-4-methoxy-benzoate: A mixture of 2-amino-4-methoxy-benzoic acid (5 g, 29.94 mmol, 1 eq) in methanol (100 mL) was added H$_2$SO$_4$ (6 mL) and then allowed to reflux for 16 h. Progress of reaction was monitored by TLC. After completion, reaction mixture was cooled to RT, concentrated under reduced pressure, neutralized with saturated aq. sodium bicarbonate. Mixture was then diluted with water (100 mL) and extracted with ethyl acetate (3×100 mL). Combined organic layer was concentrated under reduced pressure to afford methyl 2-amino-4-methoxy-benzoate (3.9 g, 78%). LCMS: 182[M+1]$^+$ Step-2: Synthesis of 2-cyclopropyl-7-methoxy-1H-quinazolin-4-one: A mixture of methyl 2-amino-4-methoxy-benzoate (800 mg, 2.63 mmol, 1 eq) and cyclopropanecarbonitrile (330 mL, 2.98 mmol, 1.1 eq) in 4M HCl in dioxane (09 mL) was sonicated for 30 minutes and then heated at 100° C. for 12 h. Progress of reaction was monitored by TLC. After completion, reaction mixture was cooled to RT, poured into ice-cold water and stirred for 15 minutes. The solid obtained was filtered and dried under vacuum to afford 2-cyclopropyl-7-methoxy-1H-quinazolin-4-one (500 mg, 38%). LCMS: 217.2[M+1]$^+$.

Step-3: Synthesis of 4-chloro-1-(cyclopropylmethyl)-7-methoxy-quinazoline: A mixture of 2-cyclopropyl-7-methoxy-1H-quinazolin-4-one (200 mg, 0.92 mmol, 1 eq) in POCl$_3$ (0.4 mL) was stirred at 120° C. for 2 h. Progress of reaction was monitored by TLC. After completion, reaction mixture was cooled to RT, poured into ice-cold water (20 mL) and stirred for 15 minutes. Solid was filtered and dried under vacuum to afford 4-chloro-1-(cyclopropylmethyl)-7-methoxy-quinazoline (100 mg, 41%). LCMS: 235.2[M+1]$^+$ Step-4: Synthesis of 1-(cyclopropylmethyl)-7-methoxy-4-[3-[2-(sulfamoylamino)ethyl]azetidin-1-yl]quinazoline: A suspension of 4-chloro-1-(cyclopropylmethyl)-7-methoxy-quinazoline (100 mg, 0.42 mmol, 1.0 eq), N-[2-(azetidin-3-yl)ethyl]sulfuric diamide trifloroacetic acid (124 mg, 0.42 mmol, 1.0 eq) and N,N diisopropylethylamine (150 mg, 0.84 mmol, 2.0 eq) in DMF (2 mL) was allowed to stir at 80° C. for 2 h. Progress of reaction was monitored by TLC. Reaction mixture was cooled to RT, concentrated under vacuum to get semi-solid residue which was triturated with ether, ethyl acetate and then with pentane to afford crude solid which was purified by reversed phase HPLC to afford 1-(cyclopropylmethyl)-7-methoxy-4-[3-[2-(sulfamoylamino)ethyl]azetidin-1-yl]quinazoline (10 mg, 6%). LCMS: 378[M+1]$^+$; $^1$H NMR (400 MHz, DMSO-d6) δ ppm 7.78 (d, 1H), 6.99 (s, 1H), 6.92 (d, 1H), 6.59-6.50 (m, 3H), 4.47 (brs, 2H), 4.05 (brs, 2H), 3.85 (s, 3H), 2.95-2.78 (m, 3H), 1.98 (brs, 1H), 1.91-1.77 (m, 2H), 1.02-0.95 (m, 2H), 0.90-0.80 (m, 2H).

Example-43: Synthesis of 1-(2,2-difluoroethyl)-6,7-dimethoxy-4-[3-[2-(sulfamoylamino)ethyl]azetidin-1-yl]quinazoline, (Compound 1.43)

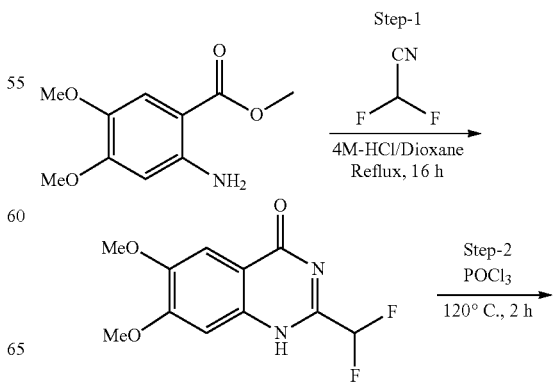

-continued

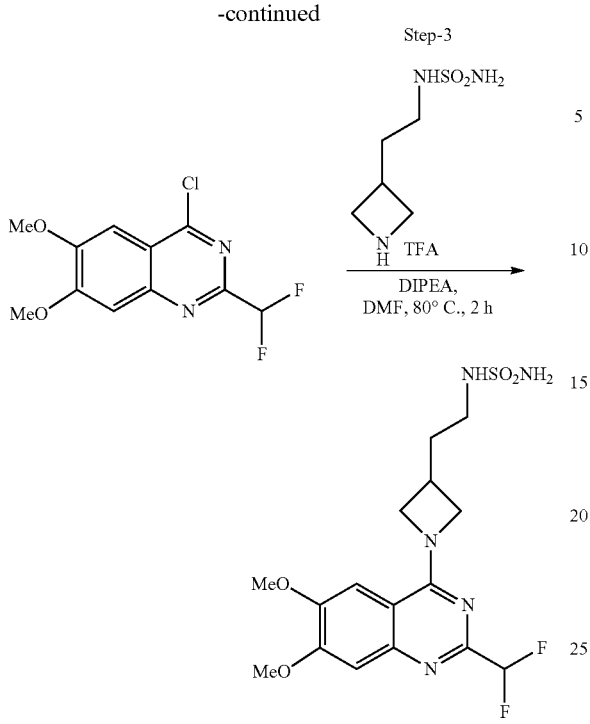

Step-1: Synthesis of 2-(difluoromethyl)-6,7-dimethoxy-1H-quinazolin-4-one: A mixture of methyl 2-amino-4,5-dimethoxy-benzoate (1 g, 4.72 mmol, 1 eq) and 2,2-difluoroacetonitrile (0.40 mL, 5.2 mmol, 1.1 eq) in 4M HCl in dioxane (10 mL) was sonicated for 30 minutes and then heated at 100° C. for 12 h. Progress of reaction was monitored by TLC. After completion, reaction mixture was cooled to RT, poured into ice-cold water and stirred for 15 minutes. The solid obtained was filtered and dried under vacuum to afford 2-(difluoromethyl)-6,7-dimethoxy-1H-quinazolin-4-one (150 mg, 11%). LCMS: 257[M+1]$^+$ Step-2: Synthesis of 4-chloro-1-(2,2-difluoroethyl)-6,7-dimethoxy-quinazoline: To a stirred solution of 2-(difluoromethyl)-6,7-dimethoxy-1H-quinazolin-4-one (190 mg, 0.92 mmol, 1 eq) in POCl$_3$ (0.4 mL) was stirred at 120° C. for 2 h. Progress of reaction was monitored by TLC. After completion, reaction mixture was cooled to RT, poured into ice-cold water (20 mL) and stirred for 15 minutes. Solid was filtered and dried under vacuum to afford 4-chloro-1-(2,2-difluoroethyl)-6,7-dimethoxy-quinazoline (110 mg, 53%). LCMS: 275[M+1]$^+$ Step-3: Synthesis of 1-(2,2-difluoroethyl)-6,7-dimethoxy-4-[3-[2-(sulfamoylamino)ethyl]azetidin-1-yl]quinazoline: A suspension of 4-chloro-1-(2,2-difluoroethyl)-6,7-dimethoxy-quinazoline (110 mg, 0.40 mmol, 1.0 eq), N-[2-(azetidin-3-yl)ethyl]sulfuric diamide trifloroacetic acid (117 mg, 0.40 mmol, 1.0 eq) and N,N diisopropylethylamine (150 mg, 0.80 mmol, 2.0 eq) in DMF (2 mL) was allowed to stir at 80° C. for 2 h. Progress of reaction was monitored by TLC. Reaction mixture was cooled to RT, concentrated under vacuum to get semi-solid residue which was triturated with ether, ethyl acetate and then with pentane to afford crude solid which was purified by reversed phase HPLC to afford 1-(2,2-difluoroethyl)-6,7-dimethoxy-4-[3-[2-(sulfamoylamino)ethyl]azetidin-1-yl]quinazoline (30 mg, 18%). LCMS: 418[M+1]$^+$; $^1$H NMR (400 MHz, DMSO-d6) δ ppm 7.23 (s, 2H), 6.62 (t, 1H), 6.70-6.40 (m, 3H), 4.65 (brs, 2H), 4.20 (brs, 2H), 3.95 (s, 6H), 3.00-2.80 (m, 3H), 1.90-1.80 (m, 2H).

Example-44: Synthesis of 4-(3-(2-sulfamoylamino-ethyl)azetidine-1-yl)-7-methoxy-2-(pyridin-3-yl) quinazoline, (Compound 1.44)

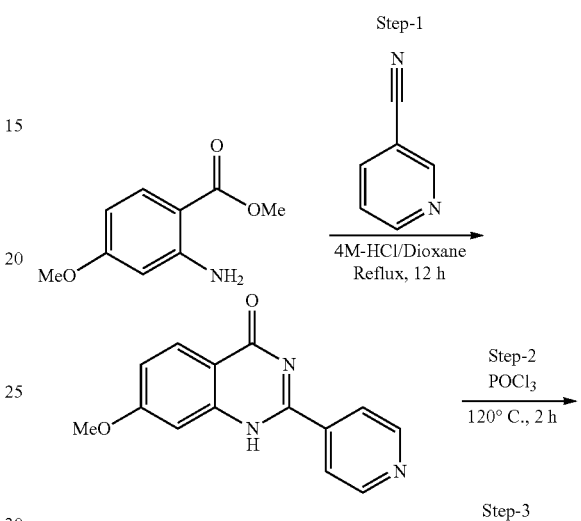

Step-1: Synthesis of 7-methoxy-2-(pyridin-3-yl)quinazolin-4 (1H)-one: A mixture of methyl 2-amino-4-methoxy-benzoate (800 mg, 4.47 mmol, 1 eq) and pyridine-3-carbonitrile (548 mg, 5.26 mmol, 1.1 eq) in 4M HCl in dioxane (10 mL) was heated at 100° C. for 12 h. Progress of reaction was monitored by TLC. After completion reaction mixture was cooled to RT. It was poured into ice cold water and stirred for 15 minutes. The solid obtained was filtered and dried under vacuum to give 7-methoxy-2-(pyridin-3-yl)quinazolin-4 (1H)-one (550 mg, 30%). LCMS: 253 [M+1]$^+$ Step-2: Synthesis of 4-chloro-7-methoxy-2-(pyridin-3-yl) quinazoline: A mixture of 7-methoxy-2-(pyridin-3-yl) quinazolin-4 (1H)-one (250 mg, 1.0 mmol, 1 eq) in POCl$_3$ (0.3 mL) was stirred at 120° C. for 2 h. Progress of reaction was monitored by TLC. After completion reaction mixture was cooled to RT, poured to ice (10 mL) and stirred for 15 minutes. Solid was filtered and dried to afford 4-chloro-7-methoxy-2-(pyridin-3-yl)quinazoline (70 mg, 47%). LCMS: 271[M+1]$^+$ Step-3: Synthesis of 4-(3-(2-sulfamoylaminoethyl)azetidine-1-yl)-7-methoxy-2-(pyridin-3-yl)quinazoline: A suspension of 4-chloro-7-methoxy-2-(pyridin-3-yl)quinazoline (70 mg, 0.258 mmol, 1.0 eq), 3-(2-sulfamoylaminoethyl) azetidine trifluoroacetate (75 mg, 0.258 mmol, 1.0 eq) and N,N diisopropylethylamine (42 mg, 0.51 mmol, 2.0 eq) in DMF (1 mL) was allowed to stir at 80° C. for 2 h. Progress of reaction was monitored by TLC. Reaction mixture was cooled to RT, DMF was removed under reduced pressure, crude obtained was purified by reversed phase HPLC to afford 4-(3-(2-sulfamoylaminoethyl)azetidine-1-yl)-7-methoxy-2-(pyridin-3-yl)quinazoline (30 mg, 17%). LCMS: 415[M+1]$^+$; $^1$H NMR (400 MHz, DMSO-d$_6$) δ ppm 9.58 (s, 1H), 8.70-8.62 (m, 2H), 7.90 (d, 1H), 7.53 (t, 1H), 7.22 (s, 1H), 7.06 (d, 1H), 6.62 (brs, 1H), 6.55 (s, 2H), 4.63 (brs, 2H), 4.22 (brs, 2H), 3.95 (s, 3H), 3.00-2.82 (m, 3H), 1.92-1.83 (m, 2H).

Example-45: Synthesis of 2-(1-adamantyl)-7-methoxy-4-[3-[2-(sulfamoylamino)ethyl]azetidin-1-yl]quinazoline, (Compound 1.45)

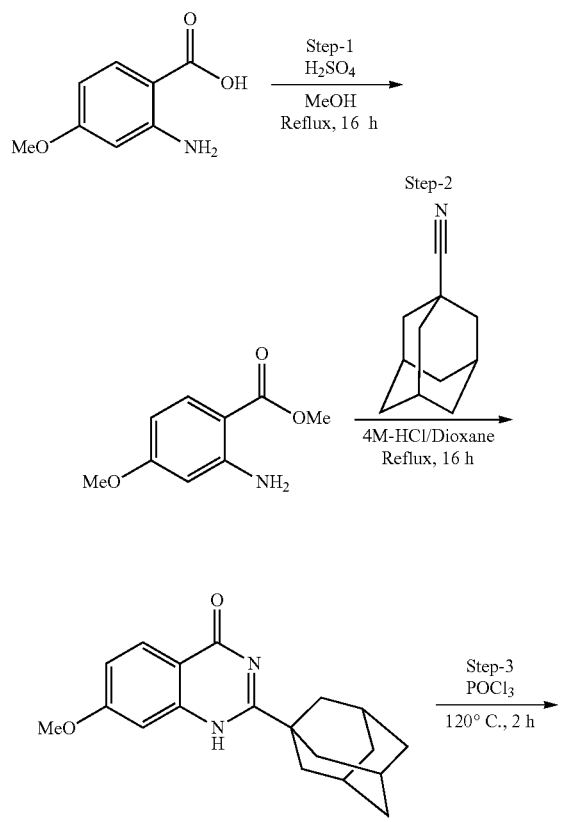

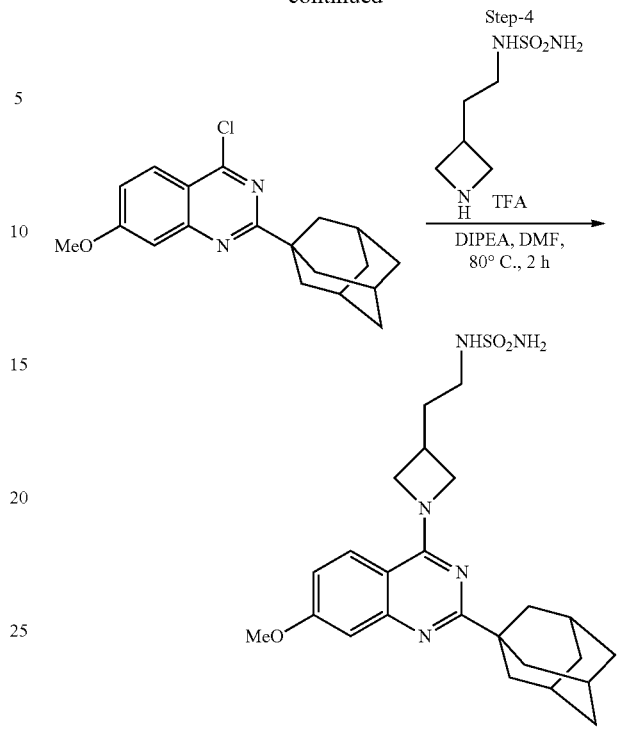

Step-1: Synthesis of methyl 2-amino-4-methoxy-benzoate: A mixture of 2-amino-4-methoxy-benzoic acid (5 g, 29.94 mmol, 1 eq) in methanol (100 mL) was added H$_2$SO$_4$ (6 mL) and then allowed to reflux for 16 h. Progress of reaction was monitored by TLC. After completion, reaction mixture was cooled to RT, concentrated under reduced pressure, neutralized with sodium bicarbonate, diluted with water (100 mL) and extracted with ethyl acetate (3×100 mL). Combined organic layer was washed with water (100 mL) and dried over anhydrous sodium. Removal of solvent under reduced pressure afforded methyl 2-amino-4-methoxy-benzoate (3.9 g, 78%). LCMS: 182 [M+1]$^+$ Step-2: Synthesis of 2-(1-adamantyl)-7-methoxy-1H-quinazolin-4-one: A mixture of methyl 2-amino-4-methoxy-benzoate (500 mg, 2.76 mmol, 1 eq) and adamantane-1-carbonitrile (533 mL, 3.31 mmol, 1.1 eq) in 4M HCl in dioxane (09 mL) was sonicated for 30 minutes and then heated at 100° C. for 12 h. Progress of reaction was monitored by TLC. After completion, reaction mixture was cooled to RT, poured into ice-cold water and stirred for 15 minutes. The solid obtained was filtered and dried under vacuum to afford 2-(1-adamantyl)-7-methoxy-1H-quinazolin-4-one (35 mg, 4%). LCMS: 311 [M+1]$^+$ Step-3: Synthesis of 2-(1-adamantyl)-4-chloro-7-methoxy-quinazoline: A mixture of 2-(1-adamantyl)-7-methoxy-1H-quinazolin-4-one (200 mg, 0.65 mmol, 1 eq) in POCl$_3$ (0.2 mL) was stirred at 120° C. for 2 h. Progress of reaction was monitored by TLC. After completion, reaction mixture was cooled to RT, poured into ice-cold water (20 mL) and stirred for 15 minutes. Solid was filtered and dried under vacuum to afford 2-(1-adamantyl)-4-chloro-7-methoxy-quinazoline (40 mg, 19%). LCMS: 328 [M+1]$^+$ Step-4: Synthesis of 2-(1-adamantyl)-7-methoxy-4-[3-[2-(sulfamoylamino)ethyl]azetidin-1-yl]quinazoline: A suspension of 2-(1-adamantyl)-4-chloro-7-methoxy-quinazoline (40 mg, 0.121 mmol, 1.0 eq), N-[2-(azetidin-3-yl)ethyl] sulfuric diamide trifloroacetic acid (24 mg, 0.121 mmol, 1.0 eq) and N,N-diisopropylethylamine (40 mg, 0.24 mmol, 2.0 eq) in DMF (2 mL) was allowed to stir at 80° C. for 2 h. Progress of reaction was monitored by TLC. Reaction mixture was cooled to RT, concentrated under vacuum to get semi-solid residue which was triturated with ether, ethyl acetate and then with pentane to afford crude solid which was purified by reversed phase HPLC to afford 2-(1-adamantyl)-7-methoxy-4-[3-[2-(sulfamoylamino)ethyl]azetidin-1-yl]quinazoline (5 mg, 9%). LCMS: 473 [M+1]$^+$; $^1$H NMR (400 MHz, DMSO-d$_6$) δ ppm 7.79 (d, 1H), 7.03 (s, 1H), 7.97 (d, 1H), 6.60 (brs, 1H), 6.55 (brs, 2H), 4.52 (brs, 2H), 4.07 (brs, 2H), 3.86 (s, 3H), 2.95-2.78 (m, 3H), 2.10-1.97 (m, 6H), 1.92-1.80 (m, 2H), 1.79-1.61 (m, 9H).

Example-46: Synthesis of N-[2-(6,7-di-methoxyquinazoline-4-yl)-2-azaspiro[3.3]hept-6-yl]-N-methyl-sulfuric diamide, (Compound 1.46)

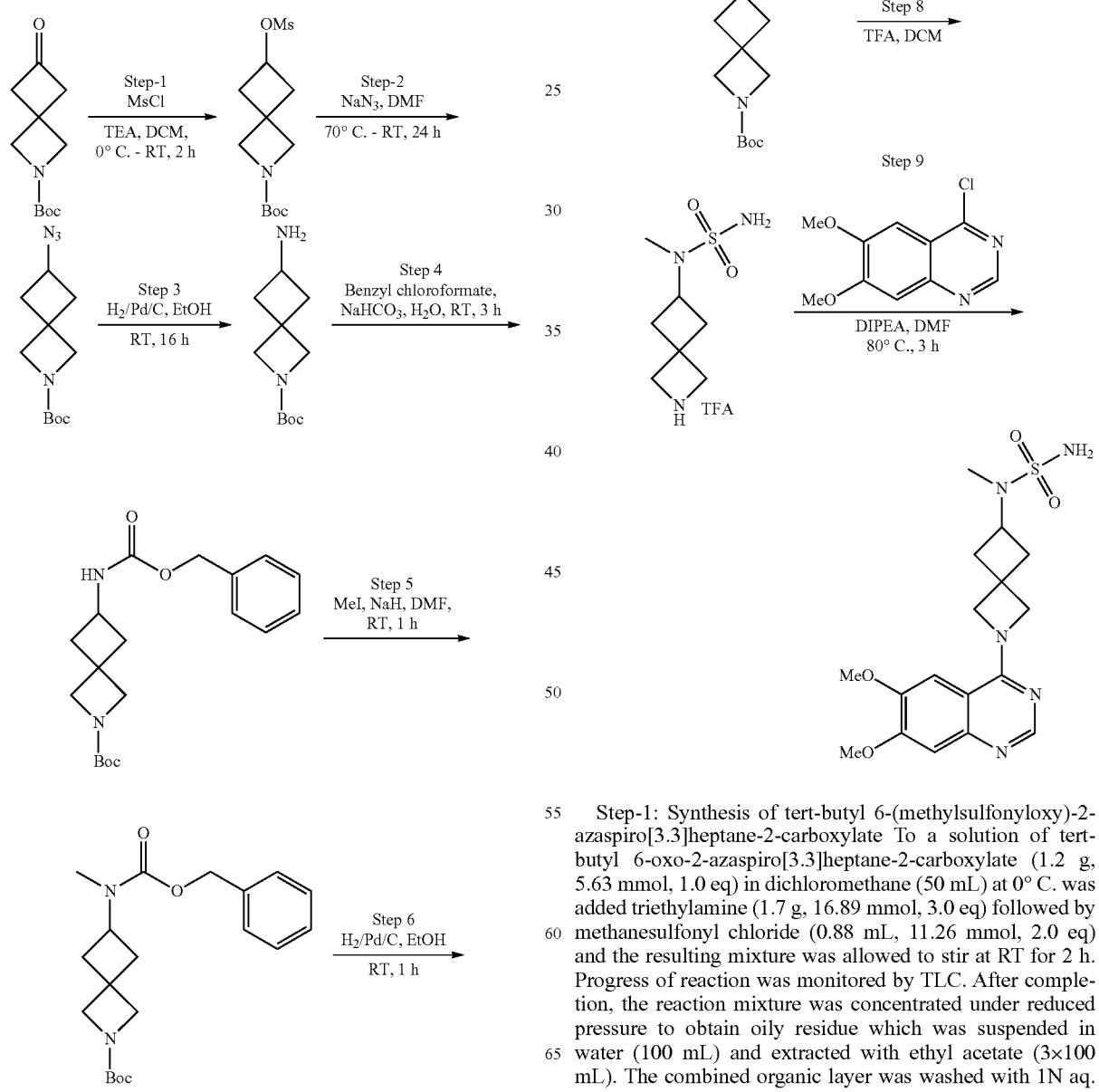

Step-1: Synthesis of tert-butyl 6-(methylsulfonyloxy)-2-azaspiro[3.3]heptane-2-carboxylate To a solution of tert-butyl 6-oxo-2-azaspiro[3.3]heptane-2-carboxylate (1.2 g, 5.63 mmol, 1.0 eq) in dichloromethane (50 mL) at 0° C. was added triethylamine (1.7 g, 16.89 mmol, 3.0 eq) followed by methanesulfonyl chloride (0.88 mL, 11.26 mmol, 2.0 eq) and the resulting mixture was allowed to stir at RT for 2 h. Progress of reaction was monitored by TLC. After completion, the reaction mixture was concentrated under reduced pressure to obtain oily residue which was suspended in water (100 mL) and extracted with ethyl acetate (3×100 mL). The combined organic layer was washed with 1N aq. HCl (50 mL) followed by brine (50 mL) and dried over sodium sulphate. Removal of solvent under reduced pressure afforded tert-butyl 6-(methylsulfonyloxy)-2-azaspiro[3.3]heptane-2-carboxylate (1.3 g, 79%) which was used in the next step without purification.

Step-2: Synthesis tert-butyl 6-azido-2-azaspiro[3.3]heptane-2-carboxylate To a solution of tert-butyl 6-(methylsulfonyloxy)-2-azaspiro[3.3]heptane-2-carboxylate (2.7 g, 9.28 mmol, 1.0 eq) in DMF (10 mL) at RT was added sodium azide (1.80 g, 27.84 mmol, 3.0 eq) and the reaction mixture was allowed to stir at 70° C. for 24 h. Progress of reaction was monitored by TLC. After completion, the reaction mixture was cooled to RT, diluted with water (100 mL) and extracted with ethyl acetate (3×100 mL). The combined organic layer was washed with water (2×100 mL) followed by brine and dried over anhydrous sodium sulphate. Removal of solvent under reduced pressure afforded tert-butyl 6-azido-2-azaspiro[3.3]heptane-2-carboxylate (2.1 g, 95%) which was used in the next step without purification.

Step-3: Synthesis of tert-butyl 6-amino-2-azaspiro[3.3]heptane-2-carboxylate To a stirred solution of tert-butyl 6-azido-2-azaspiro[3.3]heptane-2-carboxylate (2.5 g, 0.01 mol, 1.0 eq) in 100 mL of ethanol was added Pd/C (1 g, 10% on charcoal) and the reaction was allowed to stir at RT for 16 h. After completion, reaction mixture was filtered through the bed of celite and concentrated under reduced pressure to get tert-butyl 6-amino-2-azaspiro[3.3]heptane-2-carboxylate (2.3 g) which was used as such for next step without further purification.

Step-4: Synthesis of tert-butyl 6-(benzyloxycarbonylamino)-2-azaspiro[3.3]heptane-2-carboxylate To a stirred solution of tert-butyl 6-amino-2-azaspiro[3.3]heptane-2-carboxylate (0.24 g, 0.94 mmol, 1.0 eq) in 4 mL of water was added benzyl chloroformate (0.31 mL, 50% in toluene, 0.94 mmol, 1.0 eq) and sodium bicarbonate (0.15 g, 1.88 mmol, 2.0 eq). The resulting reaction mixture was allowed to stir at RT for 3 h. After completion, reaction mixture was diluted with water (50 mL) and extracted using ethyl acetate (3×30 mL). The combined organic layer was washed with brine (50 mL) dried over anhydrous sodium sulphate filtered and concentrated under vacuum to get the crude product which was purified by normal phase silica gel column chromatography to get the desired tert-butyl 6-(benzyloxycarbonylamino)-2-azaspiro[3.3]heptane-2-carboxylate (190 mg, 58%).

Step-5: Synthesis of tert-butyl 6-((benzyloxycarbonyl)(methyl)amino)-2-azaspiro[3.3]heptane-2-carboxylate To a stirred solution of tert-butyl 6-(benzyloxycarbonylamino)-2-azaspiro[3.3]heptane-2-carboxylate (0.19 g, 0.54 mmol, 1.0 eq) in 5 mL of DMF was added NaH (0.043 g, 60% in mineral oil, 1.09 mmol, 2.0 eq) and allowed the reaction mixture to stir at RT. After 15 min MeI (0.1 mL, 1.64 mmol, 3.0 eq) was added and reaction was allowed to stir at RT for 1 h. After completion, reaction mixture was diluted with water (100 mL) and extracted using diethyl ether (3×150 mL), dried (anhydrous sodium sulphate), filtered and concentrated under reduced pressure to get crude tert-butyl 6-((benzyloxycarbonyl(methyl)amino)-2-azaspiro[3.3]heptane-2-carboxylate (160 mg).

Step-6: Synthesis of tert-butyl 6-(methylamino)-2-azaspiro[3.3]heptane-2-carboxylate To a stirred solution of tert-butyl 6-((benzyloxycarbonyl)(methyl)amino)-2-azaspiro[3.3]heptane-2-carboxylate (0.16 g, 0.44 mmol, 1.0 eq) in 10 mL of ethanol was added Pd/C (0.1 g, 10% on charcoal) and allowed the reaction mixture to stir at RT under hydrogen atmosphere. After completion, reaction mixture was filtered through celite bed, filtrate was concentrated under reduced pressure to get crude tert-butyl 6-(methylamino)-2-azaspiro[3.3]heptane-2-carboxylate (100 mg) which was used as such for next step without further purification.

Step-7: Synthesis of tert-butyl 6-(methyl(sulfamoyl)amino)-2-azaspiro[3.3]heptane-2-carboxylate To a solution of N-methyl-2-azaspiro[3.3]heptan-6-amine (100 mg, 0.44 mmol, 1.0 eq) in dichloromethane (5 mL) was added N-(tert-butoxycarbonyl)-N-[4-(dimethylazaniumylidene)-1,4-dihydropyridin-1ylsulfonyl]azanide (199 mg, 0.66 mmol, 1.5 eq) and N,N-diisopropylethylamine (0.154 mL, 0.88 mmol, 2 eq) and the reaction mixture was allowed to stir at RT for 48 h. After completion, reaction mixture was concentrated under reduced pressure to get crude which was purified by normal phase silica gel column chromatography to afford tert-butyl 6-(methyl(sulfamoyl)amino)-2-azaspiro[3.3]heptane-2-carboxylate (70 mg, 52%).

Step-8: Synthesis of 2-azaspiro[3.3]heptan-6-methylamine trifluoroacetate salt To a solution of tert-butyl 3-(2-((N-(tert-butoxycarbonyl)sulfamoyl)(methyl)amino)ethyl)azetidine-1-carboxylate (180 mg, 0.46 mmol, 1 eq) in DCM (5 mL) was added TFA (1.5 mL) and the mixture was allowed to stir at RT for 2 h. After completion, reaction mixture was concentrated under reduced pressure to afford crude which was triturated with diethyl ether to afford 3-(2-sulfamoylmethylaminoethyl)azetidine trifluoroacetate salt (120 mg, 85%).

Step-9: Synthesis of N-[2-(6,7-di-methoxyquinazoline-4-yl)-2-azaspiro[3.3]hept-6-yl]-N-methylsulfuric diamide A suspension of 2-azaspiro[3.3]heptan-6-methylamine trifluoroacetate salt (50 mg, 0.15 mmol, 1 eq), 4-chloro-6,7-dimethoxyquinazoline (52 mg, 0.22 mmol, 1.5 eq) and DIPEA (0.06 mL, 0.3 mmol, 2.0 eq) in DMF (1 mL) was allowed to stir at 80° C. for 3 h. Progress of the reaction was monitored by TLC. After completion, reaction mixture was concentrated under reduced pressure to get residue which was purified by RP-HPLC to afford N-[2-(6,7-di-methoxyquinazoline-4-yl)-2-azaspiro[3.3]hept-6-yl]-N-methylsulfuric diamide (13 mg, 21% yield). LCMS: 394.4 [M+1]$^+$; $^1$H NMR (400 MHz, DMSO-d6) δ ppm 8.33 (s, 1H), 7.16 (s, 1H), 7.12 (s, 1H), 6.71 (br. s., 2H), 4.53 (br. s., 2H), 4.40 (br. s., 2H), 3.89 (d, J=3.07 Hz, 6H), 3.76-3.85 (m, 1H), 2.55 (s, 3H), 2.45-2.35 (m, 4H).

Example-47: Synthesis of 4-(3-(2-sulfamoylmethylaminoethyl)azetidine-1-yl)-6,7-di-methoxyquinazoline, (Compound 1.47)

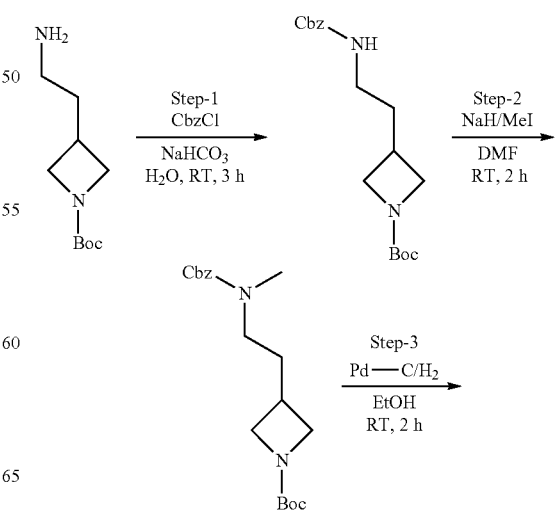

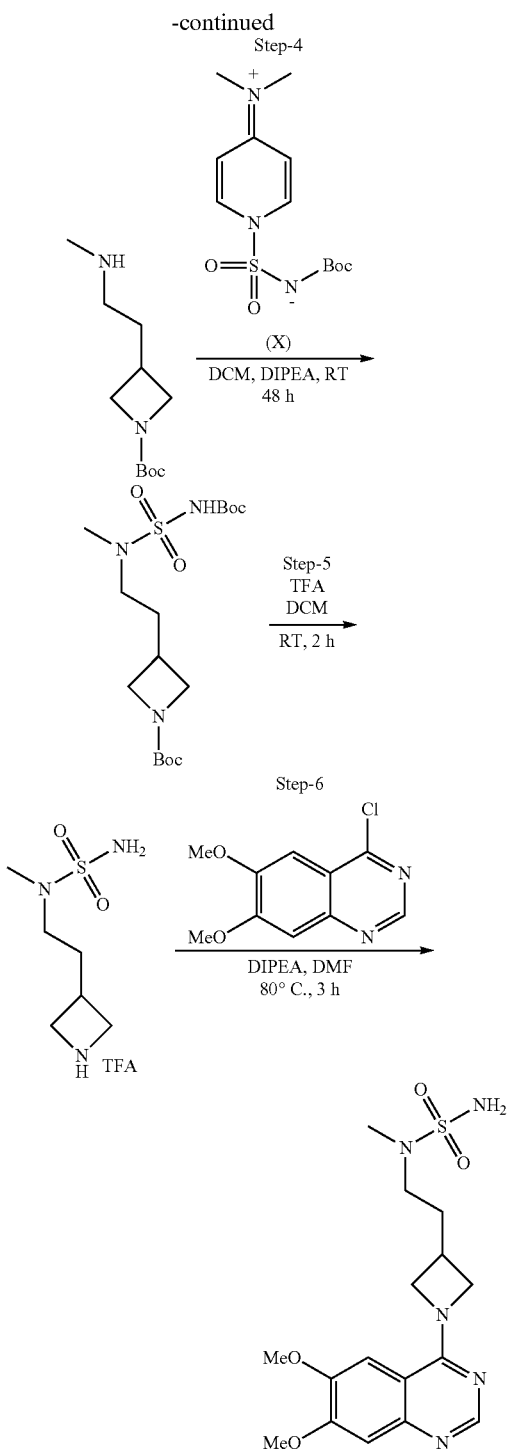

Step-1: Synthesis of tert-butyl 3-(2-(benzyloxycarbonylamino)ethyl)azetidine-1-carboxylate: To a solution of tert-butyl 3-(2-aminoethyl)azetidine-1-carboxylate (0.2 g, 1.0 mmol, 1 eq) in H₂O (5 mL), was added NaHCO₃ (0.168 g, 2.0 mmol, 2.0 eq) and benzyl chloroformate (171 mg, 1.0 mmol, 1 eq). The reaction mixture was allowed to stir at RT for 3 h. Progress of the reaction was monitored by $^1$H NMR. After completion, reaction mixture was diluted with water (100 mL) and extracted with EtOAc (3×100 mL). Combined organic layer was washed with brine (150 mL) and dried over anhydrous sodium sulfate. Removal of solvent under reduced pressure afforded tert-butyl 3-(2-(benzyloxycarbonylamino)ethyl)azetidine-1-carboxylate (0.25 g, 74%) which was used in the next step without further purification.

Step-2: Synthesis of tert-butyl 3-(2-((benzyloxycarbonyl)(methyl)amino)ethyl)azetidine-1-carboxylate: To a solution of tert-butyl 3-(2-(benzyloxycarbonylamino)ethyl)azetidine-1-carboxylate (0.25 g, 0.75 mmol, 1 eq) in DMF (5 mL), was added NaH (60 mg, 1.5 mmol, 2.0 eq, ~60% in paraffin oil) and the resulting mixture was stirred at RT for 10 minutes. To the mixture was then added methyl iodide (0.213 g, 1.5 mmol, 2 eq) and the reaction mixture was allowed to stir at RT for 2 h. Progress of reaction is monitored by $^1$H NMR. After completion, reaction mixture was diluted with water (100 mL) and extracted with EtOAc (3×100 mL). Combined organic layer was washed with water (2×100 mL) followed by brine (150 mL) and dried over anhydrous sodium sulfate. Removal of solvent under reduced pressure afforded tert-butyl 3-(2-((benzyloxycarbonyl)(methyl)amino)ethyl)azetidine-1-carboxylate (0.210 g, 80%) which was used in the next step without purification.

Step-3: Synthesis of tert-butyl 3-(2-(methylamino)ethyl)azetidine-1-carboxylate: To a solution of tert-butyl 3-(2-((benzyloxycarbonyl)(methyl)amino)ethyl)azetidine-1-carboxylate (210 mg, 0.6 mmol, 1 eq) in ethanol (30 mL) was added Pd/C (100 mg) and the reaction mixture was allowed to stir at RT under H₂ atmosphere using balloon for 2 h. Progress of reaction was monitored by TLC. After completion, reaction mixture was filtered through celite-bed. Removal of solvent under reduced pressure afforded crude tert-butyl 3-(2-(methylamino)ethyl)azetidine-1-carboxylate (130 mg, crude) which was used in the next step without purification.

Step-4: Synthesis of tert-butyl 3-(2-((N-(tert-butoxycarbonyl)sulfamoyl)(methyl)amino)ethyl)azetidine-1-carboxylate: To a solution of tert-butyl 3-(2-(methylamino)ethyl)azetidine-1-carboxylate (150 mg, 0.7 mmol, 1 eq) in dichloromethane (10 ML) were added N-(tert-butoxycarbonyl)-N-[4-(dimethylazaniumylidene)-1,4-dihydropyridin-1ylsulfonyl]azanide (317 mg, 1.05 mmol, 1.5 eq) and N,N-diisopropylethylamine (271 mg, 2.1 mmol, 3 eq) and the reaction mixture was allowed to stir at RT for 48 h. Progress of reaction was monitored by TLC. After completion, reaction mixture was concentrated under reduced pressure to get crude which was purified by Combi-Flash using ethyl acetate-hexane system as eluent to afford tert-butyl 3-(2-((N-(tert-butoxycarbonyl)sulfamoyl)(methyl)amino)ethyl)azetidine-1-carboxylate (180 mg, 65%).

Step-5: Synthesis of 3-(2-sulfamoylmethylaminoethyl)azetidine trifluoroacetate: To a solution of tert-butyl 3-(2-((N-(tert-butoxycarbonyl)sulfamoyl)(methyl)amino)ethyl)azetidine-1-carboxylate (180 mg, 0.46 mmol, 1 eq) in DCM (5 mL) was added TFA (1.5 mL) and the mixture was allowed to stir at RT for 2 h. Progress of reaction was monitored by $^1$H NMR. After completion, reaction mixture was concentrated under reduced pressure to afford crude which was triturated with diethyl ether to afford 3-(2-sulfamoylmethylaminoethyl)azetidine trifluoroacetate (120 mg, 85%).

Step-6: Synthesis of 4-(3-(2-sulfamoylmethylaminoethyl)azetidine-1-yl)-6,7-di-methoxyquinazoline: A suspension of 3-(2-sulfamoylmethylaminoethyl)azetidine trifluoroacetate (54 mg, 0.24 mmol, 1.5 eq), 4-chloro-6,7-dimethoxyquinazoline (50 mg, 0.16 mmol, 1.0 eq) and DIPEA (0.05 mL, 0.32 mmol, 2.0 eq) in DMF (1 mL) was allowed to stir at 80° C. for 3 h. Progress of reaction was monitored by TLC. After 3 h, reaction mixture was concentrated under reduced pressure to afford crude product which was purified using RP-HPLC to afford 4-(3-(2-sulfamoylmethylaminoethyl)azetidine-1-yl)-6,7-di-methoxyquinazoline (18 mg, 29%). LCMS: 382 [M+1]+; 1H NMR (400 MHz, DMSO-d6) δ ppm 8.33 (s, 1H), 7.19 (s, 1H), 7.12 (s, 1H), 6.71 (s, 2H), 4.57 (br. s., 3H), 4.14 (br. s., 2H), 3.90 (s, 3H), 3.87 (s, 3H), 2.96 (t, J=7.02 Hz, 2H), 2.83 (d, J=8.33 Hz, 2H), 2.62-2.67 (m, 3H), 1.85-1.95 (m, 3H).

Example-48: Synthesis of N-[2-(6,7-di-methoxyquinazoline-4-yl)-2-azaspiro[3.3]hept-6-yl]-N-cyclopropylsulfuric diamide, (Compound 1.48)

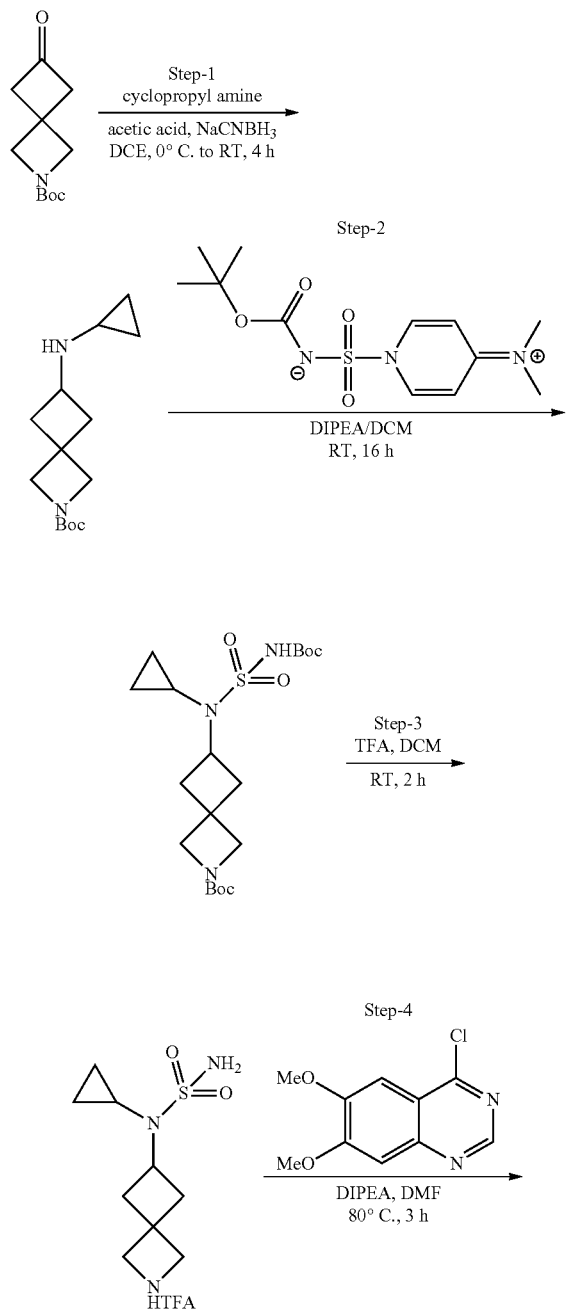

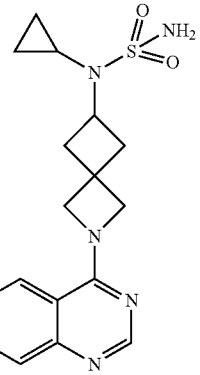

Step-1: Synthesis of tert-butyl 6-(cyclopropylamino)-2-azaspiro[3.3]heptane-2-carboxylate: A suspension of tert-butyl 6-oxo-2-azaspiro[3.3]heptane-2-carboxylate (500 mg, 2.3 mmol, 1 eq), cyclopropyl amine (135 mg, 2.3 mmol, 1.0 eq) and acetic acid (0.4 mL, 6.9 mmol, 3 eq) in DCE (10 mL) was stirred at 0° C. for 30 minutes. After 30 minutes, NaCNBH3 (0.44 g, 6.9 mmol, 3 eq) was added into above reaction mixture and then resultant reaction mixture was allowed to stir at RT for 4 h. Progress of reaction was monitored by TLC. After completion, reaction mixture was concentrated under reduced pressure to get residue which was diluted with saturated aqueous NaHCO3 solution (100 mL) and extracted with ethyl acetate (3×150 mL). Combined organic layer was washed with brine (3×50 mL) and dried over anhydrous sodium sulfate. Removal of solvent under reduced pressure to afford tert-butyl 6-(cyclopropylamino)-2-azaspiro[3.3]heptane-2-carboxylate (710 mg) which was used in the next step without purification.

Step-2: Synthesis of tert-butyl 6-((N-(tert-butoxycarbonyl)sulfamoyl)(cyclopropyl)amino)-2-azaspiro[3.3]heptane-2-carboxylate: To a solution of tert-butyl 6-(cyclopropylamino)-2-azaspiro[3.3]heptane-2-carboxylate (710 mg, 2.8 mmol, 1 eq) in DCM (50 mL) were added N-(tert-butoxycarbonyl)-N-[4-(dimethylazaniumylidene)-1,4-dihydropyridin-1ylsulfonyl]azanide (1.27 g, 4.2 mmol, 1.5 eq) and DIPEA (0.98 Ml, 5.6 mmol, 2 eq) and the mixture was allowed to stir at RT for 16 h. Progress of reaction was monitored by TLC. After completion, reaction mixture was concentrated under reduced pressure to get crude product which was purified using combi flash column chromatography to afford tert-butyl 6-((N-(tert-butoxycarbonyl)sulfamoyl)(cyclopropyl)amino)-2-azaspiro[3.3]heptane-2-carboxylate (0.4 g, 33%).

Step-3: Synthesis of (6-N-sulfamoylcyclopropylamino)-2-azaspiro[3.3]heptane trifluoroacetate: To a solution of tert-butyl 6-((N-(tert-butoxycarbonyl)sulfamoyl)(cyclopropyl)amino)-2-azaspiro[3.3]heptane-2-carboxylate (400 mg, 0.92 mmol, 1 eq) in DCM (10 mL) was added TFA (3 mL) and was allowed to stir at RT for 2 h. Progress of reaction was monitored by TLC. After completion, reaction mixture was concentrated under reduced pressure to afford crude which was triturated with diethyl ether to afford (6-N-sulfamoylcyclopropylamino)-2-azaspiro[3.3]heptane trifluoroacetate (300 mg, 94%) as TFA salt.

Step-4: Synthesis of N-[2-(6,7-di-methoxyquinazoline-4-yl)-2-azaspiro[3.3]hept-6-yl]-N-cyclopropylsulfuric diamide: A suspension of (6-N-sulfamoylcyclopropylamino)-2-azaspiro[3.3]heptane trifluoroacetate (100 mg, 0.28 mmol, 1 eq), 4-chloro-6,7-dimethoxyquinazoline (78 mg, 0.34 mmol, 1.2 eq) and DIPEA (0.1 mL, 0.56 mmol, 2.0 eq) in DMF (1 mL) was allowed to stir at 80° C. for 3 h. Progress of reaction was monitored by LCMS. After 3 h, reaction mixture was concentrated under reduced pressure to get crude which was purified using reversed phase HPLC to afford N-[2-(6,7-di-methoxyquinazoline-4-yl)-2-azaspiro[3.3]hept-6-yl]-N-cyclopropylsulfuric diamide (16 mg, 13%). LCMS: 420 [M+1]+; $^1$H NMR (400 MHz, DMSO-d6) δ ppm 8.33 (s, 1H), 7.17 (s, 1H), 7.12 (s, 1H), 6.85 (br. s., 2H), 4.54 (br. s., 2H), 4.40 (br. s., 2H), 3.89 (d, J=2.19 Hz, 6H), 2.07 (br. s., 1H), 1.65 (s, 4H), 1.23 (br. s., 1H), 0.70 (d, J=6.58 Hz, 4H)

Example-49: Synthesis of N-(2-(6,7-dimethoxyquinazolin-4-yl)-2-azaspiro[3.3]heptan-6-yl)methanesulfonamide, (Compound 1.49)

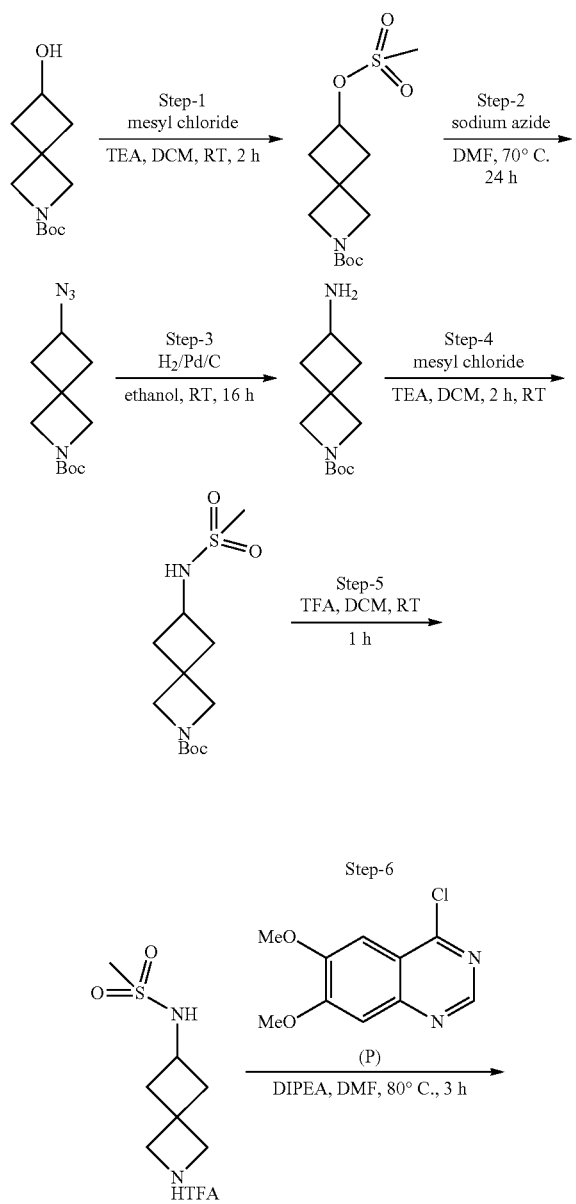

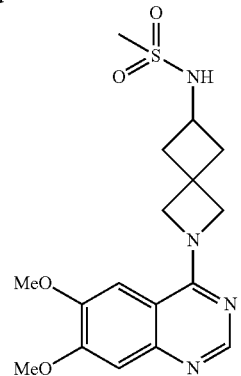

Step-1: Synthesis of tert-butyl 6-(methylsulfonyloxy)-2-azaspiro[3.3]heptane-2-carboxylate: To a solution of tert-butyl 6-hydroxy-2-azaspiro[3.3]heptane-2-carboxylate (1.2 g, 5.63 mmol, 1 eq) in DCM (50 mL) were added triethylamine (1.7 g, 16.89 mmol, 3 eq) and mesyl chloride (1.3 g, 11.26 mmol, 2 eq) and reaction mixture was allowed to stir at RT for 2 h. Progress of reaction was monitored by $^1$H NMR. After completion, reaction mixture was concentrated, diluted with water (100 mL) and extracted with ethyl acetate (3×100 mL). Combined organic layer was washed with brine (150 mL) and dried over anhydrous sodium sulfate. Removal of solvent under reduced pressure to afford tert-butyl 6-(methylsulfonyloxy)-2-azaspiro[3.3]heptane-2-carboxylate (1.3 g, 79%) which was used in the next step without purification.

Step-2: Synthesis of tert-butyl 6-azido-2-azaspiro[3.3]heptane-2-carboxylate: To a solution of tert-butyl 6-(methylsulfonyloxy)-2-azaspiro[3.3]heptane-2-carboxylate (2.7 g, 9.28 mmol, 1 eq) in DMF (10 mL) was added sodium azide (1.8 g, 27.8 mmol, 3 eq) and the reaction mixture was allowed to stir at 70° C. for 24 h. Progress of reaction is monitored by $^1$H NMR. After completion, reaction mixture was cooled, diluted with water (100 mL) and extracted with diethyl ether (3×150 mL). Combined organic layer was washed with water (2×100 mL) followed by brine (150 mL) and dried over anhydrous sodium sulfate. Removal of solvent under reduced pressure to afford tert-butyl 6-azido-2-azaspiro[3.3]heptane-2-carboxylate (2.1 g, 95%) which was used in the next step without purification.

Step-3: Synthesis of tert-butyl 6-amino-2-azaspiro[3.3]heptane-2-carboxylate: To a solution of tert-butyl 6-azido-2-azaspiro[3.3]heptane-2-carboxylate (2.5 g, 10 mmol, 1 eq) in ethanol (100 mL) was added Pd/C (1 g, ~10% on charcoal) and the reaction mixture was allowed to stir at RT for 16 h under hydrogen atmosphere. Progress of reaction was monitored by TLC. After completion, reaction mixture was filtered through celite bed and filtrate so obtained was concentrated under reduced pressure to afford tert-butyl 6-amino-2-azaspiro[3.3]heptane-2-carboxylate (2.3 g) which was used in the next step without purification.

Step-4: Synthesis of tert-butyl 6-(methylsulfonamido)-2-azaspiro[3.3]heptane-2-carboxylate: To a solution of Compound (D) (0.2 g, 0.94 mmol, 1 eq) in DCM (5 mL) were added TEA (0.397 mL, 2.82 mmol, 3 eq) and mesyl chloride (0.145 mL, 1.88 mmol, 2 eq) and then reaction mixture was allowed to stir at RT for 2 h. Progress of reaction was monitored by TLC. After 2 h, reaction mixture was cooled, diluted with aqueous saturated NaHCO$_3$ solution (100 mL) and extracted with DCM (3×150 mL). Combined organic layer was washed with water (2×100 mL) followed by brine (150 mL) and dried over anhydrous sodium sulfate. Removal of solvent under reduced pressure to afford tert-butyl 6-(methylsulfonamido)-2-azaspiro[3.3]heptane-2-carboxylate (0.23 g, 84%) which was used in the next step without purification.

Step-5: Synthesis of N-(-2-azaspiro[3.3]heptan-6-yl) methanesulfonamide trifluoroacetate: To a solution of tert-butyl 6-(methylsulfonamido)-2-azaspiro[3.3]heptane-2-carboxylate (230 mg, 0.79 mmol, 1 eq) in DCM (5 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-(-2-azaspiro[3.3]heptan-6-yl)methanesulfonamide trifluoroacetate (200 mg, 83%) as TFA salt.

Step-6: Synthesis of N-(2-(6,7-dimethoxyquinazolin-4-yl)-2-azaspiro[3.3]heptan-6-yl)methanesulfonamide: A suspension of N-(-2-azaspiro[3.3]heptan-6-yl)methanesulfonamide trifluoroacetate (100 mg, 0.32 mmol, 1 eq), 4-chloro-6,7-dimethoxyquinazoline (88 mg, 0.39 mmol, 1.2 eq) and DIPEA (0.1 mL, 0.65 mmol, 2.0 eq) in DMF (1 mL) was allowed to stir at 80° C. for 3 h. Progress of reaction was monitored by LCMS. After 3 h, reaction mixture was concentrated under reduced pressure to get crude which was purified using reversed phase HPLC to afford N-(2-(6,7-dimethoxyquinazolin-4-yl)-2-azaspiro[3.3]heptan-6-yl) methanesulfonamide (18 mg, 14%). LCMS: 379 [M+1]$^+$; $^1$H NMR (400 MHz, DMSO-d$_6$) δ ppm 8.33 (s, 1H), 7.42 (d, J=7.45 Hz, 1H), 7.16 (s, 1H), 7.12 (s, 1H), 4.54 (br. s., 2H), 4.39 (br. s., 2H), 3.89 (d, J=1.75 Hz, 6H), 3.73 (br. s., 1H), 2.86 (s, 3H), 2.65 (d, J=16.66 Hz, 4H).

Example-50: Synthesis of 4-(3-(2-sulfamoylamino-ethyl)azetidine-1-yl)-6,8-di-methoxyquinazoline, (Compound 1.50)

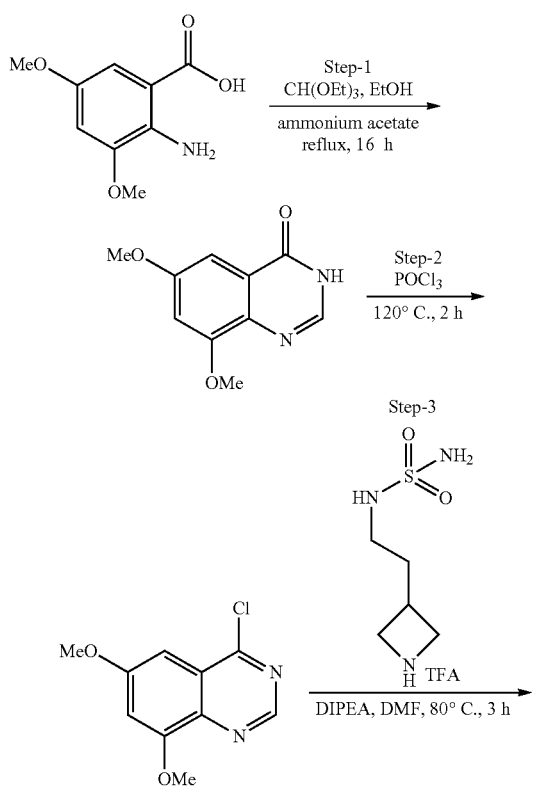

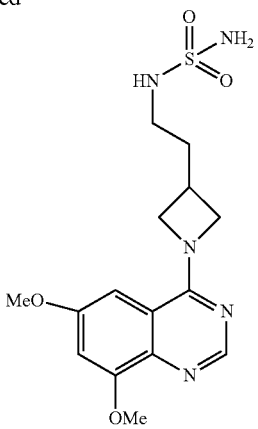

Step-1: Synthesis of 6,8-dimethoxyquinazolin-4 (3H)-one: A mixture of 2-amino-3,5-dimethoxybenzoic acid (0.25 g, 1.2 mmol, 1 eq), ammonium acetate (0.127 g, 1.5 mmol, 1.3 eq) and triethylorthoformate (0.33 mL, 1.9 mmol, 1.6 eq) in ethanol (5 mL) was allowed to stir at 90° C. for 16 h. Progress of reaction was monitored by TLC. Reaction mixture was cooled to RT, solid was filtered, washed with hexane and dried to afford 6,8-dimethoxyquinazolin-4 (3H)-one (200 mg, 76%). LCMS: 207 [M+1]$^+$ Step-2: Synthesis of 4-chloro-6,8-dimethoxyquinazoline: The stirred solution of 6,8-dimethoxyquinazolin-4 (3H)-one (0.2 g, 0.96 mmol, 1 eq) in 2 mL of POCl$_3$ was heated at 120° C. for 2 h. After completion reaction mixture was diluted with water (50 mL), precipitates so formed were filtered and dried under vacuum to afford desired 4-chloro-6,8-dimethoxyquinazoline (100 mg, 46%). LCMS: 225 [M+1]$^+$ Step-3: Synthesis of 4-(3-(2-sulfamoylaminoethyl)azetidine-1-yl)-6,8-di-methoxyquinazoline: A suspension of 4-chloro-6,8-dimethoxyquinazoline (45 mg, 0.20 mmol, 1.2 eq), 3-(2-sulfamoylaminoethyl)azetidine trifluoroacetate (50 mg, 0.17 mmol, 1.0 eq) and DIPEA (0.06 mL, 0.34 mmol, 2.0 eq) in DMF (1 mL) was allowed to stir at 80° C. for 3 h. Progress of reaction was monitored by TLC. After 3 h, reaction mixture was concentrated under reduced pressure to afford crude which was purified using RP-HPLC to afford 4-(3-(2-sulfamoylaminoethyl)azetidine-1-yl)-6,8-di-methoxyquinazoline (29 mg, 46%). LCMS: 368 [M+1]$^+$; $^1$H NMR (400 MHz, DMSO-d6) δ 8.31 (s, 1H), 6.88 (d, J=2.63 Hz, 1H), 6.79 (d, J=2.19 Hz, 1H), 6.60 (br. s., 1H), 6.54 (br. s., 2H), 4.58 (br. s., 2H), 4.14 (br. s., 2H), 3.74-3.96 (m, 6H), 2.91 (d, J=6.14 Hz, 2H), 2.83 (d, J=5.70 Hz, 1H), 1.80-1.91 (m, 2H),

Example-51: Synthesis of 3-(1-(6,7-dimethoxyquinazolin-4-yl)azetidin-3-yl)-N-hydroxypropanamide, (Compound 1.51)

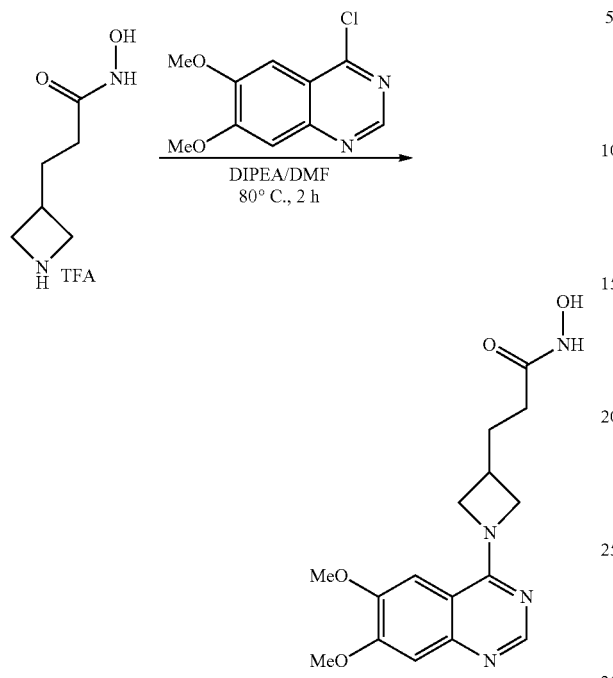

To a solution of 3-(azetidin-3-yl)-N-hydroxypropanamide (0.1 g, 0.445 mmol, 1 eq) in DMF (1 mL) were added N,N-diisopropylethylamine (0.3 mL, 1.34 mmol, 3 eq) and 4-chloro-6,7-dimethoxyquinazoline (0.1 g, 0.445 mmol, 1 eq) and the reaction mixture was allowed to stir at 80° C. for 2 h. Progress of reaction was monitored by LCMS. After completion, reaction mixture was concentrated under reduced pressure, triturated with ethyl acetate and diethyl ether to get residue which was purified by reversed phase chromatography to afford 3-(1-(6,7-dimethoxyquinazolin-4-yl)azetidin-3-yl)-N-hydroxypropanamide (04 mg, 2.71%). LCMS: 333 [M+1]$^+$. $^1$H NMR (400 MHz, DMSO-d6) δ ppm 10.0 (s, 1H), 8.75 (s, 1H), 8.62 (s, 1H), 7.30 (s, 1H), 7.20 (s, 1H), 5.00-4.20 (m, 2H), 3.99 (s, 3H), 3.98 (s, 3H), 2.90-2.80 (m, 1H), 2.08-2.00 (m, 2H), 1.95-1.85 (m, 2H).

Example-52: Synthesis of 2-(1-(6,7-dimethoxyquinazolin-4-yl)azetidin-3-yl)ethanesulfonamide, (Compound 1.52)

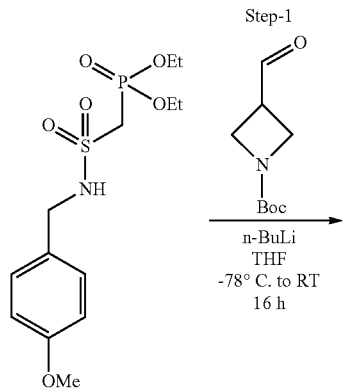

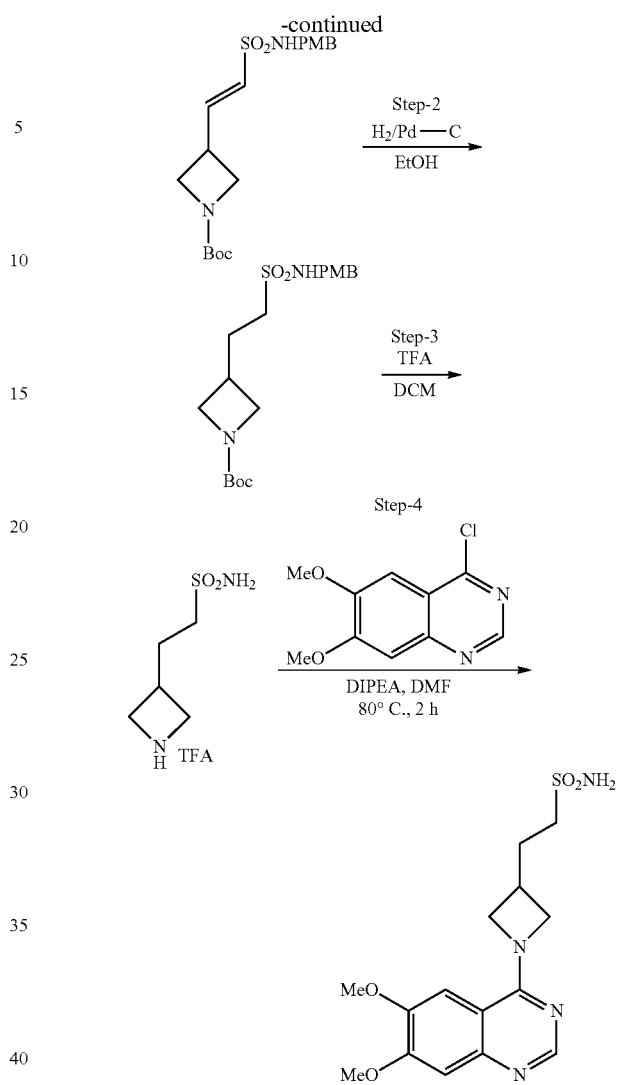

Step-1: Synthesis of (E)-tert-butyl 3 (2-(N-(4-methoxybenzyl)sulfamoyl)vinyl)azetidine-1-carboxylate: To a solution of diethyl(N-(4-methoxybenzyl)sulfamoyl)methylphosphonate (0.5 g, 1.4 mmol, 1 eq) in THF (20 ml) at −78° C. was added 2.5M n-BuLi in hexane (1.2 ml, 2.9 mmol, 2.1 eq) dropwise under nitrogen and the resulting mixture was stirred at the same temperature for 15 min. To the mixture was then added a solution of tert-butyl 3-formylazetidine-1-carboxylate (0.26 g, 1.4 mmol, 1 eq) in THF (2 ml) dropwise. Reaction mixture was warmed to RT and stirred for 16 h. Reaction mixture was diluted with saturated aq. NH$_4$Cl solution (100 mL) and extracted with ethyl acetate (3×100 mL). Combined organic layer was washed with water (2×100 mL) followed by brine (150 mL) and dried over anhydrous sodium sulfate. Removal of solvent under reduced pressure gave crude which was purified by Combi-Flash using ethyl acetate-hexane system as eluent to afford (E)-tert-butyl 3-(2-(N-(4-methoxybenzyl)sulfamoyl)vinyl)azetidine-1-carboxylate (0.3 g, 55%).

Step-2: Synthesis of tert-butyl 3-(2-(N-(4-methoxybenzyl)sulfamoyl)ethyl)azetidine-1-carboxylate: To a solution of (E)-tert-butyl 3-(2-(N-(4-methoxybenzyl)sulfamoyl)vinyl)azetidine-1-carboxylate (0.3 g, 0.78 mmol, 1 eq) in ethanol (20 mL) was added Pd/C (0.15 g) and the reaction mixture was allowed to stir at RT under H₂ atmosphere using balloon for 3 h. Progress of reaction was monitored by TLC. After completion, reaction mixture was filtered through celite-bed. Removal of solvent under reduced pressure afforded crude tert-butyl 3-(2-(N-(4-methoxybenzyl)sulfamoyl)ethyl)azetidine-1-carboxylate (0.3 g, Crude) which was used in the next step without purification.

Step-3: Synthesis of 2-(azetidin-3-yl)ethanesulfonamide trifluoroacetate: To a solution of tert-butyl 3-(2-(N-(4-methoxybenzyl)sulfamoyl)ethyl)azetidine-1-carboxylate (0.1 g, 0.26 mmol, 1 eq) in DCM (4 mL) was added TFA (1 mL) and the mixture was allowed to stir at RT for 16 h. Progress of reaction was monitored by ¹H NMR. After completion, reaction mixture was concentrated under reduced pressure to afford crude which was triturated with diethyl ether to afford 2-(azetidin-3-yl)ethanesulfonamide trifluoroacetate (0.08 g, Crude).

Step-4: Synthesis of 2-(1-(6,7-dimethoxyquinazolin-4-yl)azetidin-3-yl)ethanesulfonamide: A suspension of 2-(azetidin-3-yl)ethanesulfonamide trifluoroacetate (80 mg, 0.28 mmol, 1 eq), 4-chloro-6,7-dimethoxyquinazoline (77 mg, 0.34 mmol, 1.2 eq) and DIPEA (0.1 mL, 0.57 mmol, 2.0 eq) in DMF (1 mL) was allowed to stir at 80° C. for 2 h. Progress of reaction was monitored by TLC. After completion, reaction mixture was concentrated under reduced pressure to get residue which was purified by reversed phase HPLC to afford 2-(1-(6,7-dimethoxyquinazolin-4-yl)azetidin-3-yl)ethanesulfonamide (0.024 g, 24%). LCMS: 353 [M+1]⁺ 8.33 (s, 1H), 7.21 (s, 1H), 7.15 (s, 1H), 6.81 (s, 2H), 4.60-4.50 (m, 2H), 4.20-4.09 (m, 2H), 3.90 (s, 3H), 3.89 (s, 3H), 3.10-3.00 (m, 2H), 2.97-2.83 (m, 1H), 2.11-2.00 (m, 2H).

Example-53: Synthesis of (2-(6,7-dimethoxyquinazolin-4-yl)-2-azaspiro[3.3]heptan-6-yl)methylboronic acid, (Compound 1.53)

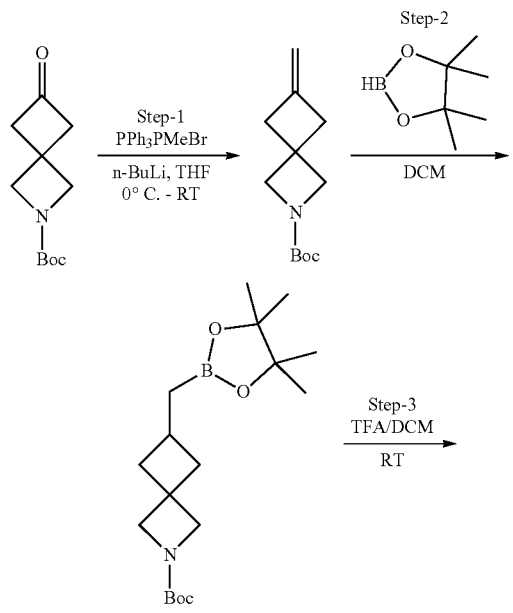

-continued

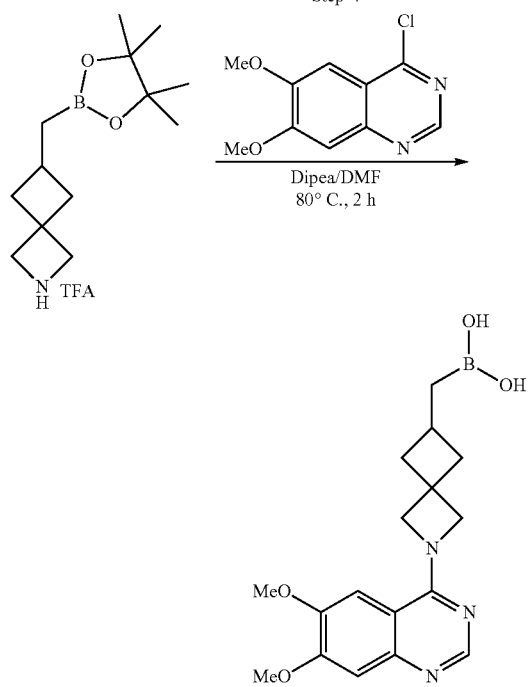

Step-1: Synthesis of tert-butyl 6-methylene-2-azaspiro[3.3]heptane-2-carboxylate: To a solution methyltriphenylphosphonium bromide (5.07 g, 14.22 mmol, 3 eq) in THF (80 mL) was added n-butyllithium (5.7 mL, 14.22 mmol, 3 eq) at 0° C. and the reaction mixture was allowed to stir at 0° C. for 1 h. To the mixture was then added a solution of tert-butyl 6-oxo-2-azaspiro[3.3]heptane-2-carboxylate (1 g, 4.74 mmol, 1 eq) in THF (10 mL) and the reaction mixture to stir at RT for overnight. Progress of reaction was monitored by TLC. After completion, reaction mixture was diluted with saturated ammonium chloride solution (100 mL) and extracted with ethyl acetate (3×100 mL). Combined organic layer was washed with brine (150 mL) and dried over anhydrous sodium sulfate. Removal of solvent under reduced pressure gave crude which was purified by normal phase silica-gel column chromatography to afford tert-butyl 6-methylene-2-azaspiro[3.3]heptane-2-carboxylate (0.680 g, 69%).

Step-2: Synthesis of tert-butyl 6-((4,4,5,5-tetramethyl-1,3,2-dioxaborolan-2-yl)methyl)-2-azaspiro[3.3]heptane-2-carboxylate: A solution of bis(1,5-cyclooctadiene)diiridium (I) dichloride (13 mg, 0.019 mmol, 0.04 eq) and ethylenebis(diphenylphosphine) (15 mg, 0.038 mmol, 0.08 eq) in DCM (5 mL) was deoxygenated by purging nitrogen for 30 minutes. To the mixture was then added a solution of tert-butyl 6-methylene-2-azaspiro[3.3]heptane-2-carboxylate (100 mg, 0.478 mmol, 1 eq) and 4,4,5,5-tetramethyl-1,3,2-dioxaborolane (91 mg, 0.717 mmol, 1.5 eq) in DCM (2 mL). Reaction mixture was allowed to stir at RT for 24 h. Progress of reaction is monitored by TLC. After completion, reaction mixture was diluted with water (20 mL) and extracted with ethyl acetate (3×15 mL). Combined organic layer was washed with brine (30 mL) and dried over anhydrous sodium sulfate. Removal of solvent under reduced pressure afforded crude which was purified using Combi-Flash to afford tert-butyl 6-((4,4,5,5-tetramethyl-1,3,2-dioxaborolan-2-yl)methyl)-2-azaspiro[3.3]heptane-2-carboxylate (0.1 g)

Step-3: Synthesis of 6-((4,4,5,5-tetramethyl-1,3,2-dioxaborolan-2-yl)methyl)-2-azaspiro[3.3]heptane: To a solution of tert-butyl 6-((4,4,5,5-tetramethyl-1,3,2-dioxaborolan-2-yl)methyl)-2-azaspiro[3.3]heptane-2-carboxylate (0.1 g, 0.297 mmol, 1 eq) in DCM (1 mL) was added TFA (0.5 mL) and the mixture was allowed to stir at RT for 1 h. Progress of reaction was monitored by $^1$H NMR. After completion, reaction mixture was concentrated under reduced pressure to afford crude which was triturated with diethyl ether to afford 6-((4,4,5,5-tetramethyl-1,3,2-dioxaborolan-2-yl)methyl)-2-azaspiro[3.3]heptane (0.1 g) as TFA salt.

Step-4: Synthesis of (2-(6,7-dimethoxyquinazolin-4-yl)-2-azaspiro[3.3]heptan-6-yl)methylboronic acid: A suspension of 4-chloro-6,7-dimethoxyquinazoline (67 mg, 0.297 mmol, 1.0 eq), 6-((4,4,5,5-tetramethyl-1,3,2-dioxaborolan-2-yl)methyl)-2-azaspiro[3.3]heptane (0.1 g, 0.297 mmol, 1.0 eq) and DIPEA (0.1 mL, 0.594 mmol, 2 eq) in DMF (1 mL) was allowed to stir at 80° C. for 2 h. Progress of reaction was monitored by TLC. After completion, reaction mixture was concentrated under reduced pressure to afford crude product which was purified by reversed phase HPLC to afford (2-(6,7-dimethoxyquinazolin-4-yl)-2-azaspiro[3.3]heptan-6-yl)methylboronic acid (5 mg, 3%). LCMS: 344 [M+1]$^+$; $^1$H NMR (400 MHz, DMSO-d$_6$) δ ppm 8.38 (s, 1H), 7.42 (s, 2H), 7.20 (s, 1H), 7.10 (s, 1H), 4.50 (brs, 2H), 4.39 (brs, 2H), 3.90 (s, 6H), 2.50-2.20 (m, 5H), 1.85-1.75 (m, 2H).

Example-54: Synthesis of N-(2-[1-(7-methoxy-6-methylquinazolin-4-yl)azetidin-3-yl]ethyl)sulfuric diamide, (Compound 1.54)

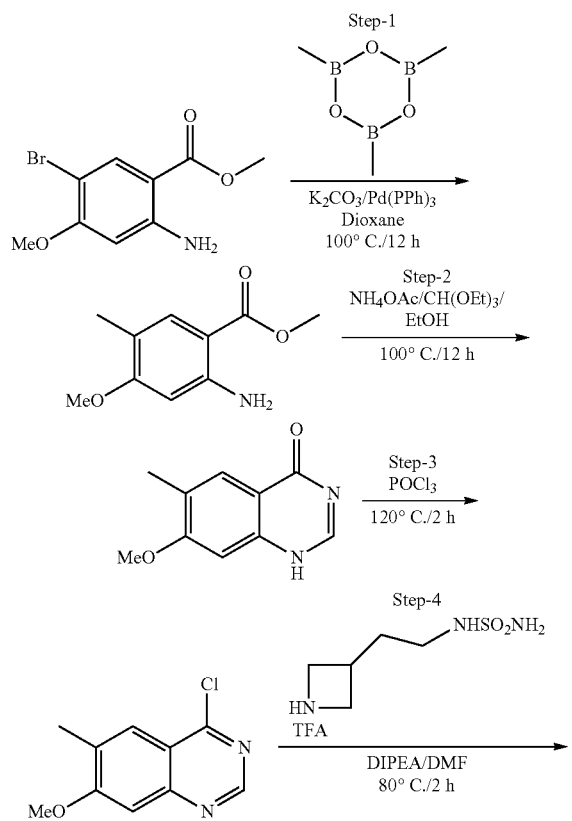

-continued

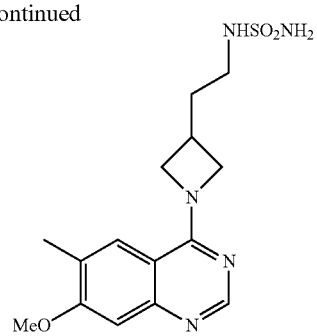

Step-1: Synthesis of methyl 2-amino-4-methoxy-5-methylbenzoate: To a solution of methyl 2-amino-5-bromo-4-methoxybenzoate (1 g, 3.84 mmol, 1 eq) in 1,4-dioxane (10 mL) was added boroxine (482 mg, 3.84 mmol, 1.0 eq) and K2CO$_3$ (1.5 g, 11.52 mmol, 3.0 eq) The reaction mixture was deoxygenated with N2 for 5 min followed by the addition of Pd(PPh$_3$) (443 mg, 0.38 mmol, 0.1 eq). The reaction mixture was again deoxygenated with N2 and the reaction mixture was allowed to heat at 100° C. for 12 h. Reaction mixture was cooled to RT, diluted with water (10 mL) and extracted with ethylacetate (3×10 mL). The organic layer was evaporated under reduced pressure to obtain the crude which was purified by normal phase column chromatography to give methyl 2-amino-4-methoxy-5-methylbenzoate (400 mg, 53%). LCMS: 195[M+1]$^+$ Step-2: Synthesis of 7-methoxy-6-methylquinazolin-4 (1H)-one: To a solution of methyl 2-amino-4-methoxy-5-methylbenzoate (400 mg, 2.04 mmol, 1.0 eq) in ethanol (10 mL) was added triethylorthoformate (485 mg, 3.27 mmol. 1.6 eq) and ammonium acetate (204 mg, 2.65 mmol, 1.3 eq), the reaction mixture was allowed to stir at 100° C. for 12 h. Progress of reaction was monitored by TLC. After completion, reaction mixture was cooled; the precipitated solid was filtered and washed with pentane (10 mL) to afford 7-methoxy-6-methylquinazolin-4 (1H)-one (252 mg, 64%) which was carried further without purification. LCMS: 190[M+1]$^+$ Step-3: Synthesis of 4-chloro-7-methoxy-6-methylquinazoline: A mixture of 7-methoxy-6-methylquinazolin-4 (1H)-one (252 mg, 4.86 mol, 1 eq) in POCl$_3$ (0.5 mL) was allowed to stir at 120° C. for 2 h. Progress of reaction was monitored by TLC. After completion reaction mixture was cooled to RT, diluted with cold water (100 mL) and allowed to stir for 5 minutes. Solid obtained was filtered, washed with water and dried under vacuum to afford 4-chloro-7-methoxy-6-methylquinazoline (100 mg, 36%). LCMS: 208 [M+1]$^+$ Step-4: Synthesis of N-{2-[1-(7-methoxy-6-methylquinazolin-4-yl)azetidin-3-yl]ethyl}sulfuric diamide: A suspension of 4-chloro-7-methoxy-6-methylquinazoline (100 mg, 0.48 mmol, 1.0 eq), N-[2-(azetidin-3-yl)ethyl]sulfuric diamide trifloroacetic acid (132 mg, 0.48 mmol, 1.0 eq) and diisopropylethylenediamine (0.2 mL, 0.96 mmol, 2.0 eq) in DMF (2.5 mL) was allowed to stir at 80° C. for 2 h. Reaction mixture was cooled to RT. The solvent was removed under reduced pressure to obtain the crude product which was purified by RP-chromatography to afford N-{2-[1-(7-methoxy-6-methylquinazolin-4-yl)azetidin-3-yl] ethyl}sulfuric diamide (30 mg, 18%). LCMS: 351[M+1]$^+$; $^1$H NMR (400 MHz, DMSO-d$_6$) ppm 8.35 (s, 1H), 7.68 (s, 1H), 7.08 (s, 1H), 6.38-6.64 (m, 3H), 4.55 (br. s., 2H), 4.11

(br. s., 2H), 3.75-3.99 (m, 3H), 2.73-3.02 (m, 3H), 2.28 (s, 3H), 1.85 (q, J=7.16 Hz, 2H).

Example-55: Synthesis of (E)-2-(1-(6,7-dimethoxyquinazolin-4-yl)azetidin-3-yl)ethenesulfonamide, (Compound 1.55)

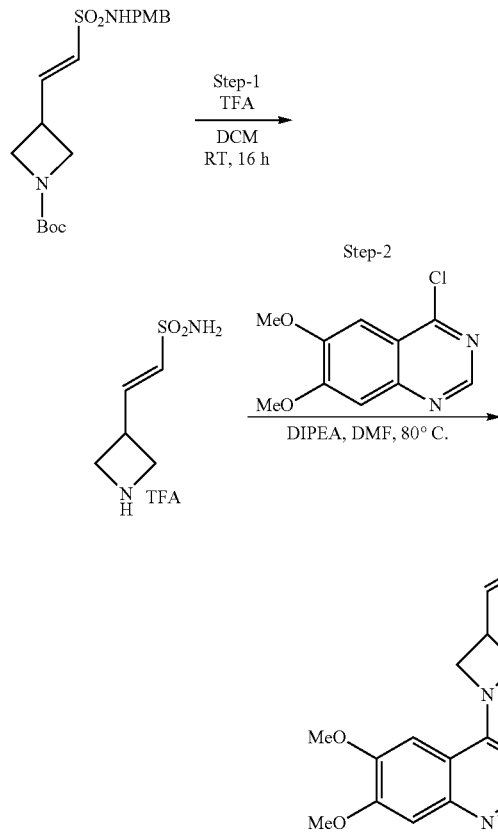

Step-1: Synthesis of (E)-2-(azetidin-3-yl)ethenesulfonamide: To a solution of (E)-tert-butyl 3-(2-(N-(4-methoxybenzyl)sulfamoyl)vinyl)azetidine-1-carboxylate (0.15 g, 0.39 mmol, 1 eq) in DCM (10 mL) was added TFA (1.5 mL) and the mixture was allowed to stir at RT for 16 h. Progress of reaction was monitored by $^1$H NMR. After completion, reaction mixture was concentrated under reduced pressure to afford crude which was triturated with diethyl ether to afford (E)-2-(azetidin-3-yl)ethenesulfonamide trifluoroacetate (0.1 g, crude).

Step-2: Synthesis of (E)-2-(1-(6,7-dimethoxyquinazolin-4-yl)azetidin-3-yl)ethenesulfonamide: A suspension of (E)-2-(azetidin-3-yl)ethenesulfonamide trifluoroacetate (100 mg, 0.36 mmol, 1 eq), 4-chloro-6,7-dimethoxyquinazoline (98 mg, 0.43 mmol, 1.2 eq) and DIPEA (0.12 mL, 0.72 mmol, 2.0 eq) in DMF (1 mL) was allowed to stir at 80° C. for 2 h. Progress of reaction was monitored by TLC. After completion, reaction mixture was concentrated under reduced pressure to get residue which was purified by reversed phase HPLC to afford (E)-2-(1-(6,7-dimethoxyquinazolin-4-yl)azetidin-3-yl)ethenesulfonamide (0.24 g, 19%). LCMS: 351 [M+1]$^+$; $^1$H NMR (400 MHz, DMSO-$d_6$) δ ppm 8.39 (s, 1H), 7.19 (s, 1H), 7.16 (s, 1H), 7.02 (brs, 2H), 6.85 (dd, 1H), 6.72 (d, 1H), 4.75-4.63 (m, 2H), 4.42-4.30 (m, 2H), 3.89 (s, 3H), 3.88 (s, 3H), 3.78-3.65 (m, 1H).

Example-56: Synthesis of 3-(1-(7-methoxyquinazolin-4-yl)azetidin-3-yl)propane-1-sulfonamide, (Compound 1.56)

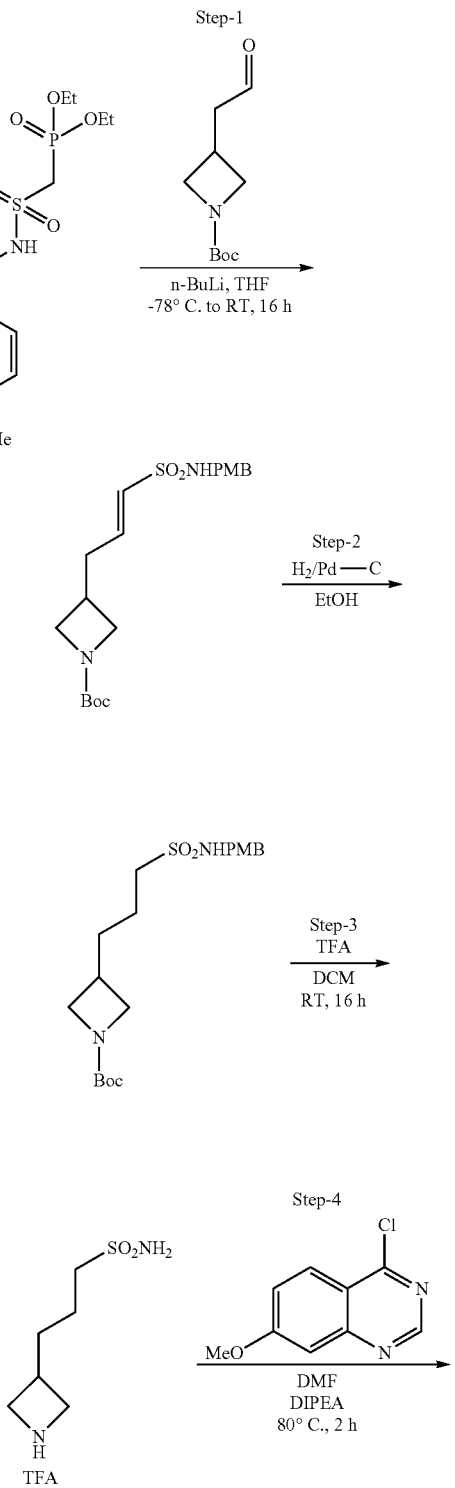

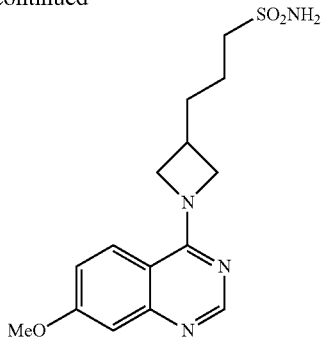

Step-1: Synthesis of (E)-tert-butyl 3-(3-(N-(4-methoxybenzyl)sulfamoyl)allyl)azetidine-1-carboxylate (0.18 g, 32.14%): To a solution of diethyl(N-(4-methoxybenzyl)sulfamoyl)methylphosphonate (0.5 g, 1.4 mmol, 1 eq) in THF (20 ml) at −78° C. was added 2.5M n-BuLi (1.2 ml, 2.9 mmol, 2.1 eq) in hexane dropwise under nitrogen and the reaction mixture was stirred at the same temperature for 15 minutes. To the mixture was then added solution of tert-butyl 3-(2-oxoethyl)azetidine-1-carboxylate (0.28 g, 1.4 mmol, 1 eq) in THF (2 mL) dropwise. Reaction mixture was gradually warmed to RT and stirred for 16 h. Progress of reaction was monitored by TLC. After completion, reaction mixture was diluted with saturated aq. NH₄Cl solution and extracted with ethyl acetate (3×100 mL). Combined organic layer was washed with water (2×100 mL) followed by brine (150 mL) and dried over anhydrous sodium sulfate. Removal of solvent under reduced gave crude which was purified by Combi-Flash using ethyl acetate-hexane system as eluent to afford (E)-tert-butyl 3-(3-(N-(4-methoxybenzyl)sulfamoyl)allyl)azetidine-1-carboxylate (0.18 g, 32.14%).

Step-2: Synthesis of tert-butyl 3-(3-(N-(4-methoxybenzyl)sulfamoyl)propyl)azetidine-1-carboxylate: To a solution of (E)-tert-butyl 3-(3-(N-(4-methoxybenzyl)sulfamoyl)allyl)azetidine-1-carboxylate (0.18 g, 0.45 mmol, 1 eq) in ethanol (10 mL) was added Pd/C (0.09 g) and the reaction mixture was allowed to stir at RT under H₂ atmosphere using balloon for 3 h. Progress of reaction was monitored by ¹H NMR. After completion, reaction mixture was filtered through celite-bed. Removal of solvent under reduced pressure afforded tert-butyl 3-(3-(N-(4-methoxybenzyl)sulfamoyl)propyl)azetidine-1-carboxylate (0.18 g, crude) which was used in the next step without purification.

Step-3: Synthesis of 3-(azetidin-3-yl)propane-1-sulfonamide 2,2,2-trifluoroacetate: To a solution of tert-butyl 3-(3-(N-(4-methoxybenzyl)sulfamoyl)propyl)azetidine-1-carboxylate (0.12 g, 0.39 mmol, 1 eq) in DCM (2 mL) was added TFA (1 mL) and the mixture was allowed to stir at RT for 16 h. Progress of reaction was monitored by ¹H NMR. After completion, reaction mixture was concentrated under reduced pressure to afford crude which was triturated with diethyl ether to afford 3-(azetidin-3-yl)propane-1-sulfonamide 2,2,2-trifluoroacetate (0.1 g, crude) which was used in the next step without purification.

Step-4: Synthesis of 3-(1-(7-methoxyquinazolin-4-yl)azetidin-3-yl)propane-1-sulfonamide: A suspension of 3-(azetidin-3-yl)propane-1-sulfonamide 2,2,2-trifluoroacetate (100 mg, 0.34 mmol, 1 eq), 4-chloro-7-methoxyquinazoline (67 mg, 0.34 mmol, 1 eq) and DIPEA (0.119 mL, 0.68 mmol, 2.0 eq) in DMF (1 mL) was allowed to stir at 80° C. for 2 h. Progress of reaction was monitored by TLC. After completion, reaction mixture was concentrated under reduced pressure to get residue which was purified by RP-HPLC to afford 3-(1-(7-methoxyquinazolin-4-yl)azetidin-3-yl)propane-1-sulfonamide (0.014 g, 12%). LCMS: 337 [M+1]⁺; ¹H NMR (400 MHz, DMSO-d6) δ ppm 8.40 (s, 1H), 7.85 (d, 1H), 7.10 (s, 1H), 7.06 (d, 1H), 6.78 (s, 2H), 4.55 (brs, 2H), 4.07 (brs, 2H), 3.87 (s, 3H), 3.00 (t, 2H), 2.87-2.75 (m, 1H), 1.85-1.62 (m, 4H).

Example-57: Synthesis of (2-(6,7-dimethoxyquinazolin-4-yl)-2-azaspiro[3.3]heptan-6-yl)methanesulfonamide, (Compound 1.57)

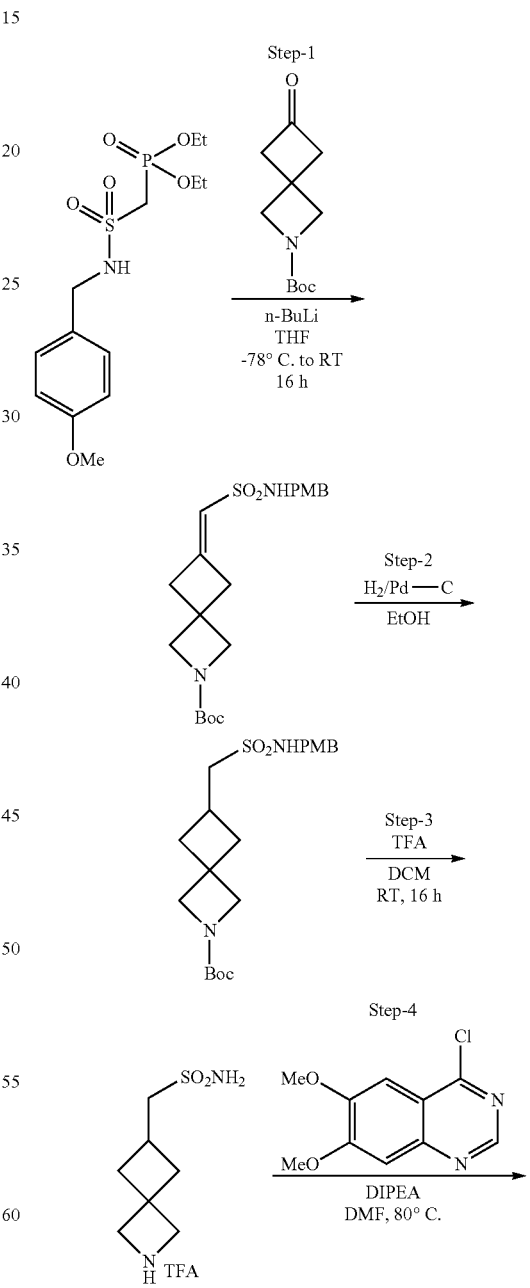

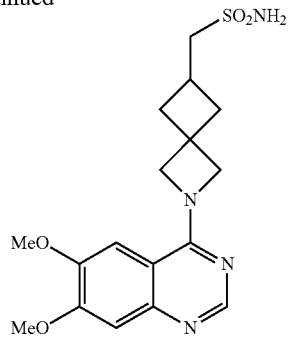

Step-1: Synthesis of tert-butyl 6-((N-(4-methoxybenzyl) sulfamoyl)methylene)-2-azaspiro[3.3]heptane-2-carboxylate: To a solution of diethyl(N-(4-methoxybenzyl)sulfamoyl)methylphosphonate (0.3 g, 0.85 mmol, 1 eq) in THF (20 mL) at −78° C. was added 2.5 M n-BuLi (0.71 mL, 1.79 mmol, 2.1 eq) dropwise under nitrogen and the resulting mixture was stirred at the same temperature for 15 minutes. To the mixture was then added a solution of tert-butyl 6-oxo-2-azaspiro[3.3]heptane-2-carboxylate (0.18 g, 0.85 mmol, 1 eq) in THF (2 mL) dropwise. Reaction mixture was warmed to RT and stirred for 16 h. Reaction mixture was diluted with saturated aq. $NH_4Cl$ solution and extracted with ethyl acetate (3×100 mL). Combined organic layer was washed with water (2×100 mL) followed by brine (150 mL) and dried over anhydrous sodium sulfate. Removal of solvent under reduced pressure gave crude which was purified by Combi-Flash using ethyl acetate-hexane system as eluent to afford tert-butyl 6-((N-(4-methoxybenzyl)sulfamoyl)methylene)-2-azaspiro[3.3]heptane-2-carboxylate (0.12 g, 34%).

Step-2: Synthesis of tert-butyl 6-((N-(4-methoxybenzyl)sulfamoyl)methyl)-2-azaspiro[3.3]heptane-2-carboxylate: To a solution of tert-butyl 6-((N-(4-methoxybenzyl)sulfamoyl)methylene)-2-azaspiro[3.3]heptane-2-carboxylate (0.12 g, 0.29 mmol, 1 eq) in ethanol (10 mL) was added Pd/C (0.06 g) and the reaction mixture was allowed to stir at RT under $H_2$ atmosphere using balloon for 3 h. Progress of reaction was monitored by TLC. After completion, reaction mixture was filtered through celite-bed. Removal of solvent under reduced pressure afforded crude tert-butyl 6-((N-(4-methoxybenzyl)sulfamoyl)methyl)-2-azaspiro[3.3]heptane-2-carboxylate (0.1 g, crude) which was used in the next step without purification.

Step-3: Synthesis of diethyl ether to afford 2-azaspiro[3.3]heptan-6-ylmethanesulfonamide 2,2,2-trifluoroacetate: To a solution of tert-butyl 6-((N-(4-methoxybenzyl)sulfamoyl)methyl)-2-azaspiro[3.3]heptane-2-carboxylate (0.1 g, 0.24 mmol, 1 eq) in DCM (4 mL) was added TFA (1 mL) and the mixture was allowed to stir at RT for 16 h. Progress of reaction was monitored by $^1H$ NMR. After completion, reaction mixture was concentrated under reduced pressure to afford crude which was triturated with diethyl ether to afford 2-azaspiro[3.3]heptan-6-ylmethanesulfonamide 2,2,2-trifluoroacetate (0.1 g, crude).

Step-4: Synthesis of (2-(6,7-dimethoxyquinazolin-4-yl)-2-azaspiro[3.3]heptan-6-yl)methanesulfonamide: A suspension of 2-azaspiro[3.3]heptan-6-ylmethanesulfonamide 2,2,2-trifluoroacetate (100 mg, 0.33 mmol, 1 eq), 4-chloro-6,7-dimethoxyquinazoline (89 mg, 0.39 mmol, 1.2 eq) and DIPEA (0.115 mL, 0.66 mmol, 2.0 eq) in DMF (1 mL) was allowed to stir at 80° C. for 2 h. Progress of reaction was monitored by TLC. After completion, reaction mixture was concentrated under reduced pressure to get residue which was purified by RP-HPLC to afford (2-(6,7-dimethoxyquinazolin-4-yl)-2-azaspiro[3.3]heptan-6-yl)methanesulfonamide (0.023 g, 18%). LCMS: 379 [M+1]$^+$; $^1H$ NMR (400 MHz, DMSO-$d_6$) δ ppm 8.31 (s, 1H), 7.19 (s, 1H), 7.09 (s, 1H), 6.75 (brs, 2H), 4.55 (brs, 2H), 4.39 (brs, 2H), 3.87 (s, 6H), 3.09 (d, 2H), 2.70-2.40 (m, 3H), 2.18-2.05 (m, 2H).

Example-58: Synthesis of 4-3-(2-(sulfamoylamino)ethyl)-3-phenylazetidin-1-yl-6,7-dimethoxyquinazoline, (Compound 1.58)

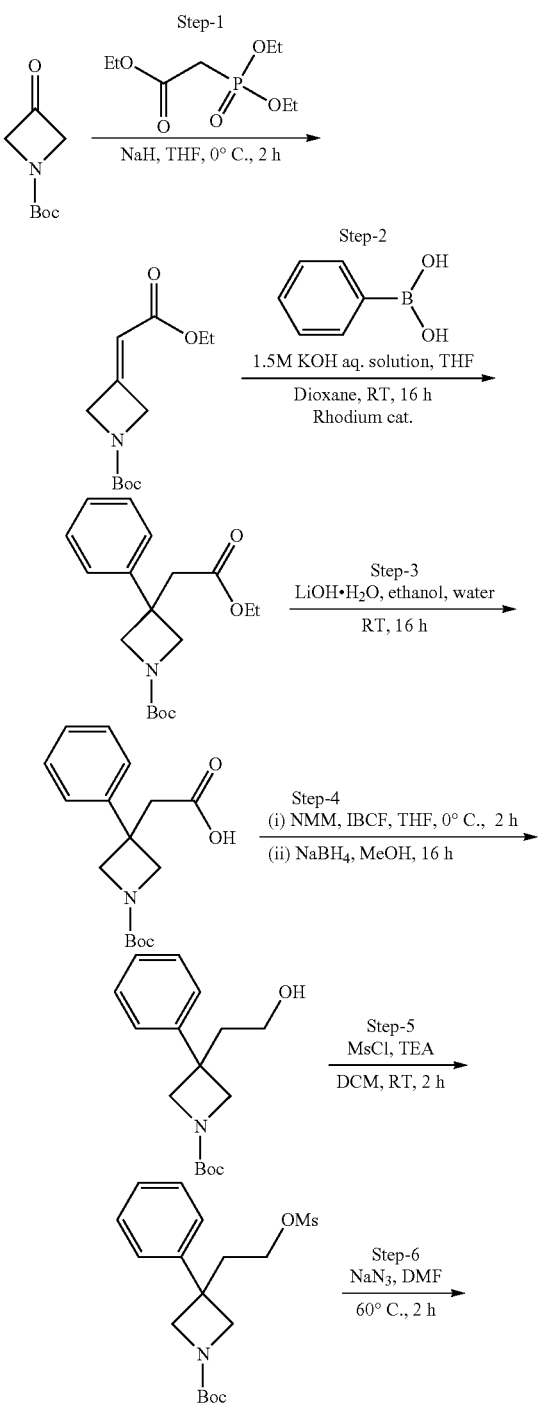

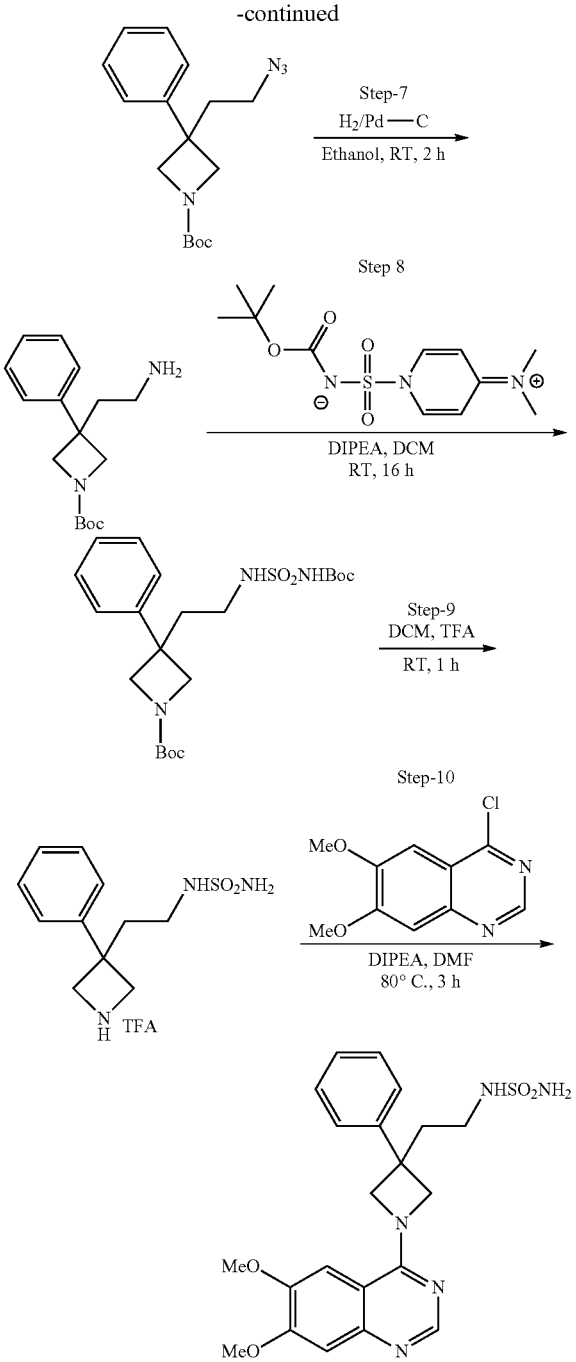

Step-1: Synthesis of tert-butyl 3-(2-ethoxy-2-oxoethylidene)azetidine-1-carboxylate: To a solution of ethyl 2-(diethoxyphosphoryl)acetate tert-butyl 3-oxoazetidine-1-carboxylate (2.75 g, 12.29 mmol, 1.05 eq) in THF (50 mL) at 0° C. was added NaH (0.7 g, 17.55 mmol, 1.5 eq) and reaction mixture was allowed to stir at 0° C. for 10 minutes. To the mixture was then added tert-butyl 3-oxoazetidine-1-carboxylate (2 g, 11.7 mmol, 1 eq) and resultant reaction mixture was allowed to stir at 0° C. for 2 h. After 2 h, reaction mixture was diluted with water (100 mL) and extracted with EtOAc (3×100 mL). Combined organic layer was washed with brine (150 mL) and dried over anhydrous sodium sulfate. Removal of solvent under reduced pressure afforded tert-butyl 3-(2-ethoxy-2-oxoethylidene)azetidine-1-carboxylate (2.8 g, crude) which was used in the next step without purification.

Step-2: Synthesis of tert-butyl 3-(2-ethoxy-2-oxoethyl)-3-phenylazetidine-1-carboxylate: To a suspension of di-μ-chlorobis[(1,2,5,6-q)-1,5-cyclooctadiene]dirhodium (12 mg, 0.024 mmol, 0.03 eq) in dioxane (2 mL) was added 1.5 M aq. KOH solution (0.093 g, 1.65 mmol, 2 eq) mixture was allowed to stir at RT for 5 minutes. To the mixture was then added phenylboronic acid (0.2 g, 1.65 mmol, 2 eq) and a solution of tert-butyl 3-(2-ethoxy-2-oxoethylidene)azetidine-1-carboxylate (0.2 g, 0.82 mmol, 1 eq) in THF (3 mL). The reaction mixture was stirred at RT for 16 h. Progress of reaction was monitored by TLC. After completion, reaction mixture was diluted with water (100 mL) and extracted with EtOAc (3×100 mL). Combined organic layer was washed with brine (150 mL) and dried over anhydrous sodium sulfate. Removal of solvent under reduced pressure gave crude which was purified by Combi-Flash to afford tert-butyl 3-(2-ethoxy-2-oxoethyl)-3-phenylazetidine-1-carboxylate (0.15 g, 56%).

Step-3: Synthesis of 2-(1-(tert-butoxycarbonyl)-3-phenylazetidin-3-yl)acetic acid: To a solution of tert-butyl 3-(2-ethoxy-2-oxoethyl)-3-phenylazetidine-1-carboxylate (1.31 g, 4.1 mmol, 1 eq) in a solution of THF-MeOH—H$_2$O (8:2:1, 50 mL)) was added LiOH·H$_2$O (0.86 g, 20 mmol, 5 eq) and mixture was allowed to stir at RT for 16 h. Progress of reaction was monitored by TLC. After completion, reaction mixture was concentrated under reduced pressure to get residue which was diluted with saturated aq. ammonium chloride solution (200 mL) and extracted with EtOAc (4×150 mL). Combined organic layer was washed with brine (150 mL) and dried over anhydrous sodium sulfate. Removal of solvent under reduced pressure afforded 2-(1-(tert-butoxycarbonyl)-3-phenylazetidin-3-yl)acetic acid (1.07 g, 89%) which was used in the next step without purification.

Step-4: Synthesis of tert-butyl 3-(2-hydroxyethyl)-3-phenylazetidine-1-carboxylate: To a solution of 2-(1-(tert-butoxycarbonyl)-3-phenylazetidin-3-yl)acetic acid (0.37 g, 1.26 mmol, 1 eq) in THF (10 mL) were added NMM (0.41 mL, 3.8 mmol, 3 eq) and isobutyl chloroformate (0.4 ml, 3.04 mmol, 2.4 eq) and reaction mixture was allowed to stir at 0° C. for 2 h. To the mixture was then added a solution of NaBH$_4$ (800 mg) in methanol (10 mL) and mixture was allowed to stir at RT for 16 h. Progress of reaction was monitored by TLC. After completion, reaction mixture was concentrated under reduced pressure to get residue and was diluted with sat. NH$_4$Cl solution (100 mL) and extracted with ethyl acetate (3×100 mL). Combined organic layer was washed with brine (150 mL) and dried over anhydrous sodium sulfate. Removal of solvent under reduced pressure to get crude which was purified by Combi-Flash using ethyl acetate-hexane system as eluent to afford tert-butyl 3-(2-hydroxyethyl)-3-phenylazetidine-1-carboxylate (240 mg, 68%).

Step-5: Synthesis of tert-butyl 3-(2-(methylsulfonyloxy)ethyl)-3-phenylazetidine-1-carboxylate: To a solution of tert-butyl 3-(2-hydroxyethyl)-3-phenylazetidine-1-carboxylate (0.7 g, 2.5 mmol, 1 eq) in DCM (50 mL) were added triethylamine (1.06 mL, 7.5 mmol, 3 eq) and mesyl chloride (0.39 mL, 5 mmol, 2 eq) and reaction mixture was allowed to stir at RT for 2 h. Progress of reaction was monitored by TLC. After completion, reaction mixture was concentrated under reduced pressure to get residue which was diluted with water (100 mL) and extracted with ethyl acetate (3×100 mL). Combined organic layer was washed with brine (150 mL) and dried over anhydrous sodium sulfate. Removal of solvent under reduced pressure afforded tert-butyl 3-(2-(methylsulfonyloxy)ethyl)-3-phenylazetidine-1-carboxylate (0.9 g, crude) which was used in the next step without purification.

Step-6: Synthesis of tert-butyl 3-(2-azidoethyl)-3-phenylazetidine-1-carboxylate: To a solution of tert-butyl 3-(2-(methylsulfonyloxy)ethyl)-3-phenylazetidine-1-carboxylate (0.26 g, 0.73 mmol, 1 eq) in DMF (4 mL) was added sodium azide (0.19 g, 2.9 mmol, 4 eq) and the reaction mixture was allowed to stir at 60° C. for 2 h. Progress of reaction is monitored by TLC. After completion, reaction mixture was diluted with water (100 mL) and extracted with ethylacetate (3×50 mL). Combined organic layer was washed with water (2×50 mL) followed by brine (50 mL) and dried over anhydrous sodium sulfate. Removal of solvent under reduced pressure afforded tert-butyl 3-(2-azidoethyl)-3-phenylazetidine-1-carboxylate (0.2 g, 90%) which was used in the next step without purification.

Step-7: Synthesis of tert-butyl 3-(2-aminoethyl)-3-phenylazetidine-1-carboxylate: To a solution of tert-butyl 3-(2-azidoethyl)-3-phenylazetidine-1-carboxylate (0.2 g, 0.66 mmol, 1 eq) in ethanol (6 mL) was added Pd—C (0.1 g, ~10% on charcoal) and reaction mixture was allowed to stir at RT under H$_2$ atmosphere using balloon for 2 h. Progress of reaction was monitored by TLC. After completion, reaction mixture was filtered through celite-bed. Removal of solvent under reduced pressure afforded crude tert-butyl 3-(2-aminoethyl)-3-phenylazetidine-1-carboxylate (0.14 g, 76%) which was used in the next step without purification.

Step-8: Synthesis of tert-butyl 3-(2-(N-(tert-butoxycarbonyl)sulfamoylamino)ethyl)-3-phenylazetidine-1-carboxylate: To a solution of tert-butyl 3-(2-aminoethyl)-3-phenylazetidine-1-carboxylate (0.6 g, 2.67 mmol, 1 eq) in dichloromethane (50 mL) were added N-(tert-butoxycarbonyl)-N-[4-(dimethylazaniumylidene)-1,4-dihydropyridin-1ylsulfonyl]azanide (0.98 g, 4 mmol, 1.5 eq) and N,N-diisopropylethylamine (0.76 mL, 5.34 mmol, 2 eq) and the reaction mixture was allowed to stir at RT for 16 h. After 16 h, reaction mixture was concentrated under reduced pressure to get crude which was purified by Combi-Flash using ethyl acetate-hexane system as eluent to afford tert-butyl 3-(2-(N-(tert-butoxycarbonyl)sulfamoylamino)ethyl)-3-phenylazetidine-1-carboxylate (0.4 g, 40%).

Step-9: Synthesis of 3-(2-(sulfamoylamino)ethyl)-3-phenylazetidine trifluoroacetate: To a solution of tert-butyl 3-(2-(N-(tert-butoxycarbonyl)sulfamoylamino)ethyl)-3-phenylazetidine-1-carboxylate (0.4 g, 0.87 mmol, 1 eq) in DCM (10 mL) was added TFA (4 mL) and the mixture was allowed to stir at RT for 1 h. Progress of reaction was monitored by TLC. After completion, reaction mixture was concentrated under reduced pressure to afford crude which was triturated with diethyl ether to afford 3-(2-(sulfamoylamino)ethyl)-3-phenylazetidine trifluoroacetate (0.3 g, 92%).

Step-10: Synthesis of 4-3-(2-(sulfamoylamino)ethyl)-3-phenylazetidin-1-yl-6,7-dimethoxyquinazoline: A mixture of 4-chloro-6,7-dimethoxyquinazoline (36 mg, 0.16 mmol, 1.2 eq), 3-(2-(sulfamoylamino)ethyl)-3-phenylazetidine trifluoroacetate (50 mg, 0.13 mmol, 1.0 eq) and DIPEA (0.05 mL, 0.27 mmol, 2.0 eq) in DMF (1 mL) was allowed to stir at 80° C. for 3 h. Progress of reaction was monitored by TLC. After completion, reaction mixture was concentrated under reduced pressure to get residue which was purified by reversed phase HPLC to afford 4-3-(2-(sulfamoylamino)ethyl)-3-phenylazetidin-1-yl-6,7-dimethoxyquinazoline (18 mg, 30%). LCMS: 444 [M+1]$^+$; $^1$HNMR (400 MHz, DMSO-d6) δ ppm 8.61 (s, 1H), 7.45-7.25 (m, 6H), 7.19 (s, 1H), 6.45 (brs, 3H), 4.85 (brs, 4H), 3.99 (s, 3H), 3.97 (s, 3H), 2.80-2.60 (m, 2H), 2.30-2.20 (m, 2H).

Example-59: Synthesis of 2-(1-(5-methylpyrrolo[1,2-f][1,2,4]triazin-4-yl)azetidin-3-yl)ethylboronic acid, (Compound 1.59)

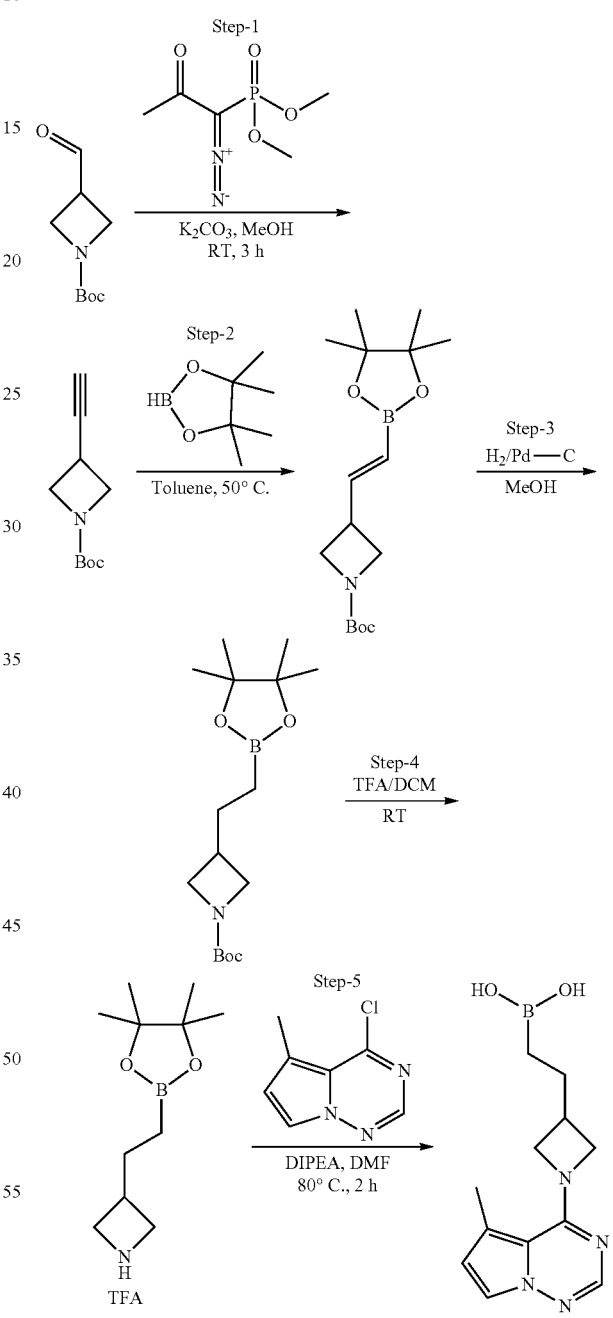

Step 1: Synthesis of tert-butyl 3-ethynylazetidine-1-carboxylate: To a solution of tert-butyl 3-formylazetidine-1-carboxylate (0.6 g, 3.24 mmol, 1 eq) in methanol (15 mL) were added potassium carbonate (0.9 g, 6.478 mmol, 2 eq) and dimethyl 1-diazo-2-oxopropylphosphonate (0.684 g, 3.564 mmol, 1.1 eq) and the reaction mixture to stir at RT for 2 h. Progress of reaction is monitored by ¹H NMR. After completion, reaction mixture was diluted with water (100 mL) and extracted with ethyl acetate (3×100 mL). Combined organic layer was washed with brine (150 mL) and dried over anhydrous sodium sulfate. Removal of solvent under reduced pressure afforded tert-butyl 3-ethynylazetidine-1-carboxylate (0.5 g, crude) which was used in the next step without purification.

Step 2: Synthesis of (E)-tert-butyl 3-(2-(4,4,5,5-tetramethyl-1,3,2-dioxaborolan-2-yl)vinyl)azetidine-1-carboxylate: A solution of tert-butyl 3-ethynylazetidine-1-carboxylate (0.45 g, 2.483 mmol, 1 eq) in toluene (10 mL) was oxygenated by purging nitrogen for 10 minutes. To the mixture was then added carbonylchlorohydrotris(triphenylphosphine)ruthenium (0.14 g, 0.149 mmol, 0.06 eq) and 4,4,5,5-tetramethyl-1,3,2-dioxaborolane (0.9 mL, 6.208 mmol, 2.5 eq). Reaction mixture was allowed to stir at 50° C. overnight. Progress of reaction is monitored by TLC. After completion, reaction mixture was diluted with water (30 mL) and extracted with ethyl acetate (3×20 mL). Combined organic layer was washed with brine (150 mL) and dried over anhydrous sodium sulfate. Removal of solvent under reduced pressure afforded crude which was purified by Combi-Flash to afford (E)-tert-butyl 3-(2-(4,4,5,5-tetramethyl-1,3,2-dioxaborolan-2-yl)vinyl)azetidine-1-carboxylate (0.6 g, 78%).

Step-3: Synthesis of tert-butyl 3-(2-(4,4,5,5-tetramethyl-1,3,2-dioxaborolan-2-yl)ethyl)azetidine-1-carboxylate: To a solution of (E)-tert-butyl 3-(2-(4,4,5,5-tetramethyl-1,3,2-dioxaborolan-2-yl)vinyl)azetidine-1-carboxylate (0.5 g, 1.62 mmol, 1 eq) in methanol (25 mL) was added Pd—C (0.225 g) and the reaction mixture was allowed to stir at RT under $H_2$ atmosphere using balloon for 2 h. Progress of reaction was monitored by ¹H NMR. After completion, reaction mixture was filtered through celite-bed. Removal of solvent under reduced pressure afforded tert-butyl 3-(2-(4,4,5,5-tetramethyl-1,3,2-dioxaborolan-2-yl)ethyl)azetidine-1-carboxylate (0.45 g, crude) which was used in the next step without purification.

Step-4: Synthesis of 3-(2-(4,4,5,5-tetramethyl-1,3,2-dioxaborolan-2-yl)ethyl)azetidine: To a solution of tert-butyl 3-(2-(4,4,5,5-tetramethyl-1,3,2-dioxaborolan-2-yl)ethyl)azetidine-1-carboxylate (0.185 g, 0.595 mmol, 1 eq) in DCM (5 mL) was added TFA (1.5 mL) and the mixture was allowed to stir at RT for 1 h. Progress of reaction was monitored by ¹H NMR. After completion, reaction mixture was concentrated under reduced pressure to afford crude which was triturated with diethyl ether to afford 3-(2-(4,4,5,5-tetramethyl-1,3,2-dioxaborolan-2-yl)ethyl)azetidine (0.183 g) as TFA salt.

Step-5: Synthesis of 2-(1-(5-methylpyrrolo[1,2-f][1,2,4]triazin-4-yl)azetidin-3-yl)ethylboronic acid: A suspension of 4-chloro-5-methylpyrrolo[1,2-f][1,2,4]triazine (0.1 g, 0.597 mmol, 1.0 eq), 3-(2-(4,4,5,5-tetramethyl-1,3,2-dioxaborolan-2-yl)ethyl)azetidine (0.183 g, 0.97 mmol, 1.0 eq) and DIPEA (0.2 mL, 1.194 mmol, 2 eq) in DMF (1 mL) was allowed to stir at 80° C. for 2 h. Progress of reaction was monitored by TLC. After completion, reaction mixture was concentrated under reduced pressure to afford crude product which was purified by reversed phase HPLC to afford 2-(1-(5-methylpyrrolo[1,2-f][1,2,4]triazin-4-yl)azetidin-3-yl)ethylboronic acid (5 mg, 3%). LCMS: 261 [M+1]⁺; ¹H NMR (400 MHz, DMSO-$d_6$) δ ppm 7.76 (s, 1H), 7.59 (s, 1H), 7.48 s, 2H), 6.45 (s, 1H), 4.43-4.35 (m, 2H), 3.96-3.85 (s, 2H), 2.50-2.45 (m, 1H), 2.41 (s, 3H), 1.70-1.56 (m, 2H), 0.60-0.50 (m, 2H).

Example-60: Synthesis of 3-(1-(6,7-dimethoxyquinazolin-4-yl)azetidin-3-yl)propylboronic acid, (Compound 1.60)

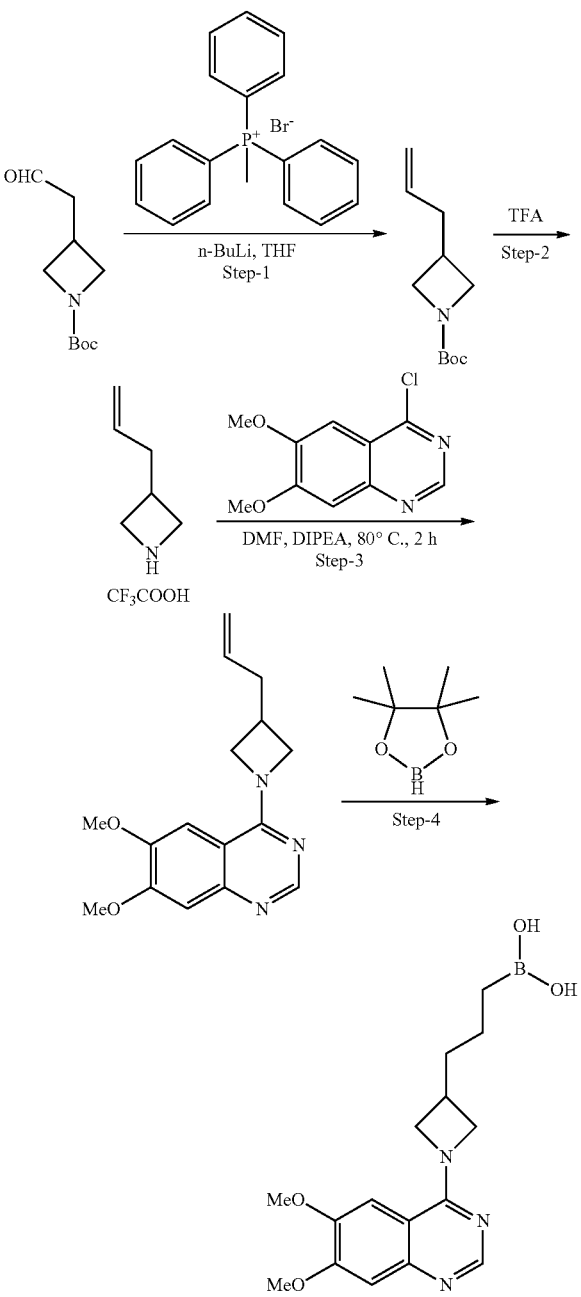

Step-1: Synthesis of tert-butyl 3-allylazetidine-1-carboxylate: To a solution of methyltriphenylphosphonium bromide (1.6 g, 4.4 mmol, 3.0 eq) in THF (2 mL) was added n-butyllithium (2.5 mol/L solution in n-hexane, 3 mL, 5 eq) at 0° C. under a nitrogen atmosphere, and the mixture was stirred at the same temperature for 10 minutes. To the reaction mixture a solution of tert-butyl 3-(2-oxoethyl)azetidine-1-carboxylate (200 mg, 1.00 mmol, 1.0 eq) in THF (3 mL) was added at the same temperature, and the mixture was stirred overnight at room temperature. To the reaction solution was added an aqueous ammonium chloride solution (10 mL), and the mixture was extracted with ethyl acetate (3×30 mL). The combined organic layer was washed with water and brine, dried over sodium sulfate, and concentrated. The residue was purified by normal phase silica gel column chromatography (eluent: ethyl acetate/n-hexane) to obtain tert-butyl 3-allylazetidine-1-carboxylate (80 mg, 41%).

Step-2: Synthesis of 3-allylazetidine 2,2,2-trifluoroacetate: To a solution of tert-butyl 3-ethenylazetidine-1-carboxylate (70 mg, 0.36 mmol, 1.0 eq) in methylene chloride (4 mL) was added 0.5 mL TFA at 0° C., and the reaction mixture was stirred at RT for 48 h. The reaction solution was concentrated and triturated with ether-hexane to get the semisolid (65 mg, 86%) which was used as such for next step without purification. $^1$H-NMR (CDCl$_3$): δ ppm 9.56 (2H, d), 5.65-5.68 (1H, m), 5.15-5.20 (2H, m), 4.1 (2H, s), 3.75 (2H, s), 3.05-3.15 (1H, m), 2.2 (2H, d)

Step-3: Synthesis of 4-(3-allylazetidin-1-yl)-6,7-dimethoxyquinazoline: To a solution of 3-allylazetidine 2,2,2-trifluoroacetate (60 mg, 0.31 mmol, 1.0 eq) in DMF (2 mL) were added 4-chloro-6,7-dimethoxyquinazoline (70 mg. 0.31 mmol, 1.0 eq) and N,N-diisopropylethylamine (0.120 g, 0.93 mmol, 3.0 eq) and the reaction mixture was allowed to stir at 80° C. for 2 h. Reaction mixture was diluted with water (10 mL) and extracted with ethyl acetate (3×30 mL). Combined organic layer was washed with brine (20 mL), dried over anhydrous sodium sulfate and concentrated under vacuum to get the residue which was purified by silica gel column chromatography (Eluent: ethyl acetate/n-hexane) to obtain the 4-(3-allylazetidin-1-yl)-6,7-dimethoxyquinazoline (80 mg, 90%). LCMS: 286[M+1]$^+$ Step-4: Synthesis of 6,7-dimethoxy-4-(3-(3-(4,4,5,5-tetramethyl-1,3,2-dioxaborolan-2-yl)propyl)azetidin-1-yl) quinazoline: To a mixture of bis(1,5-cyclooctadiene)diiridium(I) dichloride (6 mg, 4 mol %) and 1,2-bis(diphenylphosphino)ethane (6 mg, 8 mol %) was added DCM (2 mL) under nitrogen. The mixture was allowed to stir at RT for 1 h. To this reaction mixture was cooled to 0° C. and added solution of 4-(3-allylazetidin-1-yl)-6,7-dimethoxyquinazoline (0.060 g, 0.21 mmol, 1.0 eq) dissolved in DCM (1 mL) and pinacolborane (0.040 g, 0.31 mmol, 1.5 eq). The reaction was allowed to stir at RT for overnight. Progress of reaction was monitored by LCMS. The reaction was quenched by addition of water (10 mL) and extracted with DCM (3×25 mL). Combined organic layer was washed with brine (30 mL), dried over anhydrous sodium sulfate and concentrated under vacuum to get the residue which was purified by RP-column chromatography to obtain the 6,7-dimethoxy-4-(3-(3-(4,4,5,5-tetramethyl-1,3,2-dioxaborolan-2-yl)propyl)azetidin-1-yl)quinazoline (10 mg, 12%). LCMS: 414[M+1]$^+$; $^1$H NMR (400 MHz, DMSO-d$_6$) δ ppm 8.37 (s, 2H), 7.20 (br. s., 1H), 7.12 (br. s., 1H), 6.54 (br. s., 1H), 4.60 (s, 2H), 4.44 (br. s., 1H), 4.12 (s, 2H), 3.42 (d, J=5.70 Hz, 1H), 1.67 (br. s., 2H), 1.46 (d, J=8.33 Hz, 2H).

Example-61: Synthesis 2-ethyl-6,7-dimethoxy-4-[3-[2-(sulfamoylamino)ethyl]azetidin-1-yl]quinazoline, (Compound 1.61)

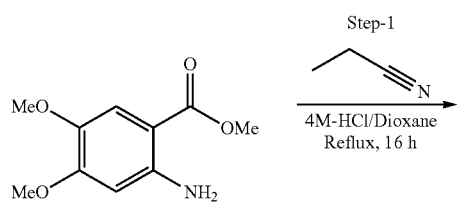

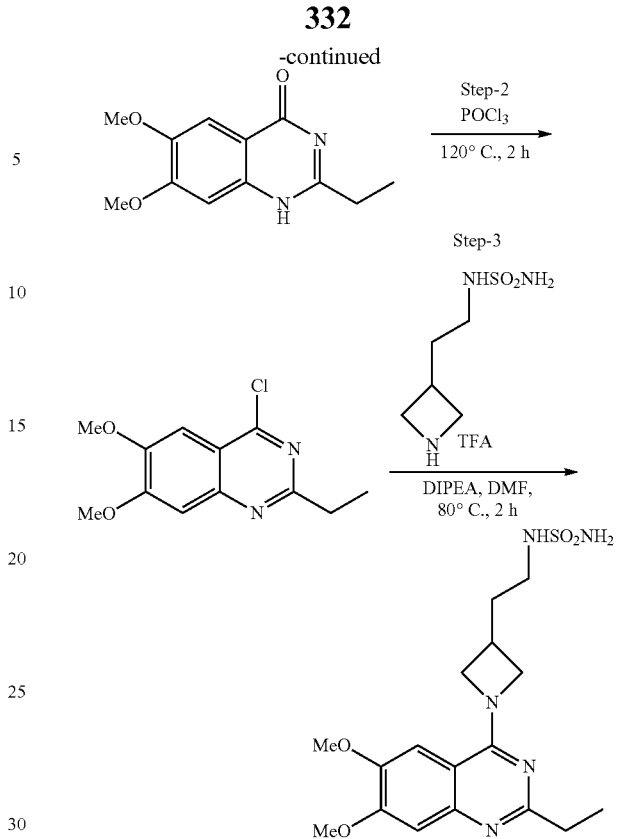

Step-1: Synthesis of 2-ethyl-6,7-dimethoxy-1H-quinazolin-4-one: A mixture of methyl 2-amino-4,5-dimethoxybenzoate (800 mg, 3.79 mmol, 1 eq) and propanenitrile (229 mg, 4.17 mmol, 1.1 eq) in 4M HCl in dioxane (10 mL) was sonicated for 30 minutes and then heated at 100° C. for 12 h. Progress of reaction was monitored by TLC. After completion, reaction mixture was cooled to RT, poured into ice-cold water and stirred for 15 minutes. The solid obtained was filtered and dried under vacuum to afford 2-ethyl-6,7-dimethoxy-1H-quinazolin-4-one (200 mg, 37%). LCMS: 234.2 [M+1]$^+$ Step-2: Synthesis of 4-chloro-2-ethyl-6,7-dimethoxy-quinazolin: A mixture of 2-ethyl-6,7-dimethoxy-1H-quinazolin-4-one (200 mg, 0.85 mmol, 1 eq) in POCl$_3$ (0.4 mL) was stirred at 120° C. for 2 h. Progress of reaction was monitored by TLC. After completion, reaction mixture was cooled to RT, poured into ice-cold water (20 mL) and stirred for 15 minutes. Solid was filtered and dried under vacuum to afford 4-chloro-2-ethyl-6,7-dimethoxy-quinazolin (52 mg, 23%). LCMS: 253.2 M+1]$^+$ Step-3: Synthesis of 2-ethyl-6,7-dimethoxy-4-[3-[2-(sulfamoylamino)ethyl]azetidin-1-yl]quinazoline: A suspension of 4-chloro-2-ethyl-6,7-dimethoxy-quinazolin (50 mg, 0.197 mmol, 1.0 eq), N-[2-(azetidin-3-yl)ethyl]sulfuric diamide triflorocetic acid (57 mg, 0.197 mmol, 1.0 eq) and N,N diisopropylethylamine (60 mg, 0.39 mmol, 2.0 eq) in DMF (2 mL) was allowed to stir at 80° C. for 2 h. Progress of reaction was monitored by TLC. Reaction mixture was cooled to RT, concentrated under vacuum to get semi-solid residue which was triturated with ether, ethyl acetate and then with pentane to afford crude solid which was purified by RP-HPLC to afford 2-ethyl-6,7-dimethoxy-4-[3-[2-(sulfamoylamino)ethyl]azetidin-1-yl]quinazoline (33 mg, 41%). LCMS: 397 [M+1]$^+$; $^1$H NMR (400 MHz, DMSO-d$_6$) δ ppm 7.19 (s, 1H), 7.12 (s, 1H), 6.56 (brs, 1H), 6.53 (s, 2H), 4.67-4.52 (m, 2H), 4.23-4.11 (m, 2H), 3.87 (s, 3H), 3.85 (s, 3H), 2.99-2.80 (m, 3H), 2.67 (t, 2H), 2.90-2.83 (m, 2H), 1.22 (t, 3H).

Example-62: Synthesis 4-(6-N-sulfamoylamino)-2-azaspiro[3.3]heptan-2-yl)-5-methylpyrrolo[1,2-f][1,2,4]triazine, (Compound 1.62)

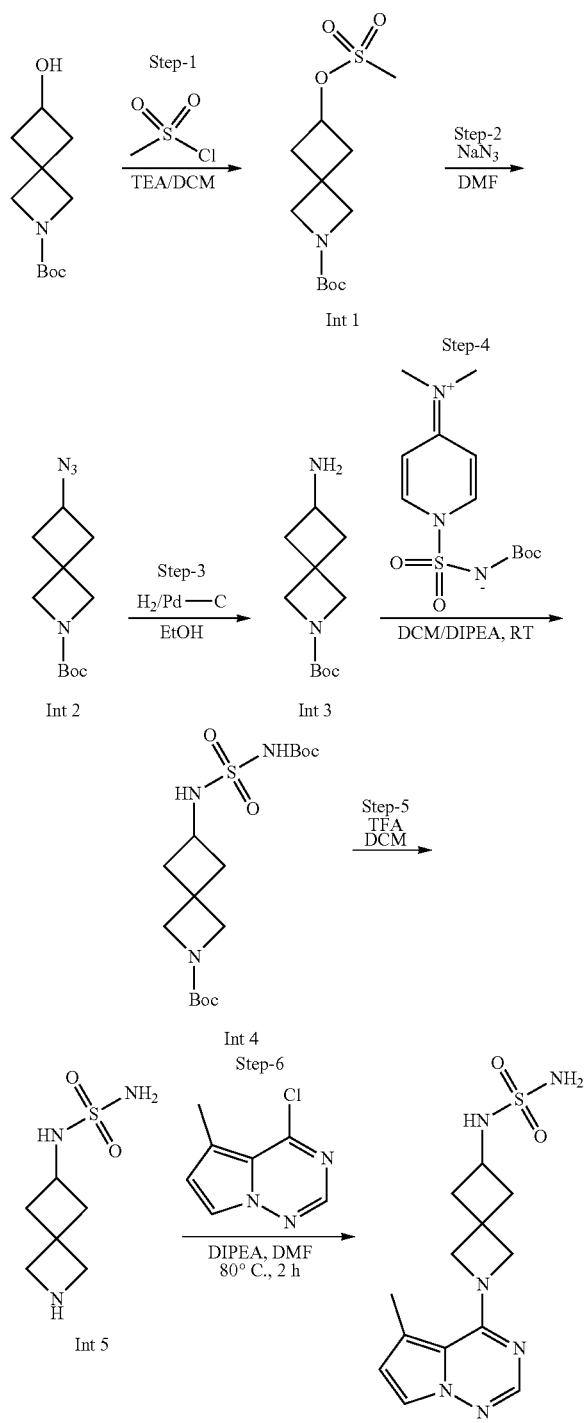

Step 1: Synthesis of tert-butyl 6-(methylsulfonyloxy)-2-azaspiro[3.3]heptane-2-carboxylate: To a solution of tert-butyl 6-hydroxy-2-azaspiro[3.3]heptane-2-carboxylate (1.2 g, 5.63 mmol, 1 eq) in DCM (50 mL) was added triethylamine (1.7 g, 16.89 mmol, 3 eq) and the reaction mixture was allowed to stir at 0° C. for 5 minutes. To the mixture was added methane sulfonyl chloride (1.3 g, 11.26 mmol, 2 eq) and the reaction mixture to stir at 0° C. for 10 minutes followed by stirring at RT for 2 h. Progress of reaction is monitored by $^1$H NMR. After completion, reaction mixture was diluted with water (100 mL) and extracted with ethyl acetate (3×100 mL). Combined organic layer was washed with brine (150 mL) and dried over anhydrous sodium sulfate. Removal of solvent under reduced pressure afforded tert-butyl 6-(methylsulfonyloxy)-2-azaspiro[3.3]heptane-2-carboxylate (1.3 g, Crude) which was used in the next step without purification.

Step-2: Synthesis of tert-butyl 6-azido-2-azaspiro[3.3]heptane-2-carboxylate: To a solution of tert-butyl 6-(methylsulfonyloxy)-2-azaspiro[3.3]heptane-2-carboxylate (1.5 g, 5.15 mmol, 1 eq) in DMF (10 mL), was added NaN$_3$ (1 g, 15.46 mmol, 3 eq) and the reaction mixture was allowed to stir at 70° C. for 16 h. Progress of reaction is monitored by $^1$H NMR. After completion, reaction mixture was diluted with water (100 mL) and extracted with diethyl ether (3×150 mL). Combined organic layer was washed with water (2×100 mL) followed by brine (150 mL) and dried over anhydrous sodium sulfate. Removal of solvent under reduced pressure afforded tert-butyl 6-azido-2-azaspiro[3.3]heptane-2-carboxylate (1.2 g, Crude) which was used in the next step without purification.

Step-3: Synthesis of tert-butyl 6-amino-2-azaspiro[3.3]heptane-2-carboxylate: To a solution of tert-butyl 6-azido-2-azaspiro[3.3]heptane-2-carboxylate (1.2 g, 5.04 mmol, 1 eq) in ethanol (50 mL) was added Pd—C (0.6 g) and the reaction mixture was allowed to stir at RT under H$_2$ atmosphere using balloon for 3 h. Progress of reaction was monitored by TLC. After completion, reaction mixture was filtered through celite-bed. Removal of solvent under reduced pressure afforded crude tert-butyl 6-amino-2-azaspiro[3.3]heptane-2-carboxylate (1 g, Crude) which was used in the next step without purification.

Step-4: Synthesis of tert-butyl 6-(N-(tert-butoxycarbonyl)sulfamoylamino)-2-azaspiro[3.3]heptane-2-carboxylate: To a solution of tert-butyl 6-amino-2-azaspiro[3.3]heptane-2-carboxylate (1 g, 4.71 mmol, 1 eq) in dichloromethane (30 mL) were added N-(tert-butoxycarbonyl)-N-[4-(dimethylazaniumylidene)-1,4-dihydropyridin-1ylsulfonyl]azanide (2.12 g, 7.07 mmol, 1.5 eq) and N,N-diisopropylethylamine (1.64 mL, 9.4 mmol, 2 eq) and the reaction mixture was allowed to stir at RT for 48 h. Progress of reaction was monitored by TLC. After completion, reaction mixture was concentrated under reduced pressure to get crude which was purified by Combi-Flash using ethyl acetate-hexane system as eluent to afford tert-butyl 6-(N-(tert-butoxycarbonyl)sulfamoylamino)-2-azaspiro[3.3]heptane-2-carboxylate (0.6 g, 32.5%).

Step-5: Synthesis of (6-N-sulfamoylamino)-2-azaspiro[3.3]heptane: To a solution of tert-butyl 6-(N-(tert-butoxycarbonyl)sulfamoylamino)-2-azaspiro[3.3]heptane-2-carboxylate (0.6 g, 1.5 mmol, 1 eq) in DCM (10 mL) was added TFA (2 mL) and the mixture was allowed to stir at RT for 1 h. Progress of reaction was monitored by $^1$H NMR. After completion, reaction mixture was concentrated under reduced pressure to afford crude which was triturated with diethyl ether to afford (6-N-sulfamoylamino)-2-azaspiro[3.3]heptane (0.5 g) as TFA salt.

Step-6: Synthesis of 4-(6-N-sulfamoylamino)-2-azaspiro[3.3]heptan-2-yl)-5-methylpyrrolo[1,2-f][1,2,4]triazine: A suspension of 4-chloro-5-methylpyrrolo[1,2-f][1,2,4]triazine (90 mg, 0.54 mmol, 1.0 eq), (6-N-sulfamoylamino)-2-azaspiro[3.3]heptane (162 mg, 0.54 mmol, 1.0 eq) and DIPEA (0.18 mL, 1.07 mmol, 2 eq) in DMF (0.9 mL) was allowed to stir at 80° C. for 2 h. Progress of reaction was monitored by TLC. After completion, reaction mixture was concentrated under reduced pressure to afford crude product which was purified by reversed phase HPLC to afford 4-(6-N-sulfamoylamino)-2-azaspiro[3.3]heptan-2-yl)-5-methylpyrrolo[1,2-f][1,2,4]triazine (43 mg, 28.66%). LCMS: 323 [M+1]+; 1H NMR (400 MHz, DMSO-$d_6$) δ ppm 7.76 (s, 1H), 7.59 (d, 1H), 6.85 (d, 1H), 6.59 (brs, 1H), 6.52 (s, 2H), 4.42 (brs, 2H), 4.25 (brs, 2H), 3.67-3.60 (m, 1H), 2.60-2.42 (m, 2H), 2.40 (s, 3H), 2.23-2.14 (m, 2H).

Example-63: Synthesis 2-(6,7-dimethoxyquinazolin-4-yl)-N-hydroxy-2-azaspiro[3.3]heptane-6-carboxamide, (Compound 1.63)

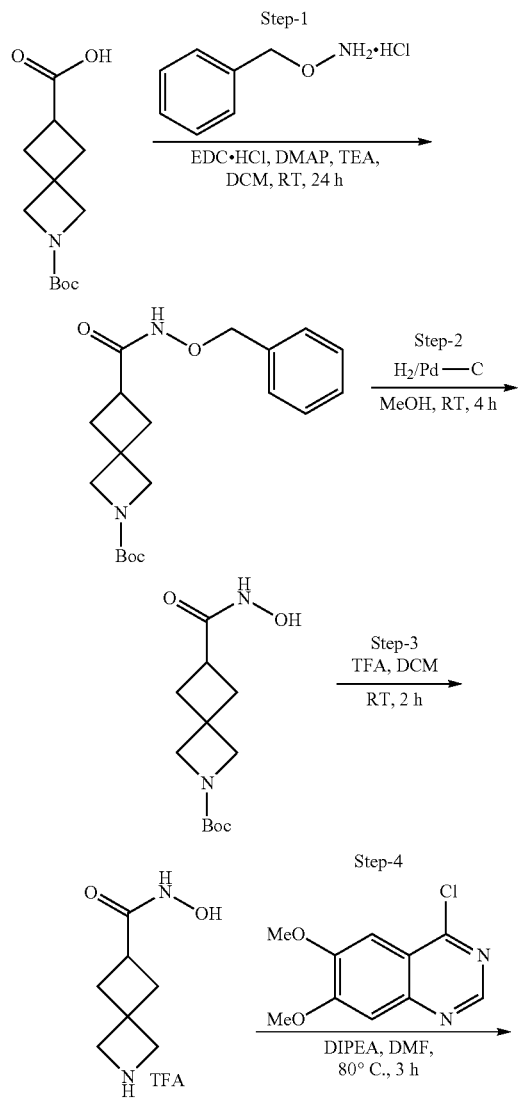

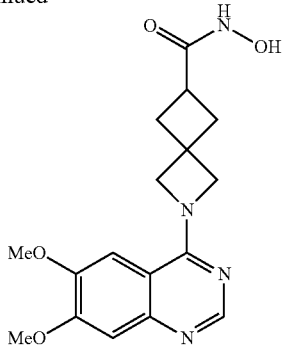

Step-1: Synthesis tert-butyl 6-(benzyloxycarbamoyl)-2-azaspiro[3.3]heptane-2-carboxylate: To a suspension of 2-(tert-butoxycarbonyl)-2-azaspiro[3.3]heptane-6-carboxylic acid (250 mg, 1.03 mmol, 1 eq), O-benzylhydroxylamine hydrochloride (180 mg, 1.13 mmol, 1.1 eq) in DCM (15 mL) were added EDC·HCl (0.23 g, 1.23 mmol, 1.2 eq), DMAP (0.19 g, 1.54 mmol, 1.5 eq) and triethylamine (0.43 mL, 3 mmol, 3 eq) and the resulting mixture was allowed to stir at RT for 24 h. Progress of reaction was monitored by TLC. After completion, reaction mixture was concentrated under reduced pressure to get residue which was diluted with cold water (50 mL) and extracted with ethyl acetate (3×100 mL). Combined organic layer was washed with brine (3×50 mL) and dried over anhydrous sodium sulfate. Removal of solvent under reduced pressure to afforded tert-butyl 6-(benzyloxycarbamoyl)-2-azaspiro[3.3]heptane-2-carboxylate (245 mg, 68%) which was used in the next step without purification.

Step-2: Synthesis of tert-butyl 6-(hydroxycarbamoyl)-2-azaspiro[3.3]heptane-2-carboxylate: To a solution of tert-butyl 6-(benzyloxycarbamoyl)-2-azaspiro[3.3]heptane-2-carboxylate (245 mg, 0.7 mmol, 1 eq) in MeOH (10 mL) was added Pd—C (70 mg, 10% on charcoal) and the mixture was allowed to stir at RT for 4 h under hydrogen atmosphere. Progress of reaction was monitored by TLC. After completion, reaction mixture was filtered through celite-bed and bed was washed with MeOH (10 mL). Filtrate was concentrated under reduced pressure to afford tert-butyl 6-(hydroxycarbamoyl)-2-azaspiro[3.3]heptane-2-carboxylate (0.15 g, 85%) which was used in the next step without purification.

Step-3: Synthesis of N-hydroxy-2-azaspiro[3.3]heptane-6-carboxamide trifluoroacetate: To a solution of tert-butyl 6-(hydroxycarbamoyl)-2-azaspiro[3.3]heptane-2-carboxylate (150 mg, 0.58 mmol, 1 eq) in DCM (4 mL) was added TFA (1 mL) and the resulting mixture was allowed to stir at RT for 2 h. Progress of reaction was monitored by TLC. After completion, reaction mixture was concentrated under reduced pressure to afford crude which was triturated with diethyl ether to afford N-hydroxy-2-azaspiro[3.3]heptane-6-carboxamide trifluoroacetate (100 mg, 63%).

Step-4: Synthesis of 2-(6,7-dimethoxyquinazolin-4-yl)-N-hydroxy-2-azaspiro[3.3]heptane-6-carboxamide: A suspension of N-hydroxy-2-azaspiro[3.3]heptane-6-carboxamide trifluoroacetate (100 mg, 0.37 mmol, 1 eq), 4-chloro-6,7-dimethoxyquinazoline (100 mg, 0.44 mmol, 1.2 eq) and DIPEA (0.13 mL, 0.74 mmol, 2.0 eq) in DMF (1 mL) was allowed to stir at 80° C. for 3 h. Progress of reaction was monitored by TLC. After 3 h, reaction mixture was concentrated under reduced pressure to afford crude which was purified using RP-HPLC to afford 2-(6,7-dimethoxyquinazolin-4-yl)-N-hydroxy-2-azaspiro[3.3]heptane-6-carboxamide (9 mg, 7%). LCMS: 345 [M+1]+; 1H NMR (400 MHz, DMSO-d6) δ ppm 10.42 (brs, 1H), 8.82 (brs, 1H), 8.33 (s, 1H), 7.20 (s, 1H), 7.11 (s, 1H), 4.50 (brs, 2H), 4.41 (brs, 2H), 3.89 (s, 6H), 2.62-2.50 (m, 1H), 2.50-2.30 (m, 4H).

Example-64: Synthesis of 4-(3-(2-sulfamoylaminoethyl)azetidine-1-yl) quinazoline, (Compound 1.64)

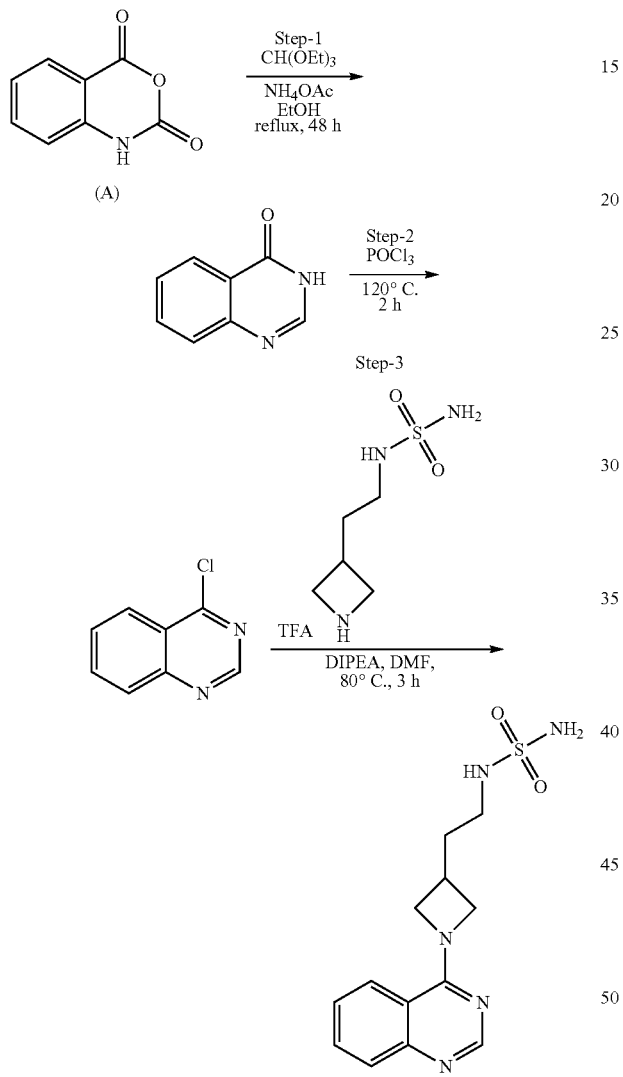

Step-1: Synthesis of quinazolin-4 (3H)-one: A mixture of 1H-benzo[d][1,3]oxazine-2,4-dione (1 g, 6.1 mmol, 1 eq), ammonium acetate (0.614 g, 7.9 mmol, 1.3 eq) and triethylorthoformate (1.63 mL, 9.7 mmol, 1.6 eq) in ethanol (10 mL) was allowed to stir at 90° C. for 48 h. Progress of reaction was monitored by TLC. Reaction mixture was cooled to RT; solid was filtered, washed with hexane and dried to quinazolin-4 (3H)-one (400 mg, 44%). LCMS: 147 [M+1]+.

Step-2: Synthesis of 4-chloroquinazoline: The stirred solution of quinazolin-4 (3H)-one (0.15 g, 1.02 mmol, 1 eq) in 1 mL of POCl3 was heated at 120° C. for 2 h. After completion reaction mixture was diluted with water (150 mL) and extracted using ethyl acetate (3×50 mL). Combined organic layer was washed with water (3×30 mL), dried over anhydrous sodium sulphate. Removal of solvent under reduced pressure afforded 4-chloroquinazoline (100 mg, 59%). LCMS: 165 [M+1]+.

Step-3: Synthesis of 4-(3-(2-sulfamoylaminoethyl)azetidine-1-yl) quinazoline: A suspension of 4-chloroquinazoline (70 mg, 0.40 mmol, 1.2 eq), 3-(2-sulfamoylaminoethyl) azetidine trifluoroacetate (100 mg, 0.34 mmol, 1.0 eq) and DIPEA (0.12 mL, 0.68 mmol, 2.0 eq) in DMF (1 mL) was allowed to stir at 80° C. for 3 h. Progress of reaction was monitored by TLC. After 3 h, reaction mixture was concentrated under reduced pressure to afford crude which was purified using reversed phase HPLC to afford 4-(3-(2-sulfamoylaminoethyl)azetidine-1-yl) quinazoline (33 mg, 31%). LCMS: 308 [M+1]+; 1H NMR (400 MHz, DMSO-d6) δ ppm 8.44 (s, 1H), 7.95 (d, 1H), 7.76 (t, 1H), 7.68 (d, 1H), 7.46 (t, 1H), 6.58 (brs, 1H), 6.55 (brs, 2H), 4.55 (brs, 2H), 4.18 (brs, 2H), 3.00-2.80 (m, 3H), 1.90-1.80 (m, 2H).

Example-65: Synthesis 3-(1-(6,7-dimethoxyquinazolin-4-yl)azetidin-3-yl)propane-1-sulfonic acid, (Compound 1.65)

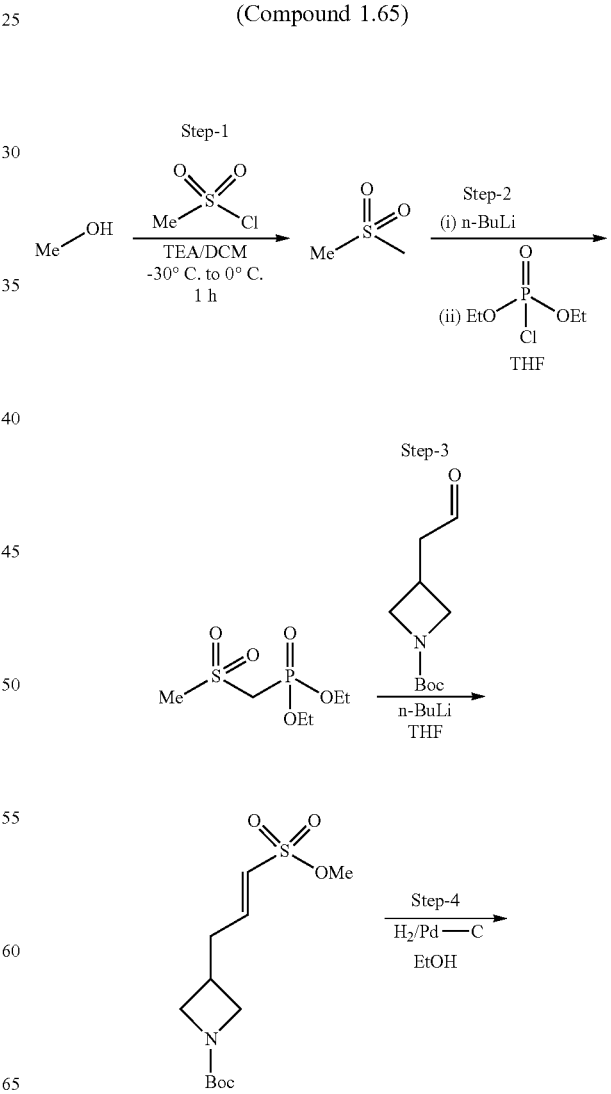

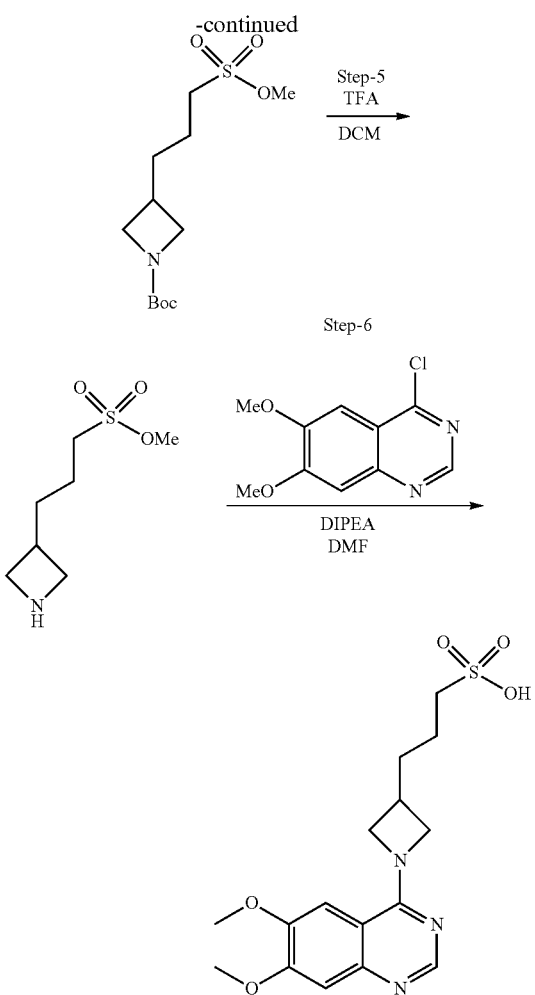

Step-1: Synthesis of methyl methanesulfonate: To a solution of methanol (5 g, S156 mmol, 1 eq) in DCM (100 mL) was added triethylamine (42.5 mL, 312 mmol, 2 eq) and the reaction mixture was allowed to stir at −30° C. for 5 minutes. To the mixture was added methane sulfonyl chloride (13.2 mL, 171 mmol, 1.1 eq) and the reaction mixture allowed to stir at 0° C. for 1 h. Progress of reaction is monitored by $^1$H NMR. After completion, reaction mixture was diluted with water (100 mL) and extracted with ethyl acetate (3×100 mL). Combined organic layer was washed with aq. NaHCO$_3$ (150 mL) followed by brine (150 mL) and dried over anhydrous sodium sulfate. Removal of solvent under reduced pressure afforded methyl methanesulfonate (5.5 g, Crude) which was used in the next step without purification.

Step-2: Synthesis of methyl(diethoxyphosphoryl)methanesulfonate): To a solution of methyl methanesulfonate (2 g, 18.18 mmol, 1 eq) in THF (20 ml) at −78° C. was added 2.5M n-BuLi (14.5 ml, 36.36 mmol, 2 eq) dropwise under nitrogen and the reaction mixture was stirred at the same temperature for 1 h. To the mixture was added a solution of diethyl chlorophosphate (1.4 ml, 9 mmol, 0.5 eq) in THF (2 ml) dropwise. Reaction mixture was warmed to 0° C. and stirred at the same temperature for 1 h. Progress of reaction was monitored by TLC. After completion, reaction mixture was diluted with saturated aq. NH$_4$Cl (100 mL) and extracted with ethyl acetate (3×100 mL). Combined organic layer was washed with water (2×100 mL) followed by brine (150 mL) and dried over anhydrous sodium sulfate. Removal of solvent under reduced pressure gave crude which was purified by Combi-Flash using ethyl acetate-hexane system as eluent to afford methyl(diethoxyphosphoryl)methanesulfonate) (1 g, 22%).

Step-3: Synthesis of (E)-tert-butyl 3-(3-(methoxysulfonyl)allyl)azetidine-1-carboxylate: To a solution of methyl (diethoxyphosphoryl)methanesulfonate) (0.5 g, 2.03 mmol, 1 eq) in THF (10 ml) at −78° C. was added 2.5M n-BuLi (1.7 ml, 4.2 mmol, 2.1 eq) dropwise under nitrogen and the reaction mixture was stirred at the same temperature for 15 minutes. To the reaction mixture was then added a solution of tert-butyl 3-(2-oxoethyl)azetidine-1-carboxylate (0.404 g, 2.03 mmol, 1 eq) in THF (2 ml) dropwise. Reaction mixture was warmed to RT and stirred for 16 h. Progress of reaction was monitored by TLC. After completion, reaction mixture was diluted with saturated aq. NH$_4$Cl (100 mL) and extracted with ethyl acetate (3×100 mL). Combined organic layer was washed with water (2×100 mL) followed by brine (150 mL) and dried over anhydrous sodium sulfate. Removal of solvent under reduced pressure gave crude which was purified by Combi-Flash using ethyl acetate-hexane system as eluent to afford (E)-tert-butyl 3-(3-(methoxysulfonyl)allyl)azetidine-1-carboxylate (0.1 g, 17%).

Step-4: Synthesis of tert-butyl 3-(3-(methoxysulfonyl)propyl)azetidine-1-carboxylate: To a solution of (E)-tert-butyl 3-(3-(methoxysulfonyl)allyl)azetidine-1-carboxylate (0.1 g, 0.34 mmol, 1 eq) in ethanol (10 mL) was added Pd/C (0.05 g) and the reaction mixture was allowed to stir at RT under H$_2$ atmosphere using balloon for 3 h. Progress of reaction was monitored by TLC. After completion, reaction mixture was filtered through celite-bed. Removal of solvent under reduced pressure afforded crude tert-butyl 3-(3-(methoxysulfonyl)propyl)azetidine-1-carboxylate (0.09 g, Crude) which was used in the next step without purification.

Step-5: Synthesis of methyl 3-(azetidin-3-yl)propane-1-sulfonate: To a solution of tert-butyl 3-(3-(methoxysulfonyl)propyl)azetidine-1-carboxylate (0.09 g, 0.306 mmol, 1 eq) in DCM (2 mL) was added TFA (1 mL) and the mixture was allowed to stir at RT for 1 h. Progress of reaction was monitored by $^1$H NMR. After completion, reaction mixture was concentrated under reduced pressure to afford crude which was triturated with diethyl ether to afford methyl 3-(azetidin-3-yl)propane-1-sulfonate (0.09 g, Crude) as TFA salt.

Step-6: Synthesis 3-(1-(6,7-dimethoxyquinazolin-4-yl)azetidin-3-yl)propane-1-sulfonic acid: A suspension of methyl 3-(azetidin-3-yl)propane-1-sulfonate (90 mg, 0.29 mmol, 1 eq), 4-chloro-6,7-dimethoxyquinazoline (80 mg, 0.35 mmol, 1.2 eq) and DIPEA (0.1 mL, 0.59 mmol, 2.0 eq) in DMF (1 mL) was allowed to stir at 80° C. for 2 h. Progress of reaction was monitored by TLC. After completion, reaction mixture was concentrated under reduced pressure to get residue which was purified by RP-HPLC to afford 3-(1-(6,7-dimethoxyquinazolin-4-yl)azetidin-3-yl)propane-1-sulfonic acid (0.022 g, 21%). LCMS: 368 [M+1]$^+$; $^1$H NMR (400 MHz, DMSO-d6) δ ppm 8.31 (s, 1H), 7.22 (s, 1H), 7.11 (s, 1H), 4.62-4.48 (m, 2H), 4.12-4.02 (m, 2H), 3.90 (s, 3H), 3.89 (s, 3H), 2.82-2.70 (m, 1H), 2.50-2.40 (m, 2H), 1.80-1.58 (m, 4H).

Example-66: Synthesis 4-(3-(2-sulfamoylamino-ethyl)azetidine-1-yl)-6-fluoro-7-methoxy quinazoline, (Compound 1.66)

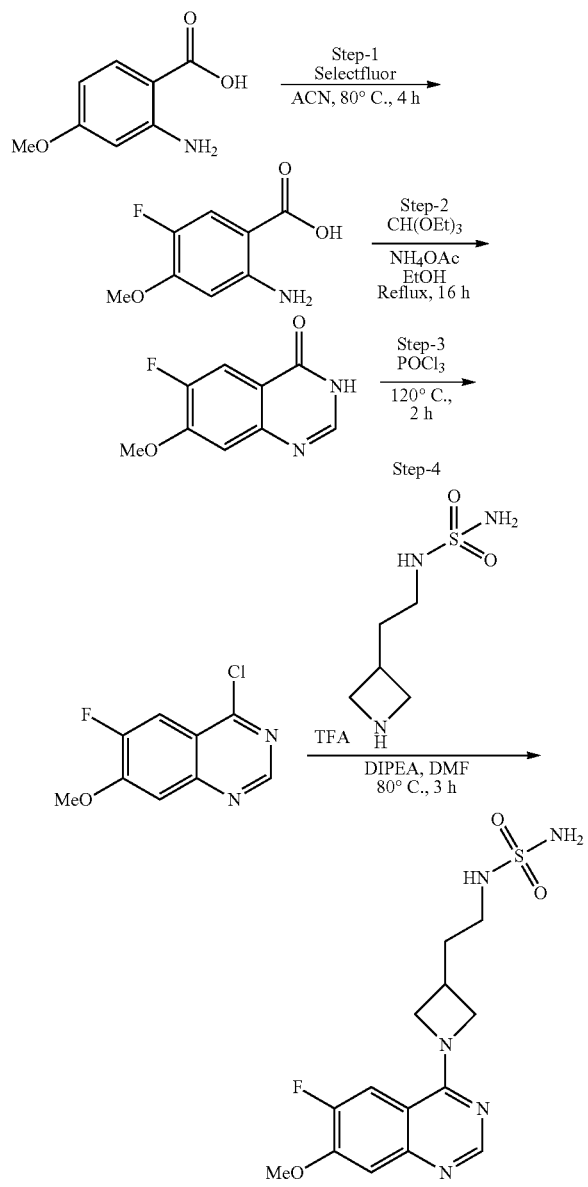

Step-1: Synthesis of 2-amino-5-fluoro-4-methoxybenzoic acid: A mixture of 2-amino-4-methoxybenzoic acid (1 g, 5.9 mmol, 1 eq) and selectfluor (2 g, 5.9 mmol, 1 eq) in acetonitrile (50 mL) was allowed to stir at 80° C. for 4 h. Progress of reaction was monitored by TLC. After 4 h, water (200 mL) was added into reaction mixture and was extracted using ethyl acetate (3×50 mL). The combined organic layer was washed with brine (50 mL) and dried over anhydrous sodium sulphate. Removal of solvent under reduced pressure gave crude which was purified by Combi-Flash to afford 2-amino-5-fluoro-4-methoxybenzoic acid (150 mg, 13%). LCMS: 186 [M+1]+.

Step-2: Synthesis of 6-fluoro-7-methoxyquinazolin-4 (3H)-one: A mixture of 2-amino-5-fluoro-4-methoxybenzoic acid (0.17 g, 0.91 mmol, 1 eq), ammonium acetate (0.1 g, 1.19 mmol, 1.3 eq) and triethylorthoformate (0.24 mL, 1.45 mmol, 1.6 eq) in ethanol (4 mL) was allowed to stir at 90° C. for 16 h. Progress of reaction was monitored by TLC. Reaction mixture was cooled to RT, solid was filtered, washed with hexane and dried under vacuum to afford 6-fluoro-7-methoxyquinazolin-4 (3H)-one (56 mg, 31%). LCMS: 195 [M+1]+.

Step-3: Synthesis of 4-chloro-6-fluoro-7-methoxyquinazoline: A mixture of 6-fluoro-7-methoxyquinazolin-4 (3H)-one (0.05 g, 0.28 mmol, 1 eq) in POCl₃ (1 mL) was stirred at 120° C. for 2 h. After completion, reaction mixture was diluted with water (150 mL) and extracted with ethyl acetate (3×50 mL). Combined organic layer was washed with water (3×30 mL) and dried over anhydrous sodium sulphate. Removal of solvent under reduced pressure afforded 4-chloro-6-fluoro-7-methoxyquinazoline (50 mg, 81%). LCMS: 213 [M+1]+.

Step-4: Synthesis 4-(3-(2-sulfamoylaminoethyl)azetidine-1-yl)-6-fluoro-7-methoxy quinazoline: A suspension of 4-chloro-6-fluoro-7-methoxyquinazoline (43 mg, 0.20 mmol, 1.2 eq), 3-(2-sulfamoylaminoethyl) azetidine trifluoroacetate (50 mg, 0.17 mmol, 1.0 eq) and DIPEA (0.06 mL, 0.34 mmol, 2.0 eq) in DMF (1 mL) was allowed to stir at 80° C. for 3 h. Progress of reaction was monitored by TLC. After 3 h, reaction mixture was concentrated under reduced pressure to afford crude which was purified using reversed phase HPLC to afford 4-(3-(2-sulfamoylaminoethyl)azetidine-1-yl)-6-fluoro-7-methoxy quinazoline (7 mg, 11%). LCMS: 356 [M+1]+; ¹H NMR (400 MHz, DMSO-d6) δ ppm 8.40 (s, 1H), 7.63 (d, 1H), 7.30 (d, 1H), 6.58 (brs, 1H), 6.56 (s, 2H), 4.55 (brs, 2H), 4.10 (brs, 2H), 3.98 (s, 3H), 2.96-2.80 (m, 3H), 1.95-1.79 (m, 2H).

Example-67: Synthesis N-(2-(1-(6,7-dimethoxyquinazolin-4-yl)azetidin-3-yl)ethyl)-1,1,1-trifluoromethanesulfonamide, (Compound 1.67)

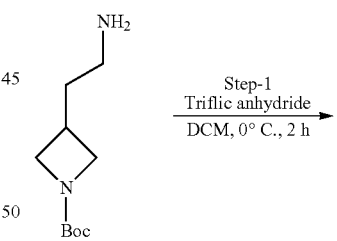

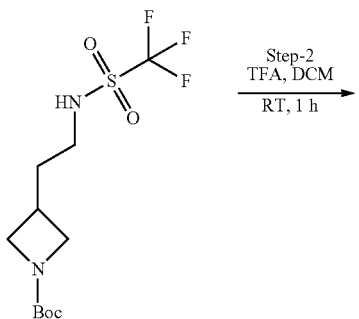

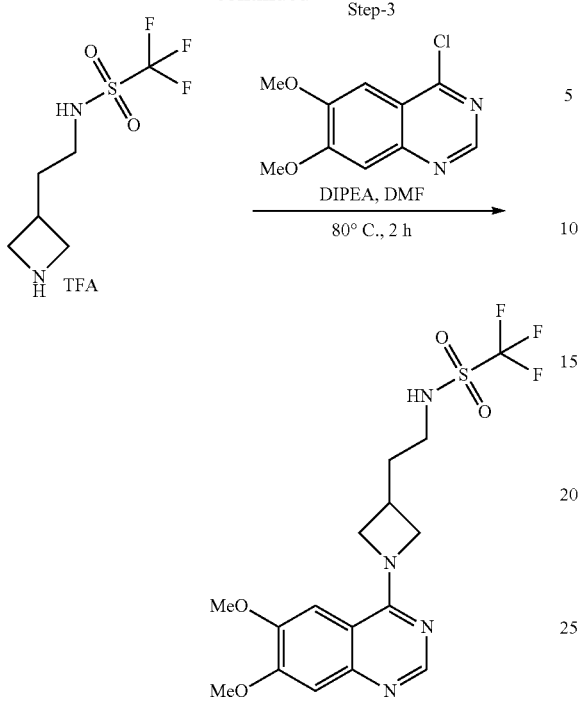

Step-1: Synthesis of tert-butyl 3-(2-(trifluoromethylsulfonamido)ethyl)azetidine-1-carboxylate: To a solution of tert-butyl 3-(2-aminoethyl)azetidine-1-carboxylate (0.1 g, 0.49 mmol, 1 eq) in DCM (3 mL) was added triflic anhydride (0.14 g, 0.49 mmol, 1 eq) and the reaction mixture was allowed to stir at 0° C. for 2 h. Progress of reaction was monitored by $^1$H NMR. After completion, reaction mixture was concentrated under reduced pressure to afford 3-(2-(trifluoromethylsulfonamido)ethyl)azetidine-1-carboxylate (0.15 g, 90%) which was used in the next step without purification.

Step-2: Synthesis of N-(2-(azetidin-3-yl)ethyl)-1,1,1-trifluoromethanesulfonamide trifluoroacetate: To a solution of 3-(2-(trifluoromethylsulfonamido)ethyl)azetidine-1-carboxylate (150 mg, 0.45 mmol, 1 eq) in DCM (4 mL) was added TFA (1 mL) and the reaction mixture was allowed to stir at RT for 1 h. Progress of reaction was monitored by NMR. After completion, reaction mixture was concentrated under reduced pressure to afford crude which was triturated with diethyl ether to afford N-(2-(azetidin-3-yl)ethyl)-1,1,1-trifluoromethanesulfonamide trifluoroacetate (100 mg, 64%).

Step-3: Synthesis of N-(2-(1-(6,7-dimethoxyquinazolin-4-yl)azetidin-3-yl)ethyl)-1,1,1-trifluoromethanesulfonamide: A suspension of 4-chloro-6,7-dimethoxyquinazoline (40 mg, 0.17 mmol, 1.2 eq), N-(2-(azetidin-3-yl)ethyl)-1,1,1-trifluoromethanesulfonamide trifluoroacetate (50 mg, 0.14 mmol, 1.0 eq) and DIPEA (0.05 mL, 0.28 mmol, 2.0 eq) in DMF (1 mL) was allowed to stir at 80° C. for 2 h. Progress of reaction was monitored by TLC. After 2 h, reaction mixture was concentrated under reduced pressure to afford crude which was purified using RP-HPLC to afford N-(2-(1-(6,7-dimethoxyquinazolin-4-yl)azetidin-3-yl)ethyl)-1,1,1-trifluoromethanesulfonamide (2.7 mg, 5%). LCMS: 421 [M+1]$^+$; $^1$H NMR (400 MHz, DMSO-d6) δ ppm 8.31 (s, 1H), 7.21 (s, 1H), 7.10 (s, 1H), 4.60-4.46 (m, 2H), 4.18-4.02 (m, 2H), 3.88 (s, 3H), 3.86 (s, 3H), 2.96-2.78 (m, 3H), 1.80-1.62 (m, 2H).

Example-68: Synthesis 4 (6-N-methylsulfamoylamino)-2-azaspiro[3.3]heptan-2-yl-6,7-dimethoxycinnoline, (Compound 1.68)

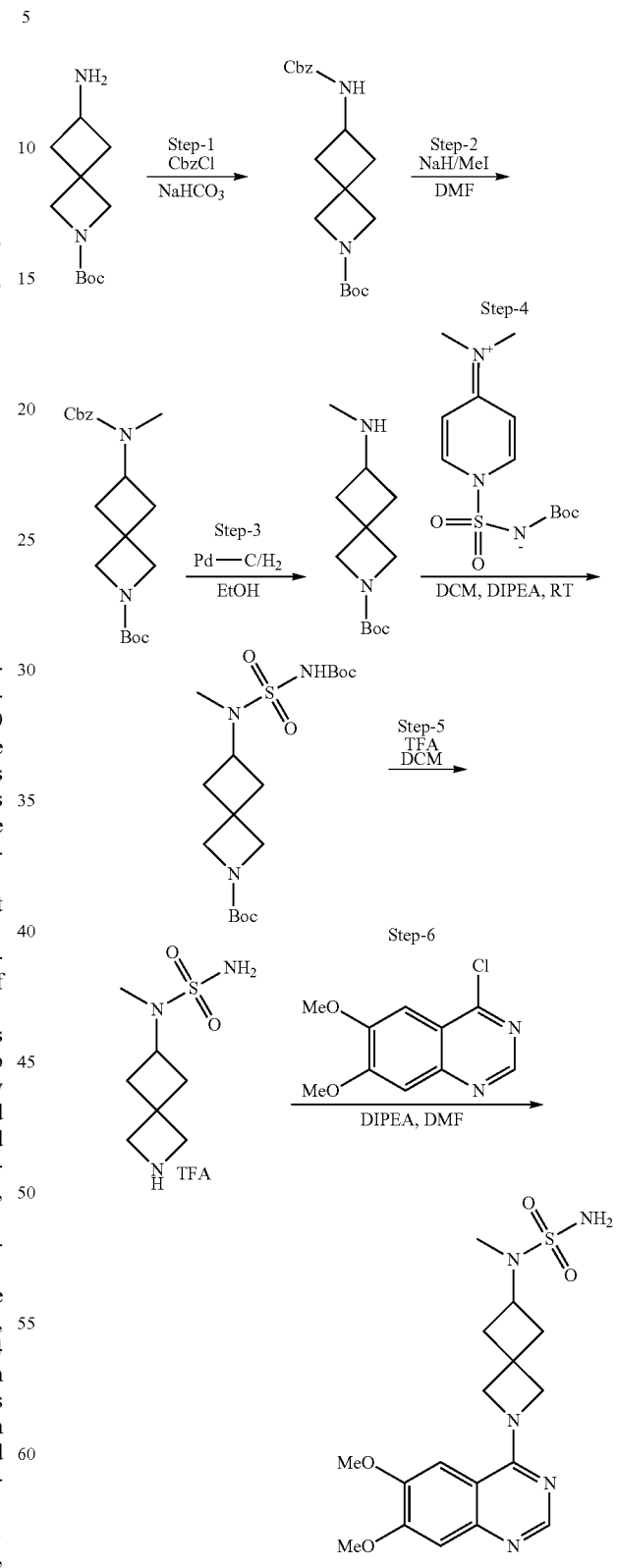

Step-1: Synthesis of tert-butyl 6-(benzyloxycarbonylamino)-2-azaspiro[3.3]heptane-2-carboxylate: To a solution of tert-butyl 6-amino-2-azaspiro[3.3]heptane-2-carboxylate (1 g, 4.7 mmol, 1 eq) in H₂O (50 mL), was added NaHCO₃ (0.791 g, 9.4 mmol, 2.0 eq) and benzyl chloroformate (1.6 mL, 4.7 mmol, 1 eq). The reaction mixture was allowed to stir at RT for 2 h. Progress of reaction is monitored by ¹H NMR. After completion, reaction mixture was diluted with water (100 mL) and extracted with EtOAc (3×100 mL). Combined organic layer was washed with brine (150 mL) and dried over anhydrous sodium sulfate. Removal of solvent under reduced pressure afforded tert-butyl 6-(benzyloxycarbonylamino)-2-azaspiro[3.3]heptane-2-carboxylate (0.7 g, Crude) which was used in the next step without purification.

Step-2: Synthesis of tert-butyl 6-((benzyloxycarbonyl)(methyl)amino)-2-azaspiro[3.3]heptane-2-carboxylate: To a solution of tert-butyl 3-(2-(benzyloxycarbonylamino)ethyl)azetidine-1-carboxylate (0.7 g, 2.0 mmol, 1 eq) in DMF (10 mL), was added NaH (0.161 g, 4.0 mmol, 2.0 eq) and the resulting mixture was stirred at RT for 10 minutes. To the mixture was then added methyl iodide (0.37 mL, 6.0 mmol, 3 eq) and the reaction mixture was allowed to stir at RT for 2. Progress of reaction is monitored by ¹H NMR. After completion, reaction mixture was diluted with water (100 mL) and extracted with EtOAc (3×100 mL). Combined organic layer was washed with water (2×100 mL) followed by brine (150 mL) and dried over anhydrous sodium sulfate. Removal of solvent under reduced pressure afforded tert-butyl 6-((benzyloxycarbonyl)(methyl)amino)-2-azaspiro[3.3]heptane-2-carboxylate (0.63 g, Crude) which was used in the next step without purification.

Step-3: Synthesis of tert-butyl 6-(methylamino)-2-azaspiro[3.3]heptane-2-carboxylate: To a solution of tert-butyl 6-((benzyloxycarbonyl)(methyl)amino)-2-azaspiro[3.3]heptane-2-carboxylate (0.6 g, 1.6 mmol, 1 eq) in ethanol (20 mL) was added Pd/C (0.3 g) and the reaction mixture was allowed to stir at RT under H₂ atmosphere using balloon for 5 h. Progress of reaction was monitored by TLC. After completion, reaction mixture was filtered through celite-bed. Removal of solvent under reduced pressure afforded crude tert-butyl 6-(methylamino)-2-azaspiro[3.3]heptane-2-carboxylate (0.4 g, Crude) which was used in the next step without purification.

Step-4: Synthesis of tert-butyl 6-((N-(tert-butoxycarbonyl)sulfamoyl)(methyl)amino)-2-azaspiro[3.3]heptane-2-carboxylate: To a solution of tert-butyl 6-(methylamino)-2-azaspiro[3.3]heptane-2-carboxylate (0.4 g, 1.7 mmol, 1 eq) in dichloromethane (15 mL) were added N-(tert-butoxycarbonyl)-N-[4-(dimethylazaniumylidene)-1,4-dihydropyridin-1ylsulfonyl]azanide (0.798 g, 2.6 mmol, 1.5 eq) and N,N-diisopropylethylamine (0.6 mL, 3.5 mmol, 2 eq) and the reaction mixture was allowed to stir at RT for 48 h. Progress of reaction was monitored by TLC. After completion, reaction mixture was concentrated under reduced pressure to get crude which was purified by Combi-Flash using ethyl acetate-hexane system as eluent to afford tert-butyl 6-((N-(tert-butoxycarbonyl)sulfamoyl)(methyl)amino)-2-azaspiro[3.3]heptane-2-carboxylate (0.4 g, 56%).

Step-5: Synthesis of (6-N-methylsulfamoylamino)-2-azaspiro[3.3]heptane: To a solution of tert-butyl 6-((N-(tert-butoxycarbonyl)sulfamoyl)(methyl)amino)-2-azaspiro[3.3]heptane-2-carboxylate (0.4 g, 0.98 mmol, 1 eq) in DCM (5 mL) was added TFA (1 mL) and the mixture was allowed to stir at RT for 1 h. Progress of reaction was monitored by ¹H NMR. After completion, reaction mixture was concentrated under reduced pressure to afford crude which was triturated with diethyl ether to afford (6-N-methylsulfamoylamino)-2-azaspiro[3.3]heptane (0.35 g) as TFA salt.

Step-6: Synthesis of 4 (6-N-methylsulfamoylamino)-2-azaspiro[3.3]heptan-2-yl-6,7-dimethoxycinnoline: A suspension of (6-N-methylsulfamoylamino)-2-azaspiro[3.3]heptane (100 mg, 0.31 mmol, 1 eq), 4-chloro-6,7-dimethoxycinnoline (85 mg, 0.37 mmol, 1.2 eq) and DIPEA (0.11 mL, 0.6 mmol, 2.0 eq) in DMF (1 mL) was allowed to stir at 80° C. for 2 h. Progress of reaction was monitored by TLC. After completion, reaction mixture was concentrated under reduced pressure to get residue which was purified by reversed phase HPLC to afford 4 (6-N-methylsulfamoylamino)-2-azaspiro[3.3]heptan-2-yl-6,7-dimethoxycinnoline (9 mg, 7% yield). LCMS: 394.4 [M+1]⁺; H NMR (400 MHz, DMSO-d6) δ ppm 8.19 (s, 1H), 7.45 (s, 1H) 7.11 (s, 1H), 6.75 (s, 1H), 4.50 (s, 2H), 4.38 (s, 2H), 3.96 (s, 6H), 3.80 (m, 1H), 2.48 (s, 3H), 2.43 (s, 4H).

Example-69: Synthesis 4-3-(3-sulfamoylaminopropyl)azetidin-1-yl-6,7-dimethoxyquinazoline, (Compound 1.69)

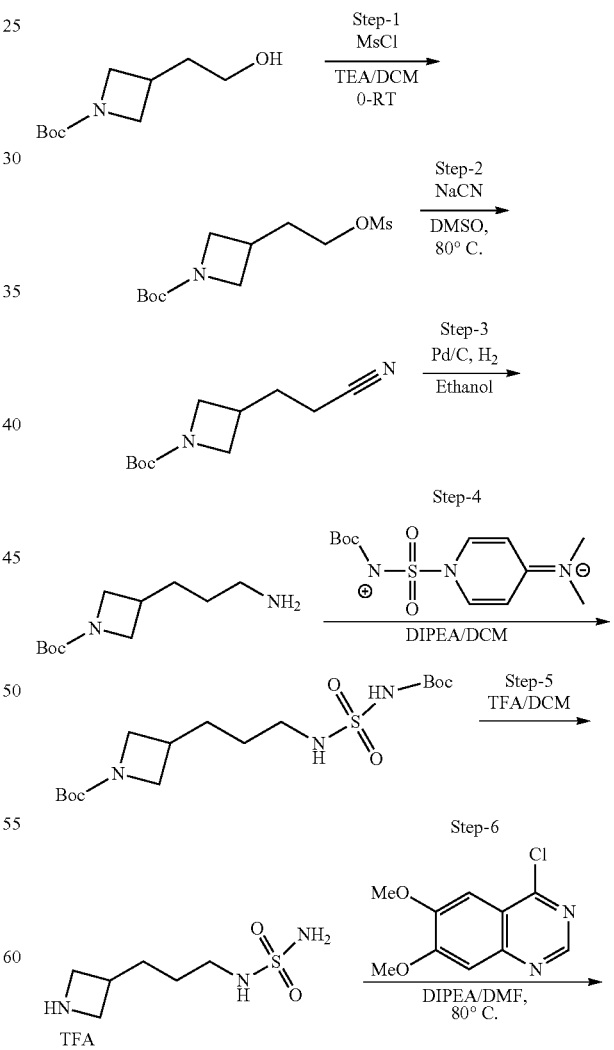

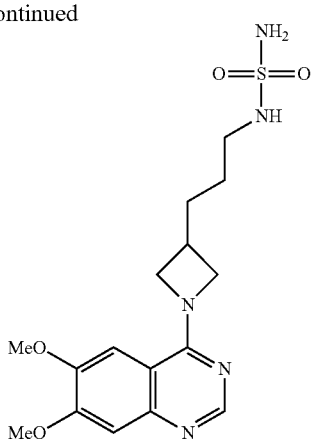

Step-1: Synthesis of tert-butyl 3-(2-(methylsulfonyloxy) ethyl)azetidine-1-carboxylate: To a solution of tert-butyl 3-(2-hydroxyethyl)azetidine-1-carboxylate (1.8 g, 8.9 mmol, 1 eq) in DCM (20 mL) was added triethylamine (2.4 mL, 17.9 mmol, 2 eq) and the reaction mixture was allowed to stir at 0° C. for 5 minutes. To the mixture was added methane sulfonyl chloride (1.1 mL, 13.4 mmol, 1.5 eq) and the reaction mixture to stir at 0° C. for 10 minutes followed by stirring at RT for 2 h. Progress of reaction was monitored by $^1$H NMR. After completion, reaction mixture was diluted with water (100 mL) and extracted with ethyl acetate (3×100 mL). Combined organic layer was washed with brine (150 mL) and dried over anhydrous sodium sulfate. Removal of solvent under reduced pressure afforded tert-butyl 3-(2-(methylsulfonyloxy)ethyl)azetidine-1-carboxylate (2.6 g, Crude) which was used in the next step without purification.

Step-2: Synthesis of tert-butyl 3-(2-cyanoethyl)azetidine-1-carboxylate: To a solution of tert-butyl 3-(2-(methylsulfonyloxy)ethyl)azetidine-1-carboxylate (2.6 g, 9.3 mmol, 1 eq) in DMSO (10 mL), was added sodium cyanide (1.16 g, 23.29 mmol, 2.5 eq) and the reaction mixture was allowed to stir at 80° C. for 16 h. Progress of reaction is monitored by $^1$H NMR. After completion, reaction mixture was diluted with water (100 mL) and extracted with diethyl ether (3×150 mL). Combined organic layer was washed with water (2×100 mL) followed by brine (150 mL) and dried over anhydrous sodium sulfate. Removal of solvent under reduced pressure afforded tert-butyl 3-(2-cyanoethyl)azetidine-1-carboxylate (1.5 g, Crude) which was used in the next step without purification.

Step-3: Synthesis of tert-butyl 3-(3-aminopropyl)azetidine-1-carboxylate: To a solution of tert-butyl 3-(2-cyanoethyl)azetidine-1-carboxylate (1.5 g, 7.1 mmol, 1 eq) in ethanol (50 mL) was added Pd/C (0.75 g) and the reaction mixture was allowed to stir at RT under $H_2$ atmosphere using balloon for 5 h. Progress of reaction was monitored by TLC. After completion, reaction mixture was filtered through celite-bed. Removal of solvent under reduced pressure afforded crude tert-butyl 3-(3-aminopropyl)azetidine-1-carboxylate (1.3 g, Crude) which was used in the next step without purification.

Step-4: Synthesis of tert-butyl 3-(3-(N-(tert-butoxycarbonyl)sulfamoylamino)propyl)azetidine-1-carboxylate: To a solution of tert-butyl 3-(3-aminopropyl)azetidine-1-carboxylate (0.2 g, 0.9 mmol, 1 eq) in dichloromethane (15 mL) were added N-(tert-butoxycarbonyl)-N-[4-(dimethylazaniumylidene)-1,4-dihydropyridin-1ylsulfonyl]azanide (0.421 mg, 1.4 mmol, 1.5 eq) and N,N-diisopropylethylamine (0.3 mL, 1.8 mmol, 2 eq) and the reaction mixture was allowed to stir at RT for 48 h. Progress of reaction was monitored by TLC. After completion, reaction mixture was concentrated under reduced pressure to get crude which was purified by Combi-Flash using ethyl acetate-hexane system as eluent to afford tert-butyl 3-(3-(N-(tert-butoxycarbonyl)sulfamoylamino)propyl)azetidine-1-carboxylate (0.15 g, 55.5%).

Step-5: Synthesis of 3-(3-sulfamoylaminopropyl)azetidine trifluoroacetate: To a solution of tert-butyl 3-(3-(N-(tert-butoxycarbonyl)sulfamoylamino)propyl)azetidine-1-carboxylate (0.15 g, 0.38 mmol, 1 eq) in DCM (5 mL) was added TFA (1 mL) and the mixture was allowed to stir at RT for 1.5 h. Progress of reaction was monitored by $^1$H NMR. After completion, reaction mixture was concentrated under reduced pressure to afford crude which was triturated with diethyl ether to afford 3-(3-sulfamoylaminopropyl)azetidine trifluoroacetate (0.15 g).

Step-6: Synthesis of 4-3-(3-sulfamoylaminopropyl)azetidin-1-yl-6,7-dimethoxyquinazoline: A mixture of 4-chloro-5-methyl-5H-pyrrolo[3,2-d]pyrimidine (38 mg, 0.17 mmol, 1 eq), 3-(3-sulfamoylaminopropyl)azetidine trifluoroacetate (50 mg, 0.17 mmol, 1.0 eq) and DIPEA (0.029 mL, 0.34 mmol, 2.0 eq) in DMF (1 ML) was allowed to stir at 80° C. for 2 h. Progress of reaction was monitored by TLC. After completion, reaction mixture was concentrated under reduced pressure to get residue which was purified by RP-HPLC to afford 4-3-(3-sulfamoylaminopropyl)azetidin-1-yl-6,7-dimethoxyquinazoline (2.1 mg, 3%). LCMS: 382.4 [M+1]$^+$; $^1$H NMR (400 MHz, DMSO-d6) δ ppm 8.35 (s, 1H), 7.20 (s, 1H), 7.12 (s, 1H), 6.50-6.42 (m, 3H), 4.62-4.50 (m, 2H), 4.17-4.02 (m, 2H), 3.88 (s, 3H), 3.87 (s, 3H), 2.92-2.81 (m, 2H), 2.60-2.68 (m, 1H)

Example-70: Synthesis 4-3-(3-sulfamoylaminopropan-2-yl)azetidin-1-yl-6,7-dimethoxyquinazoline, (Compound 1.70)

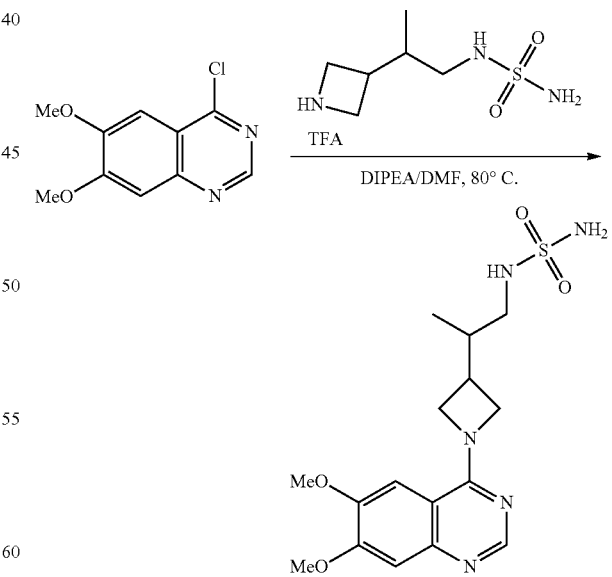

A mixture of 4-chloro-6,7-dimethoxyquinazoline (50 mg, 0.221 mmol, 1 eq), N-[2-(azetidin-3-yl)propyl]sulfuric diamide trifluoroacetate (64 mg, 0.221 mmol, 1.0 eq) and DIPEA (0.078 mL, 0.442 mmol, 2.0 eq) in DMF (2 mL) was allowed to stir at 80° C. for 2 h. Progress of reaction was monitored by TLC. After completion, reaction mixture was concentrated under reduced pressure to get residue which was purified by RP-HPLC to afford the title compound (20 mg, 23%). LCMS: 382 [M+1]$^+$; $^1$H NMR (400 MHz, METHANOL-d$_4$) δ ppm 8.28 (s, 1H), 7.28 (s, 1H), 7.08 (s, 1H), 4.71 (br. s., 1H), 4.63 (br. s., 1H), 4.44 (br. s., 1H), 3.97 (s, 3H), 3.94 (s, 3H), 2.99 (m, 2H), 2.78 (m, 1H), 2.05 (m, 1H), 1.97 (s, 1H), 1.01 (d, 2H).

Example-71: Synthesis 4-(3-(2-sulfamoylamino-ethyl)azetidine-1-yl)-2,5-di-methylpyrrolo[1,2-f][1,2,4]triazine, (Compound 1.71)

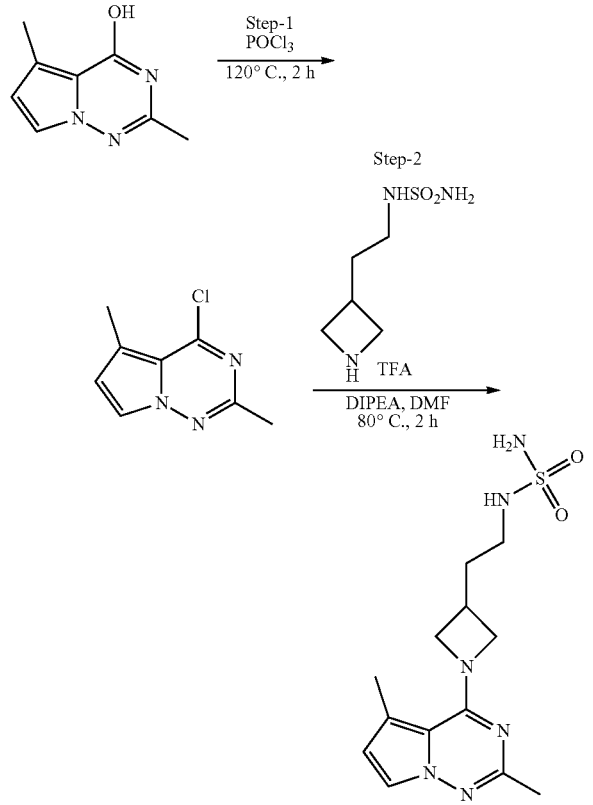

Step-1: Synthesis of 4-chloro-5-methylpyrrolo[1,2-f][1,2,4]triazine: A mixture of 2,5-dimethylpyrrolo[1,2-f][1,2,4]triazin-4-ol (100 mg, 0.613 mmol, 1 eq) in POCl$_3$ (0.3 mL) was stirred at 120° C. for 2 h. Progress of reaction was monitored by TLC. After completion reaction mixture was cooled to RT, poured to ice (10 mL) and stirred for 15 minutes. Solid was filtered and dried to afford 4-chloro-2,5-dimethylpyrrolo[1,2-f][1,2,4]triazine (70 mg, 63%). LCMS: 182 [M+1]$^+$ Step-2: Synthesis of 4-(3-(2-sulfamoylaminoethyl)azetidine-1-yl)-2,5-di-methylpyrrolo[1,2-f][1,2,4]triazine: A suspension of 4-chloro-2,5-dimethylpyrrolo[1,2-f][1,2,4]triazine (70 mg, 0.285 mmol, 1.0 eq), 3-(2-sulfamoylaminoethyl) azetidine trifluoroacetate (80 mg, 0.285 mmol, 1.0 eq) and N,N diisopropylethylamine (74 mg, 0.772 mmol, 2.0 eq) in DMF (2 mL) was allowed to stir at 80° C. for 2 h. Progress of reaction was monitored by TLC. Reaction mixture was cooled to RT, DMF was removed under reduced pressure, crude obtained was purified by RP-HPLC to afford 4-(3-(2-sulfamoylaminoethyl)azetidine-1-yl)-2,5-di-methylpyrrolo[1,2-f][1,2,4]triazine (6 mg, 20.8%). LCMS: 325.2 [M+1]$^+$; $^1$H NMR (400 MHz, METHANOL-d4) δ ppm 7.38 (d, 1H), 6.41 (d, 1H), 4.55 (t, 2H), 4.09 (dd, 2H), 3.08 (t, 2H), 2.90 (m, 1H), 2.44 (s, 3H), 2.27 (s, 3H), 1.93 (q, 2H).

Example-72: Synthesis of 4-(3-(2-sulfamoylamino-ethyl)azetidine-1-yl)-6-bromo-5-methylpyrrolo[1,2-f][1,2,4]triazine, (Compound 1.72)

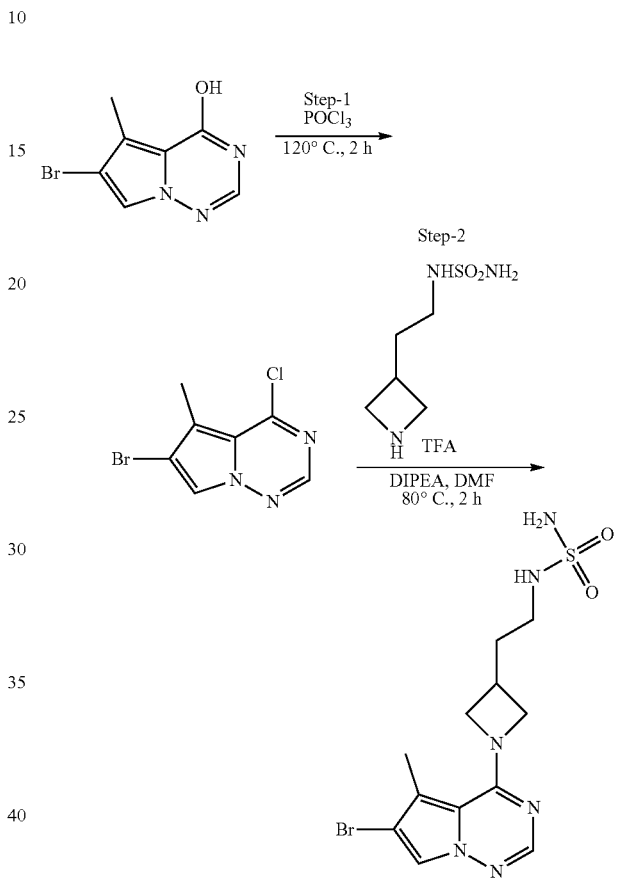

Step-1: Synthesis of 6-bromo-4-chloro-5-methylpyrrolo[1,2-f][1,2,4]triazine: A mixture of 6-bromo-5-methylpyrrolo[1,2-f][1,2,4]triazin-4-ol (100 mg, 0.440 mmol, 1 eq) in POCl$_3$ (0.3 mL) was stirred at 120° C. for 2 h. Progress of the reaction was monitored by TLC. After completion reaction mixture was cooled to RT, poured to ice (10 mL) and stirred for 15 minutes. Solid was filtered and dried to afford 6-bromo-4-chloro-5-methylpyrrolo[1,2-f][1,2,4]triazine (70 mg, 65%). LCMS: 182 [M+1]$^+$ Step-2: Synthesis of 4-(3-(2-sulfamoylaminoethyl)azetidine-1-yl)-6-bromo-5-methylpyrrolo[1,2-f][1,2,4]triazine: A suspension of 6-bromo-4-chloro-5-methylpyrrolo[1,2-f][1,2,4]triazine (70 mg, 0.285 mmol, 1.0 eq), 3-(2-sulfamoylaminoethyl)azetidine trifluoroacetate (79 mg, 0.285 mmol, 1.0 eq) and N,N diisopropylethylamine (74 mg, 0.570 mmol, 2.0 eq) in DMF (2 mL) was allowed to stir at 80° C. for 2 h. Progress of reaction was monitored by TLC. Reaction mixture was cooled to RT, DMF was removed under reduced pressure, crude obtained was purified by reversed phase HPLC to afford 4-(3-(2-sulfamoylaminoethyl)azetidine-1-yl)-6-bromo-5-methylpyrrolo[1,2-f][1,2,4]triazine (6 mg, 4%). LCMS: 389 [M+1]$^+$; $^1$H NMR (400 MHz, METHA- NOL-d4) δ ppm 7.72 (s, 1H), 7.63 (s, 1H), 4.58 (d, 3H), 4.12 (dd, 3H), 3.48 (br. s., 1H), 3.08 (t, 2H), 2.93 (d, 2H), 2.42 (s, 3H), 1.93 (q, 3H).

Example-73: Synthesis of 4-(6-N-methylsulfamoylamino)-2-azaspiro[3.3]heptan-2-yl)-5-methylpyrrolo[1,2-f][1,2,4]triazine, (Compound 1.73)

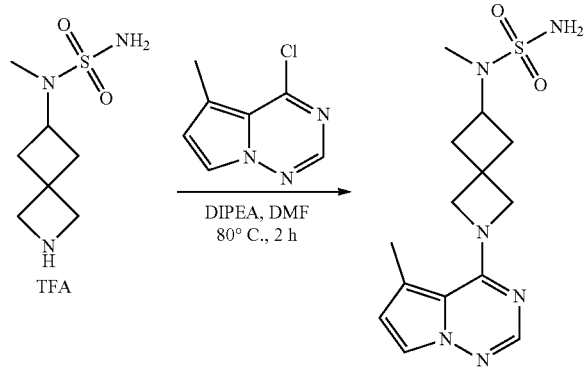 [SMILES: CN(C1CC2(CNC2)C1)S(N)(=O)=O ; Cc1ccn2ncnc(Cl)c12 ; Cc1ccn2ncnc(N3CC4(CC(N(C)S(N)(=O)=O)C4)C3)c12]

A suspension of (6-N-methylsulfamoylamino)-2-azaspiro[3.3]heptane (80 mg, 0.25 mmol, 1 eq), 4-chloro-5-methylpyrrolo[1,2-f][1,2,4]triazine (50 mg, 0.30 mmol, 1.2 eq) and DIPEA (0.08 mL, 0.50 mmol, 2.0 eq) in DMF (1 mL) was allowed to stir at 80° C. for 2 h. Progress of reaction was monitored by TLC. After completion, reaction mixture was concentrated under reduced pressure to get residue which was purified by reversed phase HPLC to afford 4-(6-N-methylsulfamoylamino)-2-azaspiro[3.3]heptan-2-yl)-5-methylpyrrolo[1,2-f][1,2,4]triazine (20 mg, 24% yield). LCMS: 337.4 [M+1]$^+$; $^1$H NMR (400 MHz, DMSO-d6) δ ppm 7.78 (s, 1H), 7.59 (s, 1H), 6.72 (s, 2H), 6.48 (s, 1H), 4.39 (brs, 2H), 4.26 (brs, 2H), 3.81-3.70 (m, 1H), 2.55 (s, 3H), 2.40 (s, 3H), 2.40-2.20 (m, 4H).

Example-74: Synthesis of N-hydroxy-3-(1-(5-methylpyrrolo[1,2-f][1,2,4]triazin-4-yl)azetidin-3-yl)propanamide, (Compound 1.74)

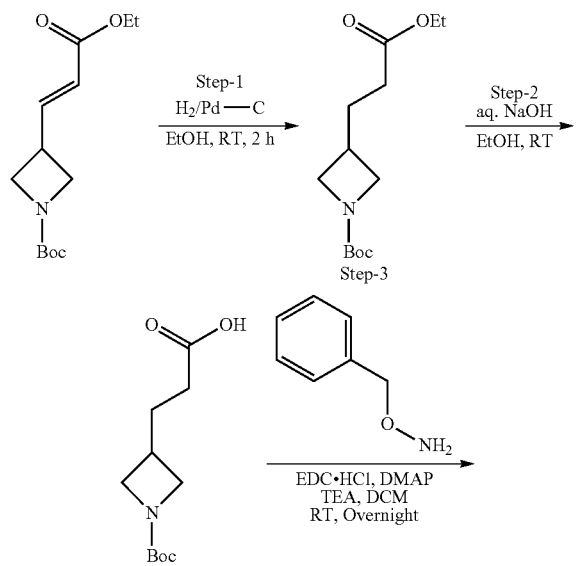

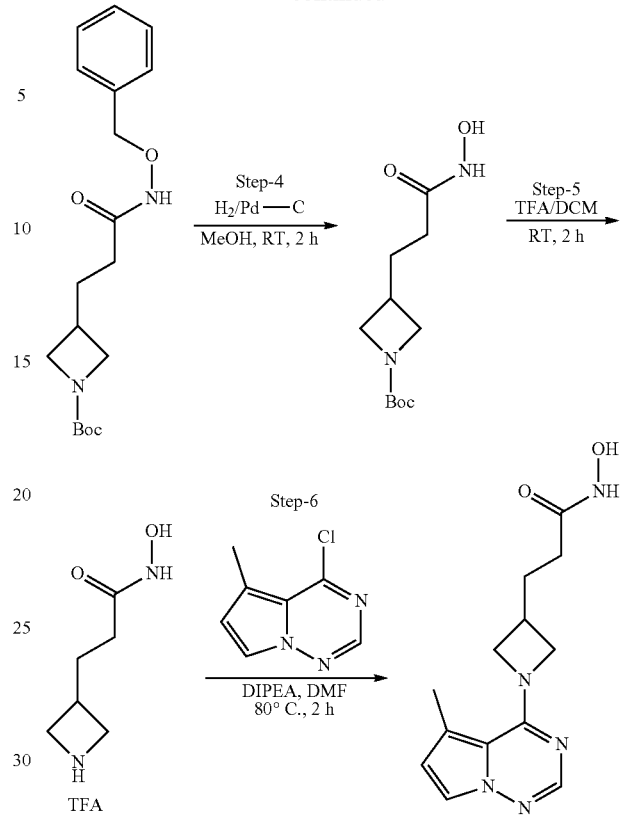

Step-1: Synthesis of tert-butyl 3-(3-ethoxy-3-oxopropyl)azetidine-1-carboxylate: To a solution of (E)-tert-butyl 3-(3-ethoxy-3-oxoprop-1-enyl)azetidine-1-carboxylate (0.6 g, 2.35 mmol, 1 eq) in ethanol (10 mL) was added Pd/C (0.2 g) and the reaction mixture was allowed to stir at RT under H$_2$ balloon for 2 h. After completion, reaction mixture was filtered using celite bed. Filtrate was concentrated under reduced pressure afforded tert-butyl 3-(3-ethoxy-3-oxopropyl)azetidine-1-carboxylate (0.600 g, crude) which was used in the next step without purification.

Step-2: Synthesis of 3-(1-(tert-butoxycarbonyl)azetidin-3-yl)propanoic acid: To a solution of tert-butyl 3-(3-ethoxy-3-oxopropyl)azetidine-1-carboxylate (0.6 g, 2.33 mmol, 1 eq) in EtOH (10 mL) was added a solution of NaOH (0.466 g, 11.65 mmol, 5 eq) in water (2 mL) and the reaction mixture was allowed to stir at RT overnight. Progress of reaction is monitored by $^1$H-NMR. After completion, solvent was removed under reduced pressure, residued was acidified with 1N HCl and extracted with ethyl acetate (3×100 mL). Combined organic layer was washed with brine (150 mL) and dried over anhydrous sodium sulfate. Removal of solvent under reduced pressure afforded 3-(1-(tert-butoxycarbonyl)azetidin-3-yl)propanoic acid (0.48 g, crude) which was used in the next step without purification.

Step-3: Synthesis of tert-butyl 3-(3-(benzyloxyamino)-3-oxopropyl)azetidine-1-carboxylate: To a solution of 3-(1-(tert-butoxycarbonyl)azetidin-3-yl)propanoic acid (0.48 g, 2.094 mmol, 1 eq) and O-benzylhydroxylamine (0.367 g, 2.301 mmol, 1.1 eq) in DCM (30 mL) were added N-(3-Dimethylaminopropyl)-N'-ethylcarbodiimide hydrochloride (0.48 g, 2.513 mmol, 1.2 eq), 4-(Dimethylamino)pyridine (0.383 g, 3.141 mmol, 1.5 eq) and triethylamine (0.9 mL, 6.282 mmol, 3 eq), the reaction mixture was allowed to stir at RT overnight. Progress of reaction is monitored by TLC. After completion, removal of solvent under reduced pressure gave residue which was diluted with water (100 mL) and extracted with ethyl acetate (3×100 mL). Combined organic layer was washed with dil. HCl and brine (150 mL) and dried over anhydrous sodium sulfate. Removal of solvent under reduced pressure afforded tert-butyl 3-(3-(benzyloxyamino)-3-oxopropyl)azetidine-1-carboxylate (0.6 g, crude) which was used in the next step without purification.

Step-4: Synthesis of tert-butyl 3-(3-(hydroxyamino)-3-oxopropyl)azetidine-1-carboxylate: To a solution of tert-butyl 3-(3-(benzyloxyamino)-3-oxopropyl)azetidine-1-carboxylate (0.6 g, 1.794 mmol, 1 eq) in methanol (25 mL) was added Pd/C (0.125 g) and the reaction mixture was allowed to stir at RT under $H_2$ atmosphere using hydrogen balloon for 2 h. After completion, reaction mixture was filtered using celite bed. Removal of solvent under reduced pressure afforded tert-butyl 3-(3-(hydroxyamino)-3-oxopropyl)azetidine-1-carboxylate (0.4 g, crude) which was used in the next step without purification.

Step-5: Synthesis of 3-(azetidin-3-yl)-N-hydroxypropanamide trifluoroacetate: To a solution of tert-butyl 3-(3-(hydroxyamino)-3-oxopropyl)azetidine-1-carboxylate (0.4 g, 1.637 mmol, 1 eq) in DCM (5 mL) was added TFA (1 mL) and the mixture was allowed to stir at RT for 2 h. Progress of reaction was monitored by $^1$H NMR. After completion, reaction mixture was concentrated under reduced pressure to afford crude which was triturated with diethyl ether to afford 3-(azetidin-3-yl)-N-hydroxypropanamide trifluoroacetate (0.250 g, crude) which was used in the next step without purification.

Step-6: Synthesis of N-hydroxy-3-(1-(5-methylpyrrolo[1,2-f][1,2,4]triazin-4-yl)azetidin-3-yl)propanamide: A suspension of 3-(azetidin-3-yl)-N-hydroxypropanamide trifluoroacetate (80 mg, 0.31 mmol, 1 eq), 4-chloro-5-methylpyrrolo[1,2-f][1,2,4]triazine (62 mg, 0.37 mmol, 1.2 eq) and DIPEA (0.1 mL, 0.62 mmol, 2.0 eq) in DMF (1 mL) was allowed to stir at 80° C. for 2 h. Progress of reaction was monitored by TLC. After completion, reaction mixture was concentrated under reduced pressure to get residue which was purified by RP-HPLC to afford N-hydroxy-3-(1-(5-methylpyrrolo[1,2-f][1,2,4]triazin-4-yl)azetidin-3-yl)propanamide (6.5 mg, 8% yield). LCMS: 276.3 [M+1]$^+$ $^1$H NMR (400 MHz, DMSO-d6) δ ppm 8.75 (brs, 1H), 7.78 (s, 1H), 7.58 (s, 1H, 6.46 (s, 1H), 4.45-4.37 (m, 2H), 4.02-3.90 (m, 2H), 2.65 (brs, 1H), 2.40 (s, 3H), 2.02-1.92 (m, 2H), 1.90-1.80 (m, 2H).

Example-75: Synthesis of N-[2-(6-chloro-5-methylpyrrolo[2,1-f][1,2,4]triazin-4-yl)-2-azaspiro[3.3]hept-6-yl]-N-methylsulfuric diamide, (Compound 1.75)

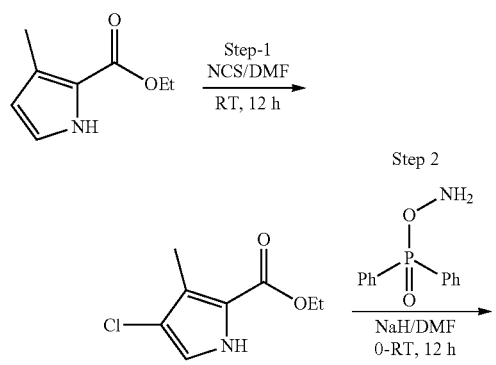

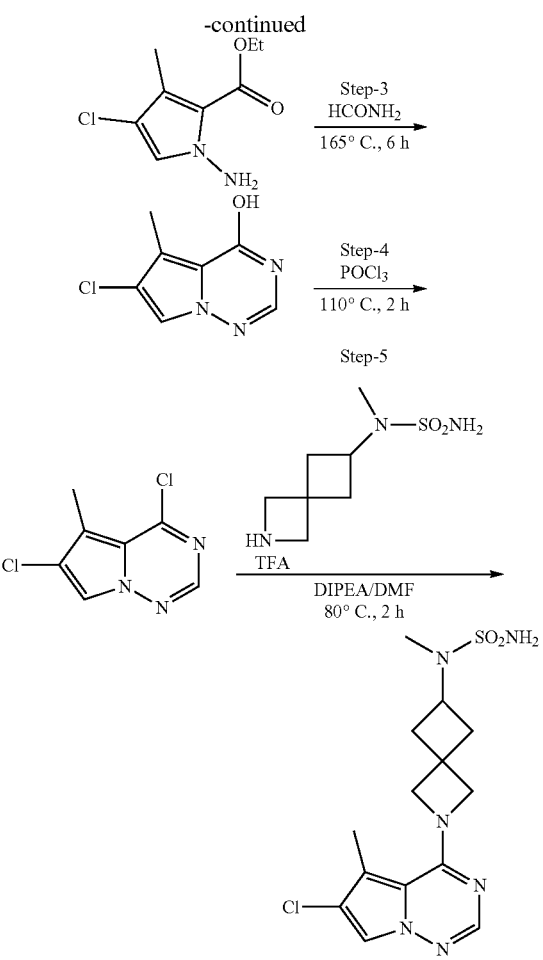

Step-1: Synthesis of ethyl 4-chloro-3-methyl-1H-pyrrole-2-carboxylate: To a solution of ethyl 3-methyl-1H-pyrrole-2-carboxylate (1 g, 6.53 mmol, 1.0 eq) in DMF (10 mL) was added a N-chlorosuccinamide (872 mg, 6.53 mmol) portion wise. The reaction mixture was allowed to stir at RT for 12 h. Progress of reaction is monitored using TLC. After completion, reaction mixture was diluted with water (100 mL) and extracted with ethyl acetate (3×100 mL). Combined organic layer was washed with brine (150 mL) and dried over anhydrous sodium sulfate. Removal of solvent under reduced pressure afforded the crude which was purified by Combi-Flash to obtain the ethyl 4-chloro-3-methyl-1H-pyrrole-2-carboxylate (600 mg, 57%). LCMS: 187[M+1]$^+$ Step-2: Synthesis of ethyl 1-amino-4-chloro-3-methyl-1H-pyrrole-2-carboxylate: To a solution of sodium hydride (0.183 g, 5.64 mmol, 1.43 eq) in DMF (50 mL) was added a solution of ethyl 4-chloro-3-methyl-1H-pyrrole-2-carboxylate. ((0.600 g, 3.20 mmol, 1 eq) in DMF (10 mL) at 0° C. and the reaction mixture was allowed to stir at 0° C. for 30 minutes, followed by addition of O-(diphenylphosphoryl)hydroxylamine (1.3 g, 5.64 mmol, 1.76 eq) portion wise. The reaction mixture was allowed to stir at RT for 12 h. Progress of reaction is monitored using TLC. After completion, DMF was removed under reduced pressure; residue was diluted with water (100 mL) and extracted with ethyl acetate (3×100 mL). Combined organic layer was washed with brine (150 mL) and dried over anhydrous sodium sulfate. Removal of solvent under reduced pressure afforded ethyl 1-amino-4-chloro-3-methyl-1H-pyrrole-2-carboxylate (0.4 g, 61%). LCMS: 202[M+1]$^+$ Step-3: Synthesis of 6-chloro-5-methylpyrrolo[2,1-f][1,2,4]triazin-4-ol: A solution of ethyl 1-amino-4-chloro-3-methyl-1H-pyrrole-2-carboxylate (0.3 g, 1.48 mmol, 1 eq) in formamide (5 mL) was allowed to stir at 165° C. for 6 h. Progress of reaction is monitored by TLC. After completion, reaction mixture was diluted with cold water (30 mL) and allowed to stir for 10 minutes. Solid was filtered, washed with water followed by hexane and dried under vacuum to afford 7-chloro-5-methylpyrrolo[2,1-f][1,2,4]triazin-4-ol (0.242 g, 83%). LCMS: 183[M+1]$^+$.

Step-4: Synthesis of 4,6-dichloro-5-methylpyrrolo[2,1-f][1,2,4]triazine: A mixture of 7-chloro-5-methylpyrrolo[2,1-f][1,2,4]triazin-4-ol (0.242 g, 1.32 mmol, 1 eq) in phosphoryl trichloride (5 mL) was allowed to stir at 110° C. for 2 h. Progress of reaction is monitored by TLC. After completion, reaction mixture was diluted with cold water (30 mL) and extracted with ethyl acetate (3×15 mL). Combined organic layer was washed with brine (20 mL) and dried over anhydrous sodium sulfate. Solvent was removed under reduced pressure to give 4,6-dichloro-5-methylpyrrolo[2,1-f][1,2,4]triazine (0.163 g, 61%). LCMS: 201[M+1]$^+$.

Step-5: Synthesis of N-[2-(6-chloro-5-methylpyrrolo[2,1-f][1,2,4]triazin-4-yl)-2-azaspiro[3.3]hept-6-yl]-N-methylsulfuic diamide: A suspension of 4,6-dichloro-5-methylpyrrolo[2,1-f][1,2,4]triazine (50 mg, 0.24 mmol, 1 eq), N-2-azaspiro[3.3]hept-6-yl-N-methylsulfuric diamide trifloroacetic acid (75 mg, 0.24 mmol, 1.0 eq) and DIPEA (0.1 mL, 0.48 mmol, 2.0 eq) in DMF (1 mL) was allowed to stir at 80° C. for 2 h. Progress of reaction was monitored by TLC. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude which was purified by reversed phase to afford N-[2-(6-chloro-5-methylpyrrolo[2,1-f][1,2,4]triazin-4-yl)-2-azaspiro[3.3]hept-6-yl]-N-methylsulfuric diamide (0.06 g). LCMS: 371 [M+1]$^+$. $^1$H NMR (400 MHz, DMSO-d6) δ ppm 7.90 (s, 1H), 7.85 (s, 1H), 6.71 (s, 2H), 4.42 (brs, 2H) 4.29 (s, 2H), 3.80-3.70 (s, 1H), 2.52 (s, 3H), 2.50-2.28 (m, 4H), 2.37 (s, 3H).

Example-76: Synthesis of N-[2-(7-chloro-5-methylpyrrolo[2,1-f][1,2,4]triazin-4-yl)-2-azaspiro[3.3]hept-6-yl]-N-methylsulfuric diamide, (Compound 1.76)

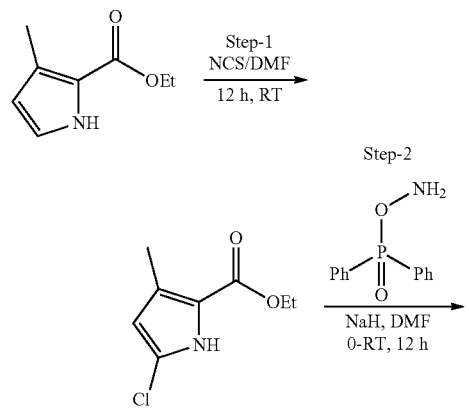

Step-1: Synthesis of ethyl 5-chloro-3-methyl-1H-pyrrole-2-carboxylate: To a solution of ethyl 3-methyl-1H-pyrrole-2-carboxylate (1 g, 6.53 mmol, 1.0 eq) in DMF (10 mL) was added a N-chlorosuccinamide (872 mg, 6.53 mmol) portion wise. The reaction mixture was allowed to stir at RT for 12 h. Progress of reaction is monitored using TLC. After completion, it was diluted with water (100 mL) and extracted with ethyl acetate (3×100 mL). Combined organic layer was washed with brine (150 mL) and dried over anhydrous sodium sulfate. Removal of solvent under reduced pressure afforded the crude which was purified by Combi-Flash to obtain the ethyl 5-chloro-3-methyl-1H-pyrrole-2-carboxylate (481 mg, 40%). LCMS: 187[M+1]$^+$ Step-2: Synthesis of ethyl 1-amino-5-chloro-3-methyl-1H-pyrrole-2-carboxylate: To a suspension of sodium hydride (0.147 g, 3.67 mmol, 1.43 eq) in DMF (25 mL) was added a solution of ethyl 5-chloro-3-methyl-1H-pyrrole-2-carboxylate (0.481 g, 2.57 mmol, 1 eq) in DMF (10 mL) at 0° C. and the reaction mixture was allowed to stir at 0° C. for 30 minutes, followed by addition of O-(diphenylphosphoryl)hydroxylamine (1.0 g, 4.52 mmol, 1.76 eq) portion wise. The reaction mixture was allowed to stir at RT for 12 h. Progress of reaction is monitored using TLC. After completion, DMF was removed under reduced pressure; residue was diluted with water (100 mL) and extracted with ethyl acetate (3×100 mL). Combined organic layer was washed with brine (150 mL) and dried over anhydrous sodium sulfate. Removal of solvent under reduced pressure afforded ethyl 1-amino-5-chloro-3-methyl-1H-pyrrole-2-carboxylate (0.3 g, 57%). LCMS: 202[M+1]⁺

Step-3: Synthesis of 7-chloro-5-methylpyrrolo[2,1-f][1,2,4]triazin-4-ol: A solution of ethyl 1-amino-5-chloro-3-methyl-1H-pyrrole-2-carboxylate (0.3 g, 1.48 mmol, 1 eq) in formamide (5 mL) was allowed to stir at 165° C. for 6 h. Progress of reaction is monitored by TLC. After completion, reaction mixture was diluted with cold water (30 mL) and allowed to stir for 10 minutes. Solid was filtered, washed with water followed by hexane and dried under vacuum to afford 7-chloro-5-methylpyrrolo[2,1-f][1,2,4]triazin-4-ol (0.225 g, 83%). LCMS:183[M+1]⁺

Step-4: Synthesis of 4,7-dichloro-5-methylpyrrolo[2,1-f][1,2,4]triazine: A mixture of 7-chloro-5-methylpyrrolo[2,1-f][1,2,4]triazin-4-ol (0.225 g, 1.22 mmol, 1 eq) in phosphoryl trichloride (5 mL) was allowed to stir at 110° C. for 2 h. Progress of reaction is monitored by TLC. After completion, reaction mixture was diluted with cold water (30 mL) and extracted with ethyl acetate (3×15 mL). Combined organic layer was washed with brine (20 mL) and dried over anhydrous sodium sulfate. Solvent was removed under reduced pressure to give 4,7-dichloro-5-methylpyrrolo[2,1-f][1,2,4]triazine 0.2 g, 87%). LCMS: 201M+1]⁺

Step-5: Synthesis of N-[2-(7-chloro-5-methylpyrrolo[2,1-f][1,2,4]triazin-4-yl)-2-azaspiro[3.3]hept-6-yl]-N-methylsulfuic diamide: A suspension of 4,7-dichloro-5-methylpyrrolo[2,1-f][1,2,4]triazine (50 mg, 0.24 mmol, 1 eq), N-2-azaspiro[3.3]hept-6-yl-N-methylsulfuric diamide trifloroacetic acid (75 mg, 0.24 mmol, 1.0 eq) and DIPEA (0.1 mL, 0.48 mmol, 2.0 eq) in DMF (1 mL) was allowed to stir at 80° C. for 2 h. Progress of reaction was monitored by TLC. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude which was purified by reversed phase to afford N-[2-(7-chloro-5-methylpyrrolo[2,1-f][1,2,4]triazin-4-yl)-2-azaspiro[3.3]hept-6-yl]-N-methylsulfuric diamide (6 mg, 7%). LCMS: 371[M+1]⁺, ¹H NMR (400 MHz, DMSO-d6) δ ppm 7.90 (s, 1H), 6.71 (s, 2H), 6.62 (s, 1H), 4.42 (brs, 2H) 4.29 (brs, 2H), 3.80-3.70 (s, 1H), 2.52 (s, 3H), 2.50-2.28 (m, 4H), 2.37 (s, 3H).

Example-77: Synthesis of N-(2-(5,7-dimethylpyrrolo[1,2-f][1,2,4]triazin-4-yl)-2-azaspiro[3.3]heptan-6-yl)-N-methylsulfamide, (Compound 1.77)

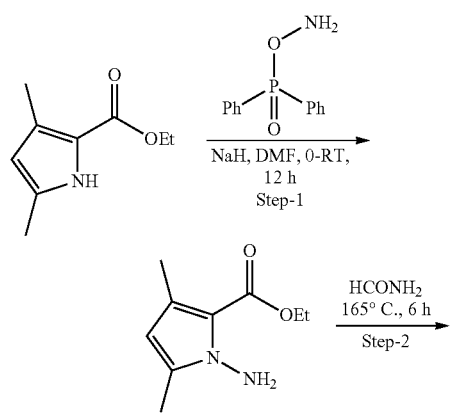

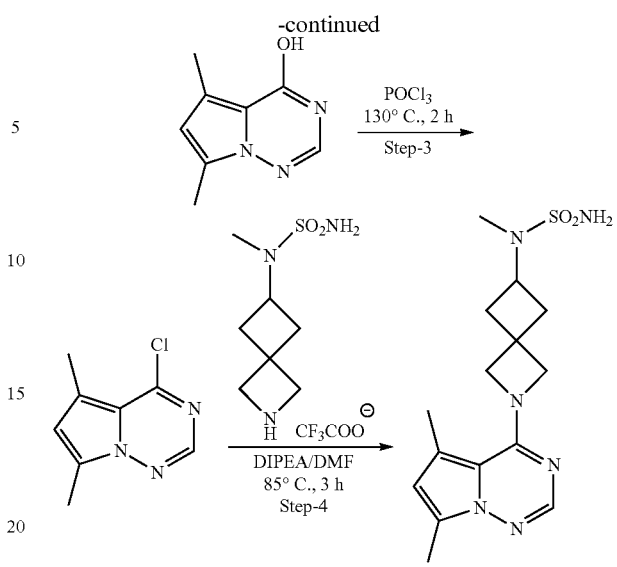

Step-1: Synthesis of ethyl 1-amino-3,5-dimethyl-1H-pyrrole-2-carboxylate: To a suspension of sodium hydride (0.720 g, 17.95 mmol, 1.5 eq) in DMF (25 mL) was added a solution of ethyl 5-chloro-3-methyl-1H-pyrrole-2-carboxylate (2.0 g, 11.97 mmol, 1 eq) in DMF (60 mL) at 0° C. and the reaction mixture was allowed to stir at 0° C. for 30 minutes, was added of O-(diphenylphosphoryl)hydroxylamine (4.45 g, 19.16 mmol, 1 eq) portion wise. The reaction mixture was allowed to stir at RT for 12 h. Progress of reaction is monitored using TLC. After completion, residue was diluted with cold water (100 mL) and extracted with ethyl acetate (3×100 mL). Combined organic layer was washed with brine (150 mL) and dried over anhydrous sodium sulfate. Removal of solvent under reduced pressure afforded ethyl 1-amino-3,5-dimethyl-1H-pyrrole-2-carboxylate (1.5 g, 69.12%). LCMS: 182 [M+1]⁺

Step-2: Synthesis of 5,7-dimethylpyrrolo[1,2-f][1,2,4]triazin-4-ol: To a solution of ethyl 1-amino-3,5-dimethyl-1H-pyrrole-2-carboxylate (1.5 g, 8.24 mmol, 1 eq) in formamide (15 mL) was allowed to stir at 165° C. for 16 h. Progress of reaction is monitored by TLC. After completion, reaction mixture was diluted with cold water (100 mL) and allowed to stir for 10 minutes. Solid was filtered, washed with water followed by hexane and dried under vacuum to afford 5,7-dimethylpyrrolo[1,2-f][1,2,4]triazin-4-ol (0.7 g, 53.84%). LCMS: 164 [M+1]⁺

Step-3: Synthesis of 4-chloro-5,7-dimethylpyrrolo[1,2-f][1,2,4]triazine: To a mixture of 5,7-dimethylpyrrolo[1,2-f][1,2,4]triazin-4-ol (0.5 g, 3.048 mmol, 1 eq) in phosphoryl oxychloride (3 mL) was allowed to stir at 130° C. for 2 h. Progress of reaction is monitored by TLC. After completion, reaction mixture was diluted with cold water (30 mL) and extracted with ethyl acetate (3×20 mL). Combined organic layer was washed with brine (20 mL) and dried over anhydrous sodium sulfate. Solvent was removed under reduced pressure to give 4-chloro-5,7-dimethylpyrrolo[1,2-f][1,2,4]triazine (0.3 g, 55%). LCMS: 182 [M+1]⁺

Step-4: Synthesis of N-(N-(2-(5,7-dimethylpyrrolo[1,2-f][1,2,4]triazin-4-yl)-2-azaspiro[3.3]heptan-6-yl)-N-methylsulfamamide: The mixture of 4-chloro-5,7-dimethylpyrrolo[1,2-f][1,2,4]triazine (200 mg, 0.828 mmol, 1 eq), N-methyl-N-(2-azaspiro[3.3]heptan-6-yl)sulfamamide, 2,2,2-trifluoroacetate salt (0.370 mg, 1.215 mmol, 1.1 eq) and DIPEA (0.26 mL, 1.542 mmol, 1.5 eq) in DMF (5 mL) was allowed to stir at 85° C. for 3 h. Progress of reaction was monitored by TLC. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford N-(N-(2-(5,7-dimethylpyrrolo[1,2-f][1,2,4]triazin-4-yl)-2-azaspiro[3.3]heptan-6-yl)-N-methylsulfamamide (15 mg, 3.88%). LCMS: 351 [M+1]$^+$; $^1$H NMR (400 MHz, DMSO-d$_6$) δ ppm 7.81 (s, 1H), 6.69 (s, 2H), 6.33 (s, 1H), 4.37 (s, 2H), 4.25 (s, 2H), 3.81-3.75 (m, 1H), 2.60-2.20 (m, 13H).

Example-78: Synthesis of N-(2-(6-cyano-5-methylpyrrolo[1,2-f][1,2,4]triazin-4-yl)-2-azaspiro[3.3]heptan-6-yl)-N-methylsulfamamide, (Compound 1.78)

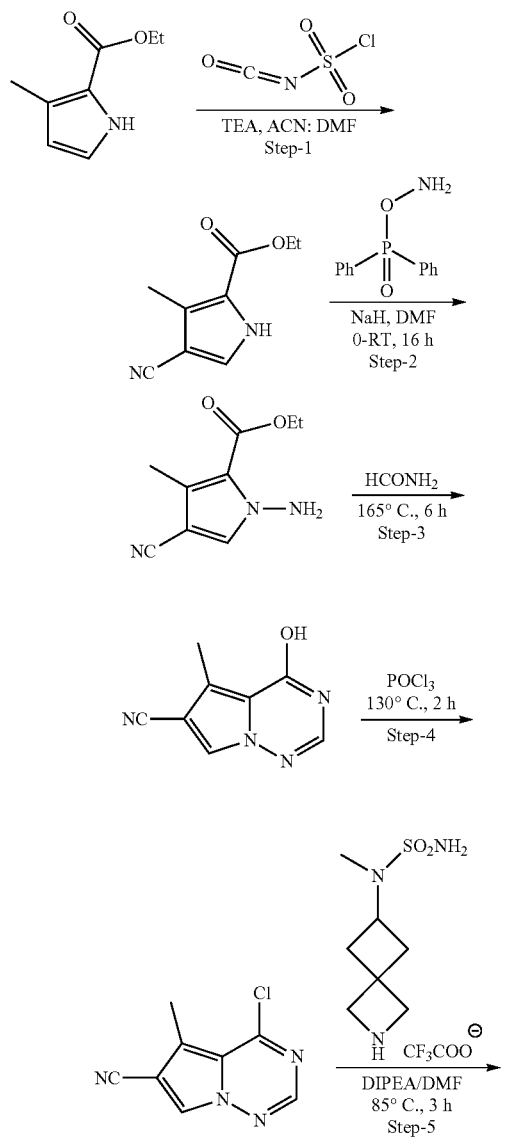

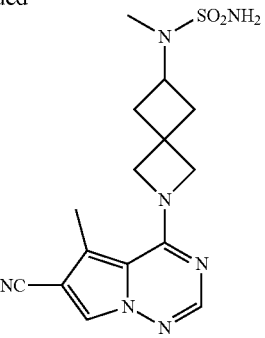

Step-1: Synthesis of ethyl 4-cyano-3-methyl-1H-pyrrole-2-carboxylate: To a solution of ethyl 3-methyl-1H-pyrrole-2-carboxylate (1.0 g, 6.535 mmol, 1.0 eq) in CH$_3$CN (5 mL) at −10° C. was added a solution of Chlorosulfonyl isocyanate (0.924 g, 6.535 mmol, 1.0 eq) in CH$_3$CN (5 mL) over 5 min. The solution rapidly became yellow and solid precipitate was deposited. N,N-dimethylformamide (1 mL) was added in reaction mixture and solution became colorless. To this reaction mixture was then added TEA (1.8 mL, 13.07 mmol, 2.0 eq) then white precipitate was formed. The reaction mixture was allowed to stir at RT for 2 h. Progress of reaction is monitored using TLC. After completion, reaction mixture poured onto ice water and extracted with ethyl acetate (3×100 mL). Combined organic layer was washed with brine (100 mL) and dried over anhydrous sodium sulfate. Removal of solvent under reduced pressure afforded ethyl 4-cyano-3-methyl-1H-pyrrole-2-carboxylate (0.9 g, 81.81%). LCMS: 179 [M+1]$^+$ Step-2: Synthesis of ethyl 1-amino-4-cyano-3-methyl-1H-pyrrole-2-carboxylate: To a suspension of sodium hydride (0.286 g, 7.162 mmol, 1.5 eq) in DMF (25 mL) was added a solution of ethyl 4-cyano-3-methyl-1H-pyrrole-2-carboxylate (0.850 g, 4.775 mmol, 1 eq) in DMF (25 mL) at 0° C. The reaction mixture was allowed to stir at 0° C. for 30 minutes and added O-(diphenylphosphoryl) hydroxylamine (1.6 g, 7.162 mmol, 1.5 eq) portion wise. The reaction mixture was allowed to stir at RT for 12 h. Progress of reaction is monitored using TLC. After completion, DMF was removed under reduced pressure; residue was diluted with water (300 mL) and extracted with ethyl acetate (3×200 mL). Combined organic layer was washed with brine (250 mL) and dried over anhydrous sodium sulfate. Removal of solvent under reduced pressure afforded ethyl 1-amino-4-cyano-3-methyl-1H-pyrrole-2-carboxylate (4.0 g, 60.60%). LCMS: 194 [M+1]$^+$ Step-3: Synthesis of 4-hydroxy-5-methylpyrrolo[1,2-f][1,2,4]triazine-6-carbonitrile: To a solution of ethyl 1-amino-4-cyano-3-methyl-1H-pyrrole-2-carboxylate (0.5 g, 2.590 mmol, 1 eq) in formamide (10 mL) was allowed to stir at 165° C. for 16 h. Progress of reaction is monitored by TLC. After completion, reaction mixture was diluted with cold water (100 mL) and allowed to stir for 10 minutes. Solid was filtered, washed with water followed by hexane and dried under vacuum to afford 4-hydroxy-5-methylpyrrolo[1,2-f][1,2,4]triazine-6-carbonitrile (0.3 g, 77.72%). LCMS: 175 [M+1]$^+$ Step-4: Synthesis of 4-chloro-5-methylpyrrolo[1,2-f][1,2,4]triazine-6-carbonitrile: To a solution of 4-hydroxy-5-methylpyrrolo[1,2-f][1,2,4]triazine-6-carbonitrile (0.3 g, 2.013 mmol, 1 eq) in N,N-Diisopropylethylamine was added a solution of phosphoryl oxychloride (0.188 mL, 2.013 mmol, 1 eq) at 0° C. and the reaction mixture was allowed to stir at 0° C. for 10 minutes. The reaction mixture was allowed to stir at 130° C. for 2 h. Progress of reaction is monitored by TLC. After completion, reaction mixture was diluted with cold water (30 mL) and extracted with ethyl acetate (3×20 mL). Combined organic layer was washed with brine (20 mL) and dried over anhydrous sodium sulfate. Solvent was removed under reduced pressure to give 4-chloro-5-methylpyrrolo[1,2-f][1,2,4]triazine-6-carbonitrile (0.22 g, 57%). LCMS: 193 [M+1]$^+$ Step-5: Synthesis of N-(2-(6-cyano-5-methylpyrrolo[1,2-f][1,2,4]triazin-4-yl)-2-azaspiro[3.3]heptan-6-yl)-N-methylsulfamamide: A mixture of 4-chloro-5-methylpyrrolo[1,2-f][1,2,4]triazine-6-carbonitrile (0.2 g, 1.04 mmol, 1 eq), N-methyl-N-(2-azaspiro[3.3]heptan-6-yl)sulfamamide, 2,2,2-trifluoroacetate salt (0.350 g, 1.14 mmol, 1.1 eq) and DIPEA (0.272 mL, 1.562 mmol, 1.5 eq) in DMF (10 mL) was allowed to stir at 85° C. for 3 h. Progress of reaction was monitored by TLC. After completion, reaction mixture was diluted with cold water (30 mL) and extracted with ethyl acetate (3×50 mL). Combined organic layer was washed with brine (3×30 mL) and dried over anhydrous sodium sulfate. Removal of solvent under reduced pressure to obtain the crude which was purified by reversed phase to afford N-(2-(6-cyano-5-methylpyrrolo[1,2-f][1,2,4]triazin-4-yl)-2-azaspiro[3.3]heptan-6-yl)-N-methylsulfamamide (10 mg, 2.65%). LCMS: 362[M+1]$^+$; $^1$H NMR (400 MHz, DMSO-d$_6$) δ ppm 8.37 (s, 1H), 7.92 (s, 1H), 6.70 (s, 2H), 4.48 (s, 2H), 4.35 (s, 2H), 3.74-3.79 (m, 1H), 2.6-2.22 (m, 10H).

Example-79: Synthesis of N-(2-(7-bromo-5-methylpyrrolo[1,2-f][1,2,4]triazin-4-yl)-2-azaspiro[3.3]heptan-6-yl)-N-methylsulfamamide, (Compound 1.79)

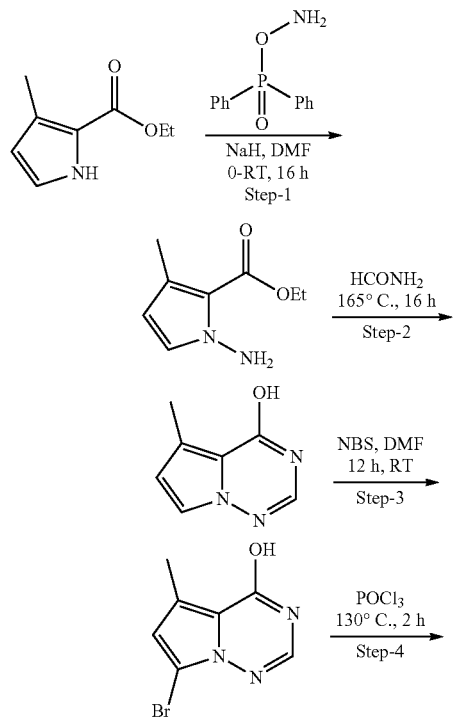

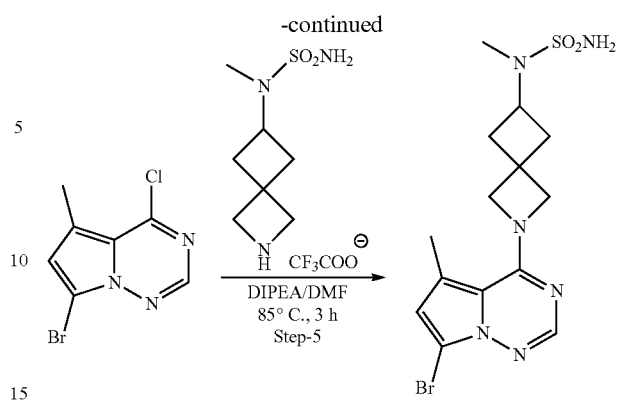

Step-1: Synthesis of ethyl 1-amino-3-methyl-1H-pyrrole-2-carboxylate: To a suspension of sodium hydride (2.352 g, 58.82 mmol, 1.5 eq) in DMF (25 mL) was added a solution of ethyl 3-methyl-1H-pyrrole-2-carboxylate (6.0 g, 39.21 mmol, 1 eq) in DMF (120 mL) at 0° C. The reaction mixture was allowed to stir at 0° C. for 30 minutes and was added O-(diphenylphosphoryl)hydroxylamine (15.53 g, 65.65 mmol, 1.7 eq) portion wise. The reaction mixture was allowed to stir at RT for 12 h. Progress of reaction was monitored by TLC. After completion, THF was removed under reduced pressure; residue was diluted with water (300 mL) and extracted with ethyl acetate (3×200 mL). Combined organic layer was washed with brine (250 mL) and dried over anhydrous sodium sulfate. Removal of solvent under reduced pressure afforded ethyl 1-amino-3-methyl-1H-pyrrole-2-carboxylate (4.0 g, 60.60%). LCMS: 169 [M+1]$^+$ Step-2: Synthesis of 5-methylpyrrolo[1,2-f][1,2,4]triazin-4-ol: A solution of ethyl 1-amino-3-methyl-1H-pyrrole-2-carboxylate (4 g, 23.95 mmol, 1 eq) in formamide (40 mL) was allowed to stir at 165° C. for 16 h. Progress of reaction is monitored by TLC. After completion, reaction mixture was cooled to RT, diluted with cold water (100 mL) under stirring. The formed precipitate was filtered and dried under vacuum to afford 5-methylpyrrolo[1,2-f][1,2,4]triazin-4-ol (3.0 g, 85.71%). LCMS: 150 [M+1]$^+$ Step-3: Synthesis of 7-bromo-5-methylpyrrolo[1,2-f][1,2,4]triazin-4-ol: To a solution of 5-methylpyrrolo[1,2-f][1,2,4]triazin-4-ol (1.0 g, 6.71 mmol, 1.0 eq) in DMF (20 mL) was added N-Bromosuccinimide (1.20 g, 6.71 mmol, 1.0 eq) portion wise. The reaction mixture was allowed to stir at RT for 72 h. Progress of reaction is monitored using TLC. After completion, reaction mixture was diluted with water (30 mL) and extracted with ethyl acetate (3×20 mL). Combined organic layer was washed with brine (3×10 mL) and dried over anhydrous sodium sulfate. Removal of solvent under reduced pressure afforded the crude which was purified by Combi-Flash to obtain 7-bromo-5-methylpyrrolo[1,2-f][1,2,4]triazin-4-ol (0.8 g, 52.63%). LCMS: 228 [M+1]$^+$ Step-4: Synthesis of 7-bromo-4-chloro-5-methylpyrrolo[1,2-f][1,2,4]triazine: A mixture of 7-bromo-5-methylpyrrolo[1,2-f][1,2,4]triazin-4-ol (0.2 g, 0.877 mmol, 1 eq) in phosphoryl oxychloride (5 mL) was allowed to stir at 130° C. for 2 h. Progress of reaction is monitored by TLC. After completion, reaction mixture was diluted with cold water (30 mL) and extracted with ethyl acetate (3×20 mL). Combined organic layer was washed with brine (20 mL) and dried over anhydrous sodium sulfate. Solvent was removed under reduced pressure to give 7-bromo-4-chloro-5-methylpyrrolo[1,2-f][1,2,4]triazine (0.15 g, 70%). LCMS: 246 [M+1]$^+$ Step-5: Synthesis of N-(2-(7-bromo-5-methylpyrrolo[1,2-f][1,2,4]triazin-4-yl)-2-azaspiro[3.3]heptan-6-yl)-N-methylsulfamamide: A mixture of 7-bromo-4-chloro-5-methylpyrrolo[1,2-f][1,2,4]triazine (0.15 g, 0.612 mmol, 1 eq), N-2-azaspiro[3.3]hept-6-yl-N-methylsulfuric diamide trifloroacetic acid (0.207 g, 0.673 mmol, 1.1 eq) and DIPEA (0.213 mL, 1.224 mmol, 2.0 eq) in DMF (10 mL) was allowed to stir at 85° C. for 3 h. Progress of reaction was monitored by TLC. After completion, reaction mixture was diluted with cold water (30 mL) and extracted with ethyl acetate (3×50 mL). Combined organic layer was washed with brine (3×30 mL) and dried over anhydrous sodium sulfate. Removal of solvent under reduced pressure to obtain the crude which was purified by reversed phase to afford N-(2-(7-bromo-5-methylpyrrolo[1,2-f][1,2,4]triazin-4-yl)-2-azaspiro[3.3]heptan-6-yl)-N-methylsulfamamide (15 mg, 6.05%). LCMS: 415[M+1]$^+$, $^1$H NMR (400 MHz, DMSO-d$_6$) δ ppm 7.91 (s, 1H), 6.72-6.69 (m, 3H), 4.42 (s, 2H), 4.29 (s, 2H), 3.80-3.76 (m, 1H), 2.54-2.38 (m, 10H).

Example-80: Synthesis of N-(2-(7-fluoro-5-methylpyrrolo[1,2-f][1,2,4]triazin-4-yl)-2-azaspiro[3.3]heptan-6-yl)-N-methylsulfamamide, (Compound 1.80)

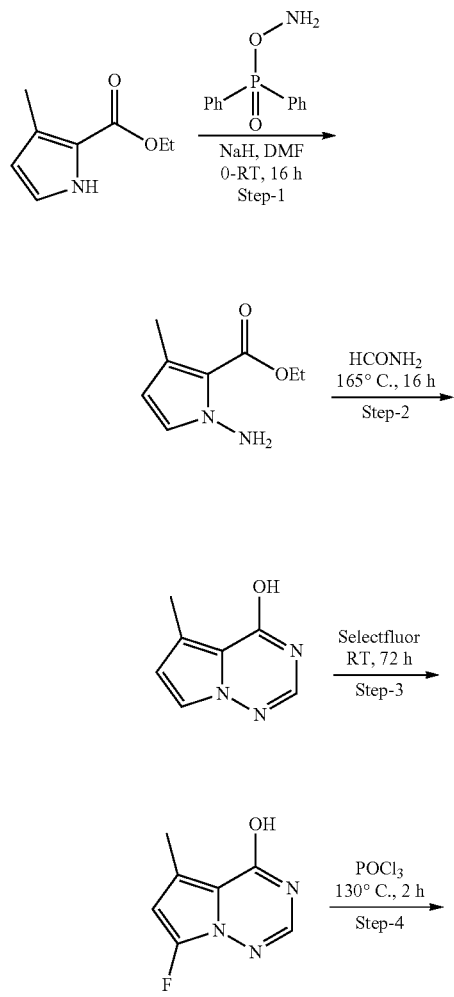

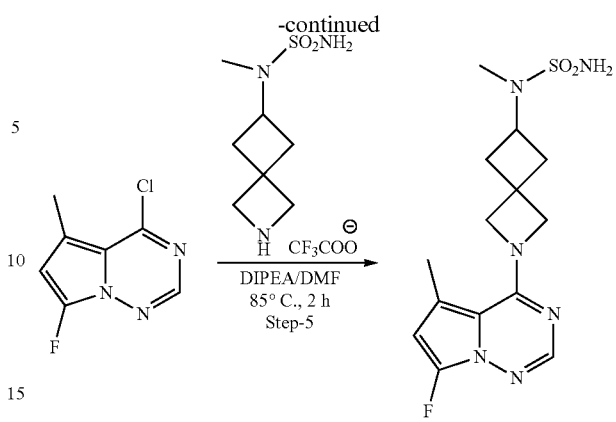

Step-1: Synthesis of ethyl 1-amino-3-methyl-1H-pyrrole-2-carboxylate: To a suspension of sodium hydride (2.352 g, 58.82 mmol, 1.5 eq) in DMF (25 mL) was added a solution of ethyl 3-methyl-1H-pyrrole-2-carboxylate (6.0 g, 39.21 mmol, 1 eq) in DMF (120 mL) at 0° C. and the reaction mixture was allowed to stir at 0° C. for 30 minutes, followed by addition of O-(diphenylphosphoryl)hydroxylamine (15.53 g, 65.65 mmol, 1.7 eq) portion wise. The reaction mixture was allowed to stir at RT for 12 h. Progress of reaction is monitored using TLC. After completion, reaction mixture was diluted with ice-cold water (300 mL) and extracted with ethyl acetate (3×200 mL). Combined organic layer was washed with brine (250 mL) and dried over anhydrous sodium sulfate. Removal of solvent under reduced pressure afforded ethyl 1-amino-3-methyl-1H-pyrrole-2-carboxylate (4.0 g, 60.60%). LCMS: 169 [M+1]$^+$ Step-2: Synthesis of 5-methylpyrrolo[1,2-f][1,2,4]triazin-4-ol: A solution of ethyl 1-amino-3-methyl-1H-pyrrole-2-carboxylate (4 g, 23.95 mmol, 1 eq) in formamide (40 mL) was allowed to stir at 165° C. for 16 h. Progress of reaction is monitored by TLC. After completion, reaction mixture was diluted with cold water (600 mL) and allowed to stir for 10 minutes. Solid was filtered, washed with water followed by hexane and dried under vacuum to afford 5-methylpyrrolo[1,2-f][1,2,4]triazin-4-ol (3.0 g, 85.71%). LCMS:150 [M+1]$^+$ Step-3: Synthesis of 7-fluoro-5-methylpyrrolo[1,2-f][1,2,4]triazin-4-ol: To a solution of ethyl 5-methylpyrrolo[1,2-f][1,2,4]triazin-4-ol (0.1 g, 0.666 mmol, 1.0 eq) in DMF (10 mL) was added Selectfluor (0.235 g, 0.666 mmol, 1.0 eq) portion wise. The reaction mixture was allowed to stir at RT for 72 h. Progress of reaction is monitored using TLC. After completion, it was diluted with water (30 mL) and extracted with ethyl acetate (3×20 mL). Combined organic layer was washed with brine (3×10 mL) and dried over anhydrous sodium sulfate. Removal of solvent under reduced pressure afforded the crude which was purified by Combi-Flash to obtain the 7-fluoro-5-methylpyrrolo[1,2-f][1,2,4]triazin-4-ol (0.12 g, 54.05%). LCMS: 168 [M+1]$^+$ Step-4: Synthesis of 4-chloro-7-fluoro-5-methylpyrrolo[1,2-f][1,2,4]triazine: A mixture of 7-fluoro-5-methylpyrrolo[1,2-f][1,2,4]triazin-4-ol (0.12 g, 0.718 mmol, 1 eq) in phosphoryl oxychloride (2 mL) was allowed to stir at 130° C. for 2 h. Progress of reaction is monitored by TLC. After completion, reaction mixture was diluted with cold water (30 mL) and extracted with ethyl acetate (3×20 mL). Combined organic layer was washed with brine (20 mL) and dried over anhydrous sodium sulfate. Solvent was removed under reduced pressure to give 4-chloro-7-fluoro-5-methylpyrrolo[1,2-f][1,2,4]triazine (0.12 g, 90%). LCMS: 186 [M+1]+

Step-5: Synthesis of N-(2-(7-fluoro-5-methylpyrrolo[1,2-f][1,2,4]triazin-4-yl)-2-azaspiro[3.3]heptan-6-yl)-N-methylsulfamamide: A mixture of 4-chloro-7-fluoro-5-methylpyrrolo[1,2-f][1,2,4]triazine (120 mg, 0.648 mmol, 1 eq), N-methyl-N-(2-azaspiro[3.3]heptan-6-yl)sulfamamide 2,2,2-trifluoroacetaldehyde (237 mg, 0.778 mmol, 1.1 eq) and DIPEA (0.169 mL, 0.972 mmol, 1.5 eq) in DMF (10 mL) was allowed to stir at 85° C. for 3 h. Progress of reaction was monitored by TLC. After completion, reaction mixture was diluted with cold water (30 mL) and extracted with ethyl acetate (3×50 mL). Combined organic layer was washed with brine (3×30 mL) and dried over anhydrous sodium sulfate. Removal of solvent under reduced pressure to obtain the crude, which was purified by reversed phase to afford N-(2-(7-fluoro-5-methylpyrrolo[1,2-f][1,2,4]triazin-4-yl)-2-azaspiro[3.3]heptan-6-yl)-N-methylsulfamamide (7 mg, 3.05%). LCMS: 355[M+1]+, $^1$H NMR (400 MHz, DMSO-$d_6$) δ ppm 7.80 (s, 1H), 6.70 (s, 2H), 6.27 (m, 1H), 4.41 (s, 2H), 4.29 (s, 2H), 3.74-3.79 (m, 1H), 2.53 (s, 3H), 2.29-2.43 (m, 7H)

Example-81: Synthesis of N-(2-(7-chloro-5-methylpyrrolo[2,1-f][1,2,4]triazin-4-yl)-2-azaspiro[3.3]heptan-6-yl)-N-cyclopropylsulfamamide, (Compound 1.81)

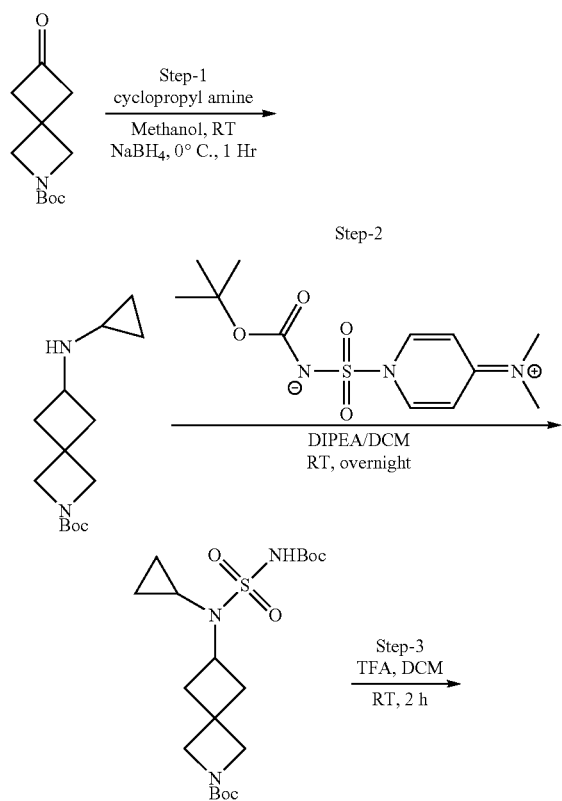

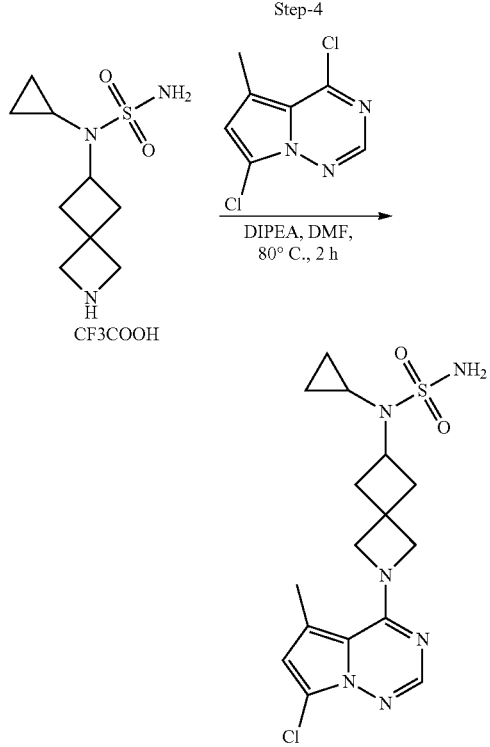

Step-1: Synthesis of tert-butyl 6-(cyclopropylamino)-2-azaspiro[3.3]heptane-2-carboxylate: A suspension of tert-butyl 6-oxo-2-azaspiro[3.3]heptane-2-carboxylate (250 mg, 1.18 mmol, 1.0 eq), cyclopropylamine (81 mg, 1.41 mmol, 1.2 eq) in methanol (3 mL) was stirred at RT for overnight. After overnight stirring, NaBH$_4$ (67 mg, 1.77 mmol, 1.5 eq) was added into above reaction mixture portion wise at 0° C. and allowed to stir for 1 h at 0° C. Progress of reaction was monitored by TLC. After completion, reaction mixture was concentrated under reduced pressure to get residue which was diluted with water (30 mL) and extracted with DCM (2×50 mL). Combined organic layer was washed with brine (1×20 mL) and dried over anhydrous sodium sulfate. Removal of solvent under reduced pressure to afford tert-butyl 6-(cyclopropylamino)-2-azaspiro[3.3]heptane-2-carboxylate (255 mg, 85%) which was used in the next step without purification.

Step-2: Synthesis of tert-butyl 6-((N-(tert-butoxycarbonyl)sulfamoyl)(cyclopropyl)amino)-2-azaspiro[3.3]heptane-2-carboxylate: To a solution of tert-butyl 6-(cyclopropylamino)-2-azaspiro[3.3]heptane-2-carboxylate (250 mg, 0.99 mmol, 1.0 eq) in DCM (8 mL) were added N-(tert-butoxycarbonyl)-N-[4-(dimethylazaniumylidene)-1,4-dihydropyridin-1-ylsulfonyl]azanide (359 mg, 1.11 mmol, 1.2 eq) and DIPEA (191 mg, 1.48 mmol, 1.5 eq) and the mixture was allowed to stir at RT for overnight. Progress of reaction was monitored by TLC. After completion, reaction mixture was diluted with water (25 mL) and extracted with DCM (2×50 mL). Combined organic layer was washed with brine (1×20 mL), dried over anhydrous sodium sulfate and concentrated under reduced pressure to afford tert-butyl 6-((N-(tert-butoxycarbonyl)sulfamoyl)(cyclopropyl)amino)-2-azaspiro[3.3]heptane-2-carboxylate (300 mg, 70%).

Step-3: Synthesis of N-cyclopropyl-N-(2-azaspiro[3.3]heptan-6-yl)sulfamamide trifluoroacetate: To a solution of tert-butyl 6-((N-(tert-butoxycarbonyl)sulfamoyl)(cyclopropyl)amino)-2-azaspiro[3.3]heptane-2-carboxylate (300 mg, 0.69 mmol, 1.0 eq) in DCM (5 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-cyclopropyl-N-(2-azaspiro[3.3]heptan-6-yl)sulfamamide trifluoroacetate (210 mg, 88%).

Step-4: Synthesis of N-(2-(7-chloro-5-methylpyrrolo[2,1-f][1,2,4]triazin-4-yl)-2-azaspiro[3.3]heptan-6-yl)-N-cyclopropylsulfamamide: A suspension of N-cyclopropyl-N-(2-azaspiro[3.3]heptan-6-yl)sulfamamide trifluoroacetate (162 mg, 0.49 mmol, 1.0 eq), 4,7-dichloro-5-methylpyrrolo[2,1-f][1,2,4]triazine (100 mg, 0.49 mmol, 1.0 eq) and DIPEA (128 mg, 0.99 mmol, 2.0 eq) in DMF (1.5 mL) was allowed to stir at 80° C. for 2 h. Progress of reaction was monitored by TLC and LCMS. After completion of reaction, reaction mixture was diluted with water (30 mL) and extracted with ethyl acetate (2×50 mL). Combined organic layer was washed with brine (1×20 mL), dried over anhydrous sodium sulfate and concentrated under reduced pressure to get crude which was purified by using reversed phase chromatography to afford N-(2-(7-chloro-5-methylpyrrolo[2,1-f][1,2,4]triazin-4-yl)-2-azaspiro[3.3]heptan-6-yl)-N-cyclopropylsulfamamide (2.56 mg, 1.3%). LCMS: 397 [M+1]$^+$; $^1$H NMR (400 MHz, DMSO-d$_6$) δ ppm 7.91 (s, 1H), 6.83 (br. s., 2H), 6.64 (s, 1H), 4.43 (br. s., 2H), 4.29 (br. s., 2H), 3.92-3.80 (m, 1H), 3.17 (d, J=5.3 Hz, 1H), 2.40 (s, 3H), 2.05 (br. s., 2H), 1.99 (br. s., 1H), 1.65 (s, 1H), 0.69 (br. s., 4H) Example-82: Synthesis of N-(2-(7-chloro-5-methylpyrrolo[2,1-f][1,2,4]triazin-4-yl)-2-azaspiro[3.3]heptan-6-yl)-N-isopropylsulfamamide, (Compound 1.82)

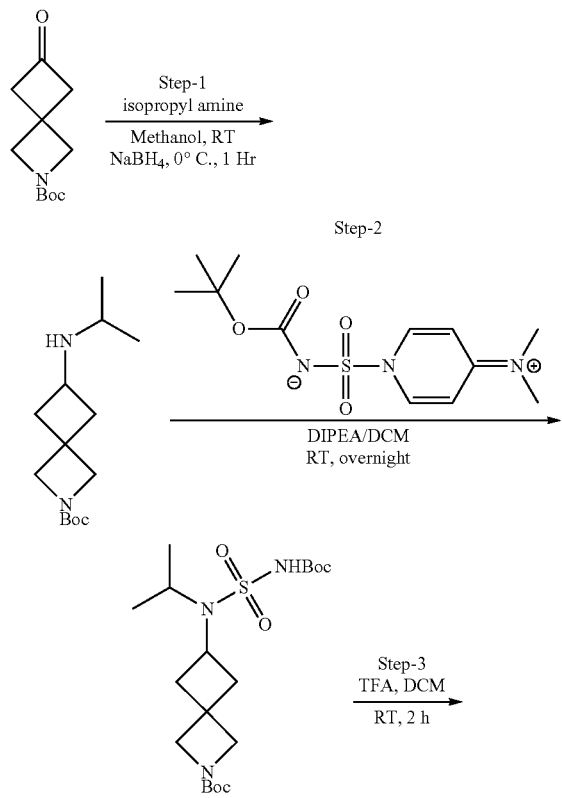

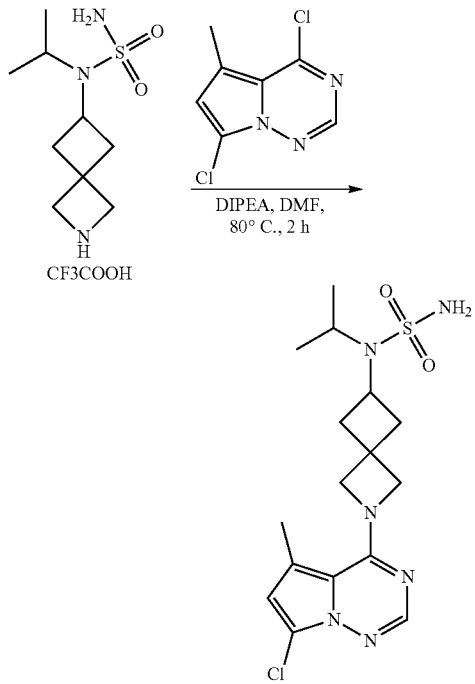

Step-1: Synthesis of tert-butyl 6-(isopropylamino)-2-azaspiro[3.3]heptane-2-carboxylate: A suspension of tert-butyl 6-oxo-2-azaspiro[3.3]heptane-2-carboxylate (250 mg, 1.18 mmol, 1.0 eq), isopropylamine (84 mg, 1.42 mmol, 1.2 eq) in methanol (3 mL) was stirred at RT for overnight. After overnight stirring, NaBH$_4$ (67 mg, 1.77 mmol, 1.5 eq) was added into above reaction mixture portion wise at 0° C. and allowed to stir the reaction mixture for 1 h at 0° C. Progress of reaction was monitored by TLC. After completion, reaction mixture was concentrated under reduced pressure to get residue which was diluted with water (20 mL) and extracted with DCM (2×50 mL). Combined organic layer was washed with brine (1×20 mL), dried over anhydrous sodium sulfate and concentrated under reduced pressure to afford tert-butyl 6-(isopropylamino)-2-azaspiro[3.3]heptane-2-carboxylate (252 mg, 84%) which was used into the next step without purification.

Step-2: Synthesis of tert-butyl 6-((N-(tert-butoxycarbonyl)sulfamoyl)(isopropyl)amino)-2-azaspiro[3.3]heptane-2-carboxylate: To a solution of tert-butyl 6-(isopropylamino)-2-azaspiro[3.3]heptane-2-carboxylate (240 mg, 0.94 mmol, 1.0 eq) in DCM (8 mL) were added N-(tert-butoxycarbonyl)-N-[4-(dimethylazaniumylidene)-1,4-dihydropyridin1ylsulfonyl]azanide (342 mg, 1.13 mmol, 1.2 eq) and DIPEA (182 mg, 1.41 mmol, 1.5 eq) and the mixture was allowed to stir at RT for overnight. Progress of reaction was monitored by TLC. After completion, reaction mixture was diluted with water (25 mL) and extracted with DCM (2×150 mL). Combined organic layer was washed with brine (1×20 mL), dried over anhydrous sodium sulfate and concentrated under reduced pressure to afford tert-butyl 6-((N-(tert-butoxycarbonyl)sulfamoyl)(isopropyl)amino)-2-azaspiro[3.3]heptane-2-carboxylate (300 mg, 73%).

Step-3: Synthesis of N-isopropyl-N-(2-azaspiro[3.3]heptan-6-yl)sulfamamide trifluoroacetate: To a solution of tert-butyl 6-((N-(tert-butoxycarbonyl)sulfamoyl)(isopropyl)amino)-2-azaspiro[3.3]heptane-2-carboxylate (300 mg, 0.692 mmol, 1.0 eq) in DCM (5 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-isopropyl-N-(2-azaspiro[3.3]heptan-6-yl)sulfamamide trifluoroacetate (250 mg, 95.8%).

Step-4: Synthesis of N-(2-(7-chloro-5-methylpyrrolo[2,1-f][1,2,4]triazin-4-yl)-2-azaspiro[3.3]heptan-6-yl)-N-isopropylsulfamamide: A suspension of N-isopropyl-N-(2-azaspiro[3.3]heptan-6-yl)sulfamamide trifluoroacetate (155 mg, 0.448 mmol, 1.0 eq), 4,7-dichloro-5-methylpyrrolo[2,1-f][1,2,4]triazine (90 mg, 0.448 mmol, 1.0 eq) and DIPEA (115 mg, 0.896 mmol, 2.0 eq) in DMF (1.5 mL) was allowed to stir at 80° C. for 2 h. Progress of reaction was monitored by TLC and LCMS. After completion, reaction mixture was diluted with water (20 mL) and extracted with ethyl acetate (1×50 mL). Combined organic layer was washed with brine (1×20 mL), dried over anhydrous sodium sulfate and concentrated under reduced pressure to get crude which was purified using reversed phase chromatography to afford N-(2-(7-chloro-5-methylpyrrolo[2,1-f][1,2,4]triazin-4-yl)-2-azaspiro[3.3]heptan-6-yl)-N-isopropylsulfamamide (9.5 mg, 5.3%). LCMS: 399 [M+1]$^+$; $^1$H NMR (400 MHz, DMSO-$d_6$) δ ppm 7.90 (s, 1H), 6.69-6.61 (m, 3H), 4.43 (s, 2H), 4.28 (s, 2H), 3.85-3.75 (m, 2H), 2.67 (t, J=10.7 Hz, 3H), 2.43-2.33 (m, 4H), 1.14 (d, J=7.0 Hz, 6H).

Example-83: Synthesis of N-(2-(1-(7-chloro-5-methylpyrrolo[2,1-f][1,2,4]triazin-4-yl)azetidin-3-yl)ethyl)-N-isopropylsulfamamide, (Compound 1.83)

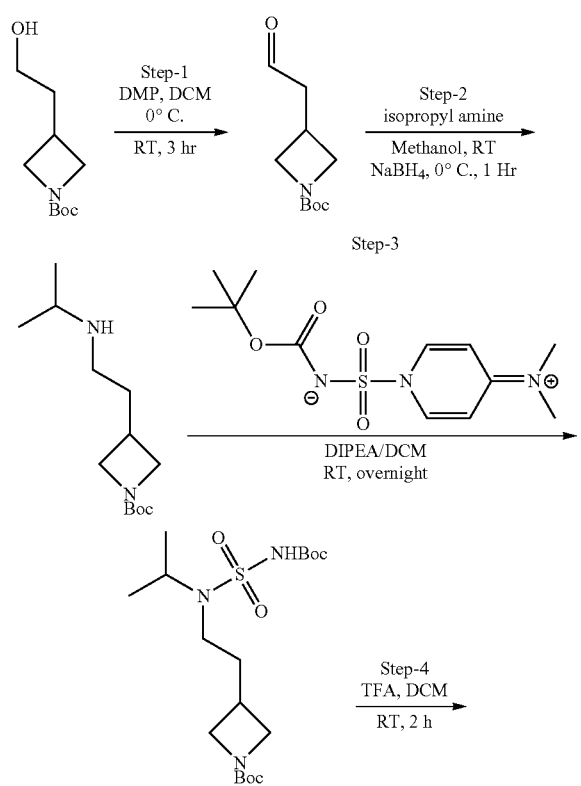

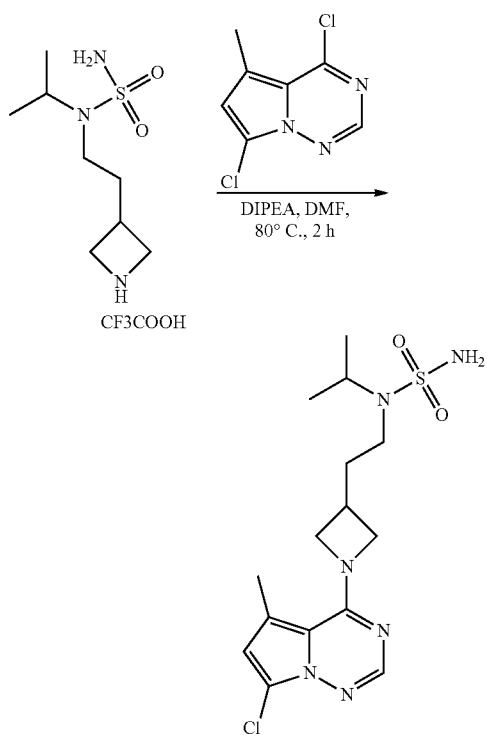

Step-1: Synthesis of tert-butyl 3-(2-oxoethyl)azetidine-1-carboxylate: A suspension of (1.0 g, 4.95 mmol, 1.0 eq) in DCM (40 mL) at 0° C. was added DMP (6.29 g, 14.8 mmol, 3.0 eq) was added portion wise at 0° C. into above reaction mixture. After addition, reaction mixture was stirred at RT for 2 h. Progress of reaction was monitored by TLC. After completion, reaction mixture was concentrated under reduced pressure to get residue which was diluted with water (150 mL) and extracted with DCM (3×250 mL). Combined organic layer was washed with brine (3×50 mL), dried over anhydrous sodium sulfate and concentrated under reduced pressure to afford tert-butyl 3-(2-oxoethyl)azetidine-1-carboxylate (1.1 g, 92%) which was used in the next step without purification.

Step-2: Synthesis of tert-butyl 3-(2-(isopropylamino)ethyl)azetidine-1-carboxylate: A suspension of (500 mg, 2.5 mmol, 1 eq), isopropylamine (177 mg, 3.01 mmol, 1.2 eq) in methanol (10 mL) was stirred at RT for overnight. After overnight stirring, NaBH$_4$ (142 mg, 3.75 mmol, 1.5 eq) was added to reaction mixture portion wise at 0° C. and allowed to stir the reaction mixture for 1 h at 0° C. Progress of reaction was monitored by TLC. After completion, reaction mixture was concentrated under reduced pressure to get residue which was diluted with water (150 mL) and extracted with ethyl acetate (3×150 mL). Combined organic layer was washed with brine (3×50 mL), dried over anhydrous sodium sulfate and concentrated under reduced pressure to afford tert-butyl 3-(2-(isopropylamino)ethyl)azetidine-1-carboxylate (470 mg, 77.5%) which was used in the next step without purification.

Step-3: Synthesis of tert-butyl 3-(2-((N-(tert-butoxycarbonyl)sulfamoyl)(isopropyl)amino)ethyl)azetidine-1-carboxylate: To a solution of tert-butyl 3-(2-(isopropylamino)ethyl)azetidine-1-carboxylate (470 mg, 1.94 mmol, 1.0 eq) in DCM (6 mL) were added N-(tert-butoxycarbonyl)-N-[4-

(dimethylazaniumylidene)-1,4-dihydropyridin1ylsulfonyl] azanide (703 mg, 2.32 mmol, 1.2 eq) and DIPEA (650 mg, 5.02 mmol, 2.5 eq) and the mixture was allowed to stir at RT for overnight. Progress of reaction was monitored by TLC. After completion, reaction mixture was diluted with water (50 mL) and extracted with DCM (2×150 mL). Combined organic layer was washed with brine (1×50 mL), dried over anhydrous sodium sulfate and concentrated under reduced pressure to afford tert-butyl tert-butyl 3-(2-((N-(tert-butoxy-carbonyl)sulfamoyl)(isopropyl)amino)ethyl)azetidine-1-carboxylate (400 mg, 51%).

Step-4: Synthesis of N-(2-(azetidin-3-yl)ethyl)-N-isopropylsulfamamide trifluoroacetate: To a solution of tert-butyl 3-(2-((N-(tert-butoxycarbonyl)sulfamoyl)(isopropyl)amino) ethyl)azetidine-1-carboxylate (400 mg, 0.922 mmol, 1 eq) in DCM (5 mL) was added TFA (1.6 mL) and was allowed to stir at RT for 2 h. Progress of reaction was monitored by TLC. After completion, reaction mixture was concentrated under reduced pressure to afford crude which was triturated with diethyl ether to afford N-(2-(azetidin-3-yl)ethyl)-N-isopropylsulfamamide trifluoroacetate (300 mg, 97%).

Step-5: Synthesis of N-(2-(1-(7-chloro-5-methylpyrrolo[2,1-f][1,2,4]triazin-4-yl)azetidin-3-yl)ethyl)-N-isopropylsulfamamide: A suspension of N-(2-(azetidin-3-yl)ethyl)-N-isopropylsulfamamide trifluoroacetate (95 mg, 0.298 mmol, 1.0 eq), 4,7-dichloro-5-methylpyrrolo[2,1-f][1,2,4] triazine (60 mg, 0.298 mmol, 1.0 eq) and DIPEA (77 mg, 0.596 mmol, 2.0 eq) in DMF (1.5 mL) was allowed to stir at 80° C. for 2 h. Progress of reaction was monitored by TLC and LCMS. After completion, reaction mixture was diluted with water (10 mL) and extracted with ethyl acetate (1×50 mL). Combined organic layer was washed with brine (1×10 mL), dried over anhydrous sodium sulfate and concentrated under reduced pressure to under reduced pressure to get crude which was purified using reversed phase chromatography to afford N-(2-(1-(7-chloro-5-methylpyrrolo[2,1-f][1,2,4]triazin-4-yl)azetidin-3-yl)ethyl)-N-isopropylsulfamamide (21.47 mg, 18.6%). LCMS: 387 [M+1]$^+$; $^1$H NMR (400 MHz, DMSO-d$_6$) δ ppm 7.90 (s, 1H), 6.63 (s, 3H), 4.46 (t, J=8.8 Hz, 2H), 4.02 (dd, J=5.7, 8.8 Hz, 2H), 3.93-3.87 (m, 1H), 2.96 (t, J=7.2 Hz, 2H), 2.77-2.68 (m, 1H), 2.39 (s, 3H), 1.94-1.87 (m, 2H), 1.11 (d, J=7.0 Hz, 6H)

Example-84: Synthesis of N-(2-(1-(7-chloro-5-methylpyrrolo[1,2-f][1,2,4]triazin-4-yl)azetidin-3-yl) ethyl)-N-methylsulfamide, (Compound 1.84)

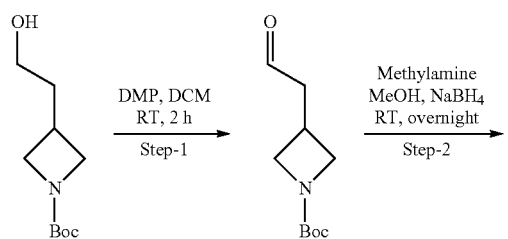

Step-1: Synthesis of tert-butyl 3-(2-oxoethyl) azetidine-1-carboxylate: To a solution of the tert-butyl 3-(2-hydroxyethyl)azetidine-1-carboxylate (0.5 g, 2.48 mmol, 1 eq) in dichloromethane (18 mL) at 0° C. was added Dess-Martin peridionane (DMP) (3.1 g, 7.46 mmol 3.0 eq) and the reaction mixture was stirred at RT for 2 h. Progress of reaction was monitored by TLC. After completion, reaction mixture poured on crushed ice and extracted with ethyl acetate (3×50 mL). Combined organic layer was washed with brine (20 mL) and dried over anhydrous sodium sulfate. Removal of solvent under reduced pressure gave crude which was triturated with pentane (100 mL) at 0° C. and filtered. Filtrate was concentrated under vacuum to afford tert-butyl 3-(2-(methylamino)ethyl)azetidine-1-carboxylate (400 mg, 80.8%). $^1$H NMR (400 MHz, CDCl$_3$-d) δ ppm 9.77 (s, 1H), 4.13-4.08 (m, 2H), 3.67-3.52-(m, 2H), 2.87-2.77 (m, 1H), 2.66-2.61 (m, 2H), 1.56 (s, 3H), 1.43 (s, 9H).

Step-2: Synthesis of tert-butyl 3-(2-((N-(tert-butoxycarbonyl) sulfamoyl)(methyl)amino)ethyl)azetidine-1-carboxylate: To a stirred solution of tert-butyl 3-(2-oxoethyl) azetidine-1-carboxylate (400 mg, 2.00 mmol, 1.0 eq) in MeOH (15.0 mL) was added Methylamine (1.5 mL, 3.011 mmol, 1.5 eq) at 0° C. The resulting mixture was stirred at room temperature for overnight. The reaction mixture was

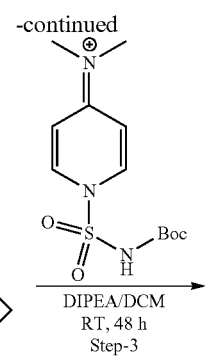

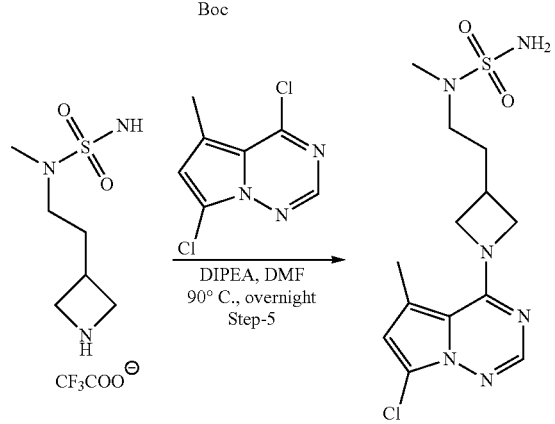

then cooled to 0° C. followed by addition of NaBH₄ (136 mg, 4.00 mmol, 3.0 eq) at 0° C. The reaction mixture was stirred at room temperature for 2 h. The progress of reaction was monitored by TLC. The reaction mixture was concentrated, basified with NaHCO₃ solution (20 mL), extracted with EtOAc (2×150 mL). The combined organic layer was washed with water (50 mL), with brine (50 mL), dried over Na₂SO₄ concentrated to get crude product. The crude product was triturated in pentane to afford tert-butyl 3-(2-(methylamino)ethyl) azetidine-1-carboxylate (500 mg, 116.27%) as liquid, which was further used further next step without purification.

Step-3: Synthesis of tert-butyl 3-(2-((N-(tert-butoxycarbonyl) sulfamoyl)(methyl)amino)ethyl)azetidine-1-carboxylate: To a solution of tert-butyl 3-((methylamino) methyl) azetidine-1-carboxylate (500 mg, 2.33 mmol, 1 eq) and N-(1-(N-(tert-butoxycarbonyl)sulfamoyl)pyridin-4 (1H)-ylidene)-N-methylmethanaminium (846 mg. 2.779 mmol, 1.2 eq) in dichloromethane (10 mL) N,N-diisopropylethylamine (1.23 ml, 6.99 mmol, 3 eq) was added and the reaction mixture was allowed to stir at RT for overnight. Progress of reaction was monitored by NMR. After completion, the reaction mixture was diluted with water (50 mL) and extracted with DCM (150 ml×2). Combined organic layer was washed with brine (50 mL), dried over anhydrous sodium sulfate and concentrated to get crude product. The crude product was triturated in pentane to afford tert-butyl 3-(2-((N-(tert-butoxycarbonyl) sulfamoyl)(methyl)amino) ethyl) azetidine-1-carboxylate (700 mg, 76.24%) as liquid which was used in the next step without purification.

Step-4: Synthesis of 3-(2-((N-sulfamoyl)(methyl)amino) ethyl)azetidine trifluoroacetate: To a solution of tert-butyl 3-(2-((N-(tert-butoxycarbonyl) sulfamoyl)(methyl)amino) ethyl)azetidine-1-carboxylate (700 mg, 1.719 mmol, 1 eq) in DCM (10 mL) was added TFA (2 mL) and the mixture was allowed to stir at RT for 2 h. Progress of reaction was monitored by NMR. After completion, reaction mixture was concentrated under reduced pressure to get of 3-(2-((N-sulfamoyl)(methyl)amino)ethyl)azetidine trifluoroacetate (500 mg) which was used in the next step without purification. ¹H NMR (400 MHz, DMSO-d₆) δ ppm 8.70 (brs., 2H), 6.69 (brs., 1H), 3.88-3.93 (m, 2H), 3.61-3.65 (m, 2H), 2.91-2.74 (m, 3H), 2.59 (s, 3H), 1.73-1.79 (m, 2H).

Step-4: Synthesis N-(2-(1-(7-chloro-5-methylpyrrolo[1,2-f][1,2,4]triazin-4-yl)azetidin-3-yl)ethyl)-N-methylsulfamide: To a solution of 3-(2-((N-sulfamoyl)(methyl)amino) ethyl)azetidine trifluoroacetate (191 mg, 0.989 mmol, 1 eq) and 4,7-dichloro-5-methylpyrrolo[1,2-f][1,2,4]triazine (100 mg, 0.494 mmol, 1 eq) in DMF (2 ml) was added N,N-diisopropylethylamine (0.12 mL, 0.741 mmol, 2 eq). The reaction mixture was allowed to stir at 90° C. for overnight. Progress of reaction was monitored by LCMS. After completion of reaction, reaction mixture was diluted with water (30 ml) extracted with ethyl acetate (150 ml×2). Combined organic layer was washed with brine (50 mL) and dried over anhydrous sodium sulfate concentrated to get crude product. which was purified by reversed phase chromatography to afford N-(2-(1-(7-chloro-5-methylpyrrolo[1,2-f][1,2,4]triazin-4-yl)azetidin-3-yl)ethyl)-N-methylsulfamide (18 mg, 5.07%). LCMS: 359.8 [M+1]⁺; ¹H NMR (400 MHz, DMSO-d₆) δ ppm 7.90 (s, 1H), 6.69 (s, 2H), 6.63 (s, 1H), 4.46-4.41 (m, 2H), 4.03-3.98 (m, 2H), 2.95-2.90 (m, 2H), 2.81-2.74 (m, 1H), 2.64 (s, 3H), 2.39 (s, 3H), 1.91-1.85 (m, 2H).

Example-85: Synthesis of N-(N-(2-(7-chloro-2-cyclopropyl-5-methylpyrrolo[1,2-f][1,2,4]triazin-4-yl)-2-azaspiro[3.3]heptan-6-yl)-N-methylsulfamoyl) acetamide, (Compound 1.85)

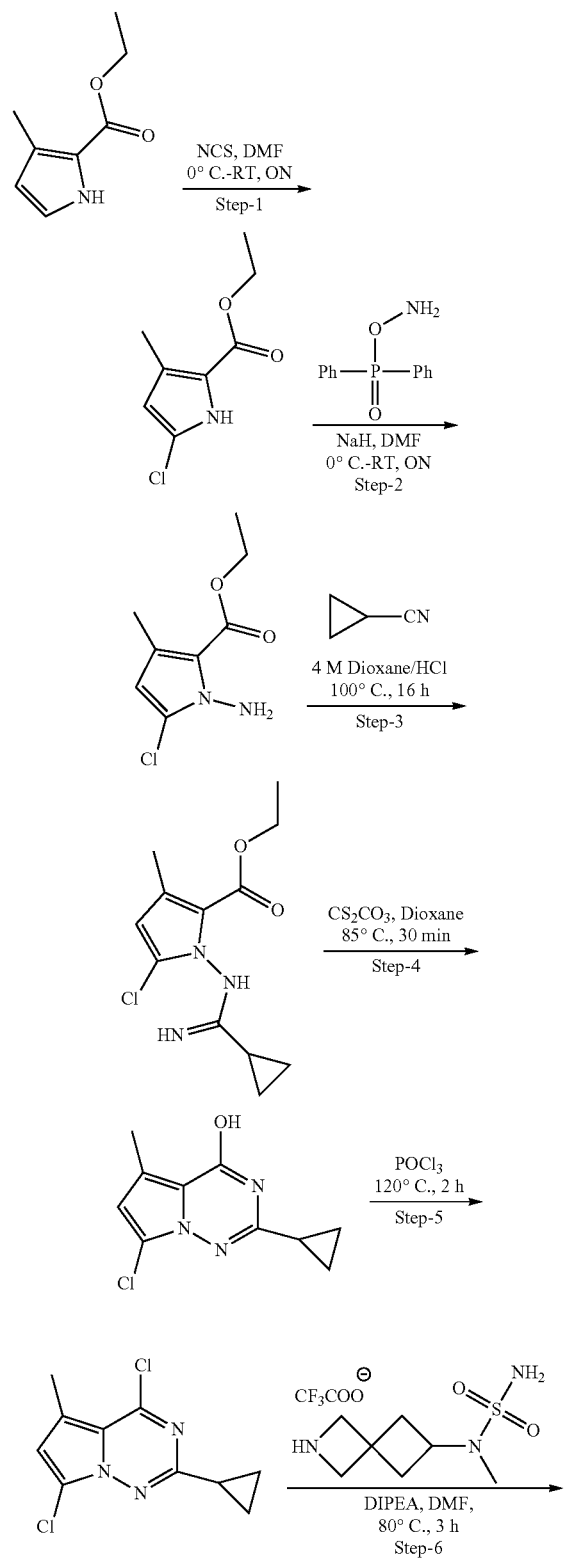

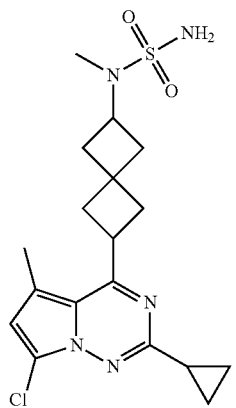

Step-1: Synthesis of ethyl 5-chloro-3-methyl-1H-pyrrole-2-carboxylate: To a solution of ethyl 3-methyl-1H-pyrrole-2-carboxylate (4 g, 26.14 mmol, 1 eq) in DMF (30 mL) was added N-chlorosuccinimide (3.47 g, 26.14 mmol, 1.1 eq) at 0° C. and the reaction mixture was allowed to stir at 0° C. for 5 minutes followed by stirring at room temperature for overnight. Progress of reaction was monitored by TLC. After completion, reaction mixture was cooled to room temperature; solid was filtered to get residue which was triturated with pentane to afford ethyl 5-chloro-3-methyl-1H-pyrrole-2-carboxylate (2.8 g, 57.25%). LCMS: 188 [M+1]$^+$ Step-2: Synthesis of ethyl 1-amino-5-chloro-3-methyl-1H-pyrrole-2-carboxylate: To a solution of ethyl 5-chloro-3-methyl-1H-pyrrole-2-carboxylate (2.8 g, 14.97 mmol, 1 eq) in DMF (120 mL) was added Sodium hydride (0.9 g, 22.42 mmol, 1.1 eq) at 0° C. and the reaction mixture was allowed to stir at 0° C. for 15 minutes. To this reaction mixture, was added O-(diphenylphosphoryl)hydroxylamine (4.53 g, 19.46 mmol, 1.3 eq) at 0° C. portion wise and allowed to stir at room temperature for overnight. Progress of reaction was monitored by TLC. After completion of reaction, the reaction mixture was diluted with water (250 mL) and extracted with MTEB (250 ml×2). The combined organic layer was washed with brine (50 mL) and dried over anhydrous sodium sulfate concentrated to get product to afford ethyl 1-amino-5-chloro-3-methyl-1H-pyrrole-2-carboxylate (3.0 g, 99.20%). LCMS: 203 [M+1]$^+$ Step-3: Synthesis of ethyl 5-chloro-1-(cyclopropanecarboximidamido)-3-methyl-1H-pyrrole-2-carboxylate: A mixture of ethyl 1-amino-5-chloro-3-methyl-1H-pyrrole-2-carboxylate (400 mg, 2.37 mmol, 1 eq) and cyclopropanecarbonitrile (191 mg, 2.85 mmol, 1.2 eq) in 4M HCl in dioxane (4 mL) was allowed to stir at 100° C. for 16 h. Progress of reaction was monitored by TLC. After completion of reaction, reaction mixture was cooled to room temperature, quenched with NaHCO$_3$ and extracted with ethyl acetate (150 ml×2). Combined organic layer was washed with brine (50 mL) and dried over anhydrous sodium sulfate concentrated to get crude product. The crude product was purified by combi flash chromatography [silica gel 100-200 mesh, elution 0-40% Ethyl acetate in hexane] to afford ethyl 5-chloro-1-(cyclopropanecarboximidamido)-3-methyl-1H-pyrrole-2-carboxylate (350 mg, 65.73%). LCMS: 270 [M+1]$^+$ Step-4: Synthesis of 7-chloro-2-cyclopropyl-5-methylpyrrolo[1,2-f][1,2,4]triazin-4-ol: To a solution of ethyl 5-chloro-1-(cyclopropanecarboximidamido)-3-methyl-1H-pyrrole-2-carboxylate (300 mg, 1.114 room temperature and the reaction mixture was allowed to stir at 85° C. for 30 min. Progress of reaction was monitored by TLC. After completion, the reaction mixture was diluted with water (150 mL) and extracted with ethyl acetate (250 ml×2), Combined organic layer was washed with brine (50 mL) and dried over anhydrous sodium sulfate concentrated to get crude which was purified by combiflash elution (0-30% ETOAc/Hexane) to afford 7-chloro-2-cyclopropyl-5-methylpyrrolo[1,2-f][1,2,4]triazin-4-ol (190 mg, 76.38%). LCMS: 224 [M+1]$^+$ Step-5: Synthesis of 4,7-dichloro-2-cyclopropyl-5-methylpyrrolo[1,2-f][1,2,4]triazine: The mixture of 7-chloro-2-cyclopropyl-5-methylpyrrolo[1,2-f][1,2,4]triazin-4-ol (190 mg, 0.849 mmol, 1 eq) in POCl$_3$ (2 mL) was allowed to stir at 120° C. for 2 h. Progress of reaction was monitored by TLC. After completion reaction mixture was cooled to room temperature, quenched with NaHCO$_3$ to maintain pH-7 and extracted with ethyl acetate (150 ml×2). Combined organic layer was washed with brine (50 mL) and dried over anhydrous sodium sulfate concentrated to get crude product. The crude product was purified by combi-flash chromatography [silica gel 100-200 mesh, elution 0-10% Ethyl acetate in hexane] to afford 4,7-dichloro-2-cyclopropyl-5-methylpyrrolo[1,2-f][1,2,4]triazine as yellow solid (110 mg, 53.64%). LCMS: 242 [M+1]$^+$ Step-6: Synthesis of N-(N-(2-(7-chloro-2-cyclopropyl-5-methylpyrrolo[1,2-f][1,2,4]triazin-4-yl)-2-azaspiro[3.3]heptan-6-yl)-N-methylsulfamoyl)acetamide: To a solution of 7-dichloro-2-cyclopropyl-5-methylpyrrolo[1,2-f][1,2,4]triazine (110 mg, 0.454 mmol, 1 eq) and N-methyl-N-(2-azaspiro[3.3]heptan-6-yl)sulfamamide trifluoroacetate (186 mg, 0.908 mmol, 1 eq) in DMF (2 ml) was added N,N-diisopropylethylamine (0.09 mL, 0.544 mmol, 1.5 eq). The reaction mixture was allowed to stir at 90° C. for overnight. Progress of reaction was monitored by LCMS. After completion, reaction mixture was diluted with water (30 ml) extracted with ethyl acetate (150 ml×2). Combined organic layer was washed with brine (50 mL) and dried over anhydrous sodium sulfate concentrated to get crude product. which was purified by combiflash (elution 0-70% EtoAc/Hexane) to afford N-(N-(2-(7-chloro-2-cyclopropyl-5-methylpyrrolo[1,2-f][1,2,4]triazin-4-yl)-2-azaspiro[3.3]heptan-6-yl)-N-methylsulfamoyl)acetamide (90 mg, 48.20%). LCMS: 411 [M+1]$^+$; $^1$H NMR (400 MHz, DMSO-d$_6$) δ ppm 6.68 (s, 2H), 6.52 (s, 1H), 4.36 (s, 2H), 4.23 (s, 2H), 3.76-3.70 (m, 1H), 2.53 (s, 3H), 2.43-2.28 (m, 7H), 1.81-1.89 (m, 1H), 0.96-0.90 (m, 2H), 0.86-0.79 (m, 2H)

Example-86: Synthesis of N-((1-(7-chloro-5-methylpyrrolo[1,2-f][1,2,4]triazin-4-yl)azetidin-3-yl)methyl) sulfamamide, (Compound 1.86)

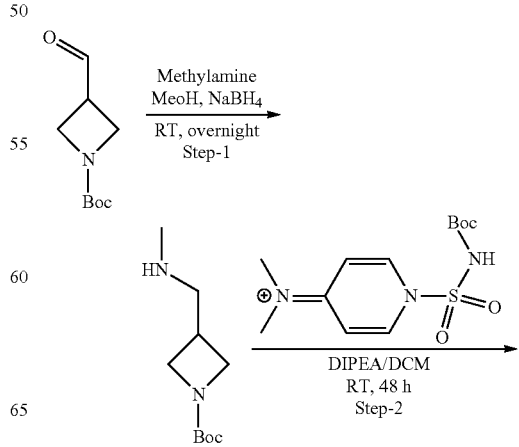

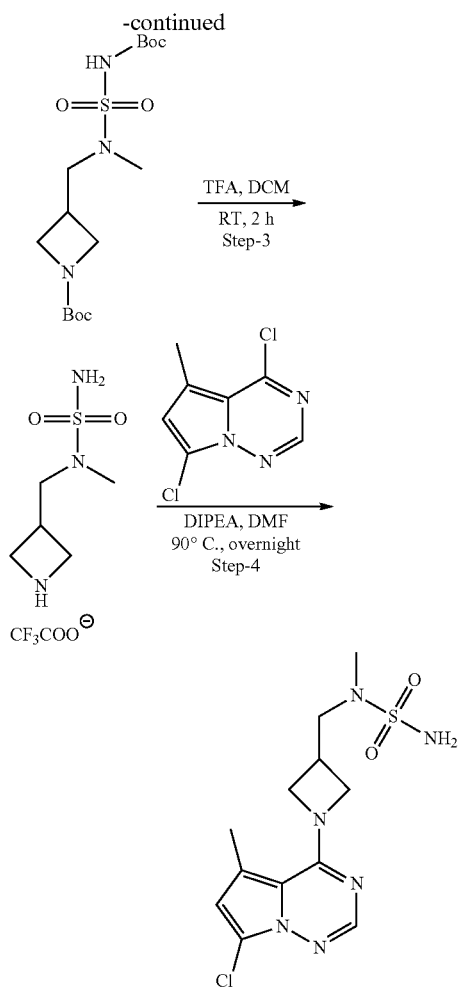

Step-1: Synthesis of tert-butyl 3-((methylamino)methyl) azetidine-1-carboxylate: To a stirred solution of tert-butyl 3-formylazetidine-1-carboxylate (500 mg, 2.69 mmol, 1.0 eq) in MeOH (10.0 mL) was added methylamine (0.38 mL, 4.04 mmol, 1.5 eq) at 0° C. The resulting mixture was stirred at room temperature for overnight. The reaction mixture was then cooled to 0° C. followed by addition of NaBH$_4$ (204 mg, 5.398 mmol, 3.0 eq) at 0° C. The reaction mixture was stirred at room temperature for 1 h. The progress of reaction was monitored by TLC & NMR. The reaction mixture was concentrated, basified with NaHCO$_3$ solution (20 mL), extracted with EtOAc (2×150 mL). The combined organic layer was washed with water (50 mL), with brine (50 mL), dried over Na$_2$SO$_4$ and concentrated to get crude product. The crude product was triturated in pentane to afford tert-butyl 3-((methylamino)methyl) azetidine-1-carboxylate (500 mg, 92.48%) as liquid. $^1$H NMR (400 MHz, CHLOROFORM-d) δ ppm 4.01-3.96 (m, 2H), 3.60-3.55 (m, 2H), 2.79-2.73 (m, 2H), 2.65-2.60 (m, 1H), 2.44 (s, 3H), 1.43 (s, 9H).

Step-2: Synthesis of tert-butyl 3-(((N-(tert-butoxycarbonyl)sulfamoyl)(methyl)amino)methyl)azetidine-1-carboxylate: To a solution of tert-butyl 3-((methylamino)methyl) azetidine-1-carboxylate (500 mg, 2.49 mmol, 1 eq) and N-(1-(N-(tert-butoxycarbonyl)sulfamoyl)pyridin-4 (1H)-ylidene)-N-methylmethanaminium (827 mg. 2.74 mmol, 1.1 eq) in dichloromethane (10 mL) was added N,N-diisopropylethylamine (1 ml, 6.22 mmol, 2.5 eq). The reaction mixture was then allowed to stir at RT for overnight. Progress of reaction was monitored by TLC & NMR. After completion, the reaction mixture was diluted with water (50 mL) and extracted with DCM (150 ml×2), Combined organic layer was washed with brine (50 mL) and dried over anhydrous sodium sulfate concentrated to get crude product. The crude product was triturated in pentane to afford tert-butyl 3-(((N-(tert-butoxycarbonyl) sulfamoyl)(methyl)amino)methyl) azetidine-1-carboxylate (500 mg, 52.77%) as liquid. $^1$H NMR (400 MHz, CHLOROFORM-d) δ ppm 4.01-3.96 (m, 2H), 3.64-3.72 (m, 2H), 3.53 (brs., 1H), 2.92 (s, 2H), 2.78-2.86 (m, 1H), 2.44 (s, 3H), 1.49-1.40 (m, 18H).

Step-3: Synthesis of 3-(N-sulfamoyl)(methyl)amino) methyl) azetidine trifluoroacetate: To a solution of tert-butyl 3-(((N-(tert-butoxycarbonyl) sulfamoyl)(methyl)amino) methyl) azetidine-1-carboxylate (500 mg, 1.318 mmol, 1 eq) in DCM (5 mL) was added TFA (1.5 mL) and the mixture was allowed to stir at RT for 2 h. Progress of reaction was monitored by TLC. After completion, reaction mixture was concentrated under reduced pressure to get of 3-(N-sulfamoyl)(methyl)amino)methyl) azetidine trifluoroacetate (500 mg) which was used in the next step without purification. $^1$H NMR (400 MHz, DMSO-d$_6$) δ ppm 8.69-8.57 (brs., 2H), 6.83 (brs., 1H), 4.05-3.89 (m, 2H), 3.74-3.63 (m, 2H), 3.21-3.10 (m, 2H), 3.05-3.01 (m, 1H), 2.61 (s, 3H).

Step-4: Synthesis N-((1-(7-chloro-5-methylpyrrolo[1,2-f][1,2,4]triazin-4-yl)azetidin-3-yl)methyl) sulfamamide: To a solution of 3-(N-sulfamoyl)(methyl)amino)methyl) azetidine trifluoroacetate (378 mg, 0.995 mmol, 1 eq) and 4,7-dichloro-5-methylpyrrolo[1,2-f][1,2,4]triazine (200 mg, 0.995 mmol, 1 eq) in DMF (3 ml), N,N-diisopropylethylamine (0.3 mL, 0.304 mmol, 2 eq) was added. The reaction mixture was allowed to stir at 90° C. for overnight. Progress of reaction was monitored by LCMS. After completion, reaction mixture was diluted with water (30 ml) extracted with ethyl acetate (150 ml×2)). Combined organic layer was washed with brine (50 mL) and dried over anhydrous sodium sulfate concentrated to get crude product. which was purified by reversed phase chromatography to afford N-((1-(7-chloro-5-methylpyrrolo[1,2-f][1,2,4]triazin-4-yl)azetidin-3-yl)methyl) sulfamamide (41 mg, 20.86%). LCMS: 345.08[M+1]$^+$; $^1$H NMR (400 MHz, DMSO-d$_6$) δ ppm 7.92 (s, 1H), 6.80 (s, 2H), 6.64 (s, 1H), 4.44-4.39 (m, 2H), 4.06-4.01 (m, 2H), 3.21-3.16 (m, 2H), 3.01-2.96 (m, 1H), 2.66 (s, 3H), 2.39 (s, 3H).

Example-87: Synthesis of N-(2-(7-methoxycinnolin-4-yl)-2-azaspiro[3.3]heptan-6-yl)-N-methylsulfamide, (Compound 1.87)

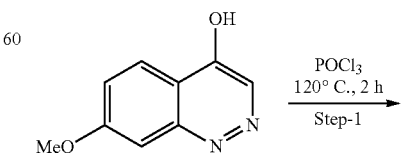

-continued

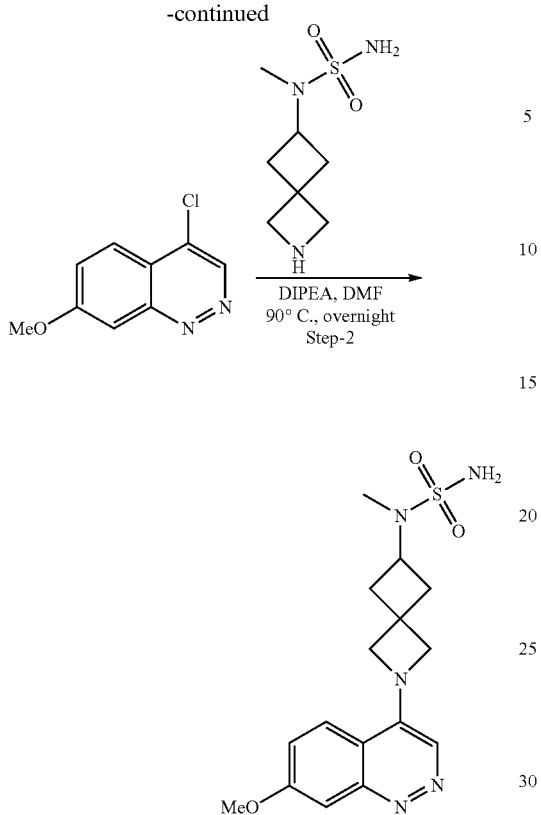

Step-1: Synthesis of 4-chloro-7-methoxycinnoline: A mixture of 7-methoxycinnolin-4-ol (200 mg, 1.135 mol, 1 eq) in POCl₃ (2.0 mL) was allowed to stir at 120° C. for 2 h. Progress of reaction was monitored by TLC. After completion reaction mixture was cooled to RT, quenched with NaHCO₃ to maintain pH-7 and extracted with ethyl acetate (150 ml×2). Combined organic layer was washed with brine (50 mL) and dried over anhydrous sodium sulfate concentrated to get crude product. The crude product was purified by combi-flash chromatography [silica gel 100-200 mesh, elution 0-10% Ethyl acetate in hexane] to 4-chloro-7-methoxycinnoline (150 mg, 67.89%) as white solid. LCMS: 195 [M+1]+

Step-2: Synthesis N-(2-(7-methoxycinnolin-4-yl)-2-azaspiro[3.3]heptan-6-yl)-N-methylsulfamide: To a solution of 4-chloro-7-methoxycinnoline (150 mg, 0.770 mmol, 1 eq) and N-methyl-N-(2-azaspiro[3.3]heptan-6-yl)sulfamamide (245 mg, 0.770 mmol, 1 eq) in Ethanol (10 ml) was added N,N-diisopropylethylamine (0.2 mL, 1.155 mmol, 1.5 eq). The reaction mixture was allowed to stir at 90° C. for overnight. Progress of reaction was monitored by LCMS. After completion, reaction mixture was concentrated under reduced pressure to get residue and diluted with water (30 ml) and extracted with ethyl acetate (150 ml×2). Combined organic layer was washed with brine (50 mL) and dried over anhydrous sodium sulfate concentrated to get crude product, which was purified by reversed phase chromatography to afford N-(2-(7-methoxycinnolin-4-yl)-2-azaspiro[3.3]heptan-6-yl)-N-methylsulfamide (41 mg, 14.63%). LCMS: 364.1 [M+1]+; ¹H NMR (400 MHz, DMSO-d₆) δ ppm 8.21 (s, 1H), 7.86 (d, J=9.65 Hz, 1H), 7.43 (d, J=2.63 Hz, 1H), 7.18 (dd, J=9.65, 2.63 Hz, 1H), 6.73 (s, 2H), 4.49 (s, 2H), 4.39 (s, 2H), 3.93 (s, 3H), 3.75-3.71 (m, 1H), 2.60-2.22 (s, 7H).

Example-88: Synthesis of N-((1-(7-chloro-5-methylpyrrolo[1,2-f][1,2,4]triazin-4-yl)azetidin-3-yl)methyl)-N-cyclopropylsulfamamide, (Compound 1.88)

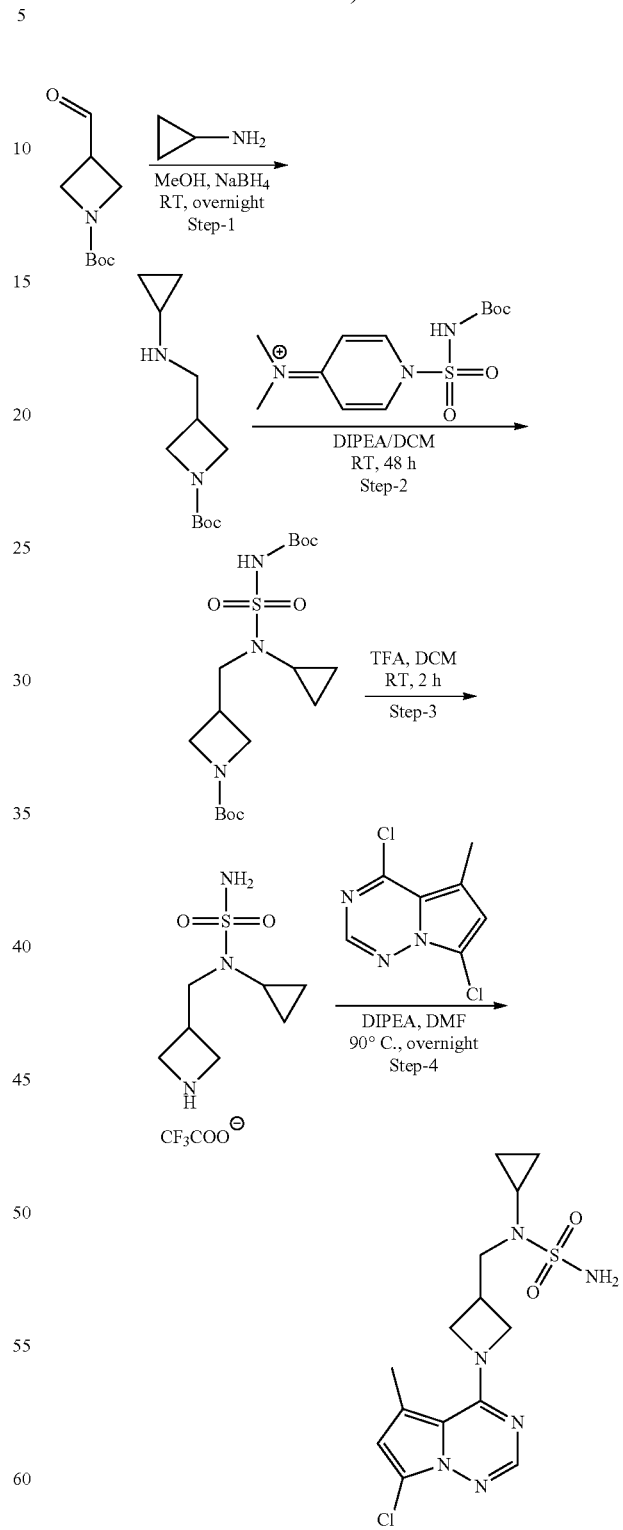

Step-1: Synthesis of tert-butyl 3-((cyclopropylamino)methyl)azetidine-1-carboxylate: To a stirred solution of tert-butyl 3-formylazetidine-1-carboxylate (500 mg, 2.69 mmol, 1.0 eq) in MeOH (10.0 mL) was added cyclopropanamine (231 mg, 4.04 mmol, 1.5 eq) at 0° C. The resulting mixture was stirred at room temperature for overnight. The reaction mixture was then cooled to 0° C. followed by addition of NaBH$_4$ (204 mg, 5.398 mmol, 3.0 eq) at 0° C. The reaction mixture was stirred at room temperature for 1 h. The progress of reaction was monitored by TLC & NMR. The reaction mixture was concentrated, basified with NaHCO$_3$ solution (20 mL), extracted with EtOAc (2×150 mL). The combined organic layer was washed with water (50 mL), with brine (50 mL), dried over Na$_2$SO$_4$ and concentrated to get crude product. The crude product was triturated in pentane to afford tert-butyl 3-((cyclopropylamino)methyl) azetidine-1-carboxylate (500 mg, 81.84%) as liquid. $^1$H NMR (400 MHz, CDC$_3$-d) δ ppm 3.99-3.93 (m, 2H), 3.61-3.55 (m, 2H), 2.85-2.90 (m, 1H), 2.65-2.60 (m, 1H), 2.08-2.02 (m, 2H), 1.43 (s, 9H), 0.43-0.38 (m, 2H), 0.25-0.30 (m, 2H).

Step-2: Synthesis of tert-butyl 3-((cyclopropylamino) methyl)azetidine-1-carboxylate: To a solution of tert-butyl 3-((methylamino)methyl) azetidine-1-carboxylate (500 mg, 2.20 mmol, 1.0 eq) and N-(1-(N-(tert-butoxycarbonyl)sulfamoyl)pyridin-4 (1H)-ylidene)-N-methylmethanaminium (732.4 mg. 2.43 mmol, 1.1 eq) in dichloromethane (10 mL) was added N,N-diisopropylethylamine (1.05 ml, 6.075 mmol, 2.5 eq) and the reaction mixture was allowed to stir at RT for overnight. Progress of reaction was monitored by NMR. After completion, the reaction mixture was diluted with water (50 mL) and extracted with DCM (150 ml×2), combined organic layer was washed with brine (50 mL) and dried over anhydrous sodium sulfate and concentrated to get crude product. The crude product was triturated in pentane (50 ml) to afford tert-butyl 3-(((N-(tert-butoxycarbonyl) sulfamoyl)(cyclopropyl)amino)methyl)azetidine-1-carboxylate (500 mg, 55.81%) as liquid which was used in the next step without purification.

Step-3: Synthesis of 3-(N-sulfamoyl) (cyclopropyl)amino)methyl) azetidine trifluoroacetate: To a solution of tertbutyl 3-(((N-(tert-butoxycarbonyl) sulfamoyl) (cyclopropyl) amino)methyl) azetidine-1-carboxylate (500 mg, 1.318 mmol, 1 eq) in DCM (10 mL) was added TFA (4 mL) and the mixture was allowed to stir at RT for 2 h. Progress of reaction was monitored by TLC. After completion, reaction mixture was concentrated under reduced pressure to get of 3-(N-sulfamoyl) (cyclopropyl)amino)methyl) azetidine trifluoroacetate (250 mg) which was used in the next step without purification.

Step-4: Synthesis of N-((1-(7-chloro-5-methylpyrrolo[1,2-f][1,2,4]triazin-4-yl)azetidin-3-yl)methyl)-N-cyclopropylsulfamamide: To a solution of 3-(N-sulfamoyl) (cyclopropyl)amino)methyl) azetidine trifluoroacetate (203.20 mg, 0.989 mmol, 2 eq) and 4,7-dichloro-5-methylpyrrolo[1,2-f][1,2,4]triazine (100 mg, 0.494 mmol, 1 eq) in DMF (2 ml) was added N,N-diisopropylethylamine (0.12 mL, 0.304 mmol, 2 eq). The reaction mixture was allowed to stir at 90° C. for overnight. Progress of reaction was monitored by LCMS. After completion, reaction mixture was diluted with water (30 ml) extracted with ethyl acetate (150 ml×2). Combined organic layer was washed with brine (50 mL) and dried over anhydrous sodium sulfate concentrated to get crude product, which was purified by reversed phase chromatography to afford N-((1-(7-chloro-5-methylpyrrolo[1,2-f][1,2,4]triazin-4-yl)azetidin-3-yl)methyl)-N-cyclopropyl sulfamamide (19 mg, 5.17%). LCMS: 371.10[M+1]$^+$; $^1$H NMR (400 MHz, DMSO-d$_6$) δ ppm 7.50 (s, 1H) 6.92 (s, 2H), 6.22 (s, 1H), 3.85-3.80 (m, 1H), 3.58-3.49 (m, 2H), 3.20-3.15-(m, 2H), 3.07-3.01 (m, 1H), 3.01-2.95 (m, 1H), 2.32 (s, 3H), 0.76-0.66 (m, 5H).

Example-89: Synthesis N-((1-(7-chloro-5-methylpyrrolo[1,2-f][1,2,4]triazin-4-yl)azetidin-3-yl) methyl)-N-isopropylsulfamide, (Compound 1.89)

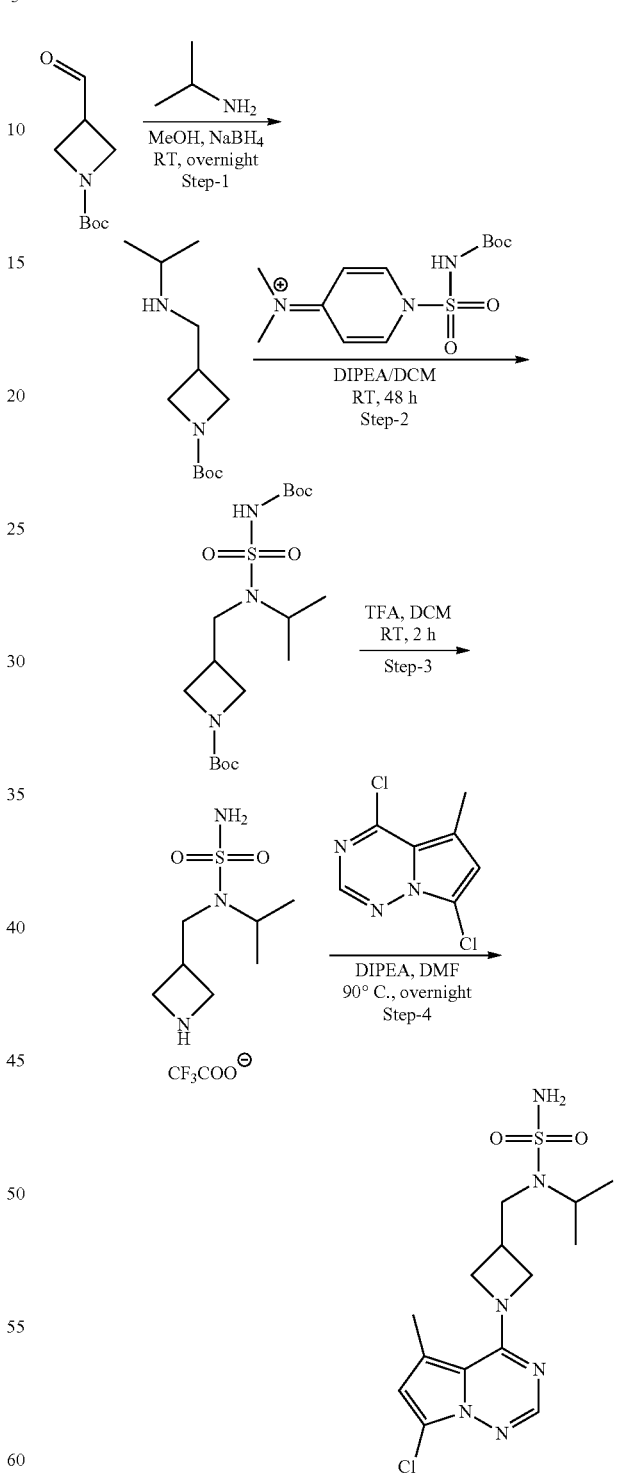

Step-1: Synthesis of tert-butyl 3-((isopropylamino) methyl)azetidine-1-carboxylate: To a stirred solution of tertbutyl 3-formylazetidine-1-carboxylate (500 mg, 2.69 mmol, 1.0 eq) in MeOH (10.0 mL) was added isopropanamine (238 mg, 4.04 mmol, 1.5 eq) at 0° C. The resulting mixture was stirred at room temperature for overnight. The reaction mixture was then cooled to 0° C. followed by addition of NaBH₄ (204 mg, 5.398 mmol, 3.0 eq) at 0° C. The reaction mixture was stirred at room temperature for 1 h. The progress of reaction was monitored by TLC. The reaction mixture was concentrated, basified with NaHCO₃ solution (20 mL), extracted with EtOAc (2×150 mL). The combined organic layer was washed with water (50 mL), with brine (50 mL), dried over Na₂SO₄ and concentrated to get crude product. The crude product was triturated using pentane (50 ml) to afford tert-butyl 3-((isopropylamino)methyl) azetidine-1-carboxylate (500 mg, 81.07%) as liquid. LCMS: 229.1 [M+1]⁺

Step-2: Synthesis of tert-butyl 3-(((N-(tert-butoxycarbonyl)sulfamoyl)(isopropyl)amino)methyl)azetidine-1-carboxylate: To a solution of tert-butyl 3-((isopropylamino) methyl) azetidine-1-carboxylate (500 mg, 2.20 mmol, 1 eq) and N-(1-(N-(tert-butoxycarbonyl)sulfamoyl)pyridin-4 (1H)-ylidene)-N-methylmethanaminium (732.4 mg. 2.43 mmol, 1.1 eq) in dichloromethane (10 mL) was added N,N-diisopropylethylamine (1.05 ml, 6.075 mmol, 2.5 eq) and the reaction mixture was allowed to stir at RT for overnight. Progress of reaction was monitored by NMR. After completion, the reaction mixture was diluted with water (50 mL) and extracted with DCM (150 ml×2). The combined organic layer was washed with brine (50 mL) and dried over anhydrous sodium sulfate concentrated to get crude product. The crude product was triturated in pentane to afford tert-butyl 3-(((N-(tert-butoxycarbonyl)sulfamoyl) (isopropyl)amino)methyl)azetidine-1-carboxylate (500 mg, 56.02%) as liquid. LCMS: 408.2 [M+1]⁺

Step-3: Synthesis of 3-(N-sulfamoyl) (isopropyl)amino) methyl) azetidine trifluoroacetate: To a solution of tert-butyl 3-(((N-(tert-butoxycarbonyl) sulfamoyl) (isopropyl)amino) methyl) azetidine-1-carboxylate (500 mg, 1.226 mmol, 1 eq) in DCM (10 mL) was added TFA (4 mL) and the mixture was allowed to stir at RT for 2 h. Progress of reaction was monitored by TLC. After completion, reaction mixture was concentrated under reduced pressure to get of 3-(N-sulfamoyl) (isopropyl)amino)methyl) azetidine trifluoroacetate (250 mg) which was used in the next step without purification. LCMS: 208.1 [M+1]⁺

Step-4: Synthesis of N-((1-(7-chloro-5-methylpyrrolo[1,2-f][1,2,4]triazin-4-yl)azetidin-3-yl)methyl)-N-isopropylsulfamide: To a solution of 3-(N-sulfamoyl) (isopropyl) amino)methyl) azetidine trifluoroacetate (205 mg, 0.989 mmol, 2 eq) and 4,7-dichloro-5-methylpyrrolo[1,2-f][1,2,4] triazine (100 mg, 0.494 mmol, 1 eq) in DMF (2 ml) was added N,N-diisopropylethylamine (0.12 mL, 0.304 mmol, 2 eq). The reaction mixture was allowed to stir at 90° C. for overnight. Progress of reaction was monitored by LCMS. After completion of reaction, reaction mixture was diluted with water (30 ml) and extracted with ethyl acetate (150 ml×2). Combined organic layer was washed with brine (50 mL) and dried over anhydrous sodium sulfate concentrated to get crude product. which was purified by reversed phase chromatography to afford N-((1-(7-chloro-5-methylpyrrolo [1,2-f][1,2,4]triazin-4-yl)azetidin-3-yl)methyl)-N-isopropylsulfamide (13 mg, 3.52%). LCMS: 373.1 [M+1]⁺; ¹H NMR (400 MHz, DMSO-d₆) δ ppm 7.91 (s, 1H), 6.71 (s, 2H), 6.63 (s, 1H), 4.39-4.34 (m, 2H), 4.11-4.06 (m, 2H), 3.93-3.88 (m, 1H), 3.27-3.22 (m, 2H), 3.05-2.99 (m, 1H), 2.39 (s, 3H), 1.19-1.03 (m, 6H).

Example-90: Synthesis of N-(2-(7-chloro-2-(difluoromethyl)-5-methyl-7αH-cyclopenta[d]pyrimidin-4-yl)-2-azaspiro[3.3]heptan-6-yl)-N-methylsulfamamide, (Compound 1.90)

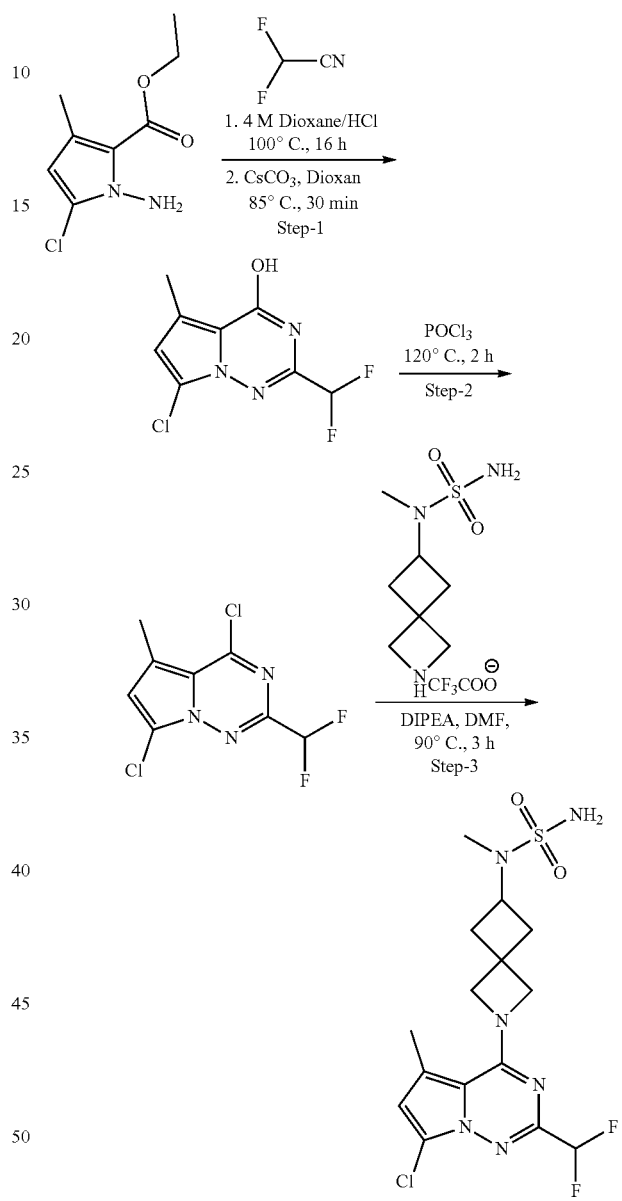

Step-1: Synthesis of 7-chloro-2-(difluoromethyl)-5-methylpyrrolo[1,2-f][1,2,4]triazin-4-ol: A mixture of ethyl 1-amino-5-chloro-3-methyl-1H-pyrrole-2-carboxylate (400 mg, 1.97 mmol, 1 eq) and 2,2-difluoroacetonitrile (182 mg, 2.36 mmol, 1.2 eq) in 4M HCl in dioxane (4 mL) was allowed to stir at 100° C. for 16 h. Progress of reaction was monitored by TLC. After completion of reaction, reaction mixture was cooled to RT, quenched with NaHCO₃ solution and extracted with ethyl acetate (50 ml×2). Combined organic layer was washed with brine (50 mL) and dried over anhydrous sodium sulfate concentrated to get crude product (440 mg). The crude product (440 mg) was dissolved in dioxane (4.0 ml) and was added CS₂CO₃ (1.28 g, 3.94 mmol, 2.0 eq). The reaction mixture was then allowed to stir at 85° C. for 30 min. The progress of reaction was monitor by LCMS. The LCMS showed the formation of desired product. The reaction mixture was diluted with DM water (150 ml) and extracted using ethyl acetate (250 ml×2). The combind organic layer was concentrated to get crude product. The crude product was purified by combi flash chromatography [silica gel 100-200 mesh, elution 0-40% Ethyl acetate in hexane] to 7-chloro-2-(difluoromethyl)-5-methylpyrrolo[1,2-f][1,2,4]triazin-4-ol (300 mg, 65.02%) LCMS: 234.2 [M+1]+

Step-2: Synthesis of 4,7-dichloro-2-isopropyl-5-methylpyrrolo[1,2-f][1,2,4]triazine: A mixture of 7-chloro-2-(difluoromethyl)-5-methylpyrrolo[1,2-f][1,2,4]triazin-4-ol (300 mg, 1.19 mmol, 1.0 eq) in POCl₃ (3 mL) was allowed to stir at 120° C. for 2 h. Progress of reaction was monitored by TLC. After completion reaction mixture was cooled to RT, quenched with NaHCO₃ to maintain pH-7 and extracted with ethyl acetate (50 ml×2). Combined organic layer was washed with brine (40 mL) and dried over anhydrous sodium sulfate concentrated to get crude product. The crude product was purified by combi-flash chromatography [silica gel 100-200 mesh, elution 0-30% Ethyl acetate in hexane] to get 4,7-dichloro-2-(difluoromethyl)-5-methylpyrrolo[1,2-f][1,2,4]triazine as viscous oil. (280 mg, 86.41%) LCMS: 252.1 [M+1]+

Step-3: Synthesis of N-(2-(7-chloro-2-(difluoromethyl)-5-methyl-7aH-cyclopenta[d]pyrimidin-4-yl)-2-azaspiro[3.3]heptan-6-yl)-N-methylsulfamamide: To a solution of, 4,7-dichloro-2-(difluoromethyl)-5-methylpyrrolo[1,2-f][1,2,4]triazine (80 mg, 0.312 mmol, 1 eq) and N-methyl-N-(2-azaspiro[3.3]heptan-6-yl)sulfamamide trifluoroacetate (98 mg, 0.476 mmol, 1.5 eq) in DMF (2 ml) was added N,N-diisopropylethylamine (0.08 mL, 0.475 mmol, 1.5 eq) was added. The reaction mixture was allowed to stir at 90° C. for 4 h. Progress of reaction was monitored by LCMS. After completion, reaction mixture was diluted with water (30 ml) extracted with ethyl acetate (150 ml×2). Combined organic layer was washed with brine (50 ml) and dried over anhydrous sodium sulfate concentrated to get crude product, which was purified by reverse phase chromatography to afford N-(2-(7-chloro-2-(difluoromethyl)-5-methyl-7aH-cyclopenta[d]pyrimidin-4-yl)-2-azaspiro[3.3]heptan-6-yl)-N-methylsulfamamide (26 mg, 15.03%) as white solid. LCMS: 421.4 [M+1]+; ¹H NMR (400 MHz, DMSO-d₆) δ ppm 6.81-6.64 (m, 4H), 4.49 (s, 2H), 4.35 (s, 2H), 3.77-3.72 (m, 1H), 2.54-2.29 (m, 10H).

Example-91: Synthesis of N-(2-(6-cyano-5-methylpyrrolo[1,2-f][1,2,4]triazin-4-yl)-2-azaspiro[3.3]heptan-6-yl)-N-methylsulfamamide, (Compound 1.91)

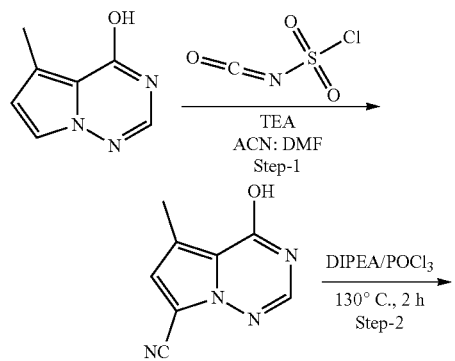

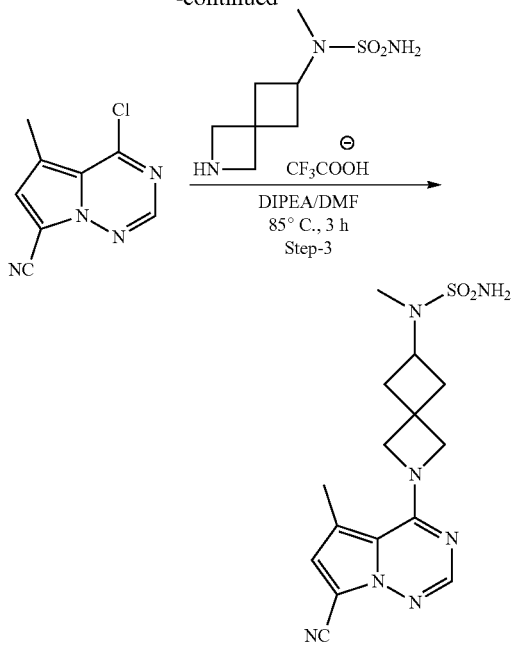

Step-1: Synthesis of 4-hydroxy-5-methylpyrrolo[1,2-f][1,2,4]triazine-7-carbonitrile: To a solution of 5-methylpyrrolo[1,2-f][1,2,4]triazin-4-ol (0.250 g, 1.67 mmol, 1.0 eq) was dissolved in CH₃CN (5 mL) and cooled to −10° C. was added a solution of Chlorosulfonyl isocyanate (0.235 g, 1.67 mmol, 1.0 eq) in CH₃CN (5 mL) was added to the reaction mixture over 5 min. The solution rapidly became yellow and solid precipitate was deposited. N,N-dimethylformamide (1 mL) was added in reaction mixture and The solution became colorless then TEA (0.455 mL, 3.333 mmol, 2.0 eq) was added to the reaction mixture turned white precipitate was formed. The reaction mixture was allowed to stir at RT for 2 h. Progress of reaction is monitored using TLC. After completion, reaction mixture poured onto ice water and extracted with ethyl acetate (3×50 mL). Combined organic layer was washed with brine (50 mL) and dried over anhydrous sodium sulfate. Removal of solvent under reduced pressure afforded 4-hydroxy-5-methylpyrrolo[1,2-f][1,2,4]triazine-7-carbonitrile (0.160 g, 55.17%). LCMS: 179 [M+1]+

Step-2: Synthesis of 4-chloro-5-methylpyrrolo[1,2-f][1,2,4]triazine-6-carbonitrile: To a solution of 4-hydroxy-5-methylpyrrolo[1,2-f][1,2,4]triazine-7-carbonitrile (0.3 g, 2.013 mmol, 1 eq) in N,N-Diisopropylethylamine was added a solution of phosphoryl oxychloride (0.188 mL, 2.013 mmol, 1 eq) at 0° C. and the reaction mixture was allowed to stir at 0° C. for 10 minutes. The reaction mixture was allowed to stir at 130° C. for 2 h. Progress of reaction is monitored by TLC. After completion, reaction mixture was diluted with cold water (30 mL) and extracted with ethyl acetate (3×20 mL). Combined organic layer was washed with brine (20 mL) and dried over anhydrous sodium sulfate. Solvent was removed under reduced pressure to give 4-chloro-5-methylpyrrolo[1,2-f][1,2,4]triazine-6-carbonitrile (0.22 g, 57%). LCMS: 193 [M+1]+

Step-3: Synthesis of N-(2-(6-cyano-5-methylpyrrolo[1,2-f][1,2,4]triazin-4-yl)-2-azaspiro[3.3]heptan-6-yl)-N-methylsulfamamide: A mixture of 4-chloro-5-methylpyrrolo[1,2-f][1,2,4]triazine-6-carbonitrile (0.2 g, 1.04 mmol, 1 eq), N-methyl-N-(2-azaspiro[3.3]heptan-6-yl)sulfamamide 2,2, 2-trifluoroacetaldehyde (0.350 g, 1.14 mmol, 1.1 eq) and DIPEA (0.272 mL, 1.562 mmol, 1.5 eq) in DMF (10 mL) was allowed to stir at 85° C. for 3 h. Progress of reaction was monitored by TLC. After completion, reaction mixture was diluted with cold water (30 mL) and extracted with ethyl acetate (3×50 mL). Combined organic layer was washed with brine (3×30 mL) and dried over anhydrous sodium sulfate. Removal of solvent under reduced pressure to obtain the crude which was purified by reversed phase to afford N-(2-(6-cyano-5-methylpyrrolo[1,2-f][1,2,4]triazin-4-yl)-2-azaspiro[3.3]heptan-6-yl)-N-methylsulfamamide (10 mg, 2.65%). LCMS: 362 [M+1]$^+$; $^1$H NMR (400 MHz, DMSO-d$_6$) δ ppm 8.06 (s, 1H), 7.24 (s, 1H), 6.70 (s, 2H), 4.48 (s, 2H), 4.35 (s, 2H), 3.82-3.74 (m, 1H), 2.58-2.22 (m, 10H).

Example-92: Synthesis of N-(2-(1-(7-chloro-5-methylpyrrolo[2,1-f][1,2,4]triazin-4-yl)azetidin-3-yl)ethyl)-N-cyclopropylsulfamamide, (Compound 1.92)

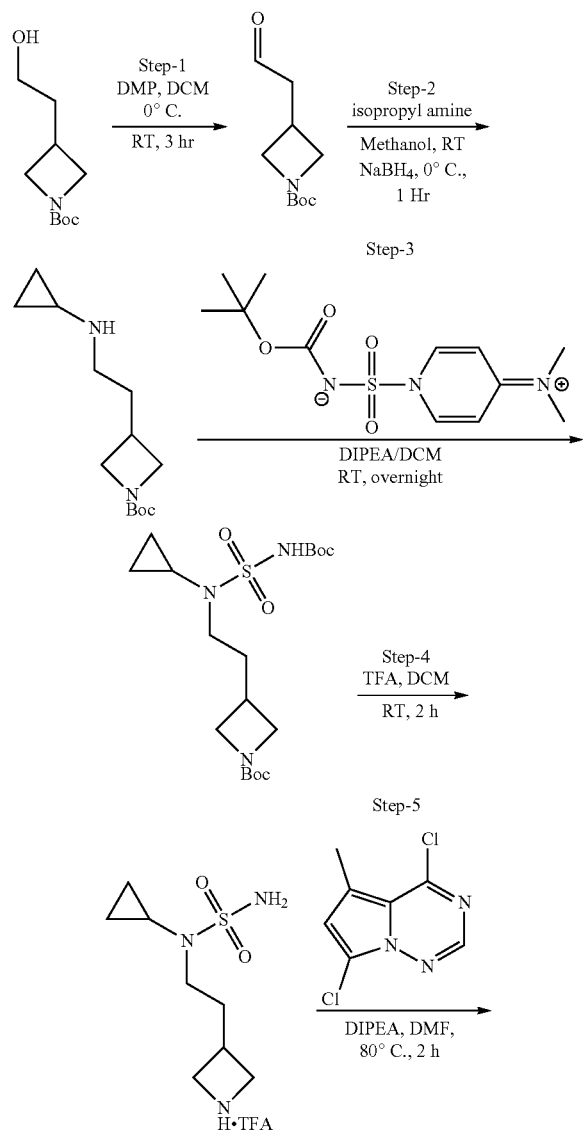

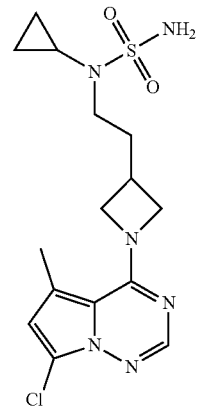

Step-1: Synthesis of tert-butyl 3-(2-oxoethyl)azetidine-1-carboxylate: A suspension of (1.0 g, 4.95 mmol, 1.0 eq) in DCM (40 mL) at 0° C. was added DMP (6.29 g, 14.8 mmol, 3.0 eq) was added portion wise at 0° C. into above reaction mixture. After addition, reaction mixture was stirred at RT for 2 h. Progress of reaction was monitored by TLC. After completion, reaction mixture was concentrated under reduced pressure to get residue which was diluted with water (150 mL) and extracted with DCM (3×250 mL). Combined organic layer was washed with brine (3×50 mL), dried over anhydrous sodium sulfate and concentrated under reduced pressure to afford tert-butyl 3-(2-oxoethyl)azetidine-1-carboxylate (1.1 g, 92.3%) which was used into the next step without purification.

Step-2: Synthesis of tert-butyl 3-(2-(cyclopropylamino)ethyl)azetidine-1-carboxylate: A suspension of (500 mg, 2.5 mmol, 1 eq), cyclopropylamine (172 mg, 3.01 mmol, 1.2 eq) in methanol (10 mL) was stirred at RT for overnight. After overnight stirring, NaBH$_4$ (142 mg, 3.75 mmol, 1.5 eq) was added portion wise at 0° C. and allowed to stir the reaction mixture for 1 h at 0° C. Progress of reaction was monitored by TLC. After completion, reaction mixture was concentrated under reduced pressure to get residue which was diluted with water (100 mL) and extracted with ethyl acetate (3×150 mL). Combined organic layer was washed with brine (3×50 mL), dried over anhydrous sodium sulfate and concentrated under reduced pressure to afford tert-butyl 3-(2-(cyclopropylamino)ethyl)azetidine-1-carboxylate (470 mg) which was used in the next step without purification (460 mg, 76.5%).

Step-3: Synthesis of tert-butyl 3-(2-((N-(tert-butoxycarbonyl)sulfamoyl)(cyclopropyl)amino)ethyl)azetidine-1-carboxylate: To a solution of tert-butyl 3-(2-(cyclopropylamino)ethyl)azetidine-1-carboxylate (460 mg, 1.91 mmol, 1.0 eq) in DCM (10 mL) was added N-(tert-butoxycarbonyl)-N-[4-(dimethylazaniumylidene)-1,4-dihydropyridin1ylsulfonyl]azanide (694 mg, 2.29 mmol, 1.2 eq) and DIPEA (370 mg, 2.86 mmol, 1.5 eq) and the mixture was allowed to stir at RT for overnight. Progress of reaction was monitored by TLC. After completion, reaction mixture was diluted with water (50 mL) and extracted with DCM (2×150 mL). Combined organic layer was washed with brine (1×50 mL), dried over anhydrous sodium sulfate and concentrated under reduced pressure to afford tert-butyl3-(2-((N-(tert-butoxycarbonyl)sulfamoyl)(cyclopropyl)amino)ethyl)azetidine-1-carboxylate (420 mg, 52%).

Step-4: Synthesis of N-(2-(azetidin-3-yl)ethyl)-N-cyclopropylsulfamamide 2,2,2-trifluoroacetate: To a solution of tert-butyl3-(2-((N-(tert-butoxycarbonyl)sulfamoyl)(cyclopropyl)amino)ethyl)azetidine-1-carboxylate (420 mg, 1.0 mmol, 1 eq) in DCM (4 mL) was added TFA (1.2 mL) and was allowed to stir at RT for 2 h. Progress of reaction was monitored by TLC. After completion, reaction mixture was concentrated under reduced pressure to afford crude which was triturated with diethyl ether to afford N-(2-(azetidin-3-yl)ethyl)-N-cyclopropylsulfamamide 2,2,2-trifluoroacetate (320 mg, 96%).

Step-5: Synthesis of N-(2-(1-(7-chloro-5-methylpyrrolo[2,1-f][1,2,4]triazin-4-yl)azetidin-3-yl)ethyl)-N-cyclopropylsulfamamide: A suspension of N-(2-(azetidin-3-yl)ethyl)-N-cyclopropylsulfamamide 2,2,2-trifluoroacetate (94 mg, 0.298 mmol, 1.0 eq), 4,7-dichloro-5-methylpyrrolo[2,1-f][1,2,4]triazine (60 mg, 0.298 mmol, 1.0 eq) and DIPEA (77 mg, 0.596 mmol, 2.0 eq) in DMF (1.5 mL) was allowed to stir at 80° C. for 2 h. Progress of reaction was monitored by TLC and LCMS. After completion of reaction, reaction mixture was diluted with water (10 mL) and extracted with ethyl acetate (1×50 mL). Combined organic layer was washed with brine (1×10 mL), dried over anhydrous sodium sulfate and concentrated under reduced pressure to obtain crude product which was purified by using reversed phase chromatography to afford N-(2-(1-(7-chloro-5-methylpyrrolo[2,1-f][1,2,4]triazin-4-yl)azetidin-3-yl)ethyl)-N-cyclopropylsulfamamide (26 mg, 22.6%). LCMS: 385 [M+1]$^+$; NMR: $^1$H NMR (400 MHz, DMSO-d$_6$) δ ppm 7.90 (s, 1H), 6.85 (s, 2H), 6.63 (s, 1H), 4.45 (t, J=8.8 Hz, 2H), 4.07-3.93 (m, 2H), 3.09 (t, J=7.0 Hz, 2H), 2.72 (br. s., 1H), 2.39 (s, 3H), 2.32 (br. s., 1H), 1.96 (d, J=7.0 Hz, 2H), 0.67 (br. s., 4H)

Example-93: Synthesis of N-(2-(7-chloro-5-methylpyrrolo[2,1-f][1,2,4]triazin-4-yl)-2-azaspiro[3.3]heptan-6-yl)-N-(3,3,3-trifluoropropyl)sulfamamide, (Compound 1.93)

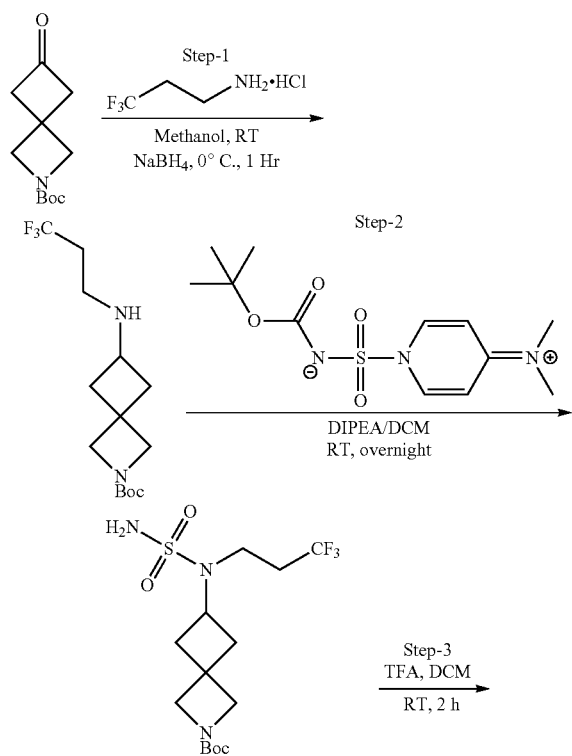

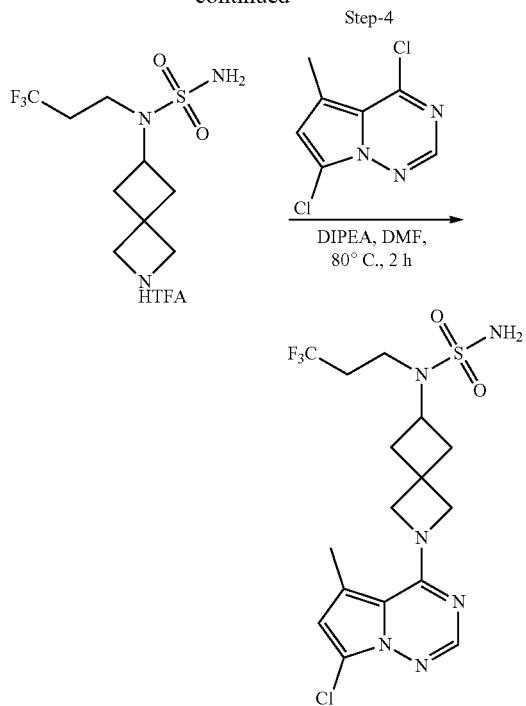

Step-1: Synthesis of tert-butyl 6-(3,3,3-trifluoropropylamino)-2-azaspiro[3.3]heptane-2-carboxylate: A suspension of tert-butyl 6-oxo-2-azaspiro[3.3]heptane-2-carboxylate (200 mg, 0.946 mmol, 1.0 eq), 3,3,3-trifluoropropan-1-amine hydrochloride (169 mg, 1.13 mmol, 1.2 eq) in methanol (5 mL) was stirred at RT for overnight. After overnight stirring, NaBH$_4$ (57 mg, 1.42 mmol, 1.5 eq) was added into above reaction mixture portion wise at 0° C. and allowed to stir the reaction mixture for 1 h at 0° C. Progress of reaction was monitored by TLC. After completion, reaction mixture was concentrated under reduced pressure to get residue which was diluted with water (30 mL) and extracted with DCM (2×50 mL). Combined organic layer was washed with brine (1×20 mL), dried over anhydrous sodium sulfate and concentrated under reduced pressure to afford tert-butyl 6-(3,3,3-trifluoropropylamino)-2-azaspiro[3.3]heptane-2-carboxylate (220 mg, 75%) which was used into the next step without purification.

Step-2: Synthesis of tert-butyl 6-((N-(tert-butoxycarbonyl)sulfamoyl)(3,3,3-trifluoropropyl)amino)-2-azaspiro[3.3]heptane-2-carboxylate: To a solution of tert-butyl 6-(cyclopropylamino)-2-azaspiro[3.3]heptane-2-carboxylate (200 mg, 0.648 mmol, 1.0 eq) in DCM (5 mL) were added N-(tert-butoxycarbonyl)-N-[4-(dimethylazaniumylidene)-1,4-dihydropyridin-1ylsulfonyl]azanide (235 mg, 0.778 mmol, 1.2 eq) and DIPEA (125 mg, 0.972 mmol, 1.5 eq) and the mixture was allowed to stir at RT for overnight. Progress of reaction was monitored by TLC. After completion, reaction mixture was diluted with water (25 mL) and extracted with DCM (2×50 mL). Combined organic layer was washed with brine (1×20 mL), dried over anhydrous sodium sulfate and concentrated under reduced pressure to obtain crude product was purified by combiflash chromatography to afford tert-butyl 6-((N-(tert-butoxycarbonyl)sulfamoyl)(3,3,3-trifluoropropyl)amino)-2-azaspiro[3.3]heptane-2-carboxylate (90 mg, 29%).

Step-3: Synthesis of N-(2-azaspiro[3.3]heptan-6-yl)-N-(3,3,3-trifluoropropyl)sulfamamide 2,2,2-trifluoroacetate:

To a solution of tert-butyl 6-((N-(tert-butoxycarbonyl)sulfamoyl)(3,3,3-trifluoropropyl)amino)-2-azaspiro[3.3]heptane-2-carboxylate (90 mg, 0.184 mmol, 1.0 eq) in DCM (3 mL) was added TFA (0.2 mL) and was allowed to stir at RT for 2 h. Progress of reaction was monitored by TLC. After completion, reaction mixture was concentrated under reduced pressure to afford crude which was triturated with diethyl ether to afford N-(2-azaspiro[3.3]heptan-6-yl)-N-(3,3,3-trifluoropropyl)sulfamamide 2,2,2-trifluoroacetate (70 mg, 94.5%).

Step-4: Synthesis of N-(2-(7-chloro-5-methylpyrrolo[2,1-f][1,2,4]triazin-4-yl)-2-azaspiro[3.3]heptan-6-yl)-N-(3,3,3-trifluoropropyl)sulfamamide:

A suspension of N-(2-azaspiro[3.3]heptan-6-yl)-N-(3,3,3-trifluoropropyl)sulfamamide 2,2,2-trifluoroacetate (76 mg, 0.199 mmol, 1.0 eq), 4,7-dichloro-5-methylpyrrolo[2,1-f][1,2,4]triazine (40 mg, 0.199 mmol, 1.0 eq) and DIPEA (51 mg, 0.398 mmol, 2.0 eq) in DMF (1.0 mL) was allowed to stir at 80° C. for 2 h. Progress of reaction was monitored by TLC and LCMS. After completion, reaction mixture was diluted with water (30 mL) and extracted with ethyl acetate (2×50 mL). Combined organic layer was washed with brine (1×20 mL), dried over anhydrous sodium sulfate and concentrated under reduced pressure to obtain crude which was purified by combiflash chromatography to afford N-(2-(7-chloro-5-methylpyrrolo[2,1-f][1,2,4]triazin-4-yl)-2-azaspiro[3.3]heptan-6-yl)-N-(3,3,3-trifluoropropyl)sulfamamide (6 mg, 6.6%). LCMS: 453 [M+1]$^+$; NMR: $^1$H NMR (400 MHz, DMSO-d$_6$) δ ppm 7.91 (s, 1H), 6.91 (br. s., 2H), 6.64 (s, 1H), 4.42 (br. s., 2H), 4.31 (br. s., 2H), 3.86 (br. s., 1H), 3.22 (br. s., 3H), 2.67 (br. s., 1H), 2.40 (s, 4H), 2.32 (br. s., 3H).

Example-94: Synthesis of N-(2-(1-(7-chloro-5-methylpyrrolo[2,1-f][1,2,4]triazin-4-yl)azetidin-3-yl)ethyl)-N-cyclobutylsulfamamide, (Compound 1.94)

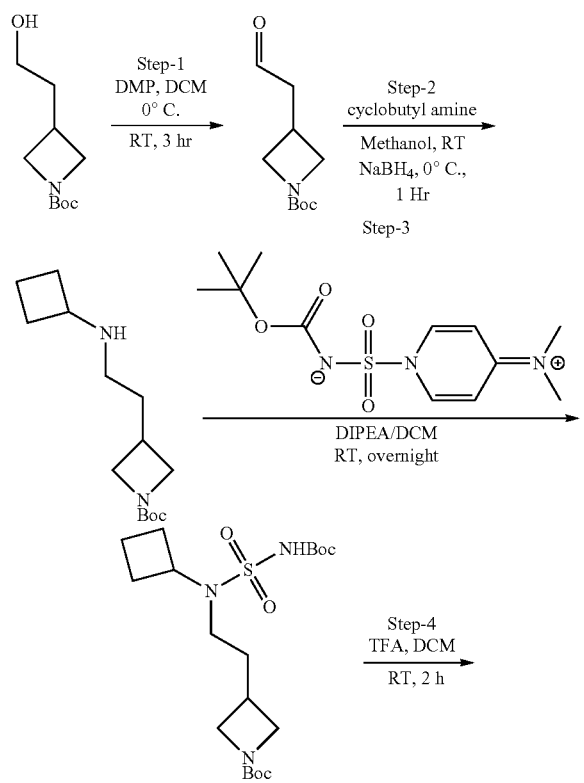

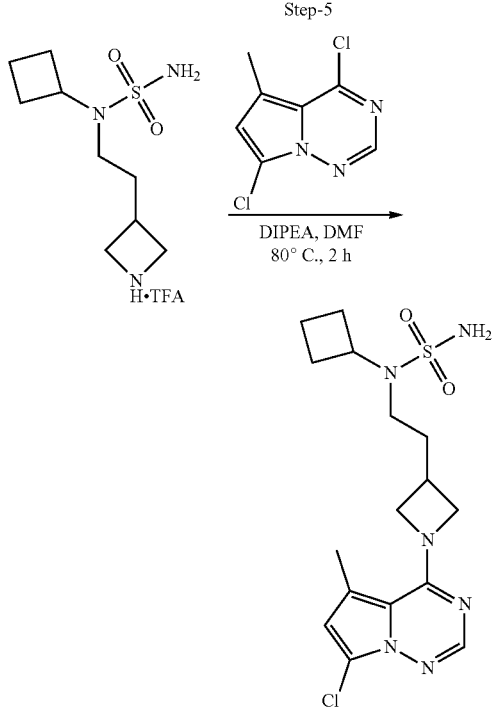

Step-1: Synthesis of tert-butyl 3-(2-oxoethyl)azetidine-1-carboxylate: A suspension of tert-butyl 3-(2-hydroxyethyl)azetidine-1-carboxylate (2.0 g, 9.93 mmol, 1.0 eq) in DCM (50 mL) at 0° C. was added DMAP (12.6 g, 29.8 mmol, 3.0 eq) was added portion wise at 0° C. into above reaction mixture. After addition, the reaction mixture was stirred at RT for 3 h. Progress of reaction was monitored by TLC. After completion, the reaction mixture was concentrated under reduced pressure to get residue which was diluted with water (150 mL) and extracted with DCM (3×250 mL). Combined organic layer was washed with brine (3×50 mL), dried over anhydrous sodium sulfate and concentrated under reduced pressure to afford tert-butyl 3-(2-oxoethyl)azetidine-1-carboxylate (1.5 g, 76%) which was used in the next step without purification.

Step-2: Synthesis of tert-butyl 3-(2-(cyclobutylamino)ethyl)azetidine-1-carboxylate: A suspension of tert-butyl 3-(2-oxoethyl)azetidine-1-carboxylate (250 mg, 1.25 mmol, 1.0 eq), cyclobutylamine (107 mg, 1.50 mmol, 1.2 eq) in methanol (5 mL) was stirred at RT for overnight. After overnight stirring, NaBH$_4$ (71 mg, 1.87 mmol, 1.5 eq) was added into above reaction mixture portion wise at 0° C. and allowed to stir the reaction mixture for 1 h at 0° C. Progress of reaction was monitored by TLC. After completion, the reaction mixture was concentrated under reduced pressure to get residue which was diluted with water (100 mL) and extracted with ethyl acetate (3×150 mL). Combined organic layer was washed with brine (3×50 mL), dried over anhydrous sodium sulfate and concentrated under reduced pressure to afford tert-butyl 3-(2-(cyclobutylamino)ethyl)azetidine-1-carboxylate (270 mg, 84.9%) which was used in the next step without purification.

Step-3: Synthesis of tert-butyl3-(2-((N-(tert-butoxycarbonyl)sulfamoyl)(cyclobut yl)amino)ethyl)azetidine-1-carboxylate: To a solution of tert-butyl3-(2-(cyclobutylamino)ethyl)azetidine-1-carboxylate (270 mg, 1.06 mmol, 1.0 eq) in DCM (5 mL) were added N-(tert-butoxycarbonyl)-N-[4-

(dimethylazaniumylidene)-1,4-dihydropyridin1ylsulfonyl]
azanide (384 mg, 1.27 mmol, 1.2 eq) and DIPEA (205 mg,
1.59 mmol, 1.5 eq) and the mixture was allowed to stir at RT
for overnight. Progress of reaction was monitored by TLC.
After completion, reaction mixture was diluted with water
(50 mL) and extracted with DCM (2×100 mL). Combined
organic layer was washed with brine (1×50 mL), dried over
anhydrous sodium sulfate and concentrated under reduced
pressure to afford tert-butyl3-(2-((N-(tert-butoxycarbonyl)
sulfamoyl)(cyclobutyl)amino)ethyl)azetidine-1-carboxylate
(350 mg, 76%).

Step-4: Synthesis of N-(2-(azetidin-3-yl)ethyl)-N-cyclobutylsulfamamide2,2,2-trifluoroacetate: To a solution of tert-butyl3-(2-((N-(tert-butoxycarbonyl)sulfamoyl)(cyclobutyl)amino)ethyl)azetidine-1-carboxylate (350 mg, 0.785 mmol, 1.0 eq) in DCM (4 mL) was added TFA (1.0 mL) and was allowed to stir at RT for 2 h. Progress of reaction was monitored by TLC. After completion, the reaction mixture was concentrated under reduced pressure to afford crude which was triturated with diethyl ether to afford N-(2-(azetidin-3-yl)ethyl)-N-cyclobutylsulfamamide 2,2,2-trifluoroacetate (250 mg, 96.5%).

Step-5: Synthesis of N-(2-(1-(7-chloro-5-methylpyrrolo[2,1-f][1,2,4]triazin-4-yl)azetidin-3-yl)ethyl)-N-cyclobutylsulfamamide: A suspension of N-(2-(azetidin-3-yl)ethyl)-N-cyclobutylsulfamamide 2,2,2-trifluoroacetate (74 mg, 0.223 mmol, 1.0 eq), 4,7-dichloro-5-methylpyrrolo[2,1-f][1,2,4]triazine (45 mg, 0.223 mmol, 1.0 eq) and DIPEA (57.5 mg, 0.446 mmol, 2.0 eq) in DMF (1.0 mL) was allowed to stir at 80° C. for 2 h. Progress of reaction was monitored by TLC and LCMS. After completion, reaction mixture was diluted with water (10 mL) and extracted with ethyl acetate (1×50 mL). Combined organic layer was washed with brine (1×10 mL), dried over anhydrous sodium sulfate and concentrated under reduced pressure to obtain crude which was purified using reversed phase chromatography to afford N-(2-(1-(7-chloro-5-methylpyrrolo[2,1-f][1,2,4]triazin-4-yl)azetidin-3-yl)ethyl)-N-cyclobutylsulfamamide (13 mg, 14.6%). LCMS: 399 [M+1]$^+$; $^1$H NMR (400 MHz, DMSO-d$_6$) δ ppm 7.90 (s, 1H), 6.63 (s, 1H), 6.66 (s, 2H), 4.45 (t, J=8.3 Hz, 2H), 4.02 (br. s., 2H), 3.96-3.87 (m, 1H), 3.01 (d, J=5.7 Hz, 2H), 2.76 (br. s., 1H), 2.39 (s, 3H), 2.06 (d, J=9.6 Hz, 4H), 1.88 (d, J=6.6 Hz, 2H), 1.63-1.48 (m, 2H).

Example-95: Synthesis of N-(2-(1-(7-chloro-5-methylpyrrolo[2,1-f][1,2,4]triazin-4-yl)azetidin-3-yl) ethyl)-N-propylsulfamamide, (Compound 1.95)

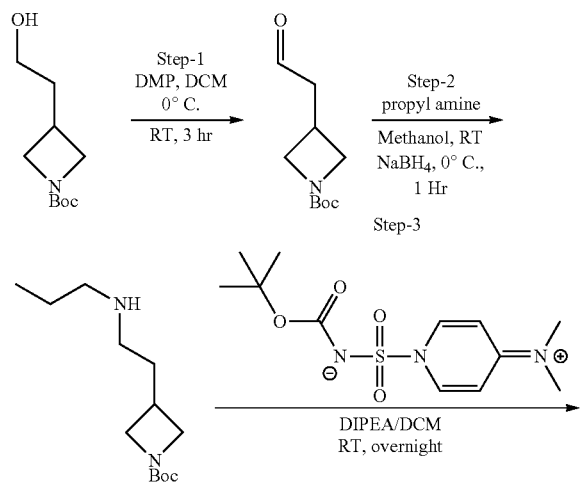

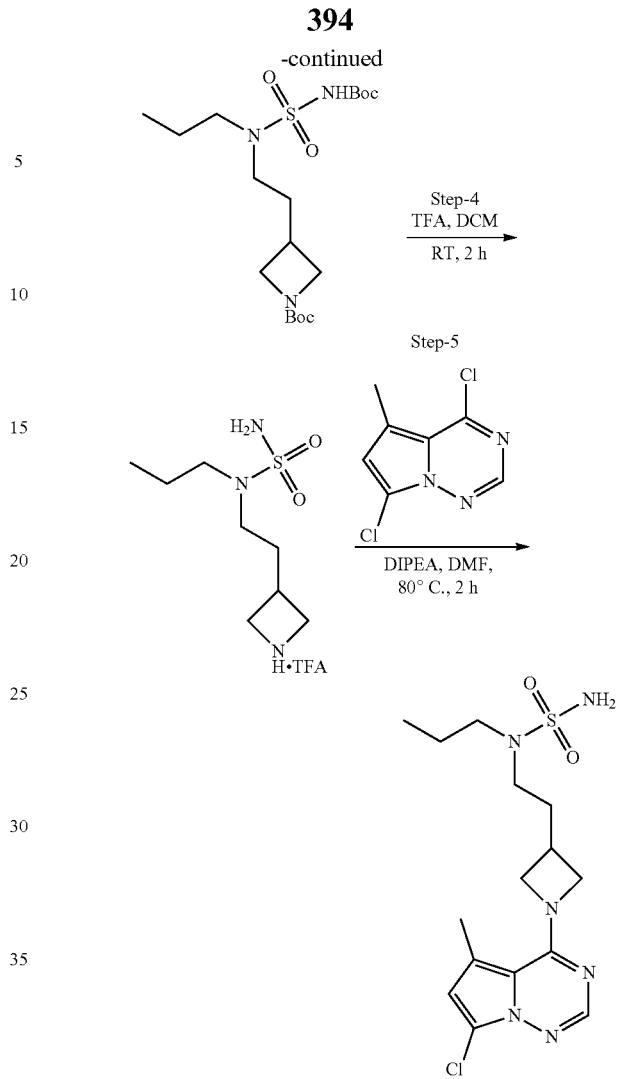

Step-1: Synthesis of tert-butyl 3-(2-oxoethyl)azetidine-1-carboxylate: A suspension of (2.0 g, 9.93 mmol, 1.0 eq) in DCM (50 mL) at 0° C. was added DMP (12.6 g, 29.8 mmol, 3.0 eq) was added portion wise at 0° C. After addition, the reaction mixture was stirred at RT for 3 h. Progress of reaction was monitored by TLC. After completion, the reaction mixture was concentrated under reduced pressure to get residue which was diluted with water (150 mL) and extracted with DCM (3×250 mL). Combined organic layer was washed with brine (3×50 mL), dried over anhydrous sodium sulfate and concentrated under reduced pressure to afford tert-butyl 3-(2-oxoethyl)azetidine-1-carboxylate (1.5 g, 76%) which was used in the next step without purification.

Step-2: Synthesis of tert-butyl 3-(2-(propylamino)ethyl)azetidine-1-carboxylate: A suspension of tert-butyl 3-(2-oxoethyl)azetidine-1-carboxylate (250 mg, 1.25 mmol, 1 eq), propylamine (89 mg, 1.50 mmol, 1.2 eq) in methanol (5 mL) was stirred at RT for overnight. After overnight stirring, NaBH$_4$ (71 mg, 1.875 mmol, 1.5 eq) was added into above reaction mixture portion wise at 0° C. and allowed to stir the reaction mixture for 1 h at 0° C. Progress of reaction was monitored by TLC. After completion, the reaction mixture was concentrated under reduced pressure to get residue which was diluted with water (100 mL) and extracted with ethyl acetate (3×100 mL). Combined organic layer was washed with brine (3×50 mL), dried over anhydrous sodium sulfate and concentrated under reduced pressure to afford tert-butyl 3-(2-(propylamino)ethyl)azetidine-1-carboxylate (200 mg, 66%) which was used in the next step without purification.

Step-3: Synthesis of tert-butyl3-(2-((N-(tert-butoxycarbonyl)sulfamoyl)(propyl)amino)ethyl)azetidine-1-carboxylate: To a solution of tert-butyl 3-(2-(propylamino)ethyl)azetidine-1-carboxylate (200 mg, 0.825 mmol, 1.0 eq) in DCM (5 mL) were added N-(tert-butoxycarbonyl)-N-[4-(dimethylazaniumylidene)-1,4-dihydropyridin1ylsulfonyl]azanide (299 mg, 0.990 mmol, 1.2 eq) and DIPEA (160 mg, 1.23 mmol, 1.5 eq) and the mixture was allowed to stir at RT for overnight. Progress of reaction was monitored by TLC. After completion, reaction mixture was diluted with water (50 mL) and extracted with DCM (2×150 mL). Combined organic layer was washed with brine (1×50 mL), dried over anhydrous sodium sulfate and concentrated under reduced pressure to afford tert-butyl3-(2-((N-(tert-butoxycarbonyl)sulfamoyl)(propyl)amino)ethyl)azetidine-1-carboxylate (270 mg, 77.58%).

Step-4: Synthesis of N-(2-(azetidin-3-yl)ethyl)-N-propylsulfamamide 2,2,2-trifluoroacetate: To a solution of tert-butyl3-(2-((N-(tert-butoxycarbonyl)sulfamoyl)(propyl)amino)ethyl)azetidine-1-carboxylate (270 mg, 0.623 mmol, 1 eq) in DCM (4 mL) was added TFA (0.7 mL) and was allowed to stir at RT for 2 h. Progress of reaction was monitored by TLC. After completion, reaction mixture was concentrated under reduced pressure to afford crude which was triturated with diethyl ether to afford N-(2-(azetidin-3-yl)ethyl)-N-propylsulfamamide 2,2,2-trifluoroacetate (170 mg, 85.85%)).

Step-5: Synthesis of N-(2-(1-(7-chloro-5-methylpyrrolo[2,1-f][1,2,4]triazin-4-yl)azetidin-3-yl)ethyl)-N-propylsulfamamide: A suspension of N-(2-(azetidin-3-yl)ethyl)-N-propylsulfamamide 2,2,2-trifluoroacetate (71 mg, 0.223 mmol, 1.0 eq), 4,7-dichloro-5-methylpyrrolo[1,2-f][1,2,4]triazine (45 mg, 0.223 mmol, 1.0 eq) and DIPEA (57.5 mg, 0.446 mmol, 2.0 eq) in DMF (1.0 mL) was allowed to stir at 80° C. for 2 h. Progress of reaction was monitored by TLC and LCMS. After completion, reaction mixture was diluted with water (10 mL) and extracted with ethyl acetate (1×50 mL). Combined organic layer was washed with brine (1×10 mL), dried over anhydrous sodium sulfate and concentrated under reduced pressure to obtain crude product which was purified using reversed phase chromatography to afford N-(2-(1-(7-chloro-5-methylpyrrolo[2,1-f][1,2,4]triazin-4-yl)azetidin-3-yl)ethyl)-N-propylsulfamamide (6.8 mg, 7.8%). LCMS: 387 [M+1]⁺; $^1$H NMR (400 MHz, DMSO-d$_6$) δ ppm 7.90 (s, 1H), 6.69-6.59 (m, 3H), 4.45 (t, J=8.8 Hz, 2H), 4.07-3.99 (m, 2H), 3.03-2.93 (m, 4H), 2.76 (br. s., 1H), 2.39 (s, 3H), 1.88 (d, J=7.0 Hz, 2H), 1.58-1.51 (m, 2H), 0.84 (t, J=7.2 Hz, 3H).

Example-96: Synthesis of N-(2-(6-chloro-1-methyl-1H-pyrazolo[3,4-d]pyrimidin-4-yl)-2-azaspiro[3.3]heptan-6-yl)-N-methylsulfamamide, (Compound 1.96)

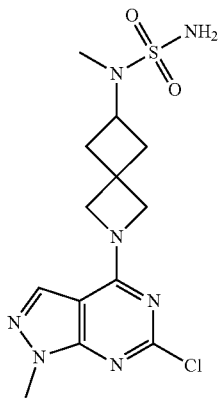

A suspension of N-methyl-N-(2-azaspiro[3.3]heptan-6-yl)sulfamamide 2,2,2-trifluoroacetate (149 mg, 0.492 mmol, 1.0 eq), 4,6-dichloro-1-methyl-1H-pyrazolo[3,4-d]pyrimidine (100 mg, 0.492 mmol, 1.0 eq) and DIPEA (127 mg, 0.984 mmol, 2.0 eq) in DMF (1 mL) was allowed to stir at 80° C. for 2 h. Progress of reaction was monitored by TLC and LCMS. After 2 h, reaction mixture was diluted with water (20 mL) and extracted with ethyl acetate (1×50 mL). Combined organic layer was washed with brine (10 mL), dried over anhydrous sodium sulfate and concentrated under reduced pressure to get crude which was purified using combiflash chromatography to afford N-(2-(6-chloro-1-methyl-1H-pyrazolo[3,4-d]pyrimidin-4-yl)-2-azaspiro[3.3]heptan-6-yl)-N-methylsulfamamide (24 mg, 13.11%) LCMS: 372 [M+1]⁺; NMR: $^1$H NMR (400 MHz, DMSO-d$_6$) δ ppm 8.03-7.99 (s, 1H), 6.73 (s, 2H), 4.52 (s, 1H), 4.40 (s, 1H), 4.28 (s, 1H), 4.16 (s, 1H), 3.85 (s, 3H), 3.76 (br. s., 1H), 2.54 (s, 3H), 2.37 (br. s., 2H), 2.33 (br. s., 2H)

Example-97: Synthesis of N-(2-(7-chloro-5-methylpyrrolo[2,1-f][1,2,4]triazin-4-yl)-2-azaspiro[3.3]heptan-6-yl)-N-propylsulfamamide, (Compound 1.97)

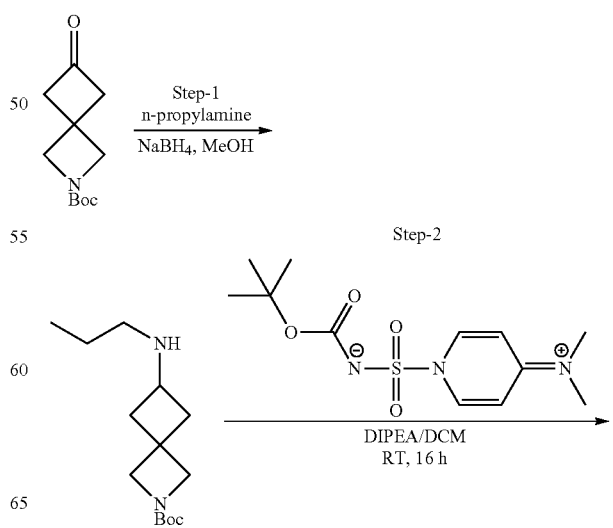

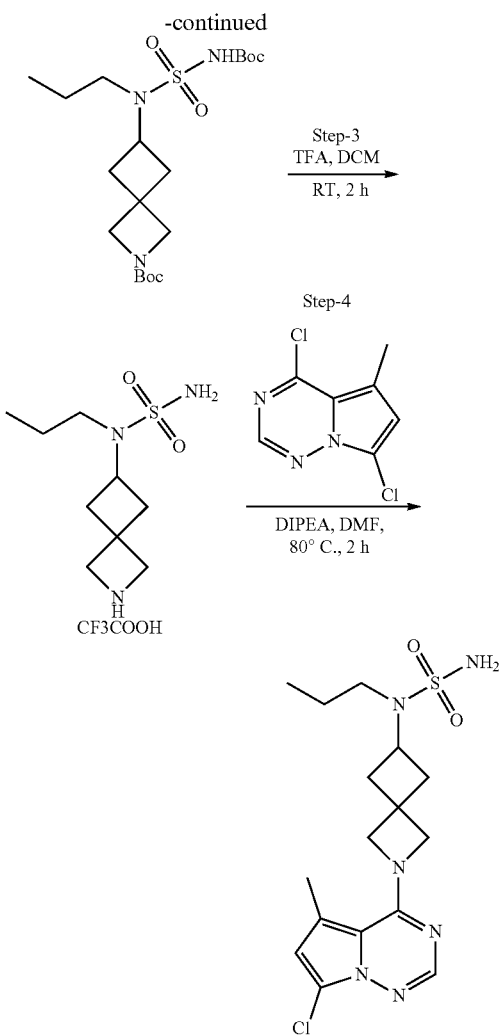

Step-1: Synthesis of tert-butyl 6-(propylamino)-2-azaspiro[3.3]heptane-2-carboxylate: To a stirred solution of tert-butyl 6-oxo-2-azaspiro[3.3]heptane-2-carboxylate (250 mg, 1.18 mmol, 1 eq) in methanol (5 ml) was added n-propylamine (84 mg, 1.42 mmol, 1.2 eq) and the reaction mixture was stirred at RT for overnight. To the reaction mixture, NaBH$_4$ (67 mg, 1.77 mmol, 1.5 eq) was added at 0° C. and then resultant reaction mixture was allowed to stir at 0° C. for 1 h. Progress of reaction was monitored by TLC and 1H-NMR. After completion, the reaction mixture was concentrated under reduced pressure to get residue which was diluted with water (100 mL) and extracted with dichloromethane (2×100 mL). Combined organic layer was dried over anhydrous sodium sulfate and concentrated under reduced pressure to afford tert-butyl 6-(propylamino)-2-azaspiro[3.3]heptane-2-carboxylate (290 mg, 96%) which was used in the next step without purification.

Step-2: Synthesis of tert-butyl 6-((N-(tert-butoxycarbonyl)sulfamoyl)(propyl)amino)-2-azaspiro[3.3]heptane-2-carboxylate: To a solution of tert-butyl 6-(propylamino)-2-azaspiro[3.3]heptane-2-carboxylate (290 mg, 1.14 mmol, 1 eq) in DCM (10 mL) were added N-(tert-butoxycarbonyl)-N-[4-(dimethylazaniumylidene)-1,4-dihydropyridin-1yl]sulfonyl]azanide (413 mg, 1.36 mmol, 1.2 eq) and DIPEA (0.29 mL, 1.71 mmol, 1.5 eq) and the mixture was allowed to stir at RT for 16 h. Progress of reaction was monitored by TLC and 1H-NMR. After completion, reaction mixture was concentrated under reduced pressure to get residue which was washed with 1N HCl solution (100 mL) and extracted with ethyl acetate (2×100 mL). Combined organic layer was dried over anhydrous sodium sulfate and concentrated under reduced pressure to afford tert-butyl 6-((N-(tert-butoxycarbonyl)sulfamoyl)(propyl)amino)-2-azaspiro[3.3]heptane-2-carboxylate (380 mg, 77%).

Step-3: Synthesis of N-propyl-N-(2-azaspiro[3.3]heptan-6-yl)sulfamamide trifluoroacetate: To a solution of tert-butyl 6-((N-(tert-butoxycarbonyl)sulfamoyl)(propyl)amino)-2-azaspiro[3.3]heptane-2-carboxylate (380 mg, 0.87 mmol, 1 eq) in DCM (10 mL) was added TFA (3 mL) and was allowed to stir at RT for 2 h. Progress of reaction was monitored by TLC. After completion, the reaction mixture was concentrated under reduced pressure to afford crude which was triturated with diethyl ether to afford N-propyl-N-(2-azaspiro[3.3]heptan-6-yl)sulfamamide trifluoroacetate (340 mg, 100%).

Step-4: Synthesis of N-(2-(7-chloro-5-methylpyrrolo[2,1-f][1,2,4]triazin-4-yl)-2-azaspiro[3.3]heptan-6-yl)-N-propylsulfamamide: A suspension of N-propyl-N-(2-azaspiro[3.3]heptan-6-yl)sulfamamide trifluoroacetate (172 mg, 0.49 mmol, 1 eq), 4,7-dichloro-5-methylpyrrolo[2,1-f][1,2,4]triazine (100 mg, 0.49 mmol, 1 eq) and DIPEA (0.12 mL, 0.74 mmol, 1.5 eq) in DMF (1 mL) was allowed to stir at 80° C. for 2 h. Progress of reaction was monitored by LCMS and TLC. After completion, reaction mixture was poured onto ice cold water (100 mL) and extracted with ethyl acetate (100 mL). Organic layer was concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-propylsulfamamide (8 mg, 7%). LCMS: 399 [M+1]$^+$; $^1$H NMR (400 MHz, DMSO-d$_6$) δ ppm 0.83 (t, J=7.45 Hz, 3H) 1.51 (d, J=7.02 Hz, 2H) 2.32 (d, J=7.89 Hz, 2H) 2.39 (s, 5H) 2.84-2.97 (m, 2H) 3.80-3.94 (m, 1H) 4.30 (br. s., 2H) 4.41 (br. s., 2H) 6.64 (d, J=9.65 Hz, 3H) 7.90 (s, 1H).

Example-98: Synthesis of N-(2-(7-chloro-5-methylpyrrolo[2,1-f][1,2,4]triazin-4-yl)-2-azaspiro[3.3]heptan-6-yl)-N-ethylsulfamamide, (Compound 1.98)

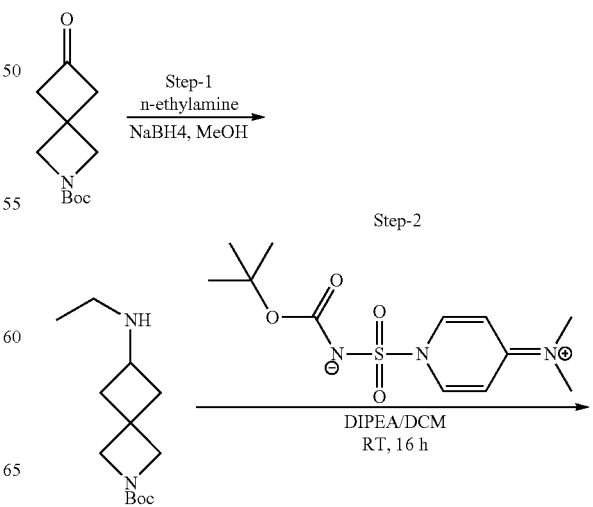

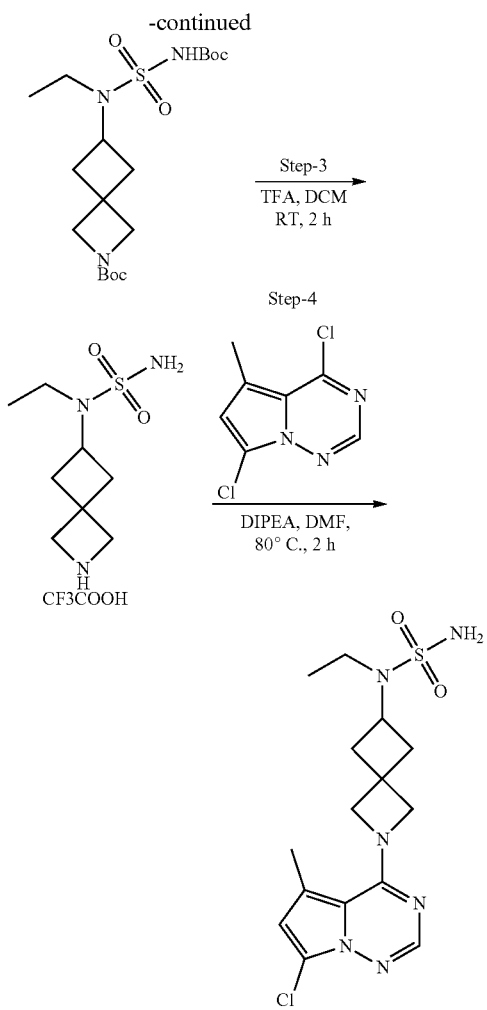

Step-1: Synthesis of tert-butyl 6-(ethylamino)-2-azaspiro[3.3]heptane-2-carboxylate: To a stirred solution of tert-butyl 6-oxo-2-azaspiro[3.3]heptane-2-carboxylate (250 mg, 1.18 mmol, 1 eq) in methanol (5 mL) was added n-ethylamine (64 mg, 1.42 mmol, 1.2 eq) and the reaction mixture was stirred at RT for overnight. To the reaction mixture, NaBH$_4$ (67 mg, 1.77 mmol, 1.5 eq) was added at 0° C. and then resultant reaction mixture was allowed to stir at 0° C. for 1 h. Progress of reaction was monitored by TLC and 1H-NMR. After completion, reaction mixture was concentrated under reduced pressure to get residue which was diluted with water (100 mL) and extracted with dichloromethane (2×100 mL). Combined organic layer was dried over anhydrous sodium sulfate and concentrated under reduced pressure to afford tert-butyl 6-(ethylamino)-2-azaspiro[3.3]heptane-2-carboxylate (250 mg, 88%) which was used in the next step without purification.

Step-2: Synthesis of tert-butyl 6-((N-(tert-butoxycarbonyl)sulfamoyl)(ethyl)amino)-2-azaspiro[3.3]heptane-2-carboxylate: To a solution of tert-butyl 6-(ethylamino)-2-azaspiro[3.3]heptane-2-carboxylate (250 mg, 1.04 mmol, 1 eq) in DCM (10 mL) were added N-(tert-butoxycarbonyl)-N-[4-(dimethylazaniumylidene)-1,4-dihydropyridin-1yl sulfonyl]azanide (377 mg, 1.24 mmol, 1.2 eq) and DIPEA (0.27 mL, 1.56 mmol, 1.5 eq) and the mixture was allowed to stir at RT for 16 h. Progress of reaction was monitored by TLC and 1H-NMR. After completion, the reaction mixture was concentrated under reduced pressure to get residue which was washed with 1N HCl solution (100 mL) and extracted with ethyl acetate (2×100 mL). Combined organic layer was dried over anhydrous sodium sulfate and concentrated it. The crude was purified by combiflash chromatography to afford tert-butyl 6-((N-(tert-butoxycarbonyl)sulfamoyl)(ethyl)amino)-2-azaspiro[3.3]heptane-2-carboxylate (190 mg, 43%).

Step-3: Synthesis of N-ethyl-N-(2-azaspiro[3.3]heptan-6-yl)sulfamamide trifluoroacetate: To a solution of tert-butyl 6-((N-(tert-butoxycarbonyl)sulfamoyl)(ethyl)amino)-2-azaspiro[3.3]heptane-2-carboxylate (190 mg, 0.45 mmol, 1 eq) in DCM (10 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-ethyl-N-(2-azaspiro[3.3]heptan-6-yl)sulfamamide trifluoroacetate (109 mg, 72.6%).

Step-4: Synthesis of N-(2-(7-chloro-5-methylpyrrolo[2,1-f][1,2,4]triazin-4-yl)-2-azaspiro[3.3]heptan-6-yl)-N-ethylsulfamamide: A suspension of N-ethyl-N-(2-azaspiro[3.3]heptan-6-yl)sulfamamide trifluoroacetate (109 mg, 0.49 mmol, 1 eq), 4,7-dichloro-5-methylpyrrolo[2,1-f][1,2,4]triazine (100 mg, 0.49 mmol, 1 eq) and DIPEA (0.17 mL, 0.99 mmol, 2 eq) in DMF (1 mL) was allowed to stir at 80° C. for 2 h. Progress of reaction was monitored by LCMS and TLC. After completion, reaction mixture was poured onto ice cold water (100 mL) and extracted with ethyl acetate (100 mL). Combined organic layer was concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-ethylsulfamamide (1 mg, 0.8%). LCMS: 385 [M+1]$^+$; $^1$H NMR (400 MHz, DMSO-d$_6$) δ ppm 1.01-1.14 (m, 3H) 2.24-2.36 (m, 2H) 2.40 (s, 3H) 2.54 (m, 2H) 3.11 (m, 2H) 3.80-3.94 (m, 1H) 4.30 (s, 2H) 4.42 (s, 2H) 6.64 (d, J=9.21 Hz, 3H) 7.90 (s, 1H).

Example-99: Synthesis of N-(2-(7-chloro-5-methylpyrrolo[2,1-f][1,2,4]triazin-4-yl)-2-azaspiro[3.3]heptan-6-yl)-N-(2,2-difluoroethyl)sulfamamide, (Compound 1.99)

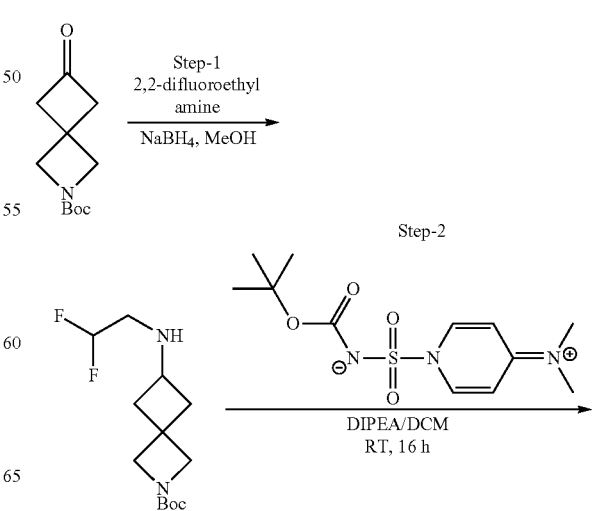

-continued

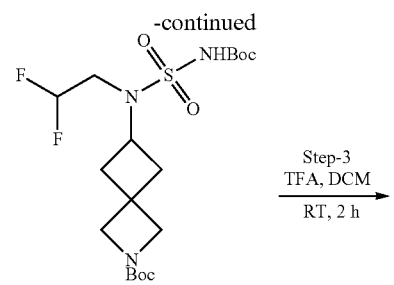

Step-3
TFA, DCM
RT, 2 h

Step-4

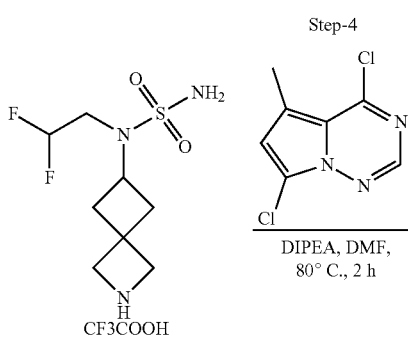

DIPEA, DMF,
80° C., 2 h

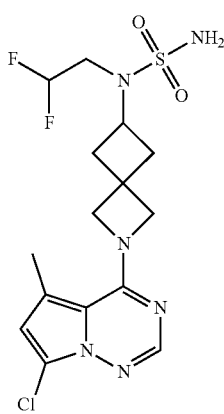

Step-1: Synthesis of tert-butyl 6-((2,2-difluoroethyl) amino)-2-azaspiro[3.3]heptane-2-carboxylate: To a stirred solution of tert-butyl 6-oxo-2-azaspiro[3.3]heptane-2-carboxylate (200 mg, 0.94 mmol, 1 eq) in methanol (5 mL) was added 2,2-difluoroethylamine (92 mg, 1.13 mmol, 1.2 eq) and the reaction mixture was stirred at RT for overnight. To the reaction mixture, NaBH$_4$ (179 mg, 4.73 mmol, 5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (100 mL) and extracted with dichloromethane (2×100 mL). Combined organic layer was dried over anhydrous sodium sulfate and concentrated under reduced pressure to afford tert-butyl 6-((2,2-difluoroethyl) amino)-2-azaspiro[3.3]heptane-2-carboxylate (290 mg, 100%) which was used in the next step without purification.

Step-2: Synthesis of tert-butyl 6-((N-(tert-butoxycarbonyl)sulfamoyl)(2,2-difluoroethyl)amino)-2-azaspiro[3.3]heptane-2-carboxylate: To a solution of tert-butyl 6-((2,2-difluoroethyl)amino)-2-azaspiro[3.3]heptane-2-carboxylate (290 mg, 1.04 mmol, 1 eq) in DCM (10 mL) were added N-(tert-butoxycarbonyl)-N-[4-(dimethylazaniumylidene)-1,4-dihydropyridin-1ylsulfonyl]azanide (380 mg, 1.25 mmol, 1.2 eq) and DIPEA (0.27 ML, 1.57 mmol, 1.5 eq) and the mixture was allowed to stir at RT for 16 h. Progress of reaction was monitored by TLC. After completion, reaction mixture was concentrated under reduced pressure to get residue which was washed with 1N HCl solution (100 mL) and extracted with ethyl acetate (2×100 mL). Combined organic layer was dried over anhydrous sodium sulfate and concentrated it. The crude was purified by combiflash chromatography to afford tert-butyl 6-((N-(tert-butoxycarbonyl) sulfamoyl)(2,2-difluoroethyl)amino)-2-azaspiro[3.3]heptane-2-carboxylate (190 mg, 38%).

Step-3: Synthesis of N-(2,2-difluoroethyl)-N-(2-azaspiro[3.3]heptan-6-yl)sulfamamide trifluoroacetate: To a solution of tert-butyl 6-((N-(tert-butoxycarbonyl)sulfamoyl)(2,2-difluoroethyl)amino)-2-azaspiro[3.3]heptane-2-carboxylate (190 mg, 0.41 mmol, 1 eq) in DCM (10 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-(2,2-difluoroethyl)-N-(2-azaspiro[3.3]heptan-6-yl)sulfamamide trifluoroacetate (88 mg, 100%).

Step-4: Synthesis of N-(2-(7-chloro-5-methylpyrrolo[2,1-f][1,2,4]triazin-4-yl)-2-azaspiro[3.3]heptan-6-yl)-N-(2,2-difluoroethyl)sulfamamide: A suspension of N-(2,2-difluoroethyl)-N-(2-azaspiro[3.3]heptan-6-yl)sulfamamide trifluoroacetate (88 mg, 0.34 mmol, 1 eq), 4,7-dichloropyrrolo[2,1-f][1,2,4]triazine (70 mg, 0.34 mmol, 1 eq) and DIPEA (0.12 mL, 0.69 mmol, 2 eq) in DMF (1 mL) was allowed to stir at 80° C. for 2 h. Progress of reaction was monitored by LCMS and TLC. After completion, reaction mixture was poured onto ice cold water (100 mL) and extracted with ethyl acetate (100 mL). Combined organic layer was dried over anhydrous sodium sulfate and concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-(2,2-difluoroethyl) sulfamamide (6 mg, 3.8%). LCMS: 421 [M+1]$^+$; $^1$H NMR (400 MHz, DMSO-d$_6$) δ ppm 2.25-2.36 (m, 4H) 2.40 (s, 5H) 3.88-4.05 (m, 1H) 4.31 (br. s., 2H) 4.40 (br. s., 2H) 6.01 (t, 1H) 6.63 (s, 1H) 7.01 (br. s., 2H) 7.90 (s, 1H).

Example-100: Synthesis of N-methyl-N-(2-(5-phenylthieno[2,3-d]pyrimidin-4-yl)-2-azaspiro[3.3]heptan-6-yl)sulfamamide, (Compound 1.100)

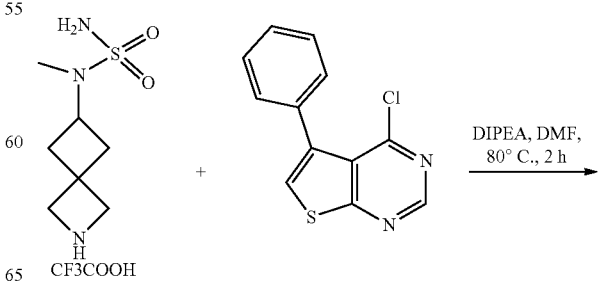

DIPEA, DMF,
80° C., 2 h

-continued

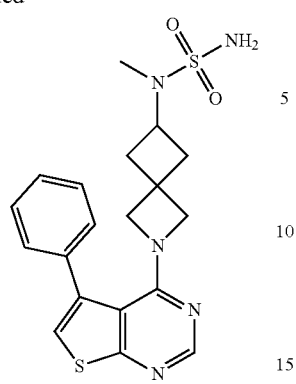

A suspension of N-methyl-N-(2-azaspiro[3.3]heptan-6-yl)sulfamamide 2,2,2-trifluoroacetate (67 mg, 0.222 mmol, 1.10 eq), 4-chloro-5-phenylthieno[2,3-d]pyrimidine (50 mg, 0.202 mmol, 1.0 eq) and DIPEA (52 mg, 0.404 mmol, 2.0 eq) in DMF (1 mL) was allowed to stir at 80° C. for 2 h. Progress of reaction was monitored by TLC and LCMS. After completion, reaction mixture was diluted with water (20 mL) and extracted with ethyl acetate (2×50 mL). Combined organic layer was washed with brine (10 mL), dried over anhydrous sodium sulfate and concentrated under reduced pressure to obtain crude product which was purified using combiflash chromatography to afford N-methyl-N-(2-(5-phenylthieno[2,3-d]pyrimidin-4-yl)-2-azaspiro[3.3]heptan-6-yl)sulfamamide (30 mg, 35.7%) LCMS: 416 [M+1]$^+$; NMR: $^1$H NMR (400 MHz, DMSO-d$_6$) δ ppm 8.46 (s, 1H), 7.54 (s, 1H), 7.54-7.46 (m, 3H), 7.45-7.38 (m, 2H), 6.62 (s, 2H), 3.64-3.36 (m, 5H), 2.40 (s, 3H), 2.14-1.95 (m, 4H).

Example-101: Synthesis of N-(2-(7-chloro-2-isopropyl-5-methylpyrrolo[1,2-f][1,2,4]triazin-4-yl)-2-azaspiro[3.3]heptan-6-yl)-N-methylsulfamide, (Compound 1.101)

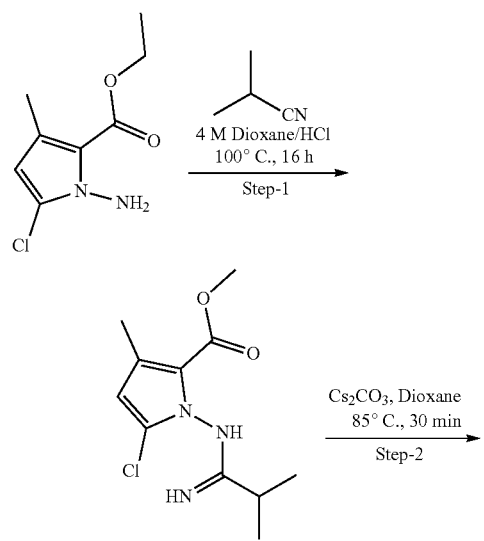

-continued

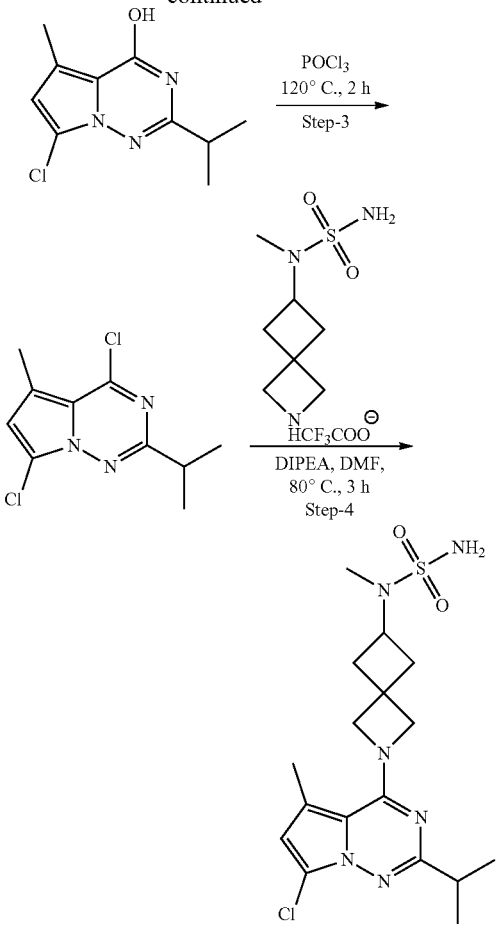

Step-1: Synthesis of ethyl 5-chloro-1-isobutyrimidamido-3-methyl-1H-pyrrole-2-carboxylate: A mixture of ethyl 1-amino-5-chloro-3-methyl-1H-pyrrole-2-carboxylate (500 mg, 2.97 mmol, 1 eq) and isobutyronitrile (246.5 mg, 3.56 mmol, 1.2 eq) in 4M HCl in dioxane (4 mL) was allowed to stir at 100° C. for 16 h. Progress of reaction was monitored by TLC. After completion of reaction, reaction mixture was cooled to RT, quenched with NaHCO$_3$ extracted with ethyl acetate (150 ml×2). Combined organic layer was washed with brine (50 mL) and dried over anhydrous sodium sulfate concentrated to get crude product. The crude product was purified by combi flash chromatography [silica gel 100-200 mesh, elution 0-40% Ethyl acetate in hexane] to ethyl 5-chloro-1-isobutyrimidamido-3-methyl-1H-pyrrole-2-carboxylate (470 mg, 70.09%) LCMS: 272.1 [M+1]$^+$ Step-2: Synthesis of 7-chloro-2-isopropyl-5-methylpyrrolo[1,2-f][1,2,4]triazin-4-ol: To a solution of ethyl 5-chloro-1-isobutyrimidamido-3-methyl-1H-pyrrole-2-carboxylate (470 mg, 2.08 mmol, 1 eq) in Dioxane (8 mL) was added Cesium carbonate (1.3 g, 4.165 mmol, 2 eq) at RT and the reaction mixture was allowed to stir at 85° C. for 30 min. Progress of reaction was monitored by TLC. After completion, the reaction mixture was diluted with water (150 mL) and extracted with ethyl acetate (250 ml×2). Combined organic layer was washed with brine (50 mL) and dried over anhydrous sodium sulfate concentrated to get crude, which was purified by combiflash elution (0-30% ETOAc/Hexane) to afford 7-chloro-2-isopropyl-5-methylpyrrolo[1,2-f][1,2,4]triazin-4-ol (140 g, 35.86%). LCMS: 226 [M+1]$^+$ Step-3: Synthesis of 4,7-dichloro-2-isopropyl-5-methylpyrrolo[1,2-f][1,2,4]triazine: A mixture of 7-chloro-2-cyclopropyl-5-methylpyrrolo[1,2-f][1,2,4]triazin-4-ol (140 mg, 0.62 mmol, 1 eq) in POCl₃ (3 mL) was allowed to stir at 120° C. for 2 h. Progress of reaction was monitored by TLC. After completion reaction mixture was cooled to RT, quenched with NaHCO₃ to maintain pH-7 and extracted with ethyl acetate (150 ml×2). Combined organic layer was washed with brine (50 mL) and dried over anhydrous sodium sulfate concentrated to get crude product. The crude product was purified by combi flash chromatography [silica gel 100-200 mesh, elution 0-10% Ethyl acetate in hexane] to 4,7-dichloro-2-isopropyl-5-methylpyrrolo[1,2-f][1,2,4]triazine as yellow solid. (100 mg, 66.03%) LCMS: 244 [M+1]⁺

Step-4: Synthesis of N-(2-(7-chloro-2-isopropyl-5-methylpyrrolo[1,2-f][1,2,4]triazin-4-yl)-2-azaspiro[3.3]heptan-6-yl)-N-methylsulfamide: To a solution of, 4,7-dichloro-2-isopropyl-5-methylpyrrolo[1,2-f][1,2,4]triazine (100 mg, 0.411 mmol, 1.0 eq) and N-methyl-N-(2-azaspiro[3.3]heptan-6-yl)sulfamamide trifluoroacetate (126 mg, 0.617 mmol, 1 eq) in DMF (2 ml) was added N,N-diisopropylethylamine (0.1 mL, 0.616 mmol, 1.5 eq). The reaction mixture was allowed to stir at 90° C. for overnight. Progress of reaction was monitored by LCMS. After completion, reaction mixture was diluted with water (30 ml) extracted with ethyl acetate (150 ml×2). Combined organic layer was washed with brine (50 mL) and dried over anhydrous sodium sulfate concentrated to get crude product, which was purified by reverse phase chromatography to afford N-(2-(7-chloro-2-isopropyl-5-methylpyrrolo[1,2-f][1,2,4]triazin-4-yl)-2-azaspiro[3.3]heptan-6-yl)-N-methylsulfamide (5 mg, 2.93%). LCMS: 413.1 [M+1]⁺; ¹H NMR (400 MHz, DMSO-d₆) δ ppm 6.69 (s, 2H), 6.56 (s, 1H), 4.41 (s, 2H), 4.28 (s, 2H), 3.76-3.71 (m, 1H), 2.81-2.76 (m, 1H), 2.53-2.33 (m, 10H), 1.22 (d, J=6.58 Hz, 6H).

Example-102: Synthesis of N-(2-(7-chloro-5,6-dimethylpyrrolo[1,2-f][1,2,4]triazin-4-yl)-2-azaspiro[3.3]heptan-6-yl)-N-methylsulfamamide, (Compound 1.102)

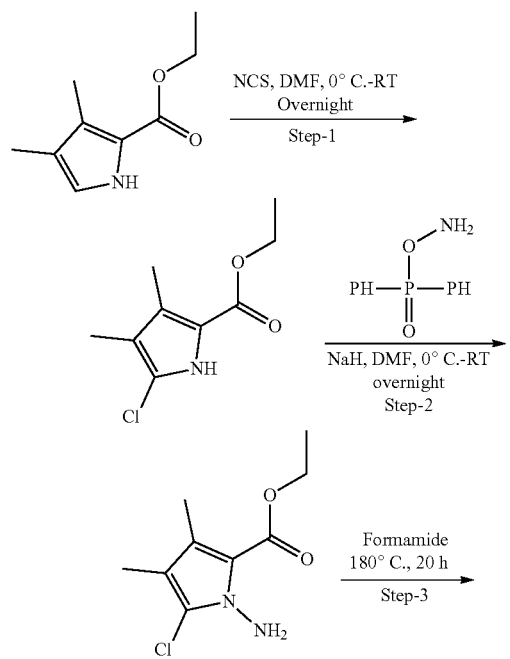

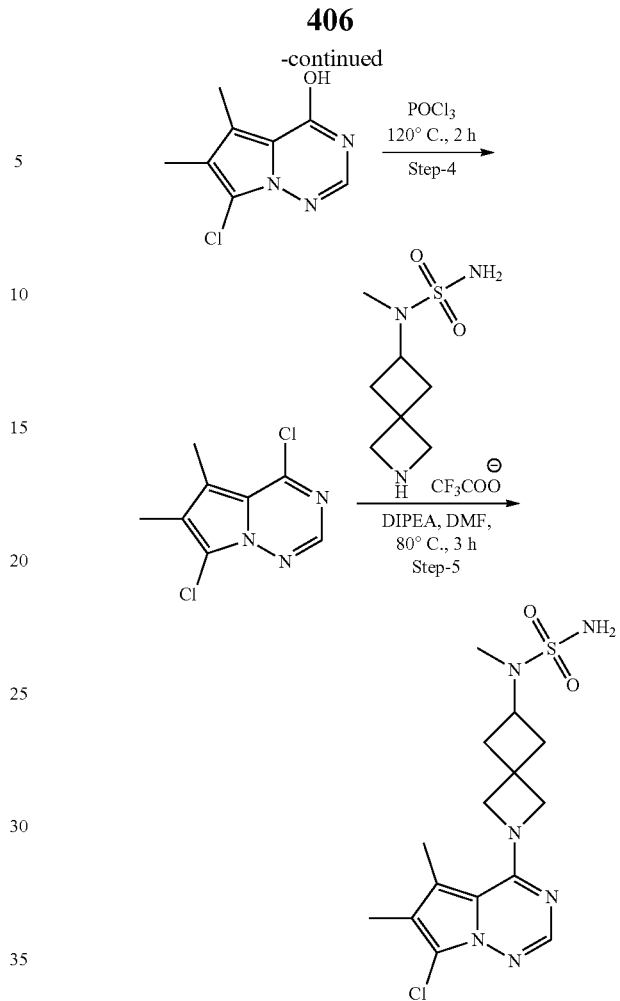

Step-1: Synthesis of ethyl 5-chloro-3,4-dimethyl-1H-pyrrole-2-carboxylate: To a solution of ethyl 3,4-dimethyl-1H-pyrrole-2-carboxylate (500 mg, 2.99 mmol, 1 eq) in DMF (5 mL) was added N-chlorosuccinimide (439 mg, 3.28 mmol, 1.1 eq) at 0° C. and the reaction mixture was allowed to stir at RT for overnight. Progress of reaction was monitored by TLC. After completion, to this reaction mixture was added ice-cold water under stirring, the formed suspension was filtered to get ethyl 5-chloro-3,4-dimethyl-1H-pyrrole-2-carboxylate (400 mg, 66.33%). LCMS: 202 [M+1]⁺

Step-2: Synthesis of ethyl 1-amino-5-chloro-3,4-dimethyl-1H-pyrrole-2-carboxylate: To a solution of ethyl 5-chloro-3,4-dimethyl-1H-pyrrole-2-carboxylate (300 mg, 1.48 mmol, 1 eq) in DMF (20 mL) was added Sodium hydride (0.9 mg, 2.23 mmol, 1.5 eq) at 0° C. and the reaction mixture was allowed to stir at 0° C. for 15 minutes. To this reaction mixture was added O-(diphenylphosphoryl)hydroxylamine (520 mg, 2.23 mmol, 1.5 eq) at 0° C. portion wise and allowed to stir at RT for overnight Progress of reaction was monitored by TLC. After completion, the reaction mixture was diluted with water (250 mL) and extracted with MTEB (250 ml×2). Combined organic layer was washed with brine (50 mL) and dried over anhydrous sodium sulfate concentrated to get product to afford ethyl 1-amino-5-chloro-3,4-dimethyl-1H-pyrrole-2-carboxylate (200 mg, 62.04%). LCMS: 217 [M+1]⁺

Step-3 Synthesis of 7-chloro-5,6-dimethylpyrrolo[1,2-f][1,2,4]triazin-4-ol: A solution of ethyl 1-amino-5-chloro-3,4-dimethyl-1H-pyrrole-2-carboxylate (200 mg, 0.92 mmol, 1 eq) in formamide (2 mL) was allowed to stir at 165° C. for overnight. Progress of reaction is monitored by TLC. After completion, reaction mixture was diluted with cold water (30 mL) and allowed to stir for 10 minutes. Solid was filtered, washed with water followed by hexane and dried under vacuum to afford 5-methylpyrrolo[1,2-f][1,2,4]triazin-4-ol (70 mg, 38.37%). LCMS: 198 [M+1]$^+$ Step-4: Synthesis of 4,7-dichloro-5,6-dimethylpyrrolo[1,2-f][1,2,4]triazine: A mixture of 7-chloro-5,6-dimethylpyrrolo[1,2-f][1,2,4]triazin-4-ol (70 mg, 0.354 mmol, 1 eq) in POCl$_3$ (1 mL) was allowed to stir at 120° C. for 2 h. Progress of reaction was monitored by TLC. After completion of reaction, reaction mixture was cooled to RT, quenched with NaHCO$_3$ to maintain pH-7 and extracted with ethyl acetate (150 ml×2). Combined organic layer was washed with brine (50 mL) and dried over anhydrous sodium sulfate concentrated to get crude product used in next step without purification 4,7-dichloro-5,6-dimethylpyrrolo[1,2-f][1,2,4]triazine as off white solid. (80 mg, LCMS: 216 [M+1]$^+$ Step-6: Synthesis of N-(2-(7-chloro-5,6-dimethylpyrrolo[1,2-f][1,2,4]triazin-4-yl)-2-azaspiro[3.3]heptan-6-yl)-N-methylsulfamamide: To a solution of, 4,7-dichloro-5,6-dimethylpyrrolo[1,2-f][1,2,4]triazine (80 mg, 0.370 mmol, 1.0 eq) and N-methyl-N-(2-azaspiro[3.3]heptan-6-yl)sulfamamide trifluoroacetate (113 mg, 0.555 mmol, 1.5 eq) in DMF (2 ml) was added N,N-diisopropylethylamine (0.09 mL, 0.555 mmol, 1.5 eq). The reaction mixture was allowed to stir at 90° C. for overnight. Progress of reaction was monitored by LCMS. After completion, reaction mixture was diluted with water (30 ml) extracted with ethyl acetate (150 ml×2). Combined organic layer was washed with brine (50 mL) and dried over anhydrous sodium sulfate and concentrated to get crude product. The crude was purified by reverse phase chromatography to get N-(2-(7-chloro-5,6-dimethylpyrrolo[1,2-f][1,2,4]triazin-4-yl)-2-azaspiro[3.3]heptan-6-yl)-N-methylsulfamamide (90 mg, 63.15%). LCMS: 385.1 [M+1]$^+$; $^1$H NMR (400 MHz, DMSO-d$_6$) δ ppm 7.87 (s, 1H), 6.67 (brs., 2H), 4.41 (s, 2H), 4.28 (s, 2H), 3.81-3.71 (m, 1H), 2.53-2.48 (m, 3H), 2.41-2.29 (m, 7H), 2.13 (s, 3H).

Example-103: Synthesis of N-(2-(7-chloro-2,5-dimethylpyrrolo[1,2-f][1,2,4]triazin-4-yl)-2-azaspiro[3.3]heptan-6-yl)-N-propylsulfatamide, (Compound 1.103)

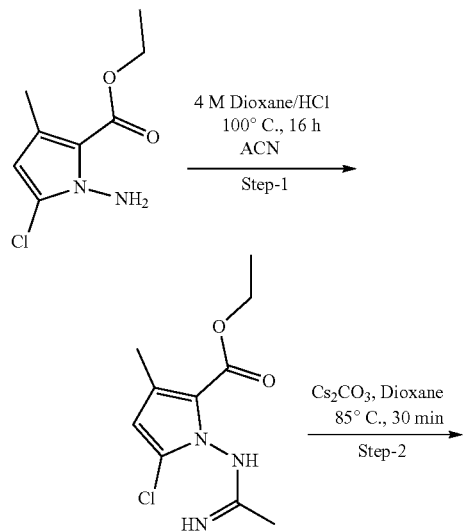

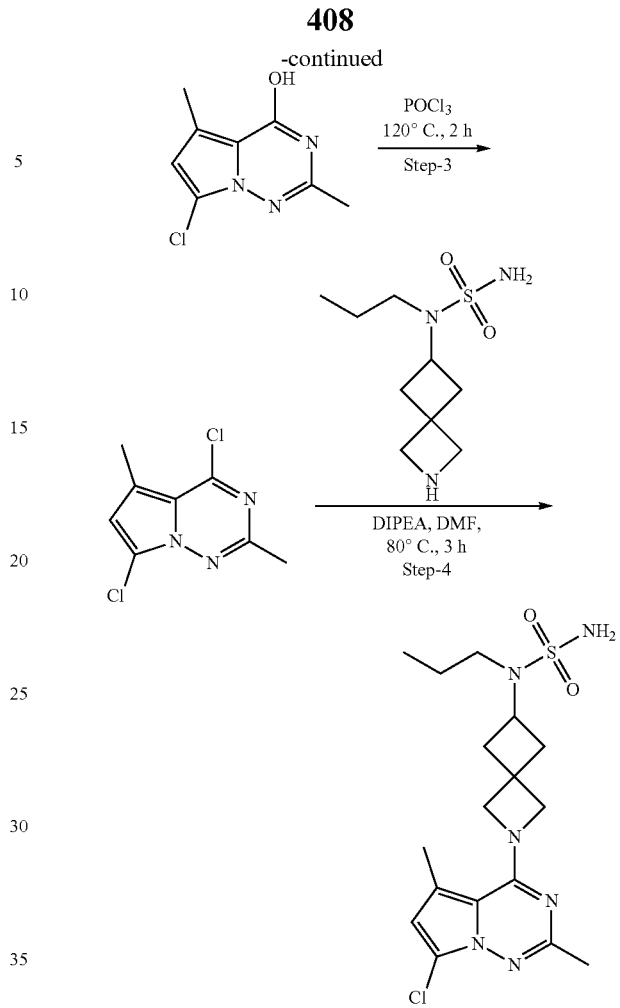

Step-1: Synthesis ethyl 1-acetimidamido-5-chloro-3-methyl-1H-pyrrole-2-carboxylate: The mixture of ethyl 1-amino-5-chloro-3-methyl-1H-pyrrole-2-carboxylate (500 mg, 2.97 mmol, 1 eq) and Acetonitrile (145.8 mg, 3.55 mmol, 1.2 eq) in 4M HCl in dioxane (4 mL) was allowed to stir at 100° C. for 16 h. Progress of reaction was monitored by TLC. After completion of reaction, reaction mixture was cooled to RT, quenched with NaHCO$_3$ extracted with ethyl acetate (150 ml×2)). Combined organic layer was washed with brine (50 mL) and dried over anhydrous sodium sulfate concentrated to get crude product which was used in next step without purification ethyl 1-acetimidamido-5-chloro-3-methyl-1H-pyrrole-2-carboxylate (800 mg, 133.04%) LCMS: 244 [M+1]$^+$ Step-2: Synthesis of 7-chloro-2,5-dimethylpyrrolo[1,2-f][1,2,4]triazin-4-ol: To a solution of ethyl 1-acetimidamido-5-chloro-3-methyl-1H-pyrrole-2-carboxylate (800 mg, 3.28 mmol, 1 eq) in Dioxane (15 mL) was added Cesium carbonate (2.13 mg, 6.56 mmol, 2 eq) at RT and the reaction mixture was allowed to stir at 85° C. for 30 min. Progress of reaction was monitored by TLC. After completion, the reaction mixture was diluted with water (150 mL) and extracted with ethyl acetate (250 ml×2), Combined organic layer was washed with brine (50 mL) and dried over anhydrous sodium sulfate concentrated to get crude was purified by combiflash elution (0-30% ETOAc/Hexane) to afford 7-chloro-2,5-dimethylpyrrolo[1,2-f][1,2,4]triazin-4-ol (385 mg, 59.34%). LCMS: 198 [M+1]$^+$ Step-3: Synthesis of 4,7-dichloro-2,5-dimethylpyrrolo[1,2-f][1,2,4]triazine: The mixture of 7-chloro-2,5-dimethylpyrrolo[1,2-f][1,2,4]triazin-4-ol (385 m g, 1.94 mmol, 1 eq) in POCl$_3$ (5 mL) was allowed to stir at 120° C. for 2 h. Progress of reaction was monitored by TLC. After completion reaction mixture was cooled to RT, quenched with NaHCO$_3$ to maintain pH-7 and extracted with ethyl acetate (150 ml×2). Combined organic layer was washed with brine (50 mL) and dried over anhydrous sodium sulfate concentrated to get crude product. The crude product was purified by combi flash chromatography [silica gel 100-200 mesh, elution 0-10% Ethyl acetate in hexane] to 4,7-dichloro-2,5-dimethylpyrrolo[1,2-f][1,2,4]triazine (300 mg, 71.26%) as yellow solid. LCMS: 216 [M+1]$^+$ Step-4: Synthesis of N-(2-(7-chloro-2,5-dimethylpyrrolo[1,2-f][1,2,4]triazin-4-yl)-2-azaspiro[3.3]heptan-6-yl)-N-propylsulfatamide: To a solution of 4,7-dichloro-2,5-dimethylpyrrolo[1,2-f][1,2,4]triazine (150 mg, 0.694 mmol, 1 eq) and N-butyl-N-(2-azaspiro[3.3]heptan-6-yl)sulfamamide trifluoroacetate (242 mg, 1.04 mmol, 1 eq) in DMF (3 ml), N,N-diisopropylethylamine (0.18 mL, 1.04 mmol, 1.5 eq) was added. The reaction mixture was allowed to stir at 90° C. for overnight. Progress of reaction was monitored by LCMS. After completion, reaction mixture was diluted with water (30 ml) extracted with ethyl acetate (150 ml×2). Combined organic layer was washed with brine (50 mL) and dried over anhydrous sodium sulfate concentrated to get crude product. which was purified by reverse phase chromatography to afford N-(2-(7-chloro-2,5-dimethylpyrrolo[1,2-f][1,2,4]triazin-4-yl)-2-azaspiro[3.3]heptan-6-yl)-N-propylsulfatamide (50 mg, 17.44%). LCMS: 413[M+1]$^+$; $^1$H NMR (400 MHz, DMSO-d$_6$) δ ppm 6.65 (s, 2H), 6.55 (s, 1H), 4.40 (s, 2H), 4.28 (s, 2H), 3.87-3.82 (m, 1H), 2.94-2.87 (m, 2H), 2.49-2.23 (m, 10H), 1.51-1.46 (m, 2H), 0.83-0.78 (m, 3H).

Example-104: Synthesis of N-(2-(1-(7-chloro-5-methylpyrrolo[1,2-f][1,2,4]triazin-4-yl)azetidin-3-yl)ethyl)sulfamamide, (Compound 1.104)

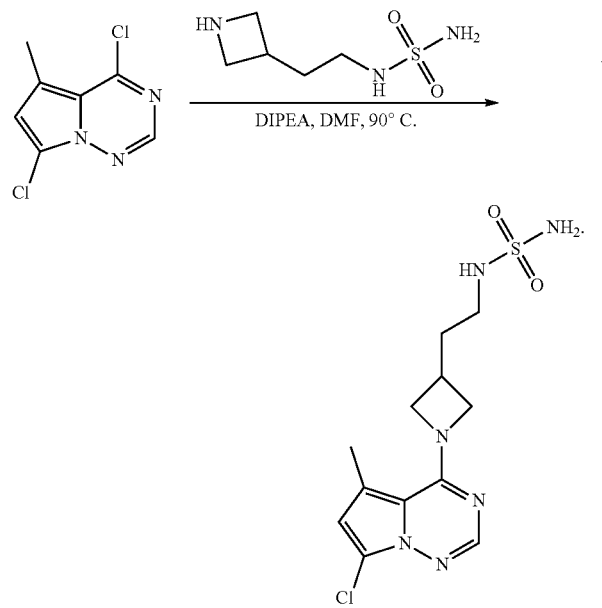

To a solution of 3-(N-sulfamoyl) (ethyl)amino) azetidine (177 mg, 0.989 mmol, 2.0 eq) and 4,7-dichloro-5-methylpyrrolo[1,2-f][1,2,4]triazine (100 mg, 0.494 mmol, 1 eq) in DMF (2 ml) was added N,N-diisopropylethylamine (0.12 mL, 0.741 mmol, 1.5 eq). The reaction mixture was allowed to stir at 90° C. for 4 h. Progress of reaction was monitored by LCMS. After completion, reaction mixture was diluted with water (30 ml) extracted with ethyl acetate (50 ml×3). Combined organic layer was washed with brine (50 mL) and dried over anhydrous sodium sulfate concentrated to get crude product. which was purified by reversed phase chromatography to afford N-(2-(1-(7-chloro-5-methylpyrrolo[1,2-f][1,2,4]triazin-4-yl)azetidin-3-yl)ethyl)sulfamamide (12 mg, 7.05%). LCMS: 345.4 [M+1]$^+$; $^1$H NMR (400 MHz, DMSO-d$_6$) δ ppm 7.90 (s, 1H), 6.63 (s, 1H), 6.53-6.48 (m, 2H), 4.46-4.41 (m, 2H), 4.02-3.97 (m, 2H), 2.91-2.85 (m, 2H), 2.84-2.77 (m, 1H), 2.39 (s, 3H), 1.85-1.78 (m, 2H).

Example-105: Synthesis of N-methyl-N-(2 (1-methyl-1H-pyrazolo[3,4-d]pyrimidin-4-yl)-2-azaspiro[3.3]heptan-6-yl)sulfamamide, (Compound 1.105)

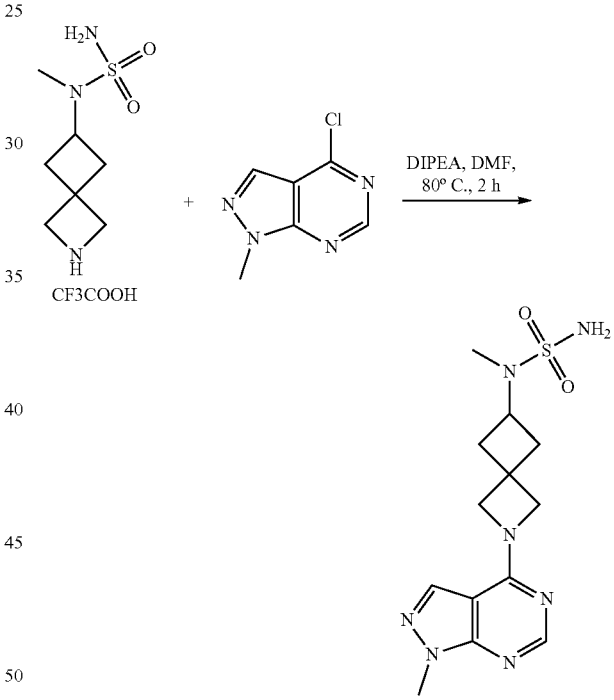

A suspension of N-methyl-N-(2-azaspiro[3.3]heptan-6-yl)sulfamamide 2,2,2-trifluoroacetate (179 mg, 0.593 mmol, 1.0 eq), 4-chloro-1-methyl-1H-pyrazolo[3,4-d]pyrimidine (100 mg, 0.593 mmol, 1.0 eq) and DIPEA (153 mg, 1.186 mmol, 2.0 eq) in DMF (1 mL) was allowed to stir at 80° C. for 2 h. Progress of reaction was monitored by TLC and LCMS. After completion, reaction mixture was diluted with water (20 mL) and extracted with ethyl acetate (2×50 mL). Combined organic layer was washed with brine (10 mL), dried over anhydrous sodium sulfate and concentrated under reduced pressure to get crude which was purified using reverse phase chromatography to afford N-methyl-N-(2-(1-methyl-1H-pyrazolo[3,4-d]pyrimidin-4-yl)-2-azaspiro[3.3] heptan-6-yl)sulfamamide (18 mg, 9%). LCMS: 338 [M+1]$^+$; NMR: $^1$H NMR (400 MHz, DMSO-d$_6$) δ ppm 8.22 (s, 1H), 7.99 (br. s., 1H), 6.72 (s, 2H), 4.61-4.05 (m, 4H) 3.89 (s, 3H), 3.82-3.61 (m, 1H), 2.55 (s, 3H), 2.45-2.30 (m, 4H).

Example-106: Synthesis of N-(2-(7-chloro-2-(4-fluorophenyl)-5-methylpyrrolo[2,1-f][1,2,4]triazin-4-yl)-2-azaspiro[3.3]heptan-6-yl)-N-methylsulfamamide, (Compound 1.106)

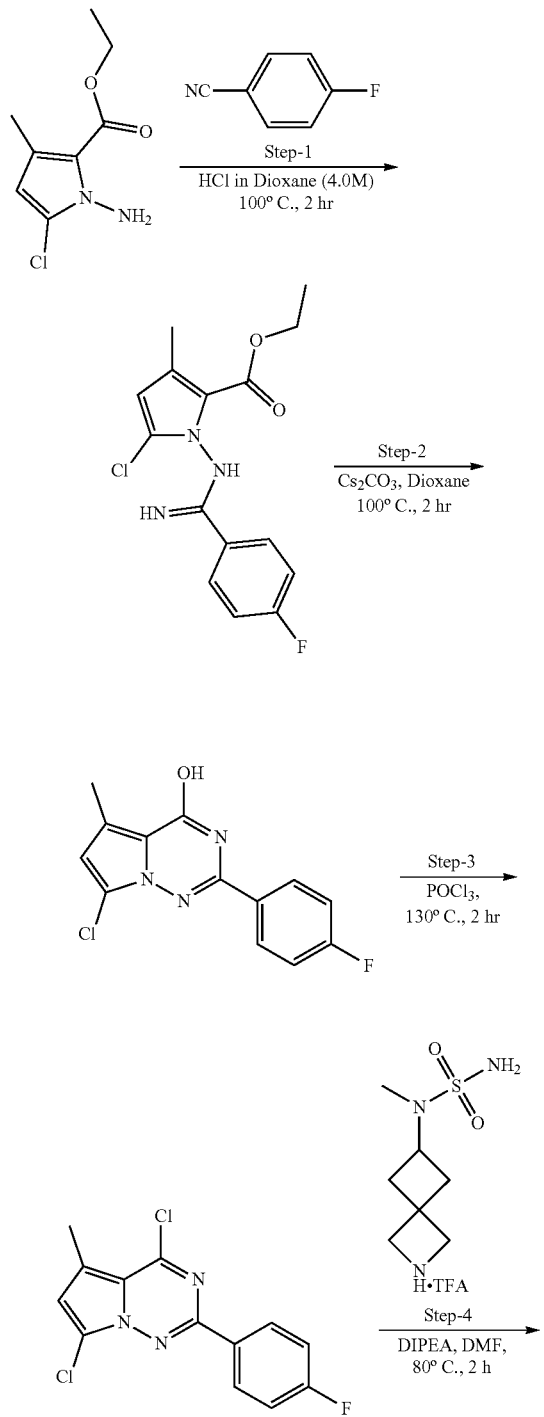

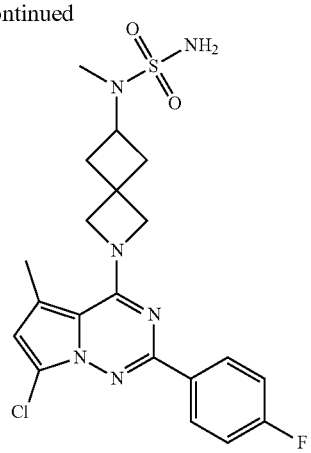

Step-1: Synthesis of ethyl 5-chloro-1-(4-fluorobenzimidamido)-3-methyl-1H-pyrrole-2-carboxylate: A mixture of ethyl 1-amino-5-chloro-3-methyl-1H-pyrrole-2-carboxylate (400 mg, 1.97 mmol, 1.0 eq), 4-fluorobenzonitrile (286 mg, 2.37 mmol, 1.2 eq) in HCl in dioxane (4.0 M) (8 mL) was allowed to stir at 100° C. for 2 h. Progress of reaction is monitored by TLC. After completion, the reaction mixture was neutralized with aqueous NaHCO₃ solution (10 mL) and extracted with ethyl acetate (2×100 mL). Combined organic layer was washed with brine (50 mL), dried over anhydrous sodium sulfate and concentrated under reduced pressure to obtain crude product which was purified by combi flash chromatography to afford ethyl 5-chloro-1-(4-fluorobenzimidamido)-3-methyl-1H-pyrrole-2-carboxylate (70 mg, 11%). LCMS: 324 [M+1]$^+$ Step-2: Synthesis of 7-chloro-2-(4-fluorophenyl)-5-methylpyrrolo[2,1-f][1,2,4]triazin-4-ol: A suspension of ethyl 5-chloro-1-(4-fluorobenzimidamido)-3-methyl-1H-pyrrole-2-carboxylate (70 mg, 0.216 mmol, 1.0 eq) Cs₂CO₃ (106 mg, 0.324 mmol, 1.5 eq) in Dioxane (3 mL) was allowed to stir at 100° C. for 2 h. Progress of reaction was monitored by TLC. After completion, reaction mixture was diluted with cold water (20 mL) and extracted with ethyl acetate (2×50 mL). Combined organic layer was washed with brine (10 mL), dried over anhydrous sodium sulfate and concentrated under reduced pressure to give 7-chloro-2-(4-fluorophenyl)-5-methylpyrrolo[2,1-f][1,2,4]triazin-4-ol (52 mg, 86.66%). LCMS: 278 [M+1]$^+$ Step-3: Synthesis of 4,7-dichloro-2-(4-fluorophenyl)-5-methylpyrrolo[2,1-f][1,2,4]triazine: A mixture of 7-chloro-2-(4-fluorophenyl)-5-methylpyrrolo[1,2-f][1,2,4]triazin-4-ol (50 mg, 0.179 mmol, 1.0 eq) in phosphoryl trichloride (0.3 mL) was allowed to stir at 130° C. for 2 h. Progress of reaction is monitored by TLC. After completion, reaction mixture was diluted with cold water (30 mL) and extracted with ethyl acetate (3×15 mL). Combined organic layer was washed with brine (20 mL), dried over anhydrous sodium sulfate and concentrated under reduced pressure to give 4,7-dichloro-2-(4-fluorophenyl)-5-methylpyrrolo[2,1-f][1,2,4]triazine (47 mg, 88.67%). LCMS: 298 [M+1]$^+$ Step-4: Synthesis of N-(2-(7-chloro-2-(4-fluorophenyl)-5-methylpyrrolo[2,1-f][1,2,4]triazin-4-yl)-2-azaspiro[3.3]heptan-6-yl)-N-methylsulfamamide: A suspension of 4,7-dichloro-2-(4-fluorophenyl)-5-methylpyrrolo[2,1-f][1,2,4]triazine (45 mg, 0.151 mmol, 1.0 eq), N-methyl-N-(2-azaspiro[3.3]heptan-6-yl)sulfamamide 2,2,2-trifluoroacetate (50 mg, 0.166 mmol, 1.1 eq) and DIPEA (40 mg, 0.302 mmol, 2.0 eq) in DMF (1 mL) was allowed to stir at 80° C.

for 2 h. Progress of reaction was monitored by TLC and LCMS. After completion, reaction mixture was diluted with water (20 mL) and extracted with ethyl acetate (1×50 mL). Combined organic layer was washed with brine (10 mL), dried over anhydrous sodium sulfate and concentrated under reduced pressure to get crude product which was purified by using combi flash chromatography to afford N-(2-(7-chloro-2-(4-fluorophenyl)-5-methylpyrrolo[2,1-f][1,2,4]triazin-4-yl)-2-azaspiro[3.3]heptan-6-yl)-N-methylsulfamamide (11 mg, 15.71%). LCMS: 465 [M+1]$^+$; NMR: 1H NMR (400 MHz, DMSO-d6) δ ppm 8.38-8.23 (m, 2H), 7.32 (t, J=8.8 Hz, 2H), 6.80-6.62 (m, 3H), 4.53 (s, 2H), 4.41 (s, 2H), 3.84-3.75 (m, 1H), 2.55 (s, 3H), 2.43 (s, 3H), 2.39-2.27 (m, 4H).

Example-107: Synthesis of N-(3-(1-(7-chloro-5-methylpyrrolo[2,1-f][1,2,4]triazin-4-yl)azetidin-3-yl)propyl)-N-methylsulfamamide, (Compound 1.107)

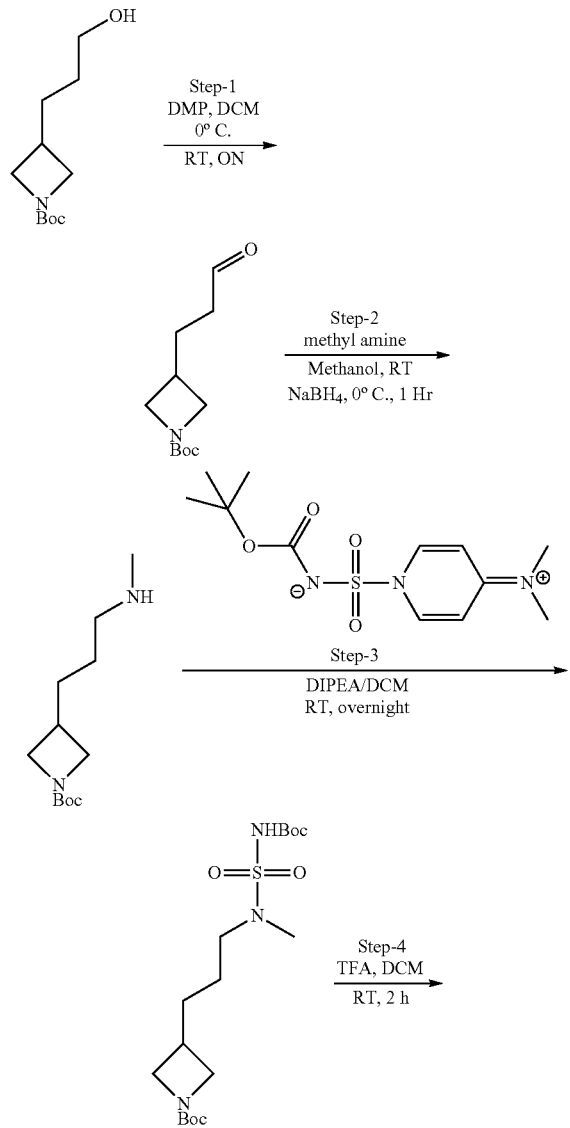

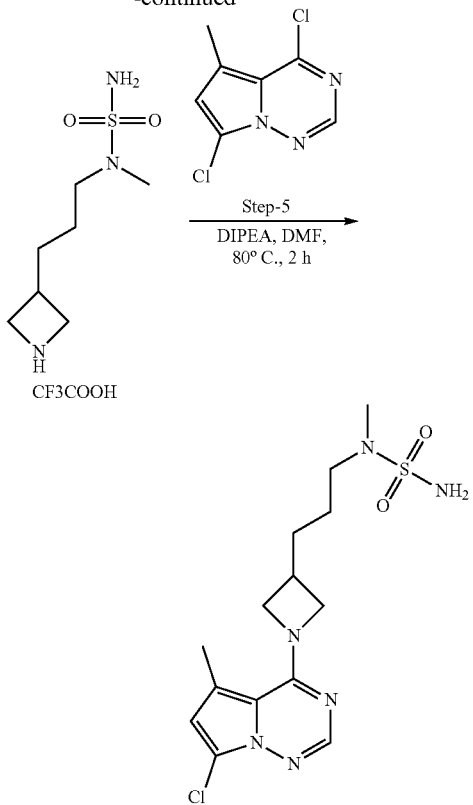

Step-1: Synthesis of tert-butyl 3-(3-oxopropyl)azetidine-1-carboxylate: A suspension of tert-butyl 3-(3-hydroxypropyl)azetidine-1-carboxylate (500 mg, 2.32 mmol, 1.0 eq) in DCM (15 mL) at 0° C. was added DMP (1.48 g, 3.48 mmol, 1.5 eq) was added portion wise at 0° C. After addition, the reaction mixture was stirred at RT for overnight. Progress of reaction was monitored by TLC. After completion, the reaction mixture was diluted with water (50 mL) and extracted with DCM (3×50 mL). Combined organic layer was washed with brine (1×50 mL), dried over anhydrous sodium sulfate and concentrated under reduced pressure to afford tert-butyl 3-(3-oxopropyl)azetidine-1-carboxylate (520 mg, 85%) which was used in the next step without purification.

Step-2: Synthesis of tert-butyl 3-(3-(methylamino)propyl)azetidine-1-carboxylate: A suspension of tert-butyl 3-(3-oxopropyl)azetidine-1-carboxylate (500 mg, 2.33 mmol, 1.0 eq), Methylamine (1.4 mL, 2.79 mmol, 1.2 eq) in methanol (10 mL) was stirred at RT for overnight. After overnight stirring, NaBH$_4$ (132 mg, 3.49 mmol, 1.5 eq) was added into above reaction mixture portion wise at 0° C. and allowed to stir the reaction mixture for 1 hr at 0° C. Progress of reaction was monitored by TLC. After completion, the reaction mixture was concentrated under reduced pressure to get residue which was diluted with water (50 mL) and extracted with ethyl acetate (3×50 mL). Combined organic layer was washed with brine (1×50 mL), dried over anhydrous sodium sulfate and concentrated under reduced pressure to afford tert-butyl 3-(3-(methylamino)propyl)azetidine-1-carboxylate (420 mg, 78.9%) which was used in the next step without purification.

Step-3: Synthesis of tert-butyl 3-(3-((N-(tert-butoxycarbonyl)sulfamoyl)(methyl)amino)propyl)azetidine-1-carboxylate: To a solution of tert-butyl 3-(3-(methylamino)

propyl)azetidine-1-carboxylate (420 mg, 1.84 mmol, 1.0 eq) in DCM (10 mL) were added N-(tert-butoxycarbonyl)-N-[4-(dimethylazaniumylidene)-1,4-dihydropyridin1ylsulfonyl]azanide (669 mg, 2.20 mmol, 1.2 eq) and DIPEA (356 mg, 2.76 mmol, 1.5 eq) and the mixture was allowed to stir at RT for overnight. Progress of reaction was monitored by TLC. After completion, reaction mixture was diluted with water (50 mL) and extracted with DCM (2×150 mL). Combined organic layer was washed with brine (1×50 mL), dried over anhydrous sodium sulfate and concentrated under reduced pressure. Crude was purified by combi flash chromatography to afford tert-butyl 3-(3-((N-(tert-butoxycarbonyl)sulfamoyl)(methyl)amino)propyl)azetidine-1-carboxylate (150 mg, 20%).

Step-4: Synthesis of N-(3-(azetidin-3-yl)propyl)-N-methylsulfamamide 2,2,2-trifluoroacetate: To a solution of tert-butyl 3-(3-((N-(tert-butoxycarbonyl)sulfamoyl)(methyl)amino)propyl)azetidine-1-carboxylate (150 mg, 0.368 mmol, 1 eq) in DCM (4 mL) was added TFA (1 mL) and was allowed to stir at RT for 2 h. Progress of reaction was monitored by TLC. After completion, reaction mixture was concentrated under reduced pressure which was triturated with diethyl ether to afford N-(3-(azetidin-3-yl)propyl)-N-methylsulfamamide 2,2,2-trifluoroacetate (130 mg, 89%).

Step-5: Synthesis of N-(3-(1-(7-chloro-5-methylpyrrolo[2,1-f][1,2,4]triazin-4-yl)azetidin-3-yl)propyl)-N-methylsulfamamide: A suspension of N-(3-(azetidin-3-yl)propyl)-N-methylsulfamamide 2,2,2-trifluoroacetate (64 mg, 0.199 mmol, 1.0 eq), 4,7-dichloro-5-methylpyrrolo[2,1-f][1,2,4]triazine (40 mg, 0.199 mmol, 1.0 eq) and DIPEA (51.3 mg, 0.398 mmol, 2.0 eq) in DMF (1.0 mL) was allowed to stir at 80° C. for 2 h. Progress of reaction was monitored by TLC and LCMS. After completion, reaction mixture was diluted with water (10 mL) and extracted with ethyl acetate (2×50 mL). Combined organic layer was washed with brine (1×10 mL), dried over anhydrous sodium sulfate and concentrated under reduced pressure to obtain crude product which was purified by reversed phase chromatography to afford N-(3-(1-(7-chloro-5-methylpyrrolo[2,1-f][1,2,4]triazin-4-yl)azetidin-3-yl)propyl)-N-methylsulfamamide (12 mg, 16.2%). LCMS: 373[M+1]$^+$; $^1$H NMR (400 MHz, DMSO-d$_6$) δ ppm 7.90 (s, 1H), 6.66 (m, 3H), 4.45 (t, J=8.8 Hz, 2H), 3.99 (dd, J=5.7, 8.8 Hz, 2H), 2.91 (t, J=6.8 Hz, 2H), 2.79-2.69 (m, 1H) 2.61 (s, 3H), 2.39 (s, 3H), 1.61 (t, J=7.7 Hz, 2H), 1.52 (d, J=7.0 Hz, 2H)

Example-108: Synthesis of N-(2-(2-amino-9H-purin-6-yl)-2-azaspiro[3.3]heptan-6-yl)-N-methylsulfamamide, (Compound 1.108)

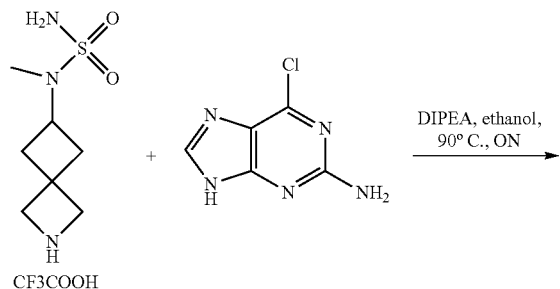

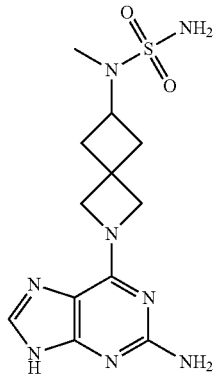

A suspension of N-methyl-N-(2-azaspiro[3.3]heptan-6-yl)sulfamamide 2,2,2-trifluoroacetate (100 mg, 0.589 mmol, 1.0 eq), 6-chloro-9H-purin-2-amine (214 mg, 0.707 mmol, 1.2 eq) and DIPEA (152 mg, 1.17 mmol, 2.0 eq) in Ethanol (4 mL) was allowed to stir at 90° C. for overnight. Progress of reaction was monitored by TLC and LCMS. After completion, solvent was removed under reduced pressure. Residue was diluted in 50 mL of water and extracted with DCM (2×50 mL). Aqueous layer was lyophilized and solid product was washed with methanol and filtered through Buchner funnel to afford N-(2-(2-amino-9H-purin-6-yl)-2-azaspiro[3.3]heptan-6-yl)-N-methylsulfamamide (48 mg, 24.12%) LCMS: 339 [M+1]$^+$; NMR: $^1$H NMR (400 MHz, DMSO-d$_6$) δ ppm 12.20 (br. s., 1H), 7.71 (br. s., 1H), 6.70 (s, 2H), 5.95 (br. s., 2H), 4.31 (br. s., 2H), 4.20 (br. s., 2H), 3.73 (td, J=8.2, 16.6 Hz, 1H), 2.53 (s, 3H), 2.46-2.37 (m, 2H), 2.37-2.24 (m, 2H)

Example-109: Synthesis of N-(2-(7-chloro-5-methylpyrrolo[2,1-f][1,2,4]triazin-4-yl)-2-azaspiro[3.3]heptan-6-yl)-N-(4-(trifluoromethyl)benzyl)sulfamamide, (Compound 1.109)

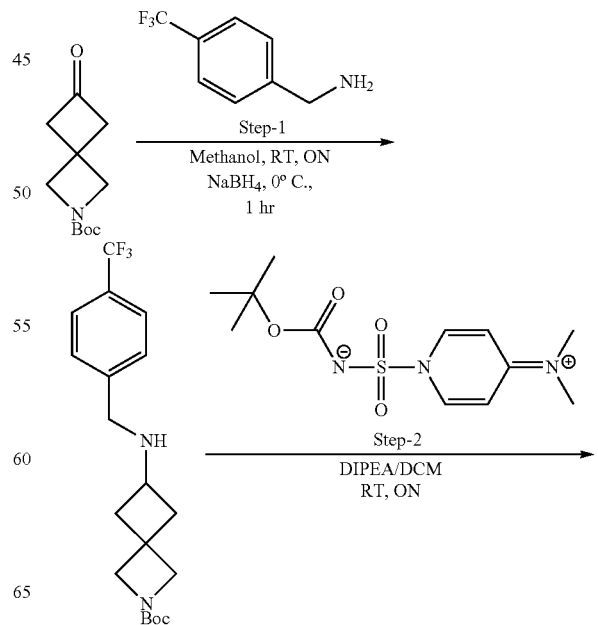

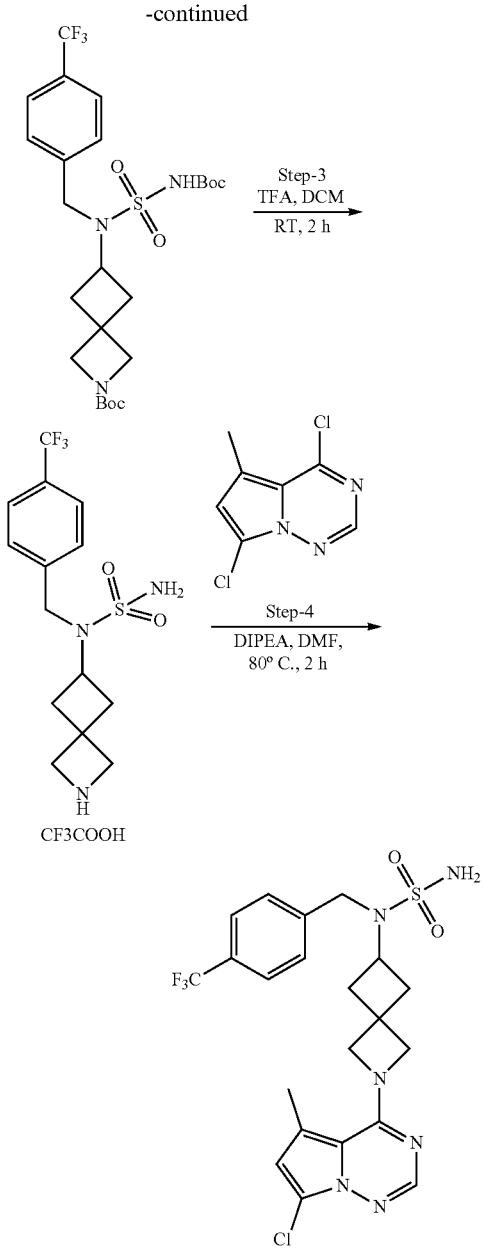

Step-1: Synthesis of tert-butyl 6-(4-(trifluoromethyl)benzylamino)-2-azaspiro[3.3]heptane-2-carboxylate: To a stirred solution of tert-butyl 6-oxo-2-azaspiro[3.3]heptane-2-carboxylate (200 mg, 0.946 mmol, 1 eq) in methanol (5 mL) was added (4-(trifluoromethyl)phenyl)methanamine (199 mg, 1.13 mmol, 1.2 eq) and the reaction mixture was stirred at RT for overnight. To the reaction mixture, NaBH$_4$ (54 mg, 1.41 mmol, 1.5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (50 mL) and extracted with dichloromethane (2×50 mL). Combined organic layer was dried over anhydrous sodium sulfate and concentrated under reduced pressure to afford tert-butyl 6-(4-(trifluoromethyl)benzylamino)-2-azaspiro[3.3]heptane-2-carboxylate (210 mg, 60%) which was used in the next step without purification.

Step-2: Synthesis of tert-butyl 6-((N-(tert-butoxycarbonyl)sulfamoyl)(4-(trifluoromethyl)benzyl)amino)-2-azaspiro[3.3]heptane-2-carboxylate: To a solution of tert-butyl 6-(4-(trifluoromethyl)benzylamino)-2-azaspiro[3.3]heptane-2-carboxylate (200 mg, 0.539 mmol, 1 eq) in DCM (10 mL) were added N-(tert-butoxycarbonyl)-N-[4-(dimethylazaniumylidene)-1,4-dihydropyridin-1ylsulfonyl]azanide (195 mg, 0.647 mmol, 1.2 eq) and DIPEA (104 mg, 0.808 mmol, 1.5 eq) and the mixture was allowed to stir at RT for overnight. Progress of reaction was monitored by TLC. After completion, the reaction mixture was concentrated under reduced pressure to get residue which was washed with 1N HCl solution (50 mL) and extracted with ethyl acetate (2×50 mL). Combined organic layer was dried over anhydrous sodium sulfate and concentrated under reduced pressure to afford tert-butyl 6-((N-(tert-butoxycarbonyl)sulfamoyl)(4-(trifluoromethyl)benzyl)amino)-2-azaspiro[3.3]heptane-2-carboxylate (260 mg, 87.8%).

Step-3: Synthesis of N-(2-azaspiro[3.3]heptan-6-yl)-N-(4-(trifluoromethyl)benzyl)sulfamamide 2,2,2-trifluoroacetate: To a solution of tert-butyl 6-((N-(tert-butoxycarbonyl)sulfamoyl)(4-(trifluoromethyl)benzyl)amino)-2-azaspiro[3.3]heptane-2-carboxylate (260 mg, 0.578 mmol, 1 eq) in DCM (5 mL) was added TFA (1.5 mL) and was allowed to stir at RT for 2 h. Progress of reaction was monitored by TLC. After completion, reaction mixture was concentrated under reduced pressure to afford crude which was triturated with diethyl ether to afford N-(2-azaspiro[3.3]heptan-6-yl)-N-(4-(trifluoromethyl)benzyl)sulfamamide 2,2,2-trifluoroacetate (180 mg, 70%).

Step-4: Synthesis of N-(2-(7-chloro-5-methylpyrrolo[2,1-f][1,2,4]triazin-4-yl)-2-azaspiro[3.3]heptan-6-yl)-N-(4-(trifluoromethyl)benzyl)sulfamamide: A suspension of N-(2-azaspiro[3.3]heptan-6-yl)-N-(4-(trifluoromethyl)benzyl)sulfamamide 2,2,2-trifluoroacetate (138 mg, 0.298 mmol, 1.0 eq), 4,7-dichloro-5-methylpyrrolo[2,1-f][1,2,4]triazine (60 mg, 0.298 mmol, 1.0 eq) and DIPEA (77 mg, 0.596 mmol, 2.0 eq) in DMF (1.0 mL) was allowed to stir at 80° C. for 2 h. Progress of reaction was monitored by LCMS and TLC. After 2 h, reaction mixture was diluted with water (10 mL) and extracted with ethyl acetate (1×50 mL). Combined organic layer was washed with brine (1×10 mL) and dried over anhydrous sodium sulfate, Concentrated under reduced pressure to obtain crude product which was purified using reversed phase chromatography to afford N-(2-(7-chloro-5-methylpyrrolo[2,1-f][1,2,4]triazin-4-yl)-2-azaspiro[3.3]heptan-6-yl)-N-(4-(trifluoromethyl)benzyl)sulfamamide (10 mg, 6.53%). LCMS: 515 [M+1]$^+$; $^1$H NMR (400 MHz, DMSO-d$_6$) δ ppm 7.92 (br. s., 1H) 7.71 (m, 2H), 7.61 (m, 2H), 6.96 (br. s., 2H), 6.73 (s, 1H), 4.31 (s, 2H), 4.28 (s, 2H), 4.22 (s, 2H), 4.12 (m, 1H), 2.43 (m, 2H), 2.42 (s, 3H), 2.37-2.24 (m, 2H).

Example-110: Synthesis of N-(2-(7-chloro-5-methylpyrrolo[2,1-f][1,2,4]triazin-4-yl)-2-azaspiro[3.3]heptan-6-yl)-N-cyclopentylsulfamamide, (Compound 1.110)

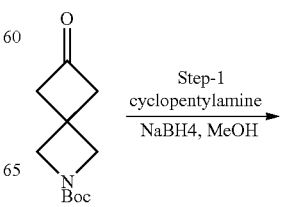

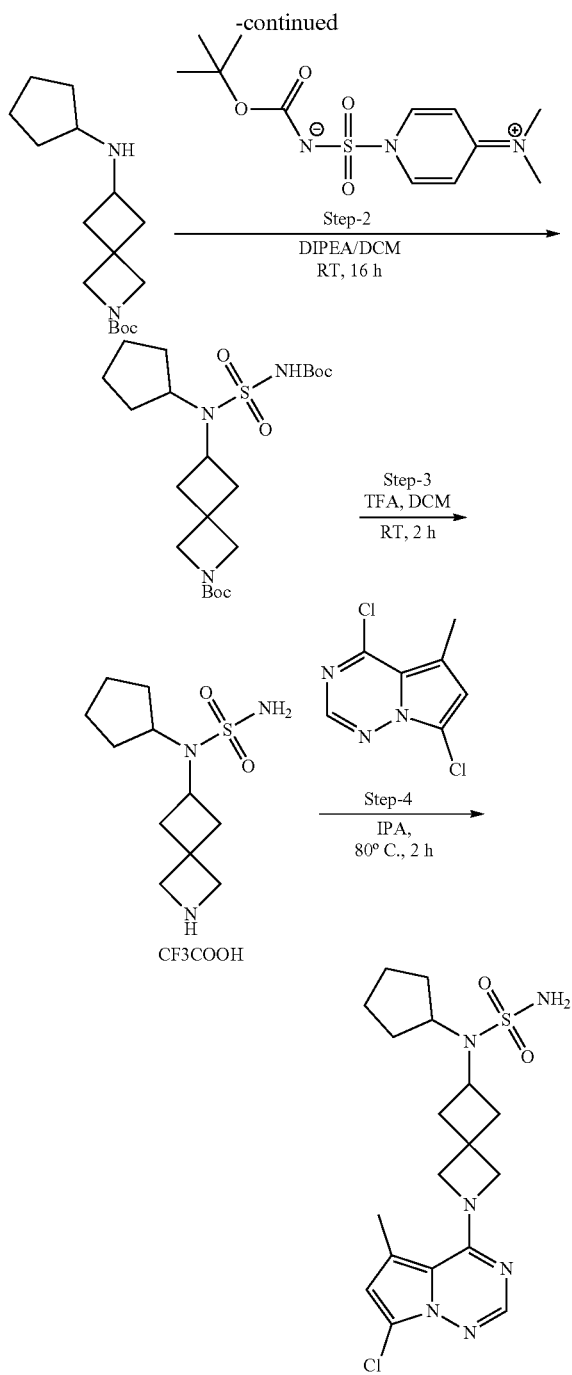

Step-1: Synthesis of ter-butyl 6-(cyclopentylamino)-2-azaspiro[3.3]heptane-2-carboxylate: To a stirred solution of tert-butyl 6-oxo-2-azaspiro[3.3]heptane-2-carboxylate (500 mg, 2.36 mmol, 1 eq) in methanol (5 mL) was added cyclopentylamine (241 mg, 2.84 mmol, 1.2 eq) and the reaction mixture was stirred at RT for overnight. To the reaction mixture, NaBH₄ (134 mg, 3.55 mmol, 1.5 eq) was added at 0° C. and then resultant reaction mixture was allowed to stir at 0° C. for 1 h. Progress of reaction was monitored by TLC and 1H-NMR. After completion, reaction mixture was concentrated under reduced pressure to get residue which was diluted with water (100 mL) and extracted with dichloromethane (2×100 mL). Combined organic layer was dried over anhydrous sodium sulfate, concentrated under reduced pressure to afford tert-butyl 6-(cyclopentylamino)-2-azaspiro[3.3]heptane-2-carboxylate (650 mg, 98%) which was used in the next step without purification.

Step-2: Synthesis of tert-butyl 6-((N-(tert-butoxycarbonyl)sulfamoyl)(cyclopentyl)amino)-2-azaspiro[3.3]heptane-2-carboxylate: To a solution of tert-butyl 6-(cyclopentylamino)-2-azaspiro[3.3]heptane-2-carboxylate (650 mg, 2.31 mmol, 1 eq) in DCM (10 mL) were added N-(tert-butoxycarbonyl)-N-[4-(dimethylazaniumylidene)-1,4-dihydropyridin-1ylsulfonyl]azanide (840 mg, 2.78 mmol, 1.2 eq) and DIPEA (0.6 mL, 3.47 mmol, 1.5 eq) and the mixture was allowed to stir at RT for 16 h. Progress of reaction was monitored by TLC and 1H-NMR. After completion, the reaction mixture was concentrated under reduced pressure to get residue which was washed with 1N HCl solution (100 mL) and extracted with ethyl acetate (2×100 mL). Combined organic layer was dried over anhydrous sodium sulfate and concentrated it. The crude was purified by combiflash chromatography to afford tert-butyl 6-((N-(tert-butoxycarbonyl)sulfamoyl)(cyclopentyl)amino)-2-azaspiro[3.3]heptane-2-carboxylate (750 mg, 70%).

Step-3: Synthesis of N-cyclopentyl-N-(2-azaspiro[3.3]heptan-6-yl)sulfamamide trifluoroacetate: To a solution of tert-butyl 6-((N-(tert-butoxycarbonyl)sulfamoyl)(cyclopentyl)amino)-2-azaspiro[3.3]heptane-2-carboxylate (750 mg, 1.63 mmol, 1 eq) in DCM (10 mL) was added TFA (4 mL) and was allowed to stir at RT for 2 h. Progress of reaction was monitored by TLC. After completion, the reaction mixture was concentrated under reduced pressure to afford crude which was triturated with diethyl ether to afford N-cyclopentyl-N-(2-azaspiro[3.3]heptan-6-yl)sulfamamide trifluoroacetate (600 mg, 98%).

Step-4: Synthesis of N-(2-(7-chloro-5-methylpyrrolo[2,1-f][1,2,4]triazin-4-yl)-2-azaspiro[3.3]heptan-6-yl)-N-cyclopentylsulfamamide: A suspension of N-cyclopentyl-N-(2-azaspiro[3.3]heptan-6-yl)sulfamamide trifluoroacetate (180 mg, 0.48 mmol, 1 eq), 4,7-dichloro-5-methylpyrrolo[2,1-f][1,2,4]triazine (67 mg, 0.33 mmol, 0.7 eq) in IPA (2.5 mL) was allowed to stir at 80° C. for 2 h. Progress of reaction was monitored by LCMS and TLC. After 2 h, the reaction mixture was concentrated under reduced pressure to obtain crude was added Water (100 mL) and extracted with ethyl acetate (100 mL). Combined organic layer was concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-cyclopentylsulfamamide (9 mg, 6.3%). LCMS: 425 [M+1]⁺; ¹H NMR (400 MHz, DMSO-d₆) δ ppm 1.42 (br. s., 2H) 1.60 (br. s., 4H) 1.76 (d, J=8.77 Hz, 2H) 2.31-2.44 (br. s., 5H) 2.64-2.70 (m, 2H) 3.71-3.75 (m, 1H) 3.81-3.90 (m, 1H) 4.26 (br. s., 2H) 4.41 (br. s., 2H) 6.61-6.67 (br. s., 3H) 7.88 (s, 1H).

Example-111: Synthesis of N-(2-(7-chloro-5-methylpyrrolo[2,1-f][1,2,4]triazin-4-yl)-2-azaspiro[3.3]heptan-6-yl)-N-cyclobutylsulfamamide, (Compound 1.111)

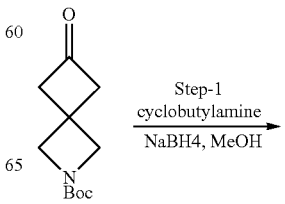

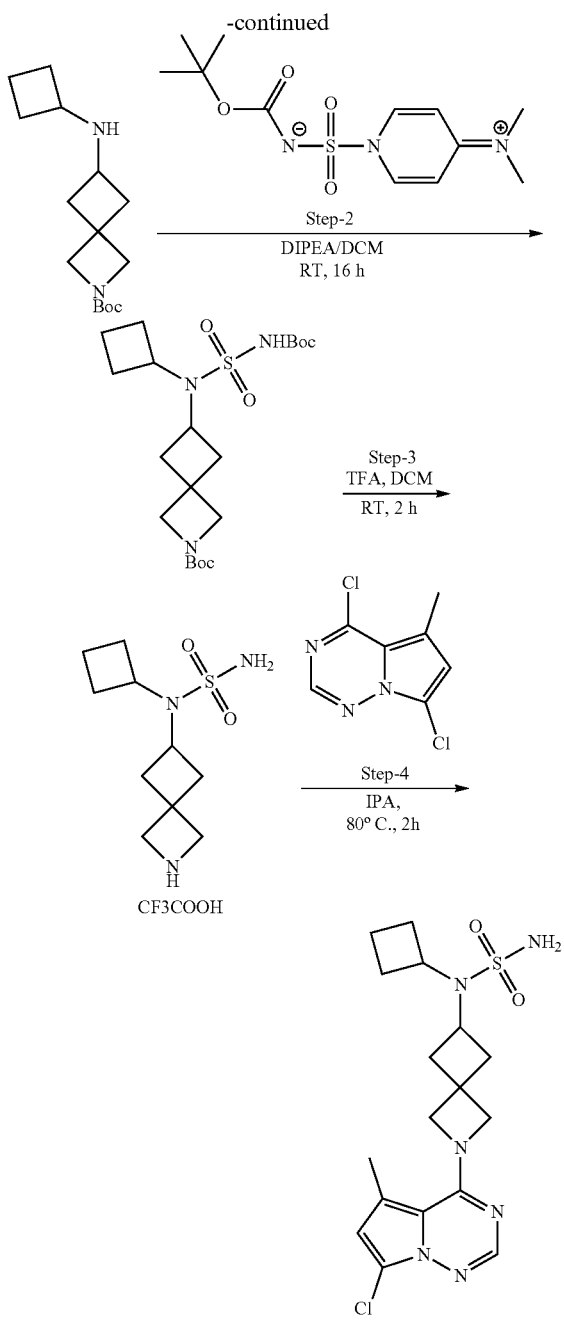

Step-1: Synthesis of tert-butyl 6-(cyclobutylamino)-2-azaspiro[3.3]heptane-2-carboxylate: To a stirred solution of tert-butyl 6-oxo-2-azaspiro[3.3]heptane-2-carboxylate (250 mg, 1.18 mmol, 1 eq) in methanol (5 mL) was added cyclobutylamine (100 mg, 1.42 mmol, 1.2 eq) and the reaction mixture was stirred at RT for overnight. To the reaction mixture, NaBH$_4$ (67 mg, 1.77 mmol, 1.5 eq) was added at 0° C. and then resultant reaction mixture was allowed to stir at 0° C. for 1 h. Progress of reaction was monitored by TLC and 1H-NMR. After completion, the reaction mixture was concentrated under reduced pressure to get residue which was diluted with water (100 mL) and extracted with dichloromethane (2×100 mL). Combined organic layer was dried over anhydrous sodium sulfate, concentrated under reduced pressure to afford tert-butyl 6-(cyclobutylamino)-2-azaspiro[3.3]heptane-2-carboxylate (200 mg, 63.4%) which was used in the next step without purification.

Step-2: Synthesis of tert-butyl 6-((N-(tert-butoxycarbonyl)sulfamoyl)(cyclobutyl)amino)-2-azaspiro[3.3]heptane-2-carboxylate: To a solution of tert-butyl 6-(cyclobutylamino)-2-azaspiro[3.3]heptane-2-carboxylate (200 mg, 0.75 mmol, 1 eq) in DCM (10 mL) were added N-(tert-butoxycarbonyl)-N-[4-(dimethylazaniumylidene)-1,4-dihydropyridin-1ylsulfonyl]azanide (272 mg, 0.90 mmol, 1.2 eq) and DIPEA (0.19 mL, 1.12 mmol, 1.5 eq) and the mixture was allowed to stir at RT for 16 h. Progress of reaction was monitored by TLC and 1H-NMR. After completion, reaction mixture was concentrated under reduced pressure to get residue which was washed with 1N HCl solution (100 mL) and extracted with ethyl acetate (2×100 mL). Combined organic layer was dried over anhydrous sodium sulfate and concentrated under reduced pressure to afford tert-butyl 6-((N-(tert-butoxycarbonyl)sulfamoyl)(cyclobutyl)amino)-2-azaspiro[3.3]heptane-2-carboxylate (320 mg, 95.8%).

Step-3: Synthesis of N-cyclobutyl-N-(2-azaspiro[3.3]heptan-6-yl)sulfamamide trifluoroacetic acid: To a solution of tert-butyl 6-((N-(tert-butoxycarbonyl)sulfamoyl)(cyclobutyl)amino)-2-azaspiro[3.3]heptane-2-carboxylate (320 mg, 0.72 mmol, 1 eq) in DCM (5 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-cyclobutyl-N-(2-azaspiro[3.3]heptan-6-yl)sulfamamide trifluoroacetic acid (225 mg, 87%) as TFA salt.

Step-4: Synthesis of N-(2-(7-chloro-5-methylpyrrolo[2,1-f][1,2,4]triazin-4-yl)-2-azaspiro[3.3]heptan-6-yl)-N-cyclobutylsulfamamide: A suspension of N-cyclobutyl-N-(2-azaspiro[3.3]heptan-6-yl)sulfamamide trifluoroacetic acid (178 mg, 0.49 mmol, 1 eq), 4,7-dichloro-5-methylpyrrolo[1,2-f][1,2,4]triazine (70 mg, 0.34 mmol, 0.7 eq) in IPA (5 mL) was allowed to stir at 80° C. for 2 h. Progress of reaction was monitored by LCMS and TLC. After 2 h, the reaction mixture was concentrated under reduced pressure. Water (100 mL) was added into the reaction mixture and extracted with ethyl acetate (100 mL). Combined organic layer was concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-cyclobutylsulfamamide (7 mg, 3.4%). LCMS: 411 [M+1]$^+$; $^1$H NMR (400 MHz, DMSO-d$_4$) δ ppm 1.35 (s, 1H) 1.44-1.67 (m, 2H) 1.99-2.13 (m, 2H) 2.18-2.31 (m, 2H) 2.35-2.48 (m, 6H) 3.68-3.81 (m, 2H) 4.28 (s, 2H) 4.42 (s, 2H) 6.63 (s, 1H) 6.70 (s, 2H) 7.90 (s, 1H).

Example-112: Synthesis of N-benzyl-N-(2-(7-chloro-5-methylpyrrolo[2,1-f][1,2,4]triazin-4-yl)-2-azaspiro[3.3]heptan-6-yl)sulfamamide, (Compound 1.112)

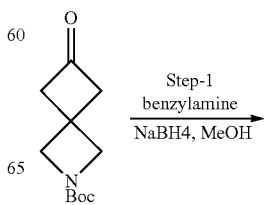

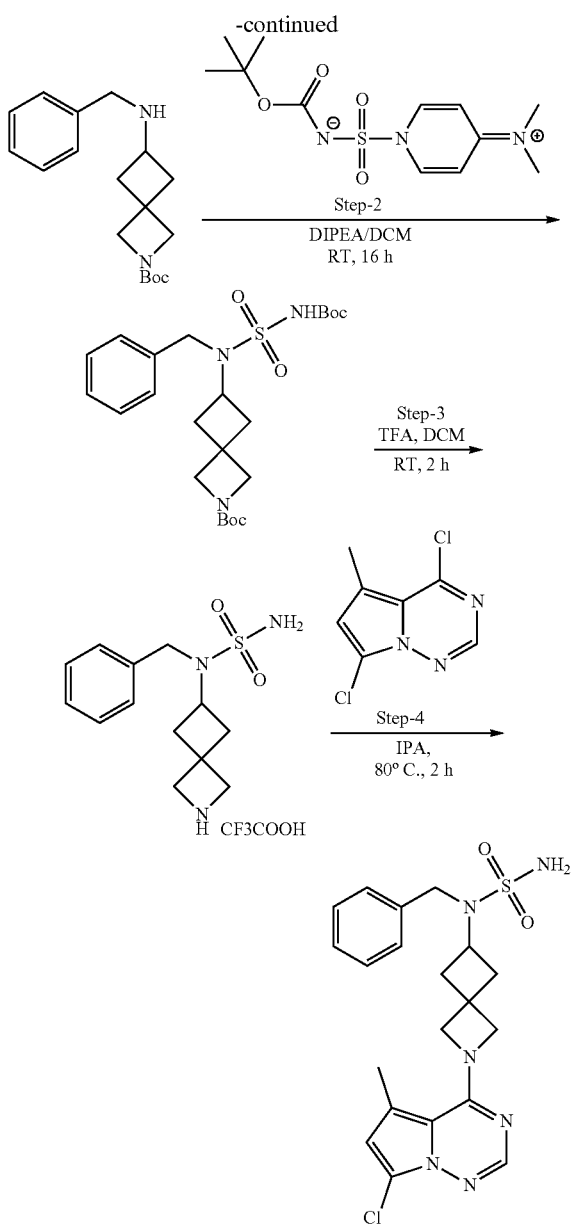

Step-1: Synthesis of tert-butyl 6-(benzylamino)-2-azaspiro[3.3]heptane-2-carboxylate: To a stirred solution of tert-butyl 6-oxo-2-azaspiro[3.3]heptane-2-carboxylate (300 mg, 1.42 mmol, 1 eq) in methanol (5 mL) was added benzylamine (182 mg, 1.70 mmol, 1.2 eq) and the reaction mixture was stirred at RT for overnight. To the reaction mixture, NaBH$_4$ (80 mg, 2.13 mmol, 1.5 eq) was added at 0° C. and then resultant reaction mixture was allowed to stir at 0° C. for 1 h. Progress of reaction was monitored by TLC and 1H-NMR. After completion, reaction mixture was concentrated under reduced pressure to get residue which was diluted with water (100 mL) and extracted with dichloromethane (2×100 mL). Combined organic layer was dried over anhydrous sodium sulfate. Removal of solvent under reduced pressure to afford tert-butyl 6-(benzylamino)-2-azaspiro[3.3]heptane-2-carboxylate (550 mg, 100%) which was used in the next step without purification.

Step-2: Synthesis of tert-butyl 6-(benzyl(N-(tert-butoxycarbonyl)sulfamoyl)amino)-2-azaspiro[3.3]heptane-2-carboxylate: To a solution of tert-butyl 6-(benzylamino)-2-azaspiro[3.3]heptane-2-carboxylate (550 mg, 1.81 mmol, 1 eq) in DCM (10 mL) were added N-(tert-butoxycarbonyl)-N-[4-(dimethylazaniumylidene)-1,4-dihydropyridin-1yl sulfonyl]azanide (659 mg, 2.18 mmol, 1.2 eq) and DIPEA (0.47 mL, 2.72 mmol, 1.5 eq) and the mixture was allowed to stir at RT for 16 h. Progress of reaction was monitored by TLC and 1H-NMR. After completion, the reaction mixture was concentrated under reduced pressure to get residue which was washed with 1N HCl solution (100 mL) and extracted with ethyl acetate (2×100 mL). Combined organic layer was dried over anhydrous sodium sulfate and concentrated under reduced pressure to afford tert-butyl 6-(benzyl(N-(tert-butoxycarbonyl)sulfamoyl)amino)-2-azaspiro[3.3]heptane-2-carboxylate (700 mg, 80%).

Step-3: Synthesis of N-benzyl-N-(2-azaspiro[3.3]heptan-6-yl)sulfamamide trifluoroacetate: To a solution of tert-butyl 6-((N-(tert-butoxycarbonyl)sulfamoyl)benzylamino)-2-azaspiro[3.3]heptane-2-carboxylate (700 mg, 1.45 mmol, 1 eq) in DCM (5 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-benzyl-N-(2-azaspiro[3.3]heptan-6-yl)sulfamamide trifluoroacetate (400 mg, 48.7%).

Step-4: Synthesis of N-benzyl-N-(2-(7-chloro-5-methylpyrrolo[2,1-f][1,2,4]triazin-4-yl)-2-azaspiro[3.3]heptan-6-yl)sulfamamide: A suspension of (6-N-sulfamoylbenzylamino)-2-azaspiro[3.3]heptane trifluoroacetate (400 mg, 1.01 mmol, 1 eq), 4,7-dichloro-5-methylpyrrolo[2,1-f][1,2,4]triazine (142 mg, 0.70 mmol, 0.7 eq) in IPA (5 mL) was allowed to stir at 80° C. for 2 h. Progress of reaction was monitored by LCMS and TLC. After 2 h, the reaction mixture was concentrated under reduced pressure to obtain crude was added water (100 mL) and extracted with ethyl acetate (2×100 mL). Combined organic layer was concentrated under reduced pressure to get crude which was purified using reverse phase column chromatography to afford N-benzyl-N-(2-(7-chloro-5-methylpyrrolo[2,1-f][1,2,4]triazin-4-yl)-2-azaspiro[3.3]heptan-6-yl)sulfamamide (10 mg, 3.17%). LCMS: 447 [M+1]$^+$; $^1$H NMR (400 MHz, DMSO-d$_6$) δ ppm 2.20-2.30 (m, 2H) 2.30-2.45 (m, 5H) 4.04 (dt, J=16.77, 8.50 Hz, 1H) 4.24 (d, J=14.91 Hz, 4H) 4.38 (s, 2H) 6.61 (s, 1H) 6.86 (s, 2H) 7.18-7.27 (m, 1H) 7.33 (q, J=7.60 Hz, 4H) 7.88 (s, 1H).

Example-113: Synthesis of N-(2-(7-chloro-5-methylpyrrolo[2,1-f][1,2,4]triazin-4-yl)-2-azaspiro[3.3]heptan-6-yl)-N-neopentylsulfamamide, (Compound 1.113)

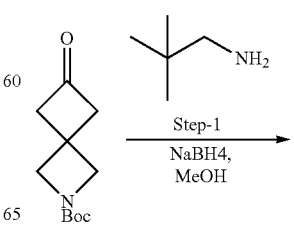

425

-continued

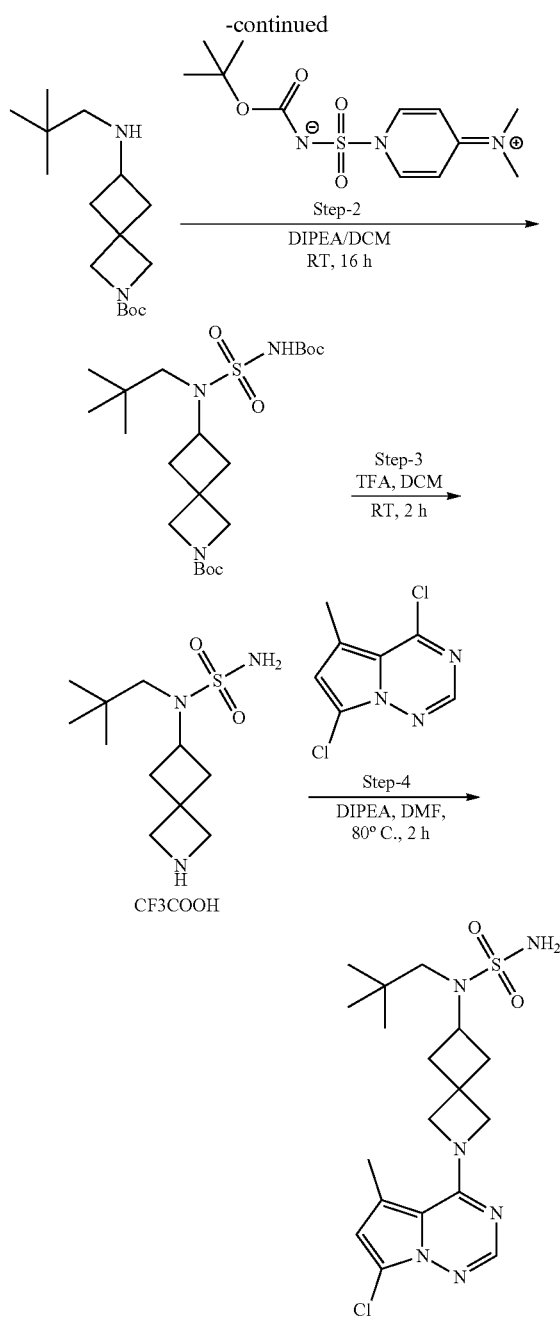

Step-1: Synthesis of tert-butyl 6-(neopentylamino)-2-azaspiro[3.3]heptane-2-carboxylate: To a stirred solution of tert-butyl 6-oxo-2-azaspiro[3.3]heptane-2-carboxylate (300 mg, 1.42 mmol, 1 eq) in methanol (5 mL) was added 2,2-dimethylpropan-1-amine (148 mg, 1.70 mmol, 1.2 eq) and the reaction mixture was stirred at RT for overnight. To the reaction mixture, NaBH₄ (80 mg, 2.13 mmol, 1.5 eq) was added at 0° C. and then resultant reaction mixture was allowed to stir at 0° C. for 1 h. Progress of reaction was monitored by TLC and 1H-NMR. After completion, reaction mixture was concentrated under reduced pressure to get residue which was diluted with water (100 mL) and extracted with dichloromethane (2×100 mL). Combined organic layer was dried over anhydrous sodium sulfate, concentrated under reduced pressure to afford tert-butyl 6-(neopentylamino)-2-azaspiro[3.3]heptane-2-carboxylate (380 mg, 94.7%) which was used in the next step without purification.

Step-2: Synthesis of tert-butyl 6-((N-(tert-butoxycarbonyl)sulfamoyl)(neopentyl)amino)-2-azaspiro[3.3]heptane-2-carboxylate: To a solution of tert-butyl 6-(ethylamino)-2-azaspiro[3.3]heptane-2-carboxylate (380 mg, 1.34 mmol, 1 eq) in DCM (10 mL) were added N-(tert-butoxycarbonyl)-N-[4-(dimethylazaniumylidene)-1,4-dihydropyridin-1ylsulfonyl]azanide (488 mg, 1.61 mmol, 1.2 eq) and DIPEA (0.35 mL, 2.01 mmol, 1.5 eq) and the Reaction mixture was allowed to stir at RT for 16 h. Progress of reaction was monitored by TLC and 1H-NMR. After completion, the reaction mixture was concentrated under reduced pressure to get residue which was washed with 1N HCl solution (100 mL) and extracted with ethyl acetate (2×100 mL). Combined organic layer was dried over anhydrous sodium sulfate and concentrated it under the reduced pressure to afford tert-butyl 6-((N-(tert-butoxycarbonyl)sulfamoyl)(neopentyl)amino)-2-azaspiro[3.3]heptane-2-carboxylate (400 mg, 64%).

Step-3: Synthesis of N-neopentyl-N-(2-azaspiro[3.3]heptan-6-yl)sulfamamide trifluoroacetate: To a solution of tert-butyl 6-((N-(tert-butoxycarbonyl)sulfamoyl)(neopentyl)amino)-2-azaspiro[3.3]heptane-2-carboxylate (400 mg, 0.86 mmol, 1 eq) in DCM (10 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-neopentyl-N-(2-azaspiro[3.3]heptan-6-yl)sulfamamide trifluoroacetate (210 mg, 64%).

Step-4: Synthesis of N-(2-(7-chloro-5-methylpyrrolo[2,1-f][1,2,4]triazin-4-yl)-2-azaspiro[3.3]heptan-6-yl)-N-neopentylsulfamamide: A suspension of N-neopentyl-N-(2-azaspiro[3.3]heptan-6-yl)sulfamamide trifluoroacetate (196 mg, 0.52 mmol, 1 eq), 4,7-dichloro-5-methylpyrrolo[2,1-f][1,2,4]triazine (73 mg, 0.36 mmol, 0.7 eq) and DIPEA (0.18 mL, 1.04 mmol, 2 eq) in DMF (1 mL) was allowed to stir at 80° C. for 2 h. Progress of reaction was monitored by LCMS and TLC. After 2 h, reaction mixture was poured onto ice cold water (100 mL) and extracted with ethyl acetate (100 mL). Combined organic layer was concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-neopentylsulfamamide (17 mg, 7.6%). LCMS: 427 [M+1]⁺; ¹H NMR (400 MHz, DMSO-$d_6$) δ ppm 0.87 (s, 9H) 2.07 (s, 1H) 2.39 (s, 3H) 2.45 (br. s., 3H) 2.80 (s, 2H) 3.72-3.86 (m, 2H) 4.29 (s, 2H) 4.40 (s, 2H) 6.64 (d, J=6.14 Hz, 2H) 7.90 (s, 1H).

Example-114: Synthesis of N-butyl-N-(2-(7-chloro-5-methylpyrrolo[2,1-f][1,2,4]triazin-4-yl)-2-azaspiro[3.3]heptan-6-yl)sulfamamide, (Compound 1.114)

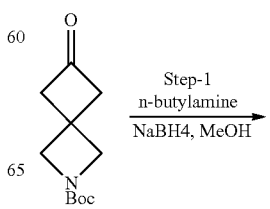

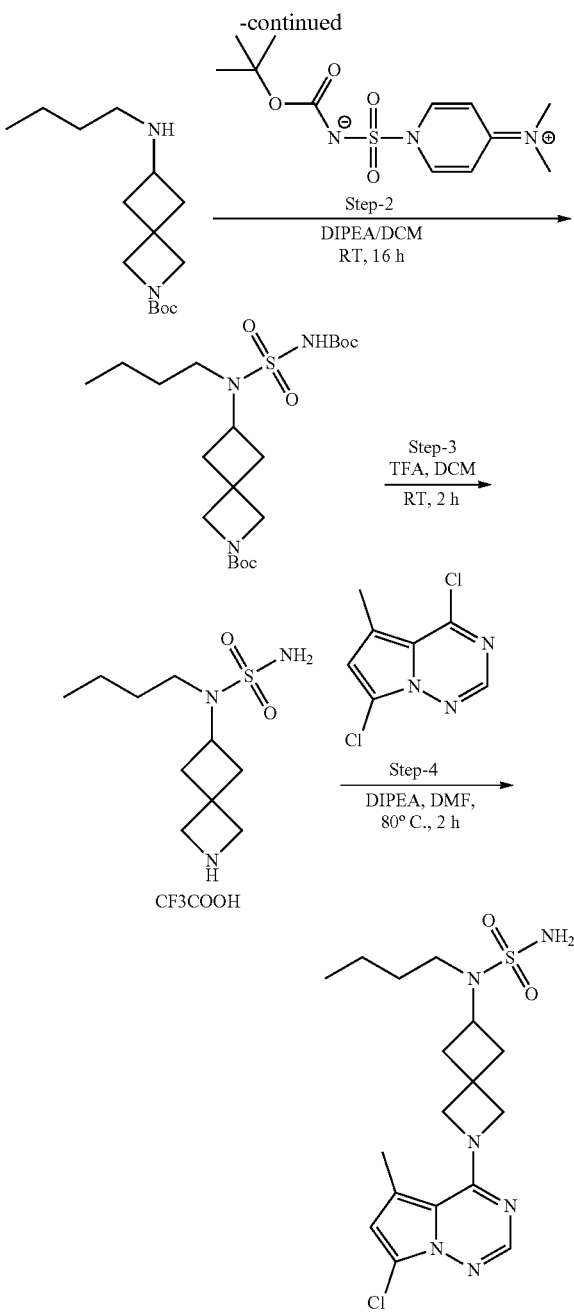

Step-1: Synthesis of tert-butyl 6-(butylamino)-2-azaspiro[3.3]heptane-2-carboxylate: To a stirred solution of tert-butyl 6-oxo-2-azaspiro[3.3]heptane-2-carboxylate (300 mg, 1.42 mmol, 1 eq) in methanol (5 mL) was added n-butylamine (124 mg, 1.70 mmol, 1.2 eq) and the reaction mixture was stirred at RT for overnight. To the reaction mixture, NaBH₄ (80 mg, 2.13 mmol, 1.5 eq) was added at 0° C. and then resultant reaction mixture was allowed to stir at 0° C. for 1 h. Progress of reaction was monitored by TLC and 1H-NMR. After completion, reaction mixture was concentrated under reduced pressure to get residue which was diluted with water (100 mL) and extracted with dichloromethane (2×100 mL). Combined organic layer was dried over anhydrous sodium sulfate, concentrated under reduced pressure to afford tert-butyl 6-(butylamino)-2-azaspiro[3.3]heptane-2-carboxylate (378 mg, 99%) which was used in the next step without purification.

Step-2: Synthesis of tert-butyl 6-((N-(tert-butoxycarbonyl)sulfamoyl)(butyl)amino)-2-azaspiro[3.3]heptane-2-carboxylate: To a solution of tert-butyl 6-(butylamino)-2-azaspiro[3.3]heptane-2-carboxylate (378 mg, 1.40 mmol, 1 eq) in DCM (10 mL) were added N-(tert-butoxycarbonyl)-N-[4-(dimethylazaniumylidene)-1,4-dihydropyridin-1ylsulfonyl]azanide (510 mg, 1.69 mmol, 1.2 eq) and DIPEA (0.36 mL, 2.11 mmol, 1.5 eq) and the mixture was allowed to stir at RT for 16 h. Progress of reaction was monitored by TLC and 1H-NMR. After completion, the reaction mixture was concentrated under reduced pressure to get residue which was washed with 1N HCl solution (100 mL) and extracted with ethyl acetate (2×100 mL). Combined organic layer was dried over anhydrous sodium sulfate. Removal of solvent under reduced pressure to afford tert-butyl 6-((N-(tert-butoxycarbonyl)sulfamoyl)(butyl)amino)-2-azaspiro[3.3]heptane-2-carboxylate (600 mg, 95%).

Step-3: Synthesis of N-butyl-N-(2-azaspiro[3.3]heptan-6-yl)sulfamamide trifluoroacetate: To a solution of tert-butyl 6-((N-(tert-butoxycarbonyl)sulfamoyl)(butyl)amino)-2-azaspiro[3.3]heptane-2-carboxylate (600 mg, 1.34 mmol, 1 eq) in DCM (10 mL) was added TFA (3 mL) and was allowed to stir at RT for 2 h. Progress of reaction was monitored by TLC. After completion, reaction mixture was concentrated under reduced pressure to afford crude which was triturated with diethyl ether to afford N-butyl-N-(2-azaspiro[3.3]heptan-6-yl)sulfamamide trifluoroacetate (340 mg, 73%).

Step-4: Synthesis of N-butyl-N-(2-(7-chloro-5-methylpyrrolo[2,1-f][1,2,4]triazin-4-yl)-2-azaspiro[3.3]heptan-6-yl)sulfamamide: A suspension of N-butyl-N-(2-azaspiro[3.3]heptan-6-yl)sulfamamide trifluoroacetate (180 mg, 0.49 mmol, 1 eq), 4,7-dichloro-5-methylpyrrolo[2,1-f][1,2,4]triazine (70 mg, 0.34 mmol, 0.7 eq) and DIPEA (0.17 mL, 0.99 mmol, 2 eq) in DMF (1 mL) was allowed to stir at 80° C. for 2 h. Progress of reaction was monitored by LCMS and TLC. After 2 h, the reaction mixture was poured onto ice cold water (100 mL) and extracted with ethyl acetate (100 mL). Combined organic layer was concentrated under reduced pressure to get crude which was purified using reverse phase column chromatography to afford N-butyl-N-(2-(7-chloro-5-methylpyrrolo[2,1-f][1,2,4]triazin-4-yl)-2-azaspiro[3.3]heptan-6-yl)sulfamamide (55 mg, 26%). LCMS: 413 [M+1]⁺; ¹H NMR (400 MHz, DMSO-d₆) δ ppm 0.88 (t, J=7.24 Hz, 3H) 1.26 (dq, J=15.02, 7.42 Hz, 2H) 1.49 (dt, J=14.91, 7.45 Hz, 2H) 2.24-2.36 (m, 2H) 2.36-2.42 (m, 3H) 2.42-2.47 (m, 2H) 2.89-3.00 (m, 2H) 3.86 (t, J=7.67 Hz, 1H) 4.30 (s, 2H) 4.41 (s, 2H) 6.64 (d, J=6.14 Hz, 3H) 7.90 (s, 1H).

Example-115: Synthesis of N-(2-(7-chloro-5-methylpyrrolo[2,1-f][1,2,4]triazin-4-yl)-2-azaspiro[3.3]heptan-6-yl)-N-(cyclopropylmethyl)sulfamamide, (Compounds 1.115)

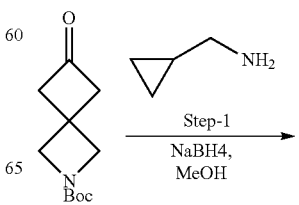

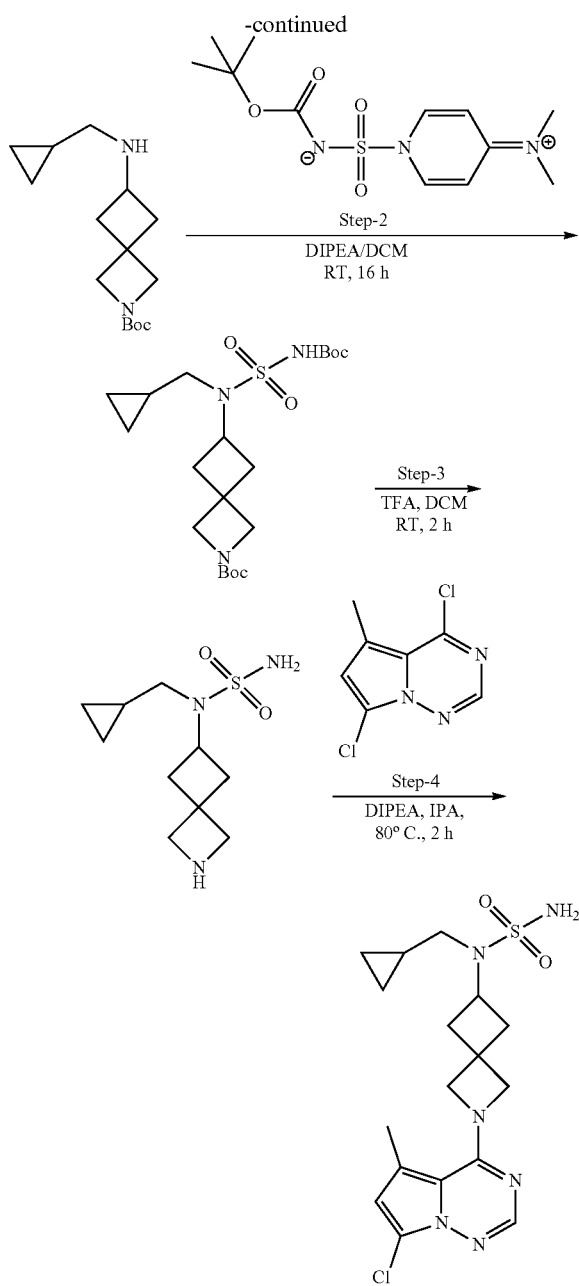

Step-1: Synthesis of tert-butyl 6-((cyclopropylmethyl)amino)-2-azaspiro[3.3]heptane-2-carboxylate: To a stirred solution of tert-butyl 6-oxo-2-azaspiro[3.3]heptane-2-carboxylate (300 mg, 1.42 mmol, 1 eq) in methanol (5 mL) was added cyclopropylmethanamine (121 mg, 1.70 mmol, 1.2 eq) and the reaction mixture was stirred at RT for overnight. To the reaction mixture, NaBH$_4$ (80 mg, 2.13 mmol, 1.5 eq) was added at 0° C. and then resultant reaction mixture was allowed to stir at 0° C. for 1 h. Progress of reaction was monitored by TLC After completion, reaction mixture was concentrated under reduced pressure to get residue which was diluted with water (100 mL) and extracted with dichloromethane (2×100 mL). Combined organic layer was dried over anhydrous sodium sulfate. Removal of solvent under reduced pressure to afford tert-butyl 6-((cyclopropylmethyl)amino)-2-azaspiro[3.3]heptane-2-carboxylate (350 mg, 92.5%) which was used in the next step without purification.

Step-2: Synthesis of tert-butyl 6-((N-(tert-butoxycarbonyl)sulfamoyl)(cyclopropylmethyl)amino)-2-azaspiro[3.3]heptane-2-carboxylate: To a solution of tert-butyl 6-((cyclopropylmethyl)amino)-2-azaspiro[3.3]heptane-2-carboxylate (350 mg, 1.31 mmol, 1 eq) in DCM (10 mL) were added N-(tert-butoxycarbonyl)-N-[4-(dimethylazaniumylidene)-1,4-dihydropyridin-1ylsulfonyl]azanide (476 mg, 1.57 mmol, 1.2 eq) and DIPEA (0.34 mL, 1.97 mmol, 1.5 eq) and the mixture was allowed to stir at RT for 16 h. Progress of reaction was monitored by TLC. After completion, reaction mixture was concentrated under reduced pressure to get residue which was washed with 1N HCl solution (100 mL) and extracted with ethyl acetate (2×100 mL). Combined organic layer was dried over anhydrous sodium sulfate and concentrated under reduced pressure to afford tert-butyl 6-((N-(tert-butoxycarbonyl)sulfamoyl)(cyclopropylmethyl)amino)-2-azaspiro[3.3]heptane-2-carboxylate (500 mg, 85.4%).

Step-3: Synthesis of N-(cyclopropylmethyl)-N-(2-azaspiro[3.3]heptan-6-yl)sulfamidetrifluoroacetic acid: To a solution of tert-butyl 6-((N-(tert-butoxycarbonyl)sulfamoyl)(cyclopropylmethyl)amino)-2-azaspiro[3.3]heptane-2-carboxylate (500 mg, 1.12 mmol, 1 eq) in DCM (5 mL) was added TFA (2 ML) and was allowed to stir at RT for 2 h. Progress of reaction was monitored by TLC. After completion, reaction mixture was concentrated under reduced pressure to afford crude which was triturated with diethyl ether to afford N-(cyclopropylmethyl)-N-(2-azaspiro[3.3]heptan-6-yl)sulfamide trifluoroacetic acid (225 mg, 55.8%).

Step-4: Synthesis of N-(2-(7-chloro-5-methylpyrrolo[2,1-f][1,2,4]triazin-4-yl)-2-azaspiro[3.3]heptan-6-yl)-N-(cyclopropylmethyl)sulfamamide: A suspension of N-(cyclopropylmethyl)-N-(2-azaspiro[3.3]heptan-6-yl)sulfamide trifluoroacetic acid (200 mg, 0.55 mmol, 1 eq), 4,7-dichloro-5-methylpyrrolo[2,1-f][1,2,4]triazine (78 mg, 0.38 mmol, 0.7 eq) in IPA (5 mL) was added DIPEA (143 mg, 1.11 mmol, 2 eq.) and the reaction mixture was allowed to stir at 80° C. for 2 h. Progress of reaction was monitored by LCMS and TLC. After 2 h, the reaction mixture was concentrated under reduced pressure. Water (100 mL) was added into the reaction mixture and extracted with ethyl acetate (100 mL×2). Combined organic layer was concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-(cyclopropylmethyl)sulfamamide (72 mg, 31.5%). LCMS: 411 [M+1]$^+$; $^1$H NMR (400 MHz, DMSO-d$_6$) δ ppm 0.14-0.27 (m, 2H) 0.39-0.50 (m, 2H) 0.96-1.08 (m, 1H) 2.25-2.42 (m, 8H) 2.86 (d, J=6.58 Hz, 2H) 3.77-3.94 (m, 1H) 4.29 (s, 2H) 4.41 (s, 2H) 6.63 (d, J=5.26 Hz, 2H) 7.90 (s, 1H).

Example-116: Synthesis of N-(2-(7-chloro-5-methylpyrrolo[2,1-f][1,2,4]triazin-4-yl)-2-azaspiro[3.3]heptan-6-yl)-N-(cyclobutylmethyl)sulfamide, (Compounds 1.116)

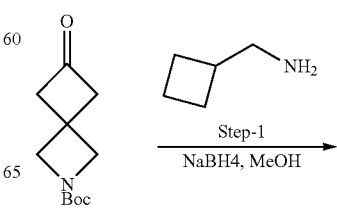

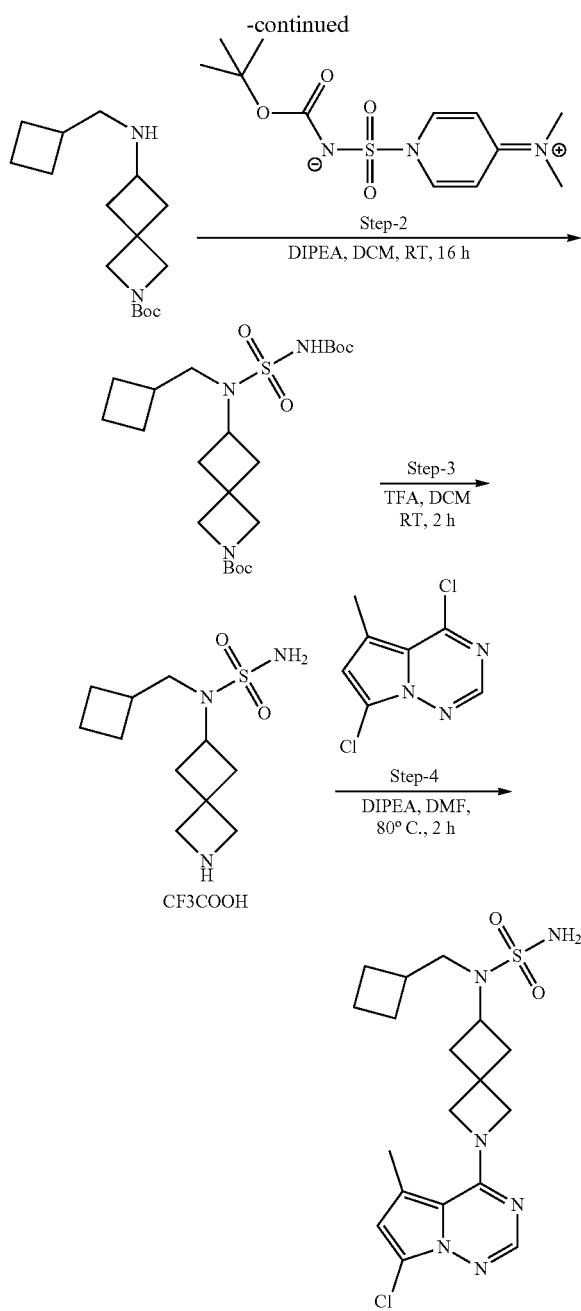

Step-2: Synthesis of tert-butyl 6-((N-(tert-butoxycarbonyl)sulfamoyl)(cyclobutylmethyl)amino)-2-azaspiro[3.3]heptane-2-carboxylate: To a solution of tert-butyl 6-((cyclobutylmethyl)amino)-2-azaspiro[3.3]heptane-2-carboxylate (350 mg, 1.24 mmol, 1 eq) in DCM (10 mL) were added N-(tert-butoxycarbonyl)-N-[4-(dimethylazaniumylidene)-1,4-dihydropyridin-1ylsulfonyl]azanide (452 mg, 1.49 mmol, 1.2 eq) and DIPEA (0.32 mL, 1.87 mmol, 1.5 eq) and the mixture was allowed to stir at RT for 16 h. Progress of reaction was monitored by TLC and 1H-NMR. After completion, reaction mixture was concentrated under reduced pressure to get residue which was washed with 1N HCl solution (100 mL) and extracted with ethyl acetate (2×100 mL). Combined organic layer was dried over anhydrous sodium sulfate and concentrated under reduced pressure to afford tert-butyl 6-((N-(tert-butoxycarbonyl)sulfamoyl)(cyclobutylmethyl)amino)-2-azaspiro[3.3]heptane-2-carboxylate (550 mg, 95.9%).

Step-3: Synthesis of N-(cyclobutylmethyl)-N-(2-azaspiro[3.3]heptan-6-yl)sulfamide trifluoroacetic acid: To a solution of tert-butyl 6-((N-(tert-butoxycarbonyl)sulfamoyl)(cyclobutylmethyl)amino)-2-azaspiro[3.3]heptane-2-carboxylate (550 mg, 1.19 mmol, 1 eq) in DCM (5 mL) was added TFA (2 mL) and was allowed to stir at RT for 2 h. Progress of reaction was monitored by TLC. After completion, reaction mixture was concentrated under reduced pressure to afford crude which was triturated with diethyl ether to afford N-(cyclobutylmethyl)-N-(2-azaspiro[3.3]heptan-6-yl)sulfamamide trifluoroacetic acid (250 mg, 56%).

Step-4: Synthesis of N-(2-(7-chloro-5-methylpyrrolo[2,1-f][1,2,4]triazin-4-yl)-2-azaspiro[3.3]heptan-6-yl)-N-(cyclobutylmethyl)sulfamide: A suspension of N-(cyclobutylmethyl)-N-(2-azaspiro[3.3]heptan-6-yl)sulfamide trifluoroacetic acid (200 mg, 0.53 mmol, 1 eq), 4,7-dichloro-5-methylpyrrolo[2,1-f][1,2,4]triazine (75 mg, 0.37 mmol, 0.7 eq) in DMF (2 mL) was added DIPEA (0.13 mL, 0.80 mmol, 1.5 eq.) and the reaction mixture was allowed to stir at 80° C. for 2 h. Progress of reaction was monitored by LCMS and TLC. After 2 h, the reaction mixture was concentrated under reduced pressure. Water (100 mL) was added into the reaction mixture and extracted with ethyl acetate (100 mL). Combined organic layer was concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-(cyclobutylmethyl)sulfamide (47 mg, 20.7%). LCMS: 424 [M+1]$^+$; $^1$H NMR (400 MHz, DMSO-$d_4$) δ ppm 1.61-1.72 (m, 2H) 1.72-1.84 (m, 2H) 1.94 (d, J=5.70 Hz, 2H) 2.24-2.37 (m, 3H) 2.40 (s, 3H) 2.67 (br. s., 1H) 2.96 (d, J=7.45 Hz, 2H) 2.95 (m, 2H) 3.76-3.90 (m, 1H) 4.31 (s, 2H) 4.41 (s, 2H) 6.64 (s, 2H) 7.91 (s, 1H).

Example-117: Synthesis of N-(2-(7-chloro-5-methylpyrrolo[2,1-f][1,2,4]triazin-4-yl)-2-azaspiro[3.3]heptan-6-yl)-N-(cyclohexylmethyl)sulfamide, (Compounds 1.117)

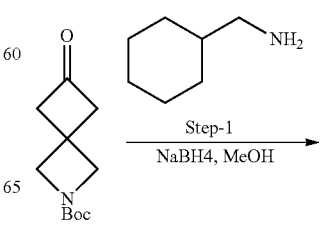

Step-1: Synthesis of tert-butyl 6-((cyclobutylmethyl)amino)-2-azaspiro[3.3]heptane-2-carboxylate: To a stirred solution of tert-butyl 6-oxo-2-azaspiro[3.3]heptane-2-carboxylate (300 mg, 1.42 mmol, 1 eq) in methanol (5 mL) was added cyclobutylmethanamine (145 mg, 1.70 mmol, 1.2 eq) and the reaction mixture was stirred at RT for overnight. To the reaction mixture, NaBH$_4$ (80 mg, 2.13 mmol, 1.5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (100 mL) and extracted with dichloromethane (2×100 mL). Combined organic layer was dried over anhydrous sodium sulfate. Removal of solvent under reduced pressure to afford tert-butyl 6-((cyclobutylmethyl)amino)-2-azaspiro[3.3]heptane-2-carboxylate (350 mg, 88%) which was used in the next step without purification.

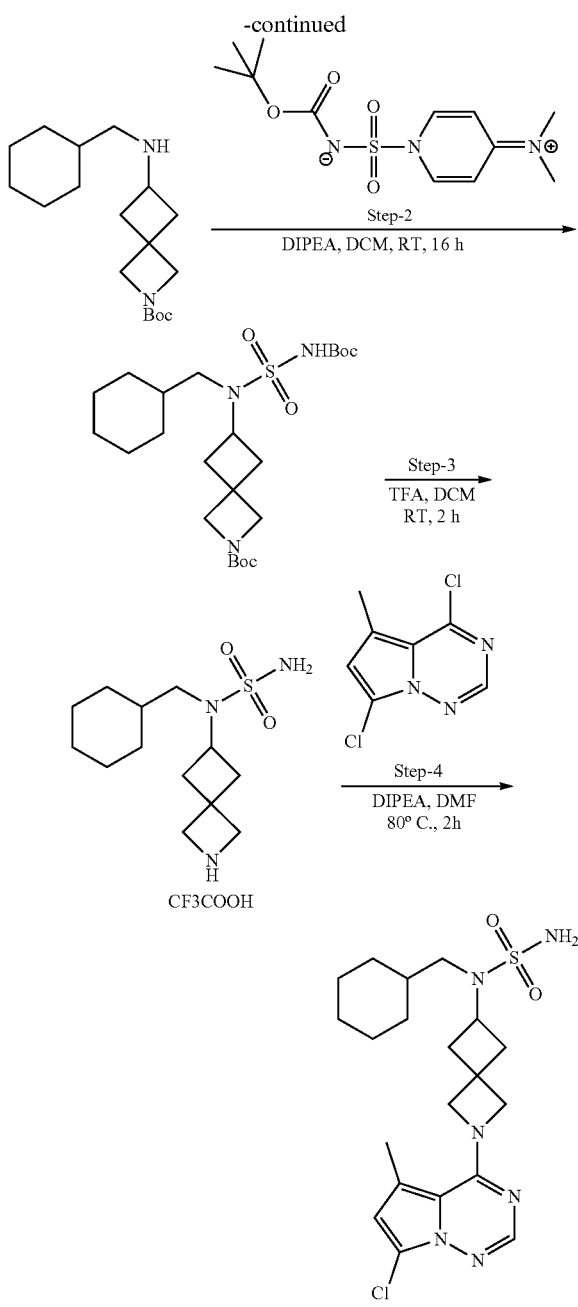

Step-2: Synthesis of tert-butyl 6-((N-(tert-butoxycarbonyl)sulfamoyl)(cyclohexylmethyl)amino)-2-azaspiro[3.3]heptane-2-carboxylate: To a solution of tert-butyl 6-((cyclohexylmethyl)amino)-2-azaspiro[3.3]heptane-2-carboxylate (400 mg, 1.29 mmol, 1 eq) in DCM (10 mL) were added N-(tert-butoxycarbonyl)-N-[4-(dimethylazaniumylidene)-1,4-dihydropyridin-1ylsulfonyl]azanide (470 mg, 1.55 mmol, 1.2 eq) and DIPEA (0.33 mL, 1.94 mmol, 1.5 eq) and the mixture was allowed to stir at RT for 16 h. Progress of reaction was monitored by TLC and 1H-NMR. After completion, reaction mixture was concentrated under reduced pressure to get residue which was washed with 1N HCl solution (100 mL) and extracted with ethyl acetate (2×100 mL). Combined organic layer was dried over anhydrous sodium sulfate and concentrated under reduced pressure to afford tert-butyl 6-((N-(tert-butoxycarbonyl)sulfamoyl)(cyclohexylmethyl)amino)-2-azaspiro[3.3]heptane-2-carboxylate (600 mg, 95%).

Step-3: Synthesis of N-(cyclohexylmethyl)-N-(2-azaspiro[3.3]heptan-6-yl)sulfamide trifluoroacetic acid: To a solution of tert-butyl 6-((N-(tert-butoxycarbonyl)sulfamoyl)(cyclohexylmethyl)amino)-2-azaspiro[3.3]heptane-2-carboxylate (600 mg, 1.23 mmol, 1 eq) in DCM (5 mL) was added TFA (3 mL) and was allowed to stir at RT for 2 h. Progress of reaction was monitored by TLC. After completion, reaction mixture was concentrated under reduced pressure to afford crude which was triturated with diethyl ether to afford N-(cyclohexylmethyl)-N-(2-azaspiro[3.3]heptan-6-yl)sulfamide trifluoroacetic acid (200 mg, 40.5%).

Step-4: Synthesis of N-(2-(7-chloro-5-methylpyrrolo[2,1-f][1,2,4]triazin-4-yl)-2-azaspiro[3.3]heptan-6-yl)-N-(cyclohexylmethyl)sulfamide: A suspension of N-(cyclohexylmethyl)-N-(2-azaspiro[3.3]heptan-6-yl)sulfamide trifluoroacetic acid (150 mg, 0.37 mmol, 1 eq), 4,7-dichloro-5-methylpyrrolo[2,1-f][1,2,4]triazine (52 mg, 0.26 mmol, 0.7 eq) in DMF (2 mL) was added DIPEA (0.1 mL, 0.56 mmol, 1.5 eq.) and the reaction mixture was allowed to stir at 80° C. for 2 h. Progress of reaction was monitored by LCMS and TLC. After 2 h, the reaction mixture was concentrated under reduced pressure. Water (100 mL) was added into the reaction mixture and extracted with ethyl acetate (100 mL). Combined organic layer was concentrated under reduced pressure to get crude which was purified using reverse phase column chromatography to afford N-(2-(7-chloro-5-methylpyrrolo[2,1-f][1,2,4]triazin-4-yl)-2-azaspiro[3.3]heptan-6-yl)-N-(cyclohexylmethyl)sulfamide (56 mg, 33.13%). LCMS: 453 [M+1]$^+$; $^1$H NMR (400 MHz, DMSO-d$_6$) δ ppm 0.75-0.90 (m, 2H) 1.10-1.25 (m, 3H) 1.70 (br. s., 6H) 2.25-2.30 (m, 3H) 2.40 (s, 5H) 2.73 (d, J=7.02 Hz, 2H) 3.90 (s, 1H) 4.30 (s, 2H) 4.40 (s, 2H) 6.63 (s, 2H) 7.90 (s, 1H).

Step-1: Synthesis of tert-butyl 6-((cyclohexylmethyl)amino)-2-azaspiro[3.3]heptane-2-carboxylate: To a stirred solution of tert-butyl 6-oxo-2-azaspiro[3.3]heptane-2-carboxylate (300 mg, 1.42 mmol, 1 eq) in methanol (5 mL) was added cyclohexylmethanamine (169 mg, 1.70 mmol, 1.2 eq) and the reaction mixture was stirred at RT for overnight. To the reaction mixture, NaBH$_4$ (80 mg, 2.13 mmol, 1.5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (100 mL) and extracted with dichloromethane (2×100 mL). Combined organic layer was dried over anhydrous sodium sulfate. Removal of solvent under reduced pressure to afford tert-butyl 6-((cyclohexylmethyl)amino)-2-azaspiro[3.3]heptane-2-carboxylate (400 mg, 91.2%) which was used in the next step without purification.

Example-118: Synthesis of N-(2-(7-chloro-5-methylpyrrolo[2,1-f][1,2,4]triazin-4-yl)-2-azaspiro[3.3]heptan-6-yl)-N-((4,4-difluorocyclohexyl)methyl)sulfamamide, (Compounds 1.118)

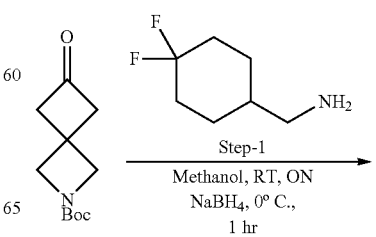

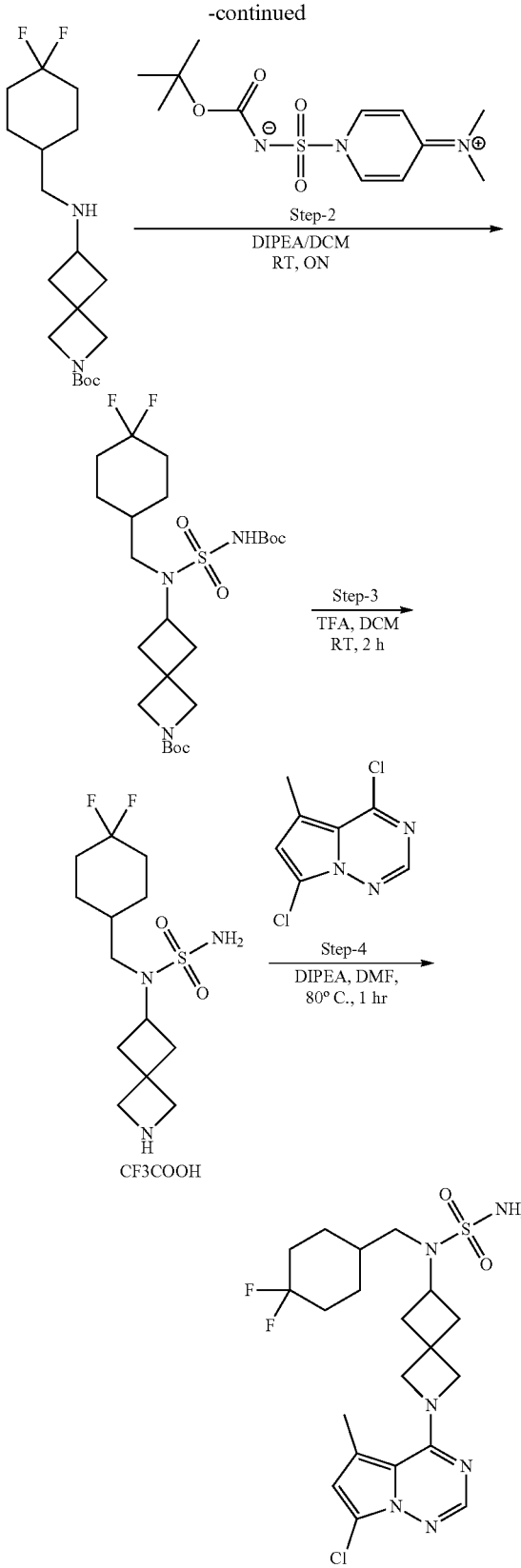

Step-1: Synthesis of tert-butyl 6-(((4,4-difluorocyclohexyl)methyl)amino)-2-azaspiro[3.3]heptane-2-carboxylate: To a stirred solution of tert-butyl 6-oxo-2-azaspiro[3.3]heptane-2-carboxylate (250 mg, 1.18 mmol, 1 eq) in methanol (8 mL) was added (4,4-difluorocyclohexyl)methanamine (211 mg, 1.42 mmol, 1.2 eq) and the reaction mixture was stirred at RT for overnight. To the reaction mixture, NaBH$_4$ (67 mg, 1.77 mmol, 1.5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (50 mL) and extracted with dichloromethane (2×50 mL). Combined organic layer was dried over anhydrous sodium sulfate. Removal of solvent under reduced pressure to afford tert-butyl 6-(((4,4-difluorocyclohexyl)methyl)amino)-2-azaspiro[3.3]heptane-2-carboxylate which was used in the next step without purification (370 mg, 91.13%).

Step-2: Synthesis of tert-butyl 6-((N-(tert-butoxycarbonyl)sulfamoyl)((4,4-difluorocyclohexyl)methyl)amino)-2-azaspiro[3.3]heptane-2-carboxylate: To a solution of tert-butyl 6-(((4,4-difluorocyclohexyl)methyl)amino)-2-azaspiro[3.3]heptane-2-carboxylate (370 mg, 1.07 mmol, 1 eq) in DCM (10 mL) were added N-(tert-butoxycarbonyl)-N-[4-(dimethylazaniumylidene)-1,4-dihydropyridin-1yl sulfonyl]azanide (389 mg, 1.29 mmol, 1.2 eq) and DIPEA (207 mg, 1.60 mmol, 1.5 eq) and the mixture was allowed to stir at RT for overnight. Progress of reaction was monitored by TLC. After completion, the reaction mixture was concentrated under reduced pressure to get residue which was washed with 1N HCl solution (50 mL) and extracted with ethyl acetate (2×150 mL). Combined organic layer was dried over anhydrous sodium sulfate and concentrated under reduced pressure to obtain tert-butyl 6-((N-(tert-butoxycarbonyl)sulfamoyl)((4,4-difluorocyclohexyl)methyl)amino)-2-azaspiro[3.3]heptane-2-carboxylate as desired product (550 mg, 98%).

Step-3: Synthesis of N-((4,4-difluorocyclohexyl)methyl)-N-(2-azaspiro[3.3]heptan-6-yl)sulfamamide 2,2,2-trifluoroacetate: To a solution of tert-butyl 6-((N-(tert-butoxycarbonyl)sulfamoyl)((4,4-difluorocyclohexyl)methyl)amino)-2-azaspiro[3.3]heptane-2-carboxylate (550 mg, 1.05 mmol, 1 eq) in DCM (6 mL) was added TFA (2.5 mL) and was allowed to stir at RT for 2 h. Progress of reaction was monitored by TLC. After completion, reaction mixture was concentrated under reduced pressure to afford crude which was triturated with diethyl ether to afford N-((4,4-difluorocyclohexyl)methyl)-N-(2-azaspiro[3.3]heptan-6-yl)sulfamamide 2,2,2-trifluoroacetate (390 mg, 84.9%).

Step-4: Synthesis of N-(2-(7-chloro-5-methylpyrrolo[2,1-f][1,2,4]triazin-4-yl)-2-azaspiro[3.3]heptan-6-yl)-N-((4,4-difluorocyclohexyl)methyl)sulfamamide: A suspension of N-((4,4-difluorocyclohexyl)methyl)-N-(2-azaspiro[3.3]heptan-6-yl)sulfamamide 2,2,2-trifluoroacetate (131 mg, 0.298 mmol, 1.0 eq), 4,7-dichloro-5-methylpyrrolo[2,1-f][1,2,4]triazine (60 mg, 0.298 mmol, 1.0 eq) and DIPEA (77 mg, 0.596 mmol, 2.0 eq) in DMF (1.0 mL) was allowed to stir at 80° C. for 1 h. Progress of reaction was monitored by LCMS and TLC. After 2 h, reaction mixture was diluted with water (10 mL) and extracted with ethyl acetate (1×50 mL). Combined organic layer was washed with brine (1×10 mL) and dried over anhydrous sodium sulfate, Concentrated under reduced pressure to obtain crude product which was purified using reversed phase HPLC chromatography to afford N-(2-(7-chloro-5-methylpyrrolo[2,1-f][1,2,4]triazin-4-yl)-2-azaspiro[3.3]heptan-6-yl)-N-((4,4-difluorocyclohexyl)methyl)sulfamamide (13 mg, 9%). LCMS: 489 [M+1]$^+$; $^1$H NMR (400 MHz, DMSO-d$_6$) δ ppm 7.91 (s, 1H), 6.70 (s, 2H), 6.63 (s, 1H), 4.40 (s, 2H), 4.31 (s, 2H), 3.88 (d, J=8.8 Hz, 1H), 2.82 (d, J=7.0 Hz, 2H), 2.40 (s, 3H), 2.32 (br. s., 3H), 1.99 (br. s., 2H), 1.79 (br. s., 4H), 1.70 (br. s., 2H), 1.20-1.06 (m, 2H).

Example-119: Synthesis of N-(2-(7-chloro-5-methylpyrrolo[2,1-f][1,2,4]triazin-4-yl)-2-azaspiro[3.3]heptan-6-yl)-N-((4-(trifluoromethyl)cyclohexyl)methyl)sulfamamide, (Compounds 1.119)

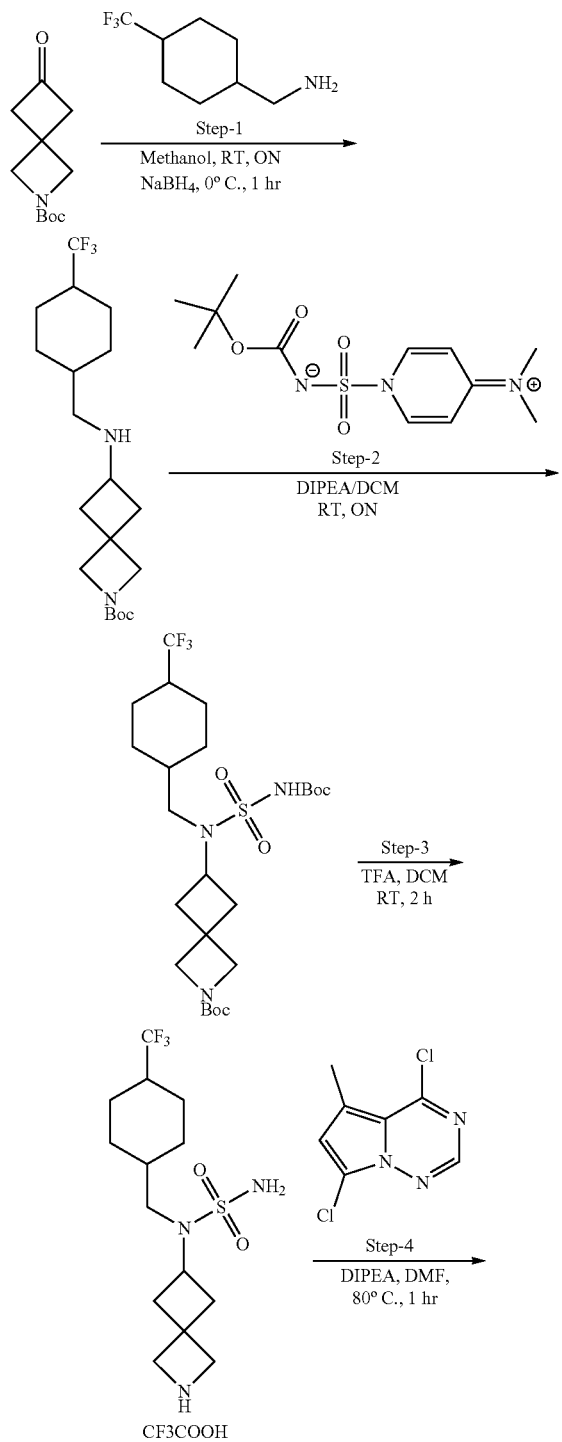

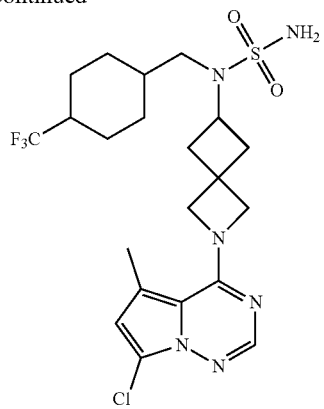

Step-1: Synthesis of tert-butyl 6-(((4-(trifluoromethyl)cyclohexyl)methyl)amino)-2-azaspiro[3.3]heptane-2-carboxylate: To a stirred solution of tert-butyl 6-oxo-2-azaspiro[3.3]heptane-2-carboxylate (250 mg, 1.18 mmol, 1 eq) in methanol (8 mL) was added (4-(trifluoromethyl)cyclohexyl)methanamine (257 mg, 1.42 mmol, 1.2 eq) and the reaction mixture was stirred at RT for overnight. To the reaction mixture, NaBH₄ (67 mg, 1.77 mmol, 1.5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (50 mL) and extracted with dichloromethane (2×150 mL). Combined organic layer was dried over anhydrous sodium sulfate. Removal of solvent under reduced pressure to afford tert-butyl 6-(((4-(trifluoromethyl)cyclohexyl)methyl)amino)-2-azaspiro[3.3]heptane-2-carboxylate (410 mg, 92.34%) which was used in the next step without purification.

Step-2: Synthesis of tert-butyl 6-((N-(tert-butoxycarbonyl)sulfamoyl)((4-(trifluoromethyl)cyclohexyl)methyl)amino)-2-azaspiro[3.3]heptane-2-carboxylate: To a solution of tert-butyl 6-(((4-(trifluoromethyl)cyclohexyl)methyl)amino)-2-azaspiro[3.3]heptane-2-carboxylate (200 mg, 0.539 mmol, 1 eq) in DCM (10 mL) were added N-(tert-butoxycarbonyl)-N-[4-(dimethylazaniumylidene)-1,4-dihydropyridin-1ylsulfonyl]azanide (195 mg, 0.647 mmol, 1.2 eq) and DIPEA (104 mg, 0.808 mmol, 1.5 eq) and the mixture was allowed to stir at RT for overnight. Progress of reaction was monitored by TLC. After completion, the reaction mixture was concentrated under reduced pressure to get residue which was washed with 1N HCl solution (50 mL) and extracted with ethyl acetate (2×150 mL). Combined organic layer was dried over anhydrous sodium sulfate and concentrated under reduced pressure to obtain tert-butyl 6-((N-(tert-butoxycarbonyl)sulfamoyl)((4-(trifluoromethyl)cyclohexyl)methyl)amino)-2-azaspiro[3.3]heptane-2-carboxylate as desired product (560 mg, 92.56%).

Step-3: Synthesis of N-(N-((4-trifluorocyclohexyl)methyl)-N-(2-azaspiro[3.3]heptan-6-yl)sulfamamide 2,2,2-trifluoroacetate: To a solution of tert-butyl 6-((N-(tert-butoxycarbonyl)sulfamoyl)((4-(trifluoromethyl)cyclohexyl)methyl)amino)-2-azaspiro[3.3]heptane-2-carboxylate (560 mg, 0.100 mmol, 1 eq) in DCM (4 mL) was added TFA (3 mL) and was allowed to stir at RT for 2 h. Progress of reaction was monitored by TLC. After completion, reaction mixture was concentrated under reduced pressure to afford crude which was triturated with diethyl ether to afford N-(2-azaspiro[3.3]heptan-6-yl)-N-((4-(trifluoromethyl)cyclohexyl)methyl)sulfamamide 2,2,2-trifluoroacetate (410 mg, 86.68%).

Step-4: Synthesis of N-(2-(7-chloro-5-methylpyrrolo[2,1-f][1,2,4]triazin-4-yl)-2-azaspiro[3.3]heptan-6-yl)-N-((4-(trifluoromethyl)cyclohexyl)methyl)sulfamamide: A suspension of N-(2-azaspiro[3.3]heptan-6-yl)-N-((4-(trifluoromethyl)cyclohexyl)methyl)sulfamamide 2,2,2-trifluoroacetate (140 mg, 0.298 mmol, 1.0 eq), 4,7-dichloro-5-methylpyrrolo[2,1-f][1,2,4]triazine (60 mg, 0.298 mmol, 1.0 eq) and DIPEA (77 mg, 0.596 mmol, 2.0 eq) in DMF (1.0 mL) was allowed to stir at 80° C. for 1 h. Progress of reaction was monitored by LCMS and TLC. After 2 h, reaction mixture was diluted with water (10 mL) and extracted with ethyl acetate (1×50 mL). Combined organic layer was washed with brine (1×10 mL) and dried over anhydrous sodium sulfate, Concentrated under reduced pressure to obtain crude product which was purified using reversed phase HPLC chromatography to afford N-(2-(7-chloro-5-methylpyrrolo[2,1-f][1,2,4]triazin-4-yl)-2-azaspiro[3.3]heptan-6-yl)-N-((4-(trifluoromethyl)cyclohexyl)methyl)sulfamamide (40 mg, 25.8% mg). LCMS: 521 [M+1]$^+$; $^1$H NMR (400 MHz, DMSO-$d_6$) δ ppm 7.91 (s, 1H), 6.73-6.67 (m, 2H), 6.64 (s, 1H), 4.41 (s, 2H), 4.31 (s, 2H), 3.83 (dd, J=7.0, 14.5 Hz, 1H), 2.90-2.76 (d, J=7.5 Hz, 2H), 2.47-2.27 (m, 7H), 1.92-1.71 (m, 3H), 1.59-1.46 (d, J=7.5 Hz, 5H), 1.20 (d, J=11.4 Hz, 1H), 0.91 (d, J=11.8 Hz, 1H).

Example-120: Synthesis of N-(2-(7-chloro-5-methylpyrrolo[2,1-f][1,2,4]triazin-4-yl)-2-azaspiro[3.3]heptan-6-yl)-N-(3,3,3-trifluoro-2-hydroxypropyl)sulfamamide, (Compounds 1.120)

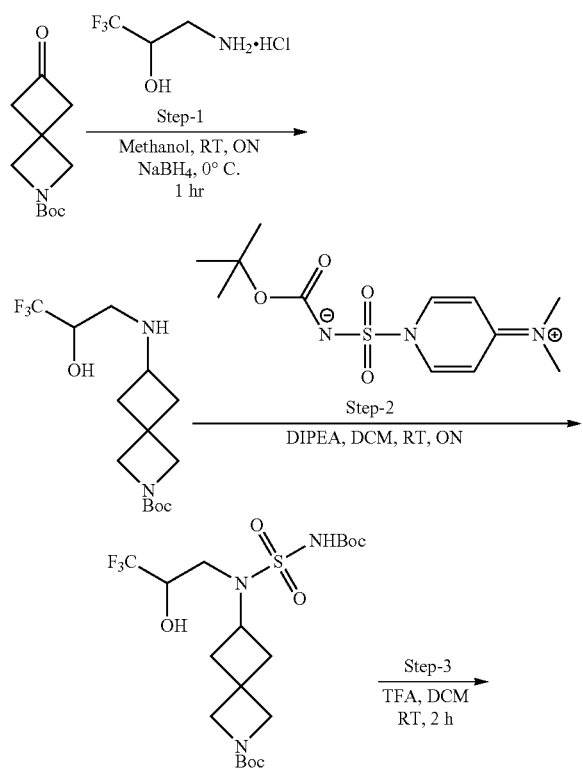

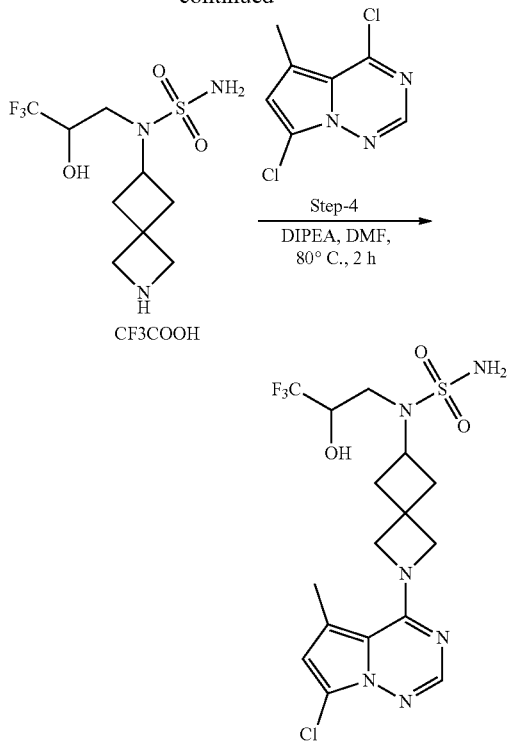

Step-1: Synthesis of tert-butyl 6-((3,3,3-trifluoro-2-hydroxypropyl)amino)-2-azaspiro[3.3]heptane-2-carboxylate: To a stirred solution of tert-butyl 6-oxo-2-azaspiro[3.3]heptane-2-carboxylate (100 mg, 0.473 mmol, 1 eq) in methanol (5 mL) was added 3-amino-1,1,1-trifluoropropan-2-ol hydrochloride (94 mg, 0.568 mmol, 1.2 eq) and the reaction mixture was stirred at RT for overnight. To the reaction mixture, NaBH$_4$ (27 mg, 0.7095 mmol, 1.5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (50 mL) and extracted with dichloromethane (2×50 mL). Combined organic layer was dried over anhydrous sodium sulfate. Removal of solvent under reduced pressure to afford tert-butyl 6-((3,3,3-trifluoro-2-hydroxypropyl)amino)-2-azaspiro[3.3]heptane-2-carboxylate which was used in the next step without purification. (140 mg, 91.5%)

Step-2: Synthesis of tert-butyl 6-((N-(tert-butoxycarbonyl)sulfamoyl)(3,3,3-trifluoro-2-hydroxypropyl)amino)-2-azaspiro[3.3]heptane-2-carboxylate: To a solution of tert-butyl 6-((3,3,3-trifluoro-2-hydroxypropyl)amino)-2-azaspiro[3.3]heptane-2-carboxylate (140 mg, 0.430 mmol, 1 eq) in DCM (5 mL) were added N-(tert-butoxycarbonyl)-N-[4-(dimethylazaniumylidene)-1,4-dihydropyridin-1ylsulfonyl]azanide (150 mg, 0.51 mmol, 1.2 eq) and DIPEA (83 mg, 0.695 mmol, 1.5 eq) and the mixture was allowed to stir at RT for overnight. Progress of reaction was monitored by TLC. After completion, the reaction mixture was concentrated under reduced pressure to get residue which was washed with 1N HCl solution (50 mL) and extracted with ethyl acetate (2×50 mL). Combined organic layer was dried over anhydrous sodium sulfate and concentrated under reduced pressure to tert-butyl 6-((N-(tert-butoxycarbonyl)sulfamoyl)(3,3,3-trifluoro-2-hydroxypropyl) amino)-2-azaspiro[3.3]heptane-2-carboxylate as desired product (160 mg, 74%).

Step-3: Synthesis of N-(2-azaspiro[3.3]heptan-6-yl)-N-(3,3,3-trifluoro-2-hydroxypropyl)sulfamamide: To a solution of tert-butyl 6-((N-(tert-butoxycarbonyl)sulfamoyl)(3,3,3-trifluoro-2-hydroxypropyl)amino)-2-azaspiro[3.3] heptane-2-carboxylate (160 mg, 0.317 mmol, 1 eq) in DCM (4 mL) was added TFA (1.0 mL) and was allowed to stir at RT for 2 h. Progress of reaction was monitored by TLC. After completion, reaction mixture was concentrated under reduced pressure to afford crude which was triturated with diethyl ether to afford N-(2-azaspiro[3.3]heptan-6-yl)-N-(3,3,3-trifluoro-2-hydroxypropyl)sulfamamide as a TFA salt (125 mg, 93%).

Step-4: Synthesis of N-(2-(7-chloro-5-methylpyrrolo[2,1-f][1,2,4]triazin-4-yl)-2-azaspiro[3.3]heptan-6-yl)-N-(3,3,3-trifluoro-2-hydroxypropyl)sulfamamide: A suspension of N-(2-azaspiro[3.3]heptan-6-yl)-N-(3,3,3-trifluoro-2-hydroxypropyl)sulfamamide as a TFA salt (124 mg, 0.298 mmol, 1.0 eq), 4,7-dichloro-5-methylpyrrolo[2,1-f][1,2,4] triazine (60 mg, 0.298 mmol, 1.0 eq) and DIPEA (77 mg, 0.596 mmol, 2.0 eq) in DMF (1.0 mL) was allowed to stir at 80° C. for 2 h. Progress of reaction was monitored by LCMS and TLC. After 2 h, reaction mixture was diluted with water (10 mL) and extracted with ethyl acetate (1×50 mL). Combined organic layer was washed with brine (1×10 mL) and dried over anhydrous sodium sulfate, Concentrated under reduced pressure to obtain crude product which was purified using reversed phase HPLC chromatography to afford N-(2-(7-chloro-5-methylpyrrolo[2,1-f][1,2,4]triazin-4-yl)-2-azaspiro[3.3]heptan-6-yl)-N-(3,3,3-trifluoro-2-hydroxypropyl)sulfamamide (7 mg, 5%). LCMS: 469 [M+1]$^+$. $^1$H NMR (400 MHz, DMSO-d$_6$) δ ppm 7.91 (s, 1H), 6.88 (br. s., 2H), 6.63 (s, 1H), 6.50 (br. s., 1H), 4.46-4.35 (m, 2H), 4.31 (s, 2H), 4.16 (br. s., 1H), 3.96-3.87 (m, 1H), 3.20-3.10 (m, 1H), 2.90 (d, J=15.3 Hz, 1H), 2.46-2.22 (m, 6H), 2.08 (s, 1H).

Example-121: Synthesis of N-(2,2-difluoroethyl)-N-(2-(1-methyl-1H-pyrazolo[3,4-d]pyrimidin-4-yl)-2-azaspiro[3.3]heptan-6-yl)sulfamamide, (Compounds 1.121)

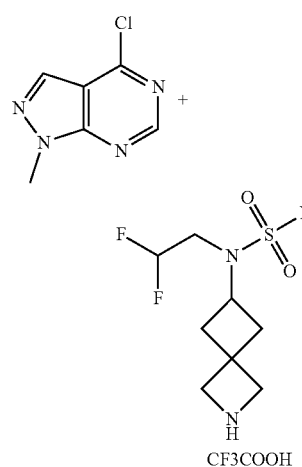

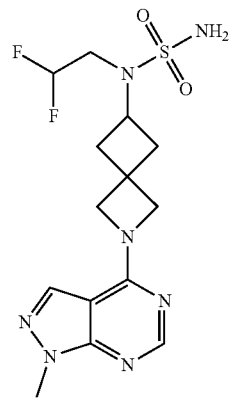

A suspension of N-(2,2-difluoroethyl)-N-(2-azaspiro[3.3] heptan-6-yl)sulfamamide 2,2,2-trifluoroacetate (119 mg, 0.3235 mmol, 1.1 eq), 4-chloro-1-methyl-1H-pyrazolo[3,4-d]pyrimidine (50 mg, 0.294 mmol, 1.0 eq) and DIPEA (0.1 mL, 0.588 mmol, 2.0 eq) in DMF (0.6 mL) was allowed to stir at 80° C. for 2 h. Progress of reaction was monitored by LCMS and TLC. After 2 h, reaction mixture was diluted with water (10 mL) and extracted with ethyl acetate (2×20 mL). Combined organic layer was washed with brine (1×10 mL) and dried over anhydrous sodium sulfate, Concentrated under reduced pressure to obtain crude product which was purified using reversed phase HPLC chromatography to afford N-(2,2-difluoroethyl)-N-(2-(1-methyl-1H-pyrazolo [3,4-d]pyrimidin-4-yl)-2-azaspiro[3.3]heptan-6-yl)sulfamamide as desired product (16 mg, 14%). LCMS:388 [M+1]$^+$; $^1$H NMR (400 MHz, DMSO-d$_6$) δ ppm 8.23 (s, 1H), 8.00 (br. s., 1H), 7.13-6.84 (m, 2H), 6.17 (br. s., 1H), 6.03 (t, J=4.2 Hz, 1H), 4.47 (br. s., 1H), 4.37 (br. s., 1H), 4.25 (br. s., 1H), 4.13 (br. s., 1H), 4.05-3.95 (m, 1H), 3.95-3.77 (m, 3H), 3.55-3.36 (m, 2H), 2.44-2.17 (m, 3H).

Example-122: Synthesis of N-(2-(7-chloro-5-methylpyrrolo[1,2-f][1,2,4]triazin-4-yl)-2-azaspiro[3.3] heptan-6-yl)-N-(2-methoxyethyl)sulfamamide, (Compound 1.122)

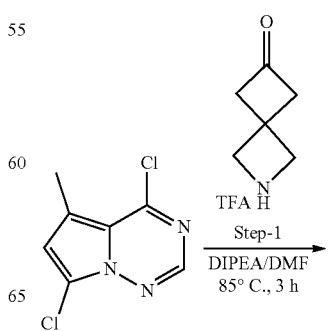

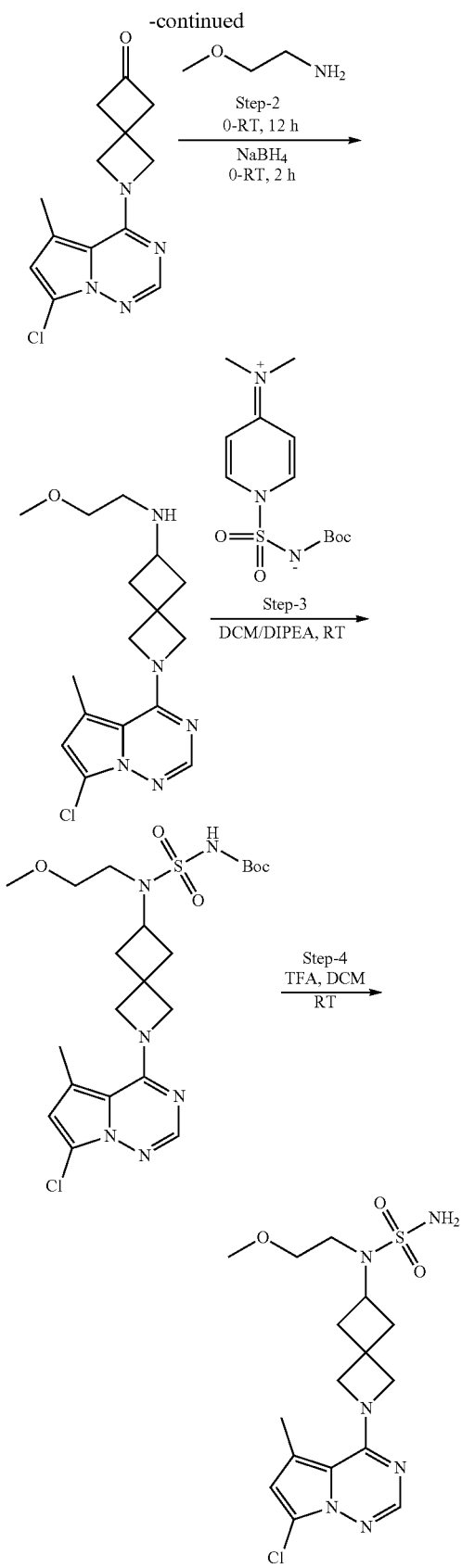

Step-1: Synthesis of 2-(7-chloro-5-methylpyrrolo[1,2-f][1,2,4]triazin-4-yl)-2-azaspiro[3.3]heptan-6-one: The mixture of 4,7-dichloro-5-methylpyrrolo[1,2-f][1,2,4]triazine (1.0 g, 4.95 mmol, 1 eq), N-methyl-N-(2-azaspiro[3.3]heptan-6-yl)sulfamamide, 2,2,2-trifluoroacetate salt (1.21 g, 5.44 mmol, 1.1 eq) and DIPEA (1.3 mL, 7.42 mmol, 1.5 eq) in DMF (10 mL) was allowed to stir at 85° C. for 3 h. Progress of reaction was monitored by TLC. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford 2-(7-chloro-5-methylpyrrolo[1,2-f][1,2,4]triazin-4-yl)-2-azaspiro[3.3]heptan-6-one (1.1 g, 80.30%). LCMS: 277.8 [M+1]+

Step-2: Synthesis of 2-(7-chloro-5-methylpyrrolo[1,2-f][1,2,4]triazin-4-yl)-N-(2-methoxyethyl)-2-azaspiro[3.3]heptan-6-amine: To a stirred solution of 2-(7-chloro-5-methylpyrrolo[1,2-f][1,2,4]triazin-4-yl)-2-azaspiro[3.3]heptan-6-one (0.160 g, 0.577 mmol, 1.0 eq) in MeOH (15.0 mL) was added 2-methoxyethanamine (0.043 g, 0.577 mmol, 1.0 eq) at 0° C. The resulting mixture was stirred at room temperature for overnight. The reaction mixture was then cooled to 0° C. followed by addition of NaBH$_4$ (0.043 mg, 1.154 mmol, 2.0 eq) at 0° C. The reaction mixture was stirred at room temperature for 2 h. The progress of reaction was monitored by TLC. The reaction mixture was concentrated, basified with NaHCO$_3$ solution (20 mL), extracted with EtOAc (2×150 mL). The combined organic layer was washed with water (50 mL), with brine (50 mL), dried over Na$_2$SO$_4$ concentrated to get crude product. The crude product was triturated in pentane to afford 2-(7-chloro-5-methylpyrrolo[1,2-f][1,2,4]triazin-4-yl)-N-(2-methoxyethyl)-2-azaspiro[3.3]heptan-6-amine (500 mg, 78.90%) as liquid, which was further used further next step without purification. LCMS: 336.8 [M+1]+

Step-3: Synthesis of tert-butyl N-(2-(7-chloro-5-methylpyrrolo[1,2-f][1,2,4]triazin-4-yl)-2-azaspiro[3.3]heptan-6-yl)-N-(2-methoxyethyl)sulfamoylcarbamate: To a solution of 2-(7-chloro-5-methylpyrrolo[1,2-f][1,2,4]triazin-4-yl)-N-(2-methoxyethyl)-2-azaspiro[3.3]heptan-6-amine (0.150 g, 0.447 mmol, 1 eq) and N-(1-(N-(tert-butoxycarbonyl)sulfamoyl)pyridin-4 (1H)-ylidene)-N-methylmethanaminium (0.161 g, 0.537 mmol, 1.2 eq) in dichloromethane (10 mL) N,N-diisopropylethylamine (0.156 ml, 0.895 mmol, 2.0 eq) was added and the reaction mixture was allowed to stir at RT for overnight. Progress of reaction was monitored by NMR. After completion, the reaction mixture was diluted with water (50 mL) and extracted with DCM (150 ml×2), combined organic layer was washed with brine (50 mL) and dried over anhydrous sodium sulfate concentrated to get crude product. The crude product was triturated in pentane to afford tert-butyl N-(2-(7-chloro-5-methylpyrrolo[1,2-f][1,2,4]triazin-4-yl)-2-azaspiro[3.3]heptan-6-yl)-N-(2-methoxyethyl)sulfamoylcarbamate (140 g, 60.85%) as liquid which was used in the next step without purification. LCMS: 516 [M+1]+

Step-4: Synthesis of N-(2-(7-chloro-5-methylpyrrolo[1,2-f][1,2,4]triazin-4-yl)-2-azaspiro[3.3]heptan-6-yl)-N-(2-methoxyethyl)sulfamamide: To a solution of tert-butyl N-(2-(7-chloro-5-methylpyrrolo[1,2-f][1,2,4]triazin-4-yl)-2-azaspiro[3.3]heptan-6-yl)-N-(2-methoxyethyl)sulfamoylcarbamate (0.1 g, 0.194 mmol, 1 eq) in DCM (10 mL) was added TFA (2 mL) and the mixture was allowed to stir at RT for 2 h. Progress of reaction was monitored by NMR. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford N-(2-(7-chloro-5-methylpyrrolo[1,2-f][1,2,4]triazin-4-yl)-2-azaspiro[3.3]heptan-6-yl)-N-(2-methoxyethyl)sulfamamide (15 mg, 18.7%). LCMS: 415.9 [M+1]+; 1H NMR (400 MHz, DMSO-d6) δ ppm 7.90 (s, 1H), 6.73 (s, 2H), 6.63 (s, 1H), 4.41 (s, 2H), 4.30 (s, 2H), 3.93-3.87 (m, 1H), 3.42-3.39 (m, 2H), 3.26 (s, 3H), 3.17-3.12 (m, 2H), 2.40-2.26 (m, 7H).

Example-123: Synthesis of N-(2-(7-chloro-5-methyl-5H-pyrrolo[3,2-d]pyrimidin-4-yl)-2-azaspiro[3.3]heptan-6-yl)-N-methylsulfamamide, (Compound 1.123)

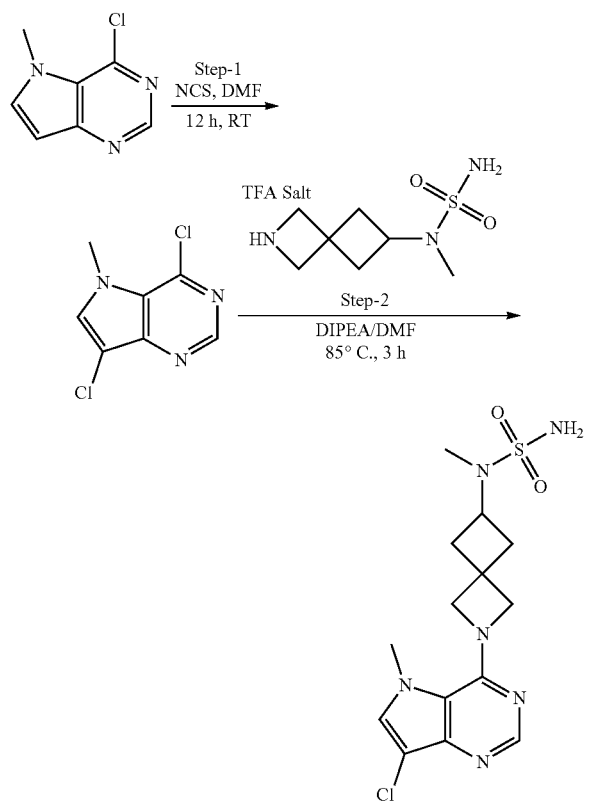

Step-1: Synthesis of 4,7-dichloro-5-methyl-5H-pyrrolo[3,2-d]pyrimidine: To a solution of 4-chloro-5-methyl-5H-pyrrolo[3,2-d]pyrimidine (0.3 g, 1.796 mmol, 1.0 eq) in DMF (100 mL) was added a N-chlorosuccinamide (0.238 g, 1.796 mmol, 1.1 eq) portion wise. The reaction mixture was allowed to stir at RT for 12 h. Progress of reaction is monitored using TLC. After completion, it was diluted with water (50 mL) and extracted with ethyl acetate (3×30 mL). Combined organic layer was washed with brine (50 mL) and dried over anhydrous sodium sulfate. Removal of solvent under reduced pressure afforded the crude which was purified by Combi-Flash to obtain the 4,7-dichloro-5-methyl-5H-pyrrolo[3,2-d]pyrimidine (0.26 g, 72.2%). LCMS: 203 [M+1]+

Step-2: Synthesis of N-(2-(7-chloro-5-methyl-5H-pyrrolo[3,2-d]pyrimidin-4-yl)-2-azaspiro[3.3]heptan-6-yl)-N-methylsulfamamide: To a solution of 4,7-dichloro-5-methyl-5H-pyrrolo[3,2-d]pyrimidine (0.1 g, 0.492 mmol, 1 eq), N-2-azaspiro[3.3]hept-6-yl-N-methylsulfuric diamide trifloroacetic acid (0.163 g, 0.541 mmol, 1.1 eq) and DIPEA (0.130 mL, 0.738 mmol, 1.5 eq) in DMF (10 mL) was allowed to stir at 85° C. for 3 h. Progress of reaction was monitored by TLC. After completion, reaction mixture was diluted with cold water (30 mL) and extracted with ethyl acetate (3×30 mL). Combined organic layer was washed with brine (50 mL) and dried over anhydrous sodium sulfate. Removal of solvent under reduced pressure to obtain the crude, which was purified by reversed phase to afford N-(2-(7-chloro-5-methyl-5H-pyrrolo[3,2-d]pyrimidin-4-yl)-2-azaspiro[3.3]heptan-6-yl)-N-methylsulfamamide (0.010 g, 5.55%). LCMS: 371.8 [M+1]+; 1H NMR (400 MHz, DMSO-d6) δ ppm 8.48 (s, 1H), 7.95 (s, 1H), 6.72 (s, 2H), 4.55 (s, 2H), 4.43 (s, 2H), 3.95 (s, 3H), 3.80-3.75 (m, 1H), 2.55 (s, 3H), 2.45-2.34 (m, 4H).

Example-124: Synthesis of N-(2-(5-chloro-7,7α-dihydro-4αH-pyrrolo[2,3-d]pyrimidin-4-yl)-2-azaspiro[3.3]heptan-6-yl)-N-methylsulfamamide, (Compound 1.124)

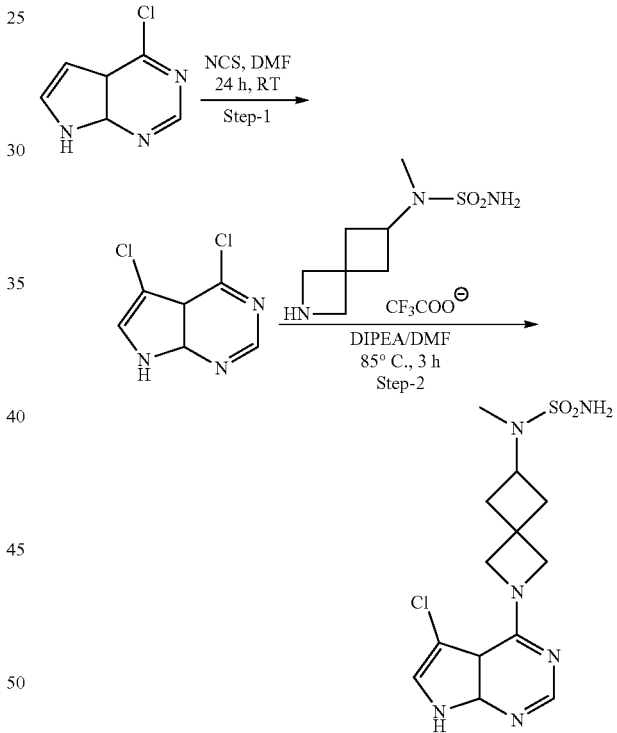

Step-1: Synthesis of 4,5-dichloro-7,7a-dihydro-4aH-pyrrolo[2,3-d]pyrimidine: To a solution of 4-chloro-7,7a-dihydro-4aH-pyrrolo[2,3-d]pyrimidine (0.5 g, 3.26 mmol, 1.0 eq) in DMF (20 mL) was added N-chlorosuccinimide (0.435 g, 3.26 mmol, 1.0 eq) portion wise. The reaction mixture was allowed to stir at RT for 24 h. Progress of reaction is monitored using TLC. After completion, reaction mixture was diluted with water (30 mL) and extracted with ethyl acetate (3×15 mL). Combined organic layer was washed with brine (3×10 mL) and dried over anhydrous sodium sulfate. Removal of solvent under reduced pressure afforded the crude which was purified by Combi-Flash to obtain 4,5-dichloro-7,7a-dihydro-4aH-pyrrolo[2,3-d]pyrimidine (0.37 g, 56.37%). LCMS: 191 [M+1]+

Step-2: Synthesis of N-(2-(5-chloro-7,7a-dihydro-4aH-pyrrolo[2,3-d]pyrimidin-4-yl)-2-azaspiro[3.3]heptan-6-yl)-N-methylsulfamamide: A mixture of 4,5-dichloro-7,7a-dihydro-4aH-pyrrolo[2,3-d]pyrimidine (0.15 g, 0.806 mmol, 1 eq), N-2-azaspiro[3.3]hept-6-yl-N-methylsulfuric diamide trifloroacetic acid (0.180 g, 0.887 mmol, 1.1 eq) and DIPEA (0.213 mL, 1.209 mmol, 2.0 eq) in DMF (10 mL) was allowed to stir at 85° C. for 3 h. Progress of reaction was monitored by TLC. After completion, reaction mixture was diluted with cold water (30 mL) and extracted with ethyl acetate (3×20 mL). Combined organic layer was washed with brine (3×15 mL) and dried over anhydrous sodium sulfate. Removal of solvent under reduced pressure to obtain the crude which was purified by reversed phase to afford N-(2-(5-chloro-7,7a-dihydro-4aH-pyrrolo[2,3-d]pyrimidin-4-yl)-2-azaspiro[3.3]heptan-6-yl)-N-methylsulfamamide (10 mg, 3.57%). LCMS: 360 [M+1]$^+$; $^1$H NMR (400 MHz, DMSO-d$_6$) δ ppm 8.48 (brs., 1H), 8.15 (s, 1H), 7.35 (s, 1H), 4.36 (s, 2H), 4.24 (s, 2H), 3.76-3.71 (m, 1H), 2.54 (s, 3H), 2.43-2.31 (m, 4H).

Example-125: Chiral Separation of N-(2-(7-chloro-5-methylpyrrolo[2,1-f][1,2,4]triazin-4-yl)-2-azaspiro[3.3]heptan-6-yl)-N-(3,3,3-trifluoro-2-hydroxypropyl)sulfamide (Compound 1.125 & 1.126)

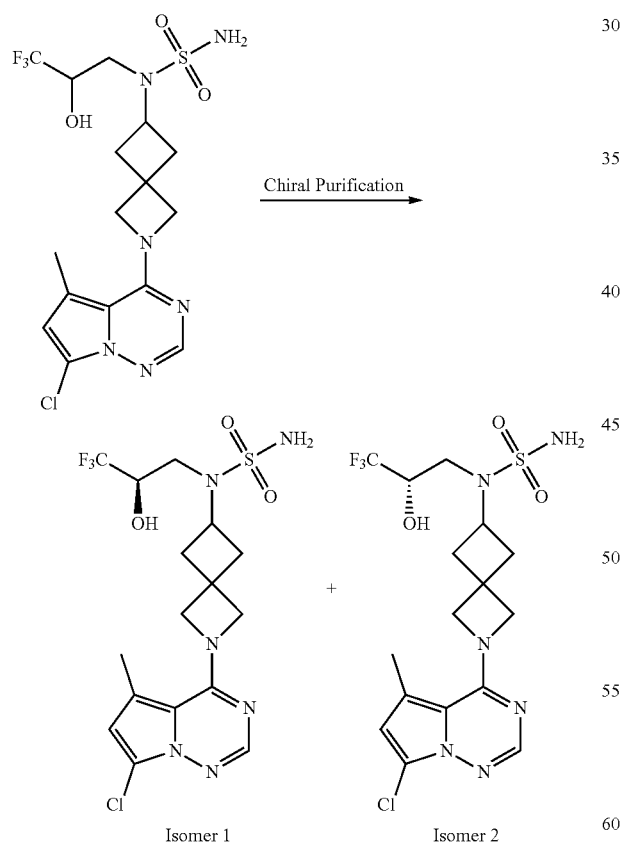

Isomer 1    Isomer 2

Enantiomers of N-(2-(7-chloro-5-methylpyrrolo[2,1-f][1,2,4]triazin-4-yl)-2-azaspiro[3.3]heptan-6-yl)-N-(3,3,3-trifluoro-2-hydroxypropyl)sulfamide (30 mg) were separated by chiral chromatography to afford Isomer 1 (13 mg, 86.66%) and Isomer 2 (14 mg, 93.33%).

Isomer 1: UPLC-MS (Method 1): Rt 4.735; LCMS: 469.1 [M+1]$^+$; $^1$H NMR (400 MHz, DMSO-d$_6$) δ ppm 7.90 (s, 1H), 6.89 (br. s., 2H), 6.63 (s, 1H), 6.51 (d, J=4.8 Hz, 1H), 4.40 (br. s., 2H), 4.31 (s, 2H), 4.16 (br. s., 1H), 3.92 (td, J=8.5, 16.8 Hz, 1H), 2.97-2.80 (m, 2H), 2.54 (s, 1H), 2.46-2.28 (m, 6H).

Isomer 2: UPLC-MS (Method 1): Rt 4.746; LCMS: 469.1 [M+1]$^+$; $^1$H NMR (400 MHz, DMSO-D$_6$) δ ppm 7.90 (s, 1H), 6.89 (br. s., 2H), 6.63 (s, 1H), 6.52 (br. s., 1H), 4.40 (br. s., 2H), 4.30 (s, 2H), 4.15 (br. s., 1H), 3.96-3.87 (m, 1H), 2.97-2.86 (m, 2H), 2.54 (s, 1H), 2.43-2.26 (m, 6H).

Example-126: Synthesis of N-[2-(7-chloro-5-methylpyrrolo[2,1-f][1,2,4]triazin-4-yl)-2-azaspiro[3.3]hept-6-yl]-2-fluoroethylsulfuric diamide, (Compound 1.127)

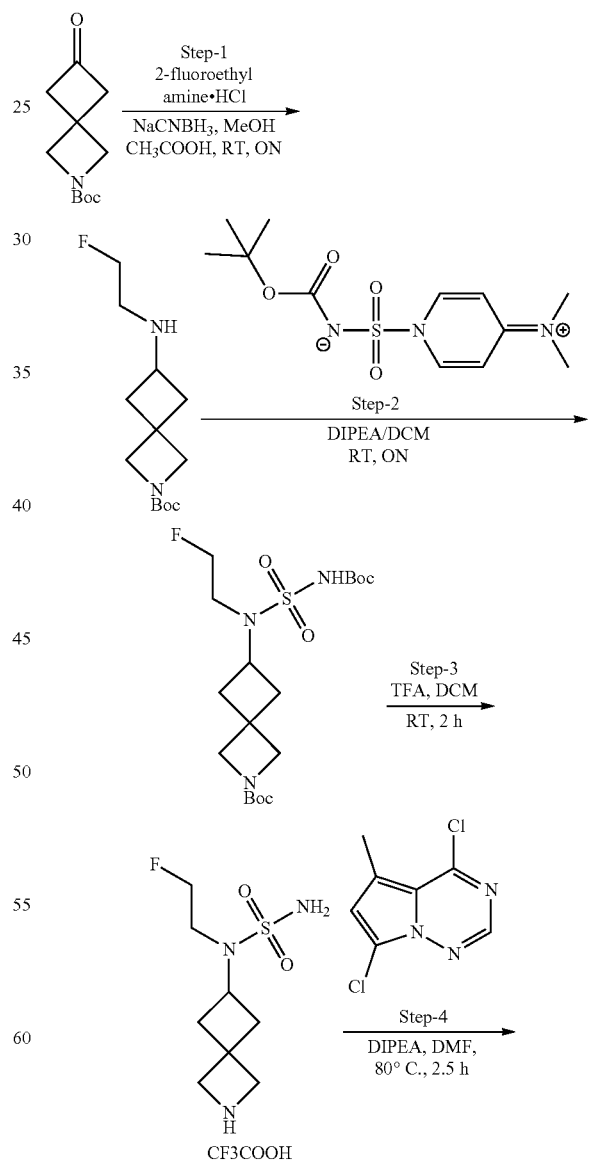

-continued

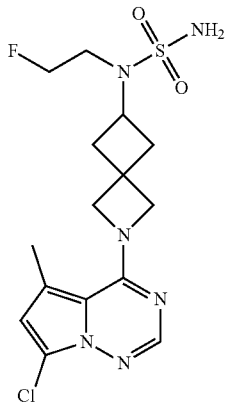

Step-1: Synthesis of tert-butyl 6-((2-fluoroethyl)amino)-2-azaspiro[3.3]heptane-2-carboxylate: To a stirred solution of tert-butyl 6-oxo-2-azaspiro[3.3]heptane-2-carboxylate (150 mg, 0.710 mmol, 1 eq) in methanol (6 ml) was added 2-fluoroethylamine·HCl (77 mg, 0.781 mmol, 1.1 eq) and molecular sieves and the reaction mixture was stirred at RT for 30 minutes. Then, NaCNBH$_3$ (89 mg, 1.420 mmol, 2.0 eq) was added at 0° C. followed by acetic acid (0.15 mL) drop wise until the pH become slightly acidic. Then, allowed the reaction mixture to stir at RT for overnight. Progress of reaction was monitored by TLC. After completion, reaction mixture was concentrated under reduced pressure to get residue which was diluted with water (40 mL) and extracted with ethyl acetate (3×30 mL). Combined organic layers were dried over anhydrous sodium sulfate. Removal of solvent under reduced pressure to afford tert-butyl 6-((2-fluoroethyl)amino)-2-azaspiro[3.3]heptane-2-carboxylate which was used in the next step without purification (180 mg, 98%).

Step-2: Synthesis of tert-butyl 6-((N-(tert-butoxycarbonyl)sulfamoyl)(2-fluoroethyl)amino)-2-azaspiro[3.3]heptane-2-carboxylate: To a solution of tert-butyl 6-((2-fluoroethyl)amino)-2-azaspiro[3.3]heptane-2-carboxylate (180 mg, 0.697 mmol, 1 eq) in DCM (5 mL) was added (tert-butoxycarbonyl)((4-(dimethyliminio)pyridin-1 (4H)-yl)sulfonyl)amide (252 mg, 0.837 mmol, 1.2 eq) and DIPEA (0.2 mL, 1.046 mmol, 1.5 eq) and the mixture was allowed to stir at RT for overnight. Progress of reaction was monitored by TLC. After completion, reaction mixture was washed with 1N HCl solution (100 mL) and extracted with DCM (2×60 mL). Combined organic layer was dried over anhydrous sodium sulfate and concentrated to afford tert-butyl 6-((N-(tert-butoxycarbonyl)sulfamoyl)(2-fluoroethyl)amino)-2-azaspiro[3.3]heptane-2-carboxylate which was used for next step without purification (180 mg, 60%).

Step-3: Synthesis of N-(2-fluoroethyl)-N-(2-azaspiro[3.3]heptan-6-yl)sulfamide 2,2,2-trifluoroacetate: To a solution of tert-butyl 6-((N-(tert-butoxycarbonyl)sulfamoyl)(2-flouroethyl)amino)-2-azaspiro[3.3]heptane-2-carboxylate (180 mg, 0.411 mmol, 1 eq) in DCM (4 mL) was added TFA (1 mL) and was allowed to stir at RT for 2 h. Progress of reaction was monitored by TLC. After completion, reaction mixture was concentrated under reduced pressure to afford crude which was triturated with diethyl ether to afford N-(2-fluoroethyl)-N-(2-azaspiro[3.3]heptan-6-yl)sulfamide 2,2,2-trifluoroacetate (175 mg, 82%).

Step-4: Synthesis of N-[2-(7-chloro-5-methylpyrrolo[2,1-f][1,2,4]triazin-4-yl)-2-azaspiro[3.3]hept-6-yl]-2-fluoroethylsulfuric diamide: A suspension of N-(2-fluoroethyl)-N-(2-azaspiro[3.3]heptan-6-yl)sulfamide 2,2,2-trifluoroacetate (175 mg, 0.5 mmol, 1 eq), 4,7-dichloro-5-methylpyrrolo[2,1-f][1,2,4]triazine (100 mg, 0.5 mmol, 1 eq) and DIPEA (0.14 mL, 0.75 mmol, 1.5 eq) in DMF (2 mL) was allowed to stir at 80° C. for 2.5 h. Progress of reaction was monitored by LCMS and TLC. After 2.5 h, reaction mixture was poured onto ice cold water (100 ml) and extracted with ethyl acetate (100 ml). Combined organic layer was concentrated under reduced pressure to get crude which was purified by combi flash and then with trituration to afford N-[2-(7-chloro-5-methylpyrrolo[2,1-f][1,2,4]triazin-4-yl)-2-azaspiro[3.3]hept-6-yl]-2-fluoroethylsulfuric diamide (14 mg, 7%). LCMS: 403 [M+1]$^+$; $^1$H NMR (400 MHz, DMSO-d$_6$) δ ppm 7.91 (s, 1H), 6.84 (s, 2H), 6.63 (s, 1H), 4.54 (t, J=5.5 Hz, 1H), 4.49-4.38 (m, 3H), 4.34-4.27 (m, 2H), 4.03-3.84 (m, 1H), 3.26 (t, J=5.3 Hz, 2H), 2.43-2.23 (m, 7H).

Example-127: Synthesis of N-(2-(7-chloro-5-methylpyrrolo[1,2-f][1,2,4]triazin-4-yl)-2-azaspiro[3.3]heptan-6-yl)-N-(2-methoxyethyl)sulfamamide, (Compound 1.128)

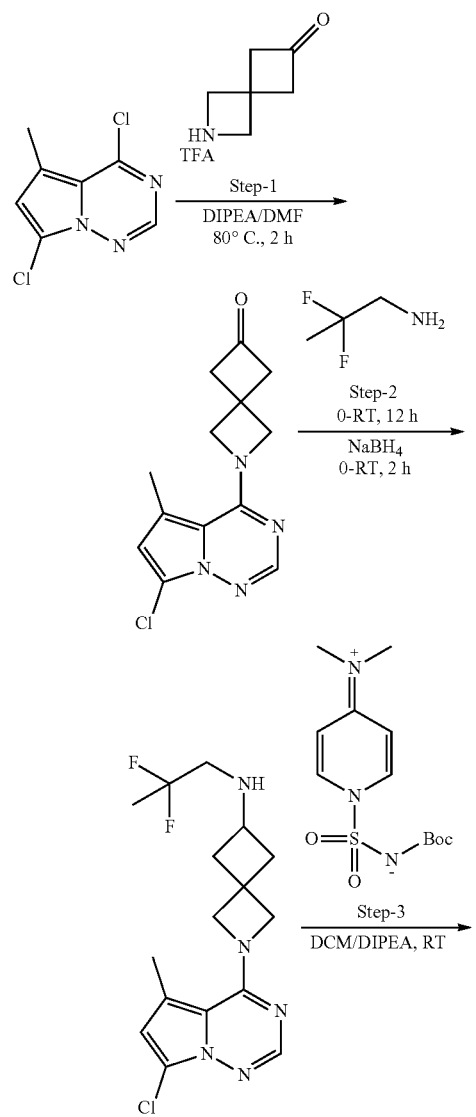

-continued

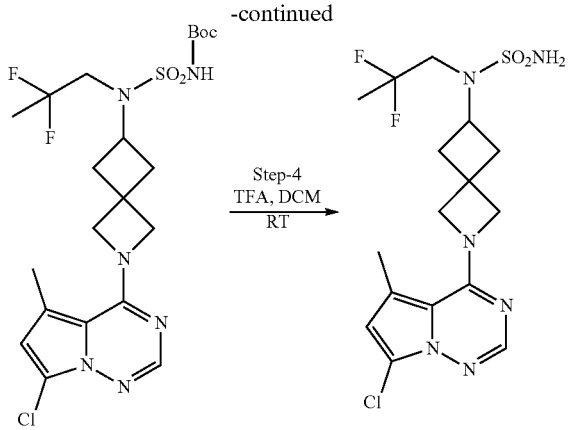

Step-4
TFA, DCM
RT

Step-1: Synthesis of 2-(7-chloro-5-methylpyrrolo[1,2-f][1,2,4]triazin-4-yl)-2-azaspiro[3.3]heptan-6-one: The mixture of 4,7-dichloro-5-methylpyrrolo[1,2-f][1,2,4]triazine (1.0 g, 4.95 mmol, 1 eq), N-methyl-N-(2-azaspiro[3.3]heptan-6-yl)sulfamamide, 2,2,2-trifluoroacetate salt (1.21 g, 5.44 mmol, 1.1 eq) and DIPEA (1.3 mL, 7.42 mmol, 1.5 eq) in DMF (10 mL) was allowed to stir at 85° C. for 3 h. Progress of reaction was monitored by TLC. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford 2-(7-chloro-5-methylpyrrolo[1,2-f][1,2,4]triazin-4-yl)-2-azaspiro[3.3]heptan-6-one (1.1 g, 80.30%). LCMS: 277.8 [M+1]$^+$ Step-2: Synthesis of 2-(7-chloro-5-methylpyrrolo[1,2-f][1,2,4]triazin-4-yl)-N-(2,2-difluoropropyl)-2-azaspiro[3.3]heptan-6-amine: To a stirred solution of 2-(7-chloro-5-methylpyrrolo[1,2-f][1,2,4]triazin-4-yl)-2-azaspiro[3.3]heptan-6-one (0.160 g, 0.578 mmol, 1.0 eq) in MeOH (15.0 mL) was added 2,2-difluoropropan-1-amine (0.055 g, 0.578 mmol, 1.0 eq) at 0° C. The resulting mixture was stirred at room temperature for overnight. The reaction mixture was then cooled to 0° C. followed by addition of NaBH$_4$ (0.043 mg, 1.159 mmol, 2.0 eq) at 0° C. The reaction mixture was stirred at room temperature for 2 h. The progress of reaction was monitored by TLC. The reaction mixture was concentrated, basified with NaHCO$_3$ solution (20 mL), extracted with EtOAc (3×50 mL). The combined organic layer was washed with water (50 mL), with brine (50 mL), dried over Na$_2$SO$_4$ concentrated to get crude product. The crude product was triturated in pentane to afford 2-(7-chloro-5-methylpyrrolo[1,2-f][1,2,4]triazin-4-yl)-N-(2,2-difluoropropyl)-2-azaspiro[3.3]heptan-6-amine (0.150 mg, 753.17%) as liquid, which was further used further next step without purification. LCMS: 356.1 [M+1]$^+$ Step-3: Synthesis of tert-butyl N-(2-(7-chloro-5-methylpyrrolo[1,2-f][1,2,4]triazin-4-yl)-2-azaspiro[3.3]heptan-6-yl)-N-(2-methoxyethyl)sulfamoylcarbamate: To a solution of 2-(7-chloro-5-methylpyrrolo[1,2-f][1,2,4]triazin-4-yl)-N-(2-methoxyethyl)-2-azaspiro[3.3]heptan-6-amine (0.150 g, 0.422 mmol, 1 eq) and N-(1-(N-(tert-butoxycarbonyl)sulfamoyl)pyridin-4 (1H)-ylidene)-N-methylmethanaminium (0.153 g, 0.507 mmol, 1.2 eq) in dichloromethane (10 mL) N,N-diisopropylethylamine (0.15 ml, 0.845 mmol, 2.0 eq) was added and the reaction mixture was allowed to stir at RT for overnight. Progress of reaction was monitored by NMR. After completion, the reaction mixture was diluted with water (50 mL) and extracted with DCM (3×50 mL), combined organic layer was washed with brine (50 mL) and dried over anhydrous sodium sulfate concentrated to get crude product. The crude product was triturated in pentane to afford tert-butyl N-(2-(7-chloro-5-methylpyrrolo[1,2-f][1,2,4]triazin-4-yl)-2-azaspiro[3.3]heptan-6-yl)-N-(2-methoxyethyl)sulfamoylcarbamate (0.130 g, 57.77%) as liquid which was used in the next step without purification. LCMS: 535.1 [M+1]$^+$ Step-4: Synthesis of N-(2-(7-chloro-5-methylpyrrolo[1,2-f][1,2,4]triazin-4-yl)-2-azaspiro[3.3]heptan-6-yl)-N-(2-methoxyethyl)sulfamamide: To a solution of tert-butyl N-(2-(7-chloro-5-methylpyrrolo[1,2-f][1,2,4]triazin-4-yl)-2-azaspiro[3.3]heptan-6-yl)-N-(2-methoxyethyl)sulfamoylcarbamate (0.130 g, 0.243 mmol, 1 eq) in DCM (10 mL) was added TFA (2 mL) and the mixture was allowed to stir at RT for 2 h. Progress of reaction was monitored by NMR. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford N-(2-(7-chloro-5-methylpyrrolo[1,2-f][1,2,4]triazin-4-yl)-2-azaspiro[3.3]heptan-6-yl)-N-(2-methoxyethyl)sulfamamide (10 mg, 9.52%). LCMS: 435.1 [M+1]$^+$; $^1$H NMR (400 MHz, DMSO-d$_6$) δ ppm 7.90 (s, 1H), 6.91 (s, 2H), 6.63 (s, 1H), 4.41 (s, 2H), 4.30 (s, 2H), 4.00-3.94 (m, 1H), 3.46-3.41 (m, 4H), 2.43-2.31 (m, 7H), 1.59-1.54 (m, 3H).

Example-128: Synthesis of N-(2-(7-chloro-5-methylpyrrolo[1,2-f][1,2,4]triazin-4-yl)-2-azaspiro[3.3]heptan-6-yl)-N-(2,2,2-trifluoroethyl)sulfamamide, (Compound 1.129)

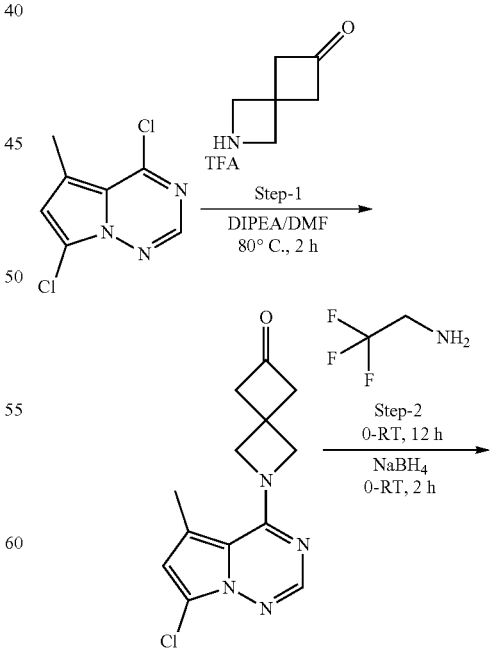

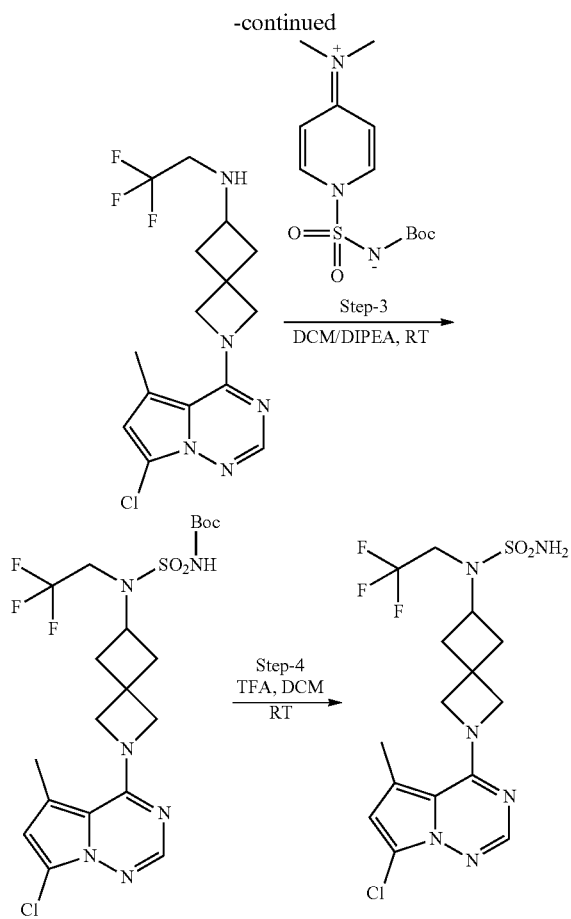

Step-1: Synthesis of 2-(7-chloro-5-methylpyrrolo[1,2-f][1,2,4]triazin-4-yl)-2-azaspiro[3.3]heptan-6-one: The mixture of 4,7-dichloro-5-methylpyrrolo[1,2-f][1,2,4]triazine (1.0 g, 4.95 mmol, 1 eq), N-methyl-N-(2-azaspiro[3.3]heptan-6-yl)sulfamamide, 2,2,2-trifluoroacetate salt (1.21 g, 5.44 mmol, 1.1 eq) and DIPEA (1.3 mL, 7.42 mmol, 1.5 eq) in DMF (10 mL) was allowed to stir at 85° C. for 3 h. Progress of reaction was monitored by TLC. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford 2-(7-chloro-5-methylpyrrolo[1,2-f][1,2,4]triazin-4-yl)-2-azaspiro[3.3]heptan-6-one (1.1 g, 80.30%). LCMS: 277.8 [M+1]$^+$ Step-2: Synthesis of 2-(7-chloro-5-methylpyrrolo[1,2-f][1,2,4]triazin-4-yl)-N-(2,2,2-trifluoroethyl)-2-azaspiro[3.3]heptan-6-amine: To a stirred solution of 2-(7-chloro-5-methylpyrrolo[1,2-f][1,2,4]triazin-4-yl)-2-azaspiro[3.3]heptan-6-one (0.160 g, 0.579 mmol, 1.0 eq) in MeOH (15.0 mL) was added 2-methoxyethanamine (0.057 g, 0.579 mmol, 1.0 eq) at 0° C. The resulting mixture was stirred at room temperature for overnight. The reaction mixture was then cooled to 0° C. followed by addition of NaBH$_4$ (0.043 g, 1.154 mmol, 2.0 eq) at 0° C. The reaction mixture was stirred at room temperature for 2 h. The progress of reaction was monitored by TLC. The reaction mixture was concentrated, basified with NaHCO$_3$ solution (20 mL), extracted with EtOAc (2×150 mL). The combined organic layer was washed with water (50 mL), with brine (50 mL), dried over Na$_2$SO$_4$ concentrated to get crude product. The crude product was triturated in pentane to afford 2-(7-chloro-5-methylpyrrolo[1,2-f][1,2,4]triazin-4-yl)-N-(2,2,2-trifluoroethyl)-2-azaspiro[3.3]heptan-6-amine (150 mg, 72.11%) as liquid, which was further used further next step without purification. LCMS: 360.1 [M+1]$^+$ Step-3: Synthesis of tert-butyl N-(2-(7-chloro-5-methylpyrrolo[1,2-f][1,2,4]triazin-4-yl)-2-azaspiro[3.3]heptan-6-yl)-N-(2-methoxyethyl)sulfamoylcarbamate: To a solution of 2-(7-chloro-5-methylpyrrolo[1,2-f][1,2,4]triazin-4-yl)-N-(2-methoxyethyl)-2-azaspiro[3.3]heptan-6-amine (0.150 g, 0.417 mmol, 1 eq) and N-(1-(N-(tert-butoxycarbonyl)sulfamoyl)pyridin-4 (1H)-ylidene)-N-methylmethanaminium (0.150 g, 0.501 mmol, 1.2 eq) in dichloromethane (10 mL) N,N-diisopropylethylamine (0.153 ml, 0.835 mmol, 2.0 eq) was added and the reaction mixture was allowed to stir at RT for overnight. Progress of reaction was monitored by NMR. After completion, the reaction mixture was diluted with water (50 mL) and extracted with DCM (150 ml×2), combined organic layer was washed with brine (50 mL) and dried over anhydrous sodium sulfate concentrated to get crude product. The crude product was triturated in pentane to afford tert-butyl N-(2-(7-chloro-5-methylpyrrolo[1,2-f][1,2,4]triazin-4-yl)-2-azaspiro[3.3]heptan-6-yl)-N-(2-methoxyethyl)sulfamoylcarbamate (130 mg, 51.38%) as liquid which was used in the next step without purification. LCMS: 539.1 [M+1]$^+$ Step-4: Synthesis of N-(2-(7-chloro-5-methylpyrrolo[1,2-f][1,2,4]triazin-4-yl)-2-azaspiro[3.3]heptan-6-yl)-N-(2,2,2-trifluoroethyl)sulfamamide: To a solution of tert-butyl N-(2-(7-chloro-5-methylpyrrolo[1,2-f][1,2,4]triazin-4-yl)-2-azaspiro[3.3]heptan-6-yl)-N-(2,2,2-trifluoroethyl) sulfamoylcarbamate (0.130 g, 0.222 mmol, 1 eq) in DCM (10 mL) was added TFA (2 mL) and the mixture was allowed to stir at RT for 2 h. Progress of reaction was monitored by NMR. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford N-(2-(7-chloro-5-methylpyrrolo[1,2-f][1,2,4]triazin-4-yl)-2-azaspiro[3.3]heptan-6-yl)-N-(2,2,2-trifluoroethyl)sulfamamide (10 mg, 10.3%). LCMS: 439.1 [M+1]$^+$; $^1$H NMR (400 MHz, DMSO-d$_6$) δ ppm 7.91 (s, 1H), 7.01 (m, 2H), 6.64 (s, 1H), 5.75 (s, 2H), 4.41 (s, 2H), 4.30 (s, 2H), 4.06-4.00 (m, 1H), 2.47-2.24 (m, 7H)

Example-129: Synthesis of N-(2-(7-chloro-5-methylpyrrolo[1,2-f][1,2,4]triazin-4-yl)-2-azaspiro[3.3]heptan-6-yl)-N-(4,4,4-trifluorobutyl)sulfamamide, (Compound 1.130)

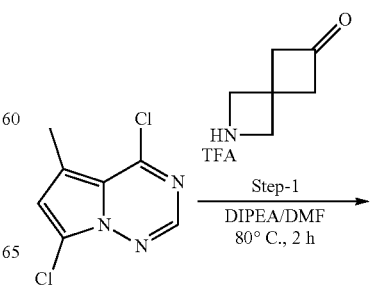

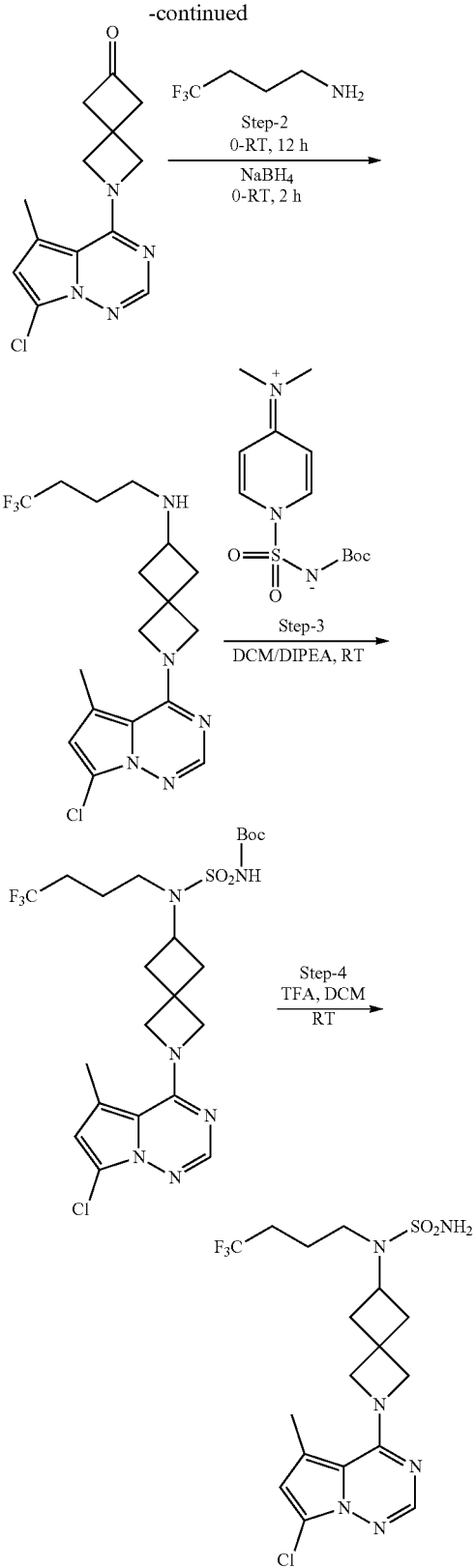

Step-1: Synthesis of 2-(7-chloro-5-methylpyrrolo[1,2-f][1,2,4]triazin-4-yl)-2-azaspiro[3.3]heptan-6-one: The mixture of 4,7-dichloro-5-methylpyrrolo[1,2-f][1,2,4]triazine (1.0 g, 4.95 mmol, 1 eq), N-methyl-N-(2-azaspiro[3.3]heptan-6-yl)sulfamamide, 2,2,2-trifluoroacetate salt (1.21 g, 5.44 mmol, 1.1 eq) and DIPEA (1.3 mL, 7.42 mmol, 1.5 eq) in DMF (10 mL) was allowed to stir at 85° C. for 3 h. Progress of reaction was monitored by TLC. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford 2-(7-chloro-5-methylpyrrolo[1,2-f][1,2,4]triazin-4-yl)-2-azaspiro[3.3]heptan-6-one (1.1 g, 80.30%). LCMS: 277.0 [M+1]$^+$ Step-2: Synthesis of 2-(7-chloro-5-methylpyrrolo[1,2-f][1,2,4]triazin-4-yl)-N-(4,4,4-trifluorobutyl)-2-azaspiro[3.3]heptan-6-amine: To a stirred solution of 2-(7-chloro-5-methylpyrrolo[1,2-f][1,2,4]triazin-4-yl)-2-azaspiro[3.3]heptan-6-one (0.160 g, 0.579 mmol, 1.0 eq) in MeOH (15.0 mL) was added 2-methoxyethanamine (0.073.5 g, 0.579 mmol, 1.0 eq) at 0° C. The resulting mixture was stirred at room temperature for overnight. The reaction mixture was then cooled to 0° C. followed by addition of NaBH$_4$ (0.043 g, 1.159 mmol, 2.0 eq) at 0° C. The reaction mixture was stirred at room temperature for 2 h. The progress of reaction was monitored by TLC. The reaction mixture was concentrated, basified with NaHCO$_3$ solution (20 mL), extracted with EtOAc (2×150 mL). The combined organic layer was washed with water (50 mL), with brine (50 mL), dried over Na$_2$SO$_4$ concentrated to get crude product. The crude product was triturated in pentane to afford 2-(7-chloro-5-methylpyrrolo[1,2-f][1,2,4]triazin-4-yl)-N-(4,4,4-trifluorobutyl)-2-azaspiro[3.3]heptan-6-amine (150 mg, 66.96%) as liquid, which was further used further next step without purification. LCMS: 388.1 [M+1]$^+$ Step-3: Synthesis of tert-butyl N-(2-(7-chloro-5-methylpyrrolo[1,2-f][1,2,4]triazin-4-yl)-2-azaspiro[3.3]heptan-6-yl)-N-(4,4,4-trifluorobutyl)sulfamoylcarbamate: To a solution of 2-(7-chloro-5-methylpyrrolo[1,2-f][1,2,4]triazin-4-yl)-N-(4,4,4-trifluorobutyl)-2-azaspiro[3.3]heptan-6-amine (0.150 g, 0.387 mmol, 1 eq) and N-(1-(N-(tert-butoxycarbonyl)sulfamoyl)pyridin-4 (1H)-ylidene)-N-methylmethanaminium (0.139 g, 0.465 mmol, 1.2 eq) in dichloromethane (10 mL) N,N-diisopropylethylamine (0.142 ml, 0.775 mmol, 2.0 eq) was added and the reaction mixture was allowed to stir at RT for overnight. Progress of reaction was monitored by NMR. After completion, the reaction mixture was diluted with water (50 mL) and extracted with DCM (150 ml×2), combined organic layer was washed with brine (50 mL) and dried over anhydrous sodium sulfate concentrated to get crude product. The crude product was triturated in pentane to afford tert-butyl N-(2-(7-chloro-5-methylpyrrolo[1,2-f][1,2,4]triazin-4-yl)-2-azaspiro[3.3]heptan-6-yl)-N-(4,4,4-trifluorobutyl)sulfamoylcarbamate (130 g, 59.36%) as liquid which was used in the next step without purification. LCMS: 567.1 [M+1]$^+$ Step-4: Synthesis of N-(2-(7-chloro-5-methylpyrrolo[1,2-f][1,2,4]triazin-4-yl)-2-azaspiro[3.3]heptan-6-yl)-N-(4,4,4-trifluorobutyl)sulfamamide: To a solution of tert-butyl N-(2-(7-chloro-5-methylpyrrolo[1,2-f][1,2,4]triazin-4-yl)-2-azaspiro[3.3]heptan-6-yl)-N-(4,4,4-trifluorobutyl)sulfamoylcarbamate (0.130 g, 0.229 mmol, 1 eq) in DCM (10 mL) was added TFA (2 mL) and the mixture was allowed to stir at RT for 2 h. Progress of reaction was monitored by NMR. After completion, reaction mixture was diluted with cold water (30 mL) and extracted with ethyl acetate (3×70 mL). Combined organic layer was washed with brine (3×50 mL) and dried over anhydrous sodium sulfate. Removal of solvent under reduced pressure to obtain the crude, which was purified by reversed phase to afford N-(2-(7-chloro-5-methylpyrrolo[1,2-f][1,2,4]triazin-4-yl)-2-azaspiro[3.3]heptan-6-yl)-N-(4,4,4-trifluorobutyl)sulfamamide (10 mg, 9.3%). LCMS: 467.1 [M+1]+; 1H NMR (400 MHz, DMSO-d6) δ ppm 7.90 (s, 1H), 6.77 (s, 2H), 6.63 (s, 1H), 4.42 (m 2H), 4.30 (m, 2H), 3.83-3.94 (m, 1H), 3.05-3.01 (m, 2H), 2.39 (s, 3H), 2.37-2.19 (m, 5H), 1.78-1.73 (m, 2H).

Example-130: Synthesis of N-(2,2-difluoroethyl)-N-(2-(7-methoxyquinazolin-4-yl)-2-azaspiro[3.3]heptan-6-yl) sulfamamide, (Compound 1.131)

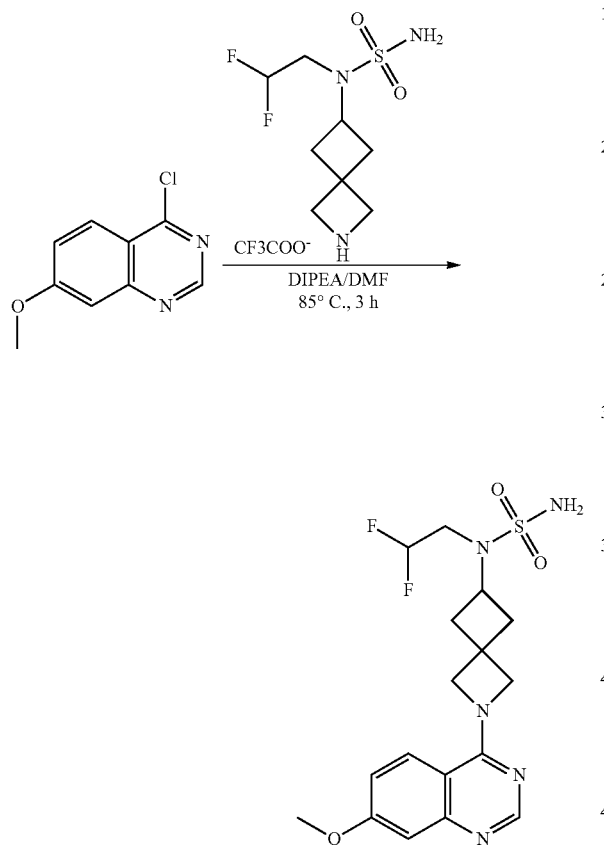

The mixture of N-(2,2-difluoroethyl)-N-(2-azaspiro[3.3]heptan-6-yl)sulfamamide (104 mg, 0.283 mmoles, 1.1 eq), 4-chloro-7-methoxyquinazoline (50 mg, 0.257 mmoles. 1.0 eq) and DIPEA (0.1 ml, 0.515 mmoles, 2.0 eq) in DMF (1.2 mL) was allowed to stir at 85° C. for 3 h. Progress of reaction was monitored by TLC. After completion, reaction mixture was diluted with cold water (10 mL) and extracted with ethyl acetate (3×10 mL). Combined organic layer was washed with cold water (2×10 mL) and dried over anhydrous sodium sulfate. Removal of solvent under reduced pressure to obtain the crude, which was purified by reversed phase chromatography to afford N-(2,2-difluoroethyl)-N-(2-(7-methoxyquinazolin-4-yl)-2-azaspiro[3.3]heptan-6-yl) sulfamamide (10 mg, 9.3%). LCMS: 414.1 [M+1]+; 1H NMR (400 MHz, DMSO-d6) δ ppm 8.37 (s, 1H), 7.82 (m, 1H), 7.12-7.01 (m, 4H), 6.23-6.17 (m, 1H), 6.03-5.97 (m, 1H), 5.88-5.82 (m, 1H), 4.48-4.41 (m, 2H), 4.39 (m, 2H), 4.00-3.92 (m, 1H), 3.88 (s, 3H), 3.48-3.37 (m, 3H), 2.39-2.29 (m, 3H).

Example-131: Synthesis of 4-(((2-(7-chloro-5-methylpyrrolo[2,1-f][1,2,4]triazin-4-yl)-2-azaspiro[3.3]heptan-6-yl)amino)methyl)benzenesulfonamide, (Compound 1.132)

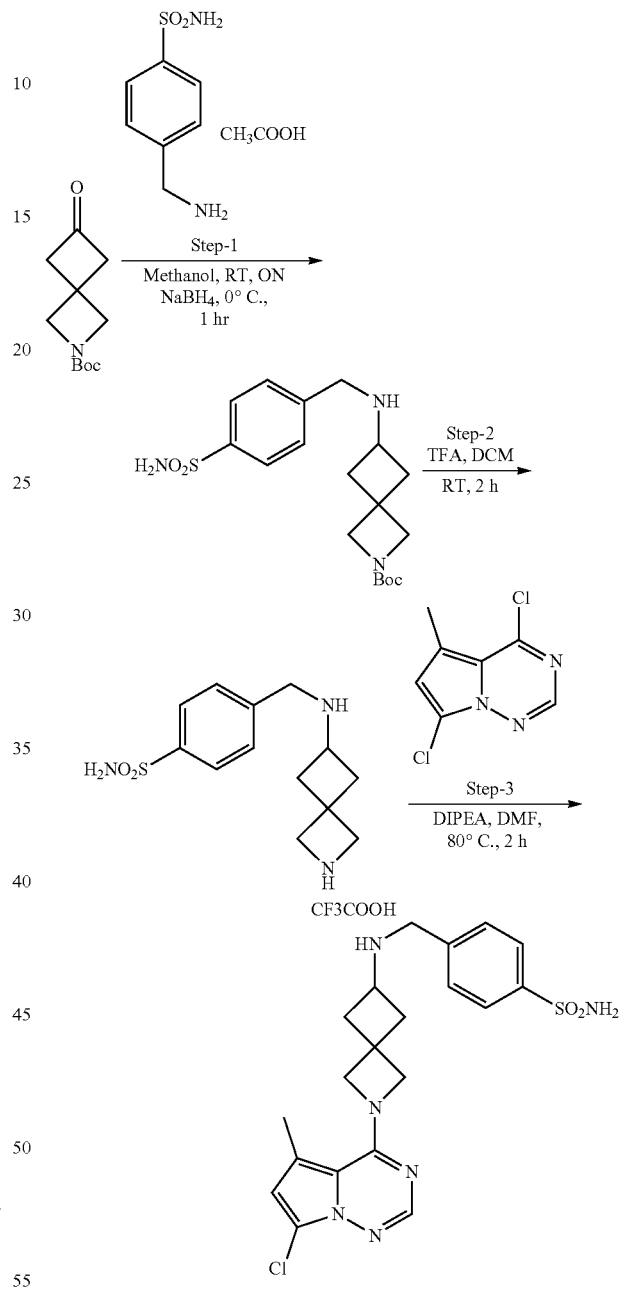

Step-1: Synthesis of tert-butyl 6-(4-sulfamoylbenzylamino)-2-azaspiro[3.3]heptane-2-carboxylate: To a stirred solution of tert-butyl 6-oxo-2-azaspiro[3.3]heptane-2-carboxylate (200 mg, 0.946 mmol, 1 eq) in methanol (5 ml) was added 4-(aminomethyl)benzenesulfonamide acetate (282 mg, 1.13 mmol, 1.2 eq) and the reaction mixture was stirred at RT for overnight. To the reaction mixture, NaBH4 (54 mg, 1.41 mmol, 1.5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (50 mL) and extracted with dichloromethane (2×50 mL). Combined organic layer was dried over anhydrous sodium sulfate. Removal of solvent under reduced pressure to afford tert-butyl 6-(4-sulfamoylbenzylamino)-2-azaspiro[3.3]heptane-2-carboxylate (310 mg, 85.87%) which was used in the next step without purification.

Step-2: Synthesis of 4-((2-azaspiro[3.3]heptan-6-ylamino)methyl)benzenesulfonamide 2,2,2-trifluoroacetate: To a solution of tert-butyl 6-(4-sulfamoylbenzylamino)-2-azaspiro[3.3]heptane-2-carboxylate (300 mg, 0.786 mmol, 1.0 eq) in DCM (5 mL) was added TFA (1.5 mL) and was allowed to stir at RT for 2 h. Progress of reaction was monitored by TLC. After completion, reaction mixture was concentrated under reduced pressure to afford crude which was triturated with diethyl ether to afford 4-((2-azaspiro[3.3]heptan-6-ylamino)methyl)benzenesulfonamide 2,2,2-trifluoroacetate (230 mg, 74.19%).

Step-3: Synthesis of 4-(((2-(7-chloro-5-methylpyrrolo[2,1-f][1,2,4]triazin-4-yl)-2-azaspiro[3.3]heptan-6-yl)amino)methyl)benzenesulfonamide: A suspension of 4-((2-azaspiro[3.3]heptan-6-ylamino)methyl)benzenesulfonamide 2,2,2-trifluoroacetate (137 mg, 0.348 mmol, 1.0 eq), 4,7-dichloro-5-methylpyrrolo[2,1-f][1,2,4]triazine (70 mg, 0.348 mmol, 1.0 eq) and DIPEA (90 mg, 0.696 mmol, 2.0 eq) in DMF (1.0 mL) was allowed to stir at 80° C. for 2 h. Progress of reaction was monitored by LCMS and TLC. After 2 h, reaction mixture was diluted with water (10 mL) and extracted with ethyl acetate (1×50 mL). Combined organic layer was washed with brine (1×10 mL) and dried over anhydrous sodium sulfate, Concentrated under reduced pressure to obtain crude product which was purified using reversed phase HPLC chromatography to afford 4-(((2-(7-chloro-5-methylpyrrolo[2,1-f][1,2,4]triazin-4-yl)-2-azaspiro[3.3]heptan-6-yl)amino)methyl)benzenesulfonamide (7 mg, 4.5%). LCMS: 447 [M+1]+; 1H NMR (400 MHz, DMSO-d$_6$) δ ppm 8.25 (br. s., 1H), 7.89 (s, 1H), 7.75 (d, J=8.3 Hz, 2H), 7.49 (d, J=7.9 Hz, 2H), 7.29 (s, 2H), 6.62 (s, 1H), 4.36 (s, 2H), 4.28 (br. s., 2H), 3.67 (s, 2H), 3.13-3.00 (m, 2H), 2.38 (s, 3H), 2.02-1.90 (m, 3H).

Example-132: Synthesis of 4-(((2-(7-chloro-5-methylpyrrolo[2,1-f][1,2,4]triazin-4-yl)-2-azaspiro[3.3]heptan-6-yl)(methyl)amino)methyl)benzenesulfonamide, (Compound 1.133)

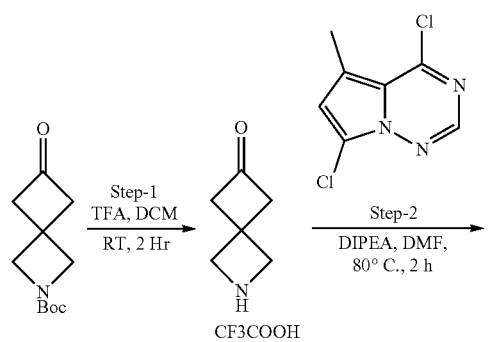

Step-1: Synthesis of 2-azaspiro[3.3]heptan-6-one 2,2,2-trifluoroacetate: To a solution of tert-butyl 6-oxo-2-azaspiro[3.3]heptane-2-carboxylate (200 mg, 0.946 mmol, 1.0 eq) in DCM (5 mL) was added TFA (1.0 mL) and was allowed to stir at RT for 2 h. Progress of reaction was monitored by TLC. After completion, reaction mixture was concentrated under reduced pressure to obtain crude which was triturated with diethyl ether to afford 2-azaspiro[3.3]heptan-6-one 2,2,2-trifluoroacetate as desired product (160 mg, 75.11%).

Step-2: Synthesis of 2-(7-chloro-5-methylpyrrolo[2,1-f][1,2,4]triazin-4-yl)-2-azaspiro[3.3]heptan-6-one: A suspension of 2-azaspiro[3.3]heptan-6-one 2,2,2-trifluoroacetate (112 mg, 0.497 mmol, 1.0 eq), 4,7-dichloro-5-methylpyrrolo[2,1-f][1,2,4]triazine (100 mg, 0.298 mmol, 1.0 eq) and DIPEA (128 mg, 0.994 mmol, 2.0 eq) in DMF (1.0 mL) was allowed to stir at 80° C. for 2 h. Progress of reaction was monitored by LCMS and TLC. After 2 h, reaction mixture was diluted with water (10 mL) and extracted with ethyl acetate (1×50 mL). Combined organic layer was washed with brine (1×10 mL) and dried over anhydrous sodium sulfate and concentrated under reduced pressure to obtain 2-(7-chloro-5-methylpyrrolo[2,1-f][1,2,4]triazin-4-yl)-2-azaspiro[3.3]heptan-6-one as crude product which was used in next step without further purification (150 mg, 87.59%). LCMS: 277 [M+1]$^+$ Step-3: Synthesis of 4-(((2-(7-chloro-5-methylpyrrolo[2,1-f][1,2,4]triazin-4-yl)-2-azaspiro[3.3]heptan-6-yl)amino)methyl)benzenesulfonamide: To a stirred solution of 2-(7-chloro-5-methylpyrrolo[2,1-f][1,2,4]triazin-4-yl)-2-azaspiro[3.3]heptan-6-one (120 mg, 0.433 mmol, 1 eq) in methanol (5 ml) was added 4-(aminomethyl)benzenesulfonamide acetate (129 mg, 0.519 mmol, 1.2 eq) and the reaction mixture was stirred at RT for overnight. To the reaction mixture, NaBH$_4$ (25 mg, 0.649 mmol, 1.5 eq) was added at 0° C. and then resultant reaction mixture was allowed to stir at 0° C. for 1 h. Progress of reaction was monitored by TLC. After completion, reaction mixture was concentrated under reduced pressure to get residue which was diluted with water (50 mL) and extracted with dichloromethane (2×50 mL). Combined organic layer was dried over anhydrous sodium sulfate. Removal of solvent under reduced pressure to afford 4-(((2-(7-chloro-5-methylpyrrolo[2,1-f][1,2,4]triazin-4-yl)-2-azaspiro[3.3]heptan-6-yl)amino)methyl)benzenesulfonamide which was used in the next step without purification (70 mg, 36.26%). LCMS: 447 [M+1]$^+$ Step-4: Synthesis of 4-(((2-(7-chloro-5-methylpyrrolo[2,1-f][1,2,4]triazin-4-yl)-2-azaspiro[3.3]heptan-6-yl)(methyl)amino)methyl)benzenesulfonamide: To a stirred solution of 4-(((2-(7-chloro-5-methylpyrrolo[2,1-f][1,2,4]triazin-4-yl)-2-azaspiro[3.3]heptan-6-yl)amino)methyl)benzenesulfonamide (70 mg, 0.156 mmol, 1 eq) in formaldehyde (2 ml) was added formic acid (2 ml) and the reaction mixture was stirred at 90° C. for overnight. Progress of reaction was monitored by TLC. After completion, reaction mixture was concentrated under reduced pressure to get residue which was diluted with water (10 mL) and extracted with dichloromethane (1×50 mL). Combined organic layer was dried over anhydrous sodium sulfate. Removal of solvent under reduced pressure which was purified by reverse phase HPLC chromatography to afford 4-(((2-(7-chloro-5-methylpyrrolo[2,1-f][1,2,4]triazin-4-yl)-2-azaspiro[3.3]heptan-6-yl)(methyl)amino)methyl)benzenesulfonamide (8 mg, 11.11%). LCMS: 461 [M+1]$^+$; $^1$H NMR (400 MHz, DMSO-d$_6$) δ ppm 7.90 (s, 1H), 7.77 (d, J=7.9 Hz, 2H), 7.47 (d, J=7.9 Hz, 2H), 7.31 (s, 2H), 6.63 (s, 1H), 4.42 (s, 2H), 4.31 (s, 2H), 3.40 (br. s., 2H), 2.83 (br. s., 1H), 2.40 (s, 3H), 2.33 (br. s., 1H), 2.09 (br. s., 2H), 1.98-1.82 (m, 3H), 1.24 (br. s., 1H).

Example-133: Synthesis of N-(2-(7-chloro-5-methyl-5H-pyrrolo[3,2-d]pyrimidin-4-yl)-2-azaspiro[3.3]heptan-6-yl)-N-(2,2-difluoroethyl)sulfamamide, (Compound 1.134)

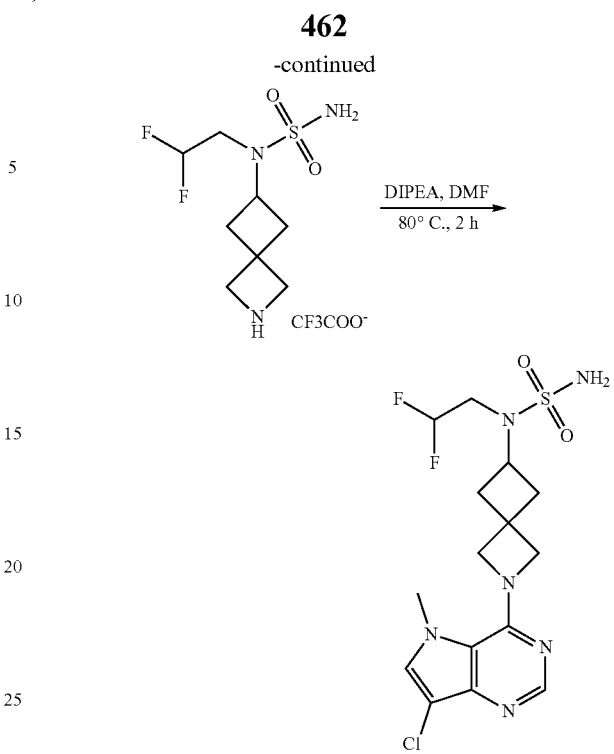

The mixture of N-(2,2-difluoroethyl)-N-(2-azaspiro[3.3]heptan-6-yl)sulfamamide 2,2,2-trifluoroacetate salt (202 mg, 0.55 mmol, 1.1 eq), 4,7-dichloro-5-methyl-5H-pyrrolo[3,2-d]pyrimidine (100 mg, 0.5 mmol, 1.0 eq) and DIPEA (0.2 ml, 1.0 mmol, 2.0 eq) in DMF (1.5 mL) was allowed to stir at 80° C. for 3 h. Progress of reaction was monitored by TLC. After completion, reaction mixture was diluted with cold water (10 mL) and extracted with ethyl acetate (3×20 mL). Combined organic layer was washed with cold water (2×10 mL) and dried over anhydrous sodium sulfate. Removal of solvent was done under reduced pressure to obtain the crude, which was purified by reverse phase chromatography to afford N-(2-(7-chloro-5-methyl-5H-pyrrolo[3,2-d]pyrimidin-4-yl)-2-azaspiro[3.3]heptan-6-yl)-N-(2,2-difluoroethyl)sulfamamide (5 mg, 23%). LCMS: 421 [M+1]$^+$; $^1$H NMR (400 MHz, DMSO-d$_6$) δ ppm 8.26 (s, 1H), 8.14 (s, 2H), 7.72 (s, 1H), 7.02 (s, 2H), 6.16-6.11 (m, 1H), 6.02 (m, 2H), 5.88-5.81 (br. s., 2H), 4.36 (s, 2H), 4.26 (s, 2H), 4.01-3.93 (m, 1H), 3.89 (s, 3H), 3.48-3.39 (m, 2H), 2.28-2.22 (m, 2H).

Example-134: Synthesis of N-(2-(7-methoxyquinazolin-4-yl)-2-azaspiro[3.3]heptan-6-yl)-N-(3,3,3-trifluoro-2-hydroxypropyl)sulfamamide, (Compound 1.135)

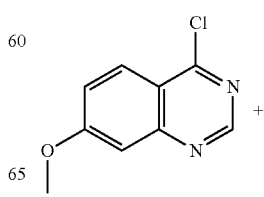

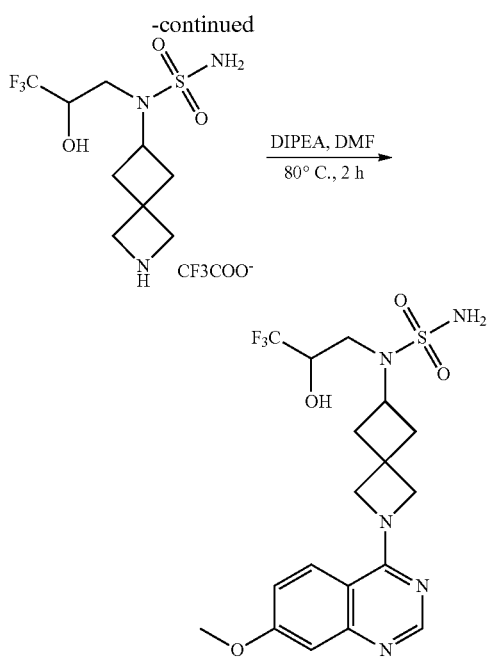

The mixture of N-(N-(2-azaspiro[3.3]heptan-6-yl)-N-(3,3,3-trifluoro-2-hydroxypropyl)sulfamamide 2,2,2-trifluoroacetate salt (261 mg, 0.567 mmol, 1.1 eq), 4-chloro-7-methoxyquinazoline (100 mg, 0.515 mmol, 1.0 eq) and DIPEA (0.2 mL, 1.030 mmol, 2.0 eq) in DMF (1 mL) was allowed to stir at 80° C. for 2 h. Progress of reaction was monitored by TLC. After completion, reaction mixture was diluted with ice cold water (15 mL) and extracted with ethyl acetate (3×15 mL). Combined organic layer was washed with cold water (2×10 mL) and dried over anhydrous sodium sulfate. Removal of solvent was done under reduced pressure to obtain the crude, which was purified by reverse phase chromatography to afford N-(2-(7-methoxyquinazolin-4-yl)-2-azaspiro[3.3]heptan-6-yl)-N-(3,3,3-trifluoro-2-hydroxypropyl)sulfamamide (20 mg, 8.4%). LCMS: 462 [M+1]$^+$; $^1$H NMR (400 MHz, DMSO-d$_6$) δ ppm 8.37 (s, 1H), 7.83-7.78 (m, 1H), 7.11-7.01 (m, 2H), 6.91-6.87 (m, 2H), 6.52-6.57 (m, 1H), 4.48-4.40 (m, 4H), 4.18-4.12 (m, 1H), 3.88 (s, 3H), 2.86-2.96 (m, 2H), 2.33-2.28 (m 3H), 1.91 (s, 2H).

Biological Examples

Example-B1: ENPP1 Inhibition Assay

IC$_{50}$ values of compounds against ENPP-1 (Ectonucleotide Pyrophosphatase/Phosphodiesterase 1) were determined at Integral BioSciences (India) using AMP Glo (Promega, Cat #V5011). Assay was performed in a 30 μL final volume in a white 96-well Half Area plate (Costar,Cat #3693). Dose response curve for the compounds were prepared in duplicates with starting conc. at 5 μM and a three-fold titration was performed. The reaction buffer consisted of 50 mM Tris (pH 8.0), 0.5 mM CaCl$_2$), 1 μM ZnCl$_2$, 250 mM NaCl and 0.1 mg/ml BSA. To the compound dilution, 15 μL of ENPP1 enzyme (R&D Systems; Cat #6136-EN-010) was added to each well (final conc. 1 nM) and the mix was pre-incubated for 15 min at RT. An equal volume (15 μL) containing cGAMP (Sigma, Cat #SML-1229) (final conc. 20 μM) was added to initiate the enzyme reaction and the reaction was incubated for 30 min at RT. The reaction was then stopped by heating at 90° C. for 3 minutes. 10 μl of reaction was then transferred to 384 well white, medium binding plates (Grenier, Cat #781075) to which 10 μl of AMP-Glo Reagent 1 was added and mixed well and incubated for 1 hour at 25° C. Following 60 min incubation, 20 μL of detection mixture was added to the enzyme reaction bringing the final volume to 40 μL. The reaction was further incubated for 60 min at RT after which the plates were read using BioTek Plate reader.

Analysis was done using the standard curve by non-linear regression, variable slope inhibitor curve fits (Graph-Pad Prism) and IC$_{50}$'s of compounds were determined wherever possible.

The results of the ENPP1 inhibition assay are shown in tables B1.

TABLE B1

| ENPP1 Inhibition Assay | |
|---|---|
| Compound No. | ENPP-1 IC$_{50}$ (cGAMP; uM) |
| 1.1 | 0.008 |
| 1.2 | >5.0 |
| 1.3 | 0.220 |
| 1.4 | 0.072 |
| 1.5 | 0.160 |
| 1.6 | 0.090 |
| 1.7 | 0.120 |
| 1.8 | 0.008 |
| 1.9 | 0.032 |
| 1.10 | 0.028 |
| 1.11 | 0.090 |
| 1.12 | 0.004 |
| 1.13 | 0.011 |
| 1.14 | 0.120 |
| 1.15 | 0.005 |
| 1.16 | 0.076 |
| 1.17 | 0.057 |
| 1.18 | >3.0 |
| 1.19 | 0.084 |
| 1.20 | 0.070 |
| 1.21 | 0.092 |
| 1.22 | 0.009 |
| 1.23 | 0.029 |
| 1.24 | 0.002 |
| 1.25 | 0.660 |
| 1.26 | 0.006 |
| 1.27 | 0.043 |
| 1.28 | 0.026 |
| 1.29 | 0.892 |
| 1.30 | 0.019 |
| 1.31 | >3.0 |
| 1.32 | >3.0 |
| 1.33 | 0.248 |
| 1.34 | >3.0 |
| 1.35 | 0.099 |
| 1.36 | 0.464 |
| 1.37 | >3.0 |
| 1.38 | >3.0 |
| 1.39 | 0.056 |
| 1.40 | 0.793 |
| 1.41 | 0.737 |
| 1.42 | >3.0 |
| 1.43 | 0.892 |
| 1.44 | >3.0 |
| 1.45 | >3.0 |
| 1.46 | 0.019 |
| 1.47 | 0.855 |
| 1.48 | 0.144 |
| 1.49 | >1.980 |
| 1.50 | 1.476 |
| 1.51 | 0.015 |
| 1.52 | 0.043 |
| 1.53 | 0.122 |
| 1.54 | 1.681 |
| 1.55 | 0.036 |
| 1.56 | 0.085 |

TABLE B1-continued

ENPP1 Inhibition Assay

| Compound No. | ENPP-1 IC$_{50}$ (cGAMP; uM) |
|---|---|
| 1.57 | 0.011 |
| 1.58 | 0.660 |
| 1.59 | >3.0 |
| 1.60 | 0.347 |
| 1.61 | 0.097 |
| 1.62 | 0.067 |
| 1.63 | 0.012 |
| 1.64 | 0.145 |
| 1.65 | 0.078 |
| 1.66 | 0.006 |
| 1.67 | ND |
| 1.68 | 0.003 |
| 1.69 | 0.003 |
| 1.70 | 0.024 |
| 1.71 | >3.0 |
| 1.72 | >3.0 |
| 1.73 | 0.247 |
| 1.74 | ND |
| 1.75 | 0.391 |
| 1.76 | 0.084 |
| 1.77 | 0.295 |
| 1.78 | 0.964 |
| 1.79 | 0.053 |
| 1.80 | 0.616 |
| 1.81 | 0.245 |
| 1.82 | 1.894 |
| 1.83 | >3.0 |
| 1.84 | >2.252 |
| 1.85 | >2.385 |
| 1.86 | 0.106 |
| 1.87 | 0.024 |
| 1.88 | ND |
| 1.89 | >3.0 |
| 1.90 | >3.0 |
| 1.91 | >3.0 |
| 1.92 | 1.505 |
| 1.93 | 0.019 |
| 1.94 | >3.0 |
| 1.95 | 1.884 |
| 1.96 | >3.0 |
| 1.97 | 0.036 |
| 1.98 | 0.055 |
| 1.99 | 0.010 |
| 1.100 | >3.0 |
| 1.101 | >3.0 |
| 1.102 | 0.812 |
| 1.103 | 0.590 |
| 1.104 | >2.71 |
| 1.105 | 0.091 |
| 1.106 | >3.0 |
| 1.107 | 0.061 |
| 1.108 | >3.0 |
| 1.109 | 0.189 |
| 1.110 | 0.395 |
| 1.111 | 0.398 |
| 1.112 | 0.141 |
| 1.113 | 0.169 |
| 1.114 | 0.039 |
| 1.115 | 0.051 |
| 1.116 | 0.069 |
| 1.117 | 0.239 |
| 1.118 | 0.072 |
| 1.119 | 0.218 |
| 1.120 | 0.018 |
| 1.121 | 0.565 |
| 1.122 | 0.062 |
| 1.123 | 0.039 |
| 1.124 | 1.86 |
| 1.125 | 0.050 |
| 1.126 | 0.023 |
| 1.127 | 0.043 |
| 1.128 | 0.030 |
| 1.129 | 0.047 |
| 1.130 | 0.081 |
| 1.131 | 0.055 |
| 1.132 | 0.181 |
| 1.133 | 0.270 |
| 1.134 | ND |
| 1.135 | ND |

*ND = Not Done

Example-B2: IP-10 Cytokine Release Assay in THP-1 Cell Lines

Percent release of Interferon gamma-induced protein 10 (IP-10) was determined in acute monocytic leukemia (THP-1; ATCC® TIB-202™) cell line. THP-1 cells (0.2×10$^6$ cells/well) were differentiated using phorbol 12-myristate 13-acetate (PMA, 10 nM (final concentration); Cat #P8139, Sigma) and incubated for 24 h at 37° C., 5% CO2 in an incubator (cell culture conditions) prior to treating with serial dilutions of compounds (3 fold, 6 point dose response starting at 10 μM). After treatment with the compounds cells were further incubated for 2 h under cell culture conditions and then exposed to 2',3'-cGAMP (c-GAMP, 1 μM (final concentration); Cat #SML 1229, Sigma). Differentiated THP-1 cells were further cultured for 24 h after which the supernatant was harvested, and ELISA was performed as per the manufacturer's protocol (BD optEIA Human IP-10 ELISA Set; Cat #550926 & 550534, BD Biosciences). Plates were read in Biotek plate reader by measuring absorbance at 450 nm.

The release of absolute IP-10 in differentiated THP-1 by compounds in the presence of cGAMP was quantified with reference to standard after subtracting blank (negative) reading from the test readings. The absolute release of IP-10 in the presence of cGAMP (1 μM) is given in the bar-graph (FIG. 1) and in the table-B2a.

TABLE B2a

Absolute percent release of IP-10 in THP-1 cell lines

| Compound/cGAMP | Percent release IP-10 (Absolute) |
|---|---|
| CGAMP (1 μM) | 5.6 |
| CGAMP (1 μM) + Compound 1.1 (10 μM) | 18.3 |
| CGAMP (1 μM) + Compound 1.1 (3.33 μM) | 13.1 |
| CGAMP (1 μM) + Compound 1.1 (1.11 μM) | 11.4 |
| CGAMP (1 μM) + Compound 1.1 (0.37 μM) | 8.9 |
| CGAMP (1 μM) + Compound 1.1 (0.12 μM) | 7.0 |
| No drug/No cGAMP | 3.4 |

The release of IP-10 in differentiated THP-1 by compounds over cGAMP induced release at four different concentrations of cGAMP (1, 5, 10 & 30 μM) was quantified with reference to standard by normalizing the blank (negative) subtracted test readings from average of cGAMP activated cells at that particular concentration. The $EC_{50}$'s was calculated by fitting the curve to the "four-parameter variable slope logistic model" using Prism Graph Pad.

The results are given in the table B2b.

TABLE B2b $EC_{50}$ of compounds at different concentration of cGAMP in THP-1 cell lines

| Compound No. | $EC_{50}$ (μM)@ 1 μM of cGAMP | $EC_{50}$ (μM)@ 5 μM of cGAMP | $EC_{50}$ (μM)@ 10 μM of cGAMP | $EC_{50}$ (μM)@ 30 μM of cGAMP |
|---|---|---|---|---|
| 1.1 | 0.308 | <0.12 | 0.471 | 0.624 |
| 1.6 | 7.78 | ND | ND | ND |
| 1.7 | >30 | ND | ND | ND |
| 1.17 | 0.129 | ND | ND | ND |
| 1.19 | <0.120 | ND | ND | ND |
| 1.20 | 5.73 | ND | ND | ND |
| 1.21 | 1.884 | ND | ND | ND |
| 1.22 | 0.490 | ND | ND | ND |
| 1.23 | 7.872 | ND | ND | ND |
| 1.26 | <0.120 | ND | ND | ND |
| 1.27 | <0.100 | ND | ND | ND |
| 1.28 | 9.559 | ND | ND | ND |
| 1.30 | <0.120 | ND | ND | ND |
| 1.35 | >30 | ND | ND | ND |
| 1.39 | 3.26 | ND | ND | ND |
| 1.46 | 0.912 | ND | ND | ND |
| 1.47 | 19.92 | ND | ND | ND |
| 1.48 | >30 | ND | ND | ND |
| 1.49 | >30 | ND | ND | ND |
| 1.50 | >30 | ND | ND | ND |
| 1.51 | >30 | ND | ND | ND |
| 1.52 | >18.6 | ND | ND | ND |
| 1.63 | <0.120 | ND | ND | ND |
| 1.66 | <0.120 | ND | ND | ND |
| 1.69 | 0.724 | ND | ND | ND |
| 1.70 | 0.304 | ND | ND | ND |
| 1.76 | 0.071 | ND | ND | ND |

*ND = Not Done

Example-B3: IFN-β Cytokine Release Assay in THP-1

Percent release of Interferon Beta (IFN-03) was determined in acute monocytic leukemia (THP-1; ATCC® TIB-202™) cell line. THP-1 cells (0.3×10⁶ cells/well) were differentiated using phorbol 12-myristate 13-acetate (PMA, 50 ng/mL; Cat #P8139, Sigma) and incubated for 24 h at 37° C., 5% $CO_2$ in an incubator (cell culture conditions) prior to treating with serial dilutions of compounds (3 fold, 5 point dose response starting at 30 PM). After treatment with the compounds cells were further incubated for 2 h under cell culture conditions and then exposed to 2',3'-cGAMP (c-GAMP, 1 μM; Cat #SML 1229, Sigma). Differentiated THP-1 cells were further cultured for 6 h after which the supernatant was harvested, and ELISA was performed as per the manufacturer's protocol (Human IFN-beta Quantikine ELISA Kit; Cat #DIFNB0, R&D systems). Plates were read in Biotek plate reader by measuring absorbance at 450 nm.

The release of IFN-β in differentiated THP-1 by compounds over cGAMP induced release, was quantified with reference to standard by normalizing the blank (negative) subtracted test readings from average of c-GAMP activated cells and the $IC_{50}$ was calculated by fitting the curve to the "four-parameter variable slope logistic model" using Prism Graph Pad.

The results are presented in the table B3.

TABLE B3

$EC_{50}$ of compounds at 1 μM concentration of cGAMP in THP-1 cell lines

| Compound No. | $EC_{50}$ (μM) @ 1 μM of cGAMP |
|---|---|
| 1.1 | <3.35 |
| 1.6 | >30 |
| 1.20 | >30 |
| 1.21 | >30 |
| 1.23 | >30 |
| 1.28 | >30 |
| 1.30 | >30 |
| 1.39 | >30 |
| 1.70 | 2.82 |
| 1.71 | >30 |
| 1.76 | <0.120 |

Example-B4. IFN-β in Mouse Splenocyte Assay

Percent release of Interferon Beta (IFN-03) is determined in mouse splenocytes isolated from Balb/c mice. Mouse splenocytes (2.5*i10⁵ cells/well) were activated with Anti-mouse CD3e (3 μg/mil, coated overnight at 4° C.; Cat #14-0032-82, eBioscience) and then incubated with Anti-mouse CD28 (3 μg/ml soluble; Cat #16-0289-81, eBiosciences) for 24 h at 37° C., 5% $CO_2$ in an incubator (cell culture conditions) prior to treating them with serial dilutions of compounds (3 fold, 6 point dose response starting at 30 μM). After treatment with the compounds cells are further incubated for 2 h under cell culture conditions and then treated with 2',3'-cGAMP (c-GAMP, 1 μM; Cat #SML 1229, Sigma). Splenocytes were further incubated under cell culture conditions for 24 hr after which the supernatant was harvested, and ELISA was performed as per the manufacturer's protocol (mIFN-β kit; Cat #MIFNB0 & DY008, R&D Systems). Plates were read in Biotek plate reader by measuring absorbance at 450 nm.

The release of IFN-0 in mouse splenocytes by compounds was quantified with reference to standard by normalizing the blank (negative) subtracted test readings from average of c-GAMP activated cells and the $IC_{50}$ was calculated by fitting the curve to the "four-parameter variable slope logistic model" using Prism Graph Pad. The results are given in the table B4.

TABLE B4

$IC_{50}$ for IFN-β in mouse splenocyte assay

| Compound No. | IFN-β in mouse splenocyte $IC_{50}$ (μM) |
|---|---|
| 1.1 | 3.088 |
| 1.76 | 3.258 |

Example-B5: IP-10 in Mouse Splenocyte Assay

Percent release of Interferon gamma-induced protein 10 (IP-10) was determined in mouse splenocytes isolated from Balb/c mice. Mouse splenocytes ($2.5*10^5$ cells/well) were activated with Anti-mouse CD3e (3 µg/ml, coated overnight at 4° C.; Cat #14-0032-82, eBioscience) and then incubated with Anti-mouse CD28 (3 µg/ml soluble; Cat #16-0289-81, eBiosciences) for 24 h at 37° C., 5% $CO_2$ in an incubator (cell culture conditions) prior to treating them with serial dilutions of compounds (3 fold, 6 point dose response starting at 30 µM). After treatment with the compounds cells were further incubated for 2 h under cell culture conditions and then treated with 2',3'-cGAMP (c-GAMP, 1 µM; Cat #SML 1229, Sigma). Splenocytes were further incubated under cell culture conditions for 48 hr after which the supernatant was harvested, and ELISA was performed as per the manufacturer's protocol (mIP-10 kit; Cat #DY466-05 & DY008, R&D Systems). Plates were read in Biotek plate reader by measuring absorbance at 450 nm.

The release of IP-10 in mouse splenocytes by compounds was quantified with reference to standard by normalizing the blank (negative) subtracted test readings from average of c-GAMP activated cells and the $IC_{50}$ was calculated by fitting the curve to the "four-parameter variable slope logistic model" using Prism Graph Pad. The results are shown in the table B5.

TABLE B5

$IC_{50}$ for IP-10 in mouse splenocyte assay

| Compound No. | IP-10 in mouse splenocyte $IC_{50}$ (µM) |
|---|---|
| 1.1 | 1.722 |
| 1.76 | 1.776 |

Example-B6: Determination of TBK1, IRF3 and NF-kB-p65 (Phosphorylated & Total) in THP-1 Assay Determination of phosphorylated and total TBK1, IRF3 and NF-kB-p65 is done in acute monocytic leukemia (THP-1; ATCC® TIB-202™) cell line. THP-1 cells ($2*10^6$ cells/well) are activated with PMA (50 ng/ml; Cat #P8139, Sigma) for 24 hour following which compound treatment for the induction of TBK1 and its phoshorylation (Ser172) expression is done. After 24 hour of incubation, the differentiated THP-1 cells are treated with 30 µM of compound for 2 hour and then exposed to cGAMP (10 µg/mL; SML 1229, Sigma) for 90 min in cell culture conditions. The cells are harvested, lysed and sonicated using 1×RIPA buffer (Cat #9806; Cell Signaling Technologies) with protease inhibitor (1×) and phosphatase inhibitor (1×). Protein estimation is done using Bradford and sample is prepared in 5× Sample loading buffer. The samples are run by SDS PAGE Electrophoresis and the protein bands are transferred onto PVDF membrane by wet transfer. The membrane is blocked in 5% nonfat dry milk and incubated with primary antibody (TBK; 1:1000, Cat #3504S; Cell Signaling Technologies) and (phoshoTBK1; 1:1000, Cat #5483S; Cell Signaling Technologies), (IRF3-1:1000, Cat #4302S; Cell Signaling Technologies) and (phoshoIRF3-1:1000, Cat #4947S; Cell Signaling Technologies), (NF-kB p65; 1:1000, Cat #8242S; Cell Signaling Technologies) and (phosho NF-kB p65; 1:1000, Cat #3033S; Cell Signaling Technologies) and secondary antibody (Anti rabbit IgG; 1:2000; Cell Signaling Technologies). The membrane is then developed using ECL reagent in a gel doc system. The expression of protein is quantified by densitometry analysis.

What is claimed is:

1. A compound selected from

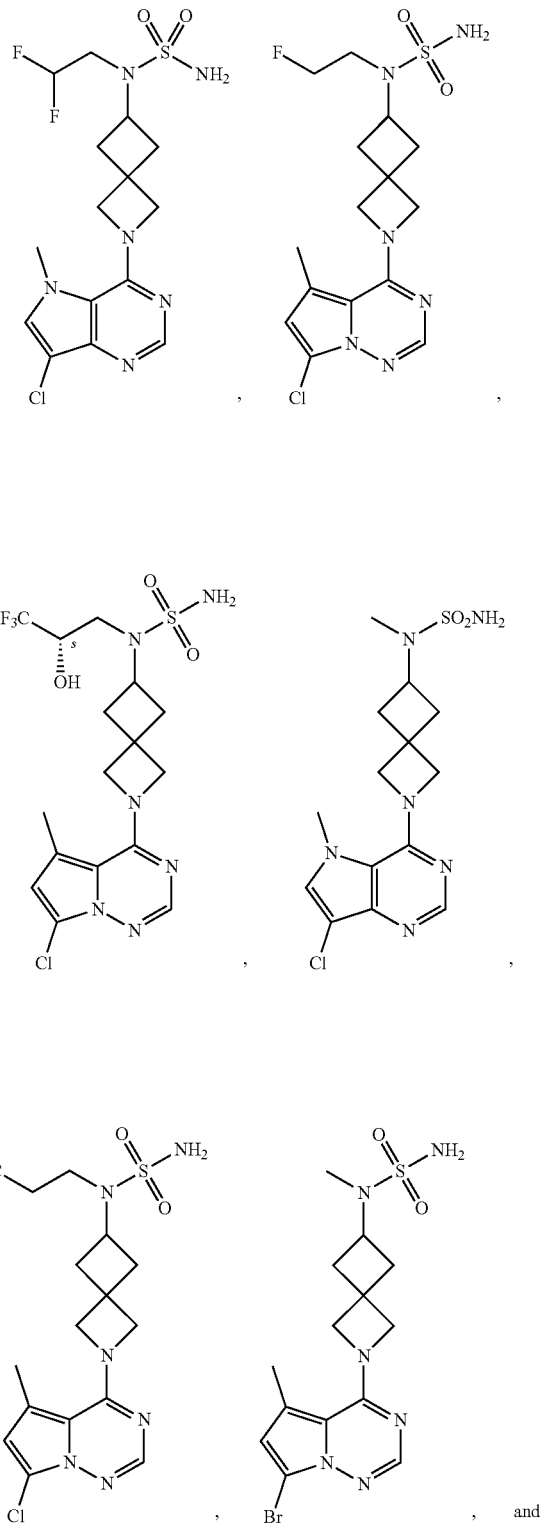

, and

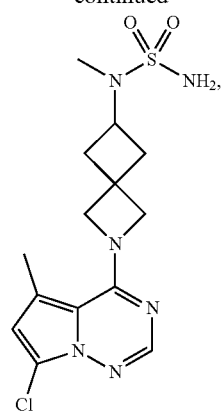
or a pharmaceutically acceptable salt thereof.
2. A compound selected from
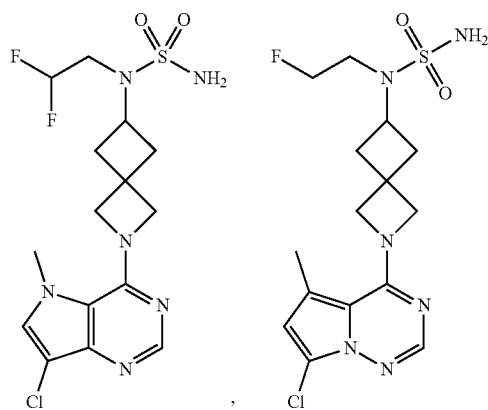
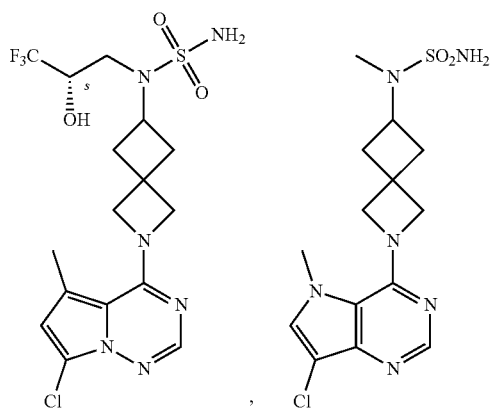
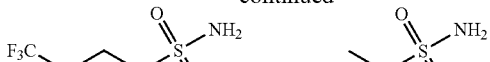
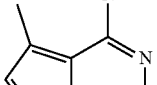 and
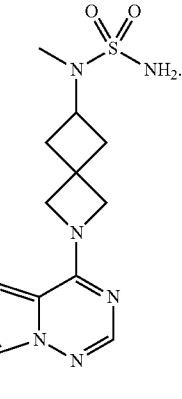
3. The compound of claim 1, which is:
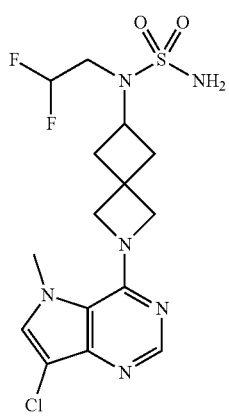 [SMILES: Cn1cc(Cl)c2ncnc(N3CC4(CC(N(CC(F)F)S(N)(=O)=O)C4)C3)c21]
or a pharmaceutically acceptable salt thereof.

4. The compound of claim 1, which is:

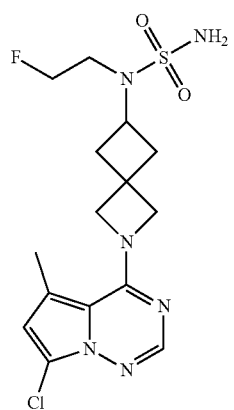 [SMILES: Cc1cc(Cl)n2ncnc(N3CC4(CC(N(CCF)S(N)(=O)=O)C4)C3)c12]

or a pharmaceutically acceptable salt thereof.

5. The compound of claim 1, which is:

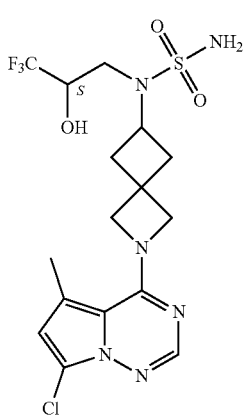

or a pharmaceutically acceptable salt thereof.

6. The compound of claim 1, which is:

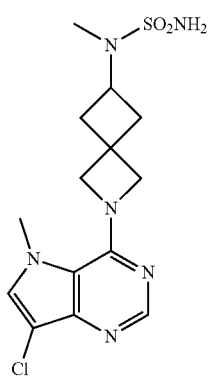 [SMILES: CN(C1CC2(C1)CN(c1ncnc3c(Cl)cn(C)c13)C2)S(N)(=O)=O]

or a pharmaceutically acceptable salt thereof.

7. The compound of claim 1, which is:

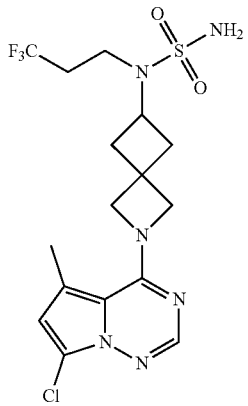 [SMILES: Cc1cc(Cl)n2ncnc(N3CC4(CC(N(CCC(F)(F)F)S(N)(=O)=O)C4)C3)c12]

or a pharmaceutically acceptable salt thereof.

8. The compound of claim 1, which is:

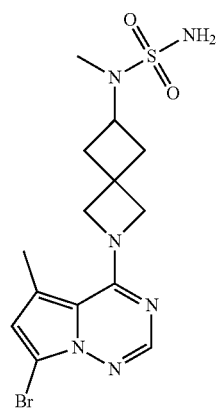 [SMILES: Cc1cc(Br)n2ncnc(N3CC4(CC(N(C)S(N)(=O)=O)C4)C3)c12]

or a pharmaceutically acceptable salt thereof.

9. The compound of claim 1, which is:

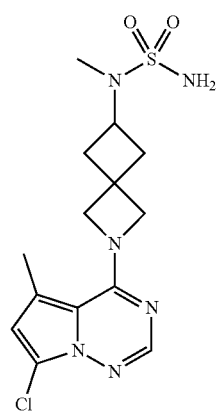 [SMILES: Cc1cc(Cl)n2ncnc(N3CC4(CC(N(C)S(N)(=O)=O)C4)C3)c12]

or a pharmaceutically acceptable salt thereof.

10. A pharmaceutical composition comprising a compound of claim 1 or a pharmaceutically acceptable salt thereof and a pharmaceutically acceptable excipient.

11. A pharmaceutical composition comprising a compound of claim 2 and a pharmaceutically acceptable excipient.

* * * * *